(12) United States Patent
Davis et al.

(10) Patent No.: US 10,202,640 B2
(45) Date of Patent: Feb. 12, 2019

(54) SINGLE CELL ANALYSIS OF T CELLS USING HIGH-THROUGHPUT MULTIPLEX AMPLIFICATION AND DEEP SEQUENCING

(71) Applicant: The Board of Trustees of the Leland Stanford Junior University, Stanford, CA (US)

(72) Inventors: Mark M. Davis, Atherton, CA (US); Jacob Glanville, San Francisco, CA (US); Arnold Han, Los Altos Hills, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 496 days.

(21) Appl. No.: 14/700,797

(22) Filed: Apr. 30, 2015

(65) Prior Publication Data
US 2015/0337369 A1  Nov. 26, 2015

Related U.S. Application Data

(60) Provisional application No. 61/990,080, filed on May 7, 2014.

(51) Int. Cl.
*C12Q 1/68* (2018.01)
*C07H 21/04* (2006.01)
(Continued)

(52) U.S. Cl.
CPC .................... *C12Q 1/686* (2013.01)

(58) Field of Classification Search
CPC .............. C12Q 1/686; C12Q 2525/191; C12Q 2535/122; C12Q 2537/143; C12Q 2563/185
See application file for complete search history.

(56) References Cited

U.S. PATENT DOCUMENTS 7,375,211 B2    5/2008   Kou et al.
7,691,994 B2    4/2010   Brewer et al.
(Continued)

FOREIGN PATENT DOCUMENTS

WO      WO-9213949 A1 *  8/1992   ......... C07K 14/7051
WO      WO 2004/033728 A2  4/2004
(Continued)

OTHER PUBLICATIONS

"Common primer sequence" from Open WetWare, Aug. 2007; downloaded from www.openwetware.org/wiki/Common_primer_sequences on Aug. 29, 2017.*
(Continued)

*Primary Examiner* — Teresa E Strzelecka
(74) *Attorney, Agent, or Firm* — Bozicevic, Field & Francis LLP; Paula A. Borden; Payal B. Sud

(57) ABSTRACT

Methods and oligonucleotide reagents for analyzing individual T cells are disclosed. In particular, the present disclosure provides methods for analyzing individual T cells using high-throughput multiplex amplification and deep sequencing of nucleic acids encoding T cell receptors (TCRs) and various other T cell phenotypic markers. The present disclosure further provides methods of reconstituting TCRs from individual T cells for functional studies, ligand discovery, or screening therapeutics.

21 Claims, 215 Drawing Sheets

Specification includes a Sequence Listing.

(51) Int. Cl.
  *C12Q 1/686* (2018.01)
  *G01N 33/535* (2006.01)

(56) References Cited

U.S. PATENT DOCUMENTS

| | | | |
|---|---|---|---|
| 8,497,071 | B2 | 7/2013 | Balazs et al. |
| 8,507,205 | B2 | 8/2013 | Faham et al. |
| 8,628,927 | B2 | 1/2014 | Faham et al. |
| 2007/0161001 | A1 | 7/2007 | Leshkowitz |
| 2010/0021896 | A1 | 1/2010 | Han |
| 2010/0255471 | A1 | 10/2010 | Clarke et al. |
| 2010/0330571 | A1* | 12/2010 | Robins ............... C12Q 1/6883 435/6.16 |
| 2012/0220466 | A1 | 8/2012 | Fire et al. |
| 2016/0024493 | A1* | 1/2016 | Robins ............... C12N 15/1065 506/2 |

FOREIGN PATENT DOCUMENTS

| | | | | |
|---|---|---|---|---|
| WO | WO-2006000830 | A2 * | 1/2006 | ......... C07K 14/7051 |
| WO | WO 2009/045898 | A2 | 9/2009 | |
| WO | WO 2011/139372 | A2 | 10/2011 | |
| WO | WO 2012/083225 | A2 | 6/2012 | |
| WO | WO-2013086450 | A1 * | 6/2013 | ............. G06F 19/22 |
| WO | WO-2013097744 | A1 * | 7/2013 | ........... C12Q 1/6881 |

OTHER PUBLICATIONS

Su, L.F. et al., Immunity, vol. 38, pp. 373-383 (Feb. 2013 ).*
Su, L.F. et al., Immunity, vol. 38, supplemental material, pp. 1-12 (Feb. 2013 ).*
Buck, G.A. et al., Biotechniques, vol. 27, pp. 528-536 (1999).*
GenBank Accession No. DQ010327 (May 2005).*
Britanova et al. (2014) Age-Related Decrease in TCR Repertoire Diversity Measured with Deep and Normalized Sequence Profiling. J. Immunol. 192(6):2689-2698.
Dash et al. (2011) Paired analysis of TCRalpha and TCRbeta chains at the single-cell level in mice. J. Clin. Invest. 121:288-295.
Dekosky et al. (2013) High-throughput sequencing of the paired human immunoglobulin heavy and light chain repertoire. Nat. Biotechnol. 31:166-169.
Estorninho et al. (2013) A novel approach to tracking antigen-experienced CD4 T cells into functional compartments via tandem deep and shallow TCR clonotyping. J. Immunol. 191(11):5430-5440.
Gerlach et al. (2010) One naive T cell, multiple fates in CD8+ T cell differentiation. J. Exp. Med. 207(6):1235-1246.
Han, et al.; "Linking T-cell receptor sequence to functional phenotype at the single-cell level"; Nat Biotechnol.; vol. 32, No. 7, pp. 684-692 (Jul. 2014).
Kim et al. (2012) Analysis of the paired TCR alpha- and beta-chains of single human T cells. PloS One 7:e37338.
Schepers et al. (2008) Dissecting T cell lineage relationships by cellular barcoding. J. Exp. Med. 205(10):2309-2318.
Shapiro et al. (2013) Single-cell sequencing-based technologies will revolutionize whole-organism science. Nature Reviews Genetics 14:618-630.
Wang et al. (2012) High-throughput, high-fidelity HLA genotyping with deep sequencing. Proc. Natl. Acad. Sci. U.S.A.109:8676-8681.
Wu et al. (2013) Quantitative assessment of single-cell RNA-sequencing methods. Nat Methods 11(1):41-46.

* cited by examiner

|  | TCRα efficiency | TCRβ efficiency |
|---|---|---|
| Plate 1 (split) | 79/88 (90%) | 80/88 (91%) |
| Plate 2 (split) | 76/88 (86%) | 83/88 (94%) |
| Split Plates | 155/176 (88%) | 163/176 (93%) |
| Plate 1 (combined) | 74/88 (84%) | 77/88 (88%) |
| Plate 2 (combined) | 64/88 (72%) | 83/88 (94%) |
| Combined Plates | 138/176 (78%) | 160/176 (91%) |
| Jurkat Wells | 16/16 (100%) | 16/16 (100%) |
| Blank Wells | 0/16 (0%) | 0/16 (0%) |

FIG. 1C

| GENE | READ/WELL |
|---|---|
| FOXP3 | 550 |
| GATA3 | 478 |
| GZMB | 353 |
| IFNG | 605 |
| IL17A | 442 |
| PRF1 | 283 |
| RORC | 974 |
| TBET | 389 |
| TGFB1 | 156 |
| TNF | 524 |
| BCL6 | 584 |
| RUNX1 | 517 |
| RUNX3 | 493 |

FIG. 8E

| Clone | TRBV | CDR3 | | | | | | | | | | | | | TRBJ |
|---|---|---|---|---|---|---|---|---|---|---|---|---|---|---|---|
| A(52) | TRBV 13 | C<br>tgt | A<br>gcc | S<br>agc | S<br>agc | L<br>cta | A<br>gcg | M | G | V<br>c | G<br>ggg | E<br>gag | L<br>ctg | F<br>ttt | F<br>ttt | TRBJ 2-2 |
| B(8) | | C<br>tgt | A<br>gcc | S<br>agc | S<br>agc | S | A | S | G | V<br>c | G<br>ggg | E<br>gag | L<br>ctg | F<br>ttt | F<br>ttt | |

| Clone | TRAV | CDR3 | | | | | | | | | | | | | TRAJ |
|---|---|---|---|---|---|---|---|---|---|---|---|---|---|---|---|
| A(52) | TRAV 38-2 | C<br>tgt | A<br>gct | Y<br>tat | R<br>agg | P | N | Y | G<br>ggt | A<br>gct | T<br>aca | N<br>aac | K<br>aag | L<br>ctc | I<br>atc | F<br>ttt | TRAJ 32 |
| B(8) | | C<br>tgt | A<br>gct | Y<br>tat | R<br>agg | P | N | Y | G<br>ggt | A<br>gct | T<br>aca | N<br>aac | K<br>aag | L<br>ctc | I<br>atc | F<br>ttt | |

Table 1.

| Primer | Reaction | Sequence | SEQ ID NO: |
|---|---|---|---|
| TRAV1 | Reaction 1 | CTGCACGTACCAGACATCTGGGTT | 7 |
| TRAV2 | Reaction 1 | GGCTCAAAGCCTTCTCAGCAGG | 8 |
| TRAV3 | Reaction 1 | GGATAACCTGGTTAAAGGCAGCTA | 9 |
| TRAV4 | Reaction 1 | GGATACAAGACAAAAGTTACAAACGA | 10 |
| TRAV5 | Reaction 1 | GCTGACGTATATTTTTTCAAATATGGA | 11 |
| TRAV6 | Reaction 1 | GGAAGAGGCCCTGTTTTCTTGCT | 12 |
| TRAV7 | Reaction 1 | GCTGGATATGAGAAGCAGAAAGGA | 13 |
| TRAV8 | Reaction 1 | AGGACTCCAGCTTCTCCTGAAGTA | 14 |
| TRAV9 | Reaction 1 | GTATGTCCAATATCCTGGAGAAGGT | 15 |
| TRAV10 | Reaction 1 | CAGTGAGAACACAAAGTCGAACGG | 16 |
| TRAV12.1 | Reaction 1 | CCTAAGTTGCTGATGTCCGTATAC | 17 |
| TRAV12.2 | Reaction 1 | GGGAAAAGCCCTGAGTTGATAATGT | 18 |
| TRAV12.3 | Reaction 1 | GCTGATGTACACATACTCCAGTGG | 19 |
| TRAV13.1 | Reaction 1 | CCCTTGGTATAAGCAAGAACTTGG | 20 |
| TRAV13.2 | Reaction 1 | CCTCAATTCATTATAGACATTCGTTC | 21 |
| TRAV14 | Reaction 1 | GCAAAATGCAACAGAAGGTCGCTA | 22 |
| TRAV16 | Reaction 1 | TAGAGAGAGCATCAAAGGCTTCAC | 23 |
| TRAV17 | Reaction 1 | CGTTCAAATGAAAGAGAGAAACACAG | 24 |
| TRAV18 | Reaction 1 | CCTGAAAAGTTCAGAAAACCAGGAG | 25 |

Figure 12B

| Primer | Reaction | Sequence | SEQ ID NO: |
|---|---|---|---|
| TRAV19 | Reaction 1 | GGTCGGTATTCTTGGAACTTCCAG | 26 |
| TRAV20 | Reaction 1 | GCTGGGGAAGAAAAGGAGAAAGAAA | 27 |
| TRAV21 | Reaction 1 | GTCAGAGAGAGCAAACAAGTGGAA | 28 |
| TRAV22 | Reaction 1 | GGACAAAACAGAATGGAAGATTAAGC | 29 |
| TRAV23 | Reaction 1 | CCAGATGTGAGTGAAAAGAAAGAAG | 30 |
| TRAV24 | Reaction 1 | GACTTTAAATGGGGATGAAAAGAAGA | 31 |
| TRAV25 | Reaction 1 | GGAGAAGTGAAGAAGCAGAAAAGAC | 32 |
| TRAV26.1 | Reaction 1 | CCAATGAAATGGCCTCTCTGATCA | 33 |
| TRAV26.2 | Reaction 1 | GCAATGTGAACAACAGAATGGCCT | 34 |
| TRAV27 | Reaction 1 | GGTGGAGAAGTGAAGAAGCTGAAG | 35 |
| TRAV29 | Reaction 1 | GGATAAAAATGAAGATGGAAGATTCAC | 36 |
| TRAV30 | Reaction 1 | CCTGATGATATTACTGAAGGGTGGA | 37 |
| TRAV34 | Reaction 1 | GGTGGGGAAGAGAAAAGTCATGAA | 38 |
| TRAV35 | Reaction 1 | GGTGAATTGACCTCAAATGGAAGAC | 39 |
| TRAV36 | Reaction 1 | GCTAACTTCAAGTGGAATTGAAAAGA | 40 |
| TRAV38 | Reaction 1 | GAAGCTTATAAGCAACAGAATGCAAC | 41 |
| TRAV39 | Reaction 1 | GGAGCAGTGAAGCAGGAGGGAC | 42 |
| TRAV40 | Reaction 1 | GAGAGACAATGGAAAACAGCAAAAAC | 43 |
| TRAV41 | Reaction 1 | GCTGAGCTCAGGGAAGAAGAAGC | 44 |
| TRBV2 | Reaction 1 | CTGAAATATTCGATGATCAATTCTCAG | 45 |
| TRBV3-1 | Reaction 1 | TCATTATAAATGAAACAGTTCCAAATCG | 46 |

Figure 12C

| Primer | Reaction | Sequence | SEQ ID NO: |
|---|---|---|---|
| TRBV4 | Reaction 1 | AGTGTGCCAAGTCGCTTCTCAC | 47 |
| TRBV5-4,8 | Reaction 1 | CAGAGGAAACTYCCCTCCTAGATT | 48 |
| TRBV5-1 | Reaction 1 | GAGACACAGAGAAACAAAGGAAACTTC | 49 |
| TRBV6-1 | Reaction 1 | GGTACCACTGACAAAGGAGAAGTCC | 50 |
| TRBV6-2,3 | Reaction 1 | GAGGGTACAACTGCCAAAGGAGAGGT | 51 |
| TRBV6-4 | Reaction 1 | GGCAAAGGAGAAGTCCCTGATGGTT | 52 |
| TRBV6-5,6 | Reaction 1 | AAGGAGAAGTCCCSAATGGCTACAA | 53 |
| TRBV6-8 | Reaction 1 | CTGACAAAGAAGTCCCCAATGGCTAC | 54 |
| TRBV6-9 | Reaction 1 | CACTGACAAAGGAGAAGTCCCCGAT | 55 |
| TRBV7-2 | Reaction 1 | AGACAAATCAGGGCTGCCCAGTGA | 56 |
| TRBV7-3 | Reaction 1 | GACTCAGGGCTGCCCAACGAT | 57 |
| TRBV7-8 | Reaction 1 | CCAGAATGAAGCTCAACTAGACAA | 58 |
| TRBV7-4,6 | Reaction 1 | GGTTCTCTGCAGAGAGGCCTGAG | 59 |
| TRBV7-7 | Reaction 1 | GGCTGCCCAGTGATCGGTTCTC | 60 |
| TRBV7-9 | Reaction 1 | GACTTACTTCCAGAATGAAGCTCAACT | 61 |
| TRBV9 | Reaction 1 | GAGCAAAAGGAAACATTCTTGAACGATT | 62 |
| TRBV10-1,3 | Reaction 1 | GGCTRATCCATTACTCATATGGTGTT | 63 |
| TRBV10-2 | Reaction 1 | GATAAAGGAGAAGTCCCCGATGGCT | 64 |
| TRBV11 | Reaction 1 | GATTCACAGTTGCCTAAGGATCGAT | 65 |
| TRBV12-3,4 | Reaction | GATTCAGGGATGCCCGAGGATCG | 66 |
| TRBV12-5 | Reaction 1 | GATTCGGGGATGCCGAAGGATCG | 67 |

Figure 12D

| Primer | Reaction | Sequence | SEQ ID NO: |
|---|---|---|---|
| TRBV13 | Reaction 1 | GCAGAGCGATAAAGGAAGCATCCCT | 68 |
| TRBV14 | Reaction 1 | TCCGGTATGCCCAACAATCGATTCT | 69 |
| TRBV15 | Reaction 1 | GATTTTAACAATGAAGCAGACACCCCT | 70 |
| TRBV16 | Reaction 1 | GATGAAACAGGTATGCCCAAGGAAAG | 71 |
| TRBV18 | Reaction 1 | TATCATAGATGAGTCAGGAATGCCAAAG | 72 |
| TRBV19 | Reaction 1 | GACTTTCAGAAAGGAGATATAGCTGAA | 73 |
| TRBV20-1 | Reaction 1 | CAAGGCCACATACGAGCAAGGCGTC | 74 |
| TRBV24-1 | Reaction 1 | CAAAGATATAAACAAAGGAGAGATCTCT | 75 |
| TRBV25-1 | Reaction 1 | AGAGAAGGGAGATCTTTCCTCTGAGT | 76 |
| TRBV27-1 | Reaction 1 | GACTGATAAGGGAGATGTTCCTGAAG | 77 |
| TRBV28 | Reaction 1 | GGCTGATCTATTTCTCATATGATGTTAA | 78 |
| TRBV29 | Reaction 1 | GCCACATATGAGAGTGGATTTGTCATT | 79 |
| TRBV30 | Reaction 1 | GGTGCCCCAGAATCTCTCAGCCT | 80 |
| TRAC | Reaction 1 | CGGTGAATAGGCAGACAGACTTGT | 81 |
| TRBC | Reaction 1 | ACCAGTGTGGCCTTTTGGGTGTG | 82 |
| TRAV1 | Reaction 2 | CCAGGGTTTTCCCAGTCACGACAGGTCGTTTTTCTTCATTCCTTAGTC | 83 |
| TRAV2 | Reaction 2 | CCAGGGTTTTCCCAGTCACGACACGATACAACATGACCTATGAACGG | 84 |
| TRAV3.1 | Reaction 2 | CCAGGGTTTTCCCAGTCACGACCTTTGAAGCTGAATTTAACAAGAGCC | 85 |
| TRAV4.1 | Reaction 2 | CCAGGGTTTTCCCAGTCACGACCTCCCTGTTTATCCCTGCCGAC | 86 |
| TRAV5.1 | Reaction 2 | CCAGGGTTTTCCCAGTCACGACAAACAAGACCAAAGACTCACTGTTC | 87 |

Figure 12E

| Primer | Reaction | Sequence | SEQ ID NO: |
|---|---|---|---|
| TRAV6 | Reaction 2 | CCAGGGTTTTCCCAGTCACGACAAGACTGAAGGTCACCTTTGATACC | 88 |
| TRAV7 | Reaction 2 | CCAGGGTTTTCCCAGTCACGACACTAAATGCTACATTACTGAAGAATGG | 89 |
| TRAV8 | Reaction 2 | CCAGGGTTTTCCCAGTCACGACGCATCAACGGTTTTGAGGCTGAATTTAA | 90 |
| TRAV9 | Reaction 2 | CCAGGGTTTTCCCAGTCACGACGAAACCACTTCTTTCCACTTGGAGAA | 91 |
| TRAV10 | Reaction 2 | CCAGGGTTTTCCCAGTCACGACTACAGCAACTCTGGATGCAGACAC | 92 |
| TRAV12 | Reaction 2 | CCAGGGTTTTCCCAGTCACGACGAAGATGGAAGGTTTACAGCACA | 93 |
| TRAV13.1 | Reaction 2 | CCAGGGTTTTCCCAGTCACGACGACATTCGTTCAAATGTGGGCGAA | 94 |
| TRAV13.2 | Reaction 2 | CCAGGGTTTTCCCAGTCACGACGGCAAGGCCAAAGAGTCACCGT | 95 |
| TRAV14 | Reaction 2 | CCAGGGTTTTCCCAGTCACGACCCAGAAGGCAAGAAAATCCGCCA | 96 |
| TRAV16 | Reaction 2 | CCAGGGTTTTCCCAGTCACGACGCTGACCTTAACAAAGGCGAGACA | 97 |
| TRAV17 | Reaction 2 | CCAGGGTTTTCCCAGTCACGACTTAAGAGTCACGCTTGACACTTCCA | 98 |
| TRAV18 | Reaction 2 | CCAGGGTTTTCCCAGTCACGACGCAGAGGTTTTCAGGCCAGTCCT | 99 |
| TRAV19 | Reaction 2 | CCAGGGTTTTCCCAGTCACGACTCCACCAGTTCCTTCAACTTCACC | 100 |
| TRAV20 | Reaction 2 | CCAGGGTTTTCCCAGTCACGACGCCACATTAACAAAGAAGGAAAGCT | 101 |
| TRAV21 | Reaction 2 | CCAGGGTTTTCCCAGTCACGACGCCTCGCTGGATAAATCATCAGGA | 102 |
| TRAV22 | Reaction 2 | CCAGGGTTTTCCCAGTCACGACACGACTGTCGCTACGGAACGCTA | 103 |
| TRAV23 | Reaction 2 | CCAGGGTTTTCCCAGTCACGACCACAATCTCCTTCAATAAAAGTGCCA | 104 |
| TRAV24 | Reaction 2 | CCAGGGTTTTCCCAGTCACGACACGAATAAGTGCCACTCTTAATACCA | 105 |
| TRAV25 | Reaction 2 | CCAGGGTTTTCCCAGTCACGACGTTTGGAGAAGCAAAAAAGAACAGCT | 106 |

Figure 12F

| Primer | Reaction | Sequence | SEQ ID NO: |
|---|---|---|---|
| TRAV26.1 | Reaction 2 | CCAGGGTTTTCCCAGTCACGACCAGAAGACAGAAAGTCCAGCACCT | 107 |
| TRAV26.2 | Reaction 2 | CCAGGGTTTTCCCAGTCACGACATCGCTGAAGACAGAAAGTCCAGT | 108 |
| TRAV27 | Reaction 2 | CCAGGGTTTTCCCAGTCACGACACTAACCTTTCAGTTTGGTGATGCAA | 109 |
| TRAV29 | Reaction 2 | CCAGGGTTTTCCCAGTCACGACCTTAAACAAAAGTGCCAAGCACCTC | 110 |
| TRAV30 | Reaction 2 | CCAGGGTTTTCCCAGTCACGACAATATCTGCTTCATTTAATGAAAAAAGC | 111 |
| TRAV34 | Reaction 2 | CCAGGGTTTTCCCAGTCACGACCAAGTTGGATGAGAAAAAGCAGCA | 112 |
| TRAV35 | Reaction 2 | CCAGGGTTTTCCCAGTCACGACCTCAGTTTGGTATAACCAGAAAGGA | 113 |
| TRAV36 | Reaction 2 | CCAGGGTTTTCCCAGTCACGACGGAAGACTAAGTAGCATATTAGATAAG | 114 |
| TRAV38 | Reaction 2 | CCAGGGTTTTCCCAGTCACGACCTGTGAACTTCCAGAAAGCAGCCA | 115 |
| TRAV39 | Reaction 2 | CCAGGGTTTTCCCAGTCACGACCCTCACTTGATACCAAAGCCCGT | 116 |
| TRAV40 | Reaction 2 | CCAGGGTTTTCCCAGTCACGACAGGCGGAAATATTAAAGACAAAAACTC | 117 |
| TRAV41 | Reaction 2 | CCAGGGTTTTCCCAGTCACGACGATTAATTGCCACAATAAACATACAGG | 118 |
| TRBV2 | Reaction 2 | CCAGGGTTTTCCCAGTCACGACGCCTGATGGATCAAATTTCACTCTG | 119 |
| TRBV3-1 | Reaction 2 | CCAGGGTTTTCCCAGTCACGACTCTCACCTAAATCTCCAGACAAAGCT | 120 |
| TRBV4 | Reaction 2 | CCAGGGTTTTCCCAGTCACGACCCTGAATGCCCCAACAGCTCTC | 121 |
| TRBV5-4,8 | Reaction 2 | CCAGGGTTTTCCCAGTCACGACCTCTGAGCTGAATGTGAACGCCT | 122 |
| TRBV5-1 | Reaction 2 | CCAGGGTTTTCCCAGTCACGACCGATTCTCAGGGCGCCAGTTCTCT | 123 |
| TRBV6-1 | Reaction 2 | CCAGGGTTTTCCCAGTCACGACTGGCTACAATGTCTCCAGATTAAACAA | 124 |
| TRBV6-2,3 | Reaction 2 | CCAGGGTTTTCCCAGTCACGACCCCTGATGGCTACAATGTCTCCAGA | 125 |

Figure 12G

| Primer | Reaction | Sequence | SEQ ID NO: |
|---|---|---|---|
| TRBV6-4 | Reaction 2 | CCAGGGTTTTCCCAGTCACGACGTGTCTCCAGAGCAAACACAGATGATT | 126 |
| TRBV6-5,6 | Reaction 2 | CCAGGGTTTTCCCAGTCACGACGTCTCCAGATCAACCACAGAGGAT | 127 |
| TRBV6-8 | Reaction 2 | CCAGGGTTTTCCCAGTCACGACGTCTCTAGATTAAACACAGAGGATTTC | 128 |
| TRBV6-9 | Reaction 2 | CCAGGGTTTTCCCAGTCACGACGGCTACAATGTATCCAGATCAAACA | 129 |
| TRBV7-2 | Reaction 2 | CCAGGGTTTTCCCAGTCACGACTCGCTTCTCTGCAGAGAGGACTGG | 130 |
| TRBV7-3 | Reaction 2 | CCAGGGTTTTCCCAGTCACGACCGGTTCTTTGCAGTCAGGCCTGA | 131 |
| TRBV7-8 | Reaction 2 | CCAGGGTTTTCCCAGTCACGACCCAGTGATCGCTTCTTTGCAGAAA | 132 |
| TRBV7-4,6 | Reaction 2 | CCAGGGTTTTCCCAGTCACGACTCTCCACTCTGAMGATCCAGCGCA | 133 |
| TRBV7-7 | Reaction 2 | CCAGGGTTTTCCCAGTCACGACGCAGAGAGGCCTGAGGGATCCAT | 134 |
| TRBV9 | Reaction 2 | CCAGGGTTTTCCCAGTCACGACCTGCAGAGAGGCCTAAGGGATCT | 135 |
| TRBV10-1,3 | Reaction 2 | CCAGGGTTTTCCCAGTCACGACCTCCGCACAACAGTTCCCTGACTT | 136 |
| TRBV10-2 | Reaction 2 | CCAGGGTTTTCCCAGTCACGACCAGATGGCTAYAGTGTCTCTAGATCAAA | 137 |
| TRBV11 | Reaction 2 | CCAGGGTTTTCCCAGTCACGACGTTGTCTCCAGATCCAAGACAGAGAA | 138 |
| TRBV12-3,4 | Reaction 2 | CCAGGGTTTTCCCAGTCACGACGCAGAGAGGCTCAAAGGAGTAGACT | 139 |
| TRBV12-5 | Reaction 2 | CCAGGGTTTTCCCAGTCACGACGCTAAGATGCCTAATGCATCATTCTC | 140 |
| TRBV13 | Reaction 2 | CCAGGGTTTTCCCAGTCACGACCTCAGCAGAGATGCCTGATGCAACT | 141 |
| TRBV14 | Reaction 2 | CCAGGGTTTTCCCAGTCACGACTCTCAGCTCAACAGTTCAGTGACTA | 142 |
| TRBV15 | Reaction 2 | CCAGGGTTTTCCCAGTCACGACGCTGAAAGGACTGGAGGGACGTAT | 143 |
| TRBV16 | Reaction 2 | CCAGGGTTTTCCCAGTCACGACGATAACTTCCAATCCAGGAGGCCG | 144 |

Figure 12H

| Primer | Reaction | Sequence | SEQ ID NO: |
|---|---|---|---|
| TRBV18 | Reaction 2 | CCAGGGTTTTCCCAGTCACGACGCTAAGTGCCTCCCAAATTCACCC | 145 |
| TRBV19 | Reaction 2 | CCAGGGTTTTCCCAGTCACGACGGAACGATTTTCTGCTGAATTTCCCA | 146 |
| TRBV20-1 | Reaction 2 | CCAGGGTTTTCCCAGTCACGACGGTACAGCGTCTCTCGGGAGAAGA | 147 |
| TRBV24-1 | Reaction 2 | CCAGGGTTTTCCCAGTCACGACGGACAAGTTTCTCATCAACCATGCAA | 148 |
| TRBV25-1 | Reaction 2 | CCAGGGTTTTCCCAGTCACGACTGGATACAGTGTCTCTCGACAGGC | 149 |
| TRBV27-1 | Reaction 2 | CCAGGGTTTTCCCAGTCACGACCAACAGTCTCCAGAATAAGGACGGA | 150 |
| TRBV28 | Reaction 2 | CCAGGGTTTTCCCAGTCACGACTACAAAGTCTCTCGAAAAGAAGAGGA | 151 |
| TRBV29 | Reaction 2 | CCAGGGTTTTCCCAGTCACGACGGGGTACAGTGTCTCTAGAGAGA | 152 |
| TRBV30 | Reaction 2 | CCAGGGTTTTCCCAGTCACGACGTTTCCCATCAGCCGCCCAAACCTA | 153 |
| TRBC | Reaction 2 | CCAGGGTTTTCCCAGTCACGACCAGACCCCAGGACCGGCAGTTCAT | 154 |
| TRAC | Reaction 2 | CAGACAGACTTGTCACTGGATTTAG | 155 |
| TRBV7-9 | Reaction 2 | CTTTTGGGTGTGGGAGATCTCTG | 156 |

Figure 13A
Table 2.

| GENE | REACTION 1 PRIMER A | REACTION 1 PRIMER B | REACTION 2 PRIMER A | REACTION 2 PRIMER B |
|---|---|---|---|---|
| GATA3 | GACGCGGCGCAGTACCCGCT (SEQ ID NO:157) | GGAGAAGGGGCTGAGATTCC AG (SEQ ID NO:158) | CCAGGGTTTTCCCAGTCACGA CGCCGGAGGAGGTGGATGTG CTT (SEQ ID NO:159) | AGCGGATAACAATTTCACACA GGAGGGGAGGCGGTGTGGTG GCT (SEQ ID NO:160) |
| TBET | GCCTGTACGTCCACCCGGACT (SEQ ID NO:161) | CTGGGTTTCTTGGAAAGTAAA GATAT (SEQ ID NO:162) | CCAGGGTTTTCCCAGTCACGA CCCAACACAGGAGCGCACTG G (SEQ ID NO:163) | AGCGGATAACAATTTCACACA GGACGTGTTGGAAGCGTTGCA GGCT (SEQ ID NO:164) |
| FOXP3 | GGCTCCTGCTGCATCGTAGCT GCT (SEQ ID NO:165) | GTCCGCTGCTTCTCTGGAGCCT (SEQ ID NO:166) | CCAGGGTTTTCCCAGTCACGA CGGCAGCCAAGGCCCTGTCGT (SEQ ID NO:167) | AGCGGATAACAATTTCACACA GGACCAGGATGGCCCAGCGG ATGA (SEQ ID NO:168) |
| RORC | CCCGGGAGGAAGTGACTGGC TA (SEQ ID NO:169) | CCATGCCACCGTATTTGCCTTC AA (SEQ ID NO:170) | CCAGGGTTTTCCCAGTCACGA CAGAGGAAGTCCATGTGGGA GATGT (SEQ ID NO:171) | AGCGGATAACAATTTCACACA GGATCAGCATTGTAGGCCCGG CACATC (SEQ ID NO:172) |
| RUNX1 | CCGCAGCATGGTGGAGGTGCT (SEQ ID NO:173) | GGTCATTAAATCTTGCAACCTG GTT (SEQ ID NO:174) | CCAGGGTTTTCCCAGTCACGA CGCGAGCTGGTGCGCACCGAC A (SEQ ID NO:175) | AGCGGATAACAATTTCACACA GGAGGCTGCGGTAGCATTTCT CAGCT (SEQ ID NO:176) |
| RUNX3 | GCGCTCGATGGTGGACGTGCT (SEQ ID NO:177) | AGCACGTCCACCATCGAGCGC (SEQ ID NO:178) | CCAGGGTTTTCCCAGTCACGA CGGACCACGCAGGCGAGCTC GT (SEQ ID NO:179) | AGCGGATAACAATTTCACACA GGACGCCGAGGCATTGCGC AGCT (SEQ ID NO:180) |
| BCL6 | GCCAAACCAGAGGGGCCTGA G (SEQ ID NO:181) | GAGAGCCGCAGGACGTGCAC TT (SEQ ID NO:182) | CCAGGGTTTTCCCAGTCACGA CCCTACACGGCCCACCTGCCT (SEQ ID NO:183) | AGCGGATAACAATTTCACACA GGAGGGTGCATGTAGAGTGG TGAGTG (SEQ ID NO:184) |
| IL2 | CTCACATTTAAGTTTTACATGC CCAA (SEQ ID NO:185) | GACAAAAGGTAATCCATCTGT TCAG (SEQ ID NO:186) | CCAGGGTTTTCCCAGTCACGA CCCACAGAACTGAAACATCTTC AGT (SEQ ID NO:187) | AGCGGATAACAATTTCACACA GGATTCTACAATGGTTGCTGT CTCA (SEQ ID NO:188) |

Figure 13B

| GENE | REACTION 1 PRIMER A | REACTION 1 PRIMER B | REACTION 2 PRIMER A | REACTION 2 PRIMER B |
|---|---|---|---|---|
| IL10 | CCAGTTTTACCTGGAGGAGGT GA (SEQ ID NO:189) | GTAGGCTTCTATGTAGTTGAT GAAGA (SEQ ID NO:190) | CCAGGGTTTTCCCAGTCACGA CCCAAGCTGAGAACCAAGAC CCA (SEQ ID NO:101) | AGCGGATAACAATTTCACACA GGAGTCAAACTCACTCATGGC TTTGTA (SEQ ID NO:192) |
| IL12A | GGGAGTTGCCTGGCCTCCAGA A (SEQ ID NO:193) | CGGTTCTTCAAGGGAGGATTT TTGT (SEQ ID NO:194) | CCAGGGTTTTCCCAGTCACGA CAGACCTCTTTTATGATGGCCC TGT (SEQ ID NO:195) | AGCGGATAACAATTTCACACA GGAGGCACAGTCTCACTGTTG AAATTCA (SEQ ID NO:196) |
| IL13 | CCCAGAACCAGAAGGCTCCGC T (SEQ ID NO:197) | CCCTCGCGAAAAAGTTTCTTTA AAT (SEQ ID NO:198) | CCAGGGTTTTCCCAGTCACGA CGGTATGGAGCATCAACCTGA CAG (SEQ ID NO:199) | AGCGGATAACAATTTCACACA GGAGGTCCTTTACAAACTGGG CCAC (SEQ ID NO:200) |
| IL17a | GACAAGAACTTCCCCCGGACT G (SEQ ID NO:201) | GGACCAGGATCTCTTGCTGGA T (SEQ ID NO:202) | CCAGGGTTTTCCCAGTCACGA CCAACCTGAACATCCATAACC GGAA (SEQ ID NO:203) | AGCGGATAACAATTTCACACA GGAGGGGACAGAGTTCATGT GGTAGT (SEQ ID NO:204) |
| IFNG | GGCTTTTCAGCTCTGCATCGTT TT (SEQ ID NO:205) | GGATGCTCTGGTCATCTTTAAA GTT (SEQ ID NO:206) | CCAGGGTTTTCCCAGTCACGA CGGGTTCTCTTGGCTGTTACTG C (SEQ ID NO:207) | AGCGGATAACAATTTCACACA GGAGTTTGAAGTAAAAGGAG ACAATTTG (SEQ ID NO:208) |
| TNFA | CATGATCCGGGACGTGGAGCT (SEQ ID NO:209) | GGGCTACAGGCTTGTCACTCG (SEQ ID NO:210) | CCAGGGTTTTCCCAGTCACGA CGGAGGCGCTCCCCAAGAAGA C (SEQ ID NO:211) | AGCGGATAACAATTTCACACA GGACGAGAAGATGATCTGACT GCCTG (SEQ ID NO:212) |
| TGFB | GCATATATATGTTCTTCAACAC ATCA (SEQ ID NO:213) | CCCTCCACGGCTCAACCACT (SEQ ID NO214) | CCAGGGTTTTCCCAGTCACGA CCCGAGAAGCGGGTACCTGAAC C (SEQ ID NO:215) | AGCGGATAACAATTTCACACA GGACCGCACAACTCCGGTGAC ATCA (SEQ ID NO:216) |
| Perforin | GTGTCTGTGGCCGGCTCACAC (SEQ ID NO:217) | CCGATATGCGGGCCACCCAGCT (SEQ ID NO:218) | CCAGGGTTTTCCCAGTCACGA CGCCAACTTTGCAGCCCAGAA GA (SEQ ID NO:219) | AGCGGATAACAATTTCACACA GGAGGGTGCCGTAGTTGGAG ATAAG (SEQ ID NO:220) |
| granzyme B | GGGAAGCTCCATAAATGTCAC CTT (SEQ ID NO:221) | GTTTTCCCAGGGGGGCCGTCT (SEQ ID NO:222) | CCAGGGTTTTCCCAGTCACGA CCCACAATATCAAAGAACAGG AGCC (SEQ ID NO:223) | AGCGGATAACAATTTCACACA GGAGCCACACTGCATGTCTGC CCT (SEQ ID NO:224) |

Figure 14A

Table 3.

| Primer | Sequence | SEQ ID NO: |
|---|---|---|
| AlphaBC1 | CTGCTGAACCGCTCTTCCGATCTNNGTTCAGTCACTGGATTTAGAGTCTCTCAG | 225 |
| AlphaBC2 | CTGCTGAACCGCTCTTCCGATCTNNCAGGAGTCACTGGATTTAGAGTCTCTCAG | 226 |
| AlphaBC3 | CTGCTGAACCGCTCTTCCGATCTNNTTATAGTCACTGGATTTAGAGTCTCTCAG | 227 |
| AlphaBC4 | CTGCTGAACCGCTCTTCCGATCTNNCCTGTGTCACTGGATTTAGAGTCTCTCAG | 228 |
| AlphaBC5 | CTGCTGAACCGCTCTTCCGATCTNNACCGCGTCACTGGATTTAGAGTCTCTCAG | 229 |
| AlphaBC6 | CTGCTGAACCGCTCTTCCGATCTNNACTTAGTCACTGGATTTAGAGTCTCTCAG | 230 |
| AlphaBC7 | CTGCTGAACCGCTCTTCCGATCTNNGCTAGGTCACTGGATTTAGAGTCTCTCAG | 231 |
| AlphaBC8 | CTGCTGAACCGCTCTTCCGATCTNNGACGTGTCACTGGATTTAGAGTCTCTCAG | 232 |
| AlphaBC9 | CTGCTGAACCGCTCTTCCGATCTNNGGCTAGTCACTGGATTTAGAGTCTCTCAG | 233 |
| AlphaBC10 | CTGCTGAACCGCTCTTCCGATCTNNGAATGGTCACTGGATTTAGAGTCTCTCAG | 234 |
| AlphaBC11 | CTGCTGAACCGCTCTTCCGATCTNNCCAACGTCACTGGATTTAGAGTCTCTCAG | 235 |
| AlphaBC12 | CTGCTGAACCGCTCTTCCGATCTNNGAGACGTCACTGGATTTAGAGTCTCTCAG | 236 |
| BetaBC1 | CTGCTGAACCGCTCTTCCGATCTNNGTTCAGAGATCTCTGCTTCTGATGGCTC | 237 |
| BetaBC2 | CTGCTGAACCGCTCTTCCGATCTNNCAGGAGAGATCTCTGCTTCTGATGGCTC | 238 |
| BetaBC3 | CTGCTGAACCGCTCTTCCGATCTNNTTATAGAGATCTCTGCTTCTGATGGCTC | 239 |
| BetaBC4 | CTGCTGAACCGCTCTTCCGATCTNNCCTGTGAGATCTCTGCTTCTGATGGCTC | 240 |
| BetaBC5 | CTGCTGAACCGCTCTTCCGATCTNNACCGCGAGATCTCTGCTTCTGATGGCTC | 241 |

Figure 14B

| Primer | Sequence | SEQ ID NO: |
|---|---|---|
| BetaBC6 | CTGCTGAACCGCTCTTCCGATCTNNACTTAGAGATCTCTGCTTCTGATGGCTC | 242 |
| BetaBC7 | CTGCTGAACCGCTCTTCCGATCTNNGCTAGGAGATCTCTGCTTCTGATGGCTC | 243 |
| BetaBC8 | CTGCTGAACCGCTCTTCCGATCTNNGACGTGAGATCTCTGCTTCTGATGGCTC | 244 |
| BetaBC9 | CTGCTGAACCGCTCTTCCGATCTNNGGCTAGAGATCTCTGCTTCTGATGGCTC | 245 |
| BetaBC10 | CTGCTGAACCGCTCTTCCGATCTNNGAATGGAGATCTCTGCTTCTGATGGCTC | 246 |
| BetaBC11 | CTGCTGAACCGCTCTTCCGATCTNNCCAACGAGATCTCTGCTTCTGATGGCTC | 247 |
| BetaBC12 | CTGCTGAACCGCTCTTCCGATCTNNGAGACGAGATCTCTGCTTCTGATGGCTC | 248 |
| Phenotype BC1 | CTGCTGAACCGCTCTTCCGATCTNNGTTCAAGCGGATAACAATTTCACACAGGA | 249 |
| Phenotype BC2 | CTGCTGAACCGCTCTTCCGATCTNNCAGGAAGCGGATAACAATTTCACACAGGA | 250 |
| Phenotype BC3 | CTGCTGAACCGCTCTTCCGATCTNNTTATAAGCGGATAACAATTTCACACAGGA | 251 |
| Phenotype BC4 | CTGCTGAACCGCTCTTCCGATCTNNCCTGTAGCGGATAACAATTTCACACAGGA | 252 |
| Phenotype BC5 | CTGCTGAACCGCTCTTCCGATCTNNACCGCAGCGGATAACAATTTCACACAGGA | 253 |
| Phenotype BC6 | CTGCTGAACCGCTCTTCCGATCTNNACTTAAGCGGATAACAATTTCACACAGGA | 254 |
| Phenotype BC7 | CTGCTGAACCGCTCTTCCGATCTNNGCTAGAGCGGATAACAATTTCACACAGGA | 255 |
| Phenotype BC8 | CTGCTGAACCGCTCTTCCGATCTNNGACGTAGCGGATAACAATTTCACACAGGA | 256 |
| Phenotype BC9 | CTGCTGAACCGCTCTTCCGATCTNNGGCTAAGCGGATAACAATTTCACACAGGA | 257 |
| Phenotype | CTGCTGAACCGCTCTTCCGATCTNNGAATGAGCGGATAACAATTTCACACAGG | 258 |

Figure 14C

| Primer | Sequence | SEQ ID NO: |
|---|---|---|
| BC10 | A | |
| Phenotype BC11 | CTGCTGAACCGCTCTTCCGATCTNNCCAACAGCGGATAACAATTTCACACAGGA | 259 |
| Phenotype BC12 | CTGCTGAACCGCTCTTCCGATCTNNGAGACAGCGGATAACAATTTCACACAGGA | 260 |
| PEprimer1 | AATGATACGGCGACCACCGAGATCTACACTCTTTCCCTACACGACGCTCTTCCGATCT | 261 |
| PEprimer2 | AAGCAGAAGACGGCATACGAGATCGGTCTCGGCATTCCTGCTGAACCGCTCTTCCGATCT | 262 |

Figure 15A
Table 4.

| Well | TCR beta V region | J region | CDR3 beta | SEQ ID NO: | Read # |
|---|---|---|---|---|---|
| 1A1 | TRBV7-9 | TRBJ1-5 | CASSFFGNQPQHF | 272 | 2759 |
| 1A2 | TRBV7-2 | TRBJ2-7 | CASSLLSGAHEQYF | 273 | 5262 |
| 1A3 | TRBV28 | TRBJ2-3 | CASSSLTSGRADTQYF | 274 | 1552 |
| 1A4 | TRBV5-4 | TRBJ1-1 | CASSLQGSMNTEAFF | 275 | 290 |
| 1A5 | TRBV6-1 | TRBJ2-4 | CASSEAGRVNIQYF | 276 | 3267 |
| 1A6 | TRBV12-3 | TRBJ1-6 | CASSLVQVNSPLHF | 277 | 4255 |
| 1A7 | TRBV19 | TRBJ1-1 | CATQDRRGTEAFF | 278 | 3080 |
| 1A8 | TRBV12-3 | TRBJ1-2 | CASSFSTCSANYGYTF | 279 | 2897 |
| 1A9 | TRBV27 | TRBJ1-2 | CASTNLRGSGGYTF | 280 | 5306 |
| 1A10 | TRBV9 | TRBJ2-2 | CASSLRTRPGAGELFF | 281 | 4939 |
| 1A11 | TRBV10-3 | TRBJ1-6 | CAISENASQNSPLHF | 282 | 660 |
| 1A12 | | | | | |
| 1B1 | TRBV6-2 | TRBJ1-6 | CASRATGNGSPLHF | 283 | 3664 |
| 1B2 | TRBV3-1 | TRBJ2-1 | CASSQEGTSGAYNEQFF | 284 | 3047 |
| 1B3 | TRBV29-1 | TRBJ2-5 | CSVHGGETQYF | 285 | 5935 |
| 1B4 | TRBV7-9 | TRBJ2-5 | CASSPEALETQYF | 286 | 7106 |
| 1B5 | TRBV29-1 | TRBJ1-1 | CSVEGEGVAFF | 287 | 2021 |
| 1B6 | TRBV5-1 | TRBJ2-1 | CASRAGLFYDNEQFF | 288 | 2759 |
| 1B7 | TRBV12-3 | TRBJ1-2 | CASSFSTCSANYGYTF | 279 | 5575 |
| 1B8 | TRBV7-3 | TRBJ2-3 | CASSQGPGADTQYF | 289 | 2368 |
| 1B9 | TRBV14 | TRBJ2-7 | CASSRTWRGYEQYF | 290 | 8285 |
| 1B10 | TRBV29-1 | TRBJ2-1 | CSVAPSGIGEQFF | 291 | 9991 |
| 1B11 | | | | | |
| 1B12 | TRBV12-3 | TRBJ1-5 | CASSLIGGNQPQHF | 292 | 5159 |
| 1C1 | TRBV27 | TRBJ1-1 | CASSFSGGRPTEAFF | 293 | 9639 |
| 1C2 | TRBV18 | TRBJ2-7 | CASSPILGVEQYF | 294 | 5014 |
| 1C3 | TRBV9 | TRBJ2-3 | CASSVTGGMGTDTQYF | 295 | 3733 |
| 1C4 | TRBV18 | TRBJ2-1 | CASSPGIAGYLGNEQFF | 296 | 2178 |
| 1C5 | TRBV5-1 | TRBJ1-1 | CASSLEGRNTEAFF | 297 | 6761 |
| 1C6 | TRBV12-3 | TRBJ1-2 | CASSFSTCSANYGYTF | 279 | 11325 |
| 1C7 | TRBV19 | TRBJ2-3 | CASSWTSGSTDTQYF | 298 | 3526 |

Figure 15B

| Well | TCR beta | | | | |
|---|---|---|---|---|---|
| | V region | J region | CDR3 beta | SEQ ID NO: | Read # |
| 1C8 | TRBV6-5 | TRBJ1-2 | CASTRDGEIYGYTF | 299 | 6236 |
| 1C9 | TRBV5-1 | TRBJ1-4 | CASSLARPSTNEKLFF | 300 | 9954 |
| 1C10 | | | | | |
| 1C11 | TRBV28 | TRBJ2-7 | CASSSLGGTGKPYEQYF | 301 | 5186 |
| 1C12 | TRBV10-3 | TRBJ2-1 | CASSGGDGTFSEQFF | 302 | 6762 |
| 1D1 | TRBV20-1 | TRBJ2-7 | CSARGQGGEQYF | 303 | 14784 |
| 1D2 | TRBV6-2 | TRBJ2-1 | CASSYSIAGGSYNEQFF | 304 | 11646 |
| 1D3 | TRBV11-2 | TRBJ1-1 | CASRGLAGRTEAFF | 305 | 3499 |
| 1D4 | TRBV5-1 | TRBJ2-3 | CASSSGLAGGGSTDTQYF | 306 | 3809 |
| 1D5 | TRBV12-3 | TRBJ1-2 | CASSFSTCSANYGYTF | 279 | 11011 |
| 1D6 | TRBV4-2 | TRBJ2-7 | CASSPSGGRSYEQYF | 307 | 15567 |
| 1D7 | | | | | |
| 1D8 | TRBV5-1 | TRBJ1-1 | CASSFNSNTEAFF | 308 | 4623 |
| 1D9 | | | | | |
| 1D10 | TRBV6-5 | TRBJ2-1 | CASRLSGSGKGNEQFF | 309 | 12982 |
| 1D11 | | | | | |
| 1D12 | TRBV9 | TRBJ2-5 | CASSVGGAAQETQYF | 310 | 5298 |
| 1E1 | TRBV14 | TRBJ2-7 | CASSLISPPPYEQYF | 311 | 13226 |
| 1E2 | TRBV11-2 | TRBJ2-1 | CASSVNEQFF | 312 | 12783 |
| 1E3 | TRBV7-3 | TRBJ2-3 | CASSWTSVGETDTQYF | 313 | 10772 |
| 1E4 | TRBV12-3 | TRBJ1-2 | CASSFSTCSANYGYTF | 279 | 8448 |
| 1E5 | | | | | |
| 1E6 | TRBV12-5 | TRBJ2-7 | CASGPRDRGGYEQYF | 314 | 7131 |
| 1E7 | TRBV6-6 | TRBJ2-5 | CASSETTATVQETQYF | 315 | 10294 |
| 1E8 | | | | | |
| 1E9 | TRBV2 | TRBJ2-5 | CASSGGGRTQETQYF | 316 | 1593 |
| 1E10 | TRBV4-2 | TRBJ2-1 | CASSQGGSGDYYNEQFF | 317 | 7782 |
| 1E11 | TRBV19 | TRBJ2-2 | CASSLRQGGSTGELFF | 318 | 1203 |
| 1E12 | TRBV11-2 | TRBJ1-1 | CASSPTTDRHWAEAFF | 319 | 1188 |
| 1F1 | TRBV3-1 | TRBJ2-1 | CASSQGGAGNGEQFF | 320 | 66 |
| 1F2 | TRBV6-1 | TRBJ1-5 | CASSEGGTTIQPQHF | 321 | 2034 |
| 1F3 | TRBV12-3 | TRBJ1-2 | CASSFSTCSANYGYTF | 279 | 4066 |
| 1F4 | TRBV9 | TRBJ2-2 | CASSVGRAGELFF | 322 | 4110 |
| 1F5 | TRBV25-1 | TRBJ2-7 | CASSSAGYEQYF | 323 | 1876 |

Figure 15C

| Well | TCR beta | | | | |
|---|---|---|---|---|---|
| | V region | J region | CDR3 beta | SEQ ID NO: | Read # |
| 1F6 | TRBV20-1 | TRBJ2-2 | CSAREAGVTGELFF | 324 | 5784 |
| 1F7 | | | | | |
| 1F8 | TRBV7-3 | TRBJ1-6 | CASSLLGGNNSPLHF | 325 | 2607 |
| 1F9 | TRBV12-3 | TRBJ1-5 | CASSPNSNQPQHF | 326 | 4275 |
| 1F10 | TRBV7-2 | TRBJ1-5 | CASSFPGAGNQPQHF | 327 | 7099 |
| 1F11 | TRBV2 | TRBJ1-5 | CASSEVWAGNQPQHF | 328 | 1928 |
| 1F12 | TRBV19 | TRBJ2-5 | CATRDRGLQETQYF | 329 | 1003 |
| 1G1 | | | | | |
| 1G2 | TRBV12-3 | TRBJ1-2 | CASSFSTCSANYGYTF | 279 | 1638 |
| 1G3 | TRBV18 | TRBJ2-1 | CASSREAGGSYNEQFF | 330 | 393 |
| 1G4 | | | | | |
| 1G5 | TRBV19 | TRBJ2-7 | CASSFGLAGSLSYEQYF | 331 | 574 |
| 1G6 | | | | | |
| 1G7 | TRBV30 | TRBJ2-7 | CAWSINLGHRSYEQYF | 332 | 2195 |
| 1G8 | | | | | |
| 1G9 | TRBV20-1 | TRBJ2-7 | CSARMGPYEQYF | 333 | 878 |
| 1G10 | TRBV7-3 | TRBJ2-1 | CASSPSGDYNEQFF | 334 | 2205 |
| 1G11 | TRBV18 | TRBJ2-7 | CASSPETGSSYEQYF | 335 | 906 |
| 1G12 | | | | | |
| 1H1 | TRBV12-3 | TRBJ1-2 | CASSFSTCSANYGYTF | 279 | 240 |
| 1H2 | TRBV28 | TRBJ2-5 | CASSLPGGVGQTQYF | 336 | 954 |
| 1H3 | TRBV6-5 | TRBJ2-1 | CASSHGGDNEQFF | 337 | 651 |
| 1H4 | TRBV4-1 | TRBJ1-2 | CASSLGNYGYTF | 338 | 574 |
| 1H5 | | | | | |
| 1H6 | TRBV2 | TRBJ1-1 | CASSVSMNTEAFF | 339 | 136 |
| 1H7 | TRBV24-1 | TRBJ2-4 | CATSEGGLAGVKNIQYF | 340 | 10 |
| 1H8 | TRBV20-1 | TRBJ2-1 | CSARDGKASTSFSSYNEQFF | 341 | 145 |
| 1H9 | TRBV10-1 | TRBJ2-7 | CASSVTTGGGEQYF | 342 | 454 |
| 1H10 | TRBV30 | TRBJ2-7 | CAGRGTSYEQYF | 343 | 853 |
| 1H11 | TRBV6-5 | TRBJ1-1 | CASKQGAYTEAFF | 344 | 341 |
| 1H12 | | | | | |
| 2A1 | TRBV4-2 | TRBJ2-1 | CASSQERVSYNEQFF | 345 | 1970 |
| 2A2 | TRBV28 | TRBJ2-1 | CASNLAGGNEQFF | 346 | 2702 |
| 2A3 | TRBV6-5 | TRBJ2-2 | CASTRDTNTGELFF | 347 | 4237 |

Figure 15D

| Well | TCR beta V region | J region | CDR3 beta | SEQ ID NO: | Read # |
|---|---|---|---|---|---|
| 2A4 | TRBV27 | TRBJ2-1 | CASSSLDRYNEQFF | 348 | 5044 |
| 2A5 | TRBV2 | TRBJ2-7 | CASYRGSGPLSYEQYF | 349 | 74 |
| 2A6 | TRBV4-2 | TRBJ2-7 | CASSPGAIEGISYEQYF | 350 | 3832 |
| 2A7 | TRBV11-2 | TRBJ1-6 | CASQKSTYNSPLHF | 351 | 4529 |
| 2A8 | TRBV12-3 | TRBJ1-2 | CASSFSTCSANYGYTF | 279 | 4137 |
| 2A9 | TRBV28 | TRBJ1-2 | CASTTTRAPGYGYTF | 352 | 6199 |
| 2A10 | TRBV12-3 | TRBJ2-1 | CASSGSPSYNEQFF | 353 | 6722 |
| 2A11 | | | | | |
| 2A12 | | | | | |
| 2B1 | TRBV28 | TRBJ2-1 | CASSLLGWTDNEQFF | 354 | 3739 |
| 2B2 | TRBV28 | TRBJ2-2 | CASSYGDPGGLDGELFF | 355 | 2157 |
| 2B3 | TRBV11-2 | TRBJ2-5 | CASSQYLAVTSGETQYF | 356 | 1382 |
| 2B4 | TRBV27 | TRBJ2-6 | CASSPDRGGANVLTF | 357 | 50 |
| 2B5 | TRBV2 | TRBJ2-6 | CASSLDNSGANVLTF | 358 | 45 |
| 2B6 | TRBV29-1 | TRBJ1-1 | CSAELVRGTEAFF | 359 | 9368 |
| 2B7 | TRBV12-3 | TRBJ1-2 | CASSFSTCSANYGYTF | 279 | 10793 |
| 2B8 | TRBV27 | TRBJ1-4 | CASRLTGSATNEKLFF | 360 | 335 |
| 2B9 | | | | | 6 |
| 2B10 | TRBV4-2 | TRBJ2-1 | CASSQDPSGEYNEQFF | 361 | 7533 |
| 2B11 | | | | | |
| 2B12 | TRBV12-3 | TRBJ2-4 | CASSSTNIQYF | 362 | 2363 |
| 2C1 | TRBV19 | TRBJ1-1 | CASSTGAGDPEAFF | 363 | 3139 |
| 2C2 | TRBV20-1 | TRBJ2-7 | CSAQTELSSYEQYF | 364 | 8728 |
| 2C3 | TRBV6-6 | TRBJ1-2 | CASSYRGDYGYTF | 365 | 8410 |
| 2C4 | TRBV12-3 | TRBJ2-2 | CASSWTSGRSNSPRELFF | 366 | 8250 |
| 2C5 | TRBV20-1 | TRBJ2-1 | CSARKHQRAESYNEQFF | 367 | 7352 |
| 2C6 | TRBV12-3 | TRBJ1-2 | CASSFSTCSANYGYTF | 279 | 11682 |
| 2C7 | TRBV20-1 | TRBJ1-4 | CSATIDSATNEKLFF | 368 | 11630 |
| 2C8 | TRBV29-1 | TRBJ2-1 | CSVAKTGGSDEQFF | 369 | 13089 |
| 2C9 | TRBV28 | TRBJ2-3 | CASSTGGTDTQYF | 370 | 15811 |
| 2C10 | | | | | |
| 2C11 | TRBV12-3 | TRBJ1-5 | CASSLGSGNQPQHF | 371 | 5472 |
| 2C12 | TRBV24-1 | TRBJ2-1 | CATSDKLAGVSYNEQFF | 372 | 27 |
| 2D1 | TRBV25-1 | TRBJ1-5 | CASSEGKGPQHF | 373 | 9544 |

Figure 15E

| Well | TCR beta | | | | |
|------|----------|---|---|---|---|
| | V region | J region | CDR3 beta | SEQ ID NO: | Read # |
| 2D2 | TRBV9 | TRBJ1-1 | CASSVGLTATEAFF | 374 | 12925 |
| 2D3 | | | | | |
| 2D4 | TRBV6-2 | TRBJ2-1 | CASRSSPLNEQFF | 375 | 12743 |
| 2D5 | TRBV12-3 | TRBJ1-2 | CASSFSTCSANYGYTF | 279 | 5178 |
| 2D6 | TRBV2 | TRBJ2-4 | CASSGASGSKNIQYF | 376 | 9198 |
| 2D7 | TRBV3-1 | TRBJ1-1 | CASSQTWDTEAFF | 377 | 182 |
| 2D8 | TRBV20-1 | TRBJ2-7 | CSARMTLDGDEQYF | 378 | 16608 |
| 2D9 | | | | | |
| 2D10 | TRBV7-3 | TRBJ2-1 | CASSTTAGGRSEQFF | 379 | 13238 |
| 2D11 | TRBV5-1 | TRBJ2-2 | CASSGAPRRNTGELFF | 380 | 17736 |
| 2D12 | TRBV2 | TRBJ2-3 | CASTLLGLAAPGTDTQYF | 381 | 5 |
| 2.00E+01 | TRBV28 | TRBJ2-2 | CASSYGDPGGLDGELFF | 355 | 3222 |
| 2.00E+02 | TRBV20-1 | TRBJ2-3 | CSARGGGRWTDTQYF | 382 | 3634 |
| 2.00E+03 | TRBV29-1 | TRBJ1-1 | CSVAQGRTEAFF | 383 | 4638 |
| 2.00E+04 | TRBV12-3 | TRBJ1-2 | CASSFSTCSANYGYTF | 279 | 4561 |
| 2.00E+05 | TRBV30 | TRBJ2-1 | CAWTLGGNEQFF | 384 | 4272 |
| 2.00E+06 | TRBV20-1 | TRBJ2-1 | CSARLAGGSSYNEQFF | 385 | 3039 |
| 2.00E+07 | TRBV30 | TRBJ2-1 | CAWTLGGNEQFF | 384 | 7412 |
| 2.00E+08 | | | | | |
| 2.00E+09 | TRBV4-2 | TRBJ2-7 | CASSPGAIEGISYEQYF | 350 | 7550 |
| 2.00E+10 | TRBV15 | TRBJ1-5 | CATSRVEGRQPQHF | 386 | 5129 |
| 2.00E+11 | TRBV30 | TRBJ1-2 | CALGYTF | 387 | 10064 |
| 2.00E+12 | TRBV9 | TRBJ1-5 | CASSAGPKNQPQHF | 388 | 4781 |
| 2F1 | TRBV5-1 | TRBJ2-7 | CASSPDRGREQYF | 389 | 944 |
| 2F2 | TRBV5-1 | TRBJ1-1 | CASSLPGGHSTEAFF | 390 | 776 |
| 2F3 | TRBV12-3 | TRBJ1-2 | CASSFSTCSANYGYTF | 279 | 1380 |
| 2F4 | TRBV2 | TRBJ1-4 | CASSAGQGEQKLFF | 391 | 48 |
| 2F5 | TRBV10-3 | TRBJ2-7 | CAITPRQDYEQYF | 392 | 481 |
| 2F6 | TRBV6-1 | TRBJ2-7 | CASSEIGVSWEQYF | 393 | 2166 |
| 2F7 | | | | | |
| 2F8 | TRBV9 | TRBJ1-5 | CASSAGPKNQPQHF | 388 | 1773 |
| 2F9 | TRBV28 | TRBJ2-3 | CASSVGLAGGPRDTQYF | 394 | 2418 |
| 2F10 | TRBV6-5 | TRBJ2-3 | CASLGPGTTQYF | 395 | 1860 |
| 2F11 | TRBV6-5 | TRBJ1-1 | CASSYAAGLQAFF | 396 | 3574 |

Figure 15F

| Well | V region | J region | CDR3 beta | SEQ ID NO: | Read # |
|---|---|---|---|---|---|
| | | | TCR beta | | |
| 2F12 | TRBV6-5 | TRBJ1-2 | CASSAQTGGWDGYTF | 397 | 910 |
| 2G1 | TRBV30 | TRBJ2-1 | CAWTLGGNEQFF | 384 | 258 |
| 2G2 | TRBV12-3 | TRBJ1-2 | CASSFSTCSANYGYTF | 279 | 393 |
| 2G3 | TRBV2 | TRBJ2-1 | CASNGLAGGRSSSYNEQFF | 398 | 23 |
| 2G4 | TRBV6-1 | TRBJ2-1 | CASSEALRGSKFF | 399 | 506 |
| 2G5 | TRBV20-1 | TRBJ1-6 | CSAAGLGHNSPLHF | 400 | 254 |
| 2G6 | | | | | |
| 2G7 | TRBV12-3 | TRBJ1-1 | CASRPGQGVTEAFF | 401 | 636 |
| 2G8 | TRBV6-1 | TRBJ2-2 | CASSPGVGTGELFF | 402 | 166 |
| 2G9 | TRBV12-3 | TRBJ2-3 | CASSPYGTSTDTQYF | 403 | 407 |
| 2G10 | TRBV19 | TRBJ2-7 | CASSGRDYKYEQYF | 404 | 180 |
| 2G11 | TRBV6-6 | TRBJ2-7 | CASSWRPNYEQYF | 405 | 338 |
| 2G12 | TRBV7-3 | TRBJ1-1 | CASSLVNTEAFF | 406 | 348 |
| 2H1 | TRBV12-3 | TRBJ1-2 | CASSFSTCSANYGYTF | 279 | 126 |
| 2H2 | TRBV28 | TRBJ1-3 | CASSPHYRGGNTIYF | 407 | 79 |
| 2H3 | TRBV28 | TRBJ2-2 | CASSYGDPGGLDGELFF | 355 | 97 |
| 2H4 | TRBV28 | TRBJ2-1 | CASSLGGSPHNEQFF | 408 | 156 |
| 2H5 | | | | | |
| 2H6 | TRBV10-3 | TRBJ2-5 | CAISESGTLQETQYF | 409 | 94 |
| 2H7 | TRBV6-5 | TRBJ2-5 | CASSQWGAGVGETQYF | 410 | 115 |
| 2H8 | TRBV11-2 | TRBJ2-1 | CASSPPWASGRVDEQFF | 411 | 36 |
| 2H9 | TRBV12-3 | TRBJ2-4 | CASSFSGGNKNIQYF | 412 | 321 |
| 2H10 | TRBV14 | TRBJ2-1 | CASSGTSSHEQFF | 413 | 227 |
| 2H11 | TRBV30 | TRBJ2-1 | CAWTLGGNEQFF | 384 | 204 |
| 2H12 | | | | | |

Figure 15G

| Well | TCR alpha (dominant) | | | | |
|---|---|---|---|---|---|
| | V region | J region | CDR3 alpha | SEQ ID NO: | Read # |
| 1A1 | TRAV20 | TRAJ57 | CAVTQGGSEKLVF | 414 | 570 |
| 1A2 | | | | | |
| 1A3 | TRAV8-6 | TRAJ15 | CAVKHQAGTALIF | 415 | 1297 |
| 1A4 | TRAV3 | TRAJ11 | CAVRDNSGYSTLTF | 416 | 1788 |
| 1A5 | TRAV3 | TRAJ35 | CAVRDAGGGFGNVLHC | 417 | 698 |
| 1A6 | TRAV12-1 | TRAJ44 | CVVPITGTASKLTF | 418 | 580 |
| 1A7 | TRAV9-1 | TRAJ26 | CALENFVF | 419 | 808 |
| 1A8 | TRAV8-4 | TRAJ3 | CAVSDLEPNSSASKIIF | 420 | 900 |
| 1A9 | TRAV23 | TRAJ22 | non-productive | | 175 |
| 1A10 | TRAV23 | TRAJ49 | CAASMANTGNQFYF | 421 | 654 |
| 1A11 | TRAV39 | TRAJ48 | non-productive | | 3026 |
| 1A12 | | | | | |
| 1B1 | TRAV21 | TRAJ49 | CAVRLPSNTGNQFYF | 422 | 190 |
| 1B2 | TRAV17 | TRAJ54 | CASVFQGAQKLVF | 423 | 1159 |
| 1B3 | TRAV17 | TRAJ32 | CATARWGATNKLIF | 424 | 21 |
| 1B4 | TRAV13-2 | TRAJ45 | CAELGADGLTF | 425 | |
| 1B5 | | | | | |
| 1B6 | TRAV26-1 | TRAJ22 | non-productive | | 1775 |
| 1B7 | TRAV8-4 | TRAJ3 | CAVSDLEPNSSASKIIF | 420 | 109 |
| 1B8 | TRAV19 | TRAJ37 | CALSPLGNTGKLIF | 426 | 2557 |
| 1B9 | TRAV23 | TRAJ37 | CASRHGSGNTGKLIF | 427 | 247 |
| 1B10 | TRAV38-1 | TRAJ44 | CAFMLTGTASKLTF | 428 | 154 |
| 1B11 | | | | | |
| 1B12 | TRAV16 | TRAJ22 | CALGSARQLTF | 429 | 1003 |
| 1C1 | TRAV4 | TRAJ15 | CLVGAGQAGTALIF | 430 | 3494 |
| 1C2 | TRAV25 | TRAJ57 | CAGPWVADGSEKLVF | 431 | 788 |
| 1C3 | TRAV8-4 | TRAJ31 | CAVSDQGARLMF | 432 | 4352 |
| 1C4 | TRAV10 | TRAJ44 | non-productive | | 5696 |
| 1C5 | TRAV13-1 | TRAJ6 | CAASLGSYIPTF | 433 | 3579 |
| 1C6 | TRAV8-4 | TRAJ3 | CAVSDLEPNSSASKIIF | 420 | 575 |
| 1C7 | TRAV26-2 | TRAJ23 | CILRDVHNQGGKLIF | 434 | 2886 |
| 1C8 | TRAV8-6 | TRAJ49 | CASSRGNQFYF | 435 | 2143 |
| 1C9 | TRAV39 | TRAJ56 | non-productive | | 2515 |

Figure 15H

| Well | TCR alpha (dominant) | | | | |
|---|---|---|---|---|---|
|  | V region | J region | CDR3 alpha | SEQ ID NO. | Read # |
| 1C10 | | | | | |
| 1C11 | TRAV12-2 | TRAJ3 | CAVNNPSSASKIIF | 436 | 1557 |
| 1C12 | TRAV13-2 | TRAJ31 | CAETPIYTRLMF | 437 | 816 |
| 1D1 | TRAV38-2 | TRAJ30 | CAYRKWMGDDKIIF | 438 | 467 |
| 1D2 | TRAV23 | TRAJ58 | CAASIETSGSRLTF | 439 | 946 |
| 1D3 | TRAV10 | TRAJ23 | CVVSANNQGGKLIF | 440 | 3712 |
| 1D4 | TRAV12-1 | TRAJ8 | CVVTTGFQKLVF | 441 | 5311 |
| 1D5 | TRAV8-4 | TRAJ3 | CAVSDLEPNSSASKIIF | 420 | 1354 |
| 1D6 | | | | | |
| 1D7 | TRAV8-4 | TRAJ23 | non-productive | | 2888 |
| 1D8 | TRAV38-1 | TRAJ53 | CAFRSGGSNYKLTF | 442 | 3839 |
| 1D9 | | | | | |
| 1D10 | TRAV4 | TRAJ12 | CLVGDMDSSYKLIF | 443 | 377 |
| 1D11 | TRAV27 | TRAJ57 | non-productive | | 11448 |
| 1D12 | TRAV12-2 | TRAJ36 | CAVRRGANNLFF | 444 | 1444 |
| 1E1 | TRAV4 | TRAJ22 | CLFAAGSARQLTF | 445 | 794 |
| 1E2 | TRAV40 | TRAJ40 | non-productive | | 241 |
| 1E3 | TRAV13-1 | TRAJ45 | CAATTYWQGGADGLTF | 446 | 521 |
| 1E4 | TRAV8-4 | TRAJ3 | CAVSDLEPNSSASKIIF | 420 | 443 |
| 1E5 | TRAV17 | TRAJ54 | CATVSIQGAQKLVF | 447 | 8450 |
| 1E6 | TRAV4 | TRAJ5 | CLVGPSAMDTGRRALTF | 448 | 407 |
| 1E7 | TRAV4 | TRAJ23 | CLVGSGGKLIF | 449 | 320 |
| 1E8 | | | | | |
| 1E9 | TRAV1-2 | TRAJ29 | CAVRLWNSGNTPLVF | 450 | 3126 |
| 1E10 | TRAV2 | TRAJ37 | CAVEPGSGNTGKLIF | 451 | 1132 |
| 1E11 | TRAV26-1 | TRAJ41 | CIVRVANSGYALNF | 452 | 3960 |
| 1E12 | TRAV8-6 | TRAJ6 | CAVIEGGSYIPTF | 453 | 2513 |
| 1F1 | TRAV1-2 | TRAJ21 | CAVREVYNFNKFYF | 454 | 5102 |
| 1F2 | TRAV1-1 | TRAJ31 | CAVPNNARLMF | 455 | 1337 |
| 1F3 | TRAV8-4 | TRAJ3 | CAVSDLEPNSSASKIIF | 420 | 1062 |
| 1F4 | TRAV41 | TRAJ49 | non-productive | | 680 |
| 1F5 | TRAV2 | TRAJ16 | CAVEDDGQKLLF | 456 | 1839 |
| 1F6 | TRAV9-1 | TRAJ35 | CALSDRGFGNVLHC | 457 | 838 |
| 1F7 | | | | | |

Figure 15I

| Well | TCR alpha (dominant) | | | | |
|---|---|---|---|---|---|
| | V region | J region | CDR3 alpha | SEQ ID NO | Read # |
| 1F8 | TRAV13-1 | TRAJ41 | non-productive | | 94 |
| 1F9 | TRAV38-1 | TRAJ49 | CAFMKPNTGNQFYF | 458 | 33 |
| 1F10 | TRAV29 | TRAJ52 | CAAGGTSYGKLTF | 459 | 6 |
| 1F11 | TRAV13-2 | TRAJ53 | CAENIPGGGSNYKLTF | 460 | 2407 |
| 1F12 | TRAV27 | TRAJ37 | CAGTHSGNTGKLIF | 461 | 964 |
| 1G1 | TRAV26-1 | TRAJ34 | CIVRAGTDKLIF | 462 | 588 |
| 1G2 | TRAV8-4 | TRAJ3 | CAVSDLEPNSSASKIIF | 420 | 298 |
| 1G3 | TRAV14 | TRAJ29 | CAMSLTFSGNTPLVF | 463 | 973 |
| 1G4 | TRAV19 | TRAJ44 | CALSEVGPGTASKLTF | 464 | 530 |
| 1G5 | TRAV8-6 | TRAJ3 | CAVSKSSASKIIF | 465 | 493 |
| 1G6 | | | | | |
| 1G7 | TRAV8-6 | TRAJ27 | CAVRPTNAGKSTF | 466 | 186 |
| 1G8 | TRAV19 | TRAJ34 | CALSEAGNTDKLIF | 467 | 1415 |
| 1G9 | TRAV26-2 | TRAJ29 | CILRVLGTPLVF | 468 | 277 |
| 1G10 | | | | | |
| 1G11 | TRAV13-1 | TRAJ34 | CAADRNTDKLIF | 469 | 346 |
| 1G12 | TRAV27 | TRAJ17 | CAGVKAAGNKLTF | 470 | 287 |
| 1H1 | TRAV8-4 | TRAJ3 | CAVSDLEPNSSASKIIF | 420 | 52 |
| 1H2 | | | | | |
| 1H3 | TRAV13-1 | TRAJ39 | CAASIRNAGNMLTF | 471 | 111 |
| 1H4 | TRAV22 | TRAJ40 | CAVETTSGTYKYIF | 472 | 20 |
| 1H5 | | | | | |
| 1H6 | TRAV23 | TRAJ31 | CAARNNARLMF | 473 | 919 |
| 1H7 | TRAV19 | TRAJ39 | CARLGAGNMLTF | 474 | 1125 |
| 1H8 | TRAV6 | TRAJ13 | CALPGRGYQKVTF | 475 | 174 |
| 1H9 | TRAV9-1 | TRAJ39 | non-productive | | 106 |
| 1H10 | TRAV14 | TRAJ21 | non-productive | | 83 |
| 1H11 | TRAV1-2 | TRAJ20 | CAVSPPRNDYKLSF | 476 | 155 |
| 1H12 | TRAV16 | TRAJ11 | non-productive | | 720 |
| 2A1 | TRAV19 | TRAJ17 | CALSEAKAAGNKLTF | 477 | 967 |
| 2A2 | TRAV12-2 | TRAJ26 | CAWTYGQNFVF | 478 | 360 |
| 2A3 | TRAV23 | TRAJ45 | CAAPSGGGADGLTF | 479 | 168 |
| 2A4 | | | | | |
| 2A5 | TRAV12-1 | TRAJ52 | CVVNVVTSYGKLTF | 480 | 3836 |

Figure 15J

| Well | TCR alpha (dominant) | | | | |
|---|---|---|---|---|---|
| | V region | J region | CDR3 alpha | SEQ ID NO. | Read # |
| 2A6 | TRAV14 | TRAJ5 | CAMSLRSRTGRRALTF | 481 | 895 |
| 2A7 | TRAV12-2 | TRAJ45 | CAVNSGGGADGLTF | 482 | 667 |
| 2A8 | TRAV8-4 | TRAJ3 | CAVSDLEPNSSASKIIF | 420 | 581 |
| 2A9 | TRAV1-2 | TRAJ37 | non-productive | | 32 |
| 2A10 | TRAV1-1 | TRAJ37 | CAVQSPHGSGNTGKLIF | 483 | 700 |
| 2A11 | TRAV12-1 | TRAJ8 | CVVFMNTGFQKLVF | 484 | 2960 |
| 2A12 | | | | | |
| 2B1 | TRAV12-2 | TRAJ37 | CAVNTNSGNTGKLIF | 485 | 992 |
| 2B2 | TRAV27 | TRAJ39 | non-productive | | 878 |
| 2B3 | TRAV14 | TRAJ37 | CAMRDSGNTGKLIF | 486 | 6374 |
| 2B4 | TRAV1-2 | TRAJ31 | CAVNNNARLMF | 487 | 3013 |
| 2B5 | TRAV10 | TRAJ17 | CVVSPKIKAAGNKLTF | 488 | 7728 |
| 2B6 | | | | | |
| 2B7 | TRAV8-4 | TRAJ3 | CAVSDLEPNSSASKIIF | 420 | 99 |
| 2B8 | TRAV1-2 | TRAJ41 | CAPINSNSGYALNF | 489 | 4845 |
| 2B9 | | | | | |
| 2B10 | TRAV2 | TRAJ6 | CAVGGAGGSYIPTF | 490 | 803 |
| 2B11 | | | | | |
| 2B12 | TRAV10 | TRAJ44 | non-productive | | 2663 |
| 2C1 | TRAV2 | TRAJ13 | CALSGGYQKVTF | 491 | 8510 |
| 2C2 | TRAV12-3 | TRAJ49 | CAMSASGNQFYF | 492 | 2149 |
| 2C3 | TRAV20 | TRAJ49 | CAVRISNTGNQFYF | 493 | 2797 |
| 2C4 | TRAV26-1 | TRAJ49 | non-productive | | 1185 |
| 2C5 | TRAV21 | TRAJ8 | CAVISFQKLVF | 494 | 1932 |
| 2C6 | TRAV8-4 | TRAJ3 | CAVSDLEPNSSASKIIF | 420 | 812 |
| 2C7 | TRAV12-3 | TRAJ6 | CAMSAAGGSYIPTF | 495 | 885 |
| 2C8 | TRAV6 | TRAJ40 | CALHTSGTYKYIF | 496 | 519 |
| 2C9 | TRAV23 | TRAJ32 | CAASNGGATNKLIF | 497 | 51 |
| 2C10 | | | | | |
| 2C11 | TRAV10 | TRAJ20 | CVNDYKLSF | 498 | 3986 |
| 2C12 | TRAV12-2 | TRAJ50 | CALKTSYDKVIF | 499 | 9573 |
| 2D1 | TRAV9-1 | TRAJ7 | CALSAYGNNRLAF | 500 | 1438 |
| 2D2 | TRAV26-1 | TRAJ42 | non-productive | | 219 |
| 2D3 | TRAV19 | TRAJ29 | CALSRGNTPLVF | 501 | 4588 |

Figure 15K

| Well | TCR alpha (dominant) | | | | |
|------|----------|----------|-------------------------|-----------|--------|
|      | V region | J region | CDR3 alpha              | SEQ ID NO | Read # |
| 2D4  | TRAV4    | TRAJ32   | CLVGGYGGATNKLIF         | 502       | 360    |
| 2D5  | TRAV8-4  | TRAJ3    | CAVSDLEPNSSASKIIF       | 420       | 1072   |
| 2D6  | TRAV13-2 | TRAJ34   | CAENTGTDKLIF            | 503       | 5320   |
| 2D7  | TRAV1-1  | TRAJ22   | non-productive          |           | 12584  |
| 2D8  | TRAV14   | TRAJ12   | CAMREGKDSSYKLIF         | 504       | 6      |
| 2D9  |          |          |                         |           |        |
| 2D10 | TRAV27   | TRAJ38   | CAGAGAGNNRKLIW          | 505       | 100    |
| 2D11 | TRAV25   | TRAJ28   | non-productive          |           | 75     |
| 2D12 |          | TRAJ12   | CAMREGKDSSYKLIF         | 506       | 11538  |
| 2E1  | TRAV8-4  | TRAJ48   | CAVSLISNFGNEKLTF        | 507       | 1286   |
| 2E2  | TRAV41   | TRAJ37   | CAVGSGNTGKLIF           | 508       | 944    |
| 2E3  | TRAV26-1 | TRAJ45   | CIVSPASGGGADGLTF        | 509       | 815    |
| 2E4  | TRAV8-4  | TRAJ3    | CAVSDLEPNSSASKIIF       | 420       | 854    |
| 2E5  | TRAV13-1 | TRAJ45   | CAASRSTAGGGADGLTF       | 510       | 563    |
| 2E6  | TRAV6    | TRAJ37   | CALVFSGNTGKLIF          | 511       | 808    |
| 2E7  | TRAV13-1 | TRAJ45   | CAASRSTAGGGADGLTF       | 510       | 78     |
| 2E8  |          |          |                         |           |        |
| 2E9  |          | TRAJ5    | CAMSLRSRTGRRALTF        | 481       | 474    |
| 2E10 | TRAV10   | TRAJ45   | CVVISTYSGGGADGLTF       | 512       | 532    |
| 2E11 | TRAV1-2  | TRAJ13   | CAVRDRQGYQKVTF          | 513       | 182    |
| 2E12 | TRAV12-2 | TRAJ23   | CAVRNQGGKLIF            | 514       | 2058   |
| 2F1  | TRAV2    | TRAJ29   | non-productive          |           | 999    |
| 2F2  | TRAV26-2 | TRAJ39   | CIRTINNAGNMLTF          | 515       | 1033   |
| 2F3  | TRAV8-4  | TRAJ3    | CAVSDLEPNSSASKIIF       | 420       | 464    |
| 2F4  | TRAV8-4  | TRAJ6    | CAVSDNPGGSYIPTF         | 516       | 2143   |
| 2F5  | TRAV6    | TRAJ36   | CALDDGANNLFF            | 517       | 1179   |
| 2F6  |          |          |                         |           |        |
| 2F7  |          |          |                         |           |        |
| 2F8  | TRAV12-2 | TRAJ23   | CAVRNQGGKLIF            | 514       | 1062   |
| 2F9  | TRAV26-1 | TRAJ23   | CIVGGFYNQGGKLIF         | 518       | 189    |
| 2F10 | TRAV27   | TRAJ58   | CARGGSRLTF              | 519       | 761    |
| 2F11 |          |          |                         |           |        |
| 2F12 | TRAV12-2 | TRAJ7    | CAVRVRRNNRLAF           | 520       | 298    |
| 2G1  | TRAV13-1 | TRAJ45   | CAASRSTAGGGADGLTF       | 510       | 42     |

Figure 15L

| Well | TCR alpha (dominant) | | | | |
|------|----------|----------|-----------|-----------|--------|
|      | V region | J region | CDR3 alpha | SEQ ID NO: | Read # |
| 2G2  | TRAV8-4  | TRAJ3    | CAVSDLFNSSASKIIF | 420 | 88 |
| 2G3  | TRAV12-3 | TRAJ17   | CASKIKAAGNKLTF | 521 | 315 |
| 2G4  |          |          |           |           |        |
| 2G5  | TRAV19   | TRAJ13   | CALSGSGGYQKVTF | 522 | 155 |
| 2G6  |          |          |           |           |        |
| 2G7  |          |          |           |           |        |
| 2G8  | TRAV1-2  | TRAJ33   | CAVRDSNYQLIW | 523 | 224 |
| 2G9  | TRAV27   | TRAJ23   | CAGASYGGKLIF | 524 | 97 |
| 2G10 | TRAV13-1 | TRAJ4    | non-productive |     | 129 |
| 2G11 | TRAV38-1 | TRAJ58   | CAFMNTLRGETSGSRLTF | 525 | 136 |
| 2G12 | TRAV13-1 | TRAJ34   | CAPRGNTDKLIF | 526 | 77 |
| 2H1  | TRAV8-4  | TRAJ3    | CAVSDLFNSSASKIIF | 420 | 41 |
| 2H2  | TRAV26-2 | TRAJ9    | CILFNTGGFKTIF | 527 | 61 |
| 2H3  | TRAV8-4  | TRAJ48   | CAVSLISNFGNEKLTF | 507 | 59 |
| 2H4  |          |          |           |           |        |
| 2H5  |          |          |           |           |        |
| 2H6  | TRAV2    | TRAJ23   | CAVNNQGGKLIF | 528 | 180 |
| 2H7  | TRAV6    | TRAJ41   | CALAAGYALNF | 529 | 64 |
| 2H8  | TRAV9-1  | TRAJ44   | CALGRTGTASKLTF | 530 | 77 |
| 2H9  |          |          |           |           |        |
| 2H10 | TRAV12-1 | TRAJ37   | CVVPLISGNTGKLIF | 531 | 42 |
| 2H11 | TRAV13-1 | TRAJ45   | CAASRSTAGGGADGLTF | 510 | 31 |
| 2H12 | TRAV8-4  | TRAJ10   | CAVNPLTGGGNKLTF | 532 | 36 |

Figure 15M

| Well | TCR alpha (secondary) | | | | |
|---|---|---|---|---|---|
| | V region | J region | CDR3 alpha | SEQ ID NO: | Read # |
| 1A1 | TRAV13-1 | TRAJ58 | non-productive | | 116 |
| 1A2 | | | | | |
| 1A3 | | | | | |
| 1A4 | TRAV12-1 | TRAJ9 | non-productive | | 330 |
| 1A5 | | | | | |
| 1A6 | | | | | |
| 1A7 | | | | | |
| 1A8 | | | | | |
| 1A9 | TRAV13-2 | TRAJ52 | CAENAGGTSYGKLTF | 533 | 56 |
| 1A10 | TRAV9-1 | TRAJ28 | non-productive | | 137 |
| 1A11 | TRAV5 | TRAJ31 | CAERNNNARLMF | 534 | 224 |
| 1A12 | | | | | |
| 1B1 | | | | | |
| 1B2 | TRAV41 | TRAJ57 | non-productive | | 435 |
| 1B3 | TRAV27 | TRAJ39 | non-productive | | 17 |
| 1B4 | | | | | |
| 1B5 | | | | | |
| 1B6 | TRAV8-4 | TRAJ17 | CAVSDEAAGNKLTF | 535 | 820 |
| 1B7 | | | | | |
| 1B8 | | | | | |
| 1B9 | | | | | |
| 1B10 | | | | | |
| 1B11 | | | | | |
| 1B12 | TRAV12-2 | TRAJ5 | non-productive | | 24 |
| 1C1 | | | | | |
| 1C2 | | | | | |
| 1C3 | TRAV12-1 | TRAJ43 | non-productive | | 351 |
| 1C4 | TRAV4 | TRAJ27 | CLVGGNTNAGKSTF | 536 | 759 |
| 1C5 | | | | | |
| 1C6 | | | | | |
| 1C7 | TRAV25 | TRAJ29 | CAGFSGNTPLVF | 537 | 354 |
| 1C8 | TRAV20 | TRAJ58 | non-productive | | 199 |
| 1C9 | TRAV30 | TRAJ54 | CGTEIWGAQKLVF | 538 | 35 |

Figure 15N

| Well | TCR alpha (secondary) | | | | |
|---|---|---|---|---|---|
| | V region | J region | CDR3 alpha | SEQ ID NO. | Read # |
| 1C10 | | | | | |
| 1C11 | TRAV13-1 | TRAJ4 | non-productive | | 775 |
| 1C12 | | | | | |
| 1D1 | TRAV25 | TRAJ34 | CAGYNNTDKLIF | 539 | 61 |
| 1D2 | | | | | |
| 1D3 | TRAV13-1 | TRAJ5 | non-productive | | 3230 |
| 1D4 | TRAV12-1 | TRAJ9 | non-productive | | 295 |
| 1D5 | | | | | |
| 1D6 | | | | | |
| 1D7 | TRAV8-6 | TRAJ8 | CAVSMNTGFQKLVF | 540 | 2046 |
| 1D8 | | | | | |
| 1D9 | | | | | |
| 1D10 | | | | | |
| 1D11 | | | | | |
| 1D12 | TRAV17 | TRAJ45 | non-productive | | 211 |
| 1.00E+01 | | | | | |
| 1.00E+02 | TRAV29 | TRAJ54 | CAASVVGAQKLVF | 541 | 19 |
| 1.00E+03 | | | | | |
| 1.00E+04 | | | | | |
| 1.00E+05 | TRAV38-2 | TRAJ30 | non-productive | | 1162 |
| 1.00E+06 | | | | | |
| 1.00E+07 | TRAV21 | TRAJ29 | non-productive | | 251 |
| 1.00E+08 | | | | | |
| 1.00E+09 | | TRAJ6 | non-productive | | 2085 |
| 1.00E+10 | | | | | |
| 1.00E+11 | TRAV9-1 | TRAJ53 | non-productive | | 1202 |
| 1.00E+12 | TRAV10 | TRAJ9 | non-productive | | 418 |
| 1F1 | | | | | |
| 1F2 | TRAV10 | TRAJ20 | non-productive | | 843 |
| 1F3 | | | | | |
| 1F4 | | | | | |
| 1F5 | | | | | |
| 1F6 | TRAV21 | TRAJ30 | non-productive | | 47 |
| 1F7 | | | | | |

Figure 15O

| Well | TCR alpha (secondary) | | | | |
|------|----------|----------|--------------------|-----------|--------|
|      | V region | J region | CDR3 alpha         | SEQ ID NO: | Read # |
| 1F8  | TRAV35   | TRAJ22   | CAGQGPYSGSARQLTF   | 542       | 7      |
| 1F9  |          |          |                    |           |        |
| 1F10 |          |          |                    |           |        |
| 1F11 |          |          |                    |           |        |
| 1F12 | TRAV17   | TRAJ54   | non-productive     |           | 11     |
| 1G1  | TRAV30   | TRAJ18   | CGTGRGSTLGRLYF     | 543       | 52     |
| 1G2  |          |          |                    |           |        |
| 1G3  | TRAV23   | TRAJ3    | CAANGRYSSASKIIF    | 544       | 263    |
| 1G4  | TRAV41   | TRAJ49   | non-productive     |           | 86     |
| 1G5  | TRAV8-4  | TRAJ27   | non-productive     |           | 246    |
| 1G6  |          |          |                    |           |        |
| 1G7  | TRAV13-1 | TRAJ5    | non-productive     |           | 61     |
| 1G8  | TRAV14   | TRAJ45   | non-productive     |           | 162    |
| 1G9  |          |          |                    |           |        |
| 1G10 |          |          |                    |           |        |
| 1G11 | TRAV13-1 | TRAJ33   | CAAPRSNYQLIW       | 545       | 180    |
| 1G12 | TRAV9-1  | TRAJ10   | non-productive     |           | 26     |
| 1H1  |          |          |                    |           |        |
| 1H2  |          |          |                    |           |        |
| 1H3  | TRAV5    | TRAJ26   | CAESPYNYGQNFVF     | 546       | 7      |
| 1H4  |          |          |                    |           |        |
| 1H5  |          |          |                    |           |        |
| 1H6  | TRAV25   | TRAJ12   | non-productive     |           | 58     |
| 1H7  |          |          |                    |           |        |
| 1H8  | TRAV2    | TRAJ3    | non-productive     |           | 131    |
| 1H9  |          |          |                    |           |        |
| 1H10 | TRAV25   | TRAJ49   | CAVSNTGNQFYF       | 547       | 68     |
| 1H11 | TRAV9-1  | TRAJ26   | CALSDGNYGQNFVF     | 548       | 142    |
| 1H12 |          |          |                    |           |        |
| 2A1  |          |          |                    |           |        |
| 2A2  |          |          |                    |           |        |
| 2A3  |          |          |                    |           |        |
| 2A4  |          |          |                    |           |        |
| 2A5  | TRAV30   | TRAJ32   | CGTGGATNKLIF       | 549       | 447    |

Figure 15P

| Well | TCR alpha (secondary) | | | | |
|---|---|---|---|---|---|
| | V region | J region | CDR3 alpha | SEQ ID NO: | Read # |
| 2A6 | | | | | |
| 2A7 | | | | | |
| 2A8 | | | | | |
| 2A9 | | | | | |
| 2A10 | | | | | |
| 2A11 | TRAV8-6 | TRAJ18 | non-productive | | 983 |
| 2A12 | | | | | |
| 2B1 | | | | | |
| 2B2 | TRAV8-4 | TRAJ48 | CAVSLISNFGNEKLTF | 507 | 866 |
| 2B3 | | | | | |
| 2B4 | TRAV6 | TRAJ39 | non-productive | | 1799 |
| 2B5 | TRAV17 | TRAJ36 | CATLQTGANNLFF | 550 | 205 |
| 2B6 | | | | | |
| 2B7 | | | | | |
| 2B8 | TRAV17 | TRAJ6 | non-productive | | 717 |
| 2B9 | | | | | |
| 2B10 | | | | | |
| 2B11 | | | | | |
| 2B12 | TRAV9-1 | TRAJ37 | CAFHGSGNTGKLIF | 551 | 325 |
| 2C1 | | | | | |
| 2C2 | TRAV12-2 | TRAJ37 | CAVNTNSGNTGKLIF | 552 | 39 |
| 2C3 | | | | | |
| 2C4 | TRAV23 | TRAJ13 | CAASIAGGYQKVTF | 553 | 1163 |
| 2C5 | TRAV23 | TRAJ38 | non-productive | | 24 |
| 2C6 | | | | | |
| 2C7 | | | | | |
| 2C8 | TRAV12-2 | TRAJ50 | CALKTSYDKVIF | 554 | 7 |
| 2C9 | | | | | |
| 2C10 | | | | | |
| 2C11 | TRAV8-6 | TRAJ4 | CAVISGGYNKLIF | 555 | 877 |
| 2C12 | TRAV25 | TRAJ39 | non-productive | | 1189 |
| 2D1 | TRAV8-6 | TRAJ37 | non-productive | | 1226 |
| 2D2 | TRAV9-1 | TRAJ7 | CALSAYGNNRLAF | 556 | 10 |
| 2D3 | TRAV26-2 | TRAJ13 | CIRTGGYQKVTF | 557 | 4252 |

Figure 15Q

| Well | TCR alpha (secondary) | | | | |
|---|---|---|---|---|---|
| | V region | J region | CDR3 alpha | SEQ ID NO: | Read # |
| 2D4 | | | | | |
| 2D5 | | | | | |
| 2D6 | | | | | |
| 2D7 | | | | | |
| 2D8 | | | | | |
| 2D9 | | | | | |
| 2D10 | | | | | |
| 2D11 | TRAV29 | TRAJ34 | CAASAVDTDKLIF | 558 | 14 |
| 2D12 | | | | | |
| 2E1 | | | | | |
| 2E2 | TRAV12-3 | TRAJ57 | non-productive | | 187 |
| 2E3 | TRAV17 | TRAJ47 | non-productive | | 16 |
| 2E4 | | | | | |
| 2E5 | TRAV22 | TRAJ9 | CAGRAGGFKTIF | 559 | 276 |
| 2E6 | TRAV14 | TRAJ16 | non-productive | | 409 |
| 2E7 | TRAV22 | TRAJ9 | CAGRAGGFKTIF | 559 | 33 |
| 2E8 | | | | | |
| 2E9 | | | | | |
| 2E10 | TRAV6 | TRAJ38 | CALGDAGNNRKLIW | 560 | 256 |
| 2E11 | TRAV1-1 | TRAJ18 | non-productive | | 8 |
| 2E12 | | | | | |
| 2F1 | | | | | |
| 2F2 | | | | | |
| 2F3 | | | | | |
| 2F4 | | | | | |
| 2F5 | TRAV23 | TRAJ37 | non-productive | | 25 |
| 2F6 | | | | | |
| 2F7 | | | | | |
| 2F8 | | | | | |
| 2F9 | TRAV13-1 | TRAJ37 | non-productive | | 144 |
| 2F10 | | | | | |
| 2F11 | | | | | |
| 2F12 | TRAV20 | TRAJ8 | non-productive | | 177 |
| 2G1 | TRAV22 | TRAJ9 | CAGRAGGFKTIF | 559 | 38 |

Figure 15R

| Well | TCR alpha (secondary) | | | | |
|---|---|---|---|---|---|
| | V region | J region | CDR3 alpha | SEQ ID NO: | Read # |
| 2G2 | | | | | |
| 2G3 | TRAV26-2 | TRAJ9 | CILFNTGGFKTIF | 561 | 7 |
| 2G4 | | | | | |
| 2G5 | TRAV2 | TRAJ23 | non-productive | | 86 |
| 2G6 | | | | | |
| 2G7 | | | | | |
| 2G8 | | | | | |
| 2G9 | | | | | |
| 2G10 | TRAV8-4 | TRAJ7 | CAAPDYGNNRLAF | 562 | 126 |
| 2G11 | TRAV41 | TRAJ34 | non-productive | | 61 |
| 2G12 | | | | | |
| 2H1 | | | | | |
| 2H2 | | | | | |
| 2H3 | TRAV27 | TRAJ39 | non-productive | | 16 |
| 2H4 | | | | | |
| 2H5 | | | | | |
| 2H6 | | | | | |
| 2H7 | | | | | |
| 2H8 | TRAV34 | TRAJ53 | non-productive | | 77 |
| 2H9 | | | | | |
| 2H10 | TRAV21 | TRAJ29 | non-productive | | 8 |
| 2H11 | TRAV22 | TRAJ9 | CAGRAGGFKTIF | 559 | 16 |
| 2H12 | TRAV13-1 | TRAJ5 | non-productive | | 8 |

Figure 16
Table 5.

| WELL | TCR BETA ||| TCR ALPHA (PRIMARY) |||| TCR ALPHA (SECONDARY) ||||
| --- | --- | --- | --- | --- | --- | --- | --- | --- | --- | --- | --- |
| | V-gene | J-gene | CDR3 | # | V-gene | J-gene | CDR3 | # | V-gene | J-gene | CDR3 | # |
| E12 | TRBV9 | TRBJ1-5 | CASSAGPKNQPQHF (SEQ ID NO:388) | 4781 | TRAV12-2 | TRAJ23 | CAVRNQGGKLIF (SEQ ID NO:514) | 2058 | | | | |
| F8 | TRBV9 | TRBJ1-5 | CASSAGPKNQPQHF (SEQ ID NO:388) | 1773 | TRAV12-2 | TRAJ23 | CAVRNQGGKLIF (SEQ ID NO:514) | 1062 | | | | |
| A6 | TRBV4-2 | TRBJ2-7 | CASSPGAIEGISYEQYF (SEQ ID NO:350) | 3832 | TRAV12-3 | TRAJ5 | CAMSLRSRTGRRALTF (SEQ ID NO:481) | 895 | | | | |
| E9 | TRBV4-2 | TRBJ2-7 | CASSPGAIEGISYEQYF (SEQ ID NO:350) | 7550 | TRAV12-3 | TRAJ5 | CAMSLRSRTGRRALTF (SEQ ID NO:481) | 474 | | | | |
| B2 | TRBV28 | TRBJ2-2 | CASSYGDPGGLDGELFF (SEQ ID NO:355) | 2157 | TRAV27 | TRAJ39 | non-productive | 878 | TRAV8-4 | TRAJ48 | CAVSLISNFGNEKLTF (SEQ ID NO:507) | 866 |
| E1 | TRBV28 | TRBJ2-2 | CASSYGDPGGLDGELFF (SEQ ID NO:355) | 3222 | TRAV8-4 | TRAJ48 | CAVSLISNFGNEKLTF (SEQ ID NO:507) | 1286 | | | | |
| H3 | TRBV28 | TRBJ2-2 | CASSYGDPGGLDGELFF (SEQ ID NO:355) | 97 | TRAV8-4 | TRAJ48 | CAVSLISNFGNEKLTF (SEQ ID NO:507) | 59 | TRAV27 | TRAJ39 | non-productive | 16 |
| E5 | TRBV30 | TRBJ2-1 | CAWTLGGNEQFF (SEQ ID NO:384) | 4272 | TRAV13-1 | TRAJ45 | CAASRSTAGGGADGLTF (SEQ ID NO:510) | 563 | TRAV22 | TRAJ9 | CAGRAGGFKTIF (SEQ ID NO:559) | 276 |
| E7 | TRBV30 | TRBJ2-1 | CAWTLGGNEQFF (SEQ ID NO:384) | 7412 | TRAV13-1 | TRAJ45 | CAASRSTAGGGADGLTF (SEQ ID NO:510) | 78 | TRAV22 | TRAJ9 | CAGRAGGFKTIF (SEQ ID NO:559) | 33 |
| G1 | TRBV30 | TRBJ2-1 | CAWTLGGNEQFF (SEQ ID NO:384) | 258 | TRAV13-1 | TRAJ45 | CAASRSTAGGGADGLTF (SEQ ID NO:510) | 42 | TRAV22 | TRAJ9 | CAGRAGGFKTIF (SEQ ID NO:559) | 38 |
| H10 | TRBV30 | TRBJ2-1 | CAWTLGGNEQFF (SEQ ID NO:384) | 204 | TRAV13-1 | TRAJ45 | CAASRSTAGGGADGLTF (SEQ ID NO:510) | 31 | TRAV22 | TRAJ9 | CAGRAGGFKTIF (SEQ ID NO:559) | 16 |

Figure 17A
Table 6.

| WELL | IL2 | IL10 | IL12A | IL13 | IL17A | IFNG | PRF1 | GZMB | TGFB | TNFA | BCL6 | TBET | GATA3 | RORC | FOXP3 | RUNX1 | RUNX3 |
|---|---|---|---|---|---|---|---|---|---|---|---|---|---|---|---|---|---|
| A1 | 325 | 0 | 0 | 0 | 0 | 0 | 0 | 0 | 98 | 338 | 0 | 512 | 0 | 796 | 0 | 459 | 0 |
| A10 | 15 | 226 | 0 | 0 | 0 | 397 | 0 | 0 | 0 | 292 | 0 | 392 | 0 | 0 | 0 | 310 | 251 |
| A11 | 52 | 0 | 0 | 0 | 0 | 595 | 0 | 0 | 0 | 396 | 0 | 459 | 0 | 0 | 0 | 273 | 384 |
| A12 | 284 | 0 | 0 | 1 | 0 | 539 | 0 | 0 | 14 | 330 | 0 | 431 | 271 | 0 | 0 | 0 | 0 |
| A2 | 294 | 0 | 0 | 237 | 0 | 2 | 0 | 0 | 168 | 241 | 0 | 469 | 315 | 1 | 0 | 446 | 0 |
| A3 | 291 | 0 | 0 | 0 | 0 | 520 | 305 | 0 | 0 | 332 | 0 | 457 | 0 | 0 | 0 | 0 | 0 |
| A4 | 0 | 0 | 0 | 0 | 0 | 718 | 0 | 0 | 11 | 414 | 0 | 0 | 323 | 0 | 0 | 449 | 0 |
| A5 | 254 | 0 | 0 | 0 | 0 | 373 | 0 | 0 | 0 | 262 | 0 | 418 | 0 | 0 | 0 | 379 | 0 |
| A6 | 298 | 0 | 0 | 0 | 0 | 515 | 0 | 0 | 5 | 372 | 0 | 492 | 328 | 0 | 0 | 0 | 0 |
| A7 | 0 | 0 | 0 | 0 | 0 | 707 | 0 | 0 | 460 | 0 | 0 | 0 | 0 | 0 | 0 | 0 | 0 |
| A8 | 40 | 0 | 0 | 0 | 0 | 536 | 0 | 0 | 127 | 333 | 0 | 399 | 0 | 0 | 0 | 390 | 0 |
| A9 | 0 | 0 | 0 | 0 | 0 | 655 | 0 | 0 | 17 | 0 | 0 | 511 | 1 | 0 | 0 | 0 | 262 |
| B1 | 297 | 0 | 0 | 0 | 0 | 492 | 0 | 0 | 25 | 315 | 0 | 468 | 0 | 0 | 0 | 449 | 0 |
| B10 | 54 | 0 | 0 | 0 | 0 | 548 | 0 | 0 | 7 | 297 | 0 | 426 | 0 | 0 | 0 | 338 | 0 |
| B11 | 36 | 0 | 0 | 0 | 0 | 622 | 0 | 0 | 0 | 434 | 0 | 554 | 0 | 0 | 0 | 522 | 0 |
| B12 | 635 | 0 | 0 | 0 | 0 | 1 | 0 | 0 | 18 | 574 | 0 | 0 | 517 | 1269 | 0 | 0 | 0 |
| B2 | 494 | 0 | 0 | 0 | 0 | 833 | 0 | 0 | 96 | 496 | 0 | 704 | 0 | 0 | 0 | 591 | 0 |
| B3 | 338 | 137 | 0 | 0 | 0 | 627 | 0 | 0 | 53 | 370 | 0 | 0 | 0 | 0 | 0 | 0 | 0 |
| B4 | 390 | 0 | 0 | 0 | 0 | 912 | 0 | 0 | 340 | 456 | 0 | 718 | 412 | 0 | 0 | 44 | 0 |
| B5 | 358 | 0 | 0 | 0 | 0 | 688 | 0 | 0 | 33 | 0 | 0 | 597 | 0 | 0 | 0 | 0 | 0 |
| B6 | 326 | 0 | 0 | 0 | 0 | 563 | 0 | 0 | 0 | 284 | 0 | 469 | 0 | 0 | 0 | 495 | 0 |
| B7 | 327 | 0 | 0 | 0 | 0 | 516 | 0 | 0 | 0 | 345 | 0 | 508 | 0 | 0 | 0 | 0 | 0 |
| B8 | 179 | 0 | 0 | 276 | 0 | 760 | 0 | 0 | 7 | 361 | 0 | 400 | 0 | 1 | 0 | 387 | 0 |

Figure 17B

| WELL | IL2 | IL10 | IL12A | IL13 | IL17A | IFNG | PRF1 | GZMB | TGFB | TNFA | BCL6 | TBET | GATA3 | RORC | FOXP3 | RUNX1 | RUNX3 |
|---|---|---|---|---|---|---|---|---|---|---|---|---|---|---|---|---|---|
| B9 | 239 | 0 | 0 | 0 | 0 | 639 | 0 | 0 | 0 | 391 | 0 | 585 | 264 | 833 | 0 | 0 | 0 |
| C1 | 319 | 0 | 0 | 0 | 0 | 460 | 0 | 0 | 269 | 321 | 0 | 493 | 0 | 0 | 0 | 0 | 0 |
| C10 | 106 | 0 | 0 | 0 | 0 | 532 | 0 | 0 | 12 | 416 | 0 | 540 | 0 | 0 | 0 | 0 | 0 |
| C11 | 0 | 0 | 0 | 0 | 0 | 728 | 0 | 0 | 0 | 320 | 0 | 320 | 0 | 0 | 0 | 588 | 0 |
| C12 | 14 | 0 | 0 | 0 | 0 | 542 | 0 | 0 | 7 | 442 | 0 | 647 | 0 | 0 | 0 | 541 | 0 |
| C2 | 301 | 0 | 0 | 272 | 0 | 442 | 0 | 0 | 0 | 328 | 0 | 485 | 0 | 0 | 0 | 528 | 0 |
| C3 | 326 | 0 | 0 | 0 | 0 | 1 | 390 | 492 | 54 | 358 | 0 | 675 | 438 | 0 | 0 | 604 | 0 |
| C4 | 0 | 0 | 0 | 0 | 0 | 742 | 0 | 0 | 25 | 413 | 0 | 0 | 0 | 0 | 0 | 573 | 0 |
| C5 | 306 | 0 | 0 | 0 | 0 | 398 | 0 | 0 | 0 | 248 | 0 | 456 | 273 | 0 | 0 | 435 | 0 |
| C6 | 0 | 0 | 0 | 0 | 0 | 565 | 0 | 0 | 433 | 0 | 0 | 0 | 0 | 0 | 0 | 490 | 0 |
| C7 | 0 | 0 | 0 | 0 | 0 | 429 | 0 | 0 | 201 | 0 | 0 | 541 | 0 | 0 | 0 | 434 | 0 |
| C8 | 139 | 0 | 0 | 0 | 0 | 616 | 266 | 0 | 0 | 333 | 0 | 477 | 0 | 0 | 0 | 472 | 0 |
| C9 | 0 | 0 | 0 | 0 | 0 | 597 | 0 | 156 | 23 | 0 | 0 | 2 | 221 | 0 | 0 | 489 | 51 |
| D1 | 258 | 0 | 0 | 0 | 0 | 507 | 0 | 0 | 0 | 280 | 0 | 454 | 302 | 0 | 0 | 394 | 0 |
| D10 | 87 | 0 | 0 | 0 | 0 | 700 | 281 | 207 | 0 | 383 | 0 | 0 | 0 | 863 | 0 | 0 | 0 |
| D11 | 6 | 43 | 0 | 0 | 277 | 815 | 0 | 0 | 0 | 485 | 0 | 640 | 0 | 0 | 0 | 551 | 0 |
| D12 | 10 | 0 | 0 | 0 | 0 | 1 | 0 | 0 | 98 | 381 | 0 | 463 | 0 | 0 | 0 | 555 | 0 |
| D2 | 0 | 0 | 0 | 0 | 0 | 399 | 0 | 0 | 0 | 329 | 0 | 0 | 0 | 0 | 0 | 410 | 0 |
| D3 | 71 | 0 | 0 | 0 | 0 | 567 | 0 | 0 | 5 | 313 | 0 | 0 | 287 | 0 | 0 | 484 | 0 |
| D4 | 239 | 0 | 0 | 333 | 0 | 833 | 0 | 0 | 29 | 428 | 0 | 0 | 0 | 0 | 0 | 505 | 0 |
| D5 | 258 | 10 | 0 | 0 | 0 | 515 | 0 | 0 | 8 | 321 | 0 | 346 | 0 | 0 | 0 | 452 | 0 |
| D6 | 185 | 0 | 0 | 0 | 0 | 453 | 0 | 0 | 0 | 215 | 0 | 422 | 282 | 0 | 0 | 341 | 0 |
| D7 | 126 | 0 | 0 | 0 | 0 | 467 | 0 | 0 | 0 | 308 | 0 | 0 | 196 | 659 | 0 | 437 | 0 |
| D8 | 222 | 0 | 0 | 0 | 0 | 801 | 0 | 0 | 0 | 395 | 0 | 0 | 0 | 1 | 0 | 468 | 0 |
| D9 | 122 | 0 | 0 | 0 | 0 | 676 | 0 | 0 | 0 | 399 | 0 | 1 | 310 | 1 | 1 | 0 | 0 |

Figure 17C

| WELL | IL2 | IL10 | IL12A | IL13 | IL17A | IFNG | PRF1 | GZMB | TGFB | TNFA | BCL6 | TBET | GATA3 | RORC | FOXP3 | RUNX1 | RUNX3 |
|---|---|---|---|---|---|---|---|---|---|---|---|---|---|---|---|---|---|
| E1 | 8 | 0 | 428 | 0 | 0 | 401 | 271 | 0 | 88 | 392 | 0 | 0 | 0 | 0 | 0 | 437 | 0 |
| E10 | 0 | 0 | 0 | 0 | 0 | 653 | 1 | 0 | 0 | 446 | 0 | 0 | 0 | 0 | 0 | 607 | 0 |
| E11 | 0 | 0 | 0 | 13 | 0 | 823 | 236 | 0 | 0 | 582 | 0 | 0 | 0 | 1045 | 0 | 293 | 0 |
| E12 | 114 | 0 | 0 | 0 | 0 | 615 | 0 | 0 | 0 | 421 | 0 | 0 | 0 | 0 | 0 | 655 | 0 |
| E2 | 0 | 0 | 0 | 0 | 0 | 448 | 394 | 407 | 109 | 345 | 0 | 0 | 0 | 0 | 0 | 592 | 0 |
| E3 | 51 | 0 | 0 | 0 | 0 | 492 | 0 | 0 | 0 | 467 | 0 | 611 | 187 | 0 | 0 | 382 | 0 |
| E4 | 1 | 0 | 0 | 0 | 0 | 915 | 0 | 0 | 0 | 557 | 0 | 669 | 0 | 1020 | 0 | 663 | 0 |
| E5 | 277 | 0 | 0 | 0 | 0 | 475 | 1 | 0 | 0 | 337 | 0 | 534 | 0 | 0 | 0 | 444 | 0 |
| E6 | 0 | 0 | 0 | 0 | 0 | 478 | 327 | 395 | 0 | 432 | 0 | 0 | 0 | 0 | 0 | 470 | 0 |
| E7 | 0 | 0 | 0 | 0 | 0 | 401 | 0 | 0 | 35 | 373 | 0 | 554 | 318 | 0 | 0 | 514 | 0 |
| E8 | 92 | 0 | 0 | 0 | 0 | 715 | 312 | 0 | 46 | 489 | 0 | 0 | 0 | 0 | 0 | 0 | 0 |
| E9 | 0 | 0 | 0 | 0 | 0 | 425 | 0 | 0 | 17 | 374 | 0 | 553 | 0 | 0 | 0 | 452 | 0 |
| F1 | 443 | 0 | 0 | 0 | 0 | 0 | 0 | 0 | 417 | 0 | 0 | 474 | 608 | 0 | 0 | 567 | 0 |
| F10 | 0 | 0 | 0 | 0 | 0 | 0 | 0 | 0 | 335 | 0 | 0 | 0 | 0 | 0 | 0 | 907 | 0 |
| F11 | 622 | 0 | 0 | 0 | 0 | 0 | 0 | 0 | 0 | 0 | 0 | 1011 | 506 | 0 | 0 | 932 | 0 |
| F12 | 0 | 0 | 0 | 0 | 0 | 0 | 0 | 0 | 37 | 402 | 0 | 0 | 0 | 1074 | 0 | 828 | 0 |
| F2 | 168 | 0 | 0 | 0 | 0 | 0 | 0 | 0 | 413 | 400 | 0 | 402 | 0 | 0 | 0 | 480 | 0 |
| F3 | 0 | 0 | 0 | 999 | 0 | 0 | 0 | 0 | 17 | 692 | 0 | 478 | 439 | 0 | 0 | 492 | 630 |
| F4 | 0 | 0 | 0 | 0 | 0 | 0 | 0 | 0 | 448 | 380 | 0 | 718 | 0 | 0 | 0 | 0 | 0 |
| F5 | 0 | 0 | 0 | 0 | 0 | 0 | 0 | 0 | 109 | 466 | 0 | 453 | 0 | 0 | 401 | 508 | 0 |
| F6 | 116 | 0 | 0 | 0 | 0 | 0 | 404 | 0 | 0 | 348 | 0 | 662 | 607 | 742 | 0 | 583 | 0 |
| F7 | 0 | 0 | 0 | 0 | 0 | 1 | 0 | 0 | 5 | 450 | 0 | 0 | 0 | 0 | 0 | 489 | 0 |
| F8 | 0 | 0 | 0 | 0 | 0 | 0 | 0 | 0 | 9 | 737 | 0 | 0 | 0 | 0 | 0 | 621 | 0 |
| F9 | 0 | 0 | 0 | 0 | 0 | 0 | 0 | 0 | 144 | 0 | 0 | 0 | 0 | 0 | 0 | 0 | 0 |
| G1 | 310 | 0 | 0 | 0 | 0 | 1 | 0 | 0 | 361 | 0 | 0 | 0 | 0 | 0 | 0 | 427 | 0 |

Figure 17D

| WELL | IL2 | IL10 | IL12A | IL13 | IL17A | IFNG | PRF1 | GZMB | TGFB | TNFA | BCL6 | TBET | GATA3 | RORC | FOXP3 | RUNX1 | RUNX3 |
|---|---|---|---|---|---|---|---|---|---|---|---|---|---|---|---|---|---|
| G10 | 184 | 0 | 0 | 0 | 0 | 0 | 0 | 0 | 44 | 495 | 0 | 0 | 477 | 0 | 0 | 706 | 0 |
| G11 | 377 | 0 | 0 | 0 | 0 | 0 | 0 | 0 | 92 | 0 | 0 | 0 | 871 | 0 | 0 | 0 | 0 |
| G12 | 0 | 0 | 0 | 0 | 0 | 0 | 0 | 0 | 0 | 624 | 664 | 963 | 0 | 0 | 0 | 1 | 0 |
| G2 | 0 | 0 | 0 | 0 | 0 | 0 | 0 | 0 | 855 | 0 | 0 | 772 | 691 | 0 | 0 | 1 | 0 |
| G3 | 0 | 0 | 0 | 0 | 0 | 0 | 0 | 0 | 685 | 0 | 0 | 0 | 0 | 0 | 0 | 0 | 0 |
| G4 | 0 | 0 | 0 | 0 | 0 | 0 | 0 | 0 | 177 | 0 | 0 | 999 | 0 | 0 | 0 | 924 | 0 |
| G5 | 0 | 0 | 0 | 0 | 0 | 0 | 0 | 0 | 0 | 0 | 0 | 0 | 518 | 0 | 0 | 870 | 0 |
| G6 | 0 | 0 | 0 | 350 | 0 | 0 | 0 | 0 | 0 | 373 | 0 | 849 | 0 | 0 | 0 | 740 | 0 |
| G7 | 0 | 0 | 0 | 0 | 0 | 0 | 0 | 0 | 352 | 400 | 0 | 0 | 532 | 0 | 0 | 0 | 0 |
| G8 | 425 | 0 | 0 | 470 | 0 | 0 | 0 | 0 | 59 | 0 | 0 | 768 | 568 | 0 | 0 | 769 | 0 |
| G9 | 0 | 0 | 0 | 0 | 0 | 0 | 0 | 0 | 366 | 0 | 0 | 0 | 0 | 0 | 0 | 933 | 0 |
| H1 | 47 | 0 | 0 | 0 | 1 | 1 | 0 | 0 | 0 | 737 | 0 | 791 | 455 | 0 | 0 | 674 | 0 |
| H10 | 0 | 0 | 0 | 0 | 0 | 0 | 0 | 0 | 0 | 491 | 0 | 0 | 0 | 0 | 0 | 0 | 0 |
| H11 | 0 | 0 | 0 | 0 | 0 | 0 | 0 | 0 | 91 | 0 | 0 | 0 | 844 | 0 | 0 | 801 | 0 |
| H12 | 0 | 0 | 0 | 0 | 0 | 0 | 0 | 0 | 19 | 0 | 0 | 865 | 0 | 0 | 0 | 0 | 0 |
| H2 | 0 | 0 | 0 | 481 | 0 | 0 | 0 | 0 | 188 | 513 | 0 | 796 | 551 | 0 | 0 | 784 | 0 |
| H3 | 246 | 0 | 0 | 0 | 0 | 0 | 0 | 0 | 0 | 732 | 621 | 864 | 0 | 0 | 0 | 1 | 0 |
| H4 | 538 | 0 | 0 | 0 | 0 | 0 | 0 | 0 | 263 | 0 | 0 | 0 | 532 | 0 | 0 | 749 | 0 |
| H5 | 0 | 0 | 0 | 0 | 0 | 0 | 0 | 0 | 0 | 693 | 0 | 0 | 0 | 0 | 0 | 0 | 0 |
| H6 | 0 | 0 | 0 | 0 | 0 | 0 | 0 | 0 | 168 | 546 | 0 | 0 | 511 | 0 | 0 | 785 | 0 |
| H7 | 2 | 0 | 0 | 0 | 0 | 0 | 0 | 0 | 0 | 0 | 0 | 0 | 0 | 0 | 0 | 1 | 1 |
| H8 | 0 | 0 | 0 | 0 | 0 | 0 | 0 | 0 | 332 | 0 | 0 | 1 | 0 | 0 | 0 | 749 | 0 |
| H9 | 0 | 0 | 0 | 0 | 0 | 0 | 0 | 0 | 0 | 0 | 0 | 9 | 0 | 0 | 0 | 0 | 0 |
| A1 | 0 | 0 | 0 | 0 | 0 | 0 | 0 | 0 | 0 | 63 | 0 | 0 | 0 | 0 | 0 | 0 | 0 |
| A10 | 0 | 0 | 0 | 1 | 0 | 3306 | 0 | 0 | 0 | 1 | 0 | 0 | 0 | 0 | 0 | 2 | 0 |

Figure 17E

| WELL | IL2 | IL10 | IL12A | IL13 | IL17A | IFNG | PRF1 | GZMB | TGFB | TNFA | BCL6 | TBET | GATA3 | RORC | FOXP3 | RUNX1 | RUNX3 |
|---|---|---|---|---|---|---|---|---|---|---|---|---|---|---|---|---|---|
| A11 | 0 | 0 | 0 | 472 | 0 | 0 | 0 | 0 | 0 | 768 | 0 | 0 | 1360 | 0 | 0 | 0 | 0 |
| A12 | 0 | 0 | 0 | 0 | 0 | 383 | 0 | 0 | 0 | 517 | 0 | 293 | 0 | 0 | 0 | 929 | 0 |
| A2 | 0 | 0 | 0 | 0 | 0 | 2400 | 0 | 0 | 0 | 965 | 0 | 2 | 0 | 19 | 0 | 1 | 0 |
| A3 | 83 | 0 | 0 | 0 | 0 | 2049 | 0 | 0 | 0 | 1 | 0 | 0 | 0 | 0 | 0 | 0 | 0 |
| A4 | 0 | 0 | 0 | 0 | 0 | 1 | 0 | 0 | 0 | 2216 | 0 | 1 | 729 | 6860 | 0 | 4694 | 0 |
| A5 | 0 | 0 | 0 | 1860 | 0 | 0 | 0 | 0 | 0 | 1991 | 0 | 0 | 1233 | 0 | 0 | 0 | 0 |
| A6 | 0 | 0 | 0 | 0 | 0 | 2402 | 0 | 0 | 0 | 1 | 0 | 0 | 749 | 0 | 0 | 0 | 0 |
| A7 | 0 | 0 | 0 | 1748 | 0 | 0 | 0 | 0 | 0 | 2090 | 0 | 2049 | 0 | 0 | 0 | 15 | 0 |
| A8 | 0 | 0 | 0 | 0 | 0 | 0 | 0 | 0 | 0 | 2030 | 0 | 293 | 0 | 0 | 1 | 434 | 0 |
| A9 | 0 | 0 | 0 | 2 | 0 | 0 | 18 | 0 | 0 | 522 | 0 | 144 | 155 | 0 | 0 | 319 | 0 |
| B1 | 0 | 0 | 0 | 0 | 0 | 0 | 0 | 0 | 0 | 121 | 0 | 6 | 0 | 0 | 0 | 1 | 0 |
| B10 | 2 | 0 | 0 | 0 | 0 | 2303 | 0 | 0 | 0 | 1 | 0 | 0 | 0 | 0 | 0 | 2 | 0 |
| B11 | 0 | 0 | 0 | 1129 | 0 | 1364 | 0 | 0 | 0 | 231 | 0 | 0 | 0 | 0 | 0 | 1 | 0 |
| B12 | 0 | 0 | 0 | 0 | 0 | 2494 | 0 | 0 | 0 | 1 | 0 | 0 | 734 | 0 | 0 | 0 | 0 |
| B2 | 1 | 0 | 0 | 0 | 0 | 2117 | 0 | 0 | 0 | 1846 | 779 | 3947 | 0 | 7507 | 0 | 1985 | 0 |
| B3 | 0 | 0 | 0 | 10 | 0 | 0 | 0 | 0 | 0 | 23 | 0 | 0 | 0 | 0 | 0 | 0 | 0 |
| B4 | 0 | 0 | 0 | 0 | 0 | 2589 | 0 | 0 | 0 | 1 | 0 | 330 | 0 | 1177 | 0 | 0 | 0 |
| B5 | 0 | 0 | 0 | 0 | 1003 | 2708 | 0 | 0 | 0 | 90 | 0 | 1 | 0 | 0 | 0 | 1388 | 0 |
| B6 | 0 | 0 | 0 | 0 | 0 | 0 | 0 | 0 | 0 | 64 | 0 | 805 | 0 | 6113 | 0 | 0 | 0 |
| B7 | 0 | 0 | 0 | 0 | 0 | 1 | 0 | 0 | 0 | 1456 | 0 | 0 | 0 | 1 | 0 | 2 | 1 |
| B8 | 0 | 0 | 0 | 0 | 0 | 2525 | 0 | 0 | 0 | 1033 | 0 | 0 | 0 | 0 | 0 | 0 | 0 |
| B9 | 0 | 0 | 0 | 0 | 0 | 137 | 0 | 0 | 1 | 0 | 0 | 389 | 17 | 1 | 0 | 168 | 0 |
| C1 | 0 | 0 | 0 | 0 | 0 | 584 | 0 | 0 | 0 | 12 | 0 | 0 | 1 | 1 | 0 | 0 | 0 |
| C10 | 0 | 0 | 0 | 0 | 0 | 0 | 0 | 0 | 0 | 715 | 0 | 389 | 1 | 1 | 0 | 168 | 0 |
| C11 | 0 | 0 | 0 | 0 | 0 | 1 | 0 | 0 | 0 | 1783 | 0 | 575 | 4 | 2299 | 0 | 384 | 0 |

Figure 17F

| WELL | IL2 | IL10 | IL12A | IL13 | IL17A | IFNG | PRF1 | GZMB | TGFB | TNFA | BCL6 | TBET | GATA3 | RORC | FOXP3 | RUNX1 | RUNX3 |
|---|---|---|---|---|---|---|---|---|---|---|---|---|---|---|---|---|---|
| C12 | 0 | 0 | 0 | 0 | 0 | 2574 | 0 | 0 | 1 | 1 | 0 | 1 | 0 | 0 | 0 | 1 | 0 |
| C2 | 178 | 0 | 0 | 1886 | 0 | 0 | 0 | 0 | 0 | 1827 | 0 | 0 | 0 | 0 | 0 | 0 | 0 |
| C3 | 14 | 0 | 0 | 1922 | 0 | 0 | 0 | 0 | 1 | 3218 | 0 | 0 | 1668 | 0 | 0 | 2463 | 0 |
| C4 | 3 | 0 | 0 | 0 | 0 | 1 | 0 | 0 | 0 | 3765 | 0 | 2181 | 7 | 11 | 0 | 8 | 0 |
| C5 | 54 | 0 | 0 | 0 | 0 | 0 | 0 | 0 | 0 | 3899 | 0 | 1802 | 0 | 4033 | 0 | 1371 | 0 |
| C6 | 0 | 1 | 0 | 1278 | 0 | 1 | 0 | 0 | 0 | 1620 | 0 | 1856 | 124 | 0 | 0 | 132 | 0 |
| C7 | 0 | 0 | 0 | 0 | 0 | 970 | 4 | 0 | 2 | 1314 | 0 | 1595 | 1 | 0 | 0 | 6 | 0 |
| C8 | 1 | 0 | 0 | 0 | 0 | 2 | 0 | 0 | 0 | 527 | 0 | 0 | 0 | 0 | 0 | 1 | 0 |
| C9 | 0 | 0 | 0 | 278 | 0 | 1 | 0 | 0 | 0 | 2 | 0 | 811 | 0 | 1 | 0 | 299 | 0 |
| D1 | 3 | 0 | 0 | 2 | 0 | 1 | 0 | 0 | 0 | 808 | 1 | 0 | 0 | 0 | 1 | 792 | 0 |
| D10 | 2 | 0 | 0 | 0 | 0 | 0 | 0 | 0 | 1 | 2724 | 0 | 1032 | 1531 | 872 | 0 | 1 | 0 |
| D11 | 2 | 0 | 0 | 2524 | 0 | 0 | 0 | 0 | 0 | 2754 | 0 | 1 | 1152 | 0 | 0 | 0 | 0 |
| D12 | 0 | 0 | 0 | 0 | 0 | 0 | 0 | 0 | 1 | 1671 | 0 | 2783 | 684 | 0 | 0 | 9 | 0 |
| D2 | 280 | 0 | 0 | 0 | 0 | 0 | 0 | 0 | 13 | 3361 | 0 | 2144 | 2608 | 1 | 0 | 917 | 0 |
| D3 | 0 | 2 | 0 | 34 | 0 | 2485 | 0 | 0 | 0 | 0 | 0 | 1 | 0 | 0 | 1536 | 2018 | 0 |
| D4 | 408 | 0 | 0 | 0 | 0 | 0 | 0 | 0 | 0 | 6341 | 0 | 334 | 5354 | 3838 | 0 | 1 | 0 |
| D5 | 0 | 0 | 0 | 2365 | 0 | 0 | 0 | 0 | 0 | 1531 | 0 | 2635 | 0 | 0 | 0 | 65 | 0 |
| D6 | 6 | 0 | 0 | 1 | 0 | 3173 | 0 | 0 | 0 | 2980 | 0 | 1410 | 0 | 0 | 0 | 3064 | 0 |
| D7 | 1 | 0 | 0 | 0 | 0 | 0 | 0 | 0 | 0 | 4225 | 0 | 0 | 0 | 0 | 0 | 1666 | 0 |
| D8 | 0 | 0 | 0 | 0 | 0 | 655 | 0 | 0 | 0 | 1 | 0 | 1206 | 0 | 0 | 0 | 0 | 0 |
| D9 | 1 | 0 | 0 | 0 | 0 | 2434 | 0 | 0 | 0 | 995 | 0 | 415 | 0 | 673 | 0 | 2 | 0 |
| E1 | 0 | 0 | 0 | 0 | 0 | 4429 | 0 | 0 | 0 | 101 | 0 | 3 | 0 | 0 | 0 | 6 | 0 |
| E10 | 0 | 0 | 0 | 0 | 0 | 0 | 0 | 0 | 0 | 3 | 0 | 566 | 0 | 5459 | 0 | 3 | 0 |
| E11 | 0 | 0 | 0 | 0 | 0 | 0 | 0 | 0 | 0 | 191 | 0 | 0 | 0 | 0 | 0 | 11 | 0 |
| E12 | 8 | 0 | 0 | 1055 | 0 | 4 | 0 | 0 | 0 | 1306 | 0 | 0 | 0 | 0 | 0 | 0 | 0 |

Figure 17G

| WELL | IL2 | IL10 | IL12A | IL13 | IL17A | IFNG | PRF1 | GZMB | TGFB | TNFA | BCL6 | TBET | GATA3 | RORC | FOXP3 | RUNX1 | RUNX3 |
|---|---|---|---|---|---|---|---|---|---|---|---|---|---|---|---|---|---|
| E2 | 243 | 0 | 0 | 0 | 0 | 0 | 0 | 0 | 22 | 1423 | 0 | 1503 | 0 | 1 | 0 | 1 | 0 |
| E3 | 0 | 0 | 0 | 0 | 0 | 2436 | 0 | 0 | 0 | 2 | 0 | 291 | 0 | 0 | 0 | 0 | 0 |
| E4 | 0 | 0 | 0 | 3106 | 0 | 0 | 0 | 0 | 0 | 4059 | 0 | 0 | 2971 | 0 | 0 | 5142 | 0 |
| E5 | 47 | 0 | 0 | 0 | 0 | 0 | 0 | 0 | 1081 | 0 | 0 | 0 | 0 | 0 | 0 | 0 | 0 |
| E6 | 0 | 0 | 0 | 0 | 0 | 2268 | 0 | 0 | 0 | 1410 | 0 | 0 | 269 | 0 | 0 | 94 | 0 |
| E7 | 2 | 0 | 0 | 0 | 0 | 0 | 0 | 0 | 1 | 2616 | 0 | 2855 | 0 | 0 | 0 | 2375 | 0 |
| E8 | 0 | 0 | 0 | 0 | 0 | 2228 | 0 | 0 | 0 | 707 | 427 | 2363 | 0 | 0 | 0 | 1515 | 0 |
| E9 | 0 | 0 | 0 | 0 | 0 | 1537 | 0 | 0 | 0 | 92 | 0 | 1 | 0 | 0 | 0 | 0 | 0 |
| F1 | 0 | 0 | 0 | 0 | 0 | 0 | 0 | 0 | 0 | 0 | 0 | 649 | 653 | 0 | 0 | 1 | 0 |
| F10 | 0 | 0 | 0 | 0 | 0 | 0 | 0 | 0 | 18 | 0 | 0 | 0 | 1423 | 0 | 0 | 1 | 0 |
| F11 | 0 | 0 | 0 | 1030 | 0 | 0 | 0 | 0 | 2 | 0 | 0 | 1338 | 0 | 0 | 0 | 1023 | 0 |
| F12 | 175 | 0 | 0 | 0 | 0 | 0 | 0 | 0 | 1 | 0 | 0 | 1746 | 0 | 0 | 0 | 0 | 0 |
| F2 | 0 | 0 | 0 | 0 | 0 | 0 | 0 | 0 | 1344 | 0 | 0 | 0 | 1293 | 0 | 0 | 0 | 0 |
| F3 | 93 | 0 | 0 | 0 | 0 | 0 | 0 | 0 | 0 | 0 | 0 | 2900 | 1939 | 0 | 0 | 1952 | 0 |
| F4 | 88 | 0 | 0 | 0 | 0 | 0 | 0 | 0 | 0 | 0 | 0 | 0 | 1 | 0 | 0 | 1738 | 0 |
| F5 | 258 | 0 | 0 | 0 | 0 | 0 | 0 | 0 | 4 | 0 | 0 | 2668 | 0 | 0 | 0 | 2931 | 0 |
| F6 | 0 | 0 | 0 | 0 | 0 | 0 | 0 | 0 | 87 | 1 | 0 | 0 | 2 | 0 | 0 | 0 | 0 |
| F7 | 0 | 0 | 0 | 0 | 0 | 0 | 0 | 0 | 284 | 0 | 0 | 0 | 0 | 0 | 1 | 1 | 0 |
| F8 | 0 | 0 | 0 | 0 | 1 | 1 | 1 | 0 | 110 | 1 | 0 | 0 | 1542 | 0 | 0 | 0 | 0 |
| F9 | 0 | 0 | 0 | 0 | 2 | 2970 | 1818 | 459 | 71 | 0 | 0 | 1978 | 0 | 0 | 0 | 1662 | 0 |
| G1 | 0 | 0 | 0 | 0 | 0 | 0 | 0 | 0 | 671 | 0 | 0 | 0 | 0 | 0 | 0 | 2067 | 0 |
| G10 | 0 | 0 | 0 | 0 | 1631 | 0 | 0 | 0 | 0 | 0 | 0 | 0 | 0 | 0 | 0 | 1802 | 0 |
| G11 | 0 | 0 | 0 | 0 | 0 | 0 | 0 | 0 | 0 | 0 | 0 | 0 | 0 | 0 | 0 | 0 | 0 |
| G12 | 0 | 0 | 0 | 0 | 0 | 0 | 0 | 0 | 0 | 0 | 0 | 0 | 0 | 0 | 0 | 0 | 0 |
| G2 | 0 | 0 | 0 | 0 | 0 | 0 | 0 | 0 | 0 | 772 | 1 | 62 | 0 | 0 | 0 | 2005 | 0 |

Figure 17H

| WELL | IL2 | IL10 | IL12A | IL13 | IL17A | IFNG | PRF1 | GZMB | TGFB | TNFA | BCL6 | TBET | GATA3 | RORC | FOXP3 | RUNX1 | RUNX3 |
|---|---|---|---|---|---|---|---|---|---|---|---|---|---|---|---|---|---|
| G3 | 0 | 0 | 0 | 0 | 0 | 1 | 0 | 0 | 100 | 0 | 0 | 1887 | 0 | 0 | 0 | 2052 | 0 |
| G4 | 0 | 0 | 0 | 0 | 0 | 0 | 0 | 0 | 91 | 0 | 0 | 1 | 0 | 0 | 1889 | 3183 | 0 |
| G5 | 0 | 0 | 0 | 0 | 0 | 0 | 0 | 0 | 72 | 1 | 1 | 2448 | 1661 | 0 | 1 | 2727 | 0 |
| G6 | 0 | 0 | 0 | 0 | 0 | 1 | 0 | 0 | 15 | 0 | 1 | 2077 | 1106 | 0 | 0 | 2159 | 1 |
| G7 | 0 | 0 | 0 | 0 | 1 | 0 | 0 | 0 | 0 | 0 | 0 | 0 | 0 | 0 | 0 | 0 | 0 |
| G8 | 0 | 0 | 0 | 0 | 0 | 1 | 0 | 0 | 0 | 1 | 0 | 0 | 0 | 0 | 0 | 1 | 0 |
| G9 | 0 | 1 | 0 | 0 | 0 | 0 | 0 | 0 | 35 | 1 | 0 | 0 | 0 | 0 | 0 | 0 | 0 |
| H1 | 0 | 0 | 0 | 0 | 0 | 1 | 0 | 0 | 253 | 0 | 0 | 1484 | 0 | 0 | 0 | 0 | 0 |
| H10 | 23 | 0 | 0 | 0 | 0 | 1 | 0 | 0 | 777 | 1 | 0 | 1027 | 2 | 1 | 0 | 1 | 0 |
| H11 | 0 | 0 | 0 | 0 | 0 | 1 | 0 | 0 | 545 | 1 | 0 | 0 | 0 | 0 | 0 | 2 | 0 |
| H12 | 0 | 0 | 0 | 0 | 0 | 0 | 0 | 0 | 430 | 0 | 0 | 2702 | 1659 | 0 | 0 | 1 | 0 |
| H2 | 0 | 0 | 0 | 0 | 0 | 1 | 0 | 0 | 351 | 0 | 0 | 0 | 0 | 0 | 0 | 0 | 0 |
| H3 | 0 | 0 | 0 | 0 | 0 | 1 | 0 | 0 | 318 | 0 | 0 | 0 | 1858 | 0 | 0 | 1 | 0 |
| H4 | 0 | 0 | 0 | 0 | 0 | 1 | 0 | 0 | 0 | 0 | 0 | 0 | 2392 | 0 | 0 | 0 | 0 |
| H5 | 173 | 0 | 0 | 0 | 0 | 1 | 0 | 0 | 155 | 0 | 0 | 0 | 0 | 0 | 0 | 1 | 0 |
| H6 | 116 | 0 | 0 | 0 | 0 | 0 | 0 | 0 | 0 | 2207 | 0 | 0 | 0 | 0 | 0 | 128 | 0 |
| H7 | 0 | 0 | 0 | 0 | 0 | 0 | 0 | 0 | 704 | 0 | 0 | 1978 | 0 | 0 | 0 | 0 | 0 |
| H8 | 0 | 0 | 0 | 0 | 1 | 0 | 0 | 0 | 18 | 0 | 0 | 1380 | 0 | 1 | 0 | 1733 | 0 |
| H9 | 0 | 0 | 0 | 0 | 0 | 0 | 0 | 0 | 2 | 2 | 4 | 2432 | 2 | 0 | 0 | 1475 | 0 |
| A1 | 2945 | 0 | 0 | 4154 | 1 | 1 | 0 | 0 | 3 | 1251 | 0 | 125 | 2 | 1 | 0 | 0 | 0 |
| A10 | 302 | 1 | 0 | 4 | 0 | 41 | 0 | 0 | 1 | 1047 | 4 | 1 | 2 | 0 | 0 | 376 | 8 |
| A11 | 229 | 1 | 11 | 2 | 301 | 0 | 0 | 0 | 0 | 1 | 0 | 3340 | 22 | 1 | 0 | 20 | 0 |
| A12 | 4 | 1 | 0 | 2 | 0 | 0 | 0 | 0 | 0 | 467 | 0 | 1 | 15 | 0 | 0 | 0 | 0 |
| A2 | 3724 | 0 | 0 | 0 | 0 | 0 | 0 | 0 | 1 | 0 | 0 | 0 | 4398 | 0 | 0 | 0 | 0 |
| A3 | 2087 | 0 | 0 | 0 | 2 | 611 | 45 | 0 | 2 | 4222 | 0 | 3 | 2546 | 1295 | 0 | 900 | 0 |

Figure 17I

| WELL | IL2 | IL10 | IL12A | IL13 | IL17A | IFNG | PRF1 | GZMB | TGFB | TNFA | BCL6 | TBET | GATA3 | RORC | FOXP3 | RUNX1 | RUNX3 |
|---|---|---|---|---|---|---|---|---|---|---|---|---|---|---|---|---|---|
| A4 | 296 | 1 | 0 | 2366 | 1 | 1 | 0 | 0 | 1 | 1759 | 234 | 452 | 151 | 0 | 0 | 6 | 0 |
| A5 | 1568 | 0 | 0 | 1 | 0 | 1 | 0 | 0 | 188 | 2 | 0 | 1 | 2 | 0 | 0 | 1686 | 0 |
| A6 | 1028 | 0 | 0 | 3320 | 1 | 2 | 0 | 0 | 0 | 0 | 2 | 0 | 2711 | 0 | 0 | 32 | 0 |
| A7 | 493 | 0 | 0 | 1647 | 672 | 0 | 0 | 0 | 0 | 212 | 4 | 1 | 1 | 0 | 0 | 0 | 0 |
| A8 | 72 | 2 | 0 | 2 | 0 | 1 | 1 | 0 | 1 | 14 | 0 | 95 | 1 | 1 | 0 | 0 | 0 |
| A9 | 213 | 1 | 0 | 1160 | 2 | 0 | 0 | 0 | 3 | 0 | 0 | 1 | 1185 | 1 | 0 | 0 | 0 |
| B1 | 1 | 0 | 0 | 3702 | 0 | 0 | 0 | 0 | 0 | 4300 | 0 | 1 | 1 | 0 | 0 | 2 | 0 |
| B10 | 606 | 0 | 0 | 1 | 0 | 80 | 0 | 0 | 199 | 0 | 0 | 969 | 1882 | 0 | 0 | 0 | 0 |
| B11 | 345 | 1 | 0 | 4 | 213 | 1 | 0 | 0 | 3 | 1086 | 0 | 611 | 1240 | 1 | 0 | 338 | 0 |
| B12 | 147 | 0 | 0 | 3 | 0 | 1 | 1 | 1 | 0 | 579 | 0 | 247 | 78 | 0 | 0 | 36 | 0 |
| B2 | 3150 | 0 | 0 | 0 | 0 | 0 | 0 | 0 | 0 | 302 | 0 | 2784 | 1 | 25 | 0 | 240 | 0 |
| B3 | 3232 | 1 | 0 | 4 | 1 | 1 | 0 | 0 | 461 | 0 | 0 | 1 | 3773 | 2430 | 312 | 2812 | 0 |
| B4 | 866 | 0 | 0 | 3390 | 0 | 0 | 0 | 0 | 1 | 2362 | 0 | 2 | 662 | 0 | 0 | 30 | 0 |
| B5 | 2025 | 0 | 0 | 4353 | 0 | 1 | 0 | 0 | 0 | 1 | 0 | 3 | 3777 | 0 | 0 | 0 | 0 |
| B6 | 2093 | 0 | 0 | 1 | 0 | 448 | 0 | 0 | 16 | 290 | 0 | 2 | 1 | 0 | 0 | 2560 | 0 |
| B7 | 1172 | 1 | 0 | 2598 | 0 | 0 | 0 | 0 | 0 | 4 | 0 | 0 | 3 | 73 | 0 | 1008 | 0 |
| B8 | 338 | 0 | 0 | 4 | 1 | 1 | 0 | 0 | 8 | 850 | 0 | 476 | 975 | 0 | 0 | 0 | 0 |
| B9 | 656 | 1 | 0 | 2 | 1 | 1 | 0 | 0 | 1075 | 1 | 0 | 2 | 2244 | 1 | 0 | 878 | 0 |
| C1 | 4246 | 0 | 0 | 1 | 0 | 0 | 0 | 0 | 0 | 0 | 0 | 3 | 3847 | 0 | 0 | 0 | 0 |
| C10 | 744 | 0 | 0 | 2188 | 0 | 0 | 0 | 0 | 0 | 1 | 0 | 1118 | 2370 | 0 | 0 | 2 | 2 |
| C11 | 662 | 0 | 0 | 2565 | 0 | 0 | 0 | 0 | 0 | 1 | 0 | 483 | 2395 | 0 | 0 | 0 | 0 |
| C12 | 717 | 1 | 0 | 2 | 0 | 0 | 0 | 0 | 0 | 1 | 0 | 842 | 1 | 0 | 0 | 648 | 0 |
| C2 | 2740 | 0 | 0 | 1 | 0 | 1 | 0 | 0 | 0 | 4763 | 0 | 2314 | 1 | 0 | 0 | 814 | 40 |
| C3 | 2888 | 0 | 0 | 4211 | 0 | 1 | 0 | 0 | 0 | 4934 | 614 | 1127 | 1759 | 0 | 0 | 20 | 0 |
| C4 | 1022 | 0 | 0 | 4985 | 0 | 0 | 0 | 0 | 1 | 2 | 0 | 760 | 4001 | 0 | 0 | 1598 | 2 |

Figure 17J

| WELL | IL2 | IL10 | IL12A | IL13 | IL17A | IFNG | PRF1 | GZMB | TGFB | TNFA | BCL6 | TBET | GATA3 | RORC | FOXP3 | RUNX1 | RUNX3 |
|---|---|---|---|---|---|---|---|---|---|---|---|---|---|---|---|---|---|
| C5 | 2741 | 696 | 0 | 1 | 0 | 0 | 0 | 0 | 88 | 0 | 0 | 1 | 1 | 3 | 0 | 3040 | 0 |
| C6 | 35 | 0 | 0 | 4 | 1647 | 0 | 0 | 0 | 30 | 1 | 0 | 1760 | 2 | 1466 | 0 | 0 | 0 |
| C7 | 1314 | 0 | 0 | 3 | 0 | 0 | 0 | 0 | 3 | 3511 | 0 | 0 | 3 | 0 | 0 | 0 | 0 |
| C8 | 898 | 0 | 0 | 3 | 1 | 0 | 0 | 0 | 10 | 2 | 0 | 568 | 2601 | 1 | 0 | 6 | 0 |
| C9 | 804 | 0 | 0 | 1 | 0 | 1 | 0 | 0 | 6 | 4 | 0 | 473 | 2415 | 811 | 0 | 740 | 0 |
| D1 | 1624 | 0 | 0 | 4417 | 2 | 276 | 0 | 0 | 1 | 1 | 0 | 56 | 1829 | 0 | 0 | 4 | 0 |
| D10 | 1583 | 0 | 0 | 4 | 0 | 199 | 0 | 0 | 40 | 0 | 0 | 1 | 2018 | 0 | 0 | 20 | 0 |
| D11 | 845 | 1205 | 0 | 5 | 0 | 0 | 0 | 0 | 0 | 2 | 0 | 1228 | 1 | 0 | 0 | 554 | 0 |
| D12 | 601 | 0 | 0 | 1 | 1 | 0 | 0 | 0 | 0 | 10 | 0 | 1 | 3 | 0 | 0 | 0 | 0 |
| D2 | 10 | 0 | 0 | 3 | 0 | 1168 | 2006 | 2399 | 572 | 2381 | 0 | 1696 | 0 | 0 | 0 | 2846 | 0 |
| D3 | 3255 | 1 | 0 | 6 | 0 | 1375 | 0 | 1 | 0 | 3735 | 0 | 2589 | 556 | 0 | 0 | 118 | 0 |
| D4 | 3362 | 1 | 0 | 0 | 2 | 3 | 0 | 1 | 1 | 19 | 2 | 4 | 764 | 0 | 0 | 12 | 0 |
| D5 | 3181 | 1 | 0 | 3 | 1 | 1018 | 0 | 1 | 7 | 1 | 0 | 3049 | 2612 | 0 | 0 | 2862 | 0 |
| D6 | 3032 | 1 | 0 | 0 | 0 | 1 | 0 | 0 | 78 | 0 | 3208 | 2864 | 2 | 0 | 0 | 2550 | 0 |
| D7 | 2080 | 1 | 0 | 0 | 0 | 0 | 0 | 1 | 773 | 2736 | 0 | 2 | 3 | 0 | 1 | 2304 | 0 |
| D8 | 480 | 0 | 0 | 3932 | 205 | 172 | 0 | 0 | 0 | 4 | 0 | 4 | 2964 | 0 | 0 | 40 | 0 |
| D9 | 1073 | 0 | 0 | 1 | 0 | 3 | 1 | 1 | 29 | 313 | 0 | 1211 | 982 | 0 | 0 | 1010 | 0 |
| E1 | 3719 | 0 | 0 | 1 | 1 | 0 | 0 | 0 | 1 | 1 | 0 | 2617 | 2033 | 0 | 0 | 0 | 0 |
| E10 | 1381 | 0 | 0 | 3 | 1533 | 0 | 0 | 0 | 0 | 2017 | 0 | 1507 | 2 | 0 | 0 | 1606 | 0 |
| E11 | 1384 | 0 | 0 | 3 | 1735 | 2 | 0 | 0 | 0 | 3517 | 0 | 0 | 2503 | 141 | 0 | 1478 | 0 |
| E12 | 1029 | 0 | 0 | 1 | 1470 | 0 | 0 | 0 | 0 | 3081 | 0 | 22 | 3 | 0 | 0 | 154 | 0 |
| E2 | 3855 | 13 | 0 | 2 | 1 | 0 | 0 | 0 | 2 | 4188 | 2054 | 0 | 3834 | 0 | 0 | 0 | 0 |
| E3 | 4247 | 0 | 0 | 5079 | 2 | 133 | 1 | 0 | 1 | 4 | 0 | 2062 | 3837 | 0 | 0 | 0 | 0 |
| E4 | 2311 | 0 | 0 | 5128 | 1 | 756 | 0 | 0 | 0 | 45 | 0 | 2 | 238 | 0 | 0 | 2 | 0 |
| E5 | 4754 | 0 | 0 | 1 | 0 | 0 | 0 | 0 | 0 | 1 | 0 | 1912 | 4750 | 0 | 0 | 4434 | 0 |

Figure 17K

| WELL | IL2 | IL10 | IL12A | IL13 | IL17A | IFNG | PRF1 | GZMB | TGFB | TNFA | BCL6 | TBET | GATA3 | RORC | FOXP3 | RUNX1 | RUNX3 |
|---|---|---|---|---|---|---|---|---|---|---|---|---|---|---|---|---|---|
| E6 | 3587 | 0 | 0 | 3 | 0 | 1158 | 1 | 0 | 3 | 1 | 0 | 2888 | 1321 | 0 | 0 | 832 | 0 |
| E7 | 2458 | 0 | 0 | 3728 | 0 | 1 | 0 | 0 | 0 | 2518 | 18 | 20 | 2556 | 0 | 0 | 376 | 10 |
| E8 | 289 | 1 | 0 | 1 | 0 | 267 | 0 | 0 | 1 | 1652 | 0 | 1617 | 3 | 1 | 0 | 818 | 0 |
| E9 | 1406 | 0 | 0 | 2 | 1 | 355 | 0 | 0 | 2 | 3493 | 2 | 821 | 735 | 0 | 0 | 0 | 0 |
| F1 | 1 | 0 | 0 | 2 | 0 | 1 | 1 | 0 | 0 | 0 | 0 | 0 | 2 | 0 | 0 | 0 | 0 |
| F10 | 0 | 0 | 0 | 1 | 0 | 494 | 1699 | 0 | 2 | 2345 | 0 | 1973 | 0 | 0 | 0 | 2496 | 0 |
| F11 | 2 | 0 | 0 | 5 | 0 | 1 | 1 | 1 | 0 | 0 | 0 | 1 | 3 | 0 | 0 | 20 | 0 |
| F12 | 1 | 2 | 0 | 4 | 0 | 1 | 0 | 0 | 3 | 0 | 0 | 1 | 0 | 0 | 0 | 3754 | 0 |
| F2 | 0 | 0 | 0 | 1 | 0 | 564 | 2609 | 3474 | 21 | 1 | 0 | 3174 | 3372 | 0 | 0 | 3260 | 0 |
| F3 | 0 | 2 | 0 | 4943 | 0 | 1 | 1 | 0 | 0 | 10 | 0 | 2 | 0 | 0 | 0 | 6 | 0 |
| F4 | 2 | 0 | 0 | 2 | 0 | 0 | 3 | 2 | 0 | 0 | 0 | 2 | 3478 | 0 | 0 | 4 | 0 |
| F5 | 1 | 1 | 0 | 3 | 0 | 1498 | 2142 | 17 | 2 | 1 | 0 | 2571 | 3 | 0 | 0 | 3436 | 0 |
| F6 | 2 | 0 | 0 | 5 | 0 | 1341 | 2777 | 708 | 95 | 0 | 0 | 2086 | 0 | 1 | 0 | 3846 | 0 |
| F7 | 3 | 1 | 0 | 1 | 0 | 162 | 2 | 1 | 61 | 1 | 0 | 3 | 1 | 1 | 0 | 4 | 0 |
| F8 | 2 | 1 | 0 | 5 | 0 | 1 | 2621 | 3922 | 0 | 1 | 0 | 2026 | 0 | 0 | 0 | 3246 | 0 |
| F9 | 1 | 1 | 0 | 0 | 0 | 2 | 2 | 0 | 4086 | 0 | 0 | 4 | 334 | 0 | 0 | 2 | 0 |
| G1 | 3 | 0 | 0 | 1 | 0 | 1 | 0 | 0 | 1 | 4 | 0 | 2 | 2 | 0 | 0 | 2 | 0 |
| G10 | 0 | 1 | 0 | 1 | 2 | 1 | 0 | 0 | 0 | 0 | 0 | 3 | 2 | 0 | 0 | 2 | 0 |
| G11 | 0 | 0 | 0 | 0 | 1 | 1411 | 2 | 0 | 0 | 0 | 0 | 0 | 0 | 1 | 0 | 0 | 0 |
| G12 | 1 | 0 | 0 | 0 | 0 | 1 | 0 | 0 | 0 | 0 | 0 | 1 | 281 | 0 | 0 | 3902 | 0 |
| G2 | 1 | 0 | 0 | 2 | 1 | 0 | 0 | 0 | 0 | 0 | 6 | 2 | 0 | 0 | 0 | 2 | 0 |
| G3 | 0 | 0 | 0 | 0 | 0 | 3 | 0 | 0 | 0 | 0 | 0 | 0 | 5 | 0 | 371 | 0 | 0 |
| G4 | 2 | 0 | 0 | 2 | 0 | 1 | 0 | 0 | 0 | 1 | 0 | 4828 | 4932 | 0 | 0 | 5716 | 0 |
| G5 | 0 | 0 | 0 | 0 | 0 | 1 | 0 | 0 | 0 | 1 | 0 | 1 | 3 | 0 | 0 | 0 | 0 |
| G6 | 0 | 0 | 0 | 2 | 0 | 1 | 0 | 0 | 2 | 2 | 0 | 2 | 0 | 0 | 0 | 0 | 0 |

Figure 17L

| WELL | IL2 | IL10 | IL12A | IL13 | IL17A | IFNG | PRF1 | GZMB | TGFB | TNFA | BCL6 | TBET | GATA3 | RORC | FOXP3 | RUNX1 | RUNX3 |
|---|---|---|---|---|---|---|---|---|---|---|---|---|---|---|---|---|---|
| G7 | 3 | 0 | 0 | 4 | 0 | 0 | 1 | 0 | 0 | 0 | 0 | 0 | 1 | 0 | 0 | 2 | 0 |
| G8 | 1 | 2 | 0 | 2 | 0 | 2 | 0 | 0 | 1 | 3 | 0 | 1 | 3 | 0 | 0 | 2 | 0 |
| G9 | 0 | 0 | 0 | 1 | 1 | 1161 | 2437 | 0 | 3 | 128 | 0 | 1 | 2012 | 3098 | 0 | 1612 | 0 |
| H1 | 2 | 0 | 0 | 2 | 1 | 0 | 0 | 3 | 0 | 0 | 2 | 4 | 1 | 0 | 1 | 2 | 0 |
| H10 | 3 | 0 | 0 | 4 | 0 | 3 | 0 | 0 | 1 | 1 | 0 | 1 | 2 | 0 | 0 | 6 | 2 |
| H11 | 3 | 0 | 0 | 3 | 0 | 1506 | 2094 | 1896 | 48 | 140 | 0 | 3 | 2 | 0 | 0 | 2530 | 0 |
| H12 | 3 | 0 | 0 | 3 | 1 | 2 | 0 | 0 | 0 | 0 | 0 | 3 | 1 | 0 | 0 | 0 | 0 |
| H2 | 2 | 0 | 0 | 0 | 1 | 1688 | 960 | 637 | 0 | 2 | 2 | 3 | 1 | 0 | 0 | 2568 | 0 |
| H3 | 4 | 1 | 0 | 0 | 1 | 0 | 1 | 1 | 3 | 4 | 0 | 1 | 3 | 0 | 0 | 6 | 0 |
| H4 | 4 | 0 | 0 | 1 | 0 | 2 | 0 | 2 | 0 | 2 | 0 | 2 | 3 | 0 | 0 | 0 | 0 |
| H5 | 596 | 1 | 0 | 3 | 0 | 0 | 0 | 0 | 0 | 1 | 0 | 3 | 2802 | 0 | 0 | 3056 | 0 |
| H6 | 4 | 0 | 0 | 0 | 1 | 1 | 2 | 0 | 0 | 0 | 0 | 1 | 1 | 0 | 0 | 2 | 0 |
| H7 | 3 | 1 | 0 | 3 | 0 | 1 | 0 | 1 | 0 | 0 | 0 | 2 | 3 | 0 | 0 | 0 | 0 |
| H8 | 0 | 0 | 1 | 3 | 1 | 2 | 0 | 0 | 0 | 2 | 0 | 3 | 4 | 0 | 0 | 2 | 0 |
| H9 | 2 | 0 | 0 | 2 | 0 | 1 | 0 | 0 | 0 | 1 | 0 | 2 | 1 | 0 | 0 | 0 | 0 |
| A1 | 2882 | 2279 | 0 | 4 | 1 | 1 | 0 | 1 | 0 | 1440 | 138 | 2 | 0 | 0 | 0 | 170 | 0 |
| A10 | 722 | 571 | 0 | 3 | 0 | 0 | 0 | 0 | 0 | 3051 | 0 | 986 | 2 | 0 | 0 | 0 | 0 |
| A11 | 2678 | 3 | 0 | 4744 | 0 | 1 | 0 | 0 | 0 | 1455 | 0 | 1156 | 2179 | 0 | 0 | 1564 | 0 |
| A12 | 1728 | 886 | 0 | 4 | 0 | 405 | 0 | 0 | 0 | 1 | 0 | 1818 | 105 | 0 | 0 | 156 | 0 |
| A2 | 2788 | 2344 | 0 | 2 | 0 | 1218 | 0 | 0 | 0 | 1335 | 0 | 1267 | 1 | 0 | 0 | 918 | 0 |
| A3 | 2622 | 1 | 0 | 4961 | 0 | 0 | 0 | 0 | 0 | 391 | 0 | 1 | 370 | 0 | 0 | 0 | 0 |
| A4 | 1425 | 353 | 0 | 4959 | 0 | 1 | 0 | 0 | 0 | 3 | 0 | 3 | 11 | 0 | 0 | 4 | 0 |
| A5 | 2806 | 32 | 0 | 5806 | 0 | 0 | 0 | 0 | 0 | 0 | 0 | 220 | 2441 | 1 | 0 | 2 | 0 |
| A6 | 644 | 242 | 0 | 4081 | 0 | 0 | 0 | 0 | 0 | 308 | 0 | 543 | 656 | 0 | 0 | 0 | 0 |
| A7 | 584 | 1 | 0 | 3782 | 0 | 0 | 0 | 0 | 0 | 0 | 6 | 332 | 1158 | 0 | 0 | 0 | 0 |

Figure 17M

| WELL | IL2 | IL10 | IL12A | IL13 | IL17A | IFNG | PRF1 | GZMB | TGFB | TNFA | BCL6 | TBET | GATA3 | RORC | FOXP3 | RUNX1 | RUNX3 |
|---|---|---|---|---|---|---|---|---|---|---|---|---|---|---|---|---|---|
| A8 | 2238 | 1609 | 0 | 4023 | 0 | 1209 | 0 | 0 | 0 | 303 | 0 | 177 | 3 | 0 | 0 | 972 | 0 |
| A9 | 27 | 1 | 0 | 1 | 0 | 0 | 0 | 0 | 0 | 30 | 0 | 45 | 2 | 0 | 0 | 4 | 0 |
| B1 | 3605 | 0 | 0 | 1 | 1 | 0 | 0 | 0 | 0 | 1147 | 994 | 2481 | 0 | 0 | 0 | 298 | 0 |
| B10 | 1166 | 1212 | 0 | 2 | 0 | 300 | 0 | 0 | 0 | 305 | 0 | 598 | 0 | 0 | 0 | 0 | 0 |
| B11 | 270 | 3341 | 0 | 5641 | 0 | 15 | 0 | 0 | 0 | 421 | 0 | 1 | 3157 | 0 | 0 | 562 | 0 |
| B12 | 1126 | 467 | 0 | 3843 | 0 | 429 | 0 | 0 | 0 | 937 | 0 | 1 | 2 | 0 | 0 | 4 | 0 |
| B2 | 3736 | 3367 | 0 | 2 | 0 | 1744 | 0 | 0 | 0 | 0 | 0 | 2581 | 3 | 0 | 0 | 918 | 0 |
| B3 | 3 | 1 | 0 | 0 | 0 | 0 | 0 | 0 | 0 | 1852 | 2 | 4767 | 5848 | 0 | 0 | 2974 | 0 |
| B4 | 2137 | 1554 | 0 | 1 | 0 | 0 | 0 | 0 | 0 | 3864 | 0 | 1849 | 258 | 0 | 0 | 428 | 0 |
| B5 | 3690 | 3403 | 0 | 2 | 0 | 0 | 0 | 0 | 0 | 1814 | 0 | 3 | 1 | 0 | 0 | 462 | 0 |
| B6 | 424 | 1502 | 0 | 2 | 0 | 0 | 1 | 0 | 0 | 2 | 0 | 937 | 1 | 0 | 0 | 958 | 0 |
| B7 | 1 | 2121 | 0 | 1 | 0 | 564 | 0 | 0 | 32 | 656 | 0 | 2061 | 3 | 0 | 118 | 0 | 448 |
| B8 | 3779 | 2553 | 0 | 1 | 3963 | 1818 | 0 | 0 | 0 | 546 | 0 | 1792 | 45 | 252 | 0 | 3 | 0 |
| B9 | 98 | 50 | 0 | 1 | 1 | 2 | 0 | 0 | 0 | 2 | 0 | 28 | 1 | 0 | 0 | 0 | 0 |
| C1 | 3 | 3114 | 0 | 1 | 1864 | 890 | 0 | 0 | 0 | 1 | 0 | 343 | 0 | 0 | 33 | 1780 | 0 |
| C10 | 3 | 1991 | 0 | 2 | 0 | 0 | 0 | 0 | 0 | 0 | 0 | 1986 | 1 | 133 | 0 | 0 | 3 |
| C11 | 382 | 3508 | 0 | 0 | 1 | 1410 | 0 | 0 | 0 | 1 | 0 | 3056 | 1 | 0 | 0 | 3532 | 0 |
| C12 | 663 | 2049 | 0 | 2 | 3833 | 2160 | 0 | 0 | 2 | 2 | 0 | 1167 | 1 | 0 | 0 | 1998 | 2 |
| C2 | 4353 | 1876 | 0 | 0 | 1 | 1 | 0 | 0 | 0 | 2 | 0 | 1436 | 0 | 0 | 0 | 0 | 0 |
| C3 | 4 | 1666 | 0 | 2 | 1 | 0 | 0 | 0 | 0 | 0 | 0 | 4137 | 1451 | 0 | 0 | 4500 | 0 |
| C4 | 1 | 1735 | 0 | 0 | 0 | 386 | 0 | 0 | 0 | 1 | 50 | 3 | 1218 | 0 | 0 | 1670 | 2 |
| C5 | 956 | 3 | 0 | 5670 | 3833 | 0 | 0 | 0 | 0 | 4534 | 0 | 0 | 1 | 0 | 0 | 2 | 0 |
| C6 | 1554 | 1461 | 0 | 2 | 1 | 1 | 0 | 0 | 0 | 1258 | 0 | 2 | 1 | 0 | 0 | 2 | 0 |
| C7 | 2594 | 2188 | 0 | 0 | 2 | 0 | 0 | 0 | 0 | 4487 | 0 | 2803 | 1 | 0 | 0 | 0 | 0 |
| C8 | 3985 | 2988 | 0 | 1 | 1 | 1 | 0 | 0 | 0 | 4487 | 0 | 2 | 3 | 2 | 0 | 0 | 0 |

Figure 17N

| WELL | IL2 | IL10 | IL12A | IL13 | IL17A | IFNG | PRF1 | GZMB | TGFB | TNFA | BCL6 | TBET | GATA3 | RORC | FOXP3 | RUNX1 | RUNX3 |
|---|---|---|---|---|---|---|---|---|---|---|---|---|---|---|---|---|---|
| C9 | 105 | 62 | 0 | 0 | 0 | 17 | 0 | 0 | 0 | 595 | 0 | 22 | 1 | 0 | 0 | 4 | 0 |
| D1 | 3 | 2626 | 0 | 1 | 4192 | 0 | 0 | 0 | 1 | 2 | 0 | 2041 | 3 | 91 | 0 | 716 | 0 |
| D10 | 2472 | 2796 | 0 | 1 | 0 | 1 | 0 | 0 | 4 | 1 | 0 | 4 | 3 | 0 | 0 | 1814 | 0 |
| D11 | 2907 | 3949 | 0 | 0 | 0 | 2 | 0 | 0 | 0 | 804 | 0 | 1989 | 1445 | 4 | 0 | 3306 | 0 |
| D12 | 4021 | 3472 | 0 | 1 | 0 | 0 | 0 | 0 | 3 | 0 | 0 | 2 | 4 | 0 | 0 | 4 | 0 |
| D2 | 3558 | 4 | 0 | 0 | 0 | 1 | 0 | 1 | 1 | 2289 | 2 | 3146 | 2356 | 49 | 33 | 1626 | 0 |
| D3 | 4978 | 2990 | 0 | 3 | 0 | 135 | 0 | 0 | 0 | 128 | 0 | 1564 | 114 | 0 | 0 | 656 | 0 |
| D4 | 3 | 3313 | 0 | 2 | 0 | 0 | 0 | 0 | 1 | 1 | 0 | 2141 | 1 | 0 | 3 | 4684 | 0 |
| D5 | 4440 | 3635 | 0 | 0 | 0 | 0 | 0 | 0 | 1 | 3 | 0 | 4 | 2 | 0 | 0 | 2 | 0 |
| D6 | 20 | 1 | 0 | 1 | 1 | 1385 | 4 | 0 | 0 | 3 | 0 | 1971 | 0 | 1 | 0 | 1296 | 0 |
| D7 | 3 | 4649 | 0 | 1 | 0 | 0 | 761 | 0 | 2 | 2839 | 0 | 1 | 2396 | 192 | 175 | 4884 | 0 |
| D8 | 4 | 444 | 0 | 2 | 0 | 1726 | 1 | 1 | 1 | 88 | 0 | 3 | 0 | 0 | 1 | 2692 | 0 |
| D9 | 183 | 1 | 0 | 2 | 0 | 22 | 0 | 0 | 2 | 0 | 10 | 211 | 3 | 0 | 0 | 22 | 0 |
| E1 | 2154 | 1343 | 0 | 1 | 1 | 2180 | 0 | 0 | 0 | 0 | 0 | 1174 | 3 | 0 | 0 | 0 | 0 |
| E10 | 29 | 3286 | 0 | 1 | 1 | 2 | 0 | 0 | 1 | 0 | 0 | 3202 | 4263 | 0 | 0 | 0 | 0 |
| E11 | 3711 | 3012 | 0 | 2 | 0 | 1796 | 0 | 0 | 0 | 0 | 0 | 1135 | 2 | 0 | 0 | 2 | 0 |
| E12 | 1677 | 3252 | 0 | 2 | 1 | 0 | 0 | 0 | 1 | 1 | 0 | 2468 | 1 | 0 | 0 | 2438 | 0 |
| E2 | 2964 | 3816 | 0 | 1 | 0 | 1 | 0 | 0 | 0 | 1 | 0 | 3 | 0 | 0 | 0 | 6 | 0 |
| E3 | 3 | 953 | 0 | 2 | 3208 | 1810 | 0 | 0 | 0 | 2 | 0 | 2380 | 31 | 454 | 141 | 332 | 2 |
| E4 | 4507 | 4348 | 0 | 4 | 1 | 0 | 0 | 0 | 1 | 17 | 2 | 549 | 505 | 0 | 0 | 22 | 0 |
| E5 | 3529 | 286 | 0 | 7712 | 0 | 0 | 0 | 0 | 0 | 3 | 4 | 1221 | 1 | 0 | 0 | 0 | 0 |
| E6 | 26 | 34 | 0 | 0 | 1 | 2 | 0 | 0 | 0 | 0 | 0 | 4 | 133 | 0 | 0 | 30 | 0 |
| E7 | 3 | 4037 | 0 | 5158 | 0 | 0 | 0 | 0 | 1 | 3 | 0 | 1290 | 4336 | 1 | 1 | 4274 | 0 |
| E8 | 4 | 2427 | 0 | 0 | 0 | 2 | 0 | 0 | 0 | 0 | 0 | 2 | 1765 | 0 | 0 | 0 | 0 |
| E9 | 2 | 217 | 0 | 1 | 0 | 0 | 0 | 0 | 0 | 532 | 0 | 130 | 2 | 22 | 0 | 342 | 0 |

Figure 17O

| WELL | IL2 | IL10 | IL12A | IL13 | IL17A | IFNG | PRF1 | GZMB | TGFB | TNFA | BCL6 | TBET | GATA3 | RORC | FOXP3 | RUNX1 | RUNX3 |
|---|---|---|---|---|---|---|---|---|---|---|---|---|---|---|---|---|---|
| F1 | 3 | 0 | 0 | 5742 | 1 | 2393 | 18 | 2 | 0 | 2 | 0 | 4 | 4 | 0 | 0 | 168 | 0 |
| F10 | 155 | 0 | 0 | 2 | 1 | 402 | 0 | 0 | 0 | 0 | 0 | 2 | 0 | 0 | 764 | 4334 | 0 |
| F11 | 2307 | 0 | 0 | 3 | 0 | 1222 | 359 | 0 | 0 | 4412 | 0 | 477 | 1 | 0 | 1 | 148 | 2 |
| F12 | 1 | 1 | 0 | 0 | 1 | 0 | 0 | 0 | 1772 | 1 | 0 | 1 | 3 | 0 | 1291 | 4 | 0 |
| F2 | 3331 | 0 | 0 | 1 | 0 | 1796 | 13 | 0 | 0 | 756 | 0 | 524 | 2 | 37 | 1 | 200 | 0 |
| F3 | 1 | 2 | 0 | 2 | 0 | 3 | 0 | 0 | 3 | 1 | 0 | 0 | 4269 | 1 | 2 | 3684 | 0 |
| F4 | 1277 | 0 | 0 | 6794 | 0 | 1704 | 2 | 0 | 0 | 74 | 0 | 20 | 2 | 0 | 0 | 4 | 2 |
| F5 | 2664 | 0 | 0 | 0 | 0 | 0 | 0 | 0 | 0 | 4748 | 2 | 96 | 1623 | 42 | 0 | 984 | 0 |
| F6 | 2358 | 0 | 0 | 1 | 0 | 1377 | 0 | 0 | 18 | 6339 | 0 | 100 | 400 | 4 | 452 | 148 | 0 |
| F7 | 2 | 0 | 0 | 0 | 0 | 0 | 0 | 0 | 0 | 1 | 0 | 5573 | 4700 | 0 | 0 | 4926 | 0 |
| F8 | 2208 | 0 | 0 | 3 | 0 | 2132 | 0 | 0 | 0 | 2 | 0 | 3326 | 1574 | 3 | 0 | 2 | 0 |
| F9 | 1592 | 1 | 0 | 1 | 0 | 0 | 1 | 0 | 3 | 3 | 0 | 1 | 2 | 0 | 124 | 1558 | 0 |
| G1 | 2 | 3 | 0 | 3 | 0 | 0 | 1 | 0 | 77 | 1 | 0 | 3 | 4723 | 0 | 0 | 2998 | 0 |
| G10 | 3735 | 2 | 0 | 1 | 0 | 0 | 0 | 0 | 0 | 2312 | 0 | 2 | 1 | 0 | 0 | 2590 | 0 |
| G11 | 3583 | 0 | 0 | 2 | 0 | 0 | 0 | 0 | 0 | 1404 | 0 | 115 | 599 | 370 | 0 | 380 | 0 |
| G12 | 4249 | 0 | 0 | 1 | 0 | 3 | 0 | 0 | 0 | 3157 | 0 | 3318 | 1370 | 0 | 1 | 118 | 0 |
| G2 | 3202 | 1 | 0 | 0 | 0 | 0 | 0 | 0 | 0 | 1118 | 0 | 1625 | 1287 | 0 | 1 | 4 | 0 |
| G3 | 4607 | 0 | 0 | 3 | 0 | 1 | 0 | 0 | 0 | 38 | 0 | 344 | 3 | 0 | 0 | 564 | 0 |
| G4 | 4311 | 0 | 0 | 0 | 0 | 0 | 0 | 0 | 0 | 4 | 0 | 2740 | 3 | 0 | 0 | 1010 | 0 |
| G5 | 3805 | 113 | 0 | 2 | 1 | 1158 | 0 | 0 | 0 | 1 | 0 | 2148 | 0 | 0 | 0 | 0 | 0 |
| G6 | 1667 | 0 | 0 | 1 | 2530 | 1 | 0 | 0 | 3 | 3968 | 0 | 1 | 2 | 0 | 0 | 1482 | 0 |
| G7 | 2405 | 1 | 0 | 2 | 1 | 759 | 0 | 0 | 2 | 11 | 0 | 2809 | 0 | 0 | 0 | 0 | 0 |
| G8 | 2694 | 0 | 0 | 1 | 1 | 0 | 0 | 0 | 18 | 778 | 0 | 2172 | 0 | 0 | 0 | 4 | 0 |
| G9 | 2298 | 0 | 0 | 2 | 1 | 0 | 0 | 0 | 0 | 4 | 0 | 1 | 0 | 0 | 0 | 0 | 0 |
| H1 | 4208 | 0 | 0 | 1 | 1 | 0 | 2 | 0 | 0 | 269 | 0 | 1476 | 25 | 0 | 0 | 0 | 0 |

Figure 17P

| WELL | IL2 | IL10 | IL12A | IL13 | IL17A | IFNG | PRF1 | GZMB | TGFB | TNFA | BCL6 | TBET | GATA3 | RORC | FOXP3 | RUNX1 | RUNX3 |
|---|---|---|---|---|---|---|---|---|---|---|---|---|---|---|---|---|---|
| H10 | 1794 | 0 | 0 | 5356 | 1 | 0 | 0 | 0 | 0 | 268 | 0 | 527 | 2446 | 0 | 0 | 0 | 2 |
| H11 | 3987 | 1 | 1 | 1 | 0 | 0 | 0 | 0 | 0 | 2 | 0 | 0 | 2 | 0 | 0 | 2 | 0 |
| H12 | 3249 | 0 | 0 | 3775 | 0 | 0 | 0 | 0 | 1 | 0 | 0 | 2 | 1095 | 0 | 0 | 0 | 0 |
| H2 | 1 | 2 | 0 | 2 | 0 | 1 | 990 | 3 | 1 | 3 | 0 | 654 | 4 | 0 | 0 | 1192 | 0 |
| H3 | 4 | 1 | 1 | 2 | 0 | 0 | 0 | 0 | 129 | 4 | 0 | 2294 | 4 | 0 | 0 | 4 | 0 |
| H4 | 3597 | 1 | 0 | 5 | 0 | 0 | 0 | 0 | 0 | 80 | 0 | 2199 | 1 | 0 | 0 | 14 | 0 |
| H5 | 4 | 1 | 0 | 2837 | 0 | 1419 | 0 | 0 | 0 | 1 | 0 | 17 | 4 | 0 | 0 | 2 | 0 |
| H6 | 4 | 0 | 0 | 3 | 0 | 1 | 0 | 0 | 85 | 1 | 0 | 4 | 1 | 0 | 0 | 0 | 0 |
| H7 | 3086 | 1 | 0 | 3 | 1 | 1373 | 0 | 0 | 0 | 1360 | 0 | 325 | 3 | 33 | 1 | 4 | 0 |
| H8 | 3273 | 0 | 0 | 0 | 0 | 2 | 0 | 0 | 66 | 1 | 0 | 2 | 4 | 0 | 0 | 1426 | 0 |
| H9 | 4 | 0 | 26 | 5499 | 0 | 2 | 0 | 0 | 1 | 2 | 0 | 2552 | 4235 | 0 | 0 | 2 | 0 |
| A1 | 1576 | 0 | 0 | 1 | 1551 | 1 | 0 | 0 | 0 | 0 | 0 | 1249 | 0 | 0 | 0 | 0 | 0 |
| A10 | 1466 | 0 | 0 | 1491 | 0 | 0 | 0 | 0 | 0 | 0 | 0 | 12 | 2 | 0 | 0 | 8 | 0 |
| A11 | 381 | 1 | 0 | 623 | 1 | 0 | 0 | 0 | 0 | 3 | 0 | 2 | 132 | 0 | 0 | 58 | 2 |
| A12 | 1603 | 0 | 0 | 1415 | 0 | 1 | 0 | 0 | 0 | 247 | 2 | 33 | 6 | 0 | 0 | 0 | 0 |
| A2 | 3 | 0 | 0 | 1552 | 1 | 1 | 0 | 0 | 1 | 628 | 0 | 3 | 1239 | 0 | 0 | 350 | 0 |
| A3 | 1963 | 1 | 0 | 2691 | 1 | 0 | 0 | 0 | 0 | 1 | 0 | 377 | 1233 | 0 | 0 | 0 | 0 |
| A4 | 3173 | 0 | 0 | 4 | 2 | 777 | 0 | 0 | 0 | 2074 | 0 | 1938 | 2 | 0 | 0 | 50 | 2 |
| A5 | 323 | 0 | 0 | 499 | 0 | 0 | 0 | 0 | 0 | 161 | 0 | 0 | 36 | 0 | 0 | 16 | 0 |
| A6 | 1676 | 0 | 0 | 3 | 0 | 709 | 0 | 0 | 0 | 1429 | 0 | 493 | 2 | 0 | 0 | 4 | 0 |
| A7 | 1092 | 0 | 0 | 1464 | 1 | 2 | 0 | 0 | 0 | 1 | 0 | 4 | 875 | 1 | 0 | 0 | 0 |
| A8 | 664 | 0 | 0 | 1065 | 0 | 0 | 0 | 0 | 0 | 1 | 0 | 5 | 423 | 0 | 0 | 4 | 0 |
| A9 | 1848 | 1 | 0 | 2023 | 1 | 1 | 0 | 0 | 0 | 93 | 0 | 0 | 1064 | 0 | 0 | 10 | 12 |
| B1 | 3 | 0 | 0 | 2924 | 1127 | 0 | 0 | 0 | 0 | 2 | 0 | 0 | 414 | 0 | 0 | 46 | 0 |
| B10 | 3392 | 0 | 0 | 4286 | 0 | 0 | 0 | 0 | 0 | 2 | 0 | 3 | 2351 | 0 | 0 | 2 | 0 |

Figure 17Q

| WELL | IL2 | IL10 | IL12A | IL13 | IL17A | IFNG | PRF1 | GZMB | TGFB | TNFA | BCL6 | TBET | GATA3 | RORC | FOXP3 | RUNX1 | RUNX3 |
|---|---|---|---|---|---|---|---|---|---|---|---|---|---|---|---|---|---|
| B11 | 1624 | 1 | 0 | 3399 | 0 | 0 | 0 | 0 | 0 | 2 | 0 | 0 | 2726 | 0 | 0 | 0 | 0 |
| B12 | 3497 | 4 | 0 | 3972 | 0 | 0 | 0 | 0 | 0 | 1 | 0 | 0 | 2142 | 0 | 0 | 0 | 0 |
| B2 | 4 | 1 | 0 | 3471 | 0 | 0 | 1 | 0 | 0 | 2 | 0 | 340 | 2063 | 1 | 0 | 4 | 0 |
| B3 | 2820 | 1 | 0 | 4006 | 0 | 0 | 0 | 0 | 0 | 25 | 0 | 4 | 881 | 2 | 0 | 36 | 0 |
| B4 | 4392 | 2 | 0 | 5561 | 1 | 0 | 0 | 0 | 0 | 2 | 0 | 4 | 1 | 0 | 0 | 2 | 0 |
| B5 | 1761 | 0 | 0 | 2909 | 0 | 1 | 0 | 0 | 0 | 1 | 0 | 465 | 883 | 0 | 0 | 8 | 0 |
| B6 | 1308 | 1 | 0 | 4842 | 0 | 0 | 0 | 0 | 0 | 1 | 0 | 48 | 2777 | 0 | 0 | 2324 | 92 |
| B7 | 539 | 0 | 0 | 3395 | 1 | 0 | 0 | 0 | 1 | 2337 | 0 | 0 | 894 | 0 | 0 | 64 | 0 |
| B8 | 1980 | 0 | 0 | 2983 | 0 | 2 | 0 | 0 | 0 | 1 | 0 | 2 | 578 | 0 | 0 | 2 | 0 |
| B9 | 3389 | 1 | 0 | 4401 | 0 | 0 | 0 | 0 | 0 | 2165 | 0 | 35 | 627 | 0 | 0 | 474 | 2 |
| C1 | 3523 | 0 | 0 | 3691 | 0 | 0 | 0 | 0 | 0 | 2 | 0 | 1 | 1027 | 0 | 0 | 0 | 0 |
| C10 | 3524 | 1 | 0 | 4083 | 0 | 1 | 0 | 0 | 1 | 3 | 0 | 1 | 326 | 0 | 0 | 310 | 10 |
| C11 | 2715 | 0 | 0 | 3881 | 0 | 0 | 0 | 0 | 0 | 2710 | 0 | 698 | 1206 | 1 | 0 | 122 | 0 |
| C12 | 4392 | 0 | 0 | 4646 | 0 | 1 | 0 | 0 | 0 | 0 | 0 | 20 | 1232 | 0 | 0 | 8 | 0 |
| C2 | 2793 | 0 | 0 | 3753 | 0 | 1 | 0 | 0 | 0 | 2 | 0 | 1 | 2639 | 0 | 0 | 166 | 0 |
| C3 | 2232 | 1 | 0 | 2625 | 0 | 0 | 0 | 1 | 1 | 584 | 0 | 2 | 2 | 0 | 0 | 162 | 0 |
| C4 | 4408 | 0 | 0 | 5397 | 0 | 1 | 0 | 0 | 0 | 5 | 2 | 2 | 1896 | 0 | 0 | 2 | 0 |
| C5 | 2714 | 0 | 0 | 3532 | 0 | 0 | 0 | 0 | 0 | 0 | 0 | 24 | 1759 | 0 | 0 | 250 | 0 |
| C6 | 2 | 1 | 0 | 4233 | 0 | 0 | 0 | 0 | 0 | 2 | 0 | 360 | 3688 | 0 | 0 | 3448 | 0 |
| C7 | 1 | 1 | 0 | 3801 | 0 | 0 | 0 | 0 | 0 | 1 | 0 | 3 | 2732 | 1 | 0 | 2560 | 0 |
| C8 | 2671 | 1081 | 0 | 4258 | 0 | 0 | 0 | 0 | 0 | 3 | 0 | 1 | 2107 | 0 | 0 | 166 | 0 |
| C9 | 3501 | 1 | 0 | 4381 | 1803 | 0 | 0 | 0 | 1 | 417 | 0 | 119 | 4 | 1 | 0 | 10 | 0 |
| D1 | 14 | 0 | 0 | 2969 | 1 | 0 | 0 | 0 | 0 | 134 | 0 | 9 | 1111 | 1 | 0 | 2 | 0 |
| D10 | 3472 | 0 | 0 | 4295 | 0 | 0 | 0 | 0 | 0 | 1 | 0 | 4 | 1881 | 0 | 0 | 2 | 0 |
| D11 | 3620 | 0 | 0 | 4359 | 0 | 1 | 0 | 0 | 0 | 2 | 0 | 37 | 358 | 0 | 0 | 4 | 0 |

Figure 17R

| WELL | IL2 | IL10 | IL12A | IL13 | IL17A | IFNG | PRF1 | GZMB | TGFB | TNFA | BCL6 | TBET | GATA3 | RORC | FOXP3 | RUNX1 | RUNX3 |
|---|---|---|---|---|---|---|---|---|---|---|---|---|---|---|---|---|---|
| D12 | 3969 | 0 | 0 | 4736 | 0 | 1 | 0 | 0 | 0 | 545 | 0 | 3 | 2718 | 0 | 0 | 60 | 0 |
| D2 | 1574 | 4 | 0 | 3543 | 1 | 1 | 1 | 0 | 18 | 1 | 0 | 2187 | 780 | 0 | 0 | 602 | 0 |
| D3 | 1897 | 0 | 0 | 2397 | 0 | 0 | 0 | 0 | 0 | 1685 | 0 | 2 | 8 | 1 | 0 | 2 | 0 |
| D4 | 4517 | 1 | 0 | 5434 | 1 | 2 | 0 | 0 | 0 | 53 | 0 | 4 | 363 | 0 | 0 | 6 | 0 |
| D5 | 1149 | 1 | 0 | 3769 | 0 | 0 | 0 | 0 | 0 | 1 | 92 | 729 | 1926 | 1912 | 0 | 1190 | 0 |
| D6 | 3699 | 0 | 0 | 4568 | 2 | 0 | 0 | 0 | 0 | 3 | 0 | 2 | 867 | 1 | 0 | 1258 | 0 |
| D7 | 4624 | 2 | 0 | 5587 | 1 | 1 | 0 | 0 | 0 | 0 | 0 | 2 | 1259 | 0 | 0 | 76 | 0 |
| D8 | 2 | 4 | 0 | 4532 | 1 | 0 | 1 | 0 | 0 | 3 | 0 | 0 | 2108 | 0 | 0 | 4 | 0 |
| D9 | 13 | 1 | 0 | 5079 | 0 | 0 | 0 | 0 | 0 | 318 | 0 | 1 | 2992 | 0 | 0 | 864 | 0 |
| E1 | 2 | 0 | 0 | 2393 | 1897 | 0 | 1 | 0 | 0 | 3 | 2 | 17 | 548 | 0 | 0 | 4 | 0 |
| E10 | 1 | 0 | 0 | 2476 | 0 | 1392 | 0 | 0 | 0 | 1 | 0 | 3 | 1640 | 1443 | 0 | 668 | 0 |
| E11 | 4 | 0 | 0 | 2 | 0 | 0 | 0 | 0 | 0 | 17 | 0 | 2423 | 1 | 0 | 0 | 2606 | 0 |
| E12 | 3345 | 1 | 0 | 3017 | 0 | 0 | 0 | 0 | 0 | 0 | 0 | 33 | 1685 | 0 | 0 | 0 | 0 |
| E2 | 2117 | 0 | 0 | 1868 | 1 | 2 | 0 | 0 | 0 | 12 | 0 | 1011 | 390 | 0 | 0 | 52 | 0 |
| E3 | 1763 | 0 | 0 | 1745 | 0 | 0 | 0 | 0 | 0 | 137 | 0 | 4 | 1016 | 1 | 0 | 402 | 0 |
| E4 | 3708 | 0 | 0 | 4159 | 1 | 0 | 0 | 0 | 0 | 4 | 0 | 4 | 1569 | 0 | 0 | 2 | 0 |
| E5 | 2425 | 0 | 0 | 2428 | 0 | 0 | 0 | 0 | 0 | 163 | 0 | 468 | 4 | 0 | 0 | 2 | 0 |
| E6 | 2588 | 0 | 0 | 2913 | 0 | 0 | 0 | 0 | 0 | 192 | 0 | 18 | 1631 | 1 | 0 | 8 | 0 |
| E7 | 2188 | 1 | 0 | 2391 | 0 | 1 | 0 | 0 | 0 | 2035 | 0 | 1 | 2068 | 0 | 0 | 656 | 0 |
| E8 | 1961 | 0 | 0 | 2239 | 0 | 0 | 0 | 0 | 0 | 1 | 0 | 2 | 1 | 1 | 0 | 16 | 0 |
| E9 | 2 | 0 | 0 | 3243 | 1 | 0 | 0 | 0 | 0 | 143 | 0 | 13 | 2921 | 0 | 0 | 142 | 0 |
| F1 | 2116 | 3 | 0 | 0 | 1 | 0 | 0 | 1 | 0 | 10 | 0 | 1592 | 3 | 1 | 1 | 0 | 0 |
| F10 | 2213 | 0 | 0 | 1 | 1 | 978 | 0 | 0 | 595 | 150 | 0 | 700 | 1274 | 0 | 0 | 748 | 2 |
| F11 | 4 | 0 | 0 | 2 | 1 | 1 | 0 | 0 | 2 | 4 | 0 | 2 | 2 | 0 | 0 | 0 | 0 |
| F12 | 2979 | 0 | 0 | 3 | 1 | 0 | 0 | 0 | 0 | 1 | 0 | 1 | 1650 | 1 | 0 | 2174 | 0 |

Figure 17S

| WELL | IL2 | IL10 | IL12A | IL13 | IL17A | IFNG | PRF1 | GZMB | TGFB | TNFA | BCL6 | TBET | GATA3 | RORC | FOXP3 | RUNX1 | RUNX3 |
|---|---|---|---|---|---|---|---|---|---|---|---|---|---|---|---|---|---|
| F2 | 2021 | 0 | 0 | 2 | 1 | 826 | 1 | 1 | 0 | 1169 | 0 | 3 | 823 | 0 | 0 | 1186 | 0 |
| F3 | 4 | 0 | 0 | 0 | 1 | 4 | 0 | 0 | 2 | 1885 | 2 | 3 | 1 | 1 | 0 | 1490 | 0 |
| F4 | 2 | 3152 | 0 | 1 | 2448 | 2 | 0 | 0 | 0 | 272 | 0 | 436 | 4 | 394 | 0 | 278 | 0 |
| F5 | 3 | 1 | 0 | 3 | 0 | 790 | 0 | 0 | 0 | 3 | 0 | 2018 | 2 | 1 | 0 | 2002 | 0 |
| F6 | 0 | 0 | 0 | 3 | 1 | 1 | 0 | 1 | 1 | 0 | 0 | 1 | 1 | 1 | 0 | 4 | 0 |
| F7 | 2242 | 1 | 0 | 0 | 0 | 0 | 0 | 0 | 0 | 2472 | 1966 | 3 | 1 | 1117 | 0 | 544 | 0 |
| F8 | 2356 | 0 | 0 | 2 | 1 | 1102 | 0 | 0 | 0 | 467 | 2 | 1529 | 1098 | 544 | 0 | 520 | 0 |
| F9 | 892 | 0 | 0 | 3 | 1470 | 0 | 0 | 0 | 0 | 2036 | 1866 | 0 | 1 | 63 | 0 | 2236 | 0 |
| G1 | 1977 | 0 | 0 | 2 | 2 | 1 | 0 | 0 | 2 | 687 | 0 | 1485 | 2 | 0 | 0 | 1414 | 0 |
| G10 | 1889 | 257 | 0 | 0 | 0 | 697 | 0 | 0 | 0 | 391 | 0 | 1261 | 1 | 1 | 0 | 1486 | 0 |
| G11 | 2 | 0 | 0 | 1 | 2 | 0 | 1 | 0 | 19 | 2 | 0 | 2 | 2316 | 0 | 572 | 2610 | 444 |
| G12 | 2232 | 0 | 0 | 2 | 0 | 687 | 0 | 0 | 1 | 964 | 0 | 1629 | 861 | 2 | 0 | 2 | 0 |
| G2 | 3 | 0 | 0 | 1 | 0 | 0 | 0 | 0 | 20 | 2 | 0 | 1846 | 2 | 0 | 0 | 1624 | 0 |
| G3 | 1 | 1 | 0 | 2 | 1 | 1219 | 0 | 0 | 229 | 2 | 0 | 863 | 1382 | 1189 | 0 | 1466 | 0 |
| G4 | 2185 | 2 | 0 | 1 | 0 | 1008 | 1 | 0 | 1 | 2508 | 0 | 2056 | 2 | 240 | 0 | 1726 | 36 |
| G5 | 1839 | 3 | 0 | 2 | 0 | 0 | 0 | 0 | 3 | 906 | 0 | 1 | 2 | 1469 | 0 | 1538 | 0 |
| G6 | 2182 | 1 | 0 | 1 | 1 | 0 | 1 | 0 | 0 | 2262 | 0 | 1311 | 2 | 0 | 1 | 1340 | 48 |
| G7 | 2841 | 2 | 0 | 1 | 0 | 0 | 0 | 0 | 3 | 1108 | 0 | 2 | 3 | 0 | 0 | 2032 | 0 |
| G8 | 2773 | 0 | 0 | 2 | 0 | 0 | 0 | 0 | 1 | 2 | 0 | 1903 | 1 | 1 | 0 | 1886 | 2 |
| G9 | 4 | 2 | 0 | 0 | 2 | 2 | 0 | 0 | 3 | 3 | 2 | 1 | 1 | 0 | 0 | 0 | 0 |
| H1 | 2255 | 0 | 0 | 2 | 1 | 1 | 0 | 0 | 1 | 3 | 1642 | 1452 | 1822 | 0 | 442 | 2 | 0 |
| H10 | 3 | 0 | 0 | 2 | 0 | 786 | 917 | 98 | 3 | 0 | 0 | 2 | 1 | 0 | 0 | 1842 | 0 |
| H11 | 2585 | 1 | 0 | 1 | 2 | 1 | 1 | 0 | 0 | 181 | 0 | 1313 | 3 | 0 | 0 | 1804 | 0 |
| H12 | 3 | 0 | 0 | 1 | 0 | 837 | 0 | 0 | 0 | 0 | 0 | 1424 | 275 | 0 | 0 | 358 | 0 |
| H2 | 2043 | 1 | 0 | 2 | 0 | 0 | 1 | 0 | 0 | 1 | 0 | 1424 | 275 | 0 | 0 | 6 | 0 |

Figure 17T

| WELL | IL2 | IL10 | IL12A | IL13 | IL17A | IFNG | PRF1 | GZMB | TGFB | TNFA | BCL6 | TBET | GATA3 | RORC | FOXP3 | RUNX1 | RUNX3 |
|---|---|---|---|---|---|---|---|---|---|---|---|---|---|---|---|---|---|
| H3 | 1368 | 2 | 0 | 1 | 1 | 1 | 0 | 0 | 0 | 1319 | 0 | 3 | 4 | 0 | 0 | 6 | 0 |
| H4 | 14 | 1 | 0 | 1 | 0 | 1 | 0 | 0 | 30 | 2 | 0 | 9 | 3374 | 1 | 1 | 3854 | 0 |
| H5 | 2 | 0 | 0 | 1 | 1 | 0 | 0 | 0 | 33 | 2 | 0 | 1902 | 6 | 0 | 1 | 2116 | 0 |
| H6 | 1 | 0 | 0 | 2 | 0 | 1 | 0 | 0 | 1 | 2164 | 0 | 1786 | 2495 | 0 | 320 | 2594 | 0 |
| H7 | 2245 | 1 | 0 | 1 | 0 | 2 | 0 | 0 | 0 | 0 | 0 | 1429 | 1178 | 1 | 0 | 1732 | 0 |
| H8 | 1864 | 0 | 0 | 1 | 1 | 965 | 0 | 0 | 0 | 2020 | 0 | 176 | 385 | 0 | 0 | 1354 | 0 |
| H9 | 2106 | 0 | 0 | 2 | 1484 | 0 | 0 | 1 | 0 | 286 | 0 | 888 | 806 | 18 | 0 | 2 | 0 |
| A1 | 0 | 0 | 0 | 2 | 1016 | 1 | 0 | 0 | 0 | 90 | 0 | 924 | 0 | 920 | 0 | 0 | 0 |
| A10 | 1 | 2 | 0 | 1 | 0 | 0 | 0 | 0 | 0 | 1 | 0 | 0 | 1 | 1 | 0 | 2 | 0 |
| A11 | 14 | 1 | 0 | 0 | 41 | 0 | 0 | 0 | 0 | 2 | 0 | 0 | 1 | 1 | 0 | 4 | 0 |
| A12 | 0 | 2 | 0 | 2 | 2 | 0 | 0 | 0 | 0 | 1 | 2 | 0 | 0 | 0 | 0 | 0 | 0 |
| A2 | 1 | 1 | 0 | 0 | 185 | 1 | 0 | 0 | 0 | 17 | 0 | 145 | 0 | 40 | 0 | 116 | 0 |
| A3 | 887 | 0 | 0 | 1 | 734 | 250 | 0 | 0 | 0 | 931 | 0 | 0 | 4 | 186 | 0 | 74 | 8 |
| A4 | 5 | 0 | 0 | 3 | 0 | 1 | 0 | 0 | 0 | 1 | 0 | 1 | 0 | 4 | 0 | 0 | 0 |
| A5 | 2 | 0 | 0 | 0 | 0 | 0 | 0 | 0 | 0 | 1 | 0 | 0 | 0 | 0 | 0 | 0 | 0 |
| A6 | 317 | 0 | 0 | 766 | 466 | 0 | 0 | 0 | 0 | 298 | 2 | 3 | 0 | 0 | 0 | 48 | 0 |
| A7 | 445 | 2 | 0 | 0 | 502 | 0 | 0 | 0 | 0 | 452 | 0 | 0 | 0 | 0 | 0 | 2 | 0 |
| A8 | 3 | 0 | 0 | 0 | 3 | 0 | 0 | 0 | 0 | 0 | 2 | 2 | 0 | 1 | 0 | 2 | 0 |
| A9 | 1 | 0 | 0 | 1 | 2 | 0 | 0 | 0 | 0 | 2 | 0 | 0 | 0 | 1 | 0 | 0 | 0 |
| B1 | 2 | 2 | 0 | 3190 | 2260 | 0 | 0 | 0 | 0 | 1 | 0 | 3 | 1949 | 0 | 0 | 132 | 0 |
| B10 | 9 | 0 | 0 | 2 | 10 | 1 | 0 | 0 | 0 | 2 | 0 | 1 | 0 | 0 | 0 | 4 | 10 |
| B11 | 60 | 1 | 0 | 3 | 195 | 0 | 0 | 0 | 0 | 2 | 0 | 3 | 0 | 0 | 0 | 2 | 0 |
| B12 | 3 | 0 | 0 | 0 | 1 | 1 | 0 | 0 | 2 | 0 | 0 | 0 | 2 | 0 | 0 | 0 | 0 |
| B2 | 3 | 38 | 0 | 0 | 896 | 1 | 0 | 0 | 0 | 25 | 0 | 220 | 143 | 813 | 29 | 978 | 0 |
| B3 | 1546 | 0 | 0 | 2 | 1484 | 0 | 0 | 0 | 0 | 233 | 0 | 0 | 2 | 1 | 0 | 836 | 0 |

Figure 17U

| WELL | IL2 | IL10 | IL12A | IL13 | IL17A | IFNG | PRF1 | GZMB | TGFB | TNFA | BCL6 | TBET | GATA3 | RORC | FOXP3 | RUNX1 | RUNX3 |
|---|---|---|---|---|---|---|---|---|---|---|---|---|---|---|---|---|---|
| B4 | 725 | 0 | 0 | 6 | 721 | 0 | 0 | 0 | 0 | 326 | 0 | 139 | 1 | 0 | 0 | 2 | 0 |
| B5 | 499 | 0 | 0 | 0 | 565 | 0 | 0 | 0 | 0 | 322 | 0 | 271 | 1 | 0 | 0 | 210 | 0 |
| B6 | 1 | 0 | 0 | 2 | 684 | 1 | 0 | 0 | 0 | 347 | 0 | 163 | 1 | 12 | 0 | 576 | 0 |
| B7 | 62 | 0 | 0 | 1943 | 1143 | 0 | 0 | 0 | 0 | 3 | 0 | 1 | 13 | 0 | 0 | 0 | 0 |
| B8 | 2 | 0 | 0 | 0 | 670 | 0 | 0 | 0 | 0 | 2 | 0 | 12 | 11 | 1 | 0 | 356 | 0 |
| B9 | 1 | 1 | 0 | 2 | 188 | 0 | 0 | 0 | 0 | 1 | 0 | 68 | 1 | 0 | 0 | 10 | 0 |
| C1 | 2421 | 0 | 0 | 2 | 1981 | 1 | 0 | 0 | 0 | 53 | 698 | 771 | 93 | 69 | 3 | 1362 | 0 |
| C10 | 4 | 0 | 0 | 1 | 210 | 14 | 0 | 0 | 0 | 13 | 0 | 3 | 24 | 1 | 0 | 44 | 0 |
| C11 | 0 | 0 | 0 | 329 | 3 | 0 | 0 | 0 | 0 | 1 | 0 | 2 | 0 | 1 | 0 | 2 | 0 |
| C12 | 1 | 1 | 0 | 0 | 110 | 1 | 0 | 0 | 0 | 0 | 0 | 1 | 1 | 0 | 0 | 2 | 0 |
| C2 | 1019 | 0 | 0 | 3 | 922 | 250 | 0 | 0 | 0 | 2 | 2 | 609 | 39 | 0 | 0 | 8 | 0 |
| C3 | 964 | 0 | 0 | 2 | 944 | 0 | 0 | 0 | 0 | 678 | 0 | 3 | 2 | 3 | 0 | 6 | 0 |
| C4 | 728 | 0 | 0 | 3 | 700 | 0 | 0 | 0 | 0 | 12 | 2 | 47 | 233 | 420 | 0 | 0 | 0 |
| C5 | 668 | 0 | 0 | 1516 | 768 | 0 | 0 | 0 | 0 | 2 | 2 | 1 | 0 | 10 | 0 | 108 | 0 |
| C6 | 284 | 0 | 0 | 0 | 760 | 0 | 0 | 0 | 0 | 1 | 0 | 1 | 4 | 0 | 0 | 0 | 0 |
| C7 | 680 | 1 | 0 | 1 | 629 | 1 | 0 | 1 | 0 | 0 | 0 | 1 | 3 | 0 | 0 | 0 | 0 |
| C8 | 314 | 1 | 0 | 0 | 458 | 1 | 1 | 0 | 0 | 29 | 0 | 43 | 3 | 1 | 0 | 18 | 0 |
| C9 | 226 | 0 | 0 | 1 | 303 | 0 | 0 | 0 | 0 | 2 | 2 | 2 | 1 | 46 | 0 | 122 | 6 |
| D1 | 3241 | 0 | 0 | 4 | 2752 | 1215 | 0 | 0 | 0 | 252 | 0 | 117 | 100 | 1 | 1 | 120 | 0 |
| D10 | 2 | 0 | 0 | 1 | 512 | 2 | 0 | 0 | 0 | 1 | 26 | 3 | 2 | 0 | 0 | 40 | 2 |
| D11 | 188 | 2 | 0 | 4 | 503 | 0 | 0 | 0 | 0 | 17 | 0 | 3 | 2 | 2 | 0 | 8 | 0 |
| D12 | 222 | 1 | 0 | 1 | 293 | 1 | 349 | 0 | 0 | 95 | 462 | 1 | 3 | 0 | 0 | 1146 | 0 |
| D2 | 6 | 0 | 0 | 1 | 3 | 333 | 0 | 0 | 0 | 50 | 0 | 510 | 48 | 0 | 0 | 228 | 0 |
| D3 | 1629 | 0 | 0 | 2 | 1373 | 0 | 0 | 0 | 0 | 4 | 0 | 4 | 4 | 0 | 0 | 228 | 0 |
| D4 | 8 | 0 | 0 | 4 | 1726 | 0 | 0 | 0 | 0 | 694 | 0 | 2 | 1 | 301 | 0 | 1238 | 0 |

Figure 17V

| WELL | IL2 | IL10 | IL12A | IL13 | IL17A | IFNG | PRF1 | GZMB | TGFB | TNFA | BCL6 | TBET | GATA3 | RORC | FOXP3 | RUNX1 | RUNX3 |
|---|---|---|---|---|---|---|---|---|---|---|---|---|---|---|---|---|---|
| D5 | 1260 | 0 | 0 | 0 | 0 | 1 | 0 | 0 | 0 | 4 | 0 | 3 | 33 | 0 | 0 | 448 | 0 |
| D6 | 1199 | 0 | 0 | 2 | 1335 | 236 | 0 | 0 | 1 | 184 | 2 | 2 | 6 | 23 | 0 | 114 | 10 |
| D7 | 6 | 1 | 0 | 1 | 1205 | 2 | 0 | 0 | 0 | 0 | 0 | 1 | 1 | 0 | 134 | 990 | 0 |
| D8 | 671 | 1 | 0 | 3 | 890 | 83 | 1 | 0 | 0 | 11 | 0 | 4 | 1 | 0 | 0 | 10 | 0 |
| D9 | 5 | 1 | 0 | 1462 | 354 | 2 | 1 | 0 | 0 | 3 | 0 | 2 | 203 | 1 | 0 | 0 | 0 |
| E1 | 1731 | 0 | 0 | 1760 | 1449 | 1 | 0 | 0 | 0 | 2 | 0 | 3 | 77 | 3 | 0 | 140 | 0 |
| E10 | 3 | 1 | 0 | 925 | 561 | 1 | 0 | 0 | 0 | 0 | 0 | 3 | 2 | 0 | 0 | 0 | 0 |
| E11 | 308 | 0 | 0 | 1 | 363 | 30 | 0 | 0 | 0 | 2 | 0 | 1 | 1 | 1 | 0 | 124 | 0 |
| E12 | 262 | 0 | 0 | 7 | 321 | 0 | 0 | 0 | 0 | 2 | 0 | 0 | 0 | 0 | 0 | 2 | 0 |
| E2 | 1066 | 0 | 0 | 528 | 0 | 307 | 0 | 0 | 0 | 0 | 0 | 587 | 861 | 0 | 0 | 0 | 0 |
| E3 | 3 | 0 | 0 | 5 | 961 | 0 | 0 | 0 | 0 | 2 | 0 | 2 | 309 | 11 | 0 | 2 | 0 |
| E4 | 996 | 0 | 0 | 3 | 947 | 2 | 0 | 0 | 0 | 516 | 306 | 14 | 49 | 0 | 0 | 438 | 0 |
| E5 | 826 | 0 | 0 | 1 | 0 | 283 | 0 | 0 | 0 | 839 | 0 | 1 | 0 | 0 | 0 | 446 | 0 |
| E6 | 3 | 0 | 0 | 1 | 614 | 0 | 0 | 0 | 0 | 3 | 0 | 1 | 2 | 14 | 0 | 610 | 0 |
| E7 | 681 | 0 | 0 | 662 | 595 | 2 | 0 | 0 | 0 | 2 | 0 | 0 | 2 | 0 | 0 | 62 | 0 |
| E8 | 433 | 0 | 0 | 1416 | 775 | 0 | 0 | 0 | 0 | 3 | 0 | 3 | 1 | 0 | 0 | 2 | 0 |
| E9 | 533 | 0 | 0 | 2 | 582 | 2 | 0 | 0 | 0 | 67 | 0 | 15 | 1373 | 0 | 0 | 70 | 0 |
| F1 | 1491 | 0 | 0 | 1889 | 0 | 0 | 0 | 0 | 0 | 1 | 0 | 2 | 1 | 0 | 0 | 308 | 0 |
| F10 | 517 | 0 | 0 | 1 | 0 | 187 | 0 | 0 | 0 | 0 | 0 | 1 | 189 | 0 | 0 | 470 | 0 |
| F11 | 328 | 0 | 0 | 764 | 0 | 0 | 0 | 0 | 0 | 4 | 0 | 1 | 4 | 0 | 0 | 1 | 0 |
| F12 | 376 | 0 | 0 | 3 | 0 | 1 | 0 | 0 | 0 | 470 | 2 | 2 | 284 | 0 | 0 | 334 | 0 |
| F2 | 991 | 0 | 0 | 1094 | 0 | 0 | 0 | 0 | 0 | 309 | 0 | 2 | 573 | 0 | 0 | 2 | 0 |
| F3 | 1303 | 0 | 0 | 1568 | 0 | 1 | 0 | 1 | 0 | 19 | 0 | 76 | 1276 | 0 | 0 | 6 | 0 |
| F4 | 1348 | 0 | 0 | 1964 | 0 | 1 | 0 | 0 | 0 | 5 | 0 | 203 | 1441 | 0 | 0 | 18 | 0 |
| F5 | 1366 | 0 | 0 | 2 | 0 | 1 | 0 | 0 | 0 | 1 | 0 | 298 | | 0 | 0 | 2 | 0 |

Figure 17W

| WELL | IL2 | IL10 | IL12A | IL13 | IL17A | IFNG | PRF1 | GZMB | TGFB | TNFA | BCL6 | TBET | GATA3 | RORC | FOXP3 | RUNX1 | RUNX3 |
|---|---|---|---|---|---|---|---|---|---|---|---|---|---|---|---|---|---|
| F6 | 775 | 0 | 0 | 937 | 0 | 1 | 0 | 0 | 0 | 295 | 0 | 2 | 209 | 0 | 0 | 70 | 0 |
| F7 | 895 | 0 | 0 | 0 | 1 | 0 | 0 | 0 | 0 | 823 | 0 | 1 | 0 | 0 | 0 | 810 | 0 |
| F8 | 628 | 1 | 0 | 7 | 1 | 228 | 0 | 0 | 0 | 580 | 0 | 361 | 3 | 0 | 0 | 2 | 0 |
| F9 | 576 | 0 | 0 | 2 | 0 | 0 | 0 | 0 | 0 | 513 | 0 | 472 | 1 | 0 | 0 | 472 | 0 |
| G1 | 1504 | 0 | 0 | 4 | 1 | 676 | 0 | 0 | 0 | 768 | 0 | 682 | 1 | 0 | 0 | 674 | 0 |
| G10 | 440 | 26 | 0 | 2 | 0 | 127 | 0 | 0 | 0 | 96 | 0 | 173 | 1 | 0 | 0 | 340 | 2 |
| G11 | 372 | 0 | 0 | 1 | 0 | 79 | 0 | 0 | 0 | 95 | 0 | 43 | 0 | 1 | 1 | 268 | 0 |
| G12 | 5 | 1 | 0 | 0 | 0 | 107 | 0 | 0 | 0 | 1 | 0 | 267 | 0 | 0 | 0 | 2 | 354 |
| G2 | 4 | 2 | 0 | 1 | 0 | 389 | 0 | 8 | 0 | 1147 | 1008 | 657 | 373 | 0 | 0 | 0 | 0 |
| G3 | 213 | 4 | 0 | 3 | 0 | 333 | 500 | 215 | 68 | 247 | 0 | 674 | 0 | 0 | 0 | 674 | 0 |
| G4 | 1406 | 0 | 0 | 1 | 0 | 1 | 1 | 0 | 0 | 5 | 0 | 1061 | 655 | 0 | 0 | 714 | 0 |
| G5 | 901 | 1 | 0 | 2 | 0 | 1 | 0 | 0 | 0 | 878 | 0 | 668 | 242 | 0 | 0 | 2 | 0 |
| G6 | 803 | 0 | 0 | 0 | 0 | 2 | 0 | 0 | 0 | 256 | 0 | 598 | 0 | 71 | 0 | 714 | 0 |
| G7 | 741 | 2 | 0 | 2 | 1 | 294 | 0 | 0 | 1 | 4 | 0 | 612 | 369 | 0 | 0 | 522 | 0 |
| G8 | 757 | 0 | 0 | 0 | 0 | 0 | 0 | 0 | 0 | 2 | 0 | 652 | 3 | 0 | 0 | 332 | 2 |
| G9 | 559 | 1 | 0 | 2 | 1 | 1 | 0 | 0 | 0 | 1 | 0 | 3 | 340 | 1 | 0 | 400 | 0 |
| H1 | 1816 | 0 | 0 | 0 | 4 | 2 | 351 | 0 | 0 | 141 | 0 | 0 | 0 | 0 | 0 | 2 | 2 |
| H10 | 581 | 1 | 0 | 1674 | 0 | 0 | 0 | 0 | 0 | 2 | 6 | 429 | 2 | 0 | 0 | 0 | 0 |
| H11 | 194 | 0 | 0 | 0 | 0 | 33 | 0 | 28 | 0 | 2 | 0 | 2 | 470 | 1 | 0 | 0 | 0 |
| H12 | 5 | 1 | 0 | 591 | 0 | 0 | 1 | 0 | 0 | 1 | 0 | 1 | 3 | 0 | 0 | 504 | 0 |
| H2 | 1004 | 0 | 0 | 0 | 0 | 0 | 0 | 0 | 0 | 2 | 0 | 3 | 2 | 2 | 0 | 2 | 0 |
| H3 | 959 | 1 | 0 | 3 | 0 | 0 | 0 | 0 | 0 | 256 | 0 | 733 | 702 | 0 | 0 | 2 | 0 |
| H4 | 1633 | 0 | 0 | 3 | 0 | 3 | 0 | 0 | 0 | 129 | 0 | 132 | 4 | 0 | 0 | 2 | 0 |
| H5 | 891 | 0 | 0 | 2 | 1 | 370 | 0 | 0 | 0 | 787 | 0 | 4 | 1 | 0 | 0 | 590 | 0 |
| H6 | 928 | 0 | 0 | 3 | 0 | 0 | 0 | 0 | 0 | 951 | 994 | 3 | 2 | 0 | 0 | 0 | 0 |

Figure 17X

| WELL | IL2 | IL10 | IL12A | IL13 | IL17A | IFNG | PRF1 | GZMB | TGFB | TNFA | BCL6 | TBET | GATA3 | RORC | FOXP3 | RUNX1 | RUNX3 |
|---|---|---|---|---|---|---|---|---|---|---|---|---|---|---|---|---|---|
| H7 | 831 | 0 | 0 | 978 | 0 | 0 | 0 | 0 | 0 | 0 | 0 | 1 | 452 | 0 | 0 | 142 | 0 |
| H8 | 728 | 0 | 0 | 5 | 0 | 2 | 0 | 0 | 0 | 1 | 0 | 404 | 447 | 1 | 0 | 0 | 0 |
| H9 | 592 | 0 | 0 | 3 | 0 | 1 | 0 | 0 | 4 | 2 | 0 | 1 | 3 | 0 | 0 | 0 | 0 |
| A1 | 0 | 0 | 0 | 0 | 0 | 0 | 0 | 0 | 3 | 0 | 0 | 0 | 468 | 0 | 2454 | 2598 | 0 |
| A10 | 0 | 0 | 0 | 0 | 0 | 0 | 0 | 0 | 0 | 0 | 1008 | 0 | 1 | 0 | 1229 | 2 | 0 |
| A11 | 0 | 0 | 0 | 0 | 0 | 0 | 26 | 0 | 516 | 0 | 0 | 0 | 0 | 0 | 1472 | 2400 | 0 |
| A12 | 0 | 0 | 0 | 0 | 0 | 0 | 0 | 0 | 0 | 0 | 0 | 0 | 0 | 0 | 872 | 1445 | 0 |
| A2 | 0 | 0 | 0 | 0 | 0 | 0 | 0 | 0 | 538 | 0 | 0 | 0 | 1326 | 0 | 3690 | 0 | 0 |
| A3 | 0 | 0 | 0 | 0 | 0 | 0 | 0 | 0 | 0 | 0 | 0 | 0 | 1970 | 0 | 5435 | 2341 | 0 |
| A4 | 0 | 0 | 0 | 0 | 0 | 0 | 0 | 0 | 0 | 0 | 0 | 0 | 1306 | 0 | 806 | 335 | 0 |
| A5 | 0 | 0 | 0 | 0 | 0 | 0 | 0 | 0 | 1 | 0 | 0 | 777 | 535 | 0 | 2636 | 826 | 0 |
| A6 | 0 | 0 | 0 | 0 | 0 | 0 | 36 | 0 | 1 | 0 | 0 | 0 | 1 | 0 | 3152 | 2908 | 0 |
| A7 | 0 | 0 | 0 | 0 | 0 | 0 | 0 | 0 | 0 | 0 | 0 | 0 | 1273 | 0 | 2703 | 0 | 0 |
| A8 | 0 | 0 | 0 | 0 | 0 | 0 | 0 | 0 | 4 | 0 | 0 | 0 | 1521 | 0 | 3646 | 927 | 0 |
| A9 | 0 | 0 | 0 | 0 | 0 | 0 | 0 | 0 | 0 | 1137 | 0 | 0 | 1318 | 5264 | 3441 | 916 | 0 |
| B1 | 0 | 0 | 0 | 0 | 0 | 0 | 1128 | 0 | 159 | 0 | 4792 | 0 | 0 | 0 | 4558 | 1 | 0 |
| B10 | 0 | 0 | 0 | 0 | 0 | 0 | 0 | 0 | 0 | 0 | 0 | 0 | 0 | 0 | 5330 | 1 | 0 |
| B11 | 0 | 0 | 0 | 0 | 0 | 0 | 1124 | 0 | 1881 | 2283 | 0 | 0 | 2119 | 0 | 5086 | 3985 | 0 |
| B12 | 0 | 0 | 0 | 0 | 0 | 0 | 1745 | 0 | 280 | 0 | 0 | 0 | 1255 | 0 | 4955 | 2825 | 0 |
| B2 | 0 | 0 | 0 | 0 | 0 | 0 | 0 | 0 | 28 | 0 | 0 | 0 | 3861 | 3 | 2343 | 1 | 0 |
| B3 | 0 | 0 | 0 | 0 | 0 | 0 | 0 | 0 | 0 | 0 | 0 | 1 | 0 | 0 | 5735 | 0 | 0 |
| B4 | 0 | 0 | 0 | 0 | 0 | 0 | 0 | 0 | 44 | 0 | 0 | 0 | 0 | 0 | 6551 | 0 | 0 |
| B5 | 0 | 0 | 0 | 0 | 0 | 0 | 0 | 0 | 0 | 0 | 1895 | 0 | 1525 | 0 | 5878 | 4324 | 0 |
| B6 | 0 | 0 | 1774 | 0 | 0 | 0 | 0 | 0 | 0 | 0 | 0 | 0 | 0 | 4283 | 1683 | 2598 | 0 |
| B7 | 0 | 0 | 0 | 0 | 0 | 0 | 0 | 0 | 0 | 2118 | 0 | 0 | 0 | 0 | 5342 | 1 | 0 |

Figure 17Y

| WELL | IL2 | IL10 | IL12A | IL13 | IL17A | IFNG | PRF1 | GZMB | TGFB | TNFA | BCL6 | TBET | GATA3 | RORC | FOXP3 | RUNX1 | RUNX3 |
|---|---|---|---|---|---|---|---|---|---|---|---|---|---|---|---|---|---|
| B8 | 0 | 0 | 0 | 0 | 0 | 0 | 0 | 0 | 0 | 0 | 0 | 0 | 0 | 5132 | 4835 | 2806 | 0 |
| B9 | 0 | 0 | 1 | 0 | 0 | 0 | 65 | 0 | 0 | 1 | 0 | 0 | 1695 | 0 | 6444 | 1605 | 0 |
| C1 | 0 | 0 | 0 | 0 | 0 | 0 | 0 | 0 | 417 | 0 | 0 | 0 | 2075 | 1 | 6780 | 4377 | 0 |
| C10 | 0 | 0 | 0 | 0 | 0 | 0 | 0 | 0 | 0 | 0 | 1 | 0 | 3 | 0 | 8859 | 1 | 0 |
| C11 | 0 | 0 | 0 | 0 | 0 | 0 | 0 | 0 | 2273 | 113 | 0 | 2 | 0 | 0 | 2109 | 859 | 0 |
| C12 | | 0 | 0 | 0 | 0 | 0 | 0 | 0 | 2311 | 0 | 2 | 0 | 0 | 0 | 4 | 0 | 0 |
| C2 | 0 | 0 | 0 | 0 | 0 | 0 | 0 | 0 | 32 | 0 | 1 | 0 | 2 | 0 | 3266 | 4309 | 0 |
| C3 | 0 | 0 | 0 | 0 | 0 | 0 | 0 | 0 | 0 | 454 | 0 | 0 | 0 | 0 | 6960 | 4250 | 0 |
| C4 | 0 | 0 | 0 | 0 | 0 | 0 | 0 | 0 | 0 | 0 | 0 | 1113 | 1706 | 0 | 4782 | 1362 | 0 |
| C5 | 0 | 0 | 0 | 0 | 0 | 0 | 585 | 0 | 24 | 0 | 0 | 0 | 3708 | 0 | 8323 | 0 | 0 |
| C6 | 0 | 0 | 0 | 0 | 0 | 0 | 0 | 0 | 0 | 0 | 0 | 2950 | 1841 | 1 | 1795 | 3155 | 0 |
| C7 | 0 | 0 | 0 | 0 | 0 | 0 | 0 | 0 | 2 | 0 | 0 | 0 | 3667 | 0 | 5737 | 3906 | 0 |
| C8 | 0 | 0 | 0 | 0 | 0 | 0 | 0 | 0 | 1480 | 0 | 0 | 1 | 1 | 0 | 7351 | 5387 | 0 |
| C9 | 0 | 0 | 0 | 0 | 0 | 0 | 1368 | 0 | 2472 | 0 | 0 | 1 | 4157 | 0 | 2 | 2 | 0 |
| D1 | 0 | 0 | 0 | 0 | 0 | 0 | 0 | 0 | 24 | 0 | 0 | 0 | 4249 | 0 | 6103 | 4054 | 0 |
| D10 | 0 | 0 | 0 | 0 | 0 | 0 | 0 | 0 | 175 | 0 | 1 | 2961 | 1 | 0 | 8163 | 4369 | 0 |
| D11 | 0 | 0 | 0 | 0 | 0 | 0 | 0 | 0 | 0 | 0 | 8132 | 0 | 0 | 0 | 5541 | 5661 | 0 |
| D12 | 0 | 0 | 0 | 0 | 0 | 0 | 0 | 0 | 5183 | 0 | 7303 | 0 | 3470 | 0 | 8588 | 4849 | 0 |
| D2 | 0 | 0 | 0 | 0 | 0 | 0 | 0 | 0 | 34 | 0 | 5660 | 0 | 1 | 0 | 2 | 0 | 0 |
| D3 | 0 | 0 | 0 | 0 | 0 | 0 | 0 | 0 | 0 | 1349 | 0 | 0 | 0 | 0 | 8728 | 2 | 0 |
| D4 | 0 | 0 | 0 | 0 | 0 | 0 | 2 | 0 | 20 | 0 | 0 | 3851 | 3425 | 0 | 2465 | 4773 | 0 |
| D5 | 0 | 0 | 0 | 0 | 0 | 0 | 9455 | 0 | 0 | 0 | 0 | 0 | 0 | 0 | 5712 | 2198 | 0 |
| D6 | 0 | 0 | 0 | 0 | 0 | 0 | 0 | 0 | 1 | 0 | 0 | 0 | 1 | 0 | 0 | 2 | 0 |
| D7 | 0 | 0 | 0 | 0 | 0 | 0 | 0 | 0 | 0 | 0 | 0 | 0 | 0 | 0 | 8820 | 8028 | 0 |
| D8 | 0 | 0 | 0 | 0 | 0 | 0 | 0 | 0 | 1514 | 0 | 0 | 0 | 5848 | 0 | 1 | 9066 | 0 |

Figure 17Z

| WELL | IL2 | IL10 | IL12A | IL13 | IL17A | IFNG | PRF1 | GZMB | TGFB | TNFA | BCL6 | TBET | GATA3 | RORC | FOXP3 | RUNX1 | RUNX3 |
|---|---|---|---|---|---|---|---|---|---|---|---|---|---|---|---|---|---|
| D9 | 0 | 0 | 0 | 0 | 0 | 0 | 0 | 0 | 22 | 0 | 0 | 0 | 0 | 0 | 7830 | 3795 | 0 |
| E1 | 0 | 0 | 0 | 0 | 0 | 0 | 0 | 0 | 1239 | 2987 | 1 | 0 | 0 | 0 | 6951 | 0 | 0 |
| E10 | 0 | 0 | 0 | 0 | 0 | 0 | 0 | 0 | 375 | 0 | 0 | 0 | 1 | 0 | 5277 | 5036 | 0 |
| E11 | 0 | 0 | 0 | 0 | 0 | 0 | 0 | 0 | 18 | 0 | 0 | 0 | 5045 | 0 | 8598 | 0 | 0 |
| E12 | 0 | 0 | 0 | 0 | 0 | 0 | 0 | 0 | 0 | 0 | 0 | 0 | 4252 | 0 | 9681 | 0 | 0 |
| E2 | 0 | 0 | 0 | 0 | 0 | 0 | 0 | 0 | 1 | 0 | 0 | 0 | 0 | 0 | 5473 | 5379 | 0 |
| E3 | 0 | 0 | 0 | 0 | 0 | 0 | 0 | 0 | 276 | 0 | 0 | 0 | 4633 | 0 | 9776 | 0 | 0 |
| E4 | 0 | 0 | 0 | 0 | 0 | 0 | 0 | 0 | 164 | 0 | 0 | 0 | 2 | 0 | 10252 | 0 | 0 |
| E5 | 0 | 0 | 0 | 0 | 0 | 0 | 0 | 0 | 1681 | 1 | 0 | 0 | 0 | 0 | 5701 | 1690 | 0 |
| E6 | 0 | 0 | 0 | 0 | 0 | 0 | 0 | 0 | 998 | 0 | 0 | 0 | 3067 | 0 | 5071 | 3832 | 0 |
| E7 | 0 | 0 | 0 | 0 | 0 | 0 | 0 | 0 | 3448 | 1 | 0 | 3327 | 0 | 0 | 1 | 0 | 0 |
| E8 | 0 | 0 | 0 | 0 | 0 | 0 | 0 | 0 | 0 | 0 | 8842 | 1 | 2256 | 0 | 3218 | 4112 | 0 |
| E9 | 0 | 0 | 0 | 0 | 0 | 0 | 0 | 0 | 1 | 0 | 4 | 0 | 0 | 0 | 6692 | 3559 | 0 |
| F1 | 0 | 0 | 0 | 0 | 0 | 0 | 0 | 0 | 0 | 0 | 6853 | 0 | 1 | 0 | 0 | 1 | 0 |
| F10 | 0 | 0 | 0 | 0 | 0 | 0 | 0 | 0 | 2235 | 0 | 6013 | 0 | 2671 | 0 | 1 | 6925 | 0 |
| F11 | 0 | 0 | 0 | 0 | 0 | 0 | 0 | 0 | 2750 | 0 | 5 | 0 | 0 | 0 | 2 | 1 | 0 |
| F12 | 0 | 0 | 0 | 0 | 0 | 0 | 0 | 0 | 1 | 0 | 2 | 0 | 0 | 0 | 0 | 5237 | 0 |
| F2 | 0 | 0 | 0 | 0 | 0 | 0 | 0 | 0 | 5538 | 0 | 1 | 0 | 1 | 0 | 2 | 289 | 0 |
| F3 | 0 | 0 | 0 | 0 | 0 | 0 | 0 | 0 | 7369 | 0 | 8761 | 0 | 1 | 0 | 1 | 1 | 0 |
| F4 | 0 | 0 | 0 | 0 | 0 | 0 | 0 | 0 | 1926 | 0 | 2 | 0 | 1 | 0 | 0 | 7329 | 0 |
| F5 | 0 | 0 | 0 | 0 | 0 | 0 | 0 | 0 | 1 | 0 | 8856 | 0 | 1 | 0 | 0 | 1 | 0 |
| F6 | 0 | 0 | 0 | 0 | 0 | 0 | 0 | 0 | 2206 | 0 | 0 | 0 | 0 | 0 | 1 | 7044 | 0 |
| F7 | 0 | 0 | 0 | 0 | 0 | 0 | 1542 | 0 | 181 | 0 | 0 | 0 | 0 | 0 | 0 | 0 | 0 |
| F8 | 0 | 0 | 0 | 0 | 0 | 0 | 0 | 0 | 1536 | 0 | 0 | 0 | 0 | 0 | 1 | 6667 | 0 |
| F9 | 0 | 0 | 0 | 0 | 0 | 0 | 0 | 0 | 2970 | 0 | 6 | 0 | 3884 | 0 | 2 | 5792 | 0 |

Figure 17AA

| WELL | IL2 | IL10 | IL12A | IL13 | IL17A | IFNG | PRF1 | GZMB | TGFB | TNFA | BCL6 | TBET | GATA3 | RORC | FOXP3 | RUNX1 | RUNX3 |
|---|---|---|---|---|---|---|---|---|---|---|---|---|---|---|---|---|---|
| G1 | 0 | 0 | 0 | 0 | 0 | 0 | 0 | 0 | 2657 | 0 | 5067 | 0 | 0 | 0 | 0 | 1243 | 0 |
| G10 | 0 | 0 | 0 | 0 | 0 | 0 | 0 | 0 | 914 | 0 | 3 | 0 | 1 | 0 | 0 | 6059 | 0 |
| G11 | 0 | 0 | 0 | 0 | 0 | 0 | 0 | 0 | 191 | 0 | 1 | 0 | 0 | 0 | 0 | 6984 | 0 |
| G12 | 0 | 0 | 0 | 0 | 0 | 0 | 0 | 0 | 286 | 0 | 0 | 0 | 0 | 0 | 0 | 6292 | 0 |
| G2 | 0 | 0 | 0 | 0 | 0 | 0 | 0 | 0 | 2161 | 0 | 3 | 4932 | 0 | 0 | 0 | 0 | 0 |
| G3 | 0 | 0 | 0 | 0 | 0 | 0 | 0 | 0 | 2 | 0 | 2 | 0 | 1 | 0 | 0 | 0 | 0 |
| G4 | 0 | 0 | 0 | 0 | 0 | 0 | 0 | 0 | 0 | 0 | 5296 | 0 | 2588 | 0 | 0 | 3876 | 0 |
| G5 | 0 | 0 | 0 | 0 | 0 | 0 | 0 | 0 | 1312 | 0 | 6180 | 0 | 1 | 0 | 0 | 0 | 0 |
| G6 | 0 | 0 | 0 | 0 | 0 | 3655 | 1547 | 0 | 1308 | 0 | 1 | 0 | 0 | 0 | 0 | 0 | 0 |
| G7 | 0 | 0 | 0 | 0 | 0 | 0 | 0 | 0 | 3 | 0 | 0 | 0 | 4562 | 0 | 0 | 8383 | 0 |
| G8 | 0 | 0 | 0 | 0 | 0 | 0 | 0 | 0 | 0 | 0 | 6316 | 0 | 0 | 0 | 0 | 5933 | 0 |
| G9 | 0 | 0 | 0 | 0 | 0 | 0 | 0 | 0 | 3163 | 0 | 0 | 0 | 0 | 0 | 0 | 4866 | 0 |
| H1 | 0 | 0 | 0 | 0 | 0 | 0 | 0 | 0 | 1037 | 0 | 4661 | 0 | 0 | 0 | 0 | 3527 | 0 |
| H10 | 0 | 0 | 0 | 0 | 0 | 0 | 0 | 0 | 2745 | 0 | 3 | 0 | 3376 | 0 | 0 | 6411 | 0 |
| H11 | 0 | 0 | 0 | 0 | 0 | 0 | 0 | 0 | 4738 | 0 | 0 | 0 | 0 | 0 | 0 | 0 | 0 |
| H12 | 0 | 0 | 0 | 0 | 0 | 0 | 0 | 0 | 0 | 0 | 1 | 0 | 0 | 0 | 0 | 1 | 0 |
| H2 | 0 | 0 | 0 | 0 | 0 | 0 | 0 | 0 | 1715 | 0 | 6090 | 0 | 2714 | 0 | 0 | 2 | 0 |
| H3 | 0 | 0 | 0 | 0 | 0 | 0 | 0 | 0 | 1430 | 0 | 6838 | 0 | 4345 | 0 | 0 | 0 | 0 |
| H4 | 0 | 0 | 0 | 0 | 0 | 0 | 0 | 0 | 19 | 0 | 0 | 0 | 2980 | 0 | 0 | 6942 | 0 |
| H5 | 0 | 0 | 0 | 0 | 0 | 0 | 0 | 0 | 2101 | 0 | 6281 | 0 | 0 | 0 | 0 | 0 | 0 |
| H6 | 0 | 0 | 0 | 0 | 0 | 0 | 0 | 0 | 189 | 0 | 4720 | 0 | 0 | 0 | 0 | 4880 | 0 |
| H7 | 0 | 0 | 0 | 0 | 0 | 0 | 0 | 0 | 0 | 0 | 5619 | 0 | 0 | 0 | 0 | 4437 | 0 |
| H8 | 0 | 0 | 0 | 0 | 0 | 0 | 0 | 0 | 29 | 0 | 8406 | 0 | 0 | 0 | 0 | 1 | 0 |
| H9 | 0 | 0 | 0 | 0 | 0 | 0 | 0 | 0 | 24 | 0 | 4647 | 0 | 0 | 0 | 0 | 3489 | 0 |

Figure 18
Table 7.

| | # positive /60 positive | Sensitivity | # positive /36 negative | Specificity | Prevalence (% positive CD45RO/total CD45RO) | Positive Predictive Value | Negative Predictive Value |
|---|---|---|---|---|---|---|---|
| IFNγ | 55 | 91.67% | 0 | 100.00% | 6.25% | 100.00% | 99.40% |
| TNFα | 46 | 76.67% | 2 | 94.44% | 35.48% | 88.30% | 88.00% |
| IL2 | 57 | 95.00% | 1 | 97.22% | 65.70% | 98.50% | 91.00% |
| IL10 | 50 | 83.33% | 1 | 97.22% | 2.46% | 43.10% | 99.60% |
| IL13 | 56 | 93.33% | 0 | 100.00% | 26.03% | 100.00% | 97.70% |
| IL17 | 49 | 81.67% | 0 | 100.00% | 4.26% | 100.00% | 99.20% |
| FOXP3 | 54 | 90.00% | 0 | 100.00% | 3.80% | 100.00% | 99.62% |

Figure 19A
Table 8.

| TCR # | TCR BETA ||||| TCR ALPHA (FIRST) ||||
|---|---|---|---|---|---|---|---|---|---|
| | TRBV | TRBJ | CDR3B | SEQ ID NO: | | TRAV | TRAJ | CDR3A | SEQ ID NO: |
| 1 | TRBV13 | TRBJ2-2 | CASSLASMGVGELFF | 265 | | TRAV38/DV8 | TRAJ32 | CAYRPNYGGATNKLIF | 269 |
| 2 | TRBV6-1 | TRBJ2-1 | CASPGGWTGGGNEQFF | 563 | | TRAV1-2 | TRAJ42 | CAVDGEGGSQGNLIF | 860 |
| 3 | TRBV6-5 | TRBJ2-7 | CASNTLGAGGREQYF | 564 | | TRAV26-1 | TRAJ43 | CIVRVKGQYNNNDMRF | 861 |
| 4 | TRBV6-1 | TRBJ2-1 | CASSEAGGQDYGNEQFF | 565 | | TRAV1-1 | TRAJ11 | CAVNGYSTLTF | 862 |
| 5 | TRBV3-1 | TRBJ2-7 | CASSQGLAAPYEQYF | 566 | | TRAV23/DV6 | TRAJ10 | CAATTGGGNKLTF | 863 |
| 6 | TRBV30 | TRBJ1-4 | CAWSDGVVGEKLFF | 567 | | TRAV19 | TRAJ10 | CALKGGTGGGNKLTF | 864 |
| 7 | TRBV5-1 | TRBJ2-6 | CASRENSGANVLTF | 568 | | TRAV23/DV6 | TRAJ57 | CAAKLGGSEKLVF | 865 |
| 8 | TRBV20-1 | TRBJ2-3 | CSAGTYRTDTQYF | 569 | | TRAV6 | TRAJ45 | CAFSMYSGGGADGLTF | 866 |
| 9 | TRBV28 | TRBJ2-1 | CASSLGGGSYNEQFF | 570 | | | | | |
| 10 | TRBV13 | TRBJ2-2 | CASSSASGGVGELFF | 267 | | TRAV38/DV8 | TRAJ32 | CAYRPNYGGATNKLIF | 269 |
| 11 | TRBV4-2 | TRBJ2-1 | CASSQDGAGGREQFF | 571 | | TRAV19 | TRAJ23 | CALSYNQGGKLIF | 867 |
| 12 | TRBV30 | TRBJ2-5 | CAWSPGGETQYF | 572 | | TRAV41 | TRAJ35 | CAANFGSFGNVLHC | 868 |
| 13 | TRBV5-1 | TRBJ2-5 | CASSFSPGLETQYF | 573 | | TRAV38/DV8 | TRAJ37 | CAYVGSSNTGKLIF | 869 |
| 14 | TRBV12-3 | TRBJ1-6 | CASSLVSSPLHF | 574 | | TRAV23/DV6 | TRAJ26 | CAASKGNYGQNFVF | 870 |
| 15 | TRBV14 | TRBJ2-5 | CASSSGTGGLETQYF | 575 | | TRAV26-1 | TRAJ7 | CIVRVEGNNRLAF | 871 |
| 16 | TRBV15 | TRBJ1-2 | CATSRDGTDYGYTF | 576 | | TRAV9-1 | TRAJ10 | CALSPGGGGNKLTF | 872 |

Figure 19B

| TCR # | TCR BETA ||| SEQ ID NO: | TCR ALPHA (FIRST) ||| SEQ ID NO: |
| --- | --- | --- | --- | --- | --- | --- | --- | --- |
| | TRBV | TRBJ | CDR3B | | TRAV | TRAJ | CDR3A | |
| 17 | TRBV15 | TRBJ2-7 | CATSREWGEAYEQYF | 577 | TRAV21 | TRAJ31 | CAVSYNARLMF | 873 |
| 18 | TRBV20-1 | TRBJ1-5 | CSAATLDGSNQPQHF | 578 | TRAV12-3 | TRAJ9 | CAMSTNTGGFKTIF | 874 |
| 19 | TRBV28 | TRBJ2-5 | CASSATGLAGGGETQYF | 579 | TRAV12-2 | TRAJ6 | CAVRRGGGSYIPTF | 875 |
| 20 | TRBV6-1 | TRBJ2-1 | CASSEPGEQFF | 580 | TRAV26-1 | TRAJ54 | CIVRSYNQGAQKLVF | 876 |
| 21 | TRBV5-1 | TRBJ2-3 | CASSLAPLQGTFRADTQYF | 581 | TRAV19 | TRAJ29 | CALTPNSGNTPLVF | 877 |
| 22 | TRBV9 | TRBJ1-4 | CASSLSGEKLFF | 582 | TRAV36/DV7 | TRAJ13 | CAVQAPGGYQKVTF | 878 |
| 23 | TRBV18 | TRBJ1-6 | CASSPTGGTTYNSPLHF | 583 | TRAV35 | TRAJ15 | CAGQLLIGQAGTALIF | 879 |
| 24 | TRBV14 | TRBJ1-1 | CASSQDEVGGRRAFF | 584 | TRAV26-1 | TRAJ32 | CIVRVFGGATNKLIF | 880 |
| 25 | TRBV4-2 | TRBJ1-2 | CASSQDWGDYGYTF | 585 | TRAV27 | TRAJ47 | CAAEREGNKLVF | 881 |
| 26 | TRBV4-2 | TRBJ2-1 | CASSQDYQGLDGEQFF | 586 | TRAV17 | TRAJ53 | CASGGGSNYKLTF | 882 |
| 27 | TRBV6-5 | TRBJ2-6 | CASSSPGVGANVLTF | 587 | TRAV36/DV7 | TRAJ53 | CAVQAPGGSNYKLTF | 883 |
| 28 | TRBV6-2 | TRBJ2-3 | CASSWIAGVAGGAVADTQYF | 588 | TRAV9-1 | TRAJ20 | CALPLNDYKLSF | 884 |
| 29 | TRBV10-3 | TRBJ2-2 | CAISAVGDRGTGELFF | 589 | TRAV38/DV8 | TRAJ41 | CAYRSPNSGYALNF | 885 |
| 30 | TRBV28 | TRBJ1-4 | CASIPPRAGPIANEKLFF | 590 | TRAV8-4 | TRAJ31 | CVVSDHARLMF | 886 |
| 31 | TRBV10-1 | TRBJ1-5 | CASRDGVQPQHF | 591 | TRAV26-1 | TRAJ8 | CIVRVVSFQKLVF | 887 |
| 32 | TRBV12-3 | TRBJ2-5 | CASRKGTEGTQYF | 592 | TRAV12-1 | TRAJ43 | CVVNEGNDMRF | 888 |
| 33 | TRBV12-3 | TRBJ2-1 | CASRTERESINEQFF | 593 | TRAV23/DV6 | TRAJ24 | CAATDSWGKLQF | 889 |
| 34 | TRBV25-1 | TRBJ2-1 | CASSEGGDHEQFF | 594 | TRAV39 | TRAJ49 | CAVVNTGNQFYF | 890 |

Figure 19C

| TCR # | TCR BETA | | | | TCR ALPHA (FIRST) | | | |
|---|---|---|---|---|---|---|---|---|
| | TRBV | TRBJ | CDR3B | SEQ ID NO: | TRAV | TRAJ | CDR3A | SEQ ID NO: |
| 35 | TRBV25-1 | TRBJ2-1 | CASSEVWGSTHNEQFF | 595 | TRAV27 | TRAJ30 | CARNRDDKIIF | 891 |
| 36 | TRBV11-2 | TRBJ2-7 | CASSFHTGEAYEQYF | 596 | TRAV12-2 | TRAJ53 | CAFKGSGGSNYKLTF | 892 |
| 37 | TRBV5-4 | TRBJ2-1 | CASSLAGTGQFF | 597 | TRAV27 | TRAJ37 | CAGELLVSVGNTGKLIF | 893 |
| 38 | TRBV5-1 | TRBJ1-2 | CASSLEGQGNGYTF | 598 | TRAV25 | TRAJ39 | CAGPTKAGNMLTF | 894 |
| 39 | TRBV11-2 | TRBJ2-2 | CASSLSQRPNTGELFF | 599 | TRAV8-4 | TRAJ31 | CAVSGIVRLMF | 895 |
| 40 | TRBV5-1 | TRBJ1-6 | CASSLTGADSPLHF | 600 | TRAV19 | TRAJ38 | CALSEASNGNNRKLIW | 896 |
| 41 | TRBV13 | TRBJ2-1 | CASSPPTSEDAYNEQFF | 601 | TRAV26-1 | TRAJ42 | CIVRSLIRGGSQGNLIF | 897 |
| 42 | TRBV7-2 | TRBJ1-2 | CASSPTIRDSGYTF | 602 | TRAV13-1 | TRAJ17 | CAAPPQLKAAGNKLTF | 898 |
| 43 | TRBV3-1 | TRBJ1-3 | CASSQASHLSGNTIYF | 603 | TRAV29/DV5 | TRAJ35 | CTASAVSFGNVLHC | 899 |
| 44 | TRBV3-1 | TRBJ1-2 | CASSQDAVQRLYGYTF | 604 | TRAV29/DV5 | TRAJ37 | CAAIGSSNTGKLIF | 900 |
| 45 | TRBV11-1 | TRBJ1-6 | CASSRGNSPLHF | 605 | TRAV13-1 | TRAJ48 | CAASKDFGNEKLTF | 901 |
| 46 | TRBV7-6 | TRBJ2-1 | CASSSGQLVHEQFF | 606 | TRAV3 | TRAJ30 | CAVRDSTNRDDKIIF | 902 |
| 47 | TRBV7-9 | TRBJ1-1 | CASSSQSNTEAFF | 607 | TRAV10 | TRAJ38 | NON-PRODUCTIVE | 903 |
| 48 | TRBV5-1 | TRBJ2-5 | CASSTGTGGEETQYF | 608 | TRAV21 | TRAJ40 | CAVTPAYKYIF | 903 |
| 49 | TRBV9 | TRBJ2-6 | CASSVDMVGANVLTF | 609 | TRAV9-1 | TRAJ15 | CALSTTNQAGTALIF | 904 |
| 50 | TRBV2 | TRBJ2-7 | CASSVFGIGVGGTYEQYF | 610 | TRAV12-1 | TRAJ24 | CVVKKDSWGKLQF | 905 |
| 51 | TRBV27 | TRBJ2-7 | CASSYPSGRICEQYF | 611 | TRAV23/DV6 | TRAJ49 | CAASMAGNQFYF | 906 |
| 52 | TRBV28 | TRBJ2-7 | CASTSGGAYEQYF | 612 | TRAV26-1 | TRAJ12 | CIVRVEDSSYKLIF | 907 |

Figure 19D

| TCR # | TCR BETA | | | | TCR ALPHA (FIRST) | | | |
|---|---|---|---|---|---|---|---|---|
| | TRBV | TRBJ | CDR3B | SEQ ID NO: | TRAV | TRAJ | CDR3A | SEQ ID NO: |
| 53 | TRBV15 | TRBJ2-1 | CATSRDLVGGNEQFF | 613 | TRAV23/DV6 | TRAJ43 | CAASKSGNNDMRF | 908 |
| 54 | TRBV30 | TRBJ2-1 | CAWSAGQGILNEQFF | 614 | TRAV38-2/DV8 | TRAJ54 | CAFMKEGAQKLVF | 909 |
| 55 | TRBV20-1 | TRBJ1-6 | CSAAPGTGDNSPLHF | 615 | TRAV12-3 | TRAJ43 | CAMSAWNNNDMRF | 910 |
| 56 | TRBV20-1 | TRBJ2-6 | CSAPTRAGANVLTF | 616 | | | | |
| 57 | TRBV20-1 | TRBJ2-2 | CSARAGGGDGELFF | 617 | TRAV22 | TRAJ30 | CALGRDDKIIF | 911 |
| 58 | TRBV20-1 | TRBJ2-3 | CSARDGTGIGDTQYF | 618 | TRAV13-1 | TRAJ54 | CAALQGAQKLVF | 912 |
| 59 | TRBV20-1 | TRBJ2-7 | CSARDRDRYYEQYF | 619 | | | | |
| 60 | TRBV20-1 | TRBJ2-2 | CSARDSAKLAGALRGGELFF | 620 | TRAV8-4 | TRAJ41 | CVVSDQNSGYALNF | 913 |
| 61 | TRBV29-1 | TRBJ1-2 | CSVAYPGQSYGYTF | 621 | TRAV12-3 | TRAJ32 | CAMSARYGGATNKLIF | 914 |
| 62 | TRBV20-1 | TRBJ2-1 | CSVGVMTYNEQFF | 622 | TRAV38/DV8 | TRAJ37 | CAYRSARGSSNTGKLIF | 915 |
| 63 | TRBV19 | TRBJ1-5 | CASNLGTADSNQPQHF | 623 | TRAV6 | TRAJ24 | CALGSWGKLQF | 916 |
| 64 | TRBV10-3 | TRBJ1-1 | CAIREQGEAFF | 624 | TRAV12-2 | TRAJ45 | CAVVNSGGGADGLTF | 917 |
| 65 | TRBV10-3 | TRBJ1-2 | CAISENGKANYGYTF | 625 | TRAV9-1 | TRAJ20 | CALTNDYKLSF | 918 |
| 66 | TRBV10-3 | TRBJ1-4 | CAISESSGGDEKLFF | 626 | TRAV38/DV8 | TRAJ49 | CAFRTNTGNQFYF | 919 |
| 67 | TRBV10-3 | TRBJ1-5 | CAISGGQDSNQPQHF | 627 | TRAV12-1 | TRAJ34 | CVVTTYNTDKLIF | 920 |
| 68 | TRBV10-3 | TRBJ2-7 | CAISSPSSGNYEQYF | 628 | TRAV13-1 | TRAJ43 | CAASDSQWYDMRF | 921 |
| 69 | TRBV30 | TRBJ2-3 | CALDGTGGNTIYF | 629 | | | | |
| 70 | TRBV7-3 | TRBJ1-1 | CASAAGWDTEAFF | 630 | | | | |

Figure 19E

| TCR # | TCR BETA | | | | TCR ALPHA (FIRST) | | | |
|---|---|---|---|---|---|---|---|---|
| | TRBV | TRBJ | CDR3B | SEQ ID NO: | TRAV | TRAJ | CDR3A | SEQ ID NO: |
| 71 | TRBV2 | TRBJ2-3 | CASAREGPDTQYF | 631 | TRAV26-2 | TRAJ48 | CILRRNEKLTF | 922 |
| 72 | TRBV27 | TRBJ2-7 | CASGDIDSARKQYF | 632 | TRAV26-1 | TRAJ9 | CIVRVAGNTGGFKTIF | 923 |
| 73 | TRBV6-5 | TRBJ1-1 | CASGGTEAFF | 633 | TRAV8-4 | TRAJ53 | CVVSVSNDSGGSNYKLTF | 924 |
| 74 | TRBV7-9 | TRBJ2-3 | CASHLVDFTDTQYF | 634 | TRAV9-1 | TRAJ5 | CALRPDTGRRALTF | 925 |
| 75 | TRBV6-1 | TRBJ2-1 | CASHSTQAGYNEQFF | 635 | | TRAJ22 | | |
| 76 | TRBV5-5 | TRBJ2-1 | CASIREGSHYNEQFF | 636 | | | | |
| 77 | TRBV27 | TRBJ2-6 | CASISMGAGGLSGANVLTF | 637 | TRAV38/DV8 | TRAJ49 | CAYRSYRTGNQFYF | 926 |
| 78 | TRBV6-1 | TRBJ2-2 | CASITSGGATGELFF | 638 | TRAV12-3 | TRAJ34 | CAPDKLIF | 927 |
| 79 | TRBV6-1 | TRBJ1-5 | CASKKGTGGNQPQHF | 639 | TRAV12-3 | TRAJ57 | CAMSQTQGGSEKLVF | 928 |
| 80 | TRBV28 | TRBJ2-7 | CASLRGYEQYF | 640 | TRAV35 | TRAJ32 | NON-PRODUCTIVE | |
| 81 | TRBV12-3 | TRBJ2-2 | CASLSDFGSANTGELFF | 641 | TRAV8-6 | TRAJ13 | CAVSSYSGGYQKVTF | 929 |
| 82 | TRBV19 | TRBJ2-6 | CASMKDVGAGANVLTF | 642 | TRAV13-1 | TRAJ42 | CAASTRGSQGNLIF | 930 |
| 83 | TRBV27 | TRBJ2-7 | CASQGQGEQYF | 643 | TRAV2 | TRAJ10 | NON-PRODUCTIVE | |
| 84 | TRBV7-9 | TRBJ1-1 | CASRAGGEAPAFF | 644 | TRAV12-1 | TRAJ34 | CVVNHNTDKLIF | 931 |
| 85 | TRBV2 | TRBJ1-2 | CASRGDRGDYGYTF | 645 | TRAV12-1 | TRAJ33 | CVVTLRPWSNYQLIW | 932 |
| 86 | TRBV2 | TRBJ1-5 | CASRIGTGSNQPQHF | 646 | TRAV29/DV5 | TRAJ39 | CAASEWTAGNMLTF | 933 |
| 87 | TRBV19 | TRBJ1-5 | CASRLAGADNQPQHF | 647 | TRAV39 | TRAJ37 | CAVDEGLGNTGKLIF | 934 |
| 88 | TRBV7-2 | TRBJ2-1 | CASRLGLAENEQFF | 648 | TRAV1-2 | TRAJ41 | CAVKDSGYALNF | 935 |

Figure 19F

| TCR # | TCR BETA | | | | TCR ALPHA (FIRST) | | | |
|---|---|---|---|---|---|---|---|---|
| | TRBV | TRBJ | CDR3B | SEQ ID NO: | TRAV | TRAJ | CDR3A | SEQ ID NO: |
| 89 | TRBV28 | TRBJ1-6 | CASRLSRDNSPLHF | 649 | TRAV10 | TRAJ13 | CVVSPGGYQKVTF | 936 |
| 90 | TRBV9 | TRBJ2-7 | CASRPGLAGDEQYF | 650 | TRAV13-1 | TRAJ29 | CAASRNSGNTPLVF | 937 |
| 91 | TRBV19 | TRBJ2-7 | CASRPGQYSYEQYF | 651 | | | | |
| 92 | TRBV2 | TRBJ1-5 | CASRPGTGRDQPQHF | 652 | | | | |
| 93 | TRBV19 | TRBJ2-2 | CASRPGTVNTGELFF | 653 | TRAV9-1 | TRAJ54 | CALSDQGIQGAQKLVF | 938 |
| 94 | TRBV6-5 | TRBJ2-7 | CASRQRDRVLEQYF | 654 | TRAV8-4 | TRAJ35 | NON-PRODUCTIVE | |
| 95 | TRBV7-3 | TRBJ2-3 | CASRQTGTSTDTQYF | 655 | TRAV8-4 | TRAJ45 | NON-PRODUCTIVE | |
| 96 | TRBV7-3 | TRBJ2-5 | CASRQTSGQETQYF | 656 | | TRAJ58 | CATDETAGGSRLTF | 939 |
| 97 | TRBV6-1 | TRBJ2-3 | CASRRTGMSTDTQYF | 657 | | | | |
| 98 | TRBV19 | TRBJ1-1 | CASRSGIYTEAFF | 658 | TRAV17 | TRAJ22 | CATGLSSGSARQLTF | 940 |
| 99 | TRBV19 | TRBJ2-3 | CASRSGLAGTTDTQYF | 659 | TRAV2 | TRAJ15 | GAVEDQAGTALIF | 941 |
| 100 | TRBV5-1 | TRBJ2-2 | CASRTGLNGELFF | 660 | TRAV41 | TRAJ34 | CAVNRSTDKLIF | 942 |
| 101 | TRBV9 | TRBJ2-3 | CASSAGQDSDTQYF | 661 | TRAV38-2/DV8 | TRAJ42 | CAYRVGGSQGNLIF | 943 |
| 102 | TRBV28 | TRBJ2-5 | CASSAPGLAGTGETQYF | 662 | TRAV12-2 | TRAJ6 | CAVRGAGGSYIPTF | 944 |
| 103 | TRBV5-1 | TRBJ2-3 | CASSAPGTGDTDTQYF | 663 | TRAV38/DV8 | TRAJ48 | CAFMKHFGNEKLTF | 945 |
| 104 | TRBV6-4 | TRBJ1-2 | CASSATLGSLHYGYTF | 664 | TRAV12-2 | TRAJ48 | CAVNTGLSNFGNEKLTF | 946 |
| 105 | TRBV7-9 | TRBJ1-3 | CASSAVEAGNTIYF | 665 | TRAV6 | TRAJ37 | CALDESNTGKLIF | 947 |
| 106 | TRBV19 | TRBJ1-5 | CASSDDGTGDQPQHF | 666 | TRAV17 | TRAJ58 | CAAGGILGETSGSRLTF | 948 |

Figure 19G

| TCR # | TCR BETA | | | | TCR ALPHA (FIRST) | | | |
|---|---|---|---|---|---|---|---|---|
| | TRBV | TRBJ | CDR3B | SEQ ID NO: | TRAV | TRAJ | CDR3A | SEQ ID NO: |
| 107 | TRBV11-2 | TRBJ2-2 | CASSDPGGGVTGELFF | 667 | | | NON-PRODUCTIVE | |
| 108 | TRBV25-1 | TRBJ1-1 | CASSDRGNTEAFF | 668 | TRAV6 | TRAJ5 | CATHNSGTYKYIF | 949 |
| 109 | TRBV25-1 | TRBJ2-7 | CASSEAGDYEQYF | 669 | TRAV17 | TRAJ40 | CAVVNTGNQFYF | 890 |
| 110 | TRBV6-1 | TRBJ1-3 | CASSEAGGNTIYF | 670 | TRAV39 | TRAJ49 | CIVRVGGTGGFKTIF | 950 |
| 111 | TRBV6-1 | TRBJ2-7 | CASSEAGVRLVSYEQYF | 671 | TRAV26-1 | TRAJ9 | CAVTRGILTGGGNKLTF | 951 |
| 112 | TRBV2 | TRBJ2-2 | CASSERAGGDTGELFF | 672 | TRAV8-4 | TRAJ10 | CAESGSFGNVLHC | 952 |
| 113 | TRBV6-1 | TRBJ2-7 | CASSEWGQGGAEQYF | 673 | TRAV13-2 | TRAJ35 | CVVNMFAGGTSYGKLTF | 953 |
| 114 | TRBV25-1 | TRBJ2-7 | CASSEYKATYEQYF | 674 | TRAV12-1 | TRAJ52 | | |
| 115 | TRBV7-2 | TRBJ1-5 | CASSFDEGTQHF | 675 | | | | |
| 116 | TRBV7-2 | TRBJ2-7 | CASSFERPYEQYF | 676 | TRAV8-4 | TRAJ42 | CVVTPWGGGSQGNLIF | 954 |
| 117 | TRBV12-3 | TRBJ2-3 | CASSFGAEDTQYF | 677 | TRAV12-2 | TRAJ6 | CAVNRGGSYIPTF | 955 |
| 118 | TRBV12-3 | TRBJ2-7 | CASSFGGPSYEQYF | 678 | | | | |
| 119 | TRBV7-9 | TRBJ1-6 | CASSFGRWVDSPLHF | 679 | TRAV8-4 | TRAJ40 | CVVSDRTPGTYKYIF | 956 |
| 120 | TRBV28 | TRBJ1-1 | CASSFPYTEAFF | 680 | TRAV16 | TRAJ20 | NON-PRODUCTIVE | |
| 121 | TRBV5-1 | TRBJ2-4 | CASSFRGDDKNIQYF | 681 | TRAV38/DV8 | TRAJ48 | CAFMKHFGNEKLTF | 945 |
| 122 | TRBV7-2 | TRBJ2-3 | CASSFSGREGVDTQYF | 682 | TRAV41 | TRAJ31 | CAVSNNARLMF | 957 |
| 123 | TRBV7-2 | TRBJ2-7 | CASSFSGSAYEQYF | 683 | TRAV6 | TRAJ10 | CALATGGGNKLTF | 958 |
| 124 | TRBV7-9 | TRBJ2-7 | CASSFSTSGEQYF | 684 | TRAV13-1 | TRAJ53 | CAASIAGSNYKLTF | 959 |

Figure 19H

| TCR # | TCR BETA ||||| TCR ALPHA (FIRST) ||||
| --- | --- | --- | --- | --- | --- | --- | --- | --- | --- |
| | TRBV | TRBJ | CDR3B | SEQ ID NO: | TRAV | TRAJ | CDR3A | SEQ ID NO: |
| 125 | TRBV12-3 | TRBJ2-2 | CASSFSTSGNTGELFF | 685 | TRAV4 | TRAJ23 | CLVGGDNQGGKLIF | 960 |
| 126 | TRBV7-2 | TRBJ1-6 | CASSFVNSPLHF | 686 | TRAV13-1 | TRAJ47 | CAASKYGNKLVF | 961 |
| 127 | TRBV28 | TRBJ1-6 | CASSFVRALGSYNSPLHF | 687 | | | | |
| 128 | TRBV28 | TRBJ2-7 | CASSGGTGNNYEQYF | 688 | TRAV12-3 | TRAJ57 | CAMGGGGGSEKLVF | 962 |
| 129 | TRBV19 | TRBJ2-5 | CASSGILETQYF | 689 | TRAV8-4 | TRAJ13 | CAVSPNSGGYQKVTF | 963 |
| 130 | TRBV2 | TRBJ1-5 | CASSGTGGHQPQHF | 690 | | | | |
| 131 | TRBV7-9 | TRBJ2-1 | CASSHSATHNEQFF | 691 | TRAV26-1 | TRAJ22 | CIVTGSARQLTF | 964 |
| 132 | TRBV19 | TRBJ1-2 | CASSIGARGYTF | 692 | TRAV23/DV6 | TRAJ12 | CAARGMDSSYKLIF | 965 |
| 133 | TRBV19 | TRBJ2-7 | CASSIGRTYEQYF | 693 | TRAV17 | TRAJ53 | CATEGGSNYKLTF | 966 |
| 134 | TRBV19 | TRBJ2-1 | CASSIRRNNEQFF | 694 | TRAV12-2 | TRAJ40 | CAPVSGTYKYIF | 967 |
| 135 | TRBV6-1 | TRBJ1-1 | CASSIWGSEAFF | 695 | | | | |
| 136 | TRBV11-2 | TRBJ2-3 | CASSKEGRITDTQYF | 696 | | | | |
| 137 | TRBV28 | TRBJ1-1 | CASSKGTDLNTEAFF | 697 | TRAV38-2/DV8 | TRAJ54 | CASYSLQGAQKLVF | 968 |
| 138 | TRBV5-4 | TRBJ1-2 | CASSLAAGPYGYTF | 698 | TRAV8-4 | TRAJ41 | NON-PRODUCTIVE | |
| 139 | TRBV5-4 | TRBJ1-6 | CASSLAANSPLHF | 699 | TRAV27 | TRAJ42 | CAGAVGAVGSQGNLIF | 969 |
| 140 | TRBV7-2 | TRBJ2-7 | CASSLAGSVYEQYF | 700 | | | | |
| 141 | TRBV7-2 | TRBJ2-5 | CASSLAPGVGETQYF | 701 | | | | |
| 142 | TRBV12-3 | TRBJ2-1 | CASSLASGIYEQFF | 702 | TRAV22 | TRAJ45 | CAVLSGGGADGLTF | 970 |

Figure 19I

| TCR # | TCR BETA | | | | TCR ALPHA (FIRST) | | | |
|---|---|---|---|---|---|---|---|---|
| | TRBV | TRBJ | CDR3B | SEQ ID NO: | TRAV | TRAJ | CDR3A | SEQ ID NO: |
| 143 | TRBV7-2 | TRBJ2-5 | CASSLASRGPQGETQYF | 703 | TRAV6 | TRAJ31 | NON-PRODUCTIVE | |
| 144 | TRBV5-1 | TRBJ2-3 | CASSLAYGTDTQYF | 704 | TRAV38-2/DV8 | TRAJ37 | CAYSLGKLIF | 971 |
| 145 | TRBV5-1 | TRBJ1-2 | CASSLDGGVVGGYTF | 705 | TRAV2 | TRAJ8 | CAVGNEGFQKLVF | 972 |
| 146 | TRBV7-2 | TRBJ2-7 | CASSLDGTSTYEQYF | 706 | | | | |
| 147 | TRBV6-6 | TRBJ2-2 | CASSLDSQNTGELFF | 707 | TRAV10 | TRAJ9 | CVVSRNTGGFKTIF | 973 |
| 148 | TRBV11-3 | TRBJ2-5 | CASSLDSTGTGKETQYF | 708 | | | | |
| 149 | TRBV7-2 | TRBJ1-5 | CASSLEATSRTQPQHF | 709 | TRAV10 | TRAJ31 | CVVANNARLMF | 974 |
| 150 | TRBV5-1 | TRBJ2-3 | CASSLEGPRDTQYF | 710 | TRAV34 | TRAJ18 | CGADRGSTLGRLYF | 975 |
| 151 | TRBV5-1 | TRBJ1-1 | CASSLEGSGGTEAFF | 711 | TRAV38/DV8 | TRAJ40 | CAYNNPGTYKYIF | 976 |
| 152 | TRBV5-1 | TRBJ2-3 | CASSLELAGVTRSTDTQYF | 712 | | | | |
| 153 | TRBV12-3 | TRBJ2-2 | CASSLEPGRQRGNTGELFF | 713 | TRAV8-4 | TRAJ56 | CAVTLPHTGANSKLTF | 977 |
| 154 | TRBV27 | TRBJ2-2 | CASSLGDTGELFF | 714 | TRAV19 | TRAJ29 | NON-PRODUCTIVE | |
| 155 | TRBV7-2 | TRBJ1-5 | CASSLGGGAEGPQHF | 715 | | | | |
| 156 | TRBV28 | TRBJ1-5 | CASSLGGTPEPQHF | 716 | | | | |
| 157 | TRBV11-2 | TRBJ2-1 | CASSLGGVTYNEQFF | 717 | TRAV9-1 | TRAJ39 | CALSDNAGNMLTF | 978 |
| 158 | TRBV28 | TRBJ2-7 | CASSLGPGLASYEQYF | 718 | TRAV8-4 | TRAJ37 | CAVSGGSSNTGKLIF | 979 |
| 159 | TRBV5-1 | TRBJ2-5 | CASSLGPGQETQYF | 719 | TRAV38/DV8 | TRAJ37 | CAYIGSSNTGKLIF | 980 |
| 160 | TRBV7-9 | TRBJ1-6 | CASSLGQEENSPLHF | 720 | TRAV6 | TRAJ41 | CAPRAFGYALNF | 981 |

Figure 19j

| TCR # | TCR BETA ||||| TCR ALPHA (FIRST) ||||
|---|---|---|---|---|---|---|---|---|---|
| | TRBV | TRBJ | CDR3B | SEQ ID NO: | TRAV | TRAJ | CDR3A | SEQ ID NO: |
| 161 | TRBV7-9 | TRBJ2-2 | CASSLGSGTNTGELFF | 721 | | | | |
| 162 | TRBV12-3 | TRBJ1-1 | CASSLGTERTEAFF | 722 | | | | |
| 163 | TRBV12-3 | TRBJ2-2 | CASSLIGASGPGELFF | 723 | TRAV12-3 | TRAJ43 | CAVSYNNDMRF | 982 |
| 164 | TRBV11-2 | TRBJ2-1 | CASSLLAGGLIVNEQFF | 724 | TRAV21 | TRAJ27 | CAGRPRHTNAGKSTF | 983 |
| 165 | TRBV11-2 | TRBJ1-3 | CASSLLRNSGNTIYF | 725 | TRAV13-1 | TRAJ17 | CAASTFAAGNKLTF | 984 |
| 166 | TRBV12-3 | TRBJ2-2 | CASSLNAPGLGSTGELFF | 726 | TRAV13-1 | TRAJ12 | CAAISMDSSYKLIF | 985 |
| 167 | TRBV28 | TRBJ1-2 | CASSLNQDGYTF | 727 | | | | |
| 168 | TRBV5-4 | TRBJ2-7 | CASSLQAGSGEQYF | 728 | TRAV8-4 | TRAJ13 | CAVTNSGGYQKVTF | 986 |
| 169 | TRBV28 | TRBJ1-3 | CASSLQGALGNTIYF | 729 | TRAV12-2 | TRAJ43 | CAVTVSNNNDMRF | 987 |
| 170 | TRBV12-3 | TRBJ2-1 | CASSLQVYNEQFF | 730 | TRAV39 | TRAJ37 | CAVDEGLGNTGKLIF | 988 |
| 171 | TRBV7-2 | TRBJ2-1 | CASSLRASGTRGEQFF | 731 | | | | |
| 172 | TRBV12-3 | TRBJ1-4 | CASSLRGQGNEKLFF | 732 | TRAV36/DV7 | TRAJ15 | NON-PRODUCTIVE | |
| 173 | TRBV5-4 | TRBJ2-5 | CASSLRGRETQYF | 733 | | TRAJ40 | CAVQYTTSGTYKYIF | 989 |
| 174 | TRBV3-1 | TRBJ1-2 | CASSLRRDYGYTF | 734 | | | | |
| 175 | TRBV5-1 | TRBJ2-3 | CASSLSSSEVDTQYF | 735 | TRAV41 | TRAJ45 | CAVPGKGGGADGLTF | 990 |
| 176 | TRBV5-4 | TRBJ1-3 | CASSLSVTDSRSGNTIYF | 736 | TRAV8-4 | TRAJ10 | CAVKRPGGGNKLTF | 991 |
| 177 | TRBV7-6 | TRBJ2-7 | CASSLTLAGGQNEQYF | 737 | TRAV2 | TRAJ20 | NON-PRODUCTIVE | |
| 178 | TRBV5-1 | TRBJ1-5 | CASSLVGGNQPQHF | 738 | TRAV14/DV4 | TRAJ57 | CAMREGQGQGGSEKLVF | 992 |

Figure 19K

| TCR # | TCR BETA ||||| TCR ALPHA (FIRST) ||||
|---|---|---|---|---|---|---|---|---|---|
| | TRBV | TRBJ | CDR3B | SEQ ID NO: | TRAV | TRAJ | CDR3A | SEQ ID NO: |
| 179 | TRBV28 | TRBJ1-5 | CASSLVIQPQHF | 739 | TRAV8-4 | TRAJ16 | NON-PRODUCTIVE | |
| 180 | TRBV28 | TRBJ1-3 | CASSLYPRRISSGNTIYF | 740 | | | | |
| 181 | TRBV11-1 | TRBJ2-2 | CASSLYTGGGSGELFF | 741 | TRAV3 | TRAJ29 | CAVRDLLNSGNTPLVF | 993 |
| 182 | TRBV19 | TRBJ2-2 | CASSMVAGNGELFF | 742 | TRAV16 | TRAJ28 | CALRGYGSGAGSYQLTF | 994 |
| 183 | TRBV19 | TRBJ1-5 | CASSNPYRGWGQNQPQHF | 743 | TRAV38/DV8 | TRAJ44 | CAYRSTVSGTASKLTF | 995 |
| 184 | TRBV11-1 | TRBJ2-7 | CASSPAGPFYEQYF | 744 | TRAV30 | TRAJ49 | | |
| 185 | TRBV5-1 | TRBJ2-3 | CASSPAPGPDTQYF | 745 | TRAV2 | TRAJ37 | CAVTYSSNTGKLIF | 996 |
| 186 | TRBV18 | TRBJ2-5 | CASSPDNDEETQYF | 746 | TRAV17 | TRAJ7 | CATGTPYYGNNRLAF | 997 |
| 187 | TRBV7-2 | TRBJ1-2 | CASSPFWDSNYGYTF | 747 | TRAV6 | TRAJ15 | CALETQAGTALIF | 998 |
| 188 | TRBV5-1 | TRBJ1-2 | CASSPGGADYGYTF | 748 | TRAV8-4 | TRAJ8 | CVLEDTGFQKLVF | 999 |
| 189 | TRBV5-1 | TRBJ1-5 | CASSPGGESNQPQHF | 749 | | | | |
| 190 | TRBV12-3 | TRBJ1-5 | CASSPGPPGLGPQHF | 750 | TRAV38/DV8 | TRAJ58 | CAYRTETSGSRLTF | 1000 |
| 191 | TRBV12-3 | TRBJ2-7 | CASSPGTQVYEQYF | 751 | TRAV38/DV8 | TRAJ40 | CASRGTGTYKYIF | 1001 |
| 192 | TRBV13 | TRBJ2-2 | CASSPGTSGVGELFF | 752 | TRAV38/DV8 | TRAJ32 | CAYRSAYGGATNKLIF | 1002 |
| 193 | TRBV28 | TRBJ2-7 | CASSPPTASGSVGQYF | 753 | TRAV19 | TRAJ27 | NON-PRODUCTIVE | |
| 194 | TRBV7-2 | TRBJ2-2 | CASSPPVWPTGELFF | 754 | TRAV2 | TRAJ26 | CAVEEGGQNFVF | 1003 |
| 195 | TRBV6-5 | TRBJ1-1 | CASSPQQAGDTEAFF | 755 | TRAV8-4 | TRAJ47 | NON-PRODUCTIVE | |
| 196 | TRBV6-1 | TRBJ2-7 | CASSPRGGAYEQYF | 756 | TRAV21 | TRAJ43 | NON-PRODUCTIVE | |

Figure 19L

| TCR # | TCR BETA | | | SEQ ID NO: | TCR ALPHA (FIRST) | | | SEQ ID NO: |
| | TRBV | TRBJ | CDR3B | | TRAV | TRAJ | CDR3A | |
|---|---|---|---|---|---|---|---|---|
| 197 | TRBV14 | TRBJ2-7 | CASSPRGYEQYF | 757 | | | | |
| 198 | TRBV18 | TRBJ2-5 | CASSPRNSAGGPETQYF | 758 | | | | |
| 199 | TRBV12-3 | TRBJ1-2 | CASSPSGREDGYTF | 759 | TRAV17 | TRAJ9 | CATSEGGFKTIF | 1004 |
| 200 | TRBV28 | TRBJ2-7 | CASSPSWAGGDYEQYF | 760 | TRAV4 | TRAJ23 | CLDQARNQGGKLIF | 1005 |
| 201 | TRBV5-1 | TRBJ2-5 | CASSPTSGETTQYF | 761 | | TRAJ24 | CAMRPGPPTDSWGKLQF | 1006 |
| 202 | TRBV18 | TRBJ1-3 | CASSPWSQSSGNTIYF | 762 | TRAV9-1 | TRAJ43 | CALSDDNNDMRF | 1007 |
| 203 | TRBV14 | TRBJ1-5 | CASSPWTGTGSYSNQPQHF | 763 | TRAV12-2 | TRAJ47 | CAAEYGNKLVF | 1008 |
| 204 | TRBV28 | TRBJ2-7 | CASSPYRDLYEQYF | 764 | TRAV19 | TRAJ53 | CALSEDSGGSNYKLTF | 1009 |
| 205 | TRBV4-1 | TRBJ1-6 | CASSQAGGNSPLHF | 765 | | | | |
| 206 | TRBV4-1 | TRBJ2-2 | CASSQDAGVGVGYTF | 766 | TRAV39 | TRAJ52 | | |
| 207 | TRBV4-1 | TRBJ2-5 | CASSQDGPRGLETQYF | 767 | TRAV14/DV4 | TRAJ56 | CAMREGYTGANSKLTF | 1010 |
| 208 | TRBV4-2 | TRBJ2-1 | CASSQDYQGVDNEQFF | 768 | TRAV17 | TRAJ53 | CATGGGSNYKLTF | 1011 |
| 209 | TRBV4-2 | TRBJ2-3 | CASSQEPDRRAQYF | 769 | TRAV13-2 | TRAJ21 | CAENFNKFYF | 1012 |
| 210 | TRBV4-1 | TRBJ2-7 | CASSQERGGKWAYEQYF | 770 | TRAV2 | TRAJ9 | NON-PRODUCTIVE | |
| 211 | TRBV3-1 | TRBJ2-7 | CASSQESRGGPVSYEQYF | 771 | | | | |
| 212 | TRBV4-2 | TRBJ2-5 | CASSQGAAGEQQYF | 772 | TRAV12-1 | TRAJ24 | CVVNTPDSWGKLQF | 1013 |
| 213 | TRBV4-1 | TRBJ1-2 | CASSQGETGEYGYTF | 773 | TRAV19 | TRAJ29 | CALSEFASGNTPLVF | 1014 |
| 214 | TRBV3-1 | TRBJ1-6 | CASSQGFVVNSPLHF | 774 | | | | |

Figure 19M

| TCR # | TCR BETA | | | | TCR ALPHA (FIRST) | | | |
|---|---|---|---|---|---|---|---|---|
| | TRBV | TRBJ | CDR3B | SEQ ID NO: | TRAV | TRAJ | CDR3A | SEQ ID NO: |
| 215 | TRBV4-1 | TRBJ2-3 | CASSQGRGVGTDTQYF | 775 | TRAV4 | TRAJ32 | CLVGDSNYGGATNKLIF | 1015 |
| 216 | TRBV4-2 | TRBJ1-6 | CASSQGRPNSPLHF | 776 | | | | |
| 217 | TRBV7-3 | TRBJ2-3 | CASSQGTSGWTDTQYF | 777 | TRAV14/DV4 | TRAJ24 | CAMRPGPPTDSWGKLQF | 1006 |
| 218 | TRBV14 | TRBJ2-1 | CASSQLSSGDYNEQFF | 778 | | | | |
| 219 | TRBV14 | TRBJ2-3 | CASSQRVGGLDTQYF | 779 | TRAV26-2 | TRAJ38 | CILMSGAGNNRKLIW | 1016 |
| 220 | TRBV5-1 | TRBJ2-2 | CASSQTDANTGELFF | 780 | TRAV14/DV4 | TRAJ31 | CAMRERGNNARLMF | 1017 |
| 221 | TRBV13 | TRBJ1-2 | CASSQTQNRGGNYGYTF | 781 | TRAV38-2/DV8 | TRAJ29 | CAYRSASGWGNTPLVF | 1018 |
| 222 | TRBV4-1 | TRBJ2-2 | CASSQVGGAFANTGELFF | 782 | TRAV16 | TRAJ57 | NON-PRODUCTIVE | |
| 223 | TRBV6-6 | TRBJ1-2 | CASSRESFAPDGYTF | 783 | TRAV3 | TRAJ37 | NON-PRODUCTIVE | |
| 224 | TRBV14 | TRBJ2-1 | CASSRGLYNEQFF | 784 | TRAV38-2/DV8 | TRAJ49 | CAASNTGNQFYF | 1019 |
| 225 | TRBV11-2 | TRBJ2-7 | CASSRSSGASSYEQYF | 785 | TRAV8-6 | TRAJ53 | CAVSVPNSGGSNYKLTF | 1020 |
| 226 | TRBV5-1 | TRBJ1-6 | CASSRSTENNSPLHF | 786 | TRAV8-6 | TRAJ52 | CAVSDPNAGGTSYGKLTF | 1021 |
| 227 | TRBV28 | TRBJ1-3 | CASSRTGGNSGNTIYF | 787 | TRAV35 | TRAJ9 | CAGPNTGGFKTIF | 1022 |
| 228 | TRBV28 | TRBJ2-7 | CASSSAGGAFSHEQYF | 788 | | | | |
| 229 | TRBV2 | TRBJ1-5 | CASSSGQGNQPHF | 789 | TRAV35 | TRAJ54 | CAGQRGRIQGAQKLVF | 1023 |
| 230 | TRBV5-1 | TRBJ2-2 | CASSSGQQLAGELFF | 790 | | | | |
| 231 | TRBV5-4 | TRBJ2-1 | CASSSPGQGWNEQFF | 791 | TRAV34 | TRAJ42 | CGADKYGGSQGNLIF | 1024 |
| 232 | TRBV5-1 | TRBJ2-7 | CASSSPSLAGPYEQYF | 792 | TRAV12-1 | TRAJ17 | CVVNKAAGNKLTF | 1025 |

Figure 19N

| TCR # | TCR BETA | | | | TCR ALPHA (FIRST) | | | |
|---|---|---|---|---|---|---|---|---|
| | TRBV | TRBJ | CDR3B | SEQ ID NO: | TRAV | TRAJ | CDR3A | SEQ ID NO: |
| 233 | TRBV18 | TRBJ2-7 | CASSSRGPPAYEQYF | 793 | TRAV8-6 | TRAJ47 | CAVSERLMEYGNKLVF | 1026 |
| 234 | TRBV7-9 | TRBJ1-2 | CASSSSSDRAHF | 794 | TRAV9-1 | TRAJ7 | CALTGDGNNRLAF | 1027 |
| 235 | TRBV7-2 | TRBJ2-1 | CASSSSDSYNEQFF | 795 | | TRAJ12 | CAMGGRDSSYKLIF | 1028 |
| 236 | TRBV11-2 | TRBJ2-3 | CASSSSGSRTDTQYF | 796 | TRAV26-2 | TRAJ49 | NON-PRODUCTIVE | |
| 237 | TRBV5-1 | TRBJ2-3 | CASSSTGQSWDTQYF | 797 | TRAV27 | TRAJ48 | CAGEGISNFGNEKLTF | 1029 |
| 238 | TRBV6-2 | TRBJ2-1 | CASSSTGTSGRMRIF | 798 | | | | |
| 239 | TRBV7-2 | TRBJ2-5 | CASSSTSGQEETQYF | 799 | | | | |
| 240 | TRBV2 | TRBJ1-2 | CASSTDSANYGYTF | 800 | TRAV12-2 | TRAJ41 | CAVPSNSGYALNF | 1030 |
| 241 | TRBV3-1 | TRBJ1-1 | CASSTHSGRTEAFF | 801 | | | | |
| 242 | TRBV19 | TRBJ1-5 | CASSTSRDRVNQPQHF | 802 | TRAV6 | TRAJ38 | CALLAGNNRKLIW | 1031 |
| 243 | TRBV18 | TRBJ1-1 | CASSTTGGTGTEAFF | 803 | TRAV17 | TRAJ52 | CATHHAGGTSYGKLTF | 1032 |
| 244 | TRBV19 | TRBJ1-4 | CASSTWTAYNEKLFF | 804 | TRAV8-4 | TRAJ48 | CVVSESGNFGNEKLTF | 1033 |
| 245 | TRBV9 | TRBJ2-3 | CASSVGGTSTDTQYF | 805 | TRAV9-1 | TRAJ42 | CALSVGSQGNLIF | 1034 |
| 246 | TRBV9 | TRBJ2-1 | CASSVSGARGYNEQFF | 806 | TRAV23/DV6 | TRAJ39 | NON-PRODUCTIVE | |
| 247 | TRBV6-5 | TRBJ2-1 | CASSYLSGGEHNEQFF | 807 | | TRAJ37 | NON-PRODUCTIVE | |
| 248 | TRBV6-6 | TRBJ2-5 | CASSYPAPSGGPETQYF | 808 | | | | |
| 249 | TRBV6-2 | TRBJ2-1 | CASSYPLVLSEQFF | 809 | TRAV3 | TRAJ39 | NON-PRODUCTIVE | |
| 250 | TRBV6-5 | TRBJ2-2 | CASSYSSGEYTGELFF | 810 | TRAV13-1 | TRAJ26 | CAASRYGQNFVF | 1035 |

Figure 19O

| TCR # | TCR BETA | | | SEQ ID NO: | TCR ALPHA (FIRST) | | | SEQ ID NO: |
|---|---|---|---|---|---|---|---|---|
| | TRBV | TRBJ | CDR3B | | TRAV | TRAJ | CDR3A | |
| 251 | TRBV6-5 | TRBJ1-6 | CASSYSYRDNSPLHF | 811 | TRAV36/DV7 | TRAJ33 | CAVQTGDSNYQLIW | 1036 |
| 252 | TRBV28 | TRBJ2-7 | CASTSSGGSPYEQYF | 812 | | | | |
| 253 | TRBV19 | TRBJ1-1 | CASTYWAGAEAFF | 813 | TRAV17 | TRAJ44 | CATVVNTGTASKLTF | 1037 |
| 254 | TRBV24-1 | TRBJ1-5 | CATSLMGQPQHF | 814 | TRAV8-6 | TRAJ52 | CAVSVRAEAGGTSYGKLTF | 1038 |
| 255 | TRBV15 | TRBJ1-1 | CATSRAFDWDRGLDTEAFF | 815 | | | | |
| 256 | TRBV15 | TRBJ2-7 | CATSRDFGDSYEQYF | 816 | TRAV9-1 | TRAJ13 | CALPNSGGYQKVTF | 1039 |
| 257 | TRBV15 | TRBJ2-3 | CATSRDPGLASTQYF | 817 | TRAV13-1 | TRAJ49 | CAATNTGNQFYF | 1040 |
| 258 | TRBV15 | TRBJ1-1 | CATSRDRADTEAFF | 818 | TRAV16 | TRAJ39 | CALSQSNAGNMLTF | 1041 |
| 259 | TRBV30 | TRBJ2-5 | CAWEKAGAGGTQYF | 819 | TRAV8-4 | TRAJ45 | CAVSDSGGGADGLTF | 1042 |
| 260 | TRBV30 | TRBJ1-2 | CAWGTNYGYTF | 820 | TRAV13-1 | TRAJ45 | CAAIGGGADGLTF | 1043 |
| 261 | TRBV30 | TRBJ2-1 | CAWMEVHEQFF | 821 | | | | |
| 262 | TRBV30 | TRBJ1-4 | CAWQYPADSEKLFF | 822 | TRAV12-3 | TRAJ11 | CAAYSGYSTLTF | 1044 |
| 263 | TRBV30 | TRBJ1-6 | CAWRSGGASPLHF | 823 | | | | |
| 264 | TRBV30 | TRBJ2-2 | CAWSAGTGVRELFF | 824 | | | | |
| 265 | TRBV30 | TRBJ2-1 | CAWSASRDAEQFF | 825 | TRAV3 | TRAJ43 | CAVRDIINDMRF | 1045 |
| 266 | TRBV30 | TRBJ1-5 | CAWSEGGIGQPQHF | 826 | TRAV38/DV8 | TRAJ26 | CAFGPGVNYGQNFVF | 1046 |
| 267 | TRBV30 | TRBJ1-2 | CAWSGANYGYTF | 827 | TRAV16 | TRAJ58 | CAPPSGSRLTF | 1047 |
| 268 | TRBV30 | TRBJ2-7 | CAWSSGTGTSEQYF | 828 | TRAV8-6 | TRAJ10 | CAVSDRRGGNKLTF | 1048 |

Figure 19P

| TCR # | TCR BETA | | | SEQ ID NO: | TCR ALPHA (FIRST) | | | SEQ ID NO: |
| | TRBV | TRBJ | CDR3B | | TRAV | TRAJ | CDR3A | |
|---|---|---|---|---|---|---|---|---|
| 269 | TRBV30 | TRBJ1-2 | CAWSVGGRIYGYTF | 829 | TRAV12-2 | TRAJ26 | CAVDNYGQNFVF | 1049 |
| 270 | TRBV30 | TRBJ2-7 | CAWSVLRGQYF | 830 | | | | |
| 271 | TRBV20-1 | TRBJ1-2 | CISQSGIGFDTF | 831 | | | | |
| 272 | TRBV20-1 | TRBJ1-5 | CSAAIVGQPQHF | 832 | TRAV26-2 | TRAJ37 | NON-PRODUCTIVE | |
| 273 | TRBV20-1 | TRBJ2-7 | CSAERSGLAGAPAYEQYF | 833 | TRAV27 | TRAJ58 | CAGSKTSGSRLTF | 1050 |
| 274 | TRBV20-1 | TRBJ2-1 | CSAGPVGAGGAGEQFF | 834 | TRAV12-3 | TRAJ41 | CAMQPVNSGYALNF | 1051 |
| 275 | TRBV20-1 | TRBJ2-7 | CSALLPTGGGEQYF | 835 | TRAV26-1 | TRAJ13 | CIVRPANSGGYQKVTF | 1052 |
| 276 | TRBV20-1 | TRBJ1-1 | CSANGLGGLNTEAFF | 836 | TRAV8-4 | TRAJ37 | CAVNPSSNTGKLIF | 1053 |
| 277 | TRBV20-1 | TRBJ2-5 | CSAPQGQETQYF | 837 | | TRAJ33 | CAIPEDSNYQLIW | 1054 |
| 278 | TRBV20-1 | TRBJ2-3 | CSARDGAGVGDTQYF | 838 | TRAV13-1 | TRAJ54 | CAALQGAQKLVF | 912 |
| 279 | TRBV20-1 | TRBJ1-4 | CSARDSDGEKLFF | 839 | TRAV26-1 | TRAJ15 | CIVYNQAGTALIF | 1055 |
| 280 | TRBV20-1 | TRBJ2-1 | CSARGGGGALGSYNEQFF | 840 | | TRAJ37 | CALATSNTGKLIF | 1056 |
| 281 | TRBV20-1 | TRBJ1-2 | CSARGSGTGDLYGYTF | 841 | TRAV12-1 | TRAJ28 | CVGRAQGGAGSYQLTF | 1057 |
| 282 | TRBV20-1 | TRBJ1-2 | CSARWEQGARGYTF | 842 | TRAV12-2 | TRAJ57 | CAVNKGGSEKLVF | 1058 |
| 283 | TRBV20-1 | TRBJ1-2 | CSASESLLLGYTF | 843 | TRAV26-1 | TRAJ49 | CIVSLNTGNQFYF | 1059 |
| 284 | TRBV20-1 | TRBJ2-1 | CSASGRAGESNEQFF | 844 | TRAV26-2 | TRAJ45 | NON-PRODUCTIVE | |
| 285 | TRBV20-1 | TRBJ2-7 | CSASKTGVHEQYF | 845 | | | | |
| 286 | TRBV20-1 | TRBJ1-1 | CSASRGNTEAFF | 846 | TRAV9-1 | TRAJ44 | CALRGNTGTASKLTF | 1060 |

Figure 19Q

| TCR # | TCR BETA ||||| TCR ALPHA (FIRST) ||||
|---|---|---|---|---|---|---|---|---|
| | TRBV | TRBJ | CDR3B | SEQ ID NO: | TRAV | TRAJ | CDR3A | SEQ ID NO: |
| 287 | TRBV20-1 | TRBJ2-3 | CSATHRENLTDTQYF | 847 | | | | |
| 288 | TRBV20-1 | TRBJ2-5 | CSATSPLSAGAYQETQYF | 848 | | | | |
| 289 | TRBV20-1 | TRBJ1-5 | CSAVGGPVSQPQHF | 849 | TRAV12-2 | TRAJ52 | CAVIGPGGTSYGKLTF | 1061 |
| 290 | TRBV20-1 | TRBJ2-7 | CSAVRTGGYYEQYF | 850 | | | | |
| 291 | TRBV20-1 | TRBJ1-1 | CSIGGQGLEAFF | 851 | TRAV12-2 | TRAJ10 | CAVIGLTGGGNKLTF | 1062 |
| 292 | TRBV29-1 | TRBJ2-7 | CSVDGALAGGTYEQYF | 852 | TRAV10 | TRAJ15 | CVVSESQAGTALIF | 1063 |
| 293 | TRBV29-1 | TRBJ2-1 | CSVDGSWQFF | 853 | TRAV12-1 | TRAJ12 | CVVNIIKGSSYKLIF | 1064 |
| 294 | TRBV29-1 | TRBJ2-7 | CSVEEGDIRPYEQYF | 854 | TRAV3 | TRAJ40 | CAVRDFSGTYKYIF | 1065 |
| 295 | TRBV29-1 | TRBJ2-2 | CSVELQGNKVGELFF | 855 | TRAV26-1 | TRAJ29 | CIVRVGLSGNTPLVF | 1066 |
| 296 | TRBV20-1 | TRBJ2-1 | CSVLAAYNEQFF | 856 | TRAV17 | TRAJ20 | CATDANDYKLSF | 1067 |
| 297 | TRBV29-1 | TRBJ1-5 | CSVRTGNSNQPQHF | 857 | TRAV2 | TRAJ5 | CAVEGGGRRALTF | 1068 |
| 298 | TRBV29-1 | TRBJ2-3 | CSVSQGRGGDTQYF | 858 | TRAV21 | TRAJ47 | CASYGNKLVF | |
| 299 | TRBV20-1 | TRBJ1-5 | CSTGGMQPQHF | 859 | TRAV3 | TRAJ40 | NON-PRODUCTIVE | 1069 |

Figure 19R

| TCR # | TCR ALPHA (SECOND) | | | SEQ ID NO: | Frequency Unstim(318) | Frequency Stim(279) | Frequency Total(597) |
|---|---|---|---|---|---|---|---|
| | TRAV | TRAJ | CDR3A | | | | |
| 1 | TRAV3 | TRAJ40 | NON-PRODUCTIVE | | 25 | 27 | 52 |
| 2 | | | | | 10 | 24 | 34 |
| 3 | | | | | 8 | 16 | 24 |
| 4 | TRAV26-1 | TRAJ8 | NON-PRODUCTIVE | | 18 | 6 | 24 |
| 5 | TRAV25 | TRAJ34 | NON-PRODUCTIVE | | 4 | 13 | 17 |
| 6 | | | | | 8 | 7 | 15 |
| 7 | TRAV35 | TRAJ42 | NON-PRODUCTIVE | | 8 | 6 | 14 |
| 8 | TRAV16 | TRAJ58 | NON-PRODUCTIVE | | 11 | 3 | 14 |
| 9 | | | | | 11 | 2 | 13 |
| 10 | TRAV26-2 | TRAJ57 | NON-PRODUCTIVE | | 6 | 2 | 8 |
| 11 | TRAV23/DV6 | TRAJ20 | CAASKEDYKLSF | 1070 | 5 | 2 | 7 |
| 12 | TRAV41 | TRAJ35 | CAANFGSFGNMLHC | 1071 | 2 | 4 | 6 |
| 13 | | | | | 5 | | 5 |
| 14 | TRAV19 | TRAJ6 | NON-PRODUCTIVE | | 5 | | 5 |
| 15 | TRAV26-1 | TRAJ7 | CIVRVEENNRLAF | 1072 | 1 | 4 | 5 |
| 16 | TRAV8-4 | TRAJ15 | NON-PRODUCTIVE | | 2 | 3 | 5 |
| 17 | TRAV6 | TRAJ5 | NON-PRODUCTIVE | | 1 | 4 | 5 |
| 18 | | | | | 4 | 1 | 5 |
| 19 | TRAV4 | TRAJ13 | NON-PRODUCTIVE | | 1 | 3 | 4 |
| 20 | TRAV26-1 | TRAJ23 | NON-PRODUCTIVE | | 1 | 3 | 4 |
| 21 | | | | | 3 | 1 | 4 |
| 22 | | | | | 2 | 1 | 3 |
| 23 | TRAV35 | TRAJ40 | NON-PRODUCTIVE | | 3 | | 3 |
| 24 | TRAV8-4 | TRAJ30 | NON-PRODUCTIVE | | 2 | 1 | 3 |

Figure 19S

| TCR # | TCR ALPHA (SECOND) | | | | Frequency | Frequency | Frequency |
|---|---|---|---|---|---|---|---|
| | TRAV | TRAJ | CDR3A | SEQ ID NO: | Unstim(318) | Stim(279) | Total(597) |
| 25 | TRAV3 | TRAJ23 | CAVRGANQGGKLIF | 1073 | 2 | 1 | 3 |
| 26 | | | | | 1 | 2 | 3 |
| 27 | | | | | 2 | 1 | 3 |
| 28 | TRAV6 | TRAJ31 | NON-PRODUCTIVE | | 2 | 1 | 3 |
| 29 | | | | | 2 | | 2 |
| 30 | TRAV26-1 | TRAJ34 | NON-PRODUCTIVE | | 1 | 1 | 2 |
| 31 | TRAV8-6 | TRAJ23 | NON-PRODUCTIVE | | | 2 | 2 |
| 32 | | | | | | 2 | 2 |
| 33 | TRAV23/DV6 | TRAJ10 | CAATTGGGNKLTF | 1074 | 1 | 1 | 2 |
| 34 | | | | | 1 | 1 | 2 |
| 35 | | | | | | 2 | 2 |
| 36 | TRAV12-2 | TRAJ48 | CAVNEPNFGNEKLTF | 1075 | 2 | | 2 |
| 37 | | | | | 1 | 1 | 2 |
| 38 | | | | | 1 | 1 | 2 |
| 39 | | | | | 2 | | 2 |
| 40 | | | | | 2 | | 2 |
| 41 | TRAV19 | TRAJ48 | NON-PRODUCTIVE | | 1 | 1 | 2 |
| 42 | | | | | 2 | | 2 |
| 43 | | | | | 2 | | 2 |
| 44 | TRAV29/DV5 | TRAJ37 | CAAIDSSNTGKLIF | 1076 | | 2 | 2 |
| 45 | | | | | 2 | | 2 |
| 46 | | | | | | 2 | 2 |
| 47 | | | | | | 2 | 2 |
| 48 | TRAV16 | TRAJ30 | NON-PRODUCTIVE | | 2 | | 2 |
| 49 | TRAV12-1 | TRAJ5 | NON-PRODUCTIVE | | 2 | | 2 |
| 50 | | | | | 2 | | 2 |

Figure 19T

| TCR # | TCR ALPHA (SECOND) | | | | Frequency | Frequency | Frequency |
|---|---|---|---|---|---|---|---|
| | TRAV | TRAJ | CDR3A | SEQ ID NO: | Unstim(318) | Stim(279) | Total(597) |
| 51 | TRAV12-2 | TRAJ32 | NON-PRODUCTIVE | | 1 | 1 | 2 |
| 52 | | | | | | 2 | 2 |
| 53 | | | | | 1 | 1 | 2 |
| 54 | | | | | | 2 | 2 |
| 55 | | | | | 1 | 1 | 2 |
| 56 | | | | | | 2 | 2 |
| 57 | TRAV21 | TRAJ16 | NON-PRODUCTIVE | | 1 | 1 | 2 |
| 58 | | | | | 1 | 1 | 2 |
| 59 | | | | | 1 | 1 | 2 |
| 60 | | | | | 2 | | 2 |
| 61 | | | | | | 2 | 2 |
| 62 | TRAV16 | TRAJ52 | NON-PRODUCTIVE | | 2 | | 2 |
| 63 | TRAV2 | TRAJ9 | | | 1 | 1 | 2 |
| 64 | | | | | | 1 | 1 |
| 65 | | | | | | 1 | 1 |
| 66 | TRAV38/DV8 | TRAJ27 | NON-PRODUCTIVE | | 1 | | 1 |
| 67 | | | | | | 1 | 1 |
| 68 | | | | | | 1 | 1 |
| 69 | | | | | 1 | | 1 |
| 70 | | | | | 1 | 1 | 1 |
| 71 | | | | | 1 | | 1 |
| 72 | | | | | 1 | | 1 |
| 73 | | | | | | 1 | 1 |
| 74 | | | | | 1 | | 1 |
| 75 | | TRAJ22 | | | | | 1 |
| 76 | | | NON-PRODUCTIVE | | | 1 | 1 |

Figure 19U

| TCR # | TCR ALPHA (SECOND) | | | SEQ ID NO: | Frequency Unstim(318) | Frequency Stim(279) | Frequency Total(597) |
|---|---|---|---|---|---|---|---|
| | TRAV | TRAJ | CDR3A | | | | |
| 77 | | | | | 1 | | 1 |
| 78 | TRAV13-1 | TRAJ29 | CAASDSGNTPLVF | 1077 | 1 | | 1 |
| 79 | | | | | | 1 | 1 |
| 80 | | | | | 1 | | 1 |
| 81 | | | | | 1 | | 1 |
| 82 | TRAV26-1 | TRAJ48 | | | | | 1 |
| 83 | | | | | 1 | | 1 |
| 84 | | | | | 1 | | 1 |
| 85 | | | | | | 1 | 1 |
| 86 | TRAV38/DV8 | TRAJ22 | NON-PRODUCTIVE | | 1 | | 1 |
| 87 | | | | | 1 | | 1 |
| 88 | | | | | | 1 | 1 |
| 89 | TRAV3 | TRAJ42 | NON-PRODUCTIVE | | 1 | | 1 |
| 90 | TRAV12-1 | TRAJ23 | CVVNKGIDQGGKLIF | 1078 | 1 | | 1 |
| 91 | | | | | | 1 | 1 |
| 92 | | | | | 1 | | 1 |
| 93 | | | | | 1 | | 1 |
| 94 | | | | | | 1 | 1 |
| 95 | | | | | 1 | | 1 |
| 96 | | | | | 1 | | 1 |
| 97 | | | | | | 1 | 1 |
| 98 | TRAV25 | TRAJ20 | NON-PRODUCTIVE | | | 1 | 1 |
| 99 | | | | | | 1 | 1 |
| 100 | | | | | | | 1 |
| 101 | | | | | 1 | | 1 |
| 102 | TRAV1-1 | TRAJ32 | NON-PRODUCTIVE | | | | 1 |

Figure 19V

| | TCR ALPHA (SECOND) | | | | Frequency | Frequency | Frequency |
|---|---|---|---|---|---|---|---|
| TCR # | TRAV | TRAJ | CDR3A | SEQ ID NO: | Unstim(318) | Stim(279) | Total(597) |
| 103 | | | | | | | 1 |
| 104 | | | | | 1 | | 1 |
| 105 | | | | | 1 | | 1 |
| 106 | TRAV38/DV8 | TRAJ44 | NON-PRODUCTIVE | | | 1 | 1 |
| 107 | | | | | 1 | | 1 |
| 108 | | | | | 1 | | 1 |
| 109 | | | | | 1 | | 1 |
| 110 | | | | | 1 | | 1 |
| 111 | TRAV1-1 | TRAJ35 | NON-PRODUCTIVE | | 1 | | 1 |
| 112 | | | | | | | 1 |
| 113 | | | | | | | 1 |
| 114 | | | | | | | 1 |
| 115 | | | | | | | 1 |
| 116 | TRAV26-2 | TRAJ23 | NON-PRODUCTIVE | | | 1 | 1 |
| 117 | | | | | | 1 | 1 |
| 118 | | | | | | 1 | 1 |
| 119 | | | | | 1 | | 1 |
| 120 | | | | | | 1 | 1 |
| 121 | | | | | | | 1 |
| 122 | | | | | | | 1 |
| 123 | | | | | 1 | | 1 |
| 124 | TRAV38/DV8 | TRAJ57 | CAYRTTQGGSEKLVF | 1079 | 1 | | 1 |
| 125 | TRAV4 | TRAJ9 | NON-PRODUCTIVE | | | 1 | 1 |
| 126 | TRAV16 | TRAJ53 | NON-PRODUCTIVE | | | 1 | 1 |
| 127 | | | | | | | 1 |
| 128 | | | | | | | 1 |

Figure 19W

| TCR # | TCR ALPHA (SECOND) | | | | Frequency | Frequency | Frequency |
| --- | --- | --- | --- | --- | --- | --- | --- |
| | TRAV | TRAJ | CDR3A | SEQ ID NO: | Unstim(318) | Stim(279) | Total(597) |
| 129 | | | | | 1 | | 1 |
| 130 | | | | | | 1 | 1 |
| 131 | | | | | | 1 | 1 |
| 132 | TRAV9-1 | TRAJ22 | NON-PRODUCTIVE | | 1 | | 1 |
| 133 | | | | | 1 | | 1 |
| 134 | TRAV12-2 | TRAJ18 | CAVRGRGSTLGRLYF | 1080 | | 1 | 1 |
| 135 | | | | | | 1 | 1 |
| 136 | | | | | | 1 | 1 |
| 137 | TRAV26-1 | TRAJ54 | NON-PRODUCTIVE | | 1 | | 1 |
| 138 | | | | | 1 | | 1 |
| 139 | | | | | | 1 | 1 |
| 140 | | | | | | 1 | 1 |
| 141 | | | | | | 1 | 1 |
| 142 | | | | | | 1 | 1 |
| 143 | | | | | | 1 | 1 |
| 144 | | | | | | 1 | 1 |
| 145 | | | | | 1 | | 1 |
| 146 | | | | | | 1 | 1 |
| 147 | TRAV16 | TRAJ3 | NON-PRODUCTIVE | | 1 | | 1 |
| 148 | | | | | 1 | | 1 |
| 149 | | | | | | 1 | 1 |
| 150 | | | | | | 1 | 1 |
| 151 | | | | | | 1 | 1 |
| 152 | | | | | | 1 | 1 |
| 153 | | | | | 1 | | 1 |
| 154 | | | | | | 1 | 1 |

Figure 19X

| TCR # | TCR ALPHA (SECOND) | | | SEQ ID NO: | Frequency Unstim(318) | Frequency Stim(279) | Frequency Total(597) |
|---|---|---|---|---|---|---|---|
| | TRAV | TRAJ | CDR3A | | | | |
| 155 | | | | | | | 1 |
| 156 | | | | | | 1 | 1 |
| 157 | | | | | 1 | | 1 |
| 158 | | | | | 1 | | 1 |
| 159 | | | | | 1 | | 1 |
| 160 | | | | | | 1 | 1 |
| 161 | | | | | 1 | | 1 |
| 162 | | | | | 1 | | 1 |
| 163 | | | | | 1 | | 1 |
| 164 | | | | | 1 | | 1 |
| 165 | TRAV8-4 | TRAJ16 | NON-PRODUCTIVE | | | | 1 |
| 166 | TRAV12-1 | TRAJ37 | NON-PRODUCTIVE | | | 1 | 1 |
| 167 | | | | | 1 | | 1 |
| 168 | | | | | 1 | | 1 |
| 169 | | | | | 1 | | 1 |
| 170 | | | | | 1 | | 1 |
| 171 | | | | | 1 | | 1 |
| 172 | | | | | 1 | | 1 |
| 173 | TRAV39 | TRAJ45 | NON-PRODUCTIVE | | 1 | | 1 |
| 174 | | | | | 1 | | 1 |
| 175 | | TRAJ52 640 | NON-PRODUCTIVE | | 1 | | 1 |
| 176 | | | | | 1 | | 1 |
| 177 | | | | | | | 1 |
| 178 | TRAV12-3 | TRAJ48 | NON-PRODUCTIVE | | | 1 | 1 |
| 179 | | | | | | | 1 |

Figure 19Y

| TCR # | TCR ALPHA (SECOND) | | | SEQ ID NO: | Frequency Unstim(318) | Frequency Stim(279) | Frequency Total(597) |
|---|---|---|---|---|---|---|---|
| | TRAV | TRAJ | CDR3A | | | | |
| 180 | | | | | | | |
| 181 | | | | | | | 1 |
| 182 | | TRAJ4 | NON-PRODUCTIVE | | | 1 | 1 |
| 183 | | | | | | 1 | 1 |
| 184 | | | | | 1 | | 1 |
| 185 | TRAV27 | TRAJ24 | CAGPTTDSWGKLQF | 1081 | | 1 | 1 |
| 186 | | | | | | 1 | 1 |
| 187 | | | | | | 1 | 1 |
| 188 | TRAV3 | TRAJ9 | NON-PRODUCTIVE | | 1 | | 1 |
| 189 | | | | | 1 | | 1 |
| 190 | TRAV38/DV8 | TRAJ40 | CAYRSAVGAYKYIF | 1082 | 1 | | 1 |
| 191 | TRAV41 | TRAJ45 | NON-PRODUCTIVE | | | | 1 |
| 192 | | | | | | | 1 |
| 193 | | | | | 1 | | 1 |
| 194 | | | | | | 1 | 1 |
| 195 | | | | | | 1 | 1 |
| 196 | | | | | 1 | | 1 |
| 197 | | | | | | 1 | 1 |
| 198 | | | | | 1 | | 1 |
| 199 | | | | | | 1 | 1 |
| 200 | | | | | | | 1 |
| 201 | TAV6 | TRAJ31 | NON-PRODUCTIVE | | | 1 | 1 |
| 202 | | | | | | | 1 |
| 203 | | | | | | 1 | 1 |
| 204 | | | | | 1 | | 1 |
| 205 | | | | | 1 | | 1 |

Figure 19Z

| TCR # | TCR ALPHA (SECOND) | | | SEQ ID NO: | Frequency Unstim(318) | Frequency Stim(279) | Frequency Total(597) |
|---|---|---|---|---|---|---|---|
| | TRAV | TRAJ | CDR3A | | | | |
| 206 | | | | | | | 1 |
| 207 | TRAV27 | TRAJ32 | NON-PRODUCTIVE | | | 1 | 1 |
| 208 | | | | | 1 | | 1 |
| 209 | | TRAJ6 | NON-PRODUCTIVE | | 1 | | 1 |
| 210 | | | | | | 1 | 1 |
| 211 | | | | | 1 | | 1 |
| 212 | TRAV19 | TRAJ41 | NON-PRODUCTIVE | | 1 | | 1 |
| 213 | | | | | | 1 | 1 |
| 214 | | | | | | 1 | 1 |
| 215 | | | | | 1 | | 1 |
| 216 | | | | | | 1 | 1 |
| 217 | TRAV6 | TRAJ31 | NON-PRODUCTIVE | | 1 | | 1 |
| 218 | | | | | | 1 | 1 |
| 219 | TRAV26-1 | TRAJ45 | CIVRVEGADGLTF | 1083 | | 1 | 1 |
| 220 | | | | | | 1 | 1 |
| 221 | | | | | | 1 | 1 |
| 222 | | | | | | 1 | 1 |
| 223 | | | | | | 1 | 1 |
| 224 | | | | | 1 | | 1 |
| 225 | | | | | | 1 | 1 |
| 226 | | | | | 1 | | 1 |
| 227 | | | | | | 1 | 1 |
| 228 | | | | | 1 | | 1 |
| 229 | | | | | 1 | | 1 |
| 230 | | | | | | 1 | 1 |
| 231 | | | | | 1 | | 1 |

Figure 19AA

| TCR # | TCR ALPHA (SECOND) | | | | Frequency | Frequency | Frequency |
|---|---|---|---|---|---|---|---|
| | TRAV | TRAJ | CDR3A | SEQ ID NO: | Unstim(318) | Stim(279) | Total(597) |
| 232 | TRAV13-1 | TRAJ5 | NON-PRODUCTIVE | | | 1 | 1 |
| 233 | TRAV25 | TRAJ20 | CAGVNDYKLSF | 1084 | | 1 | 1 |
| 234 | | | | | | 1 | 1 |
| 235 | | | | | | 1 | 1 |
| 236 | | | | | | 1 | 1 |
| 237 | | | | | | 1 | 1 |
| 238 | | | | | 1 | | 1 |
| 239 | | | | | 1 | | 1 |
| 240 | | | | | | 1 | 1 |
| 241 | | | | | | 1 | 1 |
| 242 | | | | | 1 | | 1 |
| 243 | | | | | 1 | | 1 |
| 244 | | | | | 1 | | 1 |
| 245 | | | | | | 1 | 1 |
| 246 | | | | | | 1 | 1 |
| 247 | | | | | | 1 | 1 |
| 248 | | | | | | 1 | 1 |
| 249 | | | | | | 1 | 1 |
| 250 | TRAV8-4 | TRAJ20 | NON-PRODUCTIVE | | 1 | | 1 |
| 251 | | | | | 1 | | 1 |
| 252 | | | | | | 1 | 1 |
| 253 | | | | | 1 | | 1 |
| 254 | | | | | | 1 | 1 |
| 255 | | | | | 1 | | 1 |
| 256 | | | | | | 1 | 1 |
| 257 | | | | | | 1 | 1 |

Figure 19AB

| | TCR ALPHA (SECOND) | | | SEQ ID NO: | Frequency Unstim(318) | Frequency Stim(279) | Frequency Total(597) |
|---|---|---|---|---|---|---|---|
| TCR # | TRAV | TRAJ | CDR3A | | | | |
| 258 | TRAV3 | TRAJ37 | NON-PRODUCTIVE | | | 1 | 1 |
| 259 | | | | | 1 | | 1 |
| 260 | | | | | 1 | | 1 |
| 261 | | | | | 1 | | 1 |
| 262 | | | | | 1 | | 1 |
| 263 | | | | | | 1 | 1 |
| 264 | | | | | | 1 | 1 |
| 265 | | | | | 1 | | 1 |
| 266 | | | | | 1 | | 1 |
| 267 | | | | | | 1 | 1 |
| 268 | | | | | | 1 | 1 |
| 269 | | | | | 1 | | 1 |
| 270 | | | | | | 1 | 1 |
| 271 | | | | | 1 | | 1 |
| 272 | | | | | | 1 | 1 |
| 273 | | | | | 1 | | 1 |
| 274 | | | | | 1 | | 1 |
| 275 | | | | | 1 | | 1 |
| 276 | TRAV26-2 | TRAJ24 | NON-PRODUCTIVE | | | | 1 |
| 277 | | | | | | | 1 |
| 278 | TRAV26-2 | TRAJ52 | NON-PRODUCTIVE | | | | 1 |
| 279 | | | | | | | 1 |
| 280 | | | | | | | 1 |
| 281 | | | | | | 1 | 1 |
| 282 | | | | | | 1 | 1 |
| 283 | | | | | | 1 | 1 |

Figure 19AC

| TCR # | TCR ALPHA (SECOND) | | | SEQ ID NO: | Frequency Unstim(318) | Frequency Stim(279) | Frequency Total(597) |
|---|---|---|---|---|---|---|---|
| | TRAV | TRAJ | CDR3A | | | | |
| 284 | | | | | | | 1 |
| 285 | | | | | 1 | | 1 |
| 286 | | | | | 1 | | 1 |
| 287 | | | | | 1 | | 1 |
| 288 | | | | | | 1 | 1 |
| 289 | | | | | 1 | | 1 |
| 290 | | | | | 1 | | 1 |
| 291 | | | | | | 1 | 1 |
| 292 | TRAV13-1 | TRAJ39 | CAAINAGNMLTF | 1085 | 1 | | 1 |
| 293 | | | | | | 1 | 1 |
| 294 | | | | | 1 | | 1 |
| 295 | | | | | | 1 | 1 |
| 296 | | | | | | 1 | 1 |
| 297 | | | | | 1 | | 1 |
| 298 | | | | | | 1 | 1 |
| 299 | | | | | | | 1 |

Figure 20A

Table 9.

| TCR # | TCR beta | | | SEQ ID NO: | TCR alpha (first) | | | SEQ ID NO: |
|---|---|---|---|---|---|---|---|---|
| | TRBV | TRBJ | CDR3B | | TRAV | TRAJ | CDR3A | |
| 1 | TRBV5-1 | TRBJ2-1 | CASRPGPGVGNEQFF | 1086 | TRAV23/DV6 | TRAJ3 | CAASMIGSSASKIIF | 1391 |
| 2 | TRBV5-1 | TRBJ2-3 | CASSLIMGTSGGEATIYQYF | 1087 | TRAV16 | TRAJ43 | CALRPNNNDMRF | 1392 |
| 3 | TRBV7-3 | TRBJ1-1 | CASSLLGQLNTEAFF | 1088 | TRAV17 | TRAJ52 | CATAPNAGGTSYGKLTF | 1393 |
| 4 | TRBV4-1 | TRBJ2-7 | CASSQGPVGYEQYF | 1089 | TRAV8-2 | TRAJ49 | CAVTGDTYGNQFYF | 1394 |
| 5 | TRBV7-2 | TRBJ2-6 | CAEGSNSGANVLTF | 1090 | TRAV16 | TRAJ42 | CALSGRDGGSQGNLIF | 1395 |
| 6 | TRBV10-3 | TRBJ2-5 | CAIRDRQETQYF | 1091 | TRAV1-2 | TRAJ31 | CAVRDNNARLMF | 1396 |
| 7 | TRBV10-3 | TRBJ2-7 | CAIRTGSSSYEQYF | 1092 | TRAV12-1 | TRAJ49 | CVVYVPTGNQFYF | 1397 |
| 8 | TRBV10-3 | TRBJ2-1 | CAIRVGNGNEQFF | 1093 | TRAV12-2 | TRAJ17 | CAVMGAGNKLTF | 1398 |
| 9 | TRBV10-3 | TRBJ2-1 | CAISELAGVVNEQFF | 1094 | TRAV12-3 | TRAJ32 | NON-PRODUCTIVE | |
| 10 | TRBV10-3 | TRBJ1-1 | CAISESAMDTEAFF | 1095 | TRAV1-1 | TRAJ13 | NON-PRODUCTIVE | |
| 11 | TRBV10-3 | TRBJ1-1 | CAISESKGGTEAFF | 1096 | TRAV17 | TRAJ34 | CAYDASKNTDKLIF | 1399 |
| 12 | TRBV10-3 | TRBJ1-2 | CAISESTVQNGYTF | 1097 | TRAV13-1 | TRAJ49 | CAASISGNQFYF | 1400 |
| 13 | TRBV10-3 | TRBJ1-1 | CAISFDRGTEAFF | 1098 | TRAV26-2 | TRAJ39 | CILRDSGNAGNMLTF | 1401 |
| 14 | TRBV10-3 | TRBJ2-1 | CAISGGGLAEWHEQFF | 1099 | TRAV38-1 | TRAJ37 | CVIHGSSNTGKLIF | 1402 |
| 15 | TRBV10-3 | TRBJ1-2 | CAISLQDLPSYGYTF | 1100 | TRAV17 | TRAJ41 | CATLTRSGYALNF | 1403 |
| 16 | TRBV10-3 | TRBJ2-7 | CAITAGQGTRNEQYF | 1101 | TRAV26-1 | TRAJ45 | CLVRGHSGGGADGLTF | 1404 |
| 17 | TRBV19 | TRBJ2-2 | CASAPGRGVDTGELFF | 1102 | | | | |
| 18 | TRBV2 | TRBJ1-2 | CASARDSYGYTF | 1103 | TRAV2 | TRAJ30 | CAVSNRDDKIIF | 1405 |

Figure 20B

| TCR # | TCR beta | | | SEQ ID NO: | TCR alpha (first) | | | SEQ ID NO: |
|---|---|---|---|---|---|---|---|---|
| | TRBV | TRBJ | CDR3B | | TRAV | TRAJ | CDR3A | |
| 19 | TRBV5-1 | TRBJ1-3 | CASASRDPQDTIYF | 1104 | | | | |
| 20 | TRBV2 | TRBJ2-7 | CASHGDESAQYF | 1105 | TRAV9-2 | TRAJ39 | CAVSNRDDKIIF | 1406 |
| 21 | TRBV28 | TRBJ2-7 | CASISLRGGPYEQYF | 1106 | | | | |
| 22 | TRBV28 | TRBJ2-3 | CASKQGAIDTQYF | 1107 | TRAV8-4 | TRAJ43 | NON-PRODUCTIVE | |
| 23 | TRBV6-5 | TRBJ1-4 | CASKVGAMGEKLFF | 1108 | TRAV3 | TRAJ40 | CAVRDTSGTYKYIF | 1407 |
| 24 | TRBV6-1 | TRBJ2-3 | CASRAAGTDTQYF | 1109 | TRAV26-1 | TRAJ48 | CIVRGLSNFGNEKLTF | 1408 |
| 25 | TRBV12-3 | TRBJ1-3 | CASREGGSSGNTIYF | 1110 | TRAV27 | TRAJ40 | CARTSGTYKYIF | 1409 |
| 26 | TRBV10-2 | TRBJ2-2 | CASRRQGPTQTGELFF | 1111 | TRAV9-2 | TRAJ39 | CALNNAGNMLTF | 1410 |
| 27 | TRBV7-2 | TRBJ2-1 | CASREWTSGGNEQFF | 1112 | TRAV19 | TRAJ36 | CPKIQTGANNLFF | 1411 |
| 28 | TRBV19 | TRBJ1-6 | CASRGGGTSPLHF | 1113 | TRAV12-2 | TRAJ52 | | |
| 29 | TRBV19 | TRBJ1-1 | CASRKDRDTEAFF | 1114 | TRAV13-2 | TRAJ18 | CAENIGHRGSTLGRLYF | 1412 |
| 30 | TRBV6-6 | TRBJ1-3 | CASRKGTQGARSGNTIYF | 1115 | TRAV14/DV4 | TRAJ39 | CAMREGMGNAGNMLTF | 1413 |
| 31 | TRBV5-4 | TRBJ2-5 | CASRMGSQETQYF | 1116 | TRAV14/DV4 | TRAJ43 | | |
| 32 | TRBV6-5 | TRBJ1-1 | CASRNQGGPGTEAFF | 1117 | TRAV29/DV5 | TRAJ32 | CAGGATNKLIF | 1414 |
| 33 | TRBV2 | TRBJ1-5 | CASRPGTGRDQPQHF | 1118 | TRAV27 | TRAJ47 | CAAEREGNKLVF | 1415 |
| 34 | TRBV19 | TRBJ1-1 | CASRPREHENTEAFF | 1119 | TRAV25 | TRAJ47 | CAGFEYGNKLVF | 1416 |
| 35 | TRBV6-1 | TRBJ2-3 | CASRQQTGTADTQYF | 1120 | TRAV16 | TRAJ52 | CALSGTSYGKLTF | 1417 |
| 36 | TRBV27 | TRBJ2-7 | CASRRAGGRYEQYF | 1121 | TRAV4 | TRAJ28 | CLVGDPSGAGSYQLIF | 1418 |
| 37 | TRBV6-1 | TRBJ2-3 | CASRPGLAGSDTQYF | 1122 | TRAV26-1 | TRAJ40 | CIVRVGTSGTYKYIF | 1419 |
| 38 | TRBV2 | TRBJ1-6 | CASRRQGGNSPLHF | 1123 | TRAV6 | TRAJ33 | CALDISYQLIW | 1420 |
| 39 | TRBV27 | TRBJ1-3 | CASRSTGAGYGNTIYF | 1124 | TRAV14/DV4 | TRAJ20 | CAMREFRSNDYKLSF | 1421 |
| 40 | TRBV11-2 | TRBJ2-2 | CASSAAGSSGELFF | 1125 | TRAV9-2 | TRAJ21 | CALYNFNKFYF | 1422 |
| 41 | TRBV11-3 | TRBJ2-5 | CASSAGTGEETQYF | 1126 | TRAV23/DV6 | TRAJ10 | CAASILTGGGNKLTF | 1423 |
| 42 | TRBV2 | TRBJ2-2 | CASSAIEGTSGELFF | 1127 | TRAV12-2 | TRAJ47 | CAVPKMEYGNKLVF | 1424 |

Figure 20C

| TCR # | TCR beta ||| TCR alpha (first) ||||
|---|---|---|---|---|---|---|---|
| | TRBV | TRBJ | CDR3B | SEQ ID NO: | TRAV | TRAJ | CDR3A | SEQ ID NO: |
| 43 | TRBV9 | TRBJ1-4 | CASSAPGANEKLFF | 1128 | | TRAJ40 | CAVDPSGTYKYIF | 1425 |
| 44 | TRBV2 | TRBJ2-1 | CASSAREQFF | 1129 | TRAV22 | TRAJ53 | CIVRGVNSGGSNYKLTF | 1426 |
| 45 | TRBV2 | TRBJ2-1 | CASSARQDPGLSFF | 1130 | TRAV26-1 | TRAJ17 | CALSEANRVKAAGNKLTF | 1427 |
| 46 | TRBV5-1 | TRBJ2-5 | CASSATSGKGGRETQYF | 1131 | TRAV19 | TRAJ49 | CILKPGNQFYF | 1428 |
| 47 | TRBV19 | TRBJ1-1 | CASSAYVLGTEAFF | 1132 | TRAV26-2 | TRAJ46 | CAATKKSSGDKLTF | 1429 |
| 48 | TRBV19 | TRBJ1-2 | CASSDAGGRDYGYTF | 1133 | TRAV13-1 | TRAJ16 | NON-PRODUCTIVE | |
| 49 | TRBV2 | TRBJ2-5 | CASSDGAQETQYF | 1134 | TRAV14/DV4 | TRAJ38 | NON-PRODUCTIVE | |
| 50 | TRBV10-2 | TRBJ2-7 | CASSDHERDGREQYF | 1135 | TRAV1-2 | TRAJ53 | NON-PRODUCTIVE | |
| 51 | TRBV25-1 | TRBJ1-2 | CASSDPGTGNYGYTF | 1136 | TRAV25 | | | |
| 52 | TRBV19 | TRBJ1-1 | CASSDRGDSTEAFF | 1137 | | TRAJ9 | NON-PRODUCTIVE | |
| 53 | TRBV6-1 | TRBJ2-1 | CASSDWGGRNDEQFF | 1138 | TRAV13-1 | | | |
| 54 | TRBV10-2 | TRBJ1-1 | CASSEAGRRTEAFF | 1139 | | | | |
| 55 | TRBV5-1 | TRBJ2-3 | CASSEGEVTDTQYF | 1140 | TRAV19 | TRAJ35 | NON-PRODUCTIVE | 1430 |
| 56 | TRBV2 | TRBJ1-5 | CASSEGGQNNQPQHF | 1141 | TRAV9-2 | TRAJ20 | CALSAGDYKLSF | |
| 57 | TRBV6-1 | TRBJ1-5 | CASSEGGQSNQPQHF | 1142 | TRAV17 | TRAJ49 | NON-PRODUCTIVE | |
| 58 | TRBV6-1 | TRBJ2-7 | CASSEGSPYEQYF | 1143 | TRAV9-2 | TRAJ7 | CALSQFYGNNRLAF | 1431 |
| 59 | TRBV6-1 | TRBJ1-2 | CASSEQRGGQATFYGYTF | 1144 | TRAV12-2 | TRAJ17 | CAVRAAGNKLTF | 1432 |
| 60 | TRBV25-1 | TRBJ2-1 | CASSESEGATYNEQFF | 1145 | TRAV12-1 | TRAJ28 | CVVLGAGSYQLTF | 1433 |
| 61 | TRBV9 | TRBJ2-7 | CASSETAGGMGEQYF | 1146 | | | | |
| 62 | TRBV2 | TRBJ2-7 | CASSEVGQQGYEQYF | 1147 | TRAV3 | TRAJ49 | NON-PRODUCTIVE | |
| 63 | TRBV25-1 | TRBJ1-1 | CASSEYGGRTEAFF | 1148 | TRAV21 | TRAJ37 | CAVRPRSSNTGKLIF | 1434 |
| 64 | TRBV5-1 | TRBJ2-5 | CASSFEGTQYF | 1149 | TRAV19 | TRAJ35 | NON-PRODUCTIVE | |
| 65 | TRBV28 | TRBJ2-1 | CASSFERLEVNEQFF | 1150 | TRAV5 | TRAJ18 | CAESGGGSTLGRLYF | 1435 |

Figure 20D

| TCR # | TCR beta | | | | TCR alpha (first) | | | |
|---|---|---|---|---|---|---|---|---|
| | TRBV | TRBJ | CDR3B | SEQ ID NO: | TRAV | TRAJ | CDR3A | SEQ ID NO: |
| 66 | TRBV5-6 | TRBJ1-4 | CASSFFGGNEKLFF | 1151 | | | | |
| 67 | TRBV13 | TRBJ2-1 | CASSFGLGEQFF | 1152 | TRAV38-2/DV8 | TRAJ31 | CAVRSAGNNARLMF | 1436 |
| 68 | TRBV27 | TRBJ2-3 | CASSFMVAATDTQYF | 1153 | TRAV12-2 | TRAJ8 | CAVNEGFQKLVF | 1437 |
| 69 | TRBV27 | TRBJ2-6 | CASSFQAGANVLTF | 1154 | TRAV13-1 | TRAJ26 | CAASSLVYGQNFVF | 1438 |
| 70 | TRBV7-9 | TRBJ2-2 | CASSFRGSNTGELFF | 1155 | TRAV14/DV4 | TRAJ21 | NON-PRODUCTIVE | |
| 71 | TRBV12-3 | TRBJ2-2 | CASSFRYTGELFF | 1156 | TRAV38-2/DV8 | TRAJ15 | CAYRNTLNQAGTALIF | 1439 |
| 72 | TRBV7-2 | TRBJ2-7 | CASSFSGTSPYEQYF | 1157 | TRAV2 | TRAJ22 | CAVGGVSSGSARQLTF | 1440 |
| 73 | TRBV12-3 | TRBJ2-6 | CASSFSSGANVLTF | 1158 | TRAV6 | TRAJ39 | NON-PRODUCTIVE | |
| 74 | TRBV5-1 | TRBJ1-1 | CASSFTGDPPLGTEAFF | 1159 | | | | |
| 75 | TRBV10-2 | TRBJ1-1 | CASSGEGTEAFF | 1160 | TRAV29/DV5 | TRAJ33 | CAASAHDNYQLIW | 1441 |
| 76 | TRBV27 | TRBJ1-6 | CASSGPNYNSFLHF | 1161 | TRAV12-1 | TRAJ13 | CVVPNSGGYQKVTF | 1442 |
| 77 | TRBV2 | TRBJ2-7 | CASSGQSIYEQYF | 1162 | TRAV25 | TRAJ39 | NON-PRODUCTIVE | |
| 78 | TRBV7-2 | TRBJ1-2 | CASSGKENYGYTF | 1163 | TRAV29/DV5 | TRAJ41 | CAAMSSNSGYALNF | 1443 |
| 79 | TRBV12-3 | TRBJ1-5 | CASSGTGGAADQPQHF | 1164 | TRAV9-2 | TRAJ6 | CALGSGGSYIPTF | 1444 |
| 80 | TRBV5-1 | TRBJ1-5 | CASSGTGGGPQHF | 1165 | TRAV20 | TRAJ52 | CAVTMAGGTSYGKLTF | 1445 |
| 81 | TRBV5-1 | TRBJ2-3 | CASSHGQGYADTQYF | 1166 | TRAV27 | TRAJ20 | CAGADDYKLSF | 1446 |
| 82 | TRBV19 | TRBJ2-1 | CASSIDRMAGGSYNEQFF | 1167 | TRAV26-2 | TRAJ48 | NON-PRODUCTIVE | |
| 83 | TRBV5-1 | TRBJ2-5 | CASSIQGGSVQRKTQYF | 1168 | TRAV24 | TRAJ54 | CAFNWGAQKLVF | 1447 |
| 84 | TRBV19 | TRBJ1-1 | CASSIREDTEAFF | 1169 | TRAV2 | TRAJ21 | CAVGDFNKFYF | 1448 |
| 85 | TRBV19 | TRBJ2-1 | CASSISASGGSYNEQFF | 1170 | TRAV29/DV5 | TRAJ29 | CAASVAFSGNTPLVF | 1449 |
| 86 | TRBV19 | TRBJ2-3 | CASSK.IRTGKRQAVNTDTQYF | 1171 | TRAV3 | TRAJ43 | CAVRDISDNDMRF | 1450 |
| 87 | TRBV28 | TRBJ2-7 | CASSKRAIEQYF | 1172 | TRAV21 | TRAJ27 | CAVRFPTNAGKSTF | 1451 |
| 88 | TRBV7-2 | TRBJ2-7 | CASSLAGGGSAYEQYF | 1173 | TRAV2 | TRAJ3 | CAVDSSASKIIF | 1452 |

Figure 20E

| TCR # | TCR beta | | | | TCR alpha (first) | | | |
|---|---|---|---|---|---|---|---|---|
| | TRBV | TRBJ | CDR3B | SEQ ID NO: | TRAV | TRAJ | CDR3A | SEQ ID NO: |
| 89 | TRBV28 | TRBJ2-7 | CASSLAGTGYEQYF | 1174 | TRAV14/DV4 | TRAJ49 | CAMRMMNTGNQFYF | 1453 |
| 90 | TRBV5-1 | TRBJ1-1 | CASSLAPQDQAFF | 1175 | TRAV1-2 | TRAJ32 | CAAANYGGATNKLIF | 1454 |
| 91 | TRBV12-3 | TRBJ1-2 | CASSLARQGDRNYGYTF | 1176 | TRAV9-2 | TRAJ5 | NON-PRODUCTIVE | |
| 92 | TRBV5-6 | TRBJ2-2 | CASSLASATHTGELFF | 1177 | TRAV19 | TRAJ40 | NON-PRODUCTIVE | |
| 93 | TRBV7-2 | TRBJ2-1 | CASSLDGAGVSLNEQFF | 1178 | TRAV12-1 | TRAJ6 | CVVIRSYIPTF | 1455 |
| 94 | TRBV5-1 | TRBJ2-2 | CASSLDGARDTGELFF | 1179 | TRAV6 | TRAJ48 | CAPDFGNEKLTF | 1456 |
| 95 | TRBV5-1 | TRBJ1-3 | CASSLNGGAGNTIYF | 1180 | | | | |
| 96 | TRBV5-1 | TRBJ2-3 | CASSLLDGLAGTDTQYF | 1181 | TRAV12-2 | TRAJ9 | CAVNIGGGFKTIF | 1457 |
| 97 | TRBV11-2 | TRBJ2-5 | CASSLLDWRQESETQYF | 1182 | | | | |
| 98 | TRBV28 | TRBJ2-7 | CASSLEAGDIYEQYF | 1183 | TRAV27 | TRAJ53 | NON-PRODUCTIVE | |
| 99 | TRBV11-2 | TRBJ2-2 | CASSLEGAGYTGELFF | 1184 | | | | |
| 100 | TRBV5-1 | TRBJ2-2 | CASSLEGAGQAVTGELFF | 1185 | | | | |
| 101 | TRBV7-2 | TRBJ1-2 | CASSLEGVGQNYGYTF | 1186 | TRAV8-2 | TRAJ15 | CVVRSQAGTALIF | 1458 |
| 102 | TRBV7-2 | TRBJ2-1 | CASSLERGLAGVVGHQFF | 1187 | | | | |
| 103 | TRBV7-6 | TRBJ2-7 | CASSLESSGSLGEQYF | 1188 | TRAV26-1 | TRAJ52 | CIVRGNAGGTSYGKLTF | 1459 |
| 104 | TRBV12-3 | TRBJ1-1 | CASSLETRNTEAFF | 1189 | TRAV2 | TRAJ20 | CAVSNDYKLSF | 1460 |
| 105 | TRBV7-2 | TRBJ1-1 | CASSLFLENTEAFF | 1190 | TRAV13-1 | TRAJ5 | CAASAGTGRRALITF | 1461 |
| 106 | TRBV27 | TRBJ1-3 | CASSLFLGTGNTIYF | 1191 | TRAV13-2 | TRAJ31 | NON-PRODUCTIVE | |
| 107 | TRBV7-9 | TRBJ2-5 | CASSLGAGAGALGETQYF | 1192 | TRAV19 | TRAJ52 | CALSESGGGTSYGKLTF | 1462 |
| 108 | TRBV6-4 | TRBJ2-3 | CASSLGAGGATDQYF | 1193 | TRAV22 | TRAJ20 | CAVGNYNDYKLSF | 1463 |
| 109 | TRBV5-4 | TRBJ1-4 | CASSLGGDRGAEKLFF | 1194 | TRAV26-1 | TRAJ53 | CIVIESGGSNYKLTF | 1464 |
| 110 | TRBV5-1 | TRBJ1-1 | CASSLGGGTEAFF | 1195 | TRAV19 | TRAJ49 | NON-PRODUCTIVE | |
| 111 | TRBV12-3 | TRBJ2-7 | CASSLGGSFSYEQYF | 1196 | TRAV26-1 | TRAJ49 | NON-PRODUCTIVE | |

Figure 20F

| TCR # | TCR beta ||| SEQ ID NO: | TCR alpha (first) |||| SEQ ID NO: |
|---|---|---|---|---|---|---|---|---|---|
| | TRBV | TRBJ | CDR3B | | TRAV | TRAJ | CDR3A | | |
| 112 | TRBV5-1 | TRBJ1-5 | CASSLGSGASNQPQHF | 1197 | TRAV20 | TRAJ56 | CAVRETGANSKLTF | | 1465 |
| 113 | TRBV6-1 | TRBJ1-2 | CASSLGTFNYGYTF | 1198 | | TRAJ37 | NON-PRODUCTIVE | | |
| 114 | TRBV5-1 | TRBJ2-5 | CASSLGTSQETQYF | 1199 | | | | | |
| 115 | TRBV5-4 | TRBJ2-3 | CASSLGVAPTDTQYF | 1200 | TRAV39 | TRAJ33 | CAVDRWSNYQLIW | | 1466 |
| 116 | TRBV28 | TRBJ2-7 | CASSLLANEQYF | 1201 | TRAV26-2 | TRAJ57 | NON-PRODUCTIVE | | |
| 117 | TRBV7-9 | TRBJ2-6 | CASSLIVGQTNIVSGANVLTF | 1202 | TRAV26-2 | TRAJ50 | NON-PRODUCTIVE | | |
| 118 | TRBV5-4 | TRBJ2-2 | CASSLPAGTGTGELFF | 1203 | TRAV6 | TRAJ29 | CALERGNTPLVF | | 1467 |
| 119 | TRBV12-3 | TRBJ1-5 | CASSLQGSSQPQHF | 1204 | TRAV27 | TRAJ15 | CAGVQAGTALIF | | 1468 |
| 120 | TRBV5-1 | TRBJ2-3 | CASSLRAGGSTDTQYF | 1205 | TRAV16 | TRAJ10 | CALRLTGGGNKLTF | | 1469 |
| 121 | TRBV12-3 | TRBJ1-2 | CASSLRDTGFHF | 1206 | TRAV13-1 | TRAJ21 | CAALLYNFNKFYF | | 1470 |
| 122 | TRBV2-2 | TRBJ2-2 | CASSLSALGLAGGNTGELFF | 1207 | | | | | |
| 123 | TRBV28 | TRBJ2-7 | CASSLSGQGTGEQYF | 1208 | | | | | |
| 124 | TRBV27 | TRBJ1-2 | CASSLSRIGGGYTF | 1209 | TRAV8-6 | TRAJ58 | CAVSVTSGSRLTF | | 1471 |
| 125 | TRBV7-6 | TRBJ2-3 | CASSLSTDTQYF | 1210 | TRAV9-2 | TRAJ40 | CALENSGTYKYIF | | 1472 |
| 126 | TRBV9 | TRBJ2-5 | CASSLITDRSPQYF | 1211 | TRAV13-1 | TRAJ42 | NON-PRODUCTIVE | | |
| 127 | TRBV5-1 | TRBJ1-1 | CASSLTGLTEAFF | 1212 | | | | | |
| 128 | TRBV19 | TRBJ1-2 | CASSLITGTGIGYTF | 1213 | TRAV12-2 | TRAJ52 | NON-PRODUCTIVE | | |
| 129 | TRBV18 | TRBJ2-3 | CASSLITQGITDTQYF | 1214 | | | | | |
| 130 | TRBV5-4 | TRBJ1-1 | CASSLVGMNTEAFF | 1215 | TRAV26-1 | TRAJ20 | CIVRGIDDYKLSF | | 1473 |
| 131 | TRBV27 | TRBJ2-5 | CASSLVLGETQYF | 1216 | TRAV9-2 | TRAJ30 | NON-PRODUCTIVE | | |
| 132 | TRBV27 | TRBJ2-3 | CASSLVPTYTDTQYF | 1217 | TRAV30 | TRAJ36 | CGTKLQTGANNLFF | | 1474 |
| 133 | TRBV5-1 | TRBJ2-1 | CASSLIVSDQSNEQFF | 1218 | TRAV12-1 | TRAJ15 | CVVNDQAGTALIF | | 1475 |
| 134 | TRBV7-9 | TRBJ2-3 | CASSLVYSGDRTDTQYF | 1219 | TRAV9-2 | TRAJ26 | CALRGLRNYGQNFVF | | 1476 |
| 135 | TRBV28 | TRBJ2-2 | CASSMDRGSGELFF | 1220 | TRAV20 | TRAJ27 | CAVDTNAGKSTF | | 1477 |
| 136 | TRBV7-9 | TRBJ2-6 | CASSNRPLGSGANVLTF | 1221 | TRAV12-1 | TRAJ32 | NON-PRODUCTIVE | | |

Figure 20G

| TCR # | TCR beta | | | SEQ ID NO: | TRAV | TRAJ | TCR alpha (first) CDR3A | SEQ ID NO: |
|---|---|---|---|---|---|---|---|---|
| | TRBV | TRBJ | CDR3B | | | | | |
| 137 | TRBV18 | TRBJ2-1 | CASSPRSGRYNEQFF | 1222 | TRAV19 | TRAJ40 | NON-PRODUCTIVE | |
| 138 | TRBV28 | TRBJ1-4 | CASSPFGRLWATNRKLFF | 1223 | TRAV13-1 | TRAJ10 | CAKGITGGNKLTF | 1478 |
| 139 | TRBV19 | TRBJ2-7 | CASSPGAGEQYF | 1224 | TRAV8-2 | TRAJ45 | CAVSVGSGGADGLTF | 1479 |
| 140 | TRBV11-3 | TRBJ2-2 | CASSPGAGLNTGELFF | 1225 | TRAV3 | TRAJ16 | NON-PRODUCTIVE | |
| 141 | TRBV5-4 | TRBJ1-2 | CASSPGGTGGAYGYTF | 1226 | TRAV21 | TRAJ7 | CAVFYGNNRLAF | 1480 |
| 142 | TRBV9 | TRBJ1-1 | CASSPGTRAFF | 1227 | TRAV12-1 | TRAJ36 | CVVETQTGANNLFF | 1481 |
| 143 | TRBV3-1 | TRBJ2-1 | CASSPLLASDEQFF | 1228 | TRAV6 | TRAJ22 | CALKISSGSARQLTF | 1482 |
| 144 | TRBV7-5 | TRBJ2-7 | CASSPMAGFSFYEQYF | 1229 | TRAV26-1 | TRAJ54 | CIVMGGAQKLVF | 1483 |
| 145 | TRBV18 | TRBJ2-7 | CASSPPGGPYEQYF | 1230 | TRAV26-1 | TRAJ57 | CIVRVAQGGSEKLVF | 1484 |
| 146 | TRBV18 | TRBJ1-6 | CASSPQGLGNNSPLHF | 1231 | TRAV35 | TRAJ43 | CAGRNNDMRF | 1485 |
| 147 | TRBV19 | TRBJ1-5 | CASSPQGVSFMSNQPQHF | 1232 | TRAV6 | TRAJ39 | CALENAGNMLTF | 1486 |
| 148 | TRBV12-3 | TRBJ2-7 | CASSPRLAGSYEQYF | 1233 | TRAV19 | TRAJ49 | CALSEKRTGNQFYF | 1487 |
| 149 | TRBV18 | TRBJ2-1 | CASSPRQYEQFF | 1234 | TRAV13-2 | TRAJ7 | CAENKSGNNRLAF | 1488 |
| 150 | TRBV18 | TRBJ1-4 | CASSPSDRGGKLFF | 1235 | | | | |
| 151 | TRBV18 | TRBJ1-6 | CASSPSGGRVSPLHF | 1236 | TRAV41 | TRAJ54 | CAVHLIQGAQKLVF | 1489 |
| 152 | TRBV9 | TRBJ2-1 | CASSPSGGVNEQFF | 1237 | TRAV8-2 | TRAJ54 | CAVGIQGAQKLVF | 1490 |
| 153 | TRBV6-2 | TRBJ1-1 | CASSPSRVNTEAFF | 1238 | TRAV26-1 | TRAJ53 | CIVRGNSGGSNYKLTF | 1491 |
| 154 | TRBV7-2 | TRBJ1-1 | CASSPTAAASYNEQYF | 1239 | TRAV3 | TRAJ36 | CAVRESTGANNLFF | 1492 |
| 155 | TRBV7-9 | TRBJ2-2 | CASSPVDEGTGELFF | 1240 | TRAV26-1 | TRAJ44 | NON-PRODUCTIVE | |
| 156 | TRBV5-1 | TRBJ2-3 | CASSPVSGGGDTQYF | 1241 | TRAV13-1 | TRAJ23 | CAASLNQGGKLIF | 1493 |
| 157 | TRBV5-8 | TRBJ1-1 | CASSPWGIPEAFF | 1242 | TRAV13-1 | TRAJ23 | CAASLNQGGKLIF | 1494 |
| 158 | TRBV11-2 | TRBJ2-5 | CASSQAARAETQYF | 1243 | TRAV35 | TRAJ49 | CAGHLTGNQFYF | 1495 |
| 159 | TRBV18 | TRBJ1-2 | CASSQDEGYTF | 1244 | TRAV1-1 | TRAJ32 | CAVREGYGGATNKLIF | 1496 |
| 160 | TRBV4-1 | TRBJ1-2 | CASSQDRGAANYGYTF | 1245 | TRAV39 | TRAJ44 | CAVAXDPGTASKLTF | 1497 |

Figure 20H

| TCR # | TCR beta | | | | TCR alpha (first) | | | |
|---|---|---|---|---|---|---|---|---|
| | TRBV | TRBJ | CDR3B | SEQ ID NO: | TRAV | TRAJ | CDR3A | SEQ ID NO: |
| 161 | TRBV3-1 | TRBJ2-7 | CASSQDRGVEQYF | 1246 | TRAV14/DV4 | TRAJ33 | CAMSGFDSNYQLIW | 1498 |
| 162 | TRBV3-1 | TRBJ1-2 | CASSQDSIQGSGYTF | 1247 | TRAV41 | TRAJ45 | CAVRWGGGADGLTF | 1499 |
| 163 | TRBV3-1 | TRBJ2-7 | CASSQDVSGTGGSVEQYF | 1248 | TRAV1-2 | TRAJ36 | CAVRGTTGANNLFF | 1500 |
| 164 | TRBV5-1 | TRBJ1-4 | CASSQEEGEKLFF | 1249 | TRAV6 | TRAJ27 | CALGLQNAGKSTF | 1501 |
| 165 | TRBV11-2 | TRBJ1-1 | CASSQEGQSAAFF | 1250 | TRAV17 | TRAJ47 | CATGLVEYGNKLVF | 1502 |
| 166 | TRBV4-2 | TRBJ2-7 | CASSQETSGRAYEQYF | 1251 | | | | |
| 167 | TRBV3-1 | TRBJ2-2 | CASSQFGHGPTGGQFF | 1252 | TRAV17 | TRAJ40 | CATSGTYKYIF | 1503 |
| 168 | TRBV6-6 | TRBJ1-5 | CASSQGGTGELFF | 1253 | TRAV22 | TRAJ10 | CAVVRGGGNNLTF | 1504 |
| 169 | TRBV28 | TRBJ2-7 | CASSQGPGSNQPQHF | 1254 | TRAV6 | TRAJ10 | CALYTGGGNKLTF | 1505 |
| 170 | TRBV14 | TRBJ2-2 | CASSQGRNTGELFF | 1255 | TRAV8-6 | TRAJ11 | CAVSAPSGYSTLTF | 1506 |
| 171 | TRBV3-1 | TRBJ1-2 | CASSQGTGGGYTF | 1256 | TRAV36/DV7 | TRAJ45 | CAVQSGGGADGLTF | 1507 |
| 172 | TRBV28 | TRBJ1-3 | CASSQHQGAGNTIYF | 1257 | TRAV27 | TRAJ26 | FYNYGQNFVF | 1508 |
| 173 | TRBV19 | TRBJ2-1 | CASSQPTGGAYNEQFF | 1258 | TRAV12-1 | TRAJ54 | CVVNMSWGAQKLVF | 1509 |
| 174 | TRBV5-1 | TRBJ2-2 | CASSQRGDDTGELFF | 1259 | TRAV17 | TRAJ29 | CAPSGNTPLVF | 1510 |
| 175 | TRBV4-1 | TRBJ2-7 | CASSQVPGEQREQYF | 1260 | TRAV26-1 | TRAJ54 | CIVMGGAQKLVF | 1511 |
| 176 | TRBV18 | TRBJ2-6 | CASSRAEASSGANVLTF | 1261 | TRAV9-2 | TRAJ12 | | |
| 177 | TRBV7-2 | TRBJ1-2 | CASSRALGDNYGYTF | 1262 | TRAV17 | TRAJ36 | CATVLLTGANNLFF | 1512 |
| 178 | TRBV18 | TRBJ1-4 | CASSRDLGATNEKLFF | 1263 | TRAV19 | TRAJ39 | NON-PRODUCTIVE | |
| 179 | TRBV7-9 | TRBJ1-1 | CASSRGRGKAEAFF | 1264 | TRAV19 | TRAJ32 | NON-PRODUCTIVE | |
| 180 | TRBV9 | TRBJ2-1 | CASSRGSYNEQFF | 1265 | TRAV17 | TRAJ39 | CATVLNNAGNMLTF | 1513 |
| 181 | TRBV11-2 | TRBJ1-5 | CASSRGTDQPQHF | 1266 | TRAV9-2 | TRAJ49 | NON-PRODUCTIVE | |
| 182 | TRBV7-3 | TRBJ2-2 | CASSRPFGELFF | 1267 | TRAV39 | TRAJ57 | CLITPQGGSEKLVF | 1514 |
| 183 | TRBV25-1 | TRBJ1-4 | CASSRQGRGEKLFF | 1268 | | | | |
| 184 | TRBV28 | TRBJ2-7 | CASSRRGLNYEQYF | 1269 | TRAV6 | TRAJ45 | NON-PRODUCTIVE | |

Figure 20I

| TCR # | TCR beta | | | SEQ ID NO: | TCR alpha (first) | | | SEQ ID NO: |
|---|---|---|---|---|---|---|---|---|
| | TRBV | TRBJ | CDR3B | | TRAV | TRAJ | CDR3A | |
| 185 | TRBV7-2 | TRBJ2-6 | CASSSAQVGANVLTF | 1270 | TRAV12-1 | TRAJ6 | CVVNIQSGGSYIPTF | 1515 |
| 186 | TRBV5-1 | TRBJ1-1 | CASSSDRANTEAFF | 1271 | | | | |
| 187 | TRBV12-3 | TRBJ1-1 | CASSSGGGTEAFF | 1272 | TRAV2 | TRAJ34 | CAVEAPETDKLIF | 1516 |
| 188 | TRBV6-5 | TRBJ1-1 | CASSSGQGARTEAFF | 1273 | TRAV21 | TRAJ33 | CAVRGGGYQLIW | 1517 |
| 189 | TRBV5-1 | TRBJ2-3 | CASSSGRGFDTQYF | 1274 | TRAV20 | TRAJ58 | CAVQAAETSGSRLTF | 1518 |
| 190 | TRBV7-6 | TRBJ2-5 | CASSSGSETQYF | 1275 | TRAV2 | TRAJ5 | CAVEDTGRRALTF | 1519 |
| 191 | TRBV28 | TRBJ1-2 | CASSSKRAGGYTF | 1276 | | | | |
| 192 | TRBV28 | TRBJ2-7 | CASSSLERGGRRGEQYF | 1277 | TRAV9-2 | TRAJ23 | CALSVANQGGKLIF | 1520 |
| 193 | TRBV27 | TRBJ1-4 | CASSSNQWGNEKLFF | 1278 | TRAV9-2 | TRAJ27 | CALRFRGTNAGKSTF | 1521 |
| 194 | TRBV9 | TRBJ1-3 | CASSSPSGNTIYF | 1279 | TRAV8-2 | TRAJ8 | CAVSENTGFQKLVF | 1522 |
| 195 | TRBV7-2 | TRBJ2-5 | CASSSRTGASETQYF | 1280 | TRAV20 | TRAJ32 | CAVSYGGATNKLIF | 1523 |
| 196 | TRBV19 | TRBJ1-5 | CASSSRVRQPQHF | 1281 | TRAV1-1 | TRAJ45 | NON-PRODUCTIVE | |
| 197 | TRBV5-1 | TRBJ2-1 | CASSSTGGNEQFF | 1282 | TRAV12-3 | TRAJ47 | CAMVEYGNKLVF | 1524 |
| 198 | TRBV27 | TRBJ1-1 | CASSSTQSTGLVEAFF | 1283 | TRAV29/DV5 | TRAJ40 | CAATTSGTYKYIF | 1525 |
| 199 | TRBV19 | TRBJ2-5 | CASSTGGHGTQYF | 1284 | TRAV26-1 | TRAJ48 | CIVGRTNFGNEKLTF | 1526 |
| 200 | TRBV6-1 | TRBJ2-2 | CASSTLTGAGELFF | 1285 | TRAV25 | TRAJ49 | CAVTGNQFYF | 1527 |
| 201 | TRBV28 | TRBJ2-1 | CASSTLTGGRNEQFF | 1286 | TRAV29/DV5 | TRAJ40 | CAASEGGGTYKYIF | 1528 |
| 202 | TRBV2 | TRBJ2-4 | CASSTQGNIQYF | 1287 | | | NON-PRODUCTIVE | |
| 203 | TRBV19 | TRBJ2-1 | CASSTRAQSYNEQFF | 1288 | TRAV13-1 | TRAJ32 | CALSEIGYGGATNKLIF | 1529 |
| 204 | TRBV2 | TRBJ1-2 | CASSTRTDNRGYTF | 1289 | TRAV17 | TRAJ36 | CAPSKGANNLFF | 1530 |
| 205 | TRBV2 | TRBJ2-5 | CASSTRTGGKETQYF | 1290 | TRAV26-1 | TRAJ37 | CIVRVSHGSSNTGKLIF | 1531 |
| 206 | TRBV6-1 | TRBJ2-5 | CASSTTLGTGSFQETQYF | 1291 | TRAV21 | TRAJ15 | CAVPQAGTALIF | 1532 |
| 207 | TRBV19 | TRBJ2-7 | CASSTTSGGSYEQYF | 1292 | TRAV12-1 | TRAJ53 | NON-PRODUCTIVE | |
| 208 | TRBV9 | TRBJ2-5 | CASSVGELMGPQETQYF | 1293 | TRAV12-3 | TRAJ9 | CAMANTGGFKTIF | 1533 |
| 209 | TRBV9 | TRBJ2-1 | CASSVGLAGSNEQFF | 1294 | TRAV9-2 | TRAJ27 | CALSDQGTNAGKSTF | 1534 |

Figure 20J

| TCR # | TCR beta ||||  TCR alpha (first) ||||
|---|---|---|---|---|---|---|---|---|
| | TRBV | TRBJ | CDR3B | SEQ ID NO: | TRAV | TRAJ | CDR3A | SEQ ID NO: |
| 210 | TRBV6-1 | TRBJ2-7 | CASSVGPEYEQYF | 1295 | TRAV38-1 | TRAJ44 | CAPMKATGTASKLTF | 1535 |
| 211 | TRBV6-1 | TRBJ2-1 | CASSVGRGGSNEQFF | 1296 | TRAV26-1 | TRAJ42 | CIVRAPGGSQGNLIF | 1536 |
| 212 | TRBV18 | TRBJ1-1 | CASSVKIDSEAFF | 1297 | TRAV20 | TRAJ12 | CAVQTMDSSYKLIF | 1537 |
| 213 | TRBV12-3 | TRBJ2-1 | CASSVLAGGHNEQFF | 1298 | TRAV8-2 | TRAJ9 | CAVSGNTGGFKTIF | 1538 |
| 214 | TRBV9 | TRBJ2-5 | CASSVRTSVGETQYF | 1299 | TRAV9-2 | TRAJ20 | CALSAGDYKLSF | 1539 |
| 215 | TRBV5-1 | TRBJ1-6 | CASSVTGDSNSPLHF | 1300 | TRAV25 | TRAJ49 | CAVTGNQFYF | 1540 |
| 216 | TRBV9 | TRBJ2-3 | CASSVVGLAATDTQYF | 1301 | TRAV2 | TRAJ5 | CAVEDTGRRALTF | 1541 |
| 217 | TRBV5-1 | TRBJ1-1 | CASSWSGDTEAFF | 1302 | TRAV20 | TRAJ58 | CAVQAVETSGSRLTF | 1542 |
| 218 | TRBV6-6 | TRBJ2-5 | CASSYGTSGRVIQETQYF | 1303 | TRAV38-2/DV8 | TRAJ44 | CAYSLRSGTASKLTF | 1543 |
| 219 | TRBV6-1 | TRBJ2-1 | CASSYGTSGSLGYNEQFF | 1304 | TRAV35 | TRAJ42 | CAGLGQGNLIF | 1544 |
| 220 | TRBV6-2 | TRBJ2-3 | CASSYKPGTSGGGTPDTQYF | 1305 | TRAV13-1 | TRAJ34 | CAATHLNTDKLIF | 1545 |
| 221 | TRBV6-5 | TRBJ2-2 | CASSYNKVAGGNTGELFF | 1306 | TRAV8-6 | TRAJ6 | CAVTTRGGSYIPTF | 1546 |
| 222 | TRBV28 | TRBJ1-6 | CASSYNSPLHF | 1307 | TRAV8-2 | TRAJ37 | CAVSAWGSSNTGKLIF | 1547 |
| 223 | TRBV27 | TRBJ2-1 | CASSYREYLYNEQFF | 1308 | TRAV19 | TRAJ31 | CALRNNNARLMF | 1548 |
| 224 | TRBV6-6 | TRBJ2-5 | CASSYSGGTQETQYF | 1309 | TRAV22 | TRAJ43 | CAAPNNNNNDMRF | 1549 |
| 225 | TRBV6-5 | TRBJ1-2 | CASSYTGGAGYTF | 1310 | TRAV26-1 | TRAJ41 | NON-PRODUCTIVE | |
| 226 | TRBV5-1 | TRBJ2-3 | CASTGGSTDTQYF | 1311 | TRAV29/DV5 | TRAJ6 | CAASVSGGSYIPTF | 1550 |
| 227 | TRBV28 | TRBJ2-5 | CASTLQVSETQYF | 1312 | TRAV19 | TRAJ53 | NON-PRODUCTIVE | |
| 228 | TRBV5-1 | TRBJ2-5 | CASTPQRYQETQYF | 1313 | TRAV41 | TRAJ57 | NON-PRODUCTIVE | |
| 229 | TRBV28 | TRBJ2-1 | CASTQGPNEQFF | 1314 | TRAV38-2/DV8 | TRAJ49 | CAYRTNTGNQFYF | 1551 |
| 230 | TRBV19 | TRBJ1-5 | CASTWDSNQPQHF | 1315 | TRAV41 | TRAJ54 | CAVSKGAQKIVF | 1552 |
| 231 | TRBV24-1 | TRBJ2-5 | CATGTGTVGETQYF | 1316 | TRAV35 | TRAJ7 | CAGQLPGNNRLAF | 1553 |
| 232 | TRBV2 | TRBJ1-6 | CATQRDLNSPLHF | 1317 | TRAV26-2 | TRAJ60 | CILKITXMLNF | 1554 |
| 233 | TRBV24-1 | TRBJ2-1 | CATSAPGLSGTSGYNEQFF | 1318 | TRAV6 | TRAJ39 | CAPNNAGNMLTF | 1555 |

Figure 20K

| TCR # | TCR beta ||| SEQ ID NO: | TCR alpha (first) |||  SEQ ID NO: |
|---|---|---|---|---|---|---|---|---|
| | TRBV | TRBJ | CDR3B | | TRAV | TRAJ | CDR3A | |
| 234 | TRBV24-1 | TRBJ1-2 | CATSASAFGGYTF | 1319 | TRAV27 | TRAJ42 | NON-PRODUCTIVE | |
| 235 | TRBV24-1 | TRBJ2-3 | CATSDLSQPGRMGTDTQYF | 1320 | TRAV10 | TRAJ40 | CVVILPPSGTYKYIF | 1556 |
| 236 | TRBV24-1 | TRBJ2-5 | CATSDRAVETQYF | 1321 | TRAV13-1 | TRAJ57 | CAASEEGGSEKLVF | 1557 |
| 237 | TRBV5-1 | TRBJ2-7 | CATSGTGDEQYF | 1322 | TRAV26-2 | TRAJ48 | CLPGRGNEKLTF | 1558 |
| 238 | TRBV15 | TRBJ2-3 | CATSRDYFSGATDTQYF | 1323 | TRAV38-1 | TRAJ38 | NON-PRODUCTIVE | |
| 239 | TRBV15 | TRBJ2-5 | CATSRRASGGGQETQYF | 1324 | | | | |
| 240 | TRBV15 | TRBJ2-1 | CATSRLNNEQFF | 1325 | TRAV22 | TRAJ32 | CAGYGGATNKLIF | 1559 |
| 241 | TRBV15 | TRBJ2-1 | CATSSDDLGSSYNEQFF | 1326 | TRAV16 | TRAJ53 | CALMGSNYKLTF | 1560 |
| 242 | TRBV30 | TRBJ1-5 | CAWAPVEGQPQHF | 1327 | TRAV8-2 | TRAJ10 | CAVSEANTGGGNKLTF | 1561 |
| 243 | TRBV30 | TRBJ2-7 | CAWDNKGLAGGRQYF | 1328 | TRAV23/DV6 | TRAJ16 | NON-PRODUCTIVE | |
| 244 | TRBV30 | TRBJ1-2 | CAWETAGIGYGYTF | 1329 | TRAV9-2 | TRAJ32 | CALTPGGATNKLIF | 1562 |
| 245 | TRBV30 | TRBJ1-2 | CAWKGDREGGYTF | 1330 | TRAV10 | TRAJ32 | NON-PRODUCTIVE | |
| 246 | TRBV30 | TRBJ2-5 | CAWRGTSGGAQYF | 1331 | TRAV39 | TRAJ57 | NON-PRODUCTIVE | |
| 247 | TRBV30 | TRBJ1-2 | CAWRQDLHYGYTF | 1332 | TRAV25 | TRAJ52 | NON-PRODUCTIVE | |
| 248 | TRBV30 | TRBJ1-5 | CAWSGGGENQPQHF | 1333 | TRAV2 | TRAJ16 | NON-PRODUCTIVE | |
| 249 | TRBV30 | TRBJ1-6 | CAWSGGPTNSPLHF | 1334 | TRAV2 | TRAJ30 | CAVSNRDDKIIF | 1563 |
| 250 | TRBV30 | TRBJ2-4 | CAWSISGTENIQYF | 1335 | TRAV26-1 | TRAJ27 | NON-PRODUCTIVE | |
| 251 | TRBV30 | TRBJ1-5 | CAWSMEAEGQPQHF | 1336 | TRAV26-1 | TRAJ43 | CIVRVSSRTNDMRF | 1564 |
| 252 | TRBV30 | TRBJ2-7 | CAWSPLAGVSYEQYF | 1337 | | | | |
| 253 | TRBV30 | TRBJ1-3 | CAWSRLGASGNTIYF | 1338 | TRAV27 | TRAJ37 | CATHGSSNTGKLIF | 1565 |
| 254 | TRBV30 | TRBJ1-4 | CAWSVFTGGFGTNEKLFF | 1339 | TRAV26-1 | TRAJ30 | CIVRVDLVNRDDKIIF | 1566 |
| 255 | TRBV30 | TRBJ2-7 | CAWSVIQGGTEQYF | 1340 | | | | |
| 256 | TRBV30 | TRBJ2-1 | CAWTGGTGDNEQFF | 1341 | TRAV2 | TRAJ37 | NON-PRODUCTIVE | |

Figure 20L

| TCR # | TCR beta | | | | TCR alpha (first) | | | |
|---|---|---|---|---|---|---|---|---|
| | TRBV | TRBJ | CDR3B | SEQ ID NO: | TRAV | TRAJ | CDR3A | SEQ ID NO: |
| 257 | TRBV20-1 | TRBJ2-3 | CSADSSAAGGQDTQYF | 1342 | | | | |
| 258 | TRBV29-1 | TRBJ1-1 | CSAGGQGRGNTEAFF | 1343 | TRAV26-2 | TRAJ37 | CILTSSNTGKLIF | 1567 |
| 259 | TRBV29-1 | TRBJ2-7 | CSAGLTVSGREQYF | 1344 | TRAV19 | TRAJ38 | NON-PRODUCTIVE | |
| 260 | TRBV20-1 | TRBJ1-4 | CSAGSLGGEKLFF | 1345 | TRAV8-6 | TRAJ28 | NON-PRODUCTIVE | |
| 261 | TRBV20-1 | TRBJ1-4 | CSAKDSSTNEKLFF | 1346 | TRAV38-1 | TRAJ43 | CAFMKLRGDMRF | 1568 |
| 262 | TRBV20-1 | TRBJ1-2 | CSAKTGLYYGYTF | 1347 | TRAV26-1 | TRAJ39 | CIVDNNAGNMLTF | 1569 |
| 263 | TRBV20-1 | TRBJ2-3 | CSALGGLSTDTQYF | 1348 | TRAV6 | TRAJ48 | CALDDMFGNEKLTF | 1570 |
| 264 | TRBV20-1 | TRBJ2-5 | CSALGPNQETQYF | 1349 | TRAV17 | TRAJ57 | CATVPPGGSEKLVF | 1571 |
| 265 | TRBV20-1 | TRBJ1-2 | CSALLGARGYTF | 1350 | TRAV26-2 | TRAJ41 | CILREDGRNSGYALNF | 1572 |
| 266 | TRBV20-1 | TRBJ2-1 | CSALRQGAYNEQFF | 1351 | TRAV26-1 | TRAJ42 | CIVRAPGGSQGNLIF | 1573 |
| 267 | TRBV20-1 | TRBJ2-3 | CSANPGFLTDTQYF | 1352 | TRAV13-2 | TRAJ52 | CAETGGTSYGKLTF | 1574 |
| 268 | TRBV20-1 | TRBJ1-4 | CSANSGGSEKLFF | 1353 | TRAV27 | TRAJ15 | CAGVQAGTALIF | 1575 |
| 269 | TRBV20-1 | TRBJ1-2 | CSAPTPGTGGYGYTF | 1354 | TRAV9-2 | TRAJ57 | CALTSQGGSEKLVF | 1576 |
| 270 | TRBV20-1 | TRBJ2-5 | CSARALALVQTQYF | 1355 | TRAV26-1 | TRAJ20 | CIVRVADDYKLSF | 1577 |
| 271 | TRBV20-1 | TRBJ1-1 | CSARDPRGRVITEAFF | 1356 | TRAV19 | TRAJ37 | NON-PRODUCTIVE | |
| 272 | TRBV20-1 | TRBJ2-2 | CSARDRDRAVDTGELFF | 1357 | TRAV9-2 | TRAJ9 | CALRGGGTGGFKTIF | 1578 |
| 273 | TRBV20-1 | TRBJ2-3 | CSARDRDRGTDTQYF | 1358 | TRAV29/DV5 | TRAJ53 | CAAKMGGSNYKLTF | 1579 |
| 274 | TRBV20-1 | TRBJ2-3 | CSARDRLRLGADTQYF | 1359 | TRAV1-2 | TRAJ33 | CAARDSNYQLIW | 1580 |

Figure 20M

| TCR # | TCR beta ||| | TCR alpha (first) ||| |
| --- | --- | --- | --- | --- | --- | --- | --- |
| | TRBV | TRBJ | CDR3B | SEQ ID NO: | TRAV | TRAJ | CDR3A | SEQ ID NO: |
| 275 | TRBV20-1 | TRBJ1-2 | CSARGGGQGYGYTF | 1360 | TRAV26-2 | TRAJ27 | NON-PRODUCTIVE | |
| 276 | TRBV20-1 | TRBJ1-3 | CSARGIGNTIYF | 1361 | TRAV38-1 | TRAJ53 | CAFMKHASGGSNYKLTF | 1581 |
| 277 | TRBV20-1 | TRBJ1-1 | CSARGSGPDTEAFF | 1362 | TRAV21 | TRAJ11 | CAVDYSTLTF | 1582 |
| 278 | TRBV20-1 | TRBJ1-5 | CSARGSRLRGEGVSNQPQHF | 1363 | TRAV6 | TRAJ33 | CALDISYQLIW | 1583 |
| 279 | TRBV20-1 | TRBJ2-1 | CSARSPGLAGGLNEQFF | 1364 | TRAV8-2 | TRAJ45 | CAVSGFCGGADGLTF | 1584 |
| 280 | TRBV20-1 | TRBJ2-1 | CSARSPTSGRTNEQFF | 1365 | TRAV26-1 | TRAJ37 | CIVQGNTGKLIF | 1585 |
| 281 | TRBV20-1 | TRBJ2-1 | CSASGAYNEQFF | 1366 | | | | |
| 282 | TRBV20-1 | TRBJ1-1 | CSASGWGAVF | 1367 | TRAV12-3 | TRAJ27 | CAMSANTNAGKSTF | 1586 |
| 283 | TRBV20-1 | TRBJ1-5 | CSASLGVGNQPQHF | 1368 | | | | |
| 284 | TRBV20-1 | TRBJ1-2 | CSASPNYGYTF | 1369 | TRAV17 | TRAJ49 | CATDPNTGNQFYF | 1587 |
| 285 | TRBV20-1 | TRBJ2-7 | CSASPQIAGGYEQYF | 1370 | | | | |
| 286 | TRBV20-1 | TRBJ2-7 | CSASQAGGSSYEQYF | 1371 | TRAV8-2 | TRAJ11 | CVVTRNSGYSTLTF | 1588 |
| 287 | TRBV20-1 | TRBJ1-1 | CSASRGNTEAFF | 1372 | TRAV9-2 | TRAJ44 | CALSRNTGTASKLTF | 1589 |
| 288 | TRBV20-1 | TRBJ2-3 | CSATLGTADTQYF | 1373 | TRAV38-1 | TRAJ22 | NON-PRODUCTIVE | |
| 289 | TRBV20-1 | TRBJ1-2 | CSATNDRAYGYTF | 1374 | TRAV22 | TRAJ23 | CAVGAYVGGKLIF | 1590 |
| 290 | TRBV20-1 | TRBJ1-5 | CSAYSGNPGQPQHF | 1375 | TRAV8-6 | TRAJ46 | CAVSESSGDKLTF | 1591 |
| 291 | TRBV20-1 | TRBJ2-5 | CSGTGEETQYF | 1376 | | | | |
| 292 | TRBV29-1 | TRBJ2-5 | CSSIRGGPGETQYF | 1377 | TRAV22 | TRAJ5 | NON-PRODUCTIVE | |

Figure 20N

| TCR # | TCR beta ||||| TCR alpha (first) ||||
|---|---|---|---|---|---|---|---|---|---|
| | TRBV | TRBJ | CDR3B | SEQ ID NO: | TRAV | TRAJ | CDR3A | SEQ ID NO: |
| 293 | TRBV20-1 | TRBJ1-4 | CSVAGTGEKLFF | 1378 | TRAV35 | TRAJ31 | CAGRRNNARLMF | 1592 |
| 294 | TRBV29-1 | TRBJ2-7 | CSVDGALAGGTYEQYF | 1379 | TRAV6 | TRAJ48 | CAPDFGNEKLTF | 1593 |
| 295 | TRBV29-1 | TRBJ2-3 | CSVEEGAGGTDTQYF | 1380 | TRAV4 | TRAJ48 | CLVGPSFGNEKLTF | 1594 |
| 296 | TRBV29-1 | TRBJ1-2 | CSVEGGGYGYTF | 1381 | TRAV2 | TRAJ15 | CAVGQAGTALIF | 1595 |
| 297 | TRBV29-1 | TRBJ2-7 | CSVEIPGLSFYEQYF | 1382 | TRAV29/DV5 | TRAJ41 | NON-PRODUCTIVE | |
| 298 | TRBV29-1 | TRBJ1-1 | CSVERERGRTEAFF | 1383 | TRAV8-2 | TRAJ23 | NON-PRODUCTIVE | |
| 299 | TRBV29-1 | TRBJ1-2 | CSVERSSGSFSYGYTF | 1384 | TRAV20 | TRAJ52 | CAGGAGGTSYGKLTF | 1596 |
| 300 | TRBV20-1 | TRBJ1-2 | CSVGQGVVYGYTF | 1385 | TRAV34 | TRAJ42 | CGAGGSQGNLIF | 1597 |
| 301 | TRBV29-1 | TRBJ2-7 | CSVGQTGNYEQYF | 1386 | | | | |
| 302 | TRBV29-1 | TRBJ2-5 | CSVGRDIQETQYF | 1387 | TRAV17 | TRAJ12 | CATDSSYKLIF | 1598 |
| 303 | TRBV29-1 | TRBJ2-3 | CSVIQGAGSTDTQYF | 1388 | TRAV3 | TRAJ38 | NON-PRODUCTIVE | |
| 304 | TRBV29-1 | TRBJ2-4 | CSVRTGLAKNIQYF | 1389 | TRAV19 | TRAJ17 | NON-PRODUCTIVE | |
| 305 | TRBV10-2 | TRBJ1-1 | CVTSGTVNTEAFF | 1390 | TRAV8-2 | TRAJ23 | CAVSNYNQGGKLIF | 1599 |

Figure 20O

| TCR # | TCR ALPHA (second) ||||  |
|---|---|---|---|---|---|
| | TRAV | TRAJ | CDR3A | SEQ ID NO: | Frequency |
| 1 | | | | | 2 |
| 2 | TRAV3 | TRAJ41 | CAVRVSNSNSGYALNF | 1600 | 2 |
| 3 | | | | | 2 |
| 4 | | | | | 2 |
| 5 | | | | | 1 |
| 6 | TRAV2 | TRAJ33 | NON-PRODUCTIVE | | 1 |
| 7 | | | | | 1 |
| 8 | | | | | 1 |
| 9 | | | | | 1 |
| 10 | | | | | 1 |
| 11 | TRAV20 | TRAJ27 | NON-PRODUCTIVE | | 1 |
| 12 | | | | | 1 |
| 13 | | | | | 1 |
| 14 | TRAV12-1 | TRAJ54 | NON-PRODUCTIVE | | 1 |
| 15 | | | | | 1 |
| 16 | | | | | 1 |
| 17 | | | | | 1 |
| 18 | | | | | 1 |
| 19 | | | | | 1 |
| 20 | TRAV19 | TRAJ53 | NON-PRODUCTIVE | | 1 |
| 21 | | | | | 1 |
| 22 | | | | | 1 |
| 23 | TRAV27 | TRAJ35 | NON-PRODUCTIVE | | 1 |
| 24 | | | | | 1 |
| 25 | | | | | 1 |

Figure 20P

| TCR # | TCR ALPHA (second) | | | | |
|---|---|---|---|---|---|
| | TRAV | TRAJ | CDR3A | SEQ ID NO: | Frequency |
| 26 | | | | | 1 |
| 27 | | | | | 1 |
| 28 | | | | | 1 |
| 29 | TRAV6 | TRAJ10 | CALYTGGGNKLTF | 1601 | 1 |
| 30 | | | | | 1 |
| 31 | TRAV38-2/DV8 | TRAJ31 | CAYRSPDNNARLMF | 1602 | 1 |
| 32 | | | | | 1 |
| 33 | | | | | 1 |
| 34 | TRAV9-2 | TRAJ29 | CSEWEANSGNTPLVF | 1603 | 1 |
| 35 | TRAV13-1 | TRAJ45 | NON-PRODUCTIVE | | 1 |
| 36 | | | | | 1 |
| 37 | | | | | 1 |
| 38 | | | | | 1 |
| 39 | | | | | 1 |
| 40 | | | | | 1 |
| 41 | TRAV9-2 | TRAJ42 | NON-PRODUCTIVE | | 1 |
| 42 | TRAV13-1 | TRAJ10 | NON-PRODUCTIVE | | 1 |
| 43 | | | | | 1 |
| 44 | TRAV8-6 | TRAJ29 | NON-PRODUCTIVE | | 1 |
| 45 | | | | | 1 |
| 46 | TRAV8-2 | TRAJ30 | CAVSTPNRDDKIIF | 1604 | 1 |
| 47 | TRAV38-2/DV8 | TRAJ57 | CAYEITQGGSEKLVF | 1605 | 1 |
| 48 | | | | | 1 |
| 49 | | | | | 1 |
| 50 | TRAV1-2 | TRAJ33 | CAVREDSNYQLIW | 1606 | 1 |
| 51 | | | | | 1 |

Figure 20Q

| TCR # | TCR ALPHA (second) | | | | |
|---|---|---|---|---|---|
| | TRAV | TRAJ | CDR3A | SEQ ID NO: | Frequency |
| 52 | | | | | 1 |
| 53 | | | | | 1 |
| 54 | | | | | 1 |
| 55 | TRAV3 | TRAJ23 | CAVRPRNQGGKLIF | 1607 | 1 |
| 56 | | | | | 1 |
| 57 | | | | | 1 |
| 58 | | | | | 1 |
| 59 | | | | | 1 |
| 60 | | | | | 1 |
| 61 | | | | | 1 |
| 62 | TRAV9-2 | TRAJ9 | CALKPGGTGGFKTIF | 1608 | 1 |
| 63 | | | | | 1 |
| 64 | | | | | 1 |
| 65 | TRAV26-1 | TRAJ43 | CIVRVSSRTNDMRF | 1609 | 1 |
| 66 | | | | | 1 |
| 67 | | | | | 1 |
| 68 | | | | | 1 |
| 69 | | | | | 1 |
| 70 | | | | | 1 |
| 71 | | | | | 1 |
| 72 | | | | | 1 |
| 73 | TRAV13-1 | TRAJ26 | CASNNYGQNFVF | 1610 | 1 |
| 74 | | | | | 1 |
| 75 | | | | | 1 |
| 76 | | | | | 1 |
| 77 | | | | | 1 |

Figure 20R

| TCR # | TCR ALPHA (second) | | | | |
|---|---|---|---|---|---|
| | TRAV | TRAJ | CDR3A | SEQ ID NO: | Frequency |
| 78 | TRAV26-1 | TRAJ54 | NON-PRODUCTIVE | | 1 |
| 79 | | | | | 1 |
| 80 | | | | | 1 |
| 81 | | | | | 1 |
| 82 | TRAV9-2 | TRAJ49 | CALSDPNTGNQFYF | 1611 | 1 |
| 83 | | | | | 1 |
| 84 | | | | | 1 |
| 85 | | | | | 1 |
| 86 | | | | | 1 |
| 87 | TRAV8-2 | TRAJ56 | NON-PRODUCTIVE | | 1 |
| 88 | | | | | 1 |
| 89 | | | | | 1 |
| 90 | | | | | 1 |
| 91 | TRAV17 | TRAJ29 | CATGEVSGNTPLVF | 1612 | 1 |
| 92 | | | | | 1 |
| 93 | TRAV10 | TRAJ7 | NON-PRODUCTIVE | | 1 |
| 94 | | | | | 1 |
| 95 | | | | | 1 |
| 96 | | | | | 1 |
| 97 | | | | | 1 |
| 98 | TRAV12-2 | TRAJ45 | CAVRLLGGGADGLTF | 1613 | 1 |
| 99 | | | | | 1 |
| 100 | | | | | 1 |
| 101 | | | | | 1 |
| 102 | | | | | 1 |
| 103 | | | | | 1 |

Figure 20S

| TCR # | TCR ALPHA (second) | | | | |
|---|---|---|---|---|---|
| | TRAV | TRAJ | CDR3A | SEQ ID NO: | Frequency |
| 104 | | | | | 1 |
| 105 | | | | | 1 |
| 106 | | | | | 1 |
| 107 | | | | | 1 |
| 108 | TRAV17 | TRAJ49 | NON-PRODUCTIVE | | 1 |
| 109 | | | | | 1 |
| 110 | TRAV22 | TRAJ32 | CAVERSSGATNKLIF | 1614 | 1 |
| 111 | | | | | 1 |
| 112 | | | | | 1 |
| 113 | | | | | 1 |
| 114 | | | | | 1 |
| 115 | TRAV12-3 | TRAJ42 | CAMSVPSQGNLIF | 1615 | 1 |
| 116 | TRAV8-6 | TRAJ27 | CAVSYNTNAGKSTF | 1616 | 1 |
| 117 | | | | | 1 |
| 118 | | | | | 1 |
| 119 | | | | | 1 |
| 120 | | | | | 1 |
| 121 | | | | | 1 |
| 122 | | | | | 1 |
| 123 | | | | | 1 |
| 124 | | | | | 1 |
| 125 | | | | | 1 |
| 126 | | | | | 1 |
| 127 | | | | | 1 |
| 128 | | | | | 1 |
| 129 | | | | | 1 |

Figure 20T

| TCR # | TCR ALPHA (second) | | | | |
|---|---|---|---|---|---|
| | TRAV | TRAJ | CDR3A | SEQ ID NO: | Frequency |
| 130 | TRAV16 | TRAJ28 | CALSGSGAGSYQLTF | 1617 | 1 |
| 131 | TRAV17 | TRAJ22 | CATSGSSARQLTF | 1618 | 1 |
| 132 | | | | | |
| 133 | | | | | |
| 134 | TRAV13-2 | TRAJ31 | NON-PRODUCTIVE | | 1 |
| 135 | TRAV9-2 | TRAJ30 | CALSAGRDDKIIF | 1619 | 1 |
| 136 | TRAV23/DV6 | TRAJ5 | CAAAYTGKRALTF | 1620 | 1 |
| 137 | | | | | |
| 138 | TRAV12-1 | TRAJ9 | NON-PRODUCTIVE | | 1 |
| 139 | TRAV14/DV4 | TRAJ47 | NON-PRODUCTIVE | | 1 |
| 140 | | | | | |
| 141 | | | | | |
| 142 | | | | | |
| 143 | TRAV26-1 | TRAJ17 | NON-PRODUCTIVE | | 1 |
| 144 | | | | | |
| 145 | TRAV38-1 | TRAJ18 | NON-PRODUCTIVE | | 1 |
| 146 | | | | | |
| 147 | TRAV16 | TRAJ40 | CAPPTSGTYKYIF | 1621 | 1 |
| 148 | | | | | |
| 149 | | | | | |
| 150 | | | | | |
| 151 | | | | | |
| 152 | | | | | |
| 153 | | | | | |
| 154 | | | | | |
| 155 | TRAV4 | TRAJ32 | CLVGDYEWGGATNKLIF | 1622 | 1 |

Figure 20U

| TCR # | TRAV | TRAJ | CDR3A | SEQ ID NO: | Frequency |
|---|---|---|---|---|---|
| 156 | | | | | 1 |
| 157 | | | | | 1 |
| 158 | | | | | 1 |
| 159 | | | | | 1 |
| 160 | TRAV12-2 | TRAJ54 | CAVMTIQGAQKLVF | 1623 | 1 |
| 161 | | | | | 1 |
| 162 | | | | | 1 |
| 163 | TRAV12-2 | TRAJ39 | NON-PRODUCTIVE | | 1 |
| 164 | TRAV8-6 | TRAJ45 | NON-PRODUCTIVE | | 1 |
| 165 | | | | | 1 |
| 166 | | | | | 1 |
| 167 | | | | | 1 |
| 168 | | | | | 1 |
| 169 | | | | | 1 |
| 170 | | | | | 1 |
| 171 | TRAV19 | TRAJ40 | NON-PRODUCTIVE | | 1 |
| 172 | TRAV1-2 | TRAJ16 | NON-PRODUCTIVE | | 1 |
| 173 | TRAV17 | TRAJ56 | CATDSGANSKLIF | 1624 | 1 |
| 174 | | | | | 1 |
| 175 | | | | | 1 |
| 176 | | | | | 1 |
| 177 | | | | | 1 |
| 178 | TRAV19 | TRAJ23 | CALRLYNQGGKLIF | 1625 | 1 |
| 179 | TRAV26-1 | TRAJ21 | CIVRVWNNFNKFYF | 1626 | 1 |
| 180 | | | | | 1 |
| 181 | TRAV38-1 | TRAJ39 | CAFMKHTGNMLTF | 1627 | 1 |

Figure 20V

| TCR # | TRAV | TRAJ | CDR3A | SEQ ID NO: | Frequency |
|---|---|---|---|---|---|
| 182 | | | | | 1 |
| 183 | | | | | 1 |
| 184 | TRAV14/DV4 | TRAJ32 | CAIKRRDGATNKLIF | 1628 | 1 |
| 185 | | | | | 1 |
| 186 | | | | | 1 |
| 187 | | | | | 1 |
| 188 | | | | | 1 |
| 189 | | | | | 1 |
| 190 | | | | | 1 |
| 191 | | | | | 1 |
| 192 | | | | | 1 |
| 193 | | | | | 1 |
| 194 | | | | | 1 |
| 195 | | | | | 1 |
| 196 | TRAV1-2 | TRAJ39 | CAVRDMNNAGNMLTF | 1629 | 1 |
| 197 | | | | | 1 |
| 198 | | | | | 1 |
| 199 | | | | | 1 |
| 200 | | | | | 1 |
| 201 | | | | | 1 |
| 202 | | | | | 1 |
| 203 | | | | | 1 |
| 204 | TRAV13-1 | TRAJ13 | CAARDSGGYQKVTF | 1630 | 1 |
| 205 | TRAV3 | TRAJ48 | NON-PRODUCTIVE | | 1 |
| 206 | TRAV26-2 | TRAJ53 | NON-PRODUCTIVE | | 1 |
| 207 | TRAV35 | TRAJ40 | CAGRASGTYKYIF | 1631 | 1 |

Figure 20W

| TCR # | TCR ALPHA (second) | | | | |
|---|---|---|---|---|---|
| | TRAV | TRAJ | CDR3A | SEQ ID NO: | Frequency |
| 208 | | | | | 1 |
| 209 | | | | | 1 |
| 210 | TRAV8-2 | TRAJ47 | NON-PRODUCTIVE | | 1 |
| 211 | | | | | 1 |
| 212 | TRAV9-2 | TRAJ37 | CAPPVGSNTGKLIF | 1632 | 1 |
| 213 | | | | | 1 |
| 214 | | | | | 1 |
| 215 | | | | | 1 |
| 216 | | | | | 1 |
| 217 | | | | | 1 |
| 218 | | | | | 1 |
| 219 | | | | | 1 |
| 220 | | | | | 1 |
| 221 | | | | | 1 |
| 222 | | | | | 1 |
| 223 | | | | | 1 |
| 224 | | | | | 1 |
| 225 | | | | | 1 |
| 226 | | | | | 1 |
| 227 | | | | | 1 |
| 228 | | | | | 1 |
| 229 | | | | | 1 |
| 230 | TRAV14/DV4 | TRAJ52 | NON-PRODUCTIVE | | 1 |
| 231 | | | | | 1 |
| 232 | | | | | 1 |
| 233 | TRAV6 | TRAJ40 | NON-PRODUCTIVE | | 1 |

Figure 20X

| TCR # | TCR ALPHA (second) | | | | |
|---|---|---|---|---|---|
| | TRAV | TRAJ | CDR3A | SEQ ID NO: | Frequency |
| 234 | TRAV20 | TRAJ43 | CAAVGNNNDMRF | 1633 | 1 |
| 235 | TRAV35 | TRAJ22 | CAGRPTSGSARQLTF | 1634 | 1 |
| 236 | | | | | 1 |
| 237 | | | | | 1 |
| 238 | | | | | 1 |
| 239 | | | | | 1 |
| 240 | | | | | 1 |
| 241 | | | | | 1 |
| 242 | | | | | 1 |
| 243 | | | | | 1 |
| 244 | TRAV25 | TRAJ21 | NON-PRODUCTIVE | | 1 |
| 245 | TRAV13-1 | TRAJ23 | CAARVIHNQGGKLIF | 1635 | 1 |
| 246 | TRAV12-3 | TRAJ36 | CAMSKQTGANNLFF | 1636 | 1 |
| 247 | | | | | 1 |
| 248 | TRAV3 | TRAJ8 | NON-PRODUCTIVE | | 1 |
| 249 | | | | | 1 |
| 250 | | | | | 1 |
| 251 | | | | | 1 |
| 252 | | | | | 1 |
| 253 | TRAV14/DV4 | TRAJ56 | NON-PRODUCTIVE | | 1 |
| 254 | | | | | 1 |
| 255 | | | | | 1 |
| 256 | TRAV8-6 | TRAJ24 | CAVSDPNSWGKLQF | 1637 | 1 |
| 257 | | | | | 1 |
| 258 | | | | | 1 |
| 259 | TRAV13-1 | TRAJ17 | NON-PRODUCTIVE | | 1 |

Figure 20Y

| TCR # | TCR ALPHA (second) | | | | |
|---|---|---|---|---|---|
| | TRAV | TRAJ | CDR3A | SEQ ID NO: | Frequency |
| 260 | TRAV4 | TRAJ29 | CLVGSNSGNTPLVF | 1638 | 1 |
| 261 | | | | | 1 |
| 262 | | | | | 1 |
| 263 | | | | | 1 |
| 264 | | | | | 1 |
| 265 | | | | | 1 |
| 266 | | | | | 1 |
| 267 | | | | | 1 |
| 268 | | | | | 1 |
| 269 | TRAV38-2/DV8 | TRAJ31 | NON-PRODUCTIVE | | 1 |
| 270 | TRAV23/DV6 | TRAJ45 | NON-PRODUCTIVE | | 1 |
| 271 | TRAV4 | TRAJ34 | CLVGVNTDKLIF | 1639 | 1 |
| 272 | | | | | 1 |
| 273 | | | | | 1 |
| 274 | | | | | 1 |
| 275 | | | | | 1 |
| 276 | | | | | 1 |
| 277 | TRAV14/DV4 | TRAJ20 | CAMKDDYKLSF | 1640 | 1 |
| 278 | | | | | 1 |
| 279 | | | | | 1 |
| 280 | | | | | 1 |
| 281 | | | | | 1 |
| 282 | | | | | 1 |
| 283 | | | | | 1 |
| 284 | | | | | 1 |
| 285 | | | | | 1 |

Figure 20Z

| TCR # | TCR ALPHA (second) | | | | |
|---|---|---|---|---|---|
| | TRAV | TRAJ | CDR3A | SEQ ID NO: | Frequency |
| 286 | | | | | 1 |
| 287 | | | | | 1 |
| 288 | | | | | 1 |
| 289 | | | | | 1 |
| 290 | | | | | 1 |
| 291 | | | | | 1 |
| 292 | TRAV12-1 | TRAJ26 | CVVTDYGQNFVF | 1641 | 1 |
| 293 | | | | | 1 |
| 294 | | | | | 1 |
| 295 | | | | | 1 |
| 296 | TRAV13-1 | TRAJ8 | NON-PRODUCTIVE | | 1 |
| 297 | | | | | 1 |
| 298 | TRAV1-1 | TRAJ32 | CAVREGYGGATNKLIF | 1642 | 1 |
| 299 | | | | | 1 |
| 300 | TRAV9-2 | TRAJ49 | PRRNTGNQFYF | 1643 | 1 |
| 301 | | | | | 1 |
| 302 | | | | | 1 |
| 303 | | | | | 1 |
| 304 | | | | | 1 |
| 305 | TRAV3 | TRAJ23 | NON-PRODUCTIVE | | 1 |

Figure 21A
Table 10.

| TCRB | SEQ ID NO: | Freq. | Stim/Unstim | IL2 | IL10 | IL12A | IL13 | IL17A | IFNG | PRF1 | GZMB |
|---|---|---|---|---|---|---|---|---|---|---|---|
| CASSLASMGVGELFF | 265 | 25 | Unstim | 0 | 0 | 0 | 0 | 0 | 0 | 0 | 0 |
| CASSLASMGVGELFF | | 25 | Unstim | 0 | 0 | 0 | 0 | 0 | 0 | 0 | 0 |
| CASSLASMGVGELFF | | 25 | Unstim | 0 | 0 | 0 | 0 | 0 | 0 | 0 | 0 |
| CASSLASMGVGELFF | | 25 | Unstim | 0 | 0 | 0 | 0 | 0 | 0 | 0 | 0 |
| CASSLASMGVGELFF | | 25 | Unstim | 0 | 0 | 0 | 0 | 0 | 0 | 0 | 0 |
| CASSLASMGVGELFF | | 25 | Unstim | 0 | 0 | 0 | 0 | 0 | 0 | 227 | 0 |
| CASSLASMGVGELFF | | 25 | Unstim | 0 | 0 | 0 | 0 | 0 | 0 | 0 | 0 |
| CASSLASMGVGELFF | | 25 | Unstim | 0 | 0 | 0 | 0 | 100 | 0 | 0 | 0 |
| CASSLASMGVGELFF | | 25 | Unstim | 0 | 0 | 0 | 0 | 0 | 0 | 0 | 0 |
| CASSLASMGVGELFF | | 25 | Unstim | 0 | 0 | 0 | 0 | 0 | 0 | 0 | 0 |
| CASSLASMGVGELFF | | 25 | Unstim | 0 | 0 | 0 | 0 | 0 | 1 | 0 | 0 |
| CASSLASMGVGELFF | | 25 | Unstim | 0 | 0 | 0 | 0 | 217 | 0 | 0 | 0 |
| CASSLASMGVGELFF | | 25 | Unstim | 0 | 0 | 0 | 0 | 0 | 0 | 0 | 1 |
| CASSLASMGVGELFF | | 25 | Unstim | 0 | 0 | 0 | 0 | 329 | 0 | 0 | 0 |
| CASSLASMGVGELFF | | 25 | Unstim | 0 | 0 | 0 | 0 | 0 | 0 | 0 | 0 |
| CASSLASMGVGELFF | | 25 | Unstim | 0 | 0 | 0 | 0 | 453 | 0 | 0 | 0 |
| CASSLASMGVGELFF | | 25 | Unstim | 0 | 0 | 0 | 0 | 0 | 0 | 0 | 0 |
| CASSLASMGVGELFF | | 25 | Unstim | 0 | 0 | 0 | 0 | 0 | 0 | 0 | 0 |
| CASSLASMGVGELFF | | 25 | Unstim | 0 | 0 | 0 | 0 | 0 | 0 | 0 | 0 |
| CASSLASMGVGELFF | | 25 | Unstim | 0 | 0 | 0 | 0 | 0 | 1 | 0 | 87 |

Figure 21B

| TCRB | SEQ ID NO: | Freq. | Stim/Unstim | IL2 | IL10 | IL12A | IL13 | IL17A | IFNG | PRF1 | GZMB |
|---|---|---|---|---|---|---|---|---|---|---|---|
| CASSLASMGVGELFF | | 25 | Unstim | 0 | 0 | 0 | 0 | 0 | 0 | 0 | 0 |
| CASSEAGGQDYGNEQFF | | 18 | Unstim | 0 | 0 | 0 | 0 | 0 | 0 | 0 | 0 |
| CASSEAGGQDYGNEQFF | | 18 | Unstim | 0 | 0 | 0 | 0 | 0 | 0 | 0 | 0 |
| CASSEAGGQDYGNEQFF | | 18 | Unstim | 1 | 0 | 0 | 0 | 0 | 51 | 206 | 0 |
| CASSEAGGQDYGNEQFF | | 18 | Unstim | 0 | 0 | 0 | 0 | 0 | 86 | 0 | 0 |
| CASSEAGGQDYGNEQFF | | 18 | Unstim | 0 | 0 | 0 | 0 | 0 | 0 | 0 | 0 |
| CASSEAGGQDYGNEQFF | | 18 | Unstim | 0 | 0 | 0 | 0 | 0 | 0 | 55 | 0 |
| CASSEAGGQDYGNEQFF | 565 | 18 | Unstim | 0 | 0 | 0 | 0 | 0 | 0 | 0 | 0 |
| CASSEAGGQDYGNEQFF | | 18 | Unstim | 0 | 0 | 0 | 0 | 0 | 0 | 393 | 0 |
| CASSEAGGQDYGNEQFF | | 18 | Unstim | 0 | 0 | 0 | 0 | 0 | 0 | 0 | 0 |
| CASSEAGGQDYGNEQFF | | 18 | Unstim | 0 | 0 | 0 | 0 | 0 | 0 | 0 | 0 |
| CASSEAGGQDYGNEQFF | | 18 | Unstim | 0 | 0 | 0 | 1 | 0 | 607 | 0 | 0 |
| CASSEAGGQDYGNEQFF | | 18 | Unstim | 0 | 0 | 0 | 0 | 0 | 0 | 0 | 0 |
| CASSEAGGQDYGNEQFF | | 18 | Unstim | 0 | 0 | 0 | 0 | 0 | 0 | 1567 | 0 |
| CASSEAGGQDYGNEQFF | | 18 | Unstim | 0 | 0 | 0 | 0 | 0 | 583 | 558 | 0 |
| CASSEAGGQDYGNEQFF | | 18 | Unstim | 0 | 0 | 0 | 0 | 0 | 0 | 0 | 0 |
| CASSEAGGQDYGNEQFF | | 18 | Unstim | 0 | 0 | 0 | 0 | 0 | 854 | 0 | 0 |
| CASSLGGGSYNEQFF | | 11 | Unstim | 0 | 0 | 0 | 0 | 0 | 0 | 0 | 0 |
| CASSLGGGSYNEQFF | | 11 | Unstim | 0 | 0 | 0 | 0 | 0 | 0 | 188 | 0 |
| CASSLGGGSYNEQFF | | 11 | Unstim | 0 | 0 | 0 | 0 | 0 | 0 | 0 | 0 |
| CASSLGGGSYNEQFF | 570 | 11 | Unstim | 0 | 0 | 0 | 0 | 0 | 0 | 0 | 0 |
| CASSLGGGSYNEQFF | | 11 | Unstim | 0 | 0 | 0 | 0 | 0 | 0 | 0 | 0 |
| CASSLGGGSYNEQFF | | 11 | Unstim | 0 | 0 | 0 | 0 | 0 | 638 | 0 | 0 |
| CASSLGGGSYNEQFF | | 11 | Unstim | 0 | 0 | 0 | 0 | 0 | 0 | 0 | 0 |

Figure 21C

| TCRB | SEQ ID NO: | Freq. | Stim/ Unstim | IL2 | IL10 | IL12A | IL13 | IL17A | IFNG | PRF1 | GZMB |
|---|---|---|---|---|---|---|---|---|---|---|---|
| CASSLGGGSYNEQFF |  | 11 | Unstim | 0 | 0 | 0 | 0 | 0 | 0 | 0 | 0 |
| CASSLGGGSYNEQFF |  | 11 | Unstim | 0 | 0 | 0 | 0 | 1 | 0 | 0 | 0 |
| CASSLGGGSYNEQFF |  | 11 | Unstim | 0 | 0 | 0 | 0 | 0 | 0 | 0 | 0 |
| CASSLGGGSYNEQFF |  | 11 | Unstim | 0 | 0 | 0 | 0 | 0 | 0 | 1 | 0 |
| CSAGTYRTDTQYF |  | 11 | Unstim | 0 | 0 | 0 | 0 | 0 | 0 | 0 | 0 |
| CSAGTYRTDTQYF |  | 11 | Unstim | 0 | 0 | 0 | 0 | 0 | 0 | 0 | 0 |
| CSAGTYRTDTQYF |  | 11 | Unstim | 0 | 0 | 0 | 0 | 0 | 0 | 0 | 0 |
| CSAGTYRTDTQYF | 569 | 11 | Unstim | 0 | 0 | 0 | 0 | 0 | 0 | 155 | 0 |
| CSAGTYRTDTQYF |  | 11 | Unstim | 0 | 0 | 0 | 0 | 0 | 0 | 0 | 0 |
| CSAGTYRTDTQYF |  | 11 | Unstim | 0 | 0 | 0 | 0 | 1 | 0 | 0 | 0 |
| CSAGTYRTDTQYF |  | 11 | Unstim | 0 | 0 | 0 | 0 | 0 | 1 | 0 | 0 |
| CSAGTYRTDTQYF |  | 11 | Unstim | 0 | 0 | 0 | 0 | 0 | 0 | 0 | 2 |
| CSAGTYRTDTQYF |  | 11 | Unstim | 0 | 0 | 0 | 0 | 0 | 0 | 0 | 3 |
| CSAGTYRTDTQYF |  | 11 | Unstim | 0 | 0 | 0 | 0 | 0 | 0 | 0 | 0 |
| CASPGGWTGGGNEQFF |  | 10 | Unstim | 0 | 0 | 0 | 0 | 0 | 0 | 0 | 0 |
| CASPGGWTGGGNEQFF |  | 10 | Unstim | 0 | 0 | 0 | 0 | 0 | 164 | 0 | 0 |
| CASPGGWTGGGNEQFF |  | 10 | Unstim | 0 | 0 | 0 | 0 | 0 | 0 | 1 | 0 |
| CASPGGWTGGGNEQFF |  | 10 | Unstim | 0 | 0 | 0 | 0 | 0 | 0 | 0 | 12 |
| CASPGGWTGGGNEQFF | 563 | 10 | Unstim | 0 | 0 | 0 | 0 | 0 | 0 | 0 | 8 |
| CASPGGWTGGGNEQFF |  | 10 | Unstim | 0 | 0 | 0 | 0 | 0 | 0 | 0 | 0 |
| CASPGGWTGGGNEQFF |  | 10 | Unstim | 0 | 0 | 0 | 0 | 1 | 0 | 0 | 16 |
| CASPGGWTGGGNEQFF |  | 10 | Unstim | 0 | 0 | 0 | 0 | 0 | 0 | 0 | 0 |
| CASPGGWTGGGNEQFF |  | 10 | Unstim | 0 | 0 | 0 | 0 | 0 | 2 | 0 | 0 |
| CASNTLGAGGREQYF | 564 | 8 | Unstim | 0 | 0 | 0 | 0 | 0 | 0 | 322 | 0 |

Figure 21D

| TCRB | SEQ ID NO: | Freq. | Stim/Unstim | IL2 | IL10 | IL12A | IL13 | IL17A | IFNG | PRF1 | GZMB |
|---|---|---|---|---|---|---|---|---|---|---|---|
| CASNTLGAGGREQYF | | 8 | Unstim | 0 | 0 | 0 | 0 | 0 | 0 | 0 | 0 |
| CASNTLGAGGREQYF | | 8 | Unstim | 0 | 0 | 0 | 0 | 0 | 240 | 0 | 0 |
| CASNTLGAGGREQYF | | 8 | Unstim | 0 | 0 | 0 | 0 | 0 | 0 | 0 | 0 |
| CASNTLGAGGREQYF | | 8 | Unstim | 0 | 0 | 0 | 0 | 0 | 1 | 0 | 0 |
| CASNTLGAGGREQYF | | 8 | Unstim | 0 | 0 | 0 | 0 | 0 | 0 | 0 | 0 |
| CASNTLGAGGREQYF | | 8 | Unstim | 0 | 0 | 0 | 0 | 1 | 0 | 1 | 1 |
| CASRENSGANVLTF | 568 | 8 | Unstim | 0 | 0 | 0 | 0 | 0 | 0 | 0 | 0 |
| CASRENSGANVLTF | 568 | 8 | Unstim | 0 | 0 | 0 | 0 | 343 | 0 | 0 | 0 |
| CASRENSGANVLTF | 568 | 8 | Unstim | 0 | 0 | 0 | 0 | 0 | 281 | 301 | 0 |
| CASRENSGANVLTF | 568 | 8 | Unstim | 0 | 0 | 0 | 0 | 0 | 0 | 0 | 0 |
| CASRENSGANVLTF | 568 | 8 | Unstim | 0 | 0 | 0 | 0 | 0 | 265 | 267 | 0 |
| CASRENSGANVLTF | 568 | 8 | Unstim | 0 | 0 | 0 | 0 | 0 | 1049 | 0 | 1 |
| CAWSDGVVGEKLFF | 567 | 8 | Unstim | 0 | 0 | 0 | 0 | 0 | 0 | 1382 | 0 |
| CAWSDGVVGEKLFF | 567 | 8 | Unstim | 0 | 0 | 0 | 0 | 22 | 0 | 0 | 0 |
| CAWSDGVVGEKLFF | 567 | 8 | Unstim | 0 | 0 | 0 | 0 | 0 | 0 | 0 | 0 |
| CAWSDGVVGEKLFF | 567 | 8 | Unstim | 0 | 0 | 0 | 0 | 0 | 0 | 0 | 0 |
| CAWSDGVVGEKLFF | 567 | 8 | Unstim | 0 | 0 | 0 | 0 | 0 | 0 | 0 | 0 |
| CASSSASGGVGELFF | 267 | 6 | Unstim | 0 | 0 | 0 | 0 | 0 | 0 | 0 | 0 |
| CASSSASGGVGELFF | 267 | 6 | Unstim | 0 | 0 | 0 | 0 | 0 | 0 | 0 | 0 |
| CASSSASGGVGELFF | 267 | 6 | Unstim | 0 | 0 | 0 | 0 | 0 | 0 | 0 | 34 |

Figure 21E

| TCRB | SEQ ID NO: | Freq. | Stim/Unstim | IL2 | IL10 | IL12A | IL13 | IL17A | IFNG | PRF1 | GZMB |
|---|---|---|---|---|---|---|---|---|---|---|---|
| CASSSASGGVGELFF | | 6 | Unstim | 0 | 0 | 72 | 0 | 0 | 0 | 472 | 0 |
| CASSSASGGVGELFF | | 6 | Unstim | 0 | 0 | 0 | 0 | 0 | 995 | 0 | 0 |
| CASSSASGGVGELFF | | 6 | Unstim | 0 | 0 | 0 | 0 | 0 | 0 | 0 | 0 |
| CASSFSPGLETQYF | 573 | 5 | Unstim | 0 | 0 | 0 | 0 | 255 | 350 | 0 | 0 |
| CASSFSPGLETQYF | | 5 | Unstim | 0 | 0 | 0 | 0 | 0 | 0 | 0 | 0 |
| CASSFSPGLETQYF | | 5 | Unstim | 0 | 0 | 0 | 0 | 0 | 0 | 0 | 0 |
| CASSFSPGLETQYF | | 5 | Unstim | 0 | 0 | 0 | 0 | 353 | 0 | 0 | 0 |
| CASSLVSSPLHF | 574 | 5 | Unstim | 0 | 0 | 0 | 0 | 0 | 0 | 153 | 0 |
| CASSLVSSPLHF | | 5 | Unstim | 0 | 0 | 0 | 0 | 0 | 0 | 0 | 0 |
| CASSLVSSPLHF | | 5 | Unstim | 0 | 1 | 0 | 0 | 0 | 0 | 0 | 0 |
| CASSLVSSPLHF | | 5 | Unstim | 0 | 0 | 0 | 0 | 0 | 0 | 0 | 0 |
| CASSQDGAGGREQFF | 571 | 5 | Unstim | 0 | 0 | 0 | 0 | 0 | 0 | 0 | 0 |
| CASSQDGAGGREQFF | | 5 | Unstim | 0 | 0 | 0 | 0 | 0 | 0 | 0 | 0 |
| CASSQDGAGGREQFF | | 5 | Unstim | 0 | 0 | 0 | 0 | 0 | 0 | 0 | 0 |
| CASSQDGAGGREQFF | | 5 | Unstim | 0 | 0 | 0 | 0 | 0 | 0 | 0 | 0 |
| CASSQGLAAPYEQYF | 566 | 4 | Unstim | 0 | 0 | 0 | 0 | 0 | 1 | 0 | 0 |
| CASSQGLAAPYEQYF | | 4 | Unstim | 0 | 0 | 0 | 0 | 0 | 988 | 0 | 0 |
| CASSQGLAAPYEQYF | | 4 | Unstim | 0 | 0 | 0 | 0 | 0 | 1 | 0 | 0 |
| CASSQGLAAPYEQYF | | 4 | Unstim | 0 | 0 | 0 | 0 | 0 | 0 | 0 | 0 |
| CSAATLDGSNQPQHF | 578 | 4 | Unstim | 0 | 0 | 0 | 0 | 0 | 0 | 351 | 0 |
| CSAATLDGSNQPQHF | | 4 | Unstim | 0 | 0 | 0 | 0 | 768 | 1144 | 0 | 0 |
| CSAATLDGSNQPQHF | | 4 | Unstim | 0 | 0 | 0 | 0 | 0 | 0 | 0 | 0 |
| CSAATLDGSNQPQHF | | 4 | Unstim | 0 | 0 | 0 | 0 | 0 | 0 | 0 | 0 |

Figure 21F

| TCRB | SEQ ID NO: | Freq. | Stim/ Unstim | IL2 | IL10 | IL12A | IL13 | IL17A | IFNG | PRF1 | GZMB |
|---|---|---|---|---|---|---|---|---|---|---|---|
| CASSLAPLQGTFRADTQYF | 581 | 3 | Unstim | 0 | 0 | 0 | 0 | 0 | 0 | 0 | 0 |
| CASSLAPLQGTFRADTQYF |  | 3 | Unstim | 0 | 0 | 0 | 0 | 0 | 0 | 0 | 0 |
| CASSLAPLQGTFRADTQYF |  | 3 | Unstim | 0 | 0 | 0 | 0 | 0 | 0 | 0 | 0 |
| CASSPTGGTTYNSPLHF | 583 | 3 | Unstim | 0 | 0 | 0 | 0 | 0 | 0 | 0 | 0 |
| CASSPTGGTTYNSPLHF |  | 3 | Unstim | 0 | 0 | 0 | 0 | 0 | 0 | 0 | 0 |
| CASSPTGGTTYNSPLHF |  | 3 | Unstim | 0 | 0 | 0 | 0 | 0 | 0 | 0 | 0 |
| CAISAVGDRGTGELFF | 589 | 2 | Unstim | 0 | 0 | 0 | 0 | 0 | 0 | 482 | 7 |
| CAISAVGDRGTGELFF |  | 2 | Unstim | 0 | 0 | 0 | 0 | 0 | 0 | 883 | 0 |
| CASSFHTGEAYEQYF | 596 | 2 | Unstim | 0 | 0 | 0 | 0 | 0 | 0 | 428 | 0 |
| CASSFHTGEAYEQYF |  | 2 | Unstim | 0 | 0 | 0 | 0 | 0 | 0 | 0 | 0 |
| CASSLSGEKLFF | 582 | 2 | Unstim | 0 | 0 | 0 | 0 | 0 | 0 | 0 | 0 |
| CASSLSGEKLFF |  | 2 | Unstim | 0 | 0 | 840 | 0 | 0 | 0 | 0 | 0 |
| CASSLSQRPNTGELFF | 599 | 2 | Unstim | 0 | 0 | 0 | 0 | 0 | 0 | 100 | 0 |
| CASSLSQRPNTGELFF |  | 2 | Unstim | 0 | 3 | 0 | 0 | 2 | 738 | 0 | 0 |
| CASSLTGADSPLHF | 600 | 2 | Unstim | 0 | 0 | 0 | 0 | 0 | 1 | 0 | 0 |
| CASSLTGADSPLHF |  | 2 | Unstim | 0 | 0 | 0 | 0 | 0 | 440 | 0 | 0 |
| CASSPTIRDSGYTF | 602 | 2 | Unstim | 0 | 0 | 0 | 0 | 0 | 0 | 0 | 0 |
| CASSPTIRDSGYTF |  | 2 | Unstim | 0 | 0 | 0 | 0 | 0 | 0 | 0 | 0 |
| CASSQASHLSGNTIYF | 603 | 2 | Unstim | 0 | 0 | 0 | 0 | 0 | 0 | 0 | 0 |
| CASSQASHLSGNTIYF |  | 2 | Unstim | 0 | 0 | 0 | 0 | 0 | 0 | 0 | 0 |
| CASSQDEVGGRRAFF | 584 | 2 | Unstim | 0 | 0 | 0 | 0 | 0 | 0 | 0 | 0 |
| CASSQDEVGGRRAFF |  | 2 | Unstim | 0 | 0 | 0 | 0 | 0 | 0 | 0 | 0 |
| CASSQDWGDYGYTF | 585 | 2 | Unstim | 0 | 0 | 0 | 0 | 0 | 0 | 884 | 0 |
| CASSQDWGDYGYTF |  | 2 | Unstim | 0 | 0 | 0 | 0 | 0 | 1 | 0 | 0 |
| CASSQDYQGLDGEQFF |  | 2 | Unstim | 0 | 0 | 0 | 0 | 0 | 0 | 773 | 0 |
| CASSQDYQGVDNEQFF | 586 | 2 | Unstim | 0 | 0 | 0 | 0 | 0 | 0 | 0 | 0 |

Figure 21G

| TCRB | SEQ ID NO: | Freq. | Stim/Unstim | IL2 | IL10 | IL12A | IL13 | IL17A | IFNG | PRF1 | GZMB |
|---|---|---|---|---|---|---|---|---|---|---|---|
| CASSRGNSPLHF | 605 | 2 | Unstim | 0 | 0 | 0 | 0 | 0 | 0 | 0 | 0 |
| CASSRGNSPLHF | | 2 | Unstim | 0 | 0 | 0 | 0 | 0 | 0 | 0 | 0 |
| CASSSPGVGANVLTF | 587 | 2 | Unstim | 0 | 0 | 0 | 0 | 0 | 0 | 0 | 0 |
| CASSSPGVGANVLTF | | 2 | Unstim | 0 | 0 | 0 | 0 | 0 | 0 | 0 | 0 |
| CASSTGTGGEETQYF | 608 | 2 | Unstim | 0 | 0 | 0 | 0 | 290 | 0 | 0 | 0 |
| CASSTGTGGEETQYF | | 2 | Unstim | 0 | 0 | 0 | 0 | 0 | 0 | 0 | 120 |
| CASSVDMVGANVLTF | 609 | 2 | Unstim | 0 | 0 | 0 | 0 | 0 | 0 | 0 | 0 |
| CASSVDMVGANVLTF | | 2 | Unstim | 0 | 0 | 0 | 0 | 0 | 0 | 0 | 0 |
| CASSVFGIGVGGTYEQYF | 610 | 2 | Unstim | 0 | 0 | 0 | 0 | 0 | 0 | 0 | 1 |
| CASSVFGIGVGGTYEQYF | | 2 | Unstim | 0 | 0 | 0 | 0 | 0 | 0 | 0 | 0 |
| CASSWIAGVAGGAVADTQYF | 588 | 2 | Unstim | 0 | 0 | 0 | 0 | 0 | 0 | 0 | 0 |
| CASSWIAGVAGGAVADTQYF | | 2 | Unstim | 0 | 0 | 0 | 0 | 0 | 0 | 0 | 0 |
| CATSRDGTDYGYTF | 576 | 2 | Unstim | 0 | 0 | 0 | 0 | 0 | 0 | 0 | 0 |
| CATSDGTDYGYTF | | 2 | Unstim | 0 | 0 | 0 | 0 | 0 | 0 | 0 | 0 |
| CAWSPGGETQYF | 572 | 2 | Unstim | 0 | 0 | 0 | 0 | 0 | 264 | 0 | 0 |
| CAWSPGGETQYF | | 2 | Unstim | 0 | 0 | 0 | 0 | 0 | 364 | 0 | 0 |
| CSARDSAKLAGALRGGELFF | 620 | 2 | Unstim | 0 | 0 | 0 | 0 | 0 | 0 | 0 | 0 |
| CSARDSAKLAGALRGGELFF | | 2 | Unstim | 0 | 0 | 0 | 0 | 0 | 1477 | 0 | 0 |
| CSVGVMTYNEQFF | 622 | 2 | Unstim | 0 | 0 | 0 | 0 | 0 | 0 | 0 | 0 |
| CSVGVMTYNEQFF | | 2 | Unstim | 0 | 0 | 0 | 0 | 0 | 0 | 0 | 0 |
| CAISESSSGGDEKLFF | 626 | 1 | Unstim | 0 | 0 | 0 | 0 | 0 | 0 | 0 | 0 |
| CALDGTGGNTIYF | 629 | 1 | Unstim | 0 | 0 | 0 | 0 | 0 | 0 | 0 | 0 |
| CASAREGPDTQYF | 631 | 1 | Unstim | 0 | 0 | 756 | 0 | 0 | 3 | 0 | 0 |
| CASGDIDSARKQYF | 632 | 1 | Unstim | 0 | 0 | 0 | 0 | 0 | 0 | 0 | 0 |
| CASHLVDFTDTQYF | 634 | 1 | Unstim | 0 | 0 | 0 | 0 | 0 | 0 | 91 | 0 |
| CASHSTQAGYNEQFF | 635 | 1 | Unstim | 0 | 0 | 0 | 0 | 0 | 87 | 0 | 0 |

Figure 21H

| TCRB | SEQ ID NO: | Freq. | Stim/ Unstim | IL2 | IL10 | IL12A | IL13 | IL17A | IFNG | PRF1 | GZMB |
|---|---|---|---|---|---|---|---|---|---|---|---|
| CASIPPRAGPIANEKLFF | 590 | 1 | Unstim | 0 | 0 | 0 | 0 | 0 | 0 | 197 | 0 |
| CASISMGAGGLSGANVLTF | 637 | 1 | Unstim | 0 | 0 | 0 | 0 | 0 | 0 | 0 | 651 |
| CASITSGGATGELFF | 638 | 1 | Unstim | 0 | 0 | 0 | 0 | 787 | 0 | 0 | 0 |
| CASLRGYEQYF | 640 | 1 | Unstim | 0 | 0 | 0 | 0 | 0 | 793 | 0 | 0 |
| CASLSDFGSANTGELFF | 641 | 1 | Unstim | 0 | 0 | 0 | 0 | 0 | 0 | 0 | 0 |
| CASMKDVGAGANVLTF | 642 | 1 | Unstim | 0 | 0 | 0 | 0 | 0 | 0 | 0 | 0 |
| CASNLGTADSNQPQHF | 623 | 1 | Unstim | 0 | 0 | 0 | 0 | 0 | 0 | 0 | 0 |
| CASRAGGEAPAFF | 644 | 1 | Unstim | 0 | 0 | 0 | 0 | 0 | 0 | 1 | 0 |
| CASRIGTGSNQPQHF | 646 | 1 | Unstim | 0 | 0 | 0 | 0 | 0 | 1 | 0 | 0 |
| CASRLAGADNQPQHF | 647 | 1 | Unstim | 0 | 0 | 0 | 0 | 0 | 0 | 0 | 0 |
| CASRPGLAGDEQYF | 650 | 1 | Unstim | 0 | 0 | 0 | 0 | 0 | 0 | 0 | 0 |
| CASRPGQYSYEQYF | 651 | 1 | Unstim | 0 | 0 | 0 | 0 | 0 | 0 | 0 | 0 |
| CASRPGTVNTGELFF | 653 | 1 | Unstim | 0 | 0 | 0 | 0 | 0 | 0 | 0 | 0 |
| CASRQRDRVLEQYF | 654 | 1 | Unstim | 0 | 0 | 0 | 0 | 0 | 0 | 0 | 0 |
| CASRQTSGQETQYF | 656 | 1 | Unstim | 0 | 2 | 0 | 0 | 0 | 0 | 0 | 0 |
| CASRRTGMSTDTQYF | 657 | 1 | Unstim | 1 | 0 | 0 | 0 | 0 | 0 | 0 | 0 |
| CASRTERESINEQFF | 593 | 1 | Unstim | 0 | 0 | 0 | 0 | 0 | 0 | 0 | 0 |
| CASSAPGLAGTGETQYF | 662 | 1 | Unstim | 0 | 0 | 0 | 0 | 0 | 0 | 0 | 0 |
| CASSAPGTGDTDTQYF | 663 | 1 | Unstim | 0 | 0 | 0 | 0 | 0 | 0 | 0 | 0 |
| CASSATGLAGGGETQYF | 579 | 1 | Unstim | 0 | 0 | 0 | 0 | 0 | 0 | 0 | 0 |
| CASSATLGSLHYGYTF | 664 | 1 | Unstim | 0 | 0 | 0 | 0 | 0 | 0 | 0 | 0 |
| CASSAVEAGNTIYF | 665 | 1 | Unstim | 0 | 0 | 0 | 0 | 0 | 0 | 0 | 0 |
| CASSDDGTGDQPQHF | 666 | 1 | Unstim | 0 | 0 | 0 | 0 | 0 | 0 | 0 | 0 |
| CASSDRGNTEAFF | 668 | 1 | Unstim | 0 | 0 | 0 | 0 | 0 | 0 | 0 | 0 |
| CASSEAGDYEQYF | 669 | 1 | Unstim | 0 | 0 | 0 | 0 | 1 | 0 | 0 | 0 |
| CASSEAGGNTIYF | 670 | 1 | Unstim | 0 | 0 | 0 | 0 | 0 | 0 | 0 | 0 |

Figure 21I

| TCRB | SEQ ID NO: | Freq. | Stim/ Unstim | IL2 | IL10 | IL12A | IL13 | IL17A | IFNG | PRF1 | GZMB |
|---|---|---|---|---|---|---|---|---|---|---|---|
| CASSEAGVRLVSYEQYF | 671 | 1 | Unstim | 0 | 0 | 0 | 0 | 0 | 0 | 0 | 0 |
| CASSEGGDHEQFF | 594 | 1 | Unstim | 0 | 0 | 0 | 0 | 0 | 0 | 0 | 0 |
| CASSEPGEQFF | 580 | 1 | Unstim | 0 | 0 | 0 | 0 | 0 | 471 | 251 | 0 |
| CASSERAGGDTGELFF | 672 | 1 | Unstim | 0 | 0 | 0 | 0 | 0 | 0 | 1 | 0 |
| CASSEWGQGGAEQYF | 673 | 1 | Unstim | 0 | 0 | 0 | 0 | 0 | 0 | 0 | 0 |
| CASSEYKATYEQYF | 674 | 1 | Unstim | 1 | 0 | 0 | 0 | 0 | 0 | 0 | 0 |
| CASSFDEGTQHF | 675 | 1 | Unstim | 0 | 0 | 0 | 0 | 0 | 1 | 0 | 0 |
| CASSFGRWVDSPLHF | 679 | 1 | Unstim | 0 | 0 | 63 | 0 | 0 | 0 | 0 | 0 |
| CASSFRGDDKNIQYF | 681 | 1 | Unstim | 0 | 0 | 0 | 0 | 0 | 0 | 548 | 0 |
| CASSFSGSAYEQYF | 683 | 1 | Unstim | 0 | 0 | 0 | 0 | 0 | 0 | 0 | 0 |
| CASSFSTSGEQYF | 684 | 1 | Unstim | 0 | 0 | 0 | 0 | 0 | 1 | 0 | 0 |
| CASSFSTSGNTGELFF | 685 | 1 | Unstim | 0 | 0 | 0 | 0 | 0 | 0 | 0 | 190 |
| CASSGILETQYF | 689 | 1 | Unstim | 0 | 0 | 0 | 0 | 0 | 0 | 0 | 0 |
| CASSIGARGYTF | 692 | 1 | Unstim | 0 | 0 | 0 | 0 | 0 | 0 | 758 | 0 |
| CASSIGRTYEQYF | 693 | 1 | Unstim | 0 | 0 | 0 | 0 | 230 | 0 | 0 | 0 |
| CASSLAAGPYGYTF | 698 | 1 | Unstim | 0 | 0 | 0 | 0 | 1 | 1 | 0 | 0 |
| CASSLAGSVYEQYF | 700 | 1 | Unstim | 0 | 0 | 0 | 0 | 0 | 0 | 0 | 0 |
| CASSLAGTGQFF | 597 | 1 | Unstim | 0 | 0 | 0 | 0 | 0 | 0 | 0 | 0 |
| CASSLDGTSTYEQYF | 706 | 1 | Unstim | 0 | 0 | 0 | 0 | 0 | 0 | 0 | 0 |
| CASSLEATSRTQPQHF | 709 | 1 | Unstim | 0 | 0 | 0 | 0 | 0 | 0 | 0 | 0 |
| CASSLEGQGNGYTF | 598 | 1 | Unstim | 0 | 0 | 0 | 0 | 0 | 403 | 0 | 0 |
| CASSLEGSGGTEAFF | 711 | 1 | Unstim | 0 | 0 | 0 | 0 | 0 | 0 | 0 | 0 |
| CASSLELAGVTRSTDTQYF | 712 | 1 | Unstim | 0 | 0 | 0 | 0 | 0 | 0 | 0 | 0 |
| CASSLGDTGELFF | 714 | 1 | Unstim | 0 | 0 | 0 | 0 | 0 | 0 | 0 | 0 |
| CASSLGGGAEGPQHF | 715 | 1 | Unstim | 0 | 0 | 0 | 0 | 0 | 102 | 0 | 0 |
| CASSLGGTPEPQHF | 716 | 1 | Unstim | 0 | 0 | 0 | 0 | 0 | 0 | 0 | 0 |

Figure 21J

| TCRB | SEQ ID NO: | Freq. | Stim/Unstim | IL2 | IL10 | IL12A | IL13 | IL17A | IFNG | PRF1 | GZMB |
|---|---|---|---|---|---|---|---|---|---|---|---|
| CASSLGGVTYNEQFF | 717 | 1 | Unstim | 0 | 0 | 0 | 0 | 0 | 0 | 0 | 0 |
| CASSLGPGLASYEQYF | 718 | 1 | Unstim | 0 | 0 | 0 | 0 | 0 | 0 | 0 | 1 |
| CASSLGPGQETQYF | 719 | 1 | Unstim | 0 | 0 | 0 | 0 | 7 | 0 | 0 | 0 |
| CASSLGSGTNTGELFF | 721 | 1 | Unstim | 0 | 0 | 0 | 0 | 0 | 0 | 218 | 0 |
| CASSLGTERTEAFF | 722 | 1 | Unstim | 1 | 0 | 0 | 0 | 0 | 0 | 0 | 0 |
| CASSLIGASGPGELFF | 723 | 1 | Unstim | 0 | 0 | 0 | 0 | 0 | 0 | 0 | 0 |
| CASSLLAGGLIVNEQFF | 724 | 1 | Unstim | 0 | 0 | 0 | 0 | 0 | 0 | 0 | 0 |
| CASSLLRNSGNTIYF | 725 | 1 | Unstim | 0 | 0 | 0 | 0 | 0 | 0 | 0 | 0 |
| CASSLNAPGLGSTGELFF | 726 | 1 | Unstim | 0 | 0 | 0 | 0 | 0 | 0 | 0 | 0 |
| CASSLQAGSGEQYF | 728 | 1 | Unstim | 0 | 0 | 0 | 0 | 0 | 0 | 270 | 0 |
| CASSLQGALGNTIYF | 729 | 1 | Unstim | 0 | 0 | 0 | 0 | 0 | 0 | 0 | 0 |
| CASSLQVYNEQFF | 730 | 1 | Unstim | 0 | 0 | 0 | 0 | 0 | 0 | 0 | 0 |
| CASSLRASGTRGEQFF | 731 | 1 | Unstim | 0 | 0 | 0 | 0 | 0 | 0 | 0 | 0 |
| CASSLRGQGNEKLFF | 732 | 1 | Unstim | 0 | 0 | 0 | 0 | 0 | 1 | 0 | 1 |
| CASSLRGRETQYF | 733 | 1 | Unstim | 0 | 0 | 0 | 0 | 0 | 0 | 0 | 0 |
| CASSLRRDYGYTF | 734 | 1 | Unstim | 0 | 0 | 0 | 0 | 0 | 0 | 0 | 0 |
| CASSLSSSEVDTQYF | 735 | 1 | Unstim | 0 | 0 | 0 | 0 | 0 | 0 | 0 | 0 |
| CASSLSVTDSRSGNTIYF | 736 | 1 | Unstim | 0 | 0 | 0 | 0 | 0 | 0 | 0 | 0 |
| CASSLTLAGGQNEQYF | 737 | 1 | Unstim | 0 | 0 | 0 | 0 | 0 | 0 | 0 | 0 |
| CASSLVGGGNQPQHF | 738 | 1 | Unstim | 0 | 0 | 0 | 0 | 0 | 0 | 0 | 0 |
| CASSLYPRRISSGNTIYF | 740 | 1 | Unstim | 0 | 0 | 0 | 0 | 1267 | 0 | 0 | 0 |
| CASSNPYRGWGQNQPQHF | 743 | 1 | Unstim | 0 | 0 | 0 | 0 | 0 | 0 | 0 | 0 |
| CASSPGGADYGYTF | 748 | 1 | Unstim | 0 | 0 | 0 | 0 | 0 | 0 | 0 | 0 |
| CASSPGGESNQPQHF | 749 | 1 | Unstim | 0 | 0 | 0 | 0 | 0 | 0 | 0 | 0 |
| CASSPGPPGLGPQHF | 750 | 1 | Unstim | 0 | 0 | 0 | 0 | 0 | 0 | 1306 | 1487 |
| CASSPGTQVYEQYF | 751 | 1 | Unstim | 0 | 0 | 0 | 0 | 0 | 0 | 0 | 0 |

Figure 21K

| TCRB | SEQ ID NO: | Freq. | Stim/Unstim | IL2 | IL10 | IL12A | IL13 | IL17A | IFNG | PRF1 | GZMB |
|---|---|---|---|---|---|---|---|---|---|---|---|
| CASSPPTASGSVGQYF | 753 | 1 | Unstim | 0 | 0 | 0 | 0 | 0 | 0 | 0 | 0 |
| CASSPPTSEDAYNEQFF | 601 | 1 | Unstim | 0 | 0 | 0 | 0 | 0 | 0 | 0 | 0 |
| CASSPRGGAYEQYF | 756 | 1 | Unstim | 0 | 0 | 0 | 0 | 0 | 0 | 0 | 0 |
| CASSPRGYEQYF | 757 | 1 | Unstim | 0 | 0 | 0 | 0 | 0 | 0 | 0 | 0 |
| CASSPSGREDGYTF | 759 | 1 | Unstim | 0 | 0 | 0 | 0 | 0 | 0 | 0 | 0 |
| CASSPWSQSSGNTIYF | 762 | 1 | Unstim | 0 | 0 | 0 | 0 | 0 | 0 | 0 | 0 |
| CASSPYRDLYEQYF | 764 | 1 | Unstim | 0 | 0 | 0 | 0 | 0 | 0 | 0 | 0 |
| CASSQAGGNSPLHF | 765 | 1 | Unstim | 0 | 0 | 0 | 0 | 0 | 0 | 0 | 0 |
| CASSQEPDRRAQYF | 769 | 1 | Unstim | 0 | 0 | 0 | 0 | 0 | 0 | 0 | 0 |
| CASSQESRGGPVSYEQYF | 771 | 1 | Unstim | 0 | 0 | 0 | 0 | 0 | 0 | 0 | 0 |
| CASSQGAAGEQQYF | 772 | 1 | Unstim | 0 | 0 | 0 | 0 | 0 | 0 | 0 | 0 |
| CASSQGRGVGTDTQYF | 775 | 1 | Unstim | 0 | 0 | 0 | 0 | 0 | 0 | 2 | 0 |
| CASSQLSSGDYNEQFF | 778 | 1 | Unstim | 0 | 0 | 0 | 0 | 0 | 0 | 0 | 0 |
| CASSQRVGGLDTQYF | 779 | 1 | Unstim | 0 | 0 | 0 | 0 | 0 | 0 | 0 | 0 |
| CASSRSSGASSYEQYF | 785 | 1 | Unstim | 0 | 0 | 0 | 0 | 0 | 389 | 0 | 0 |
| CASSRTGGNSGNTIYF | 787 | 1 | Unstim | 0 | 0 | 0 | 0 | 0 | 0 | 0 | 0 |
| CASSSGQGNQPQHF | 789 | 1 | Unstim | 0 | 0 | 0 | 0 | 0 | 715 | 0 | 0 |
| CASSSGQQLAGELFF | 790 | 1 | Unstim | 0 | 0 | 0 | 0 | 0 | 1 | 0 | 0 |
| CASSSGTGGLETQYF | 575 | 1 | Unstim | 0 | 0 | 0 | 0 | 92 | 0 | 0 | 0 |
| CASSSPGQGWNEQFF | 791 | 1 | Unstim | 0 | 0 | 0 | 0 | 0 | 0 | 0 | 0 |
| CASSSTGTSGRMRIF | 798 | 1 | Unstim | 0 | 0 | 0 | 0 | 0 | 1 | 0 | 0 |
| CASSSTSGQEETQYF | 799 | 1 | Unstim | 0 | 0 | 0 | 0 | 0 | 0 | 0 | 0 |
| CASSTTGGTGTEAFF | 803 | 1 | Unstim | 0 | 0 | 0 | 0 | 0 | 1 | 0 | 0 |
| CASSVGGTSTDTQYF | 805 | 1 | Unstim | 0 | 0 | 0 | 0 | 0 | 0 | 50 | 0 |
| CASSVSGARGYNEQFF | 806 | 1 | Unstim | 0 | 0 | 0 | 0 | 0 | 0 | 0 | 0 |
| CASSYLSGGEHNEQFF | 807 | 1 | Unstim | 0 | 0 | 0 | 0 | 0 | 0 | 0 | 0 |

Figure 21L

| TCRB | SEQ ID NO: | Freq. | Stim/ Unstim | IL2 | IL10 | IL12A | IL13 | IL17A | IFNG | PRF1 | GZMB |
|---|---|---|---|---|---|---|---|---|---|---|---|
| CASSYPSGRICEQYF | 611 | 1 | Unstim | 0 | 0 | 0 | 0 | 0 | 1225 | 755 | 0 |
| CASSYSYRDNSPLHF | 811 | 1 | Unstim | 0 | 0 | 0 | 0 | 0 | 0 | 0 | 0 |
| CASTSSGGSPYEQYF | 812 | 1 | Unstim | 0 | 0 | 0 | 0 | 0 | 0 | 0 | 0 |
| CATSLMGQPQHF | 814 | 1 | Unstim | 0 | 0 | 0 | 0 | 0 | 1 | 0 | 0 |
| CATSRAFDWDRGLDTEAFF | 815 | 1 | Unstim | 0 | 0 | 0 | 0 | 0 | 0 | 0 | 0 |
| CATSRDLVGGNEQFF | 613 | 1 | Unstim | 0 | 0 | 0 | 0 | 0 | 0 | 0 | 81 |
| CATSREWGEAYEQYF | 577 | 1 | Unstim | 0 | 0 | 0 | 0 | 0 | 0 | 0 | 0 |
| CAWEKAGAGGTQYF | 819 | 1 | Unstim | 0 | 0 | 0 | 0 | 0 | 0 | 0 | 0 |
| CAWGTNYGYTF | 820 | 1 | Unstim | 0 | 0 | 0 | 0 | 0 | 0 | 0 | 0 |
| CAWMEVHEQFF | 821 | 1 | Unstim | 0 | 0 | 0 | 0 | 0 | 0 | 1 | 0 |
| CAWRSGGASPLHF | 823 | 1 | Unstim | 0 | 0 | 0 | 0 | 0 | 0 | 0 | 0 |
| CAWSASRDAEQFF | 825 | 1 | Unstim | 0 | 0 | 0 | 0 | 0 | 0 | 0 | 0 |
| CAWSEGGIGQPQHF | 826 | 1 | Unstim | 0 | 0 | 0 | 0 | 1 | 0 | 0 | 0 |
| CAWSGANYGYTF | 827 | 1 | Unstim | 0 | 0 | 0 | 0 | 0 | 0 | 0 | 0 |
| CAWSVLRGQYF | 830 | 1 | Unstim | 0 | 0 | 0 | 0 | 0 | 0 | 0 | 0 |
| CSAAIVGQPQHF | 832 | 1 | Unstim | 0 | 0 | 0 | 0 | 0 | 0 | 0 | 0 |
| CSAAPGTGDNSPLHF | 615 | 1 | Unstim | 0 | 0 | 0 | 0 | 32 | 0 | 0 | 0 |
| CSALLPTGGGEQYF | 835 | 1 | Unstim | 0 | 0 | 0 | 0 | 0 | 0 | 0 | 0 |
| CSANGLGGLNTEAFF | 836 | 1 | Unstim | 0 | 0 | 0 | 0 | 0 | 0 | 0 | 0 |
| CSAPQGQETQYF | 837 | 1 | Unstim | 0 | 0 | 0 | 0 | 0 | 0 | 0 | 0 |
| CSARAGGGDGELFF | 617 | 1 | Unstim | 0 | 0 | 0 | 0 | 0 | 543 | 0 | 175 |
| CSARDGAGVGDTQYF | 838 | 1 | Unstim | 0 | 0 | 0 | 0 | 0 | 0 | 0 | 0 |
| CSARDGTGIGDTQYF | 618 | 1 | Unstim | 0 | 0 | 0 | 0 | 0 | 0 | 0 | 0 |
| CSARDRDRYYEQYF | 619 | 1 | Unstim | 0 | 0 | 0 | 0 | 0 | 0 | 0 | 0 |
| CSARDSDGEKLFF | 839 | 1 | Unstim | 0 | 0 | 0 | 0 | 0 | 1701 | 0 | 29 |
| CSARGGGGALGSYNEQFF | 840 | 1 | Unstim | 0 | 0 | 0 | 0 | 0 | 0 | 0 | 0 |

Figure 21M

| TCRB | SEQ ID NO: | Freq. | Stim/Unstim | IL2 | IL10 | IL12A | IL13 | IL17A | IFNG | PRF1 | GZMB |
|---|---|---|---|---|---|---|---|---|---|---|---|
| CSASGRAGESNEQFF | 844 | 1 | Unstim | 0 | 0 | 0 | 0 | 640 | 0 | 0 | 0 |
| CSASKTGVHEQYF | 845 | 1 | Unstim | 0 | 0 | 0 | 0 | 0 | 0 | 0 | 0 |
| CSASRGNTEAFF | 846 | 1 | Unstim | 0 | 0 | 0 | 0 | 0 | 0 | 0 | 0 |
| CSATHRENLTDTQYF | 847 | 1 | Unstim | 0 | 0 | 0 | 0 | 0 | 0 | 0 | 0 |
| CSAVGGPVSQPQHF | 849 | 1 | Unstim | 0 | 0 | 0 | 0 | 0 | 0 | 0 | 0 |
| CSAVRTGGYYEQYF | 850 | 1 | Unstim | 0 | 0 | 0 | 0 | 0 | 0 | 0 | 0 |
| CSVDGALAGGTYEQYF | 852 | 1 | Unstim | 0 | 0 | 0 | 0 | 0 | 0 | 0 | 0 |
| CSVEEGDIRPYEQYF | 854 | 1 | Unstim | 0 | 0 | 0 | 0 | 0 | 0 | 0 | 0 |
| CSVSQGRGGDTQYF | 858 | 1 | Unstim | 0 | 0 | 0 | 0 | 0 | 0 | 0 | 0 |
| CASSLASMGVGELFF | 265 | 27 | Stim | 0 | 0 | 0 | 0 | 666 | 0 | 0 | 0 |
| CASSLASMGVGELFF | | 27 | Stim | 0 | 0 | 0 | 0 | 0 | 0 | 0 | 0 |
| CASSLASMGVGELFF | | 27 | Stim | 0 | 0 | 0 | 0 | 588 | 0 | 0 | 0 |
| CASSLASMGVGELFF | | 27 | Stim | 2 | 0 | 0 | 1 | 688 | 1 | 0 | 3 |
| CASSLASMGVGELFF | | 27 | Stim | 0 | 0 | 0 | 0 | 758 | 969 | 107 | 0 |
| CASSLASMGVGELFF | | 27 | Stim | 0 | 0 | 0 | 0 | 773 | 0 | 0 | 1 |
| CASSLASMGVGELFF | | 27 | Stim | 0 | 0 | 0 | 0 | 927 | 0 | 0 | 0 |
| CASSLASMGVGELFF | | 27 | Stim | 0 | 0 | 0 | 0 | 835 | 0 | 0 | 0 |
| CASSLASMGVGELFF | | 27 | Stim | 0 | 0 | 0 | 0 | 657 | 1 | 0 | 0 |
| CASSLASMGVGELFF | | 27 | Stim | 0 | 0 | 0 | 0 | 725 | 1 | 0 | 0 |
| CASSLASMGVGELFF | | 27 | Stim | 0 | 0 | 0 | 0 | 721 | 1 | 0 | 0 |
| CASSLASMGVGELFF | | 27 | Stim | 0 | 0 | 0 | 0 | 1582 | 0 | 0 | 0 |
| CASSLASMGVGELFF | | 27 | Stim | 0 | 0 | 0 | 0 | 1444 | 1 | 0 | 0 |
| CASSLASMGVGELFF | | 27 | Stim | 0 | 0 | 0 | 0 | 335 | 0 | 0 | 0 |
| CASSLASMGVGELFF | | 27 | Stim | 0 | 0 | 0 | 0 | 485 | 0 | 0 | 0 |
| CASSLASMGVGELFF | | 27 | Stim | 0 | 0 | 0 | 0 | 106 | 0 | 0 | 0 |

Figure 21N

| TCRB | SEQ ID NO: | Freq. | Stim/ Unstim | IL2 | IL10 | IL12A | IL13 | IL17A | IFNG | PRF1 | GZMB |
|---|---|---|---|---|---|---|---|---|---|---|---|
| CASSLASMGVGELFF | | 27 | Stim | 0 | 0 | 0 | 0 | 303 | 0 | 0 | 0 |
| CASSLASMGVGELFF | | 27 | Stim | 0 | 0 | 0 | 0 | 163 | 43 | 0 | 0 |
| CASSLASMGVGELFF | | 27 | Stim | 0 | 0 | 0 | 0 | 90 | 0 | 0 | 0 |
| CASSLASMGVGELFF | | 27 | Stim | 0 | 0 | 0 | 0 | 226 | 0 | 0 | 0 |
| CASSLASMGVGELFF | | 27 | Stim | 0 | 0 | 0 | 0 | 311 | 0 | 0 | 0 |
| CASSLASMGVGELFF | | 27 | Stim | 0 | 0 | 0 | 0 | 0 | 1 | 0 | 0 |
| CASSLASMGVGELFF | | 27 | Stim | 0 | 0 | 0 | 0 | 122 | 0 | 0 | 0 |
| CASSLASMGVGELFF | | 27 | Stim | 0 | 0 | 0 | 0 | 125 | 72 | 0 | 0 |
| CASSLASMGVGELFF | | 27 | Stim | 0 | 0 | 0 | 0 | 237 | 0 | 0 | 0 |
| CASSLASMGVGELFF | | 27 | Stim | 0 | 0 | 0 | 0 | 744 | 0 | 0 | 0 |
| CASPGGWTGGGNEQFF | | 24 | Stim | 0 | 0 | 0 | 0 | 174 | 0 | 0 | 0 |
| CASPGGWTGGGNEQFF | | 24 | Stim | 0 | 0 | 0 | 0 | 202 | 0 | 0 | 0 |
| CASPGGWTGGGNEQFF | | 24 | Stim | 0 | 0 | 0 | 0 | 29 | 284 | 6 | 0 |
| CASPGGWTGGGNEQFF | | 24 | Stim | 0 | 0 | 0 | 0 | 102 | 139 | 0 | 0 |
| CASPGGWTGGGNEQFF | | 24 | Stim | 0 | 0 | 0 | 0 | 1 | 490 | 0 | 0 |
| CASPGGWTGGGNEQFF | 563 | 24 | Stim | 0 | 0 | 0 | 0 | 98 | 232 | 262 | 0 |
| CASPGGWTGGGNEQFF | | 24 | Stim | 0 | 0 | 0 | 0 | 213 | 388 | 0 | 0 |
| CASPGGWTGGGNEQFF | | 24 | Stim | 2 | 0 | 0 | 0 | 30 | 1 | 0 | 0 |
| CASPGGWTGGGNEQFF | | 24 | Stim | 0 | 0 | 0 | 0 | 6 | 1117 | 0 | 0 |
| CASPGGWTGGGNEQFF | | 24 | Stim | 0 | 0 | 0 | 0 | 370 | 583 | 0 | 0 |
| CASPGGWTGGGNEQFF | | 24 | Stim | 0 | 0 | 0 | 0 | 454 | 1050 | 0 | 0 |
| CASPGGWTGGGNEQFF | | 24 | Stim | 0 | 0 | 0 | 0 | 0 | 1679 | 0 | 0 |
| CASPGGWTGGGNEQFF | | 24 | Stim | 0 | 0 | 0 | 0 | 735 | 1410 | 0 | 0 |
| CASPGGWTGGGNEQFF | | 24 | Stim | 0 | 0 | 0 | 0 | 0 | 1 | 0 | 0 |
| CASPGGWTGGGNEQFF | | 24 | Stim | 0 | 0 | 0 | 0 | 486 | 675 | 0 | 0 |
| CASPGGWTGGGNEQFF | | 24 | Stim | 0 | 0 | 0 | 0 | 67 | 331 | 0 | 0 |

Figure 21O

| TCRB | SEQ ID NO: | Freq. | Stim/Unstim | IL2 | IL10 | IL12A | IL13 | IL17A | IFNG | PRF1 | GZMB |
|---|---|---|---|---|---|---|---|---|---|---|---|
| CASPGGWTGGGNEQFF | | 24 | Stim | 0 | 0 | 0 | 0 | 3 | 588 | 0 | 0 |
| CASPGGWTGGGNEQFF | | 24 | Stim | 0 | 0 | 0 | 0 | 175 | 365 | 0 | 0 |
| CASPGGWTGGGNEQFF | | 24 | Stim | 0 | 0 | 0 | 0 | 325 | 620 | 0 | 0 |
| CASPGGWTGGGNEQFF | | 24 | Stim | 0 | 0 | 0 | 0 | 384 | 473 | 96 | 0 |
| CASPGGWTGGGNEQFF | | 24 | Stim | 14 | 0 | 0 | 0 | 588 | 0 | 0 | 0 |
| CASPGGWTGGGNEQFF | | 24 | Stim | 0 | 0 | 0 | 0 | 267 | 439 | 450 | 0 |
| CASPGGWTGGGNEQFF | | 24 | Stim | 0 | 0 | 0 | 0 | 430 | 612 | 0 | 0 |
| CASNTLGAGGREQYF | | 16 | Stim | 0 | 0 | 0 | 0 | 92 | 0 | 0 | 0 |
| CASNTLGAGGREQYF | | 16 | Stim | 0 | 0 | 0 | 0 | 381 | 462 | 0 | 0 |
| CASNTLGAGGREQYF | | 16 | Stim | 0 | 0 | 0 | 0 | 297 | 36 | 0 | 0 |
| CASNTLGAGGREQYF | | 16 | Stim | 0 | 0 | 0 | 0 | 129 | 0 | 0 | 0 |
| CASNTLGAGGREQYF | | 16 | Stim | 0 | 0 | 0 | 0 | 117 | 1253 | 0 | 0 |
| CASNTLGAGGREQYF | 564 | 16 | Stim | 0 | 0 | 0 | 0 | 679 | 526 | 0 | 0 |
| CASNTLGAGGREQYF | | 16 | Stim | 0 | 0 | 0 | 0 | 303 | 0 | 228 | 0 |
| CASNTLGAGGREQYF | | 16 | Stim | 0 | 0 | 0 | 0 | 326 | 1 | 0 | 0 |
| CASNTLGAGGREQYF | | 16 | Stim | 0 | 0 | 0 | 0 | 1019 | 521 | 0 | 0 |
| CASNTLGAGGREQYF | | 16 | Stim | 0 | 0 | 0 | 0 | 260 | 1891 | 0 | 0 |
| CASNTLGAGGREQYF | | 16 | Stim | 0 | 0 | 0 | 0 | 967 | 1917 | 0 | 0 |
| CASNTLGAGGREQYF | | 16 | Stim | 0 | 0 | 0 | 0 | 1056 | 1 | 0 | 0 |
| CASNTLGAGGREQYF | | 16 | Stim | 0 | 0 | 0 | 0 | 630 | 0 | 0 | 0 |
| CASNTLGAGGREQYF | | 16 | Stim | 0 | 0 | 0 | 0 | 595 | 76 | 137 | 178 |
| CASNTLGAGGREQYF | | 16 | Stim | 0 | 0 | 0 | 0 | 252 | 0 | 0 | 0 |
| CASNTLGAGGREQYF | | 16 | Stim | 0 | 0 | 0 | 0 | 263 | 554 | 371 | 0 |
| CASSQGLAAPYEQYF | 566 | 13 | Stim | 0 | 0 | 0 | 0 | 1 | 923 | 0 | 0 |
| CASSQGLAAPYEQYF | | 13 | Stim | 0 | 0 | 0 | 0 | 569 | 492 | 0 | 0 |
| CASSQGLAAPYEQYF | | 13 | Stim | 0 | 0 | 0 | 0 | 381 | | | |

Figure 21P

| TCRB | SEQ ID NO: | Freq. | Stim/Unstim | IL2 | IL10 | IL12A | IL13 | IL17A | IFNG | PRF1 | GZMB |
|---|---|---|---|---|---|---|---|---|---|---|---|
| CASSQGLAAPYEQYF | | 13 | Stim | 0 | 0 | 0 | 0 | 531 | 808 | 0 | 0 |
| CASSQGLAAPYEQYF | | 13 | Stim | 0 | 0 | 0 | 0 | 655 | 852 | 0 | 0 |
| CASSQGLAAPYEQYF | | 13 | Stim | 0 | 0 | 0 | 0 | 186 | 807 | 0 | 0 |
| CASSQGLAAPYEQYF | | 13 | Stim | 0 | 0 | 0 | 0 | 468 | 732 | 0 | 0 |
| CASSQGLAAPYEQYF | | 13 | Stim | 0 | 0 | 0 | 0 | 460 | 768 | 0 | 0 |
| CASSQGLAAPYEQYF | | 13 | Stim | 0 | 0 | 0 | 0 | 120 | 834 | 0 | 0 |
| CASSQGLAAPYEQYF | | 13 | Stim | 0 | 0 | 0 | 0 | 93 | 336 | 0 | 0 |
| CASSQGLAAPYEQYF | | 13 | Stim | 0 | 0 | 0 | 0 | 0 | 139 | 0 | 0 |
| CASSQGLAAPYEQYF | | 13 | Stim | 0 | 0 | 0 | 0 | 222 | 558 | 0 | 0 |
| CASSQGLAAPYEQYF | | 13 | Stim | 0 | 0 | 0 | 0 | 11 | 100 | 0 | 0 |
| CASSQGLAAPYEQYF | | 13 | Stim | 0 | 0 | 0 | 0 | 2 | 491 | 248 | 0 |
| CAWSDGVVGEKLFF | | 7 | Stim | 0 | 0 | 0 | 0 | 0 | 0 | 0 | 0 |
| CAWSDGVVGEKLFF | 567 | 7 | Stim | 0 | 0 | 0 | 0 | 2 | 0 | 0 | 0 |
| CAWSDGVVGEKLFF | | 7 | Stim | 0 | 0 | 0 | 0 | 565 | 852 | 0 | 0 |
| CAWSDGVVGEKLFF | | 7 | Stim | 0 | 0 | 0 | 0 | 586 | 879 | 0 | 0 |
| CAWSDGVVGEKLFF | | 7 | Stim | 0 | 0 | 0 | 0 | 504 | 983 | 0 | 0 |
| CAWSDGVVGEKLFF | | 7 | Stim | 0 | 0 | 0 | 0 | 574 | 997 | 0 | 0 |
| CASRENSGANVLTF | | 6 | Stim | 0 | 0 | 0 | 0 | 330 | 0 | 0 | 0 |
| CASRENSGANVLTF | | 6 | Stim | 0 | 0 | 0 | 0 | 0 | 115 | 0 | 0 |
| CASRENSGANVLTF | 568 | 6 | Stim | 0 | 0 | 0 | 0 | 19 | 1659 | 0 | 0 |
| CASRENSGANVLTF | | 6 | Stim | 0 | 0 | 0 | 0 | 9 | 1198 | 0 | 0 |
| CASRENSGANVLTF | | 6 | Stim | 0 | 0 | 0 | 0 | 0 | 712 | 0 | 0 |
| CASRENSGANVLTF | | 6 | Stim | 0 | 0 | 1 | 0 | 0 | 516 | 0 | 0 |
| CASRENSGANVLTF | | 6 | Stim | 0 | 0 | 0 | 0 | 0 | 764 | 64 | 0 |
| CASSEAGGQDYGNEQFF | 565 | 6 | Stim | 0 | 0 | 0 | 0 | 23 | 181 | 0 | 0 |
| CASSEAGGQDYGNEQFF | | 6 | Stim | 0 | 0 | 0 | 0 | 205 | 259 | 0 | 0 |

Figure 21Q

| TCRB | SEQ ID NO: | Freq. | Stim/ Unstim | IL2 | IL10 | IL12A | IL13 | IL17A | IFNG | PRF1 | GZMB |
|---|---|---|---|---|---|---|---|---|---|---|---|
| CASSEAGGQDYGNEQFF | | 6 | Stim | 0 | 0 | 0 | 0 | 0 | 645 | 80 | 0 |
| CASSEAGGQDYGNEQFF | | 6 | Stim | 0 | 0 | 0 | 0 | 0 | 1735 | 0 | 0 |
| CASSEAGGQDYGNEQFF | | 6 | Stim | 0 | 0 | 0 | 0 | 399 | 444 | 0 | 0 |
| CASSEAGGQDYGNEQFF | | 6 | Stim | 0 | 0 | 0 | 0 | 438 | 428 | 14 | 0 |
| CASSEPGEQFF | | 4 | Stim | 0 | 0 | 0 | 0 | 148 | 179 | 0 | 0 |
| CASSEPGEQFF | 580 | 4 | Stim | 0 | 0 | 0 | 0 | 113 | 1 | 0 | 1005 |
| CASSEPGEQFF | | 4 | Stim | 0 | 0 | 0 | 0 | 4 | 763 | 0 | 0 |
| CASSEPGEQFF | | 4 | Stim | 0 | 0 | 0 | 0 | 1 | 124 | 0 | 0 |
| CASSSGTGGLETQYF | | 4 | Stim | 0 | 0 | 0 | 0 | 310 | 0 | 0 | 1 |
| CASSSGTGGLETQYF | 575 | 4 | Stim | 0 | 0 | 0 | 0 | 1472 | 0 | 0 | 0 |
| CASSSGTGGLETQYF | | 4 | Stim | 0 | 0 | 0 | 0 | 690 | 0 | 0 | 0 |
| CASSSGTGGLETQYF | | 4 | Stim | 0 | 0 | 0 | 0 | 124 | 85 | 0 | 0 |
| CATSREWGEAYEQYF | | 4 | Stim | 0 | 0 | 0 | 0 | 270 | 415 | 0 | 0 |
| CATSREWGEAYEQYF | 577 | 4 | Stim | 0 | 0 | 0 | 0 | 495 | 0 | 0 | 0 |
| CATSREWGEAYEQYF | | 4 | Stim | 0 | 0 | 0 | 0 | 1174 | 0 | 0 | 0 |
| CATSREWGEAYEQYF | | 4 | Stim | 0 | 0 | 0 | 0 | 960 | 0 | 0 | 0 |
| CAWSPGGETQYF | | 4 | Stim | 0 | 0 | 0 | 0 | 185 | 577 | 369 | 0 |
| CAWSPGGETQYF | 572 | 4 | Stim | 0 | 0 | 0 | 0 | 544 | 945 | 0 | 0 |
| CAWSPGGETQYF | | 4 | Stim | 0 | 0 | 0 | 0 | 121 | 0 | 0 | 0 |
| CAWSPGGETQYF | | 4 | Stim | 1 | 0 | 0 | 0 | 16 | 457 | 0 | 0 |
| CASSATGLAGGGETQYF | | 3 | Stim | 0 | 0 | 0 | 0 | 453 | 969 | 0 | 0 |
| CASSATGLAGGGETQYF | 579 | 3 | Stim | 0 | 0 | 0 | 0 | 0 | 664 | 0 | 0 |
| CASSATGLAGGGETQYF | | 3 | Stim | 0 | 0 | 0 | 0 | 451 | 740 | 0 | 0 |
| CATSRDGTDYGYTF | | 3 | Stim | 0 | 0 | 0 | 0 | 512 | 886 | 0 | 0 |
| CATSRDGTDYGYTF | 576 | 3 | Stim | 0 | 0 | 0 | 0 | 0 | 0 | 0 | 0 |
| CATSRDGTDYGYTF | | 3 | Stim | 0 | 0 | 0 | 0 | 0 | 473 | 26 | 0 |

Figure 21R

| TCRB | SEQ ID NO: | Freq. | Stim/ Unstim | IL2 | IL10 | IL12A | IL13 | IL17A | IFNG | PRF1 | GZMB |
|---|---|---|---|---|---|---|---|---|---|---|---|
| CSAGTYRTDTQYF | 569 | 3 | Stim | 0 | 0 | 0 | 0 | 196 | 0 | 0 | 0 |
| CSAGTYRTDTQYF | | 3 | Stim | 0 | 0 | 0 | 0 | 424 | 756 | 0 | 0 |
| CSAGTYRTDTQYF | | 3 | Stim | 0 | 0 | 0 | 0 | 0 | 683 | 0 | 0 |
| CASRKGTEGTQYF | 592 | 2 | Stim | 0 | 0 | 0 | 0 | 0 | 2776 | 0 | 0 |
| CASRKGTEGTQYF | | 2 | Stim | 0 | 0 | 0 | 0 | 336 | 0 | 0 | 0 |
| CASSEVWGSTHNEQFF | 595 | 2 | Stim | 0 | 0 | 0 | 0 | 233 | 404 | 0 | 0 |
| CASSEVWGSTHNEQFF | | 2 | Stim | 0 | 0 | 0 | 0 | 0 | 2 | 0 | 0 |
| CASSKGTDLNTEAFF | 697 | 2 | Stim | 0 | 0 | 0 | 0 | 0 | 0 | 0 | 0 |
| CASSKGTDLNTEAFF | | 2 | Stim | 0 | 0 | 0 | 0 | 0 | 0 | 0 | 0 |
| CASSLAPGVGETQYF | 701 | 2 | Stim | 0 | 0 | 0 | 0 | 0 | 0 | 0 | 0 |
| CASSLAPGVGETQYF | | 2 | Stim | 0 | 0 | 0 | 0 | 201 | 468 | 0 | 0 |
| CASSLGGGSYNEQFF | 570 | 2 | Stim | 0 | 0 | 0 | 0 | 107 | 204 | 0 | 0 |
| CASSLGGGSYNEQFF | | 2 | Stim | 0 | 0 | 0 | 0 | 0 | 0 | 0 | 0 |
| CASSPAGPFYEQYF | 744 | 2 | Stim | 4 | 0 | 0 | 0 | 0 | 0 | 0 | 0 |
| CASSPAPGPDTQYF | 745 | 2 | Stim | 0 | 0 | 0 | 0 | 0 | 817 | 1 | 0 |
| CASSQDAVQRLYGYTF | 604 | 2 | Stim | 0 | 0 | 0 | 0 | 291 | 0 | 0 | 0 |
| CASSQDAVQRLYGYTF | | 2 | Stim | 0 | 0 | 0 | 0 | 254 | 498 | 0 | 0 |
| CASSQDGAGGREQFF | 571 | 2 | Stim | 0 | 0 | 0 | 0 | 414 | 0 | 0 | 0 |
| CASSQDGAGGREQFF | | 2 | Stim | 0 | 0 | 0 | 0 | 245 | 0 | 0 | 0 |
| CASSSASGGVGELFF | 267 | 2 | Stim | 0 | 0 | 0 | 0 | 213 | 1087 | 329 | 0 |
| CASSSASGGVGELFF | | 2 | Stim | 20 | 0 | 0 | 0 | 0 | 0 | 0 | 0 |
| CASSSGQLVHEQFF | 606 | 2 | Stim | 0 | 0 | 0 | 0 | 0 | 0 | 0 | 0 |
| CASSSGQLVHEQFF | | 2 | Stim | 0 | 0 | 0 | 0 | 0 | 193 | 0 | 0 |
| CASSSQSNTEAFF | 607 | 2 | Stim | 0 | 0 | 0 | 0 | 375 | 303 | 0 | 0 |
| CASSSQSNTEAFF | | 2 | Stim | 0 | 0 | 0 | 0 | 447 | 631 | 0 | 0 |
| CASSSSDRAHF | 794 | 2 | Stim | 0 | 0 | 0 | 0 | | | | |

Figure 21S

| TCRB | SEQ ID NO: | Freq. | Stim/ Unstim | IL2 | IL10 | IL12A | IL13 | IL17A | IFNG | PRF1 | GZMB |
|---|---|---|---|---|---|---|---|---|---|---|---|
| CASSSSDRAHF | | 2 | Stim | 0 | 0 | 0 | 0 | 0 | 0 | 0 | 0 |
| CASTSGGAYEQYF | 612 | 2 | Stim | 0 | 0 | 0 | 0 | 1 | 448 | 0 | 0 |
| CASTSGGAYEQYF | 612 | 2 | Stim | 0 | 0 | 0 | 0 | 1 | 0 | 0 | 1623 |
| CAWSAGQGILNEQFF | 614 | 2 | Stim | 0 | 0 | 0 | 0 | 267 | 0 | 0 | 0 |
| CAWSAGQGILNEQFF | 614 | 2 | Stim | 0 | 1 | 0 | 0 | 568 | 2 | 0 | 0 |
| CSAPTRAGANVLTF | 616 | 2 | Stim | 0 | 0 | 0 | 0 | 292 | 393 | 0 | 0 |
| CSAPTRAGANVLTF | 616 | 2 | Stim | 0 | 0 | 0 | 0 | 502 | 531 | 0 | 0 |
| CSVAYPGQSYGYTF | 621 | 2 | Stim | 0 | 0 | 0 | 0 | 315 | 383 | 0 | 0 |
| CSVAYPGQSYGYTF | 621 | 2 | Stim | 0 | 0 | 0 | 0 | 0 | 0 | 0 | 0 |
| CAIREQGEAFF | 624 | 1 | Stim | 0 | 0 | 0 | 0 | 208 | 618 | 0 | 0 |
| CAISENGKANYGYTF | 625 | 1 | Stim | 0 | 0 | 0 | 0 | 844 | 0 | 0 | 0 |
| CAISGGGQDSNQPQHF | 627 | 1 | Stim | 0 | 0 | 0 | 306 | 1 | 680 | 0 | 0 |
| CAISSPSSGNYEQYF | 628 | 1 | Stim | 0 | 0 | 0 | 0 | 409 | 550 | 0 | 0 |
| CASAAGWDTEAFF | 630 | 1 | Stim | 0 | 0 | 0 | 0 | 0 | 638 | 0 | 0 |
| CASGGTEAFF | 633 | 1 | Stim | 0 | 0 | 0 | 0 | 146 | 704 | 0 | 0 |
| CASIPPRAGPIANEKLFF | 590 | 1 | Stim | 55 | 0 | 0 | 0 | 0 | 0 | 0 | 0 |
| CASIREGSHYNEQFF | 636 | 1 | Stim | 0 | 0 | 0 | 0 | 1123 | 0 | 0 | 0 |
| CASKKGTGGNQPQHF | 639 | 1 | Stim | 0 | 0 | 0 | 0 | 826 | 1484 | 0 | 0 |
| CASNLGTADSNQPQHF | 623 | 1 | Stim | 1 | 0 | 0 | 0 | 161 | 186 | 0 | 0 |
| CASQGQGEQYF | 643 | 1 | Stim | 0 | 0 | 0 | 0 | 292 | 0 | 0 | 0 |
| CASRDGVQPQHF | 591 | 1 | Stim | 0 | 0 | 0 | 0 | 429 | 711 | 0 | 0 |
| CASRDGVQPQHF | 591 | 1 | Stim | 0 | 0 | 0 | 0 | 1028 | 0 | 0 | 0 |
| CASRGDRGDYGYTF | 645 | 1 | Stim | 0 | 0 | 0 | 0 | 0 | 0 | 0 | 0 |
| CASRLGLAENEQFF | 648 | 1 | Stim | 0 | 0 | 0 | 0 | 1389 | 0 | 0 | 0 |
| CASRLSRDNSPLHF | 649 | 1 | Stim | 0 | 0 | 0 | 0 | 983 | 0 | 0 | 0 |
| CASRPGTGRDQPQHF | 652 | 1 | Stim | 0 | 0 | 0 | 0 | 0 | 122 | 56 | 0 |

Figure 21T

| TCRB | SEQ ID NO: | Freq. | Stim/Unstim | IL2 | IL10 | IL12A | IL13 | IL17A | IFNG | PRF1 | GZMB |
|---|---|---|---|---|---|---|---|---|---|---|---|
| CASRQTGTSTDTQYF | 655 | 1 | Stim | 0 | 0 | 0 | 0 | 547 | 992 | 0 | 0 |
| CASRSGIYTEAFF | 658 | 1 | Stim | 0 | 0 | 0 | 0 | 0 | 2 | 0 | 0 |
| CASRSGLAGTTDTQYF | 659 | 1 | Stim | 0 | 0 | 0 | 0 | 0 | 0 | 349 | 0 |
| CASTERESINEQFF | 593 | 1 | Stim | 0 | 0 | 0 | 0 | 953 | 1599 | 0 | 1 |
| CASRTGLNGELFF | 660 | 1 | Stim | 0 | 0 | 0 | 0 | 640 | 1061 | 0 | 0 |
| CASSAGQDSDTQYF | 661 | 1 | Stim | 0 | 0 | 0 | 0 | 0 | 0 | 0 | 0 |
| CASSDPGGGVTGELFF | 667 | 1 | Stim | 0 | 0 | 0 | 0 | 0 | 1040 | 36 | 0 |
| CASSEGGDHEQFF | 594 | 1 | Stim | 0 | 0 | 0 | 39 | 686 | 945 | 0 | 0 |
| CASSFERPYEQYF | 676 | 1 | Stim | 0 | 0 | 0 | 0 | 0 | 425 | 0 | 0 |
| CASSFGAEDTQYF | 677 | 1 | Stim | 0 | 0 | 0 | 0 | 0 | 728 | 5 | 0 |
| CASSFGGPSYEQYF | 678 | 1 | Stim | 0 | 0 | 0 | 0 | 536 | 965 | 0 | 0 |
| CASSFPYTEAFF | 680 | 1 | Stim | 0 | 0 | 0 | 0 | 146 | 0 | 14 | 0 |
| CASSFSGREGVDTQYF | 682 | 1 | Stim | 0 | 0 | 0 | 0 | 0 | 0 | 0 | 0 |
| CASSFVNSPLHF | 686 | 1 | Stim | 0 | 0 | 0 | 0 | 286 | 804 | 0 | 0 |
| CASSFVRALGSYNSPLHF | 687 | 1 | Stim | 1 | 0 | 0 | 0 | 580 | 1 | 0 | 0 |
| CASSGGGTGNNYEQYF | 688 | 1 | Stim | 0 | 0 | 0 | 0 | 775 | 1 | 0 | 0 |
| CASSGTGGHQPQHF | 690 | 1 | Stim | 0 | 0 | 0 | 0 | 220 | 191 | 0 | 0 |
| CASSHSATHNEQFF | 691 | 1 | Stim | 0 | 199 | 0 | 0 | 0 | 0 | 0 | 0 |
| CASSIRRNNEQFF | 694 | 1 | Stim | 0 | 0 | 0 | 0 | 0 | 0 | 0 | 0 |
| CASSIWGSEAFF | 695 | 1 | Stim | 0 | 0 | 0 | 0 | 233 | 0 | 0 | 0 |
| CASSKEGRITDTQYF | 696 | 1 | Stim | 0 | 0 | 0 | 0 | 0 | 1455 | 0 | 0 |
| CASSLAANSPLHF | 699 | 1 | Stim | 0 | 0 | 0 | 0 | 150 | 329 | 0 | 0 |
| CASSLAGTGQFF | 597 | 1 | Stim | 0 | 0 | 0 | 0 | 691 | 1101 | 0 | 0 |
| CASSLAPLQGTFRADTQYF | 581 | 1 | Stim | 0 | 0 | 36 | 0 | 0 | 1315 | 0 | 0 |
| CASSLASGIYEQFF | 702 | 1 | Stim | 62 | 0 | 0 | 0 | 0 | 0 | 0 | 0 |
| CASSLASRGPQGETQYF | 703 | 1 | Stim | 0 | 0 | 0 | 0 | 0 | 0 | 0 | 0 |

Figure 21U

| TCRB | SEQ ID NO: | Freq. | Stim/Unstim | IL2 | IL10 | IL12A | IL13 | IL17A | IFNG | PRF1 | GZMB |
|---|---|---|---|---|---|---|---|---|---|---|---|
| CASSLAYGTDTQYF | 704 | 1 | Stim | 0 | 0 | 0 | 0 | 0 | 1 | 0 | 0 |
| CASSLDGGVVGGYTF | 705 | 1 | Stim | 0 | 0 | 0 | 0 | 1 | 478 | 0 | 0 |
| CASSLDSQNTGELFF | 707 | 1 | Stim | 0 | 0 | 0 | 0 | 355 | 0 | 1 | 0 |
| CASSLDSTGTGKETQYF | 708 | 1 | Stim | 0 | 0 | 0 | 0 | 4 | 1005 | 246 | 379 |
| CASSLEGPRDTQYF | 710 | 1 | Stim | 0 | 0 | 0 | 0 | 0 | 479 | 0 | 0 |
| CASSLEGQGNGYTF | 598 | 1 | Stim | 0 | 0 | 0 | 0 | 0 | 972 | 0 | 0 |
| CASSLEPGRQGNTGELFF | 713 | 1 | Stim | 0 | 0 | 0 | 0 | 604 | 0 | 0 | 0 |
| CASSLGGTPEPQHF | 716 | 1 | Stim | 0 | 0 | 0 | 0 | 0 | 123 | 0 | 0 |
| CASSLGQEENSPLHF | 720 | 1 | Stim | 0 | 0 | 0 | 0 | 206 | 2218 | 0 | 0 |
| CASSLNQDGYTF | 727 | 1 | Stim | 0 | 0 | 0 | 0 | 612 | 0 | 0 | 0 |
| CASSLSGEKLFF | 582 | 1 | Stim | 0 | 0 | 0 | 0 | 91 | 877 | 305 | 0 |
| CASSLVIQPQHF | 739 | 1 | Stim | 0 | 0 | 0 | 0 | 324 | 542 | 0 | 0 |
| CASSLYTGGGSGELFF | 741 | 1 | Stim | 900 | 0 | 0 | 0 | 0 | 0 | 0 | 0 |
| CASSMVAGNGELFF | 742 | 1 | Stim | 0 | 0 | 0 | 0 | 0 | 1 | 426 | 0 |
| CASSPDNDEETQYF | 746 | 1 | Stim | 0 | 1 | 0 | 0 | 0 | 0 | 0 | 0 |
| CASSPFWDSNYGYTF | 747 | 1 | Stim | 0 | 0 | 0 | 646 | 0 | 1400 | 0 | 0 |
| CASSPGTSGVGELFF | 752 | 1 | Stim | 0 | 0 | 0 | 0 | 0 | 1929 | 0 | 0 |
| CASSPPTSEDAYNEQFF | 601 | 1 | Stim | 0 | 0 | 0 | 0 | 961 | 1719 | 0 | 0 |
| CASSPPVWPTGELFF | 754 | 1 | Stim | 0 | 0 | 0 | 0 | 0 | 0 | 0 | 0 |
| CASSPQQAGDTEAFF | 755 | 1 | Stim | 0 | 0 | 0 | 0 | 783 | 0 | 0 | 0 |
| CASSPRNSAGGPETQYF | 758 | 1 | Stim | 0 | 0 | 0 | 0 | 35 | 1400 | 0 | 0 |
| CASSPSWAGGDYEQYF | 760 | 1 | Stim | 0 | 0 | 0 | 0 | 832 | 0 | 0 | 0 |
| CASSPTSGETTQYF | 761 | 1 | Stim | 0 | 0 | 0 | 0 | 0 | 0 | 0 | 0 |
| CASSPWTGTGSYSNQPQHF | 763 | 1 | Stim | 0 | 0 | 0 | 0 | 0 | 808 | 0 | 0 |
| CASSQDAGVGVGYTF | 766 | 1 | Stim | 0 | 0 | 0 | 0 | 0 | 916 | 0 | 0 |
| CASSQDEVGGRRAFF | 584 | 1 | Stim | 0 | 0 | 0 | 0 | 379 | 511 | 0 | 0 |

Figure 21V

| TCRB | SEQ ID NO: | Freq. | Stim/Unstim | IL2 | IL10 | IL12A | IL13 | IL17A | IFNG | PRF1 | GZMB |
|---|---|---|---|---|---|---|---|---|---|---|---|
| CASSQDGPRGLETQYF | 767 | 1 | Stim | 0 | 0 | 0 | 0 | 1 | 1 | 0 | 0 |
| CASSQDWGDYGYTF | 585 | 1 | Stim | 0 | 0 | 0 | 0 | 0 | 0 | 0 | 0 |
| CASSQDYQGLDGEQFF | 586 | 1 | Stim | 0 | 0 | 0 | 0 | 524 | 915 | 0 | 0 |
| CASSQDYQGVDNEQFF | 768 | 1 | Stim | 0 | 0 | 0 | 0 | 112 | 506 | 0 | 0 |
| CASSQERGGKWAYEQYF | 779 | 1 | Stim | 0 | 0 | 0 | 0 | 568 | 1083 | 79 | 0 |
| CASSQGETGEYGYTF | 773 | 1 | Stim | 0 | 0 | 0 | 0 | 91 | 0 | 0 | 0 |
| CASSQGFVVNSPLHF | 774 | 1 | Stim | 0 | 0 | 0 | 0 | 1258 | 2 | 0 | 0 |
| CASSQGRPNSPLHF | 776 | 1 | Stim | 0 | 0 | 0 | 0 | 0 | 0 | 0 | 0 |
| CASSQGTSGWTDTQYF | 777 | 1 | Stim | 1 | 0 | 0 | 0 | 0 | 805 | 129 | 0 |
| CASSQTDANTGELFF | 780 | 1 | Stim | 0 | 0 | 0 | 0 | 481 | 0 | 0 | 0 |
| CASSQTQNRGGNYGYTF | 781 | 1 | Stim | 0 | 0 | 0 | 0 | 1371 | 1 | 548 | 86 |
| CASSQVGGAFANTGELFF | 782 | 1 | Stim | 0 | 0 | 0 | 12 | 791 | 0 | 0 | 19 |
| CASSRESFAPDGYTF | 783 | 1 | Stim | 0 | 0 | 0 | 0 | 655 | 1247 | 0 | 0 |
| CASSRGLYNEQFF | 784 | 1 | Stim | 0 | 0 | 0 | 0 | 601 | 0 | 0 | 0 |
| CASSRSTENNSPLHF | 786 | 1 | Stim | 0 | 0 | 0 | 572 | 4 | 5 | 0 | 0 |
| CASSSAGGAFSHEQYF | 788 | 1 | Stim | 0 | 0 | 0 | 1 | 0 | 462 | 0 | 0 |
| CASSSPGVGANVLTF | 587 | 1 | Stim | 0 | 0 | 0 | 0 | 75 | 0 | 0 | 0 |
| CASSSPSLAGPYEQYF | 792 | 1 | Stim | 0 | 0 | 0 | 0 | 669 | 860 | 0 | 0 |
| CASSSRGPPAYEQYF | 793 | 1 | Stim | 0 | 5 | 0 | 0 | 0 | 0 | 0 | 0 |
| CASSSSDSYNEQFF | 795 | 1 | Stim | 0 | 0 | 0 | 0 | 123 | 735 | 0 | 0 |
| CASSSSGSRTDTQYF | 796 | 1 | Stim | 0 | 0 | 0 | 0 | 876 | 1363 | 0 | 0 |
| CASSSTGQSWDTQYF | 797 | 1 | Stim | 1 | 0 | 0 | 0 | 248 | 455 | 0 | 0 |
| CASSTDSANYGYTF | 800 | 1 | Stim | 0 | 0 | 0 | 0 | 1297 | 0 | 0 | 0 |
| CASSTHSGRTEAFF | 801 | 1 | Stim | 0 | 0 | 0 | 0 | 0 | 0 | 0 | 0 |
| CASSTSRDRVNQPQHF | 802 | 1 | Stim | 0 | 0 | 0 | 0 | 0 | 0 | 0 | 0 |
| CASSTWAYNEKLFF | 804 | 1 | Stim | 0 | 0 | 0 | 0 | 0 | 0 | 0 | 0 |

Figure 21W

| TCRB | SEQ ID NO: | Freq. | Stim/Unstim | IL2 | IL10 | IL12A | IL13 | IL17A | IFNG | PRF1 | GZMB |
|---|---|---|---|---|---|---|---|---|---|---|---|
| CASSWIAGVAGGAVADTQYF | 588 | 1 | Stim | 28 | 0 | 0 | 0 | 0 | 1469 | 0 | 0 |
| CASSYPAPSGGPETQYF | 808 | 1 | Stim | 0 | 0 | 0 | 0 | 592 | 1 | 0 | 0 |
| CASSYPLVLSEQFF | 809 | 1 | Stim | 0 | 0 | 0 | 0 | 839 | 0 | 0 | 0 |
| CASSYPSGRICEQYF | 611 | 1 | Stim | 0 | 0 | 0 | 0 | 1 | 0 | 0 | 0 |
| CASSYSSGEYTGELFF | 810 | 1 | Stim | 0 | 0 | 0 | 0 | 0 | 777 | 0 | 0 |
| CASTYWAGAEAFF | 813 | 1 | Stim | 0 | 0 | 0 | 0 | 289 | 0 | 0 | 0 |
| CATSRDFGDSYEQYF | 816 | 1 | Stim | 0 | 0 | 0 | 41 | 18 | 947 | 0 | 0 |
| CATSRDLVGGNEQFF | 613 | 1 | Stim | 0 | 0 | 0 | 0 | 224 | 0 | 0 | 0 |
| CATSRDPGLASTQYF | 817 | 1 | Stim | 0 | 0 | 0 | 0 | 1 | 1 | 0 | 0 |
| CATSRDRADTEAFF | 818 | 1 | Stim | 0 | 0 | 0 | 0 | 0 | 778 | 0 | 0 |
| CAWQYPADSEKLFF | 822 | 1 | Stim | 0 | 0 | 0 | 0 | 22 | 501 | 0 | 0 |
| CAWSAGTGVRELFF | 824 | 1 | Stim | 0 | 0 | 0 | 0 | 0 | 0 | 0 | 0 |
| CAWSSGTGTSEQYF | 828 | 1 | Stim | 0 | 0 | 0 | 0 | 0 | 0 | 0 | 0 |
| CAWSVGGRIYGYTF | 829 | 1 | Stim | 0 | 0 | 0 | 0 | 0 | 0 | 0 | 0 |
| CISQSGIGFDTF | 831 | 1 | Stim | 0 | 0 | 0 | 0 | 0 | 342 | 224 | 0 |
| CSAAPGTGDNSPLHF | 615 | 1 | Stim | 0 | 0 | 0 | 0 | 794 | 0 | 0 | 0 |
| CSAATLDGSNQPQHF | 578 | 1 | Stim | 0 | 0 | 0 | 0 | 270 | 0 | 0 | 0 |
| CSAERSGLAGAPAYEQYF | 833 | 1 | Stim | 0 | 0 | 0 | 0 | 977 | 0 | 0 | 0 |
| CSAGPVGAGGAGEQFF | 834 | 1 | Stim | 0 | 0 | 0 | 0 | 0 | 0 | 0 | 0 |
| CSARAGGGDGELFF | 617 | 1 | Stim | 0 | 0 | 0 | 0 | 0 | 759 | 0 | 0 |
| CSARDGTGIGDTQYF | 618 | 1 | Stim | 0 | 0 | 0 | 0 | 431 | 0 | 0 | 0 |
| CSARDRDRYYEQYF | 619 | 1 | Stim | 0 | 0 | 14 | 0 | 402 | 0 | 0 | 0 |
| CSARGSGTGDLYGYTF | 841 | 1 | Stim | 0 | 0 | 0 | 0 | 1453 | 0 | 0 | 0 |
| CSARWEQGARGYTF | 842 | 1 | Stim | 0 | 0 | 0 | 0 | 137 | 656 | 0 | 0 |
| CSASESLLLGYTF | 843 | 1 | Stim | 0 | 0 | 0 | 0 | 0 | 187 | 0 | 0 |
| CSATSPLSAGAYQETQYF | 848 | 1 | Stim | 0 | 0 | 0 | 0 | 409 | 0 | 0 | 0 |

Figure 21X

| TCRB | SEQ ID NO: | Freq. | Stim/Unstim | IL2 | IL10 | IL12A | IL13 | IL17A | IFNG | PRF1 | GZMB |
|---|---|---|---|---|---|---|---|---|---|---|---|
| CSIGGQQGLEAFF | 851 | 1 | Stim | 0 | 0 | 0 | 0 | 0 | 1 | 0 | 0 |
| CSVDGSWQFF | 853 | 1 | Stim | 0 | 0 | 0 | 0 | 0 | 0 | 0 | 0 |
| CSVELQGNKVGELFF | 855 | 1 | Stim | 0 | 0 | 0 | 0 | 359 | 581 | 0 | 0 |
| CSVHGGETQYF | 285 | 1 | Stim | 0 | 0 | 0 | 0 | 0 | 0 | 0 | 0 |
| CSVLAAYNEQFF | 856 | 1 | Stim | 0 | 0 | 0 | 0 | 289 | 0 | 0 | 0 |
| CSVRTGNSNQPQHF | 857 | 1 | Stim | 0 | 0 | 0 | 0 | 287 | 373 | 0 | 0 |

Figure 21Y

| TCRB | SEQ ID NO: | Freq. | Stim/ Unstim | TGF B | TNFA | BCL6 | TBET | GATA 3 | RORC | FOXP 3 | RUNX 1 | RUNX 3 |
|---|---|---|---|---|---|---|---|---|---|---|---|---|
| CASSLASMGVGELFF | | 25 | Unstim | 0 | 0 | 0 | 0 | 0 | 0 | 0 | 0 | 0 |
| CASSLASMGVGELFF | | 25 | Unstim | 0 | 0 | 0 | 0 | 0 | 0 | 0 | 0 | 0 |
| CASSLASMGVGELFF | | 25 | Unstim | 0 | 0 | 0 | 49 | 0 | 153 | 0 | 74 | 0 |
| CASSLASMGVGELFF | | 25 | Unstim | 1 | 0 | 0 | 0 | 0 | 339 | 0 | 0 | 0 |
| CASSLASMGVGELFF | | 25 | Unstim | 0 | 0 | 396 | 0 | 0 | 289 | 0 | 342 | 0 |
| CASSLASMGVGELFF | | 25 | Unstim | 17 | 0 | 0 | 0 | 0 | 0 | 0 | 0 | 0 |
| CASSLASMGVGELFF | 265 | 25 | Unstim | 2 | 0 | 0 | 0 | 0 | 0 | 274 | 181 | 336 |
| CASSLASMGVGELFF | | 25 | Unstim | 0 | 300 | 0 | 0 | 0 | 0 | 0 | 233 | 0 |
| CASSLASMGVGELFF | | 25 | Unstim | 15 | 0 | 216 | 0 | 0 | 36 | 0 | 57 | 0 |
| CASSLASMGVGELFF | | 25 | Unstim | 26 | 0 | 0 | 0 | 0 | 0 | 0 | 398 | 0 |
| CASSLASMGVGELFF | | 25 | Unstim | 8 | 0 | 1 | 1 | 1 | 0 | 0 | 0 | 534 |
| CASSLASMGVGELFF | | 25 | Unstim | 0 | 0 | 0 | 0 | 0 | 5 | 0 | 0 | 0 |
| CASSLASMGVGELFF | | 25 | Unstim | 4 | 0 | 414 | 0 | 0 | 0 | 0 | 377 | 0 |
| CASSLASMGVGELFF | | 25 | Unstim | 1 | 0 | 0 | 0 | 977 | 0 | 0 | 1453 | 773 |
| CASSLASMGVGELFF | | 25 | Unstim | 0 | 0 | 0 | 0 | 0 | 0 | 446 | 35 | 0 |
| CASSLASMGVGELFF | | 25 | Unstim | 840 | 0 | 0 | 0 | 1025 | 0 | 1 | 0 | 0 |
| CASSLASMGVGELFF | | 25 | Unstim | 460 | 0 | 0 | 0 | 408 | 1049 | 0 | 522 | 0 |
| CASSLASMGVGELFF | | 25 | Unstim | 0 | 529 | 0 | 0 | 0 | 0 | 532 | 562 | 0 |
| CASSLASMGVGELFF | | 25 | Unstim | 29 | 1 | 0 | 0 | 551 | 0 | 0 | 550 | 0 |
| CASSLASMGVGELFF | | 25 | Unstim | 696 | 0 | 0 | 0 | 880 | 0 | 0 | 1087 | 0 |
| CASSLASMGVGELFF | | 25 | Unstim | 165 | 0 | 0 | 0 | 0 | 0 | 0 | 0 | 0 |
| CASSLASMGVGELFF | | 25 | Unstim | 0 | 0 | 0 | 0 | 412 | 0 | 447 | 675 | 0 |
| CASSLASMGVGELFF | | 25 | Unstim | 7 | 0 | 0 | 0 | 0 | 0 | 0 | 643 | 0 |
| CASSLASMGVGELFF | | 25 | Unstim | 395 | 0 | 0 | 0 | 0 | 0 | 0 | 0 | 0 |
| CASSEAGGQDYGNEQFF | 565 | 18 | Unstim | 0 | 0 | 0 | 0 | 0 | 0 | 0 | 0 | 0 |

Figure 21Z

| TCRB | SEQ ID NO: | Freq. | Stim/ Unstim | TGF B | TNFA | BCL6 | TBET | GATA 3 | RORC | FOXP 3 | RUNX 1 | RUNX 3 |
|---|---|---|---|---|---|---|---|---|---|---|---|---|
| CASSEAGGQDYGNEQFF | | 18 | Unstim | 0 | 0 | 0 | 0 | 0 | 0 | 0 | 0 | 0 |
| CASSEAGGQDYGNEQFF | | 18 | Unstim | 0 | 0 | 0 | 66 | 98 | 0 | 0 | 172 | 0 |
| CASSEAGGQDYGNEQFF | | 18 | Unstim | 0 | 0 | 199 | 103 | 0 | 0 | 0 | 72 | 128 |
| CASSEAGGQDYGNEQFF | | 18 | Unstim | 5 | 0 | 0 | 0 | 0 | 402 | 0 | 220 | 0 |
| CASSEAGGQDYGNEQFF | | 18 | Unstim | 0 | 0 | 0 | 2 | 20 | 0 | 0 | 0 | 0 |
| CASSEAGGQDYGNEQFF | | 18 | Unstim | 1 | 1 | 163 | 0 | 0 | 0 | 0 | 126 | 0 |
| CASSEAGGQDYGNEQFF | | 18 | Unstim | 56 | 0 | 0 | 0 | 1153 | 0 | 0 | 0 | 18 |
| CASSEAGGQDYGNEQFF | | 18 | Unstim | 0 | 0 | 0 | 0 | 0 | 0 | 0 | 340 | 0 |
| CASSEAGGQDYGNEQFF | | 18 | Unstim | 40 | 0 | 0 | 0 | 0 | 0 | 0 | 635 | 0 |
| CASSEAGGQDYGNEQFF | | 18 | Unstim | 0 | 0 | 1 | 0 | 702 | 0 | 0 | 863 | 0 |
| CASSEAGGQDYGNEQFF | | 18 | Unstim | 0 | 0 | 683 | 0 | 444 | 1767 | 0 | 578 | 0 |
| CASSEAGGQDYGNEQFF | | 18 | Unstim | 17 | 0 | 0 | 0 | 0 | 0 | 0 | 0 | 0 |
| CASSEAGGQDYGNEQFF | | 18 | Unstim | 0 | 2 | 2373 | 0 | 0 | 0 | 0 | 2342 | 0 |
| CASSEAGGQDYGNEQFF | | 18 | Unstim | 0 | 779 | 0 | 519 | 516 | 0 | 0 | 745 | 0 |
| CASSEAGGQDYGNEQFF | | 18 | Unstim | 0 | 0 | 0 | 0 | 1 | 1 | 0 | 0 | 0 |
| CASSEAGGQDYGNEQFF | | 18 | Unstim | 0 | 618 | 0 | 530 | 0 | 1 | 0 | 648 | 0 |
| CASSEAGGQDYGNEQFF | | 18 | Unstim | 0 | 0 | 429 | 421 | 0 | 0 | 0 | 398 | 0 |
| CASSLGGGSYNEQFF | | 11 | Unstim | 0 | 0 | 0 | 307 | 0 | 0 | 0 | 0 | 0 |
| CASSLGGGSYNEQFF | | 11 | Unstim | 0 | 0 | 0 | 0 | 0 | 0 | 0 | 0 | 0 |
| CASSLGGGSYNEQFF | | 11 | Unstim | 0 | 75 | 79 | 42 | 46 | 0 | 0 | 0 | 0 |
| CASSLGGGSYNEQFF | 570 | 11 | Unstim | 15 | 0 | 0 | 0 | 0 | 0 | 0 | 602 | 0 |
| CASSLGGGSYNEQFF | | 11 | Unstim | 0 | 618 | 1 | 45 | 552 | 1 | 0 | 0 | 0 |
| CASSLGGGSYNEQFF | | 11 | Unstim | 20 | 0 | 0 | 1 | 2044 | 2 | 1 | 3244 | 0 |
| CASSLGGGSYNEQFF | | 11 | Unstim | 2 | 1 | 2386 | 1 | 1557 | 0 | 1895 | 2362 | 0 |
| CASSLGGGSYNEQFF | | 11 | Unstim | 0 | 0 | 0 | 0 | 0 | 1740 | 874 | 0 | 0 |

Figure 21AA

| TCRB | SEQ ID NO: | Freq. | Stim/Unstim | TGF B | TNFA | BCL6 | TBET | GATA 3 | RORC | FOXP 3 | RUNX 1 | RUNX 3 |
|---|---|---|---|---|---|---|---|---|---|---|---|---|
| CASSLGGGSYNEQFF | | 11 | Unstim | 0 | 0 | 0 | 370 | 0 | 724 | 0 | 328 | 0 |
| CASSLGGGSYNEQFF | | 11 | Unstim | 42 | 0 | 0 | 240 | 0 | 0 | 0 | 491 | 0 |
| CSAGTYRTDTQYF | | 11 | Unstim | 0 | 0 | 375 | 1 | 144 | 0 | 0 | 326 | 0 |
| CSAGTYRTDTQYF | | 11 | Unstim | 1 | 0 | 0 | 265 | 0 | 0 | 0 | 285 | 0 |
| CSAGTYRTDTQYF | | 11 | Unstim | 0 | 0 | 0 | 358 | 402 | 0 | 0 | 489 | 0 |
| CSAGTYRTDTQYF | 569 | 11 | Unstim | 0 | 1 | 0 | 44 | 0 | 0 | 0 | 0 | 522 |
| CSAGTYRTDTQYF | | 11 | Unstim | 1 | 0 | 0 | 1051 | 1 | 0 | 0 | 1152 | 0 |
| CSAGTYRTDTQYF | | 11 | Unstim | 0 | 0 | 915 | 958 | 0 | 0 | 0 | 0 | 0 |
| CSAGTYRTDTQYF | | 11 | Unstim | 642 | 0 | 0 | 0 | 1407 | 0 | 0 | 2016 | 0 |
| CSAGTYRTDTQYF | | 11 | Unstim | 433 | 0 | 0 | 599 | 0 | 0 | 0 | 539 | 0 |
| CSAGTYRTDTQYF | | 11 | Unstim | 102 | 0 | 0 | 0 | 290 | 0 | 1 | 340 | 0 |
| CSAGTYRTDTQYF | | 11 | Unstim | 1 | 0 | 0 | 728 | 0 | 1311 | 0 | 733 | 0 |
| CSAGTYRTDTQYF | | 11 | Unstim | 0 | 0 | 0 | 0 | 0 | 1101 | 0 | 501 | 0 |
| CASPGGWTGGGNEQFF | | 10 | Unstim | 0 | 0 | 101 | 0 | 30 | 1 | 0 | 0 | 0 |
| CASPGGWTGGGNEQFF | | 10 | Unstim | 0 | 0 | 343 | 110 | 0 | 0 | 0 | 0 | 0 |
| CASPGGWTGGGNEQFF | | 10 | Unstim | 0 | 0 | 1078 | 353 | 743 | 0 | 0 | 929 | 0 |
| CASPGGWTGGGNEQFF | | 10 | Unstim | 0 | 527 | 0 | 0 | 356 | 852 | 0 | 405 | 0 |
| CASPGGWTGGGNEQFF | 563 | 10 | Unstim | 11 | 0 | 0 | 170 | 1753 | 453 | 0 | 211 | 0 |
| CASPGGWTGGGNEQFF | | 10 | Unstim | 0 | 0 | 0 | 2314 | 807 | 4434 | 1 | 0 | 0 |
| CASPGGWTGGGNEQFF | | 10 | Unstim | 23 | 0 | 1110 | 257 | 0 | 2353 | 0 | 1336 | 0 |
| CASPGGWTGGGNEQFF | | 10 | Unstim | 3 | 0 | 0 | 0 | 543 | 0 | 0 | 408 | 0 |
| CASPGGWTGGGNEQFF | | 10 | Unstim | 231 | 0 | 0 | 0 | 485 | 1 | 0 | 907 | 0 |
| CASNTLGAGGREQYF | | 10 | Unstim | 0 | 0 | 0 | 0 | 143 | 0 | 0 | 780 | 0 |
| CASNTLGAGGREQYF | 564 | 8 | Unstim | 0 | 569 | 0 | 0 | 0 | 1208 | 1 | 328 | 0 |
| CASNTLGAGGREQYF | | 8 | Unstim | 0 | 263 | 0 | 40 | 0 | 0 | 0 | 0 | 0 |

Figure 21AB

| TCRB | SEQ ID NO: | Freq. | Stim/Unstim | TGF B | TNFA | BCL6 | TBET | GATA 3 | RORC | FOXP 3 | RUNX 1 | RUNX 3 |
|---|---|---|---|---|---|---|---|---|---|---|---|---|
| CASNTLGAGGREQYF | | 8 | Unstim | 0 | 0 | 0 | 0 | 0 | 0 | 0 | 31 | 0 |
| CASNTLGAGGREQYF | | 8 | Unstim | 0 | 348 | 0 | 310 | 298 | 0 | 0 | 22 | 0 |
| CASNTLGAGGREQYF | | 8 | Unstim | 165 | 1 | 0 | 0 | 0 | 0 | 0 | 0 | 0 |
| CASNTLGAGGREQYF | | 8 | Unstim | 28 | 0 | 1 | 794 | 1 | 2 | 0 | 1 | 0 |
| CASNTLGAGGREQYF | | 8 | Unstim | 78 | 0 | 1178 | 1 | 1 | 0 | 0 | 1307 | 0 |
| CASRENSGANVLTF | | 8 | Unstim | 1 | 1 | 0 | 62 | 48 | 0 | 50 | 70 | 0 |
| CASRENSGANVLTF | | 8 | Unstim | 0 | 2 | 0 | 1344 | 1281 | 0 | 0 | 1451 | 0 |
| CASRENSGANVLTF | 568 | 8 | Unstim | 0 | 0 | 0 | 431 | 480 | 0 | 636 | 287 | 2 |
| CASRENSGANVLTF | | 8 | Unstim | 0 | 0 | 0 | 0 | 0 | 600 | 0 | 0 | 0 |
| CASRENSGANVLTF | | 8 | Unstim | 35 | 0 | 0 | 0 | 0 | 0 | 0 | 550 | 0 |
| CASRENSGANVLTF | | 8 | Unstim | 0 | 0 | 15 | 88 | 0 | 0 | 267 | 241 | 0 |
| CASRENSGANVLTF | | 8 | Unstim | 1 | 0 | 0 | 843 | 1025 | 2937 | 0 | 0 | 0 |
| CASRENSGANVLTF | | 8 | Unstim | 17 | 0 | 0 | 0 | 1114 | 0 | 0 | 0 | 0 |
| CAWSDGVVGEKLFF | | 8 | Unstim | 0 | 509 | 0 | 260 | 154 | 980 | 0 | 511 | 8 |
| CAWSDGVVGEKLFF | | 8 | Unstim | 0 | 0 | 0 | 0 | 0 | 0 | 0 | 0 | 0 |
| CAWSDGVVGEKLFF | | 8 | Unstim | 1 | 0 | 316 | 0 | 0 | 357 | 0 | 179 | 0 |
| CAWSDGVVGEKLFF | 567 | 8 | Unstim | 0 | 1 | 0 | 0 | 2 | 3415 | 0 | 2159 | 0 |
| CAWSDGVVGEKLFF | | 8 | Unstim | 84 | 0 | 0 | 0 | 668 | 93 | 0 | 460 | 0 |
| CAWSDGVVGEKLFF | | 8 | Unstim | 223 | 0 | 0 | 0 | 0 | 0 | 0 | 0 | 0 |
| CAWSDGVVGEKLFF | | 8 | Unstim | 30 | 0 | 0 | 0 | 447 | 1456 | 0 | 711 | 0 |
| CAWSDGVVGEKLFF | | 6 | Unstim | 8 | 0 | 0 | 0 | 522 | 2 | 0 | 858 | 0 |
| CASSSASGGVGELFF | | 6 | Unstim | 0 | 0 | 0 | 182 | 0 | 0 | 192 | 1 | 0 |
| CASSSASGGVGELFF | | 6 | Unstim | 0 | 0 | 590 | 0 | 0 | 808 | 0 | 550 | 0 |
| CASSSASGGVGELFF | 267 | 6 | Unstim | 0 | 0 | 0 | 490 | 391 | 0 | 0 | 0 | 0 |
| CASSSASGGVGELFF | | 6 | Unstim | 0 | 0 | 0 | 1 | 339 | 0 | 0 | 425 | 0 |
| CASSSASGGVGELFF | | 6 | Unstim | 0 | 0 | 0 | 603 | 0 | 0 | 0 | 572 | 0 |

Figure 21AC

| TCRB | SEQ ID NO: | Freq. | Stim/ Unstim | TGF B | TNFA | BCL6 | TBET | GATA 3 | RORC | FOXP 3 | RUNX 1 | RUNX 3 |
|---|---|---|---|---|---|---|---|---|---|---|---|---|
| CASSSASGGVGELFF | | 6 | Unstim | 34 | 0 | 0 | 0 | 0 | 0 | 0 | 637 | 0 |
| CASSFSPGLETQYF | | 5 | Unstim | 0 | 355 | 0 | 0 | 234 | 0 | 0 | 0 | 0 |
| CASSFSPGLETQYF | 573 | 5 | Unstim | 13 | 0 | 1 | 0 | 978 | 1 | 0 | 1 | 0 |
| CASSFSPGLETQYF | | 5 | Unstim | 4 | 0 | 0 | 482 | 0 | 0 | 524 | 522 | 0 |
| CASSFSPGLETQYF | | 5 | Unstim | 239 | 0 | 0 | 0 | 0 | 0 | 0 | 0 | 0 |
| CASSFSPGLETQYF | | 5 | Unstim | 0 | 488 | 0 | 612 | 291 | 0 | 0 | 533 | 0 |
| CASSLVSSPLHF | | 5 | Unstim | 2 | 0 | 0 | 0 | 90 | 288 | 0 | 179 | 0 |
| CASSLVSSPLHF | 574 | 5 | Unstim | 0 | 616 | 0 | 116 | 0 | 938 | 0 | 0 | 0 |
| CASSLVSSPLHF | | 5 | Unstim | 21 | 0 | 1 | 1 | 0 | 0 | 0 | 28 | 0 |
| CASSLVSSPLHF | | 5 | Unstim | 0 | 0 | 0 | 0 | 0 | 0 | 0 | 0 | 0 |
| CASSLVSSPLHF | | 5 | Unstim | 337 | 0 | 0 | 0 | 0 | 0 | 0 | 413 | 0 |
| CASSQDGAGGREQFF | | 5 | Unstim | 23 | 0 | 0 | 1 | 0 | 0 | 0 | 0 | 0 |
| CASSQDGAGGREQFF | | 5 | Unstim | 0 | 0 | 0 | 247 | 0 | 0 | 282 | 288 | 0 |
| CASSQDGAGGREQFF | 571 | 5 | Unstim | 1 | 325 | 0 | 0 | 0 | 418 | 0 | 340 | 0 |
| CASSQDGAGGREQFF | | 5 | Unstim | 1 | 1 | 0 | 0 | 347 | 0 | 406 | 595 | 0 |
| CASSQDGAGGREQFF | | 5 | Unstim | 333 | 0 | 0 | 1 | 271 | 1 | 0 | 499 | 0 |
| CASSQGLAAPYEQYF | | 4 | Unstim | 0 | 252 | 0 | 0 | 121 | 0 | 0 | 255 | 0 |
| CASSQGLAAPYEQYF | 566 | 4 | Unstim | 0 | 0 | 0 | 0 | 0 | 1 | 495 | 434 | 0 |
| CASSQGLAAPYEQYF | | 4 | Unstim | 0 | 494 | 0 | 0 | 0 | 0 | 0 | 538 | 0 |
| CASSQGLAAPYEQYF | | 4 | Unstim | 3 | 0 | 0 | 589 | 0 | 192 | 0 | 622 | 0 |
| CSAATLDGSNQPQHF | | 4 | Unstim | 1 | 139 | 0 | 0 | 96 | 0 | 0 | 181 | 0 |
| CSAATLDGSNQPQHF | 578 | 4 | Unstim | 1 | 0 | 0 | 0 | 204 | 802 | 0 | 347 | 0 |
| CSAATLDGSNQPQHF | | 4 | Unstim | 0 | 0 | 0 | 283 | 630 | 0 | 0 | 930 | 0 |
| CSAATLDGSNQPQHF | | 4 | Unstim | 0 | 0 | 0 | 1151 | 940 | 0 | 0 | 0 | 2199 |
| CASSLAPLQGTFRADTQYF | 581 | 3 | Unstim | 0 | 0 | 0 | 309 | 123 | 476 | 0 | 393 | 0 |
| CASSLAPLQGTFRADTQYF | | 3 | Unstim | 1 | 0 | 109 | 83 | 62 | 0 | 0 | 79 | 0 |

Figure 21AD

| TCRB | SEQ ID NO: | Freq. | Stim/ Unstim | TGF B | TNFA | BCL6 | TBET | GATA 3 | RORC | FOXP 3 | RUNX 1 | RUNX 3 |
|---|---|---|---|---|---|---|---|---|---|---|---|---|
| CASSLAPLQGTFRADTQYF | | 3 | Unstim | 175 | 0 | 0 | 0 | 0 | 0 | 0 | 610 | 0 |
| CASSPTGGTTYNSPLHF | 583 | 3 | Unstim | 55 | 0 | 0 | 0 | 41 | 0 | 0 | 608 | 0 |
| CASSPTGGTTYNSPLHF | | 3 | Unstim | 125 | 0 | 0 | 1568 | 0 | 0 | 1 | 1 | 0 |
| CASSPTGGTTYNSPLHF | | 3 | Unstim | 6 | 0 | 0 | 0 | 0 | 1727 | 876 | 0 | 0 |
| CAISAVGDRGTGELFF | 589 | 2 | Unstim | 540 | 1 | 0 | 691 | 0 | 0 | 0 | 0 | 0 |
| CAISAVGDRGTGELFF | | 2 | Unstim | 7 | 1 | 0 | 0 | 904 | 644 | 0 | 1289 | 0 |
| CASSFHTGEAYEQYF | 596 | 2 | Unstim | 10 | 0 | 384 | 0 | 0 | 0 | 0 | 1 | 707 |
| CASSFHTGEAYEQYF | | 2 | Unstim | 4 | 0 | 0 | 0 | 0 | 0 | 966 | 884 | 0 |
| CASSLSGEKLFF | 582 | 2 | Unstim | 13 | 0 | 0 | 0 | 1152 | 0 | 0 | 0 | 0 |
| CASSLSGEKLFF | | 2 | Unstim | 3 | 1 | 0 | 0 | 713 | 1 | 0 | 982 | 0 |
| CASSLSQRPNTGELFF | 599 | 2 | Unstim | 2 | 0 | 0 | 120 | 0 | 0 | 0 | 0 | 0 |
| CASSLSQRPNTGELFF | | 2 | Unstim | 0 | 678 | 0 | 572 | 0 | 0 | 0 | 0 | 0 |
| CASSLTGADSPLHF | 600 | 2 | Unstim | 1 | 0 | 0 | 0 | 2257 | 0 | 0 | 2 | 0 |
| CASSLTGADSPLHF | | 2 | Unstim | 1 | 0 | 922 | 351 | 0 | 0 | 0 | 0 | 0 |
| CASSPTIRDSGYTF | 602 | 2 | Unstim | 37 | 0 | 0 | 869 | 497 | 0 | 0 | 829 | 0 |
| CASSPTIRDSGYTF | | 2 | Unstim | 523 | 0 | 0 | 1054 | 678 | 0 | 0 | 860 | 0 |
| CASSQASHLSGNTIYF | 603 | 2 | Unstim | 0 | 638 | 0 | 492 | 572 | 0 | 0 | 0 | 0 |
| CASSQASHLSGNTIYF | | 2 | Unstim | 11 | 0 | 0 | 0 | 1018 | 0 | 1516 | 1480 | 0 |
| CASSQDEVGGRRAFF | 584 | 2 | Unstim | 0 | 0 | 0 | 0 | 0 | 0 | 0 | 0 | 0 |
| CASSQDEVGGRRAFF | | 2 | Unstim | 2 | 0 | 0 | 0 | 746 | 1 | 0 | 0 | 0 |
| CASSQDWGDYGYTF | 585 | 2 | Unstim | 0 | 0 | 0 | 0 | 0 | 1496 | 0 | 737 | 1 |
| CASSQDWGDYGYTF | | 2 | Unstim | 2 | 0 | 993 | 808 | 0 | 0 | 0 | 993 | 0 |
| CASSQDYQGLDGEQFF | 586 | 2 | Unstim | 0 | 0 | 0 | 0 | 596 | 0 | 0 | 863 | 0 |
| CASSQDYQGVDNEQFF | | 2 | Unstim | 1 | 0 | 0 | 129 | 0 | 0 | 0 | 113 | 0 |
| CASSRGNSPLHF | 605 | 2 | Unstim | 285 | 1 | 0 | 1 | 0 | 0 | 0 | 1 | 0 |
| CASSRGNSPLHF | | 2 | Unstim | | | | | | | | | |

Figure 21AE

| TCRB | SEQ ID NO: | Freq. | Stim/ Unstim | TGF B | TNFA | BCL6 | TBET | GATA 3 | RORC | FOXP 3 | RUNX 1 | RUNX 3 |
|---|---|---|---|---|---|---|---|---|---|---|---|---|
| CASSSPGVGANVLTF | 587 | 2 | Unstim | 0 | 0 | 0 | 606 | 522 | 0 | 0 | 777 | 0 |
| CASSSPGVGANVLTF | | 2 | Unstim | 116 | 0 | 0 | 0 | 368 | 0 | 0 | 635 | 0 |
| CASSTGTGGEETQYF | 608 | 2 | Unstim | 0 | 346 | 0 | 0 | 208 | 0 | 0 | 330 | 0 |
| CASSTGTGGEETQYF | | 2 | Unstim | 0 | 0 | 0 | 627 | 538 | 0 | 0 | 785 | 0 |
| CASSVDMVGANVLTF | 609 | 2 | Unstim | 528 | 0 | 1 | 0 | 0 | 0 | 0 | 763 | 0 |
| CASSVDMVGANVLTF | | 2 | Unstim | 20 | 0 | 0 | 0 | 1062 | 2541 | 0 | 1576 | 0 |
| CASSVFGIGVGGTYEQYF | 610 | 2 | Unstim | 0 | 0 | 0 | 0 | 448 | 0 | 599 | 660 | 0 |
| CASSVFGIGVGGTYEQYF | | 2 | Unstim | 205 | 0 | 0 | 0 | 0 | 0 | 268 | 294 | 0 |
| CASSWIAGVAGGAVADTQYF | 588 | 2 | Unstim | 63 | 0 | 0 | 0 | 0 | 0 | 0 | 984 | 0 |
| CASSWIAGVAGGAVADTQYF | | 2 | Unstim | 16 | 0 | 0 | 0 | 540 | 0 | 0 | 0 | 1216 |
| CATSRDGTDYGYTF | 576 | 2 | Unstim | 60 | 0 | 0 | 0 | 0 | 0 | 0 | 0 | 0 |
| CATSRDGTDYGYTF | | 2 | Unstim | 7 | 0 | 0 | 1129 | 0 | 0 | 0 | 1038 | 0 |
| CAWSPGGETQYF | 572 | 2 | Unstim | 0 | 0 | 552 | 107 | 301 | 743 | 0 | 190 | 0 |
| CAWSPGGETQYF | | 2 | Unstim | 0 | 0 | 0 | 0 | 0 | 0 | 0 | 0 | 0 |
| CSARDSAKLAGALRGGELFF | 620 | 2 | Unstim | 0 | 0 | 0 | 347 | 385 | 1007 | 0 | 524 | 0 |
| CSARDSAKLAGALRGGELFF | | 2 | Unstim | 0 | 0 | 0 | 0 | 703 | 0 | 0 | 1165 | 0 |
| CSVGVMTYNEQFF | 622 | 2 | Unstim | 0 | 495 | 0 | 73 | 428 | 934 | 0 | 446 | 0 |
| CSVGVMTYNEQFF | | 2 | Unstim | 0 | 1039 | 0 | 0 | 723 | 1889 | 0 | 1115 | 0 |
| CAISESSGGDEKLFF | 626 | 1 | Unstim | 2 | 0 | 292 | 270 | 157 | 0 | 0 | 0 | 0 |
| CALDGTGGNTIYF | 629 | 1 | Unstim | 5 | 0 | 0 | 1811 | 1158 | 0 | 0 | 1 | 0 |
| CASAREGPDTQYF | 631 | 1 | Unstim | 223 | 0 | 0 | 0 | 420 | 0 | 0 | 0 | 0 |
| CASGDIDSARKQYF | 632 | 1 | Unstim | 2 | 0 | 0 | 0 | 501 | 0 | 1 | 759 | 863 |
| CASHLVDFTDTQYF | 634 | 1 | Unstim | 0 | 0 | 0 | 15 | 67 | 0 | 83 | 75 | 0 |
| CASHSTQAGYNEQFF | 635 | 1 | Unstim | 0 | 0 | 68 | 0 | 89 | 0 | 0 | 99 | 0 |
| CASIPPRAGPIANEKLFF | 590 | 1 | Unstim | 0 | 178 | 0 | 0 | 820 | 0 | 245 | 224 | 0 |
| CASISMGAGGLSGANVLTF | 637 | 1 | Unstim | 0 | 1078 | 0 | 533 | 0 | 2391 | 0 | 1252 | 0 |

Figure 21AF

| TCRB | SEQ ID NO: | Freq. | Stim/ Unstim | TGF B | TNFA | BCL6 | TBET | GATA 3 | RORC | FOXP 3 | RUNX 1 | RUNX 3 |
|---|---|---|---|---|---|---|---|---|---|---|---|---|
| CASITSGGATGELFF | 638 | 1 | Unstim | 10 | 0 | 0 | 0 | 377 | 0 | 0 | 0 | 0 |
| CASLRGYEQYF | 640 | 1 | Unstim | 0 | 0 | 0 | 1160 | 670 | 0 | 0 | 1110 | 0 |
| CASLSDFGSANTGELFF | 641 | 1 | Unstim | 1 | 0 | 789 | 0 | 0 | 0 | 0 | 848 | 0 |
| CASMKDVGAGANVLTF | 642 | 1 | Unstim | 1 | 0 | 0 | 206 | 0 | 581 | 0 | 0 | 0 |
| CASNLGTADSNQPQHF | 623 | 1 | Unstim | 2 | 0 | 0 | 44 | 117 | 0 | 0 | 187 | 0 |
| CASRAGGEAPAFF | 644 | 1 | Unstim | 0 | 0 | 0 | 0 | 527 | 0 | 542 | 755 | 0 |
| CASRIGTGSNQPQHF | 646 | 1 | Unstim | 23 | 0 | 0 | 327 | 0 | 0 | 0 | 0 | 0 |
| CASRLAGADNQPQHF | 647 | 1 | Unstim | 0 | 0 | 0 | 419 | 0 | 756 | 0 | 372 | 84 |
| CASRPGLAGDEQYF | 650 | 1 | Unstim | 579 | 0 | 0 | 0 | 1 | 0 | 0 | 0 | 0 |
| CASRPGQYSYEQYF | 651 | 1 | Unstim | 225 | 0 | 0 | 0 | 0 | 0 | 0 | 555 | 0 |
| CASRPGTVNTGELFF | 653 | 1 | Unstim | 524 | 0 | 0 | 0 | 0 | 0 | 0 | 0 | 0 |
| CASRQRDRVLEQYF | 654 | 1 | Unstim | 0 | 507 | 676 | 0 | 0 | 0 | 0 | 565 | 0 |
| CASRQTSGQETQYF | 656 | 1 | Unstim | 0 | 0 | 0 | 0 | 0 | 0 | 0 | 0 | 0 |
| CASRRTGMSTDTQYF | 657 | 1 | Unstim | 0 | 122 | 0 | 0 | 0 | 0 | 0 | 968 | 0 |
| CASRTERESINEQFF | 593 | 1 | Unstim | 8 | 0 | 0 | 0 | 414 | 1665 | 881 | 580 | 0 |
| CASSAPGLAGTGETQYF | 662 | 1 | Unstim | 0 | 0 | 0 | 990 | 633 | 2127 | 1050 | 1110 | 0 |
| CASSAPGTGDTDTQYF | 663 | 1 | Unstim | 0 | 0 | 0 | 1 | 107 | 0 | 0 | 0 | 0 |
| CASSATGLAGGGETQYF | 579 | 1 | Unstim | 0 | 642 | 0 | 672 | 1 | 0 | 568 | 587 | 0 |
| CASSATLGSLHYGYTF | 664 | 1 | Unstim | 0 | 0 | 0 | 573 | 446 | 1240 | 0 | 712 | 0 |
| CASSAVEAGNTIYF | 665 | 1 | Unstim | 0 | 0 | 0 | 0 | 775 | 0 | 919 | 600 | 0 |
| CASSDDGTGDQPQHF | 666 | 1 | Unstim | 0 | 0 | 0 | 0 | 0 | 0 | 0 | 0 | 0 |
| CASSDRGNTEAFF | 668 | 1 | Unstim | 0 | 0 | 1 | 0 | 598 | 0 | 1019 | 965 | 0 |
| CASSEAGDYEQYF | 669 | 1 | Unstim | 0 | 0 | 383 | 0 | 158 | 0 | 269 | 0 | 0 |
| CASSEAGGNTIYF | 670 | 1 | Unstim | 1 | 0 | 0 | 0 | 1115 | 1 | 1447 | 158 | 0 |
| CASSEAGVRLVSYEQYF | 671 | 1 | Unstim | 14 | 0 | 0 | 0 | 0 | 0 | 0 | 0 | 0 |
| CASSEGGDHEQFF | 594 | 1 | Unstim | 5 | 0 | 236 | 157 | 105 | 0 | 0 | 225 | 0 |

Figure 21AG

| TCRB | SEQ ID NO: | Freq. | Stim/ Unstim | TGF B | TNFA | BCL6 | TBET | GATA 3 | RORC | FOXP 3 | RUNX 1 | RUNX 3 |
|---|---|---|---|---|---|---|---|---|---|---|---|---|
| CASSEPGEQFF | 580 | 1 | Unstim | 0 | 2 | 0 | 171 | 206 | 1 | 0 | 321 | 0 |
| CASSERAGGDTGELFF | 672 | 1 | Unstim | 5 | 0 | 0 | 881 | 611 | 0 | 0 | 300 | 0 |
| CASSEWGQGGAEQYF | 673 | 1 | Unstim | 0 | 700 | 0 | 784 | 553 | 0 | 660 | 730 | 0 |
| CASSEYKATYEQYF | 674 | 1 | Unstim | 0 | 0 | 0 | 0 | 0 | 1 | 0 | 0 | 0 |
| CASSFDEGTQHF | 675 | 1 | Unstim | 0 | 359 | 0 | 0 | 0 | 0 | 0 | 0 | 0 |
| CASSFGRWVDSPLHF | 679 | 1 | Unstim | 10 | 0 | 0 | 0 | 0 | 0 | 0 | 132 | 0 |
| CASSFRGDDKNIQYF | 681 | 1 | Unstim | 0 | 0 | 0 | 0 | 525 | 0 | 671 | 715 | 0 |
| CASSFSGSAYEQYF | 683 | 1 | Unstim | 37 | 0 | 1 | 0 | 0 | 0 | 0 | 0 | 0 |
| CASSFSTSGEQYF | 684 | 1 | Unstim | 918 | 0 | 0 | 0 | 1467 | 0 | 0 | 0 | 0 |
| CASSFSTSGNTGELFF | 685 | 1 | Unstim | 27 | 0 | 1 | 509 | 0 | 0 | 370 | 445 | 1 |
| CASSGILETQYF | 689 | 1 | Unstim | 0 | 0 | 0 | 0 | 382 | 0 | 594 | 430 | 0 |
| CASSIGARGYTF | 692 | 1 | Unstim | 0 | 0 | 0 | 778 | 0 | 1 | 0 | 979 | 0 |
| CASSIGRTYEQYF | 693 | 1 | Unstim | 3 | 0 | 471 | 498 | 0 | 0 | 1 | 23 | 0 |
| CASSLAAGPYGYTF | 698 | 1 | Unstim | 0 | 0 | 0 | 0 | 486 | 1 | 875 | 739 | 0 |
| CASSLAGSVYEQYF | 700 | 1 | Unstim | 0 | 0 | 0 | 0 | 1066 | 2765 | 0 | 1501 | 0 |
| CASSLAGTGQFF | 597 | 1 | Unstim | 4 | 0 | 796 | 591 | 0 | 0 | 0 | 725 | 0 |
| CASSLDGTSTYEQYF | 706 | 1 | Unstim | 0 | 0 | 0 | 261 | 399 | 0 | 431 | 393 | 0 |
| CASSLEATSRTQPQHF | 709 | 1 | Unstim | 9 | 1 | 0 | 752 | 0 | 0 | 0 | 589 | 0 |
| CASSLEGQGNGYTF | 598 | 1 | Unstim | 0 | 0 | 393 | 55 | 0 | 1 | 0 | 345 | 3 |
| CASSLEGSGGTEAFF | 711 | 1 | Unstim | 0 | 0 | 0 | 0 | 451 | 0 | 602 | 697 | 0 |
| CASSLELAGVTRSTDTQYF | 712 | 1 | Unstim | 0 | 0 | 1 | 0 | 69 | 0 | 0 | 280 | 0 |
| CASSLGDTGELFF | 714 | 1 | Unstim | 0 | 0 | 0 | 111 | 0 | 0 | 0 | 149 | 0 |
| CASSLGGGAEGPQHF | 715 | 1 | Unstim | 0 | 0 | 0 | 7 | 3 | 119 | 0 | 13 | 0 |
| CASSLGGTPEPQHF | 716 | 1 | Unstim | 0 | 0 | 0 | 0 | 102 | 0 | 0 | 215 | 0 |
| CASSLGGVTYNEQFF | 717 | 1 | Unstim | 44 | 0 | 0 | 1290 | 0 | 0 | 0 | 0 | 0 |
| CASSLGPGLASYEQYF | 718 | 1 | Unstim | 13 | 0 | 0 | 0 | 0 | 419 | 0 | 0 | 0 |

Figure 21AH

| TCRB | SEQ ID NO: | Freq. | Stim/Unstim | TGF B | TNFA | BCL6 | TBET | GATA 3 | RORC | FOXP 3 | RUNX 1 | RUNX 3 |
|---|---|---|---|---|---|---|---|---|---|---|---|---|
| CASSLGPGQETQYF | 719 | 1 | Unstim | 0 | 0 | 0 | 273 | 0 | 0 | 307 | 0 | 0 |
| CASSLGSGTNTGELFF | 721 | 1 | Unstim | 0 | 0 | 0 | 54 | 128 | 0 | 167 | 0 | 0 |
| CASSLGTERTEAFF | 722 | 1 | Unstim | 0 | 0 | 0 | 0 | 0 | 0 | 0 | 0 | 723 |
| CASSLIGASGPGELFF | 723 | 1 | Unstim | 0 | 0 | 0 | 0 | 0 | 198 | 0 | 108 | 0 |
| CASSLLAGGLIVNEQFF | 724 | 1 | Unstim | 0 | 0 | 0 | 0 | 147 | 0 | 163 | 0 | 0 |
| CASSLLRNSGNTIYF | 725 | 1 | Unstim | 0 | 0 | 421 | 0 | 0 | 925 | 0 | 539 | 0 |
| CASSLNAPGLGSTGELFF | 726 | 1 | Unstim | 0 | 0 | 678 | 472 | 462 | 0 | 0 | 602 | 0 |
| CASSLQAGSGEQYF | 728 | 1 | Unstim | 0 | 309 | 0 | 0 | 98 | 1 | 243 | 0 | 0 |
| CASSLQGALGNTIYF | 729 | 1 | Unstim | 2 | 0 | 982 | 971 | 0 | 0 | 0 | 952 | 0 |
| CASSLQVYNEQFF | 730 | 1 | Unstim | 2 | 0 | 659 | 0 | 0 | 1 | 0 | 566 | 0 |
| CASSLRASGTRGEQFF | 731 | 1 | Unstim | 0 | 0 | 0 | 0 | 830 | 0 | 0 | 1298 | 0 |
| CASSLRGQGNEKLFF | 732 | 1 | Unstim | 1 | 0 | 0 | 208 | 141 | 675 | 0 | 0 | 0 |
| CASSLRGRETQYF | 733 | 1 | Unstim | 0 | 0 | 1 | 0 | 816 | 0 | 854 | 1184 | 0 |
| CASSLRRDYGYTF | 734 | 1 | Unstim | 25 | 0 | 0 | 424 | 1 | 0 | 0 | 319 | 0 |
| CASSLSSSEVDTQYF | 735 | 1 | Unstim | 0 | 0 | 990 | 0 | 0 | 1529 | 0 | 799 | 0 |
| CASSLSVTDSRSGNTIYF | 736 | 1 | Unstim | 1 | 0 | 302 | 0 | 0 | 0 | 0 | 255 | 0 |
| CASSLTLAGGQNEQYF | 737 | 1 | Unstim | 18 | 0 | 1 | 0 | 629 | 0 | 0 | 0 | 0 |
| CASSLVGGGNQPQHF | 738 | 1 | Unstim | 0 | 0 | 0 | 0 | 251 | 0 | 409 | 447 | 0 |
| CASSLYPRRISSGNTIYF | 740 | 1 | Unstim | 0 | 0 | 0 | 0 | 1250 | 2837 | 0 | 1042 | 1247 |
| CASSNPYRGWGQNQPQHF | 743 | 1 | Unstim | 30 | 0 | 0 | 0 | 236 | 0 | 0 | 0 | 0 |
| CASSPGGADYGYTF | 748 | 1 | Unstim | 41 | 0 | 0 | 0 | 163 | 0 | 0 | 213 | 0 |
| CASSPGGESNQPQHF | 749 | 1 | Unstim | 1 | 0 | 0 | 293 | 176 | 0 | 0 | 0 | 0 |
| CASSPGPPGLGPQHF | 750 | 1 | Unstim | 261 | 0 | 0 | 0 | 0 | 0 | 0 | 0 | 0 |
| CASSPGTQVYEQYF | 751 | 1 | Unstim | 23 | 0 | 0 | 0 | 0 | 0 | 1781 | 1864 | 0 |
| CASSPPTASGSVGQYF | 753 | 1 | Unstim | 0 | 0 | 0 | 0 | 0 | 0 | 324 | 373 | 0 |
| CASSPPTSEDAYNEQFF | 601 | 1 | Unstim | 15 | 1 | 1133 | 1 | 861 | 1 | 0 | 1246 | 0 |

Figure 21AI

| TCRB | SEQ ID NO: | Freq. | Stim/Unstim | TGFB | TNFA | BCL6 | TBET | GATA3 | RORC | FOXP3 | RUNX1 | RUNX3 |
|---|---|---|---|---|---|---|---|---|---|---|---|---|
| CASSPRGGAYEQYF | 756 | 1 | Unstim | 498 | 0 | 0 | 2 | 1 | 3 | 0 | 552 | 0 |
| CASSPRGYEQYF | 757 | 1 | Unstim | 0 | 0 | 1216 | 1087 | 0 | 2028 | 0 | 948 | 0 |
| CASSPSGREDGYTF | 759 | 1 | Unstim | 12 | 0 | 458 | 544 | 312 | 0 | 0 | 500 | 0 |
| CASSPWSQSSGNTIYF | 762 | 1 | Unstim | 1 | 0 | 0 | 0 | 73 | 0 | 0 | 0 | 0 |
| CASSPYRDLYEQYF | 764 | 1 | Unstim | 0 | 0 | 0 | 0 | 0 | 71 | 411 | 371 | 0 |
| CASSQAGGNSPLHF | 765 | 1 | Unstim | 0 | 0 | 0 | 0 | 0 | 0 | 0 | 0 | 0 |
| CASSQEPDRRAQYF | 769 | 1 | Unstim | 0 | 0 | 0 | 0 | 0 | 0 | 0 | 0 | 0 |
| CASSQESRGGPVSYEQYF | 771 | 1 | Unstim | 0 | 0 | 0 | 0 | 635 | 1883 | 1 | 931 | 0 |
| CASSQGAAGEQQYF | 772 | 1 | Unstim | 0 | 235 | 0 | 87 | 0 | 390 | 0 | 1 | 0 |
| CASSQGRGVGTDTQYF | 775 | 1 | Unstim | 0 | 1261 | 0 | 1373 | 889 | 0 | 0 | 1 | 0 |
| CASSQLSSGDYNEQFF | 778 | 1 | Unstim | 60 | 0 | 0 | 0 | 1 | 0 | 0 | 0 | 0 |
| CASSQRVGGLDTQYF | 779 | 1 | Unstim | 0 | 0 | 0 | 6 | 25 | 0 | 0 | 40 | 0 |
| CASSRSSGASSYEQYF | 785 | 1 | Unstim | 0 | 0 | 0 | 24 | 424 | 0 | 0 | 0 | 1386 |
| CASSRTGGNSGNTIYF | 787 | 1 | Unstim | 1 | 528 | 418 | 0 | 0 | 0 | 0 | 0 | 0 |
| CASSSGQGNQPQHF | 789 | 1 | Unstim | 4 | 0 | 0 | 539 | 0 | 0 | 0 | 0 | 0 |
| CASSSGQQLAGELFF | 790 | 1 | Unstim | 96 | 0 | 0 | 0 | 2281 | 0 | 0 | 3248 | 0 |
| CASSSGTGGLETQYF | 575 | 1 | Unstim | 0 | 0 | 1064 | 0 | 588 | 0 | 0 | 754 | 0 |
| CASSSPGQGWNEQFF | 791 | 1 | Unstim | 3 | 0 | 0 | 145 | 1 | 0 | 0 | 0 | 0 |
| CASSSTGTSGRMRIF | 798 | 1 | Unstim | 0 | 350 | 0 | 0 | 698 | 0 | 1063 | 721 | 0 |
| CASSSTSGQEETQYF | 799 | 1 | Unstim | 2 | 0 | 0 | 0 | 0 | 0 | 0 | 1 | 0 |
| CASSTTGGTGTEAFF | 803 | 1 | Unstim | 8 | 1352 | 1 | 0 | 930 | 0 | 0 | 1353 | 0 |
| CASSVGGTSTDTQYF | 805 | 1 | Unstim | 0 | 0 | 124 | 0 | 14 | 0 | 176 | 32 | 0 |
| CASSVSGARGYNEQFF | 806 | 1 | Unstim | 0 | 701 | 0 | 1 | 0 | 0 | 0 | 729 | 0 |
| CASSYLSGGEHNEQFF | 807 | 1 | Unstim | 2 | 0 | 0 | 0 | 637 | 0 | 913 | 63 | 0 |
| CASSYPSGRICEQYF | 611 | 1 | Unstim | 0 | 0 | 0 | 0 | 649 | 0 | 0 | 706 | 0 |
| CASSYSYRDNSPLHF | 811 | 1 | Unstim | 0 | 0 | 0 | 0 | 0 | 0 | 0 | 24 | 0 |

Figure 21AJ

| TCRB | SEQ ID NO: | Freq. | Stim/Unstim | TGF B | TNFA | BCL6 | TBET | GATA 3 | RORC | FOXP 3 | RUNX 1 | RUNX 3 |
|---|---|---|---|---|---|---|---|---|---|---|---|---|
| CASTSGGGSPYEQYF | 812 | 1 | Unstim | 0 | 0 | 1464 | 756 | 1013 | 0 | 1442 | 1267 | 0 |
| CATSLMGQPQHF | 814 | 1 | Unstim | 58 | 0 | 743 | 0 | 0 | 0 | 0 | 673 | 0 |
| CATSRAFDWDRGLDTEAFF | 815 | 1 | Unstim | 1 | 0 | 1063 | 529 | 718 | 39 | 1024 | 0 | 0 |
| CATSRDLVGGNEQFF | 613 | 1 | Unstim | 16 | 0 | 0 | 673 | 0 | 0 | 0 | 472 | 0 |
| CATSREWGEAYEQYF | 577 | 1 | Unstim | 1 | 0 | 193 | 137 | 0 | 0 | 0 | 0 | 0 |
| CAWEKAGAGGTQYF | 819 | 1 | Unstim | 250 | 0 | 0 | 1033 | 716 | 0 | 0 | 1008 | 0 |
| CAWGTNYGYTF | 820 | 1 | Unstim | 0 | 489 | 761 | 133 | 478 | 0 | 0 | 627 | 1 |
| CAWMEVHEQFF | 821 | 1 | Unstim | 10 | 0 | 0 | 1598 | 1180 | 0 | 0 | 0 | 0 |
| CAWRSGGASPLHF | 823 | 1 | Unstim | 0 | 0 | 0 | 0 | 0 | 0 | 0 | 0 | 0 |
| CAWSASRDAEQFF | 825 | 1 | Unstim | 0 | 0 | 0 | 453 | 877 | 0 | 1126 | 1166 | 0 |
| CAWSEGGIGQPQHF | 826 | 1 | Unstim | 2 | 0 | 0 | 0 | 522 | 1424 | 0 | 819 | 0 |
| CAWSGANYGYTF | 827 | 1 | Unstim | 1 | 0 | 0 | 480 | 0 | 1 | 0 | 0 | 867 |
| CAWSVLRGQYF | 830 | 1 | Unstim | 399 | 0 | 0 | 1230 | 695 | 1259 | 0 | 0 | 1427 |
| CSAAIVGQPQHF | 832 | 1 | Unstim | 0 | 749 | 0 | 0 | 0 | 0 | 0 | 753 | 0 |
| CSAAPGTGDNSPLHF | 615 | 1 | Unstim | 1 | 0 | 0 | 0 | 0 | 0 | 0 | 313 | 0 |
| CSALLPTGGGEQYF | 835 | 1 | Unstim | 0 | 0 | 0 | 687 | 376 | 0 | 0 | 599 | 0 |
| CSANGLGGLNTEAFF | 836 | 1 | Unstim | 0 | 0 | 0 | 0 | 738 | 0 | 1234 | 1159 | 0 |
| CSAPQGQETQYF | 837 | 1 | Unstim | 0 | 0 | 291 | 0 | 111 | 0 | 0 | 270 | 0 |
| CSARAGGGDGELFF | 617 | 1 | Unstim | 5 | 0 | 0 | 0 | 0 | 0 | 0 | 410 | 0 |
| CSARDGAGVGDTQYF | 838 | 1 | Unstim | 0 | 0 | 0 | 14 | 0 | 106 | 0 | 71 | 0 |
| CSARDGTGIGDTQYF | 618 | 1 | Unstim | 662 | 0 | 0 | 0 | 0 | 0 | 0 | 525 | 0 |
| CSARDRDRYYEQYF | 619 | 1 | Unstim | 25 | 0 | 0 | 894 | 509 | 1602 | 0 | 881 | 0 |
| CSARDSDGEKLFF | 839 | 1 | Unstim | 1 | 0 | 0 | 664 | 778 | 1 | 0 | 0 | 0 |
| CSARGGGGALGSYNEQFF | 840 | 1 | Unstim | 0 | 0 | 0 | 0 | 111 | 0 | 0 | 270 | 0 |
| CSASGRAGESNEQFF | 844 | 1 | Unstim | 0 | 0 | 0 | 772 | 422 | 1226 | 0 | 674 | 0 |
| CSASKTGVHEQYF | 845 | 1 | Unstim | 2 | 0 | 0 | 0 | 65 | 0 | 0 | 0 | 0 |

Figure 21AK

| TCRB | SEQ ID NO: | Freq. | Stim/Unstim | TGF B | TNFA | BCL6 | TBET | GATA 3 | RORC | FOXP 3 | RUNX 1 | RUNX 3 |
|---|---|---|---|---|---|---|---|---|---|---|---|---|
| CSASRGNTEAFF | 846 | 1 | Unstim | 1 | 0 | 0 | 83 | 60 | 0 | 0 | 93 | 0 |
| CSATHRENLTDTQYF | 847 | 1 | Unstim | 0 | 0 | 0 | 1 | 684 | 0 | 984 | 1004 | 0 |
| CSAVGGPVSQPQHF | 849 | 1 | Unstim | 0 | 0 | 0 | 0 | 709 | 0 | 989 | 840 | 0 |
| CSAVRTGGYYEQYF | 850 | 1 | Unstim | 9 | 0 | 0 | 0 | 872 | 0 | 0 | 0 | 0 |
| CSVDGALAGGTYEQYF | 852 | 1 | Unstim | 0 | 0 | 0 | 0 | 314 | 0 | 496 | 342 | 0 |
| CSVEEGDIRPYEQYF | 854 | 1 | Unstim | 0 | 205 | 285 | 0 | 30 | 0 | 0 | 240 | 0 |
| CSVSQGRGGDTQYF | 858 | 1 | Unstim | 90 | 784 | 0 | 0 | 0 | 1 | 0 | 0 | 0 |
| CASSLASMGVGELFF | 265 | 27 | Stim | 4 | 0 | 0 | 0 | 0 | 992 | 0 | 778 | 0 |
| CASSLASMGVGELFF | 265 | 27 | Stim | 0 | 872 | 0 | 0 | 0 | 4762 | 0 | 2417 | 0 |
| CASSLASMGVGELFF | 265 | 27 | Stim | 0 | 0 | 0 | 0 | 1499 | 1401 | 0 | 718 | 0 |
| CASSLASMGVGELFF | 265 | 27 | Stim | 0 | 689 | 821 | 167 | 0 | 0 | 0 | 1 | 0 |
| CASSLASMGVGELFF | 265 | 27 | Stim | 0 | 934 | 0 | 51 | 2 | 1553 | 0 | 927 | 0 |
| CASSLASMGVGELFF | 265 | 27 | Stim | 0 | 830 | 0 | 0 | 0 | 217 | 0 | 603 | 1166 |
| CASSLASMGVGELFF | 265 | 27 | Stim | 0 | 857 | 0 | 0 | 0 | 0 | 0 | 971 | 0 |
| CASSLASMGVGELFF | 265 | 27 | Stim | 1 | 909 | 0 | 0 | 0 | 0 | 0 | 864 | 0 |
| CASSLASMGVGELFF | 265 | 27 | Stim | 0 | 678 | 0 | 0 | 0 | 0 | 0 | 830 | 0 |
| CASSLASMGVGELFF | 265 | 27 | Stim | 0 | 0 | 0 | 154 | 0 | 1534 | 0 | 0 | 0 |
| CASSLASMGVGELFF | 265 | 27 | Stim | 0 | 836 | 0 | 0 | 1102 | 3266 | 1 | 2034 | 0 |
| CASSLASMGVGELFF | 265 | 27 | Stim | 0 | 1498 | 1775 | 0 | 0 | 0 | 0 | 1558 | 120 |
| CASSLASMGVGELFF | 265 | 27 | Stim | 0 | 487 | 0 | 0 | 0 | 965 | 0 | 327 | 0 |
| CASSLASMGVGELFF | 265 | 27 | Stim | 0 | 427 | 0 | 0 | 0 | 1377 | 0 | 79 | 0 |
| CASSLASMGVGELFF | 265 | 27 | Stim | 0 | 0 | 0 | 2 | 0 | 0 | 0 | 140 | 0 |
| CASSLASMGVGELFF | 265 | 27 | Stim | 0 | 485 | 0 | 2 | 0 | 743 | 0 | 28 | 0 |
| CASSLASMGVGELFF | 265 | 27 | Stim | 0 | 386 | 0 | 0 | 0 | 0 | 0 | 102 | 0 |

Figure 21AL.

| TCRB | SEQ ID NO: | Freq. | Stim/ Unstim | TGF B | TNFA | BCL6 | TBET | GATA 3 | RORC | FOXP 3 | RUNX 1 | RUNX 3 |
|---|---|---|---|---|---|---|---|---|---|---|---|---|
| CASSLASMGVGELFF | | 27 | Stim | 0 | 174 | 0 | 3 | 0 | 235 | 124 | 0 | 0 |
| CASSLASMGVGELFF | | 27 | Stim | 0 | 469 | 253 | 0 | 0 | 7 | 0 | 228 | 0 |
| CASSLASMGVGELFF | | 27 | Stim | 0 | 498 | 0 | 0 | 0 | 828 | 1 | 0 | 0 |
| CASSLASMGVGELFF | | 27 | Stim | 0 | 0 | 0 | 0 | 0 | 0 | 0 | 363 | 0 |
| CASSLASMGVGELFF | | 27 | Stim | 0 | 228 | 0 | 0 | 0 | 288 | 0 | 19 | 0 |
| CASSLASMGVGELFF | | 27 | Stim | 0 | 157 | 0 | 0 | 0 | 327 | 0 | 0 | 1 |
| CASSLASMGVGELFF | | 27 | Stim | 0 | 426 | 0 | 0 | 0 | 673 | 0 | 161 | 0 |
| CASSLASMGVGELFF | | 27 | Stim | 0 | 0 | 0 | 0 | 0 | 2 | 0 | 0 | 0 |
| CASPGGWTGGGNEQFF | | 24 | Stim | 0 | 320 | 71 | 16 | 0 | 505 | 0 | 13 | 0 |
| CASPGGWTGGGNEQFF | | 24 | Stim | 0 | 427 | 0 | 0 | 0 | 770 | 0 | 180 | 0 |
| CASPGGWTGGGNEQFF | | 24 | Stim | 0 | 415 | 0 | 0 | 0 | 105 | 0 | 0 | 0 |
| CASPGGWTGGGNEQFF | | 24 | Stim | 0 | 273 | 0 | 0 | 0 | 63 | 0 | 1 | 1 |
| CASPGGWTGGGNEQFF | | 24 | Stim | 0 | 597 | 12 | 0 | 0 | 721 | 0 | 0 | 0 |
| CASPGGWTGGGNEQFF | 563 | 24 | Stim | 0 | 0 | 0 | 0 | 0 | 0 | 0 | 311 | 0 |
| CASPGGWTGGGNEQFF | | 24 | Stim | 0 | 327 | 0 | 1 | 0 | 109 | 0 | 25 | 0 |
| CASPGGWTGGGNEQFF | | 24 | Stim | 0 | 438 | 551 | 45 | 0 | 1038 | 0 | 0 | 0 |
| CASPGGWTGGGNEQFF | | 24 | Stim | 0 | 873 | 0 | 0 | 0 | 572 | 0 | 858 | 0 |
| CASPGGWTGGGNEQFF | | 24 | Stim | 0 | 436 | 6 | 0 | 0 | 0 | 0 | 2 | 0 |
| CASPGGWTGGGNEQFF | | 24 | Stim | 0 | 777 | 0 | 0 | 0 | 954 | 0 | 328 | 0 |
| CASPGGWTGGGNEQFF | | 24 | Stim | 0 | 1251 | 0 | 0 | 0 | 0 | 0 | 0 | 0 |
| CASPGGWTGGGNEQFF | | 24 | Stim | 0 | 844 | 0 | 0 | 0 | 1330 | 0 | 0 | 0 |
| CASPGGWTGGGNEQFF | | 24 | Stim | 1 | 1390 | 0 | 341 | 1057 | 2531 | 0 | 1558 | 0 |
| CASPGGWTGGGNEQFF | | 24 | Stim | 0 | 760 | 7 | 0 | 0 | 0 | 0 | 27 | 0 |
| CASPGGWTGGGNEQFF | | 24 | Stim | 0 | 201 | 0 | 0 | 0 | 299 | 0 | 0 | 0 |
| CASPGGWTGGGNEQFF | | 24 | Stim | 0 | 635 | 0 | 0 | 0 | 0 | 0 | 19 | 0 |
| CASPGGWTGGGNEQFF | | 24 | Stim | 0 | 235 | 0 | 52 | 0 | 0 | 0 | 0 | 0 |

Figure 21AM

| TCRB | SEQ ID NO: | Freq. | Stim/ Unstim | TGF B | TNFA | BCL6 | TBET | GATA 3 | RORC | FOXP 3 | RUNX 1 | RUNX 3 |
|---|---|---|---|---|---|---|---|---|---|---|---|---|
| CASPGGWTGGGNEQFF | | 24 | Unstim | 0 | 449 | 0 | 0 | 23 | 389 | 0 | 5 | 0 |
| CASPGGWTGGGNEQFF | | 24 | Stim | 0 | 495 | 13 | 24 | 1 | 289 | 0 | 157 | 0 |
| CASPGGWTGGGNEQFF | | 24 | Stim | 0 | 401 | 0 | 141 | 78 | 1207 | 0 | 510 | 0 |
| CASPGGWTGGGNEQFF | | 24 | Stim | 0 | 1 | 575 | 69 | 0 | 896 | 0 | 372 | 0 |
| CASPGGWTGGGNEQFF | | 24 | Stim | 0 | 566 | 0 | 0 | 0 | 922 | 0 | 74 | 0 |
| CASPGGWTGGGNEQFF | | 24 | Stim | 0 | 172 | 0 | 0 | 0 | 338 | 0 | 177 | 0 |
| CASNTLGAGGREQYF | | 16 | Stim | 0 | 601 | 0 | 0 | 0 | 0 | 0 | 406 | 0 |
| CASNTLGAGGREQYF | | 16 | Stim | 0 | 0 | 0 | 0 | 0 | 312 | 0 | 301 | 0 |
| CASNTLGAGGREQYF | | 16 | Stim | 0 | 46 | 0 | 0 | 0 | 286 | 0 | 152 | 0 |
| CASNTLGAGGREQYF | | 16 | Stim | 0 | 204 | 0 | 0 | 0 | 0 | 0 | 0 | 0 |
| CASNTLGAGGREQYF | | 16 | Stim | 0 | 497 | 0 | 0 | 6 | 786 | 0 | 797 | 0 |
| CASNTLGAGGREQYF | | 16 | Stim | 0 | 305 | 0 | 0 | 0 | 820 | 0 | 236 | 0 |
| CASNTLGAGGREQYF | 564 | 16 | Stim | 0 | 423 | 0 | 5 | 0 | 826 | 126 | 389 | 0 |
| CASNTLGAGGREQYF | | 16 | Stim | 0 | 1271 | 1318 | 0 | 0 | 2442 | 1330 | 1283 | 1 |
| CASNTLGAGGREQYF | | 16 | Stim | 0 | 541 | 0 | 0 | 0 | 1178 | 0 | 224 | 0 |
| CASNTLGAGGREQYF | | 16 | Stim | 0 | 796 | 0 | 1 | 0 | 1561 | 0 | 1 | 0 |
| CASNTLGAGGREQYF | | 16 | Stim | 0 | 990 | 876 | 0 | 0 | 0 | 0 | 894 | 0 |
| CASNTLGAGGREQYF | | 16 | Stim | 0 | 580 | 0 | 2 | 147 | 1352 | 237 | 89 | 0 |
| CASNTLGAGGREQYF | | 16 | Stim | 5 | 0 | 0 | 0 | 446 | 0 | 0 | 0 | 0 |
| CASNTLGAGGREQYF | | 16 | Stim | 0 | 202 | 0 | 36 | 0 | 496 | 0 | 236 | 0 |
| CASNTLGAGGREQYF | | 16 | Stim | 0 | 359 | 0 | 0 | 0 | 836 | 350 | 289 | 0 |
| CASNTLGAGGREQYF | | 16 | Stim | 0 | 479 | 0 | 53 | 147 | 51 | 0 | 366 | 0 |
| CASSQGLAAPYEQYF | | 13 | Stim | 0 | 900 | 0 | 0 | 0 | 1205 | 0 | 3 | 0 |
| CASSQGLAAPYEQYF | 566 | 13 | Stim | 0 | 380 | 0 | 0 | 0 | 0 | 0 | 0 | 0 |
| CASSQGLAAPYEQYF | | 13 | Stim | 0 | 745 | 0 | 0 | 0 | 0 | 0 | 0 | 0 |
| CASSQGLAAPYEQYF | | 13 | Stim | 0 | 853 | 0 | 2 | 0 | 6 | 0 | 1 | 0 |

Figure 21AN

| TCRB | SEQ ID NO: | Freq. | Stim/ Unstim | TGF B | TNFA | BCL6 | TBET | GATA 3 | RORC | FOXP 3 | RUNX 1 | RUNX 3 |
|---|---|---|---|---|---|---|---|---|---|---|---|---|
| CASSQGLAAPYEQYF | | 13 | Stim | 0 | 185 | 0 | 0 | 0 | 0 | 0 | 0 | 0 |
| CASSQGLAAPYEQYF | | 13 | Stim | 0 | 590 | 0 | 0 | 0 | 1107 | 0 | 97 | 821 |
| CASSQGLAAPYEQYF | | 13 | Stim | 0 | 754 | 0 | 1 | 0 | 0 | 0 | 90 | 54 |
| CASSQGLAAPYEQYF | | 13 | Stim | 0 | 827 | 0 | 0 | 0 | 175 | 0 | 0 | 0 |
| CASSQGLAAPYEQYF | | 13 | Stim | 0 | 490 | 0 | 1 | 0 | 0 | 0 | 0 | 0 |
| CASSQGLAAPYEQYF | | 13 | Stim | 0 | 292 | 0 | 0 | 0 | 1 | 0 | 0 | 0 |
| CASSQGLAAPYEQYF | | 13 | Stim | 0 | 609 | 0 | 1 | 0 | 0 | 0 | 0 | 0 |
| CASSQGLAAPYEQYF | | 13 | Stim | 0 | 73 | 0 | 0 | 0 | 30 | 0 | 0 | 0 |
| CASSQGLAAPYEQYF | | 13 | Stim | 0 | 517 | 0 | 1 | 0 | 0 | 0 | 0 | 0 |
| CAWSDGVVGEKLFF | 567 | 7 | Stim | 0 | 0 | 0 | 0 | 258 | 938 | 0 | 501 | 0 |
| CAWSDGVVGEKLFF | | 7 | Stim | 0 | 0 | 2411 | 0 | 0 | 3725 | 0 | 2121 | 0 |
| CAWSDGVVGEKLFF | | 7 | Stim | 0 | 655 | 0 | 0 | 2 | 708 | 0 | 1 | 0 |
| CAWSDGVVGEKLFF | | 7 | Stim | 0 | 679 | 0 | 0 | 1 | 1034 | 8 | 298 | 0 |
| CAWSDGVVGEKLFF | | 7 | Stim | 0 | 546 | 0 | 0 | 1 | 1193 | 0 | 12 | 0 |
| CAWSDGVVGEKLFF | | 7 | Stim | 0 | 717 | 0 | 0 | 0 | 0 | 0 | 0 | 0 |
| CAWSDGVVGEKLFF | | 7 | Stim | 0 | 376 | 616 | 553 | 1 | 1165 | 0 | 251 | 0 |
| CASRENSGANVLTF | 568 | 6 | Stim | 0 | 266 | 0 | 0 | 11 | 0 | 0 | 0 | 0 |
| CASRENSGANVLTF | | 6 | Stim | 0 | 1229 | 0 | 3 | 0 | 1033 | 0 | 168 | 0 |
| CASRENSGANVLTF | | 6 | Stim | 0 | 394 | 0 | 1 | 21 | 701 | 0 | 0 | 0 |
| CASRENSGANVLTF | | 6 | Stim | 0 | 520 | 0 | 0 | 0 | 417 | 40 | 8 | 0 |
| CASRENSGANVLTF | | 6 | Stim | 0 | 490 | 0 | 0 | 0 | 0 | 0 | 0 | 0 |
| CASRENSGANVLTF | | 6 | Stim | 0 | 814 | 0 | 53 | 0 | 1219 | 1 | 251 | 0 |
| CASSEAGGQDYGNEQFF | 565 | 6 | Stim | 0 | 393 | 1 | 3 | 0 | 38 | 0 | 0 | 0 |
| CASSEAGGQDYGNEQFF | | 6 | Stim | 0 | 478 | 0 | 0 | 0 | 11 | 0 | 0 | 0 |
| CASSEAGGQDYGNEQFF | | 6 | Stim | 0 | 444 | 0 | 0 | 0 | 977 | 0 | 402 | 0 |
| CASSEAGGQDYGNEQFF | | 6 | Stim | 0 | 1103 | 0 | 32 | 0 | 1692 | 1 | 956 | 0 |

Figure 21AO

| TCRB | SEQ ID NO: | Freq. | Stim/Unstim | TGFB | TNFA | BCL6 | TBET | GATA3 | RORC | FOXP3 | RUNX1 | RUNX3 |
|---|---|---|---|---|---|---|---|---|---|---|---|---|
| CASSEAGGQDYGNEQFF | | 6 | Stim | 0 | 494 | 0 | 0 | 0 | 0 | 1 | 78 | 0 |
| CASSEAGGQDYGNEQFF | | 6 | Stim | 0 | 547 | 0 | 0 | 0 | 955 | 0 | 1 | 0 |
| CASSEPGEQFF | | 4 | Stim | 0 | 202 | 0 | 0 | 0 | 21 | 106 | 0 | 0 |
| CASSEPGEQFF | 580 | 4 | Stim | 0 | 889 | 0 | 844 | 674 | 0 | 0 | 0 | 0 |
| CASSEPGEQFF | | 4 | Stim | 0 | 774 | 0 | 0 | 0 | 3 | 0 | 0 | 0 |
| CASSEPGEQFF | | 4 | Stim | 0 | 248 | 0 | 0 | 0 | 0 | 1 | 0 | 0 |
| CASSSGTGGLETQYF | | 4 | Stim | 0 | 444 | 0 | 0 | 0 | 0 | 465 | 0 | 723 |
| CASSSGTGGLETQYF | 575 | 4 | Stim | 0 | 1443 | 0 | 0 | 0 | 3205 | 0 | 1733 | 0 |
| CASSSGTGGLETQYF | | 4 | Stim | 0 | 799 | 0 | 0 | 0 | 1754 | 1 | 0 | 0 |
| CASSSGTGGLETQYF | | 4 | Stim | 0 | 379 | 0 | 0 | 0 | 215 | 213 | 2 | 0 |
| CATSREWGEAYEQYF | | 4 | Stim | 0 | 274 | 0 | 0 | 1 | 221 | 0 | 20 | 0 |
| CATSREWGEAYEQYF | 577 | 4 | Stim | 0 | 654 | 0 | 0 | 0 | 1388 | 0 | 710 | 0 |
| CATSREWGEAYEQYF | | 4 | Stim | 0 | 1292 | 1523 | 0 | 0 | 2648 | 0 | 1504 | 0 |
| CATSREWGEAYEQYF | | 4 | Stim | 0 | 1149 | 437 | 0 | 0 | 2316 | 1 | 7 | 0 |
| CAWSPGGETQYF | | 4 | Stim | 0 | 494 | 0 | 0 | 0 | 0 | 0 | 9 | 0 |
| CAWSPGGETQYF | 572 | 4 | Stim | 0 | 659 | 1 | 0 | 0 | 347 | 0 | 4 | 0 |
| CAWSPGGETQYF | | 4 | Stim | 0 | 282 | 0 | 0 | 0 | 36 | 19 | 0 | 0 |
| CAWSPGGETQYF | | 4 | Stim | 0 | 557 | 0 | 0 | 0 | 274 | 0 | 0 | 0 |
| CASSATGLAGGGETQYF | | 3 | Stim | 0 | 945 | 0 | 4 | 0 | 0 | 0 | 27 | 0 |
| CASSATGLAGGGETQYF | 579 | 3 | Stim | 0 | 0 | 0 | 1201 | 952 | 2361 | 0 | 1395 | 0 |
| CASSATGLAGGGETQYF | | 3 | Stim | 0 | 525 | 0 | 85 | 0 | 961 | 0 | 513 | 0 |
| CATSRDGTDYGYTF | | 3 | Stim | 0 | 687 | 0 | 0 | 0 | 118 | 2 | 1 | 0 |
| CATSRDGTDYGYTF | 576 | 3 | Stim | 0 | 810 | 0 | 0 | 0 | 970 | 0 | 125 | 0 |
| CATSRDGTDYGYTF | | 3 | Stim | 0 | 442 | 0 | 0 | 1 | 747 | 0 | 0 | 0 |
| CSAGTYRTDTQYF | 569 | 3 | Stim | 0 | 329 | 0 | 0 | 0 | 566 | 0 | 4 | 0 |
| CSAGTYRTDTQYF | | 3 | Stim | 0 | 589 | 0 | 102 | 0 | 613 | 0 | 506 | 0 |

Figure 21AP

| TCRB | SEQ ID NO: | Freq. | Stim/ Unstim | TGF B | TNFA | BCL6 | TBET | GATA 3 | RORC | FOXP 3 | RUNX 1 | RUNX 3 |
|---|---|---|---|---|---|---|---|---|---|---|---|---|
| CSAGTYRTDTQYF | | 3 | Stim | 0 | 521 | 301 | 1 | 0 | 35 | 0 | 15 | 0 |
| CASRKGTEGTQYF | 592 | 2 | Stim | 0 | 1168 | 0 | 0 | 0 | 3242 | 0 | 0 | 0 |
| CASRKGTEGTQYF | | 2 | Stim | 0 | 0 | 0 | 447 | 321 | 47 | 0 | 445 | 0 |
| CASSEVWGSTHNEQFF | 595 | 2 | Stim | 0 | 434 | 0 | 0 | 0 | 0 | 0 | 2 | 0 |
| CASSEVWGSTHNEQFF | | 2 | Stim | 1 | 0 | 0 | 0 | 930 | 0 | 0 | 1397 | 0 |
| CASSKGTDLNTEAFF | 697 | 2 | Stim | 0 | 0 | 0 | 0 | 26 | 54 | 0 | 233 | 0 |
| CASSKGTDLNTEAFF | | 2 | Stim | 0 | 0 | 0 | 0 | 0 | 0 | 0 | 0 | 0 |
| CASSLAPGVGETQYF | 701 | 2 | Stim | 0 | 0 | 0 | 424 | 0 | 0 | 339 | 452 | 0 |
| CASSLAPGVGETQYF | | 2 | Stim | 0 | 0 | 0 | 1 | 0 | 0 | 0 | 1 | 0 |
| CASSLGGGSYNEQFF | 570 | 2 | Stim | 0 | 385 | 0 | 85 | 0 | 776 | 0 | 0 | 0 |
| CASSLGGGSYNEQFF | | 2 | Stim | 0 | 121 | 0 | 63 | 72 | 0 | 0 | 72 | 0 |
| CASSPAGPFYEQYF | 744 | 2 | Stim | 0 | 496 | 0 | 465 | 0 | 0 | 1 | 480 | 0 |
| CASSPAPGPDTQYF | 745 | 2 | Stim | 0 | 1 | 418 | 0 | 0 | 1 | 0 | 412 | 6 |
| CASSQDAVQRLYGYTF | 604 | 2 | Stim | 0 | 592 | 0 | 13 | 0 | 1154 | 0 | 149 | 0 |
| CASSQDAVQRLYGYTF | | 2 | Stim | 0 | 244 | 0 | 160 | 0 | 707 | 342 | 232 | 0 |
| CASSQDGAGGREQFF | 571 | 2 | Stim | 0 | 451 | 122 | 0 | 0 | 0 | 0 | 127 | 0 |
| CASSQDGAGGREQFF | | 2 | Stim | 0 | 325 | 0 | 0 | 0 | 1049 | 0 | 449 | 0 |
| CASSSASGGVGELFF | 267 | 2 | Stim | 0 | 374 | 0 | 0 | 0 | 0 | 0 | 254 | 0 |
| CASSSASGGVGELFF | | 2 | Stim | 0 | 583 | 2224 | 0 | 0 | 1160 | 0 | 647 | 0 |
| CASSSGQLVHEQFF | 606 | 2 | Stim | 2 | 1959 | 0 | 1 | 641 | 0 | 0 | 0 | 0 |
| CASSSGQLVHEQFF | | 2 | Stim | 0 | 0 | 0 | 0 | 0 | 3104 | 0 | 0 | 0 |
| CASSSQSNTEAFF | 607 | 2 | Stim | 0 | 344 | 0 | 0 | 0 | 1155 | 0 | 460 | 0 |
| CASSSQSNTEAFF | | 2 | Stim | 0 | 469 | 0 | 0 | 304 | 0 | 0 | 0 | 0 |
| CASSSSDRAHF | 794 | 2 | Stim | 0 | 386 | 0 | 0 | 0 | 703 | 0 | 0 | 0 |
| CASSSSDRAHF | | 2 | Stim | 0 | 0 | 0 | 0 | 0 | 0 | 0 | 0 | 0 |
| CASTSGGAYEQYF | 612 | 2 | Stim | 0 | 308 | 0 | 3 | 0 | 0 | 0 | 316 | 0 |

Figure 21AQ

| TCRB | SEQ ID NO: | Freq. | Stim/ Unstim | TGF B | TNFA | BCL6 | TBET | GATA 3 | RORC | FOXP 3 | RUNX 1 | RUNX 3 |
|---|---|---|---|---|---|---|---|---|---|---|---|---|
| CASTSGGAYEQYF | | 2 | Stim | 1 | 0 | 0 | 0 | 0 | 1 | 0 | 1549 | 0 |
| CAWSAGQGILNEQFF | 614 | 2 | Stim | 0 | 390 | 0 | 0 | 0 | 826 | 288 | 308 | 54 |
| CAWSAGQGILNEQFF | | 2 | Stim | 4 | 0 | 0 | 0 | 0 | 1223 | 0 | 664 | 0 |
| CSAPTRAGANVLTF | | 2 | Stim | 1 | 0 | 0 | 0 | 0 | 0 | 0 | 0 | 0 |
| CSAPTRAGANVLTF | 616 | 2 | Stim | 1 | 0 | 0 | 0 | 0 | 1541 | 0 | 818 | 0 |
| CSVAYPGQSYGYTF | | 2 | Stim | 0 | 0 | 0 | 0 | 0 | 0 | 0 | 0 | 0 |
| CSVAYPGQSYGYTF | 621 | 2 | Stim | 0 | 313 | 0 | 0 | 0 | 653 | 1 | 1 | 0 |
| CAIREQGEAFF | 624 | 1 | Stim | 0 | 468 | 0 | 0 | 1 | 9 | 0 | 871 | 0 |
| CAISENGKANYGYTF | 625 | 1 | Stim | 0 | 0 | 0 | 0 | 0 | 1829 | 0 | 41 | 0 |
| CAISGGQDSNQPQHF | 627 | 1 | Stim | 0 | 556 | 0 | 1 | 0 | 0 | 7 | 0 | 0 |
| CAISSPSSGNYEQYF | 628 | 1 | Stim | 0 | 397 | 0 | 0 | 77 | 0 | 0 | 0 | 0 |
| CASAAGWDTEAFF | 630 | 1 | Stim | 0 | 0 | 0 | 0 | 1 | 0 | 0 | 0 | 0 |
| CASGGTEAFF | 633 | 1 | Stim | 0 | 827 | 0 | 0 | 0 | 393 | 0 | 1 | 0 |
| CASIPPRAGPIANEKLFF | 590 | 1 | Stim | 0 | 538 | 0 | 887 | 523 | 0 | 989 | 285 | 421 |
| CASIREGSHYNEQFF | 636 | 1 | Stim | 0 | 833 | 0 | 0 | 0 | 2084 | 0 | 0 | 0 |
| CASKKGTGGNQPQHF | 639 | 1 | Stim | 0 | 1004 | 0 | 0 | 0 | 426 | 0 | 0 | 0 |
| CASNLGTADSNQPQHF | 623 | 1 | Stim | 0 | 26 | 0 | 2 | 0 | 233 | 0 | 35 | 0 |
| CASQGQGEQYF | 643 | 1 | Stim | 0 | 517 | 781 | 674 | 1 | 0 | 0 | 0 | 0 |
| CASRDGVQPQHF | 591 | 1 | Stim | 0 | 579 | 0 | 1 | 1 | 1102 | 0 | 2 | 0 |
| CASRDGVQPQHF | 591 | 1 | Stim | 0 | 1202 | 677 | 4 | 0 | 2659 | 0 | 1389 | 0 |
| CASRGDRGDYGYTF | 645 | 1 | Stim | 0 | 1 | 0 | 0 | 0 | 0 | 376 | 251 | 151 |
| CASRLGLAENEQFF | 648 | 1 | Stim | 0 | 0 | 0 | 2227 | 0 | 0 | 0 | 0 | 0 |
| CASRLSRDNSPLHF | 649 | 1 | Stim | 0 | 1224 | 0 | 489 | 837 | 0 | 0 | 1285 | 0 |
| CASRPGTGRDQPQHF | 652 | 1 | Stim | 0 | 65 | 16 | 0 | 0 | 0 | 0 | 0 | 0 |
| CASRQTGTSTDTQYF | 655 | 1 | Stim | 0 | 430 | 0 | 6 | 0 | 0 | 0 | 176 | 288 |
| CASRSGIYTEAFF | 658 | 1 | Stim | 0 | 0 | 0 | 0 | 0 | 1921 | 0 | 796 | 0 |

Figure 21AR

| TCRB | SEQ ID NO: | Freq. | Stim/ Unstim | TGF B | TNFA | BCL6 | TBET | GATA 3 | RORC | FOXP 3 | RUNX 1 | RUNX 3 |
|---|---|---|---|---|---|---|---|---|---|---|---|---|
| CASRSGLAGTTDTQYF | 659 | 1 | Stim | 0 | 1 | 482 | 330 | 0 | 0 | 0 | 0 | 0 |
| CASRTERESINEQFF | 593 | 1 | Stim | 0 | 1243 | 0 | 98 | 0 | 2102 | 0 | 1114 | 0 |
| CASRTGLNGELFF | 660 | 1 | Stim | 0 | 878 | 0 | 0 | 0 | 616 | 0 | 476 | 0 |
| CASSAGQDSDTQYF | 661 | 1 | Stim | 0 | 122 | 0 | 138 | 79 | 0 | 131 | 140 | 0 |
| CASSDPGGGVTGELFF | 667 | 1 | Stim | 1 | 35 | 0 | 8 | 0 | 0 | 0 | 1 | 0 |
| CASSEGGDHEQFF | 594 | 1 | Stim | 0 | 287 | 0 | 0 | 458 | 0 | 0 | 586 | 0 |
| CASSFERPYEQYF | 676 | 1 | Stim | 0 | 2 | 0 | 0 | 267 | 0 | 0 | 367 | 0 |
| CASSFGAEDTQYF | 677 | 1 | Stim | 0 | 86 | 0 | 0 | 0 | 924 | 0 | 372 | 311 |
| CASSFGGPSYEQYF | 678 | 1 | Stim | 0 | 723 | 0 | 1 | 0 | 0 | 0 | 354 | 245 |
| CASSFPYTEAFF | 680 | 1 | Stim | 0 | 441 | 0 | 0 | 0 | 205 | 286 | 127 | 0 |
| CASSFSGREGVDTQYF | 682 | 1 | Stim | 0 | 758 | 0 | 0 | 0 | 0 | 0 | 844 | 0 |
| CASSFVNSPLHF | 686 | 1 | Stim | 0 | 475 | 0 | 1 | 0 | 0 | 0 | 0 | 0 |
| CASSFVRALGSYNSPLHF | 687 | 1 | Stim | 0 | 560 | 0 | 1 | 0 | 1375 | 0 | 389 | 0 |
| CASSGGTGNNYEQYF | 688 | 1 | Stim | 0 | 879 | 0 | 0 | 0 | 1 | 0 | 793 | 0 |
| CASSGTGGHQPQHF | 690 | 1 | Stim | 0 | 0 | 0 | 0 | 0 | 196 | 132 | 0 | 0 |
| CASSHSATHNEQFF | 691 | 1 | Stim | 0 | 0 | 0 | 727 | 0 | 0 | 616 | 567 | 0 |
| CASSIRRNNEQFF | 694 | 1 | Stim | 0 | 0 | 0 | 0 | 0 | 0 | 768 | 383 | 994 |
| CASSIWGSEAFF | 695 | 1 | Stim | 0 | 504 | 0 | 0 | 0 | 509 | 0 | 31 | 542 |
| CASSKEGRITDTQYF | 696 | 1 | Stim | 0 | 866 | 0 | 0 | 1 | 0 | 0 | 277 | 33 |
| CASSLAANSPLHF | 699 | 1 | Stim | 0 | 208 | 0 | 10 | 21 | 384 | 0 | 147 | 0 |
| CASSLAGTGQFF | 597 | 1 | Stim | 0 | 833 | 0 | 0 | 0 | 1122 | 0 | 441 | 0 |
| CASSLAPLQGTFRADTQYF | 581 | 1 | Stim | 0 | 836 | 0 | 0 | 0 | 1701 | 0 | 0 | 0 |
| CASSLASGIYEQFF | 702 | 1 | Stim | 0 | 487 | 0 | 0 | 0 | 0 | 0 | 0 | 0 |
| CASSLASRGPQGETQYF | 703 | 1 | Stim | 0 | 1 | 0 | 821 | 0 | 0 | 618 | 712 | 0 |
| CASSLAYGTDTQYF | 704 | 1 | Stim | 0 | 0 | 0 | 0 | 1 | 0 | 1172 | 977 | 0 |
| CASSLDGGVVGGYTF | 705 | 1 | Stim | 0 | 118 | 0 | 0 | 0 | 0 | 453 | 0 | 0 |

Figure 21AS

| TCRB | SEQ ID NO: | Freq. | Stim/Unstim | TGFB | TNFA | BCL6 | TBET | GATA3 | RORC | FOXP3 | RUNX1 | RUNX3 |
|---|---|---|---|---|---|---|---|---|---|---|---|---|
| CASSLDSQNTGELFF | 707 | 1 | Stim | 0 | 478 | 0 | 0 | 353 | 1081 | 0 | 0 | 0 |
| CASSLDSTGTGKETQYF | 708 | 1 | Stim | 0 | 806 | 0 | 1 | 163 | 0 | 0 | 0 | 0 |
| CASSLEGPRDTQYF | 710 | 1 | Stim | 0 | 0 | 0 | 132 | 407 | 0 | 669 | 493 | 0 |
| CASSLEGQGNGYTF | 598 | 1 | Stim | 0 | 0 | 0 | 0 | 0 | 0 | 0 | 0 | 0 |
| CASSLEPGRQGNTGELFF | 713 | 1 | Stim | 0 | 0 | 0 | 0 | 0 | 0 | 0 | 709 | 0 |
| CASSLGGTPEPQHF | 716 | 1 | Stim | 0 | 336 | 0 | 0 | 0 | 254 | 0 | 0 | 0 |
| CASSLGQEENSPLHF | 720 | 1 | Stim | 0 | 35 | 533 | 609 | 802 | 1965 | 0 | 1 | 0 |
| CASSLNQDGYTF | 727 | 1 | Stim | 0 | 684 | 0 | 0 | 0 | 1426 | 524 | 768 | 0 |
| CASSLSGEKLFF | 582 | 1 | Stim | 0 | 0 | 0 | 0 | 0 | 1352 | 1 | 774 | 0 |
| CASSLVIQPQHF | 739 | 1 | Stim | 0 | 0 | 0 | 7 | 0 | 0 | 0 | 6 | 0 |
| CASSLYTGGGSGELFF | 741 | 1 | Stim | 52 | 1522 | 0 | 0 | 742 | 0 | 0 | 0 | 0 |
| CASSMVAGNGELFF | 742 | 1 | Stim | 0 | 450 | 0 | 412 | 0 | 0 | 386 | 378 | 0 |
| CASSPDNDEETQYF | 746 | 1 | Stim | 0 | 0 | 0 | 0 | 0 | 0 | 272 | 188 | 0 |
| CASSPFWDSNYGYTF | 747 | 1 | Stim | 0 | 641 | 0 | 451 | 0 | 0 | 0 | 0 | 0 |
| CASSPGTSGVGELFF | 752 | 1 | Stim | 0 | 1505 | 886 | 4 | 45 | 3 | 399 | 174 | 0 |
| CASSPPTSEDAYNEQFF | 601 | 1 | Stim | 0 | 0 | 0 | 0 | 877 | 0 | 0 | 1079 | 0 |
| CASSPPVWPTGELFF | 754 | 1 | Stim | 0 | 616 | 0 | 0 | 367 | 0 | 548 | 0 | 0 |
| CASSPQQAGDTEAFF | 755 | 1 | Stim | 0 | 1002 | 0 | 0 | 257 | 1051 | 0 | 0 | 0 |
| CASSPRNSAGGPETQYF | 758 | 1 | Stim | 0 | 1348 | 0 | 3 | 0 | 0 | 0 | 1 | 0 |
| CASSPSWAGGDYEQYF | 760 | 1 | Stim | 0 | 1080 | 0 | 1 | 0 | 1416 | 0 | 962 | 0 |
| CASSPTSGETTQYF | 761 | 1 | Stim | 228 | 0 | 0 | 0 | 0 | 0 | 0 | 0 | 0 |
| CASSPWTGTGSYSNQPQHF | 763 | 1 | Stim | 0 | 667 | 0 | 0 | 0 | 0 | 0 | 0 | 0 |
| CASSQDAGVGVGYTF | 766 | 1 | Stim | 0 | 691 | 187 | 0 | 0 | 0 | 0 | 1 | 0 |
| CASSQDEVGGRRAFF | 584 | 1 | Stim | 0 | 423 | 0 | 0 | 0 | 552 | 0 | 343 | 0 |
| CASSQDGPRGLETQYF | 767 | 1 | Stim | 0 | 0 | 0 | 0 | 0 | 1 | 0 | 0 | 0 |
| CASSQDWGDYGYTF | 585 | 1 | Stim | 0 | 445 | 0 | 0 | 0 | 0 | 0 | 0 | 0 |

Figure 21AT

| TCRB | SEQ ID NO: | Freq. | Stim/ Unstim | TGF B | TNFA | BCL6 | TBET | GATA 3 | RORC | FOXP 3 | RUNX 1 | RUNX 3 |
|---|---|---|---|---|---|---|---|---|---|---|---|---|
| CASSQDYQGLDGEQFF | 586 | 1 | Stim | 0 | 563 | 0 | 1 | 0 | 970 | 0 | 518 | 0 |
| CASSQDYQGVDNEQFF | 768 | 1 | Stim | 0 | 561 | 320 | 1 | 0 | 66 | 0 | 3 | 0 |
| CASSQERGGKWAYEQYF | 779 | 1 | Stim | 0 | 783 | 0 | 0 | 0 | 1089 | 0 | 741 | 0 |
| CASSQGETGEYGYTF | 773 | 1 | Stim | 0 | 176 | 157 | 0 | 0 | 294 | 0 | 62 | 0 |
| CASSQGFVVNSPLHF | 774 | 1 | Stim | 0 | 870 | 0 | 502 | 0 | 1849 | 0 | 986 | 0 |
| CASSQGRPNSPLHF | 776 | 1 | Stim | 0 | 0 | 0 | 0 | 0 | 0 | 744 | 0 | 0 |
| CASSQGTSGWTDTQYF | 777 | 1 | Stim | 0 | 948 | 0 | 0 | 0 | 84 | 0 | 0 | 0 |
| CASSQTDANTGELFF | 780 | 1 | Stim | 0 | 1070 | 0 | 860 | 924 | 0 | 1457 | 1298 | 0 |
| CASSQTQNRGGNYGYTF | 781 | 1 | Stim | 0 | 751 | 0 | 503 | 0 | 1392 | 0 | 595 | 0 |
| CASSQVGGAFANTGELFF | 782 | 1 | Stim | 0 | 1474 | 0 | 1 | 908 | 2533 | 0 | 592 | 1530 |
| CASSRESFAPDGYTF | 783 | 1 | Stim | 0 | 960 | 0 | 0 | 0 | 198 | 0 | 0 | 0 |
| CASSRGLYNEQFF | 784 | 1 | Stim | 0 | 0 | 0 | 798 | 0 | 982 | 0 | 0 | 0 |
| CASSRSTENNSPLHF | 786 | 1 | Stim | 0 | 906 | 0 | 0 | 0 | 2 | 0 | 840 | 0 |
| CASSSAGGAFSHEQYF | 788 | 1 | Stim | 0 | 0 | 0 | 0 | 0 | 0 | 0 | 0 | 0 |
| CASSSPGVGANVLTF | 587 | 1 | Stim | 0 | 385 | 0 | 1 | 0 | 0 | 0 | 188 | 0 |
| CASSSPSLAGPYEQYF | 792 | 1 | Stim | 0 | 230 | 178 | 33 | 0 | 0 | 0 | 117 | 0 |
| CASSSRGPPAYEQYF | 793 | 1 | Stim | 0 | 781 | 0 | 0 | 0 | 1610 | 294 | 811 | 0 |
| CASSSSDSYNEQFF | 795 | 1 | Stim | 0 | 0 | 0 | 1382 | 926 | 0 | 1412 | 1134 | 0 |
| CASSSSGGSRTDTQYF | 796 | 1 | Stim | 0 | 269 | 0 | 0 | 0 | 1424 | 0 | 7 | 0 |
| CASSSTGQSWDTQYF | 797 | 1 | Stim | 0 | 1144 | 1 | 1 | 0 | 1650 | 1265 | 881 | 0 |
| CASSTDSANYGYTF | 800 | 1 | Stim | 0 | 388 | 0 | 0 | 0 | 430 | 0 | 0 | 0 |
| CASSTHSGRTEAFF | 801 | 1 | Stim | 0 | 0 | 0 | 0 | 0 | 0 | 0 | 1 | 0 |
| CASSTSRDRVNQPQHF | 802 | 1 | Stim | 0 | 0 | 0 | 0 | 0 | 0 | 376 | 398 | 0 |
| CASSTWTAYNEKLFF | 804 | 1 | Stim | 0 | 796 | 0 | 0 | 0 | 0 | 707 | 0 | 0 |
| CASSWIAGVAGGAVADTQYF | 588 | 1 | Stim | 0 | 0 | 0 | 0 | 0 | 0 | 0 | 0 | 0 |
| CASSYPAPSGGPETQYF | 808 | 1 | Stim | 0 | 561 | 0 | 442 | 0 | 0 | 0 | 674 | 0 |

Figure 21AU

| TCRB | SEQ ID NO: | Freq. | Stim/ Unstim | TGF B | TNFA | BCL6 | TBET | GATA 3 | RORC | FOXP 3 | RUNX 1 | RUNX 3 |
|---|---|---|---|---|---|---|---|---|---|---|---|---|
| CASSYPLVLSEQFF | 809 | 1 | Stim | 0 | 722 | 1011 | 392 | 0 | 0 | 1 | 895 | 0 |
| CASSYPSGRICEQYF | 611 | 1 | Stim | 0 | 571 | 0 | 686 | 0 | 1312 | 0 | 0 | 0 |
| CASSYSSGEYTGELFF | 810 | 1 | Stim | 0 | 730 | 22 | 0 | 0 | 694 | 0 | 3 | 0 |
| CASTYWAGAEAFF | 813 | 1 | Stim | 0 | 426 | 0 | 196 | 155 | 0 | 0 | 445 | 0 |
| CATSRDFGDSYEQYF | 816 | 1 | Stim | 0 | 869 | 0 | 0 | 0 | 6 | 537 | 0 | 0 |
| CATSRDLVGGNEQFF | 613 | 1 | Stim | 0 | 0 | 0 | 349 | 0 | 0 | 0 | 321 | 0 |
| CATSRDPGLASTQYF | 817 | 1 | Stim | 0 | 0 | 0 | 0 | 1668 | 0 | 0 | 0 | 0 |
| CATSRDRADTEAFF | 818 | 1 | Stim | 0 | 0 | 0 | 116 | 473 | 3 | 0 | 1 | 0 |
| CAWQYPADSEKLFF | 822 | 1 | Stim | 0 | 560 | 0 | 0 | 0 | 0 | 0 | 0 | 0 |
| CAWSAGTGVRELFF | 824 | 1 | Stim | 0 | 200 | 0 | 0 | 8 | 0 | 143 | 76 | 350 |
| CAWSSGTGTSEQYF | 828 | 1 | Stim | 0 | 0 | 0 | 0 | 0 | 0 | 450 | 225 | 651 |
| CAWSVGGRIYGYTF | 829 | 1 | Stim | 0 | 0 | 394 | 0 | 0 | 0 | 0 | 258 | 0 |
| CISQSGIGFDTF | 831 | 1 | Stim | 0 | 359 | 1 | 0 | 0 | 0 | 8 | 0 | 0 |
| CSAAPGTGDNSPLHF | 615 | 1 | Stim | 0 | 731 | 0 | 448 | 1 | 0 | 0 | 809 | 1 |
| CSAATLDGSNQPQHF | 578 | 1 | Stim | 0 | 487 | 0 | 15 | 263 | 0 | 0 | 7 | 995 |
| CSAERSGLAGAPAYEQYF | 833 | 1 | Stim | 0 | 1153 | 0 | 0 | 512 | 2057 | 0 | 0 | 0 |
| CSAGPVGAGAGEQFF | 834 | 1 | Stim | 0 | 343 | 0 | 125 | 0 | 0 | 321 | 361 | 0 |
| CSARAGGGDGELFF | 617 | 1 | Stim | 0 | 616 | 0 | 0 | 0 | 35 | 0 | 9 | 0 |
| CSARDGTGIGDTQYF | 618 | 1 | Stim | 0 | 600 | 410 | 88 | 0 | 0 | 0 | 0 | 0 |
| CSARDRDRYYEQYF | 619 | 1 | Stim | 0 | 523 | 0 | 0 | 2 | 1188 | 0 | 226 | 568 |
| CSARGSGTGDLYGYTF | 841 | 1 | Stim | 13 | 0 | 0 | 0 | 0 | 0 | 321 | 0 | 0 |
| CSARWEQGARGYTF | 842 | 1 | Stim | 0 | 11 | 0 | 0 | 0 | 0 | 0 | 0 | 0 |
| CSASESLLLGYTF | 843 | 1 | Stim | 0 | 0 | 0 | 0 | 0 | 0 | 0 | 0 | 0 |
| CSATSPLSAGAYQETQYF | 848 | 1 | Stim | 0 | 0 | 0 | 0 | 0 | 0 | 503 | 0 | 0 |
| CSIGGQGLEAFF | 851 | 1 | Stim | 0 | 0 | 0 | 1282 | 836 | 0 | 1091 | 1145 | 0 |
| CSVDGSWQFF | 853 | 1 | Stim | 6 | 0 | 0 | 0 | 111 | 0 | 496 | 575 | 0 |

Figure 21AV

| TCRB | SEQ ID NO: | Freq. | Stim/ Unstim | TGF B | TNFA | BCL6 | TBET | GATA 3 | RORC | FOXP 3 | RUNX 1 | RUNX 3 |
|---|---|---|---|---|---|---|---|---|---|---|---|---|
| CSVELQGNKVGELFF | 855 | 1 | Stim | 0 | 484 | 0 | 12 | 0 | 490 | 0 | 370 | 0 |
| CSVHGGETQYF | 285 | 1 | Stim | 0 | 0 | 0 | 0 | 0 | 0 | 0 | 0 | 0 |
| CSVLAAYNEQFF | 856 | 1 | Stim | 234 | 340 | 0 | 0 | 0 | 0 | 372 | 403 | 0 |
| CSVRTGNSNQPQHF | 857 | 1 | Stim | 0 | 541 | 0 | 0 | 0 | 424 | 0 | 0 | 0 |

Figure 22A

Table 11.

| TCRB | SEQ ID NO: | IL2 | IL10 | IL12A | IL13 | IL17A | IFNG | PRF1 | GZMB |
|---|---|---|---|---|---|---|---|---|---|
| CASRPGPGVGNEQFF | 1086 | 0 | 0 | 0 | 2 | 0 | 174 | 19 | 0 |
| CASRPGPGVGNEQFF | | 0 | 0 | 0 | 1 | 0 | 262 | 2 | 0 |
| CASSLIMGTSGGATDTQYF | 1087 | 0 | 0 | 0 | 0 | 0 | 583 | 0 | 6 |
| CASSLIMGTSGGATDTQYF | | 0 | 0 | 0 | 0 | 0 | 407 | 47 | 1 |
| CASSLLGQLNTEAFF | 1088 | 0 | 0 | 0 | 0 | 0 | 648 | 0 | 0 |
| CASSLLGQLNTEAFF | | 0 | 0 | 0 | 0 | 0 | 293 | 0 | 0 |
| CASSQGPVGYEQYF | 1089 | 0 | 0 | 0 | 0 | 1 | 1 | 0 | 0 |
| CASSQGPVGYEQYF | | 0 | 0 | 0 | 0 | 0 | 141 | 0 | 0 |
| CAEGSNSGANVLTF | 1090 | 0 | 0 | 0 | 0 | 1 | 1 | 0 | 0 |
| CAIRDRQETQYF | 1091 | 0 | 0 | 0 | 0 | 0 | 634 | 0 | 0 |
| CAIRTGSSSYEQYF | 1092 | 0 | 0 | 0 | 0 | 0 | 0 | 0 | 0 |
| CAIRVGNGNEQFF | 1093 | 0 | 0 | 0 | 0 | 0 | 0 | 0 | 0 |
| CAISELAGVVNEQFF | 1094 | 0 | 0 | 0 | 0 | 0 | 0 | 0 | 0 |
| CAISESAMDTEAFF | 1095 | 0 | 0 | 0 | 0 | 0 | 0 | 216 | 0 |
| CAISESKGGTEAFF | 1096 | 0 | 0 | 0 | 0 | 0 | 0 | 0 | 0 |
| CAISESTVQNGYTF | 1097 | 0 | 0 | 0 | 0 | 0 | 0 | 0 | 0 |
| CAISFDRGTEAFF | 1098 | 0 | 0 | 0 | 0 | 0 | 500 | 27 | 174 |
| CAISGGLAEWHEQFF | 1099 | 0 | 0 | 0 | 0 | 0 | 0 | 0 | 0 |
| CAISLQDLPSYGYTF | 1100 | 0 | 0 | 0 | 0 | 0 | 1 | 0 | 0 |
| CAITAGQGTRNEQYF | 1101 | 0 | 32 | 0 | 0 | 0 | 0 | 0 | 0 |
| CASAPGRGVDTGELFF | 1102 | 0 | 0 | 0 | 0 | 0 | 0 | 0 | 0 |
| CASARDSYGYTF | 1103 | 0 | 0 | 0 | 0 | 0 | 1 | 0 | 0 |
| CASASRDPQDTIYF | 1104 | 0 | 0 | 0 | 0 | 0 | 0 | 0 | 0 |
| CASHGDDSAQYF | 1105 | 0 | 0 | 0 | 0 | 0 | 574 | 0 | 0 |
| CASISLRGGPYEQYF | 1106 | 0 | 0 | 0 | 0 | 0 | 0 | 0 | 0 |
| CASKQGAIDTQYF | 1107 | 0 | 0 | 0 | 0 | 0 | 268 | 0 | 0 |
| CASKVGAMGEKLFF | 1108 | 0 | 0 | 0 | 0 | 0 | 0 | 0 | 0 |
| CASRAAGTDTQYF | 1109 | 0 | 0 | 0 | 0 | 0 | 0 | 0 | 0 |
| CASREGGSSGNTIYF | 1110 | 0 | 0 | 0 | 0 | 0 | 0 | 0 | 0 |
| CASREQGPTQTGELFF | 1111 | 0 | 0 | 0 | 0 | 0 | 422 | 0 | 0 |
| CASREWTSGGNEQFF | 1112 | 0 | 0 | 0 | 0 | 0 | 0 | 0 | 0 |
| CASRGGGTSPLHF | 1113 | 0 | 0 | 0 | 0 | 0 | 739 | 0 | 0 |
| CASRKDRDTEAFF | 1114 | 0 | 0 | 0 | 0 | 0 | 0 | 0 | 0 |

Figure 22B

| TCRB | SEQ ID NO: | IL2 | IL10 | IL12A | IL13 | IL17A | IFNG | PRF1 | GZMB |
|---|---|---|---|---|---|---|---|---|---|
| CASRKGTQGARSGNTIYF | 1115 | 0 | 0 | 0 | 0 | 0 | 0 | 0 | 0 |
| CASRMGSQETQYF | 1116 | 0 | 0 | 0 | 0 | 0 | 0 | 0 | 0 |
| CASRNQGGFGTEAFF | 1117 | 0 | 0 | 0 | 0 | 0 | 1 | 0 | 0 |
| CASRPGTGRDQPQHF | 1118 | 0 | 0 | 0 | 0 | 0 | 162 | 15 | 0 |
| CASRPREENTEAFF | 1119 | 0 | 0 | 0 | 0 | 0 | 0 | 0 | 0 |
| CASRQQTGTADTQYF | 1120 | 0 | 0 | 0 | 0 | 0 | 5 | 0 | 1 |
| CASRRAGGRYEQYF | 1121 | 0 | 0 | 0 | 0 | 0 | 2 | 0 | 0 |
| CASRRGLAGSDTQYF | 1122 | 0 | 0 | 0 | 0 | 0 | 231 | 0 | 0 |
| CASRRQGGNSPLHF | 1123 | 0 | 0 | 0 | 0 | 0 | 419 | 0 | 0 |
| CASRSTGAGYGNTIYF | 1124 | 0 | 0 | 0 | 0 | 0 | 1 | 0 | 0 |
| CASSAAGSSGELFF | 1125 | 0 | 0 | 0 | 0 | 0 | 0 | 0 | 0 |
| CASSAGTGEETQYF | 1126 | 0 | 0 | 0 | 0 | 0 | 294 | 0 | 0 |
| CASSAIEGTSGELFF | 1127 | 0 | 0 | 0 | 0 | 1 | 0 | 0 | 0 |
| CASSAPGANEKLFF | 1128 | 0 | 0 | 0 | 0 | 0 | 688 | 0 | 0 |
| CASSAREQFF | 1129 | 0 | 0 | 0 | 0 | 0 | 0 | 0 | 0 |
| CASSARQDPGLSFF | 1130 | 0 | 0 | 0 | 0 | 217 | 540 | 0 | 0 |
| CASSATSGGGGRETQYF | 1131 | 0 | 0 | 0 | 0 | 0 | 280 | 0 | 0 |
| CASSAYVLGTEAFF | 1132 | 0 | 0 | 0 | 0 | 0 | 0 | 0 | 0 |
| CASSDAGGRDYGYTF | 1133 | 0 | 0 | 0 | 0 | 0 | 0 | 0 | 0 |
| CASSDGAQETQYF | 1134 | 0 | 0 | 0 | 0 | 0 | 228 | 0 | 0 |
| CASSDHERDGREQYF | 1135 | 0 | 0 | 0 | 0 | 0 | 0 | 0 | 0 |
| CASSDPGTGNYGYTF | 1136 | 0 | 0 | 0 | 0 | 0 | 0 | 0 | 0 |
| CASSDRGDSTEAFF | 1137 | 0 | 0 | 0 | 0 | 0 | 0 | 243 | 0 |
| CASSDWGGRNDEQFF | 1138 | 0 | 0 | 0 | 0 | 0 | 256 | 0 | 0 |
| CASSEAGRRTEAFF | 1139 | 0 | 0 | 0 | 0 | 500 | 0 | 0 | 0 |
| CASSEGEVTDTQYF | 1140 | 0 | 0 | 0 | 0 | 0 | 0 | 0 | 0 |
| CASSEGGQNNQPQHF | 1141 | 15 | 0 | 0 | 0 | 0 | 0 | 0 | 0 |
| CASSEGQSNQPQHF | 1142 | 1 | 0 | 0 | 0 | 0 | 0 | 0 | 0 |
| CASSEGSPYEQYF | 1143 | 0 | 0 | 0 | 0 | 0 | 228 | 39 | 0 |
| CASSEQRGGQATFYGYTF | 1144 | 0 | 0 | 0 | 0 | 0 | 0 | 0 | 0 |
| CASSESGGATYNEQFF | 1145 | 0 | 0 | 0 | 0 | 0 | 295 | 0 | 0 |
| CASSETAGGMGEQYF | 1146 | 0 | 0 | 0 | 0 | 0 | 0 | 0 | 0 |
| CASSEVGQQGYEQYF | 1147 | 0 | 0 | 0 | 1 | 0 | 304 | 0 | 0 |
| CASSEYGGRTEAFF | 1148 | 0 | 0 | 0 | 0 | 0 | 0 | 0 | 0 |
| CASSFEGTQYF | 1149 | 0 | 0 | 0 | 0 | 0 | 235 | 0 | 0 |
| CASSFERLEYNEQFF | 1150 | 0 | 0 | 0 | 0 | 0 | 197 | 66 | 0 |

Figure 22C

| TCRB | SEQ ID NO: | IL2 | IL10 | IL12A | IL13 | IL17A | IFNG | PRF1 | GZMB |
|---|---|---|---|---|---|---|---|---|---|
| CASSFFGGNEKLFF | 1151 | 0 | 0 | 0 | 0 | 0 | 0 | 0 | 0 |
| CASSFGLGEQFF | 1152 | 0 | 0 | 0 | 0 | 0 | 224 | 0 | 0 |
| CASSFMVAATDTQYF | 1153 | 0 | 0 | 0 | 0 | 0 | 205 | 13 | 0 |
| CASSFQAGANVLTF | 1154 | 0 | 0 | 0 | 0 | 0 | 0 | 0 | 0 |
| CASSFRGSNTGELFF | 1155 | 0 | 0 | 0 | 0 | 0 | 246 | 0 | 0 |
| CASSFRYTGELFF | 1156 | 0 | 90 | 0 | 0 | 0 | 0 | 0 | 0 |
| CASSFSGTSPYEQYF | 1157 | 0 | 0 | 0 | 0 | 0 | 1 | 0 | 0 |
| CASSFSSGANVLTF | 1158 | 0 | 0 | 0 | 0 | 0 | 0 | 0 | 0 |
| CASSFTGDPPLGTEAFF | 1159 | 0 | 0 | 0 | 0 | 0 | 324 | 199 | 0 |
| CASSGGGTEAFF | 1160 | 0 | 0 | 0 | 0 | 0 | 478 | 0 | 0 |
| CASSGPNYNSPLHF | 1161 | 0 | 0 | 0 | 0 | 0 | 0 | 0 | 0 |
| CASSGQSIYEQYF | 1162 | 0 | 75 | 0 | 0 | 0 | 0 | 0 | 0 |
| CASSGRENYGYTF | 1163 | 0 | 0 | 0 | 0 | 0 | 0 | 0 | 0 |
| CASSGTGGAADQPQHF | 1164 | 0 | 0 | 0 | 0 | 0 | 451 | 0 | 0 |
| CASSGTGGGPQHF | 1165 | 0 | 0 | 0 | 0 | 0 | 347 | 0 | 0 |
| CASSHGQGYADTQYF | 1166 | 0 | 0 | 0 | 0 | 0 | 0 | 0 | 0 |
| CASSIDRMAGSSYNEQFF | 1167 | 0 | 0 | 0 | 0 | 0 | 354 | 0 | 0 |
| CASSIQGGSVQETQYF | 1168 | 0 | 0 | 0 | 0 | 0 | 0 | 0 | 0 |
| CASSIREDTEAFF | 1169 | 0 | 0 | 0 | 0 | 0 | 0 | 0 | 0 |
| CASSISASGGSYNEQFF | 1170 | 0 | 0 | 0 | 0 | 0 | 0 | 0 | 0 |
| CASSKIRTGGRQAVNTDTQYF | 1171 | 0 | 0 | 0 | 0 | 0 | 1 | 0 | 0 |
| CASSKRAIEQYF | 1172 | 0 | 0 | 0 | 0 | 0 | 386 | 0 | 0 |
| CASSLAGGGSAYEQYF | 1173 | 0 | 0 | 0 | 0 | 0 | 0 | 0 | 0 |
| CASSLAGTGYEQYF | 1174 | 9 | 0 | 0 | 0 | 0 | 0 | 0 | 0 |
| CASSLAPQDQAFF | 1175 | 0 | 0 | 0 | 0 | 0 | 0 | 0 | 0 |
| CASSLARQGDRNYGYTF | 1176 | 0 | 0 | 0 | 0 | 0 | 0 | 0 | 0 |
| CASSLASATHTGELFF | 1177 | 0 | 0 | 0 | 0 | 0 | 361 | 0 | 0 |
| CASSLDGAGVSLNEQFF | 1178 | 0 | 0 | 0 | 0 | 0 | 0 | 0 | 0 |
| CASSLDGARDTGELFF | 1179 | 0 | 0 | 0 | 0 | 0 | 306 | 0 | 0 |
| CASSLDGGAGNTIYF | 1180 | 2 | 0 | 0 | 0 | 0 | 0 | 0 | 0 |
| CASSLDGLAGTDTQYF | 1181 | 0 | 0 | 0 | 0 | 0 | 0 | 0 | 0 |
| CASSLDWRQESETQYF | 1182 | 0 | 0 | 0 | 0 | 0 | 723 | 0 | 0 |
| CASSLEAGDLYEQYF | 1183 | 0 | 0 | 0 | 0 | 0 | 428 | 0 | 0 |
| CASSLEGAGYTGELFF | 1184 | 0 | 0 | 0 | 0 | 0 | 280 | 0 | 0 |
| CASSLEGQAVTGELFF | 1185 | 0 | 0 | 0 | 0 | 0 | 0 | 0 | 0 |
| CASSLEGVGQNYGYTF | 1186 | 0 | 0 | 0 | 0 | 85 | 248 | 0 | 0 |

Figure 22D

| TCRB | SEQ ID NO: | IL2 | IL10 | IL12A | IL13 | IL17A | IFNG | PRF1 | GZMB |
|---|---|---|---|---|---|---|---|---|---|
| CASSLERGLAGVVGEQFF | 1187 | 0 | 0 | 0 | 0 | 0 | 0 | 0 | 0 |
| CASSLESSGSLGEQYF | 1188 | 0 | 0 | 0 | 0 | 0 | 0 | 0 | 0 |
| CASSLETRNTEAFF | 1189 | 0 | 0 | 0 | 0 | 0 | 159 | 62 | 0 |
| CASSLFLENTEAFF | 1190 | 0 | 0 | 0 | 0 | 0 | 254 | 1 | 0 |
| CASSLFLGTGNTIYF | 1191 | 0 | 0 | 0 | 0 | 0 | 0 | 0 | 0 |
| CASSLGAGALGETQYF | 1192 | 0 | 0 | 0 | 1 | 0 | 0 | 0 | 0 |
| CASSLGAGGATDTQYF | 1193 | 0 | 0 | 0 | 0 | 0 | 1 | 0 | 0 |
| CASSLGGDRGAEKLFF | 1194 | 0 | 0 | 0 | 0 | 0 | 0 | 1 | 0 |
| CASSLGGGTEAFF | 1195 | 0 | 0 | 0 | 0 | 0 | 0 | 0 | 0 |
| CASSLGSFSYEQYF | 1196 | 0 | 0 | 0 | 0 | 0 | 0 | 0 | 411 |
| CASSLGSGASNQPQHF | 1197 | 0 | 0 | 0 | 0 | 0 | 0 | 0 | 0 |
| CASSLGTFNYGYTF | 1198 | 57 | 0 | 0 | 0 | 0 | 0 | 0 | 0 |
| CASSLGTSQETQYF | 1199 | 0 | 57 | 0 | 0 | 0 | 204 | 151 | 15 |
| CASSLGVAPTDTQYF | 1200 | 0 | 0 | 0 | 0 | 0 | 520 | 0 | 0 |
| CASSLLANEQYF | 1201 | 0 | 7 | 0 | 0 | 0 | 0 | 0 | 0 |
| CASSLLVGQTNIVSGANVLTF | 1202 | 0 | 0 | 0 | 0 | 0 | 0 | 0 | 0 |
| CASSLPAGTGTGELFF | 1203 | 0 | 0 | 0 | 0 | 0 | 1 | 0 | 0 |
| CASSLQGSSQPQHF | 1204 | 0 | 0 | 0 | 0 | 0 | 652 | 0 | 0 |
| CASSLRAGGSTDTQYF | 1205 | 0 | 0 | 0 | 0 | 0 | 0 | 1 | 0 |
| CASSLRDTGFHF | 1206 | 0 | 0 | 0 | 0 | 0 | 0 | 0 | 0 |
| CASSLSALGLAGGNTGELFF | 1207 | 0 | 0 | 0 | 0 | 0 | 0 | 0 | 0 |
| CASSLSGQGTGEQYF | 1208 | 0 | 0 | 0 | 0 | 0 | 1 | 0 | 0 |
| CASSLSRIGGGYTF | 1209 | 0 | 0 | 0 | 0 | 1 | 0 | 0 | 0 |
| CASSLSTDTQYF | 1210 | 0 | 0 | 0 | 0 | 0 | 394 | 0 | 0 |
| CASSLTDRSPQYF | 1211 | 0 | 0 | 0 | 0 | 0 | 0 | 0 | 0 |
| CASSLTGLTEAFF | 1212 | 0 | 0 | 0 | 0 | 0 | 3 | 0 | 0 |
| CASSLTGTGIGYTF | 1213 | 0 | 0 | 0 | 0 | 0 | 0 | 0 | 0 |
| CASSLTQGITDTQYF | 1214 | 0 | 0 | 0 | 0 | 0 | 480 | 0 | 0 |
| CASSLVGMNTEAFF | 1215 | 0 | 0 | 0 | 0 | 0 | 288 | 0 | 0 |
| CASSLVLGETQYF | 1216 | 0 | 0 | 0 | 0 | 0 | 0 | 0 | 0 |
| CASSLVPTYTDTQYF | 1217 | 0 | 0 | 0 | 0 | 0 | 444 | 1 | 0 |
| CASSLVSDQSNEQFF | 1218 | 0 | 0 | 0 | 0 | 0 | 316 | 0 | 0 |
| CASSLVYSGDRTDTQYF | 1219 | 0 | 0 | 0 | 0 | 0 | 772 | 0 | 0 |
| CASSMDRGSGELFF | 1220 | 0 | 0 | 0 | 0 | 0 | 306 | 0 | 0 |
| CASSNRGLGSGANVLTF | 1221 | 0 | 0 | 0 | 0 | 0 | 0 | 0 | 0 |
| CASSPESGRYNEQFF | 1222 | 0 | 116 | 0 | 0 | 0 | 331 | 0 | 0 |

Figure 22E

| TCRB | SEQ ID NO: | IL2 | IL10 | IL12A | IL13 | IL17A | IFNG | PRF1 | GZMB |
|---|---|---|---|---|---|---|---|---|---|
| CASSPFGRLWATNEKLFF | 1223 | 0 | 0 | 0 | 0 | 0 | 134 | 0 | 0 |
| CASSPGAGEQYF | 1224 | 0 | 0 | 0 | 0 | 0 | 244 | 0 | 0 |
| CASSPGAGLNTGELFF | 1225 | 0 | 0 | 0 | 0 | 0 | 229 | 0 | 0 |
| CASSPGGTGGAYGYTF | 1226 | 0 | 0 | 0 | 0 | 0 | 0 | 0 | 0 |
| CASSPGTRAFF | 1227 | 0 | 0 | 0 | 0 | 0 | 0 | 0 | 0 |
| CASSPLLASDEQFF | 1228 | 0 | 0 | 0 | 0 | 0 | 0 | 0 | 0 |
| CASSPMAGPSFYEQYF | 1229 | 0 | 0 | 0 | 0 | 0 | 0 | 0 | 0 |
| CASSPPGGPYEQYF | 1230 | 0 | 0 | 0 | 0 | 0 | 0 | 0 | 0 |
| CASSPQGLGNNSPLHF | 1231 | 0 | 0 | 0 | 0 | 522 | 3 | 0 | 0 |
| CASSPQGVSFMSNQPQHF | 1232 | 0 | 0 | 0 | 0 | 0 | 0 | 0 | 0 |
| CASSPRLAGSYEQYF | 1233 | 0 | 145 | 0 | 0 | 1 | 1 | 0 | 0 |
| CASSPRQYEQFF | 1234 | 0 | 0 | 0 | 0 | 0 | 351 | 0 | 0 |
| CASSPSDRGGKLFF | 1235 | 0 | 0 | 0 | 0 | 0 | 446 | 0 | 0 |
| CASSPSGGRVSPLHF | 1236 | 0 | 0 | 0 | 0 | 0 | 0 | 0 | 0 |
| CASSPSGGVNEQFF | 1237 | 0 | 0 | 0 | 0 | 0 | 3 | 0 | 0 |
| CASSPSRVNTEAFF | 1238 | 0 | 0 | 0 | 0 | 0 | 0 | 0 | 0 |
| CASSPTAAASYNEQFF | 1239 | 0 | 0 | 0 | 51 | 0 | 245 | 0 | 0 |
| CASSPVDEGTGELFF | 1240 | 0 | 0 | 0 | 0 | 0 | 0 | 0 | 0 |
| CASSPVSGGGDTQYF | 1241 | 0 | 0 | 0 | 0 | 0 | 286 | 0 | 0 |
| CASSPWGIPEAFF | 1242 | 0 | 0 | 0 | 0 | 0 | 363 | 0 | 0 |
| CASSQAARAETQYF | 1243 | 0 | 0 | 0 | 0 | 0 | 2 | 0 | 0 |
| CASSQDPEGYTF | 1244 | 0 | 0 | 0 | 0 | 0 | 1 | 0 | 0 |
| CASSQDRGAANYGYTF | 1245 | 0 | 0 | 0 | 0 | 0 | 514 | 0 | 0 |
| CASSQDRGVEQYF | 1246 | 0 | 0 | 0 | 0 | 0 | 354 | 0 | 0 |
| CASSQDSIQGSGYTF | 1247 | 0 | 0 | 0 | 0 | 0 | 715 | 0 | 0 |
| CASSQDVSGTGGSYEQYF | 1248 | 0 | 0 | 0 | 0 | 0 | 229 | 0 | 0 |
| CASSQEEGEKLFF | 1249 | 0 | 0 | 0 | 0 | 0 | 0 | 0 | 0 |
| CASSQEGQSAAFF | 1250 | 0 | 0 | 0 | 0 | 0 | 0 | 0 | 0 |
| CASSQETSGRAYEQYF | 1251 | 0 | 0 | 0 | 0 | 0 | 211 | 0 | 0 |
| CASSQFGEGPTGGQFF | 1252 | 0 | 0 | 0 | 0 | 0 | 0 | 0 | 0 |
| CASSQGGTGELFF | 1253 | 0 | 0 | 0 | 0 | 0 | 0 | 0 | 0 |
| CASSQGPGSNQPQHF | 1254 | 0 | 0 | 0 | 0 | 0 | 0 | 0 | 0 |
| CASSQGRNTGELFF | 1255 | 0 | 0 | 0 | 0 | 0 | 0 | 0 | 0 |
| CASSQGTGGGYTF | 1256 | 0 | 0 | 0 | 1 | 0 | 267 | 0 | 0 |
| CASSQHQGAGNTIYF | 1257 | 0 | 0 | 0 | 0 | 0 | 405 | 0 | 0 |
| CASSQPTGGAYNEQFF | 1258 | 0 | 0 | 0 | 0 | 0 | 0 | 0 | 0 |

Figure 22F

| TCRB | SEQ ID NO: | IL2 | IL10 | IL12A | IL13 | IL17A | IFNG | PRF1 | GZMB |
|---|---|---|---|---|---|---|---|---|---|
| CASSQRGDDTGELFF | 1259 | 0 | 0 | 0 | 0 | 1 | 0 | 0 | 0 |
| CASSQVPGEQREQYF | 1260 | 0 | 0 | 0 | 0 | 0 | 0 | 0 | 0 |
| CASSRAEASSGANVLTF | 1261 | 0 | 0 | 0 | 0 | 0 | 0 | 0 | 0 |
| CASSRALGDNYGYTF | 1262 | 0 | 0 | 0 | 329 | 1 | 332 | 15 | 0 |
| CASSRDLGATNEKLFF | 1263 | 1 | 0 | 0 | 0 | 0 | 0 | 0 | 0 |
| CASSRGEGKAEAFF | 1264 | 0 | 0 | 0 | 0 | 0 | 0 | 0 | 0 |
| CASSRGSYNEQFF | 1265 | 0 | 0 | 0 | 0 | 0 | 240 | 0 | 0 |
| CASSRGTDQPQHF | 1266 | 0 | 0 | 0 | 0 | 1 | 2 | 0 | 0 |
| CASSRPFGELFF | 1267 | 0 | 0 | 0 | 0 | 0 | 0 | 0 | 0 |
| CASSRQGRGEKLFF | 1268 | 0 | 0 | 0 | 0 | 0 | 0 | 0 | 0 |
| CASSRRGLNYEQYF | 1269 | 0 | 0 | 0 | 0 | 0 | 380 | 0 | 0 |
| CASSSAQVGANVLTF | 1270 | 0 | 0 | 0 | 0 | 0 | 670 | 0 | 0 |
| CASSSDRANTEAFF | 1271 | 0 | 0 | 0 | 0 | 0 | 1 | 0 | 0 |
| CASSSGGGTEAFF | 1272 | 0 | 0 | 0 | 0 | 0 | 0 | 0 | 0 |
| CASSSGQGARTEAFF | 1273 | 0 | 0 | 0 | 1 | 0 | 0 | 0 | 0 |
| CASSSGRGFDTQYF | 1274 | 0 | 0 | 0 | 0 | 239 | 0 | 0 | 0 |
| CASSSGSETQYF | 1275 | 0 | 0 | 0 | 0 | 0 | 0 | 0 | 0 |
| CASSSKRAGGYTF | 1276 | 0 | 0 | 0 | 0 | 0 | 444 | 0 | 0 |
| CASSSLERGGRRGEQYF | 1277 | 0 | 190 | 0 | 0 | 0 | 0 | 0 | 0 |
| CASSSNQWGNEKLFF | 1278 | 1 | 0 | 0 | 0 | 0 | 254 | 0 | 0 |
| CASSSPSGNTIYF | 1279 | 0 | 0 | 0 | 0 | 0 | 281 | 0 | 0 |
| CASSSRTGASETQYF | 1280 | 0 | 246 | 0 | 0 | 0 | 0 | 0 | 0 |
| CASSSRVRQPQHF | 1281 | 0 | 0 | 0 | 0 | 0 | 1 | 0 | 0 |
| CASSSTGGNEQFF | 1282 | 0 | 0 | 0 | 0 | 0 | 0 | 0 | 0 |
| CASSSTQSTGLVEAFF | 1283 | 0 | 0 | 0 | 0 | 0 | 458 | 0 | 0 |
| CASSTGGHGTQYF | 1284 | 0 | 1 | 0 | 0 | 0 | 0 | 0 | 0 |
| CASSTLTGAGELFF | 1285 | 0 | 0 | 0 | 0 | 0 | 0 | 0 | 0 |
| CASSTLTGGRNEQFF | 1286 | 0 | 0 | 0 | 0 | 0 | 0 | 0 | 0 |
| CASSTQGNIQYF | 1287 | 0 | 0 | 0 | 0 | 0 | 0 | 0 | 0 |
| CASSTRAQSYNEQFF | 1288 | 0 | 0 | 0 | 0 | 0 | 0 | 0 | 1 |
| CASSTRTDNRGYTF | 1289 | 0 | 136 | 0 | 0 | 0 | 1 | 0 | 0 |
| CASSTRTGGKETQYF | 1290 | 0 | 0 | 0 | 244 | 0 | 1 | 96 | 0 |
| CASSTTLGTGSFQETQYF | 1291 | 35 | 0 | 0 | 0 | 0 | 0 | 0 | 0 |
| CASSTTSGGSYEQYF | 1292 | 0 | 0 | 0 | 0 | 0 | 0 | 0 | 0 |
| CASSVGDLWGPQETQYF | 1293 | 0 | 0 | 0 | 0 | 0 | 300 | 0 | 0 |
| CASSVGLAGSNEQFF | 1294 | 0 | 0 | 0 | 0 | 0 | 670 | 0 | 0 |

Figure 22G

| TCRB | SEQ ID NO: | IL2 | IL10 | IL12A | IL13 | IL17A | IFNG | PRF1 | GZMB |
|---|---|---|---|---|---|---|---|---|---|
| CASSVGPEYEQYF | 1295 | 0 | 0 | 0 | 0 | 0 | 0 | 0 | 0 |
| CASSVGRGGSNEQFF | 1296 | 0 | 0 | 0 | 0 | 0 | 0 | 0 | 0 |
| CASSVKIDSEAFF | 1297 | 0 | 0 | 0 | 0 | 0 | 570 | 0 | 0 |
| CASSVLAGGHNEQFF | 1298 | 0 | 0 | 0 | 0 | 0 | 0 | 0 | 0 |
| CASSVRTSVGETQYF | 1299 | 0 | 0 | 0 | 0 | 0 | 0 | 0 | 0 |
| CASSVTGDSNSPLHF | 1300 | 0 | 0 | 0 | 0 | 0 | 290 | 0 | 0 |
| CASSVVGLAATDTQYF | 1301 | 0 | 0 | 0 | 0 | 0 | 171 | 0 | 0 |
| CASSWSGDTEAFF | 1302 | 0 | 0 | 0 | 0 | 0 | 0 | 0 | 0 |
| CASSYGTSGRVIQETQYF | 1303 | 0 | 0 | 0 | 0 | 0 | 302 | 0 | 0 |
| CASSYGTSGSLGYNEQFF | 1304 | 0 | 0 | 0 | 0 | 0 | 201 | 2 | 0 |
| CASSYKPGTSGGGTPDTQYF | 1305 | 0 | 0 | 0 | 0 | 0 | 293 | 0 | 0 |
| CASSYNKVAGGNTGELFF | 1306 | 0 | 0 | 0 | 0 | 0 | 2 | 0 | 0 |
| CASSYNSPLHF | 1307 | 0 | 0 | 0 | 0 | 0 | 0 | 0 | 0 |
| CASSYREYLYNEQFF | 1308 | 0 | 0 | 0 | 0 | 0 | 0 | 0 | 0 |
| CASSYSGGTQETQYF | 1309 | 0 | 0 | 0 | 0 | 0 | 268 | 5 | 0 |
| CASSYTGGAGYTF | 1310 | 0 | 0 | 0 | 436 | 0 | 0 | 0 | 0 |
| CASTGGSTDTQYF | 1311 | 0 | 0 | 0 | 0 | 0 | 2 | 0 | 0 |
| CASTLQVSETQYF | 1312 | 0 | 0 | 0 | 0 | 0 | 0 | 0 | 0 |
| CASTPQEYQETQYF | 1313 | 0 | 0 | 0 | 0 | 0 | 1 | 0 | 0 |
| CASTQGPNEQFF | 1314 | 0 | 0 | 0 | 0 | 0 | 304 | 0 | 0 |
| CASTWDSNQPQHF | 1315 | 0 | 0 | 0 | 0 | 0 | 0 | 0 | 0 |
| CATGTGTVGETQYF | 1316 | 0 | 0 | 0 | 0 | 0 | 192 | 0 | 0 |
| CATQRDLNSPLHF | 1317 | 0 | 0 | 0 | 0 | 0 | 365 | 1 | 0 |
| CATSAPGLSGTSGYNEQFF | 1318 | 0 | 0 | 0 | 0 | 0 | 214 | 3 | 0 |
| CATSASAFGGYTF | 1319 | 0 | 0 | 0 | 0 | 0 | 275 | 0 | 0 |
| CATSDLSQPGRMGTDTQYF | 1320 | 0 | 0 | 0 | 0 | 0 | 0 | 0 | 0 |
| CATSDRAVETQYF | 1321 | 0 | 0 | 0 | 0 | 0 | 0 | 0 | 0 |
| CATSGTGDEQYF | 1322 | 0 | 0 | 0 | 0 | 0 | 0 | 0 | 0 |
| CATSRDYFSGATDTQYF | 1323 | 0 | 0 | 0 | 0 | 1 | 242 | 0 | 0 |
| CATSREASGGGGQETQYF | 1324 | 0 | 0 | 0 | 0 | 0 | 572 | 0 | 0 |
| CATSRLNNEQFF | 1325 | 0 | 0 | 0 | 0 | 0 | 0 | 0 | 0 |
| CATSSDDLGSSYNEQFF | 1326 | 0 | 0 | 0 | 0 | 0 | 317 | 0 | 0 |
| CAWAPVEGQPQHF | 1327 | 0 | 0 | 0 | 0 | 0 | 364 | 42 | 0 |
| CAWDNKGLAGGRQYF | 1328 | 0 | 0 | 0 | 0 | 0 | 0 | 0 | 0 |
| CAWETAGIGYGYTF | 1329 | 0 | 0 | 0 | 0 | 0 | 1 | 0 | 0 |
| CAWKGDREGGYTF | 1330 | 0 | 0 | 0 | 0 | 0 | 0 | 0 | 0 |

Figure 22H

| TCRB | SEQ ID NO: | IL2 | IL10 | IL12A | IL13 | IL17A | IFNG | PRF1 | GZMB |
|---|---|---|---|---|---|---|---|---|---|
| CAWRGTSGGAQYF | 1331 | 0 | 0 | 0 | 0 | 0 | 0 | 0 | 0 |
| CAWRQDLHYGYTF | 1332 | 0 | 0 | 0 | 0 | 0 | 852 | 0 | 27 |
| CAWSGGENQPQHF | 1333 | 0 | 0 | 0 | 0 | 0 | 0 | 258 | 0 |
| CAWSGGPTNSPLHF | 1334 | 0 | 0 | 0 | 0 | 0 | 1 | 0 | 0 |
| CAWSISGTENIQYF | 1335 | 0 | 0 | 0 | 0 | 0 | 0 | 0 | 0 |
| CAWSMEAEGQPQHF | 1336 | 0 | 0 | 0 | 0 | 0 | 320 | 0 | 0 |
| CAWSPLAGVSYEQYF | 1337 | 0 | 0 | 0 | 0 | 0 | 211 | 0 | 0 |
| CAWSRLGASGNTIYF | 1338 | 0 | 0 | 0 | 0 | 61 | 311 | 0 | 0 |
| CAWSVFTGGFGTNEKLFF | 1339 | 0 | 0 | 0 | 0 | 0 | 0 | 0 | 0 |
| CAWSVIQGGTEQYF | 1340 | 0 | 0 | 0 | 0 | 0 | 0 | 0 | 0 |
| CAWTGGTGDNEQFF | 1341 | 0 | 0 | 0 | 0 | 247 | 0 | 0 | 0 |
| CSADSSAAGGQDTQYF | 1342 | 0 | 0 | 0 | 0 | 0 | 0 | 192 | 0 |
| CSAGGQGRGNTEAFF | 1343 | 0 | 0 | 0 | 0 | 0 | 0 | 0 | 0 |
| CSAGLTGGREQYF | 1344 | 0 | 0 | 0 | 0 | 0 | 374 | 1 | 0 |
| CSAGSLGGEKLFF | 1345 | 0 | 0 | 0 | 0 | 0 | 352 | 0 | 0 |
| CSAKDSSTNEKLFF | 1346 | 0 | 0 | 0 | 0 | 0 | 0 | 0 | 0 |
| CSAKTGLYYGYTF | 1347 | 0 | 0 | 0 | 0 | 0 | 328 | 0 | 0 |
| CSALGGISTDTQYF | 1348 | 0 | 0 | 0 | 0 | 0 | 4 | 0 | 0 |
| CSALGPNQETQYF | 1349 | 0 | 0 | 0 | 0 | 0 | 0 | 0 | 0 |
| CSALLGARGYTF | 1350 | 0 | 0 | 0 | 0 | 0 | 0 | 0 | 0 |
| CSALRQGAYNEQFF | 1351 | 0 | 0 | 0 | 0 | 0 | 459 | 0 | 0 |
| CSANPGFLTDTQYF | 1352 | 0 | 0 | 0 | 0 | 0 | 0 | 0 | 0 |
| CSANSGGSEKLFF | 1353 | 0 | 0 | 0 | 0 | 0 | 0 | 0 | 0 |
| CSAPTPGTGGYGYTF | 1354 | 0 | 0 | 0 | 0 | 0 | 0 | 0 | 0 |
| CSARALALVQTQYF | 1355 | 0 | 0 | 0 | 0 | 0 | 1 | 0 | 0 |
| CSARDPRGRVITEAFF | 1356 | 0 | 0 | 0 | 0 | 0 | 0 | 0 | 0 |
| CSARDRDRAVDTGELFF | 1357 | 0 | 0 | 0 | 0 | 0 | 605 | 0 | 0 |
| CSARDRDRGTDTQYF | 1358 | 0 | 157 | 0 | 0 | 0 | 524 | 0 | 0 |
| CSARDRLRLGADTQYF | 1359 | 0 | 0 | 0 | 0 | 0 | 226 | 0 | 0 |
| CSARGGQGQYGYTF | 1360 | 0 | 0 | 0 | 0 | 0 | 0 | 0 | 0 |
| CSARGIGNTIYF | 1361 | 0 | 0 | 0 | 0 | 0 | 0 | 0 | 0 |
| CSARGSGPDTEAFF | 1362 | 0 | 0 | 0 | 0 | 0 | 0 | 0 | 0 |
| CSARGSRLGEGVSNQPQHF | 1363 | 0 | 0 | 0 | 0 | 0 | 556 | 0 | 0 |
| CSARSPGLAGGLNEQFF | 1364 | 0 | 0 | 0 | 0 | 0 | 0 | 0 | 0 |
| CSARSPTSGRTNEQFF | 1365 | 13 | 0 | 0 | 0 | 0 | 0 | 0 | 0 |
| CSASGAYNEQFF | 1366 | 0 | 0 | 0 | 0 | 0 | 0 | 0 | 0 |

Figure 22I

| TCRB | SEQ ID NO: | IL2 | IL10 | IL12A | IL13 | IL17A | IFNG | PRF1 | GZMB |
|---|---|---|---|---|---|---|---|---|---|
| CSASGWGAVF | 1367 | 0 | 0 | 0 | 0 | 0 | 1 | 0 | 0 |
| CSASLGVGNQPQHF | 1368 | 0 | 0 | 0 | 0 | 0 | 1 | 0 | 0 |
| CSASPNYGYTF | 1369 | 0 | 0 | 0 | 0 | 0 | 245 | 75 | 0 |
| CSASPQIAGGYEQYF | 1370 | 0 | 0 | 0 | 0 | 0 | 144 | 0 | 0 |
| CSASQAGGSSYEQYF | 1371 | 0 | 0 | 0 | 0 | 0 | 0 | 0 | 0 |
| CSASRGNTEAFF | 1372 | 0 | 0 | 0 | 1 | 535 | 0 | 0 | 0 |
| CSATLGTADTQYF | 1373 | 0 | 0 | 0 | 0 | 0 | 0 | 0 | 0 |
| CSATNDRAYGYTF | 1374 | 0 | 0 | 0 | 0 | 0 | 223 | 0 | 0 |
| CSAYSGNPGQPQHF | 1375 | 8 | 0 | 0 | 0 | 0 | 0 | 0 | 0 |
| CSGTGEETQYF | 1376 | 0 | 0 | 0 | 0 | 0 | 0 | 0 | 0 |
| CSSIRGGPGETQYF | 1377 | 0 | 0 | 0 | 0 | 0 | 1 | 0 | 0 |
| CSVAGTGEKLFF | 1378 | 0 | 0 | 0 | 0 | 0 | 0 | 0 | 0 |
| CSVDGALAGGTYEQYF | 1379 | 0 | 204 | 0 | 0 | 0 | 0 | 0 | 0 |
| CSVEEGAGGTDTQYF | 1380 | 0 | 0 | 0 | 0 | 0 | 0 | 0 | 0 |
| CSVEGGGYGYTF | 1381 | 0 | 0 | 0 | 0 | 0 | 0 | 0 | 0 |
| CSVEIPGLSFYEQYF | 1382 | 0 | 0 | 0 | 0 | 0 | 0 | 0 | 0 |
| CSVERERGRTEAFF | 1383 | 0 | 0 | 0 | 0 | 0 | 0 | 0 | 0 |
| CSVERSSGSFSYGYTF | 1384 | 0 | 0 | 0 | 0 | 0 | 0 | 0 | 0 |
| CSVGQGVVYGYTF | 1385 | 0 | 0 | 0 | 0 | 0 | 221 | 71 | 0 |
| CSVGQTGNYEQYF | 1386 | 0 | 0 | 0 | 229 | 0 | 503 | 0 | 0 |
| CSVGRDIQETQYF | 1387 | 0 | 6 | 0 | 0 | 0 | 3 | 1 | 0 |
| CSVIQGAGSTDTQYF | 1388 | 0 | 0 | 0 | 0 | 0 | 269 | 0 | 0 |
| CSVRTGLAKNIQYF | 1389 | 0 | 0 | 0 | 0 | 0 | 0 | 0 | 0 |
| CVTSGTVNTEAFF | 1390 | 0 | 0 | 0 | 0 | 0 | 241 | 0 | 0 |

Figure 22J

| TCRB | SEQ ID NO: | TGFB | TNFA | BCL6 | TBET | GATA 3 | RORC | FOX P3 | RUNX 1 | RUNX 3 |
|---|---|---|---|---|---|---|---|---|---|---|
| CASRPGPGVGNEQFF | 1086 | 0 | 283 | 1 | 0 | 0 | 0 | 0 | 53 | 0 |
| CASRPGPGVGNEQFF | | 0 | 298 | 0 | 112 | 0 | 0 | 0 | 294 | 0 |
| CASSLIMGTSGGATDTQYF | 1087 | 0 | 756 | 0 | 415 | 0 | 13 | 0 | 0 | 0 |
| CASSLIMGTSGGATDTQYF | | 15 | 0 | 452 | 147 | 114 | 0 | 0 | 0 | 1 |
| CASSLLGQLNTEAFF | 1088 | 0 | 677 | 0 | 17 | 0 | 0 | 0 | 8 | 0 |
| CASSLLGQLNTEAFF | | 184 | 0 | 311 | 0 | 0 | 0 | 0 | 359 | 0 |
| CASSQGPVGYEQYF | 1089 | 251 | 0 | 461 | 0 | 1 | 0 | 500 | 0 | 0 |
| CASSQGPVGYEQYF | | 2 | 144 | 0 | 126 | 0 | 0 | 0 | 174 | 0 |
| CAEGSNSGANVLTF | 1090 | 103 | 292 | 0 | 0 | 220 | 0 | 0 | 348 | 95 |
| CAIRDRQETQYF | 1091 | 1 | 0 | 1 | 0 | 485 | 0 | 0 | 0 | 0 |
| CAIRTGSSSYEQYF | 1092 | 58 | 0 | 1 | 0 | 0 | 0 | 0 | 317 | 0 |
| CAIRVGNGNEQFF | 1093 | 186 | 0 | 0 | 0 | 215 | 0 | 0 | 0 | 0 |
| CAISELAGVVNEQFF | 1094 | 427 | 0 | 0 | 0 | 290 | 1 | 447 | 0 | 0 |
| CAISESAMDTEAFF | 1095 | 50 | 318 | 0 | 0 | 1 | 0 | 0 | 1 | 0 |
| CAISESKGGTEAFF | 1096 | 0 | 851 | 1016 | 0 | 666 | 0 | 0 | 1135 | 0 |
| CAISESTVQNGYTF | 1097 | 1 | 408 | 531 | 423 | 1 | 1 | 0 | 1 | 0 |
| CAISFDRGTEAFF | 1098 | 0 | 380 | 0 | 338 | 3 | 0 | 0 | 377 | 25 |
| CAISGGLAEWHEQFF | 1099 | 350 | 3 | 538 | 0 | 0 | 1 | 0 | 0 | 0 |
| CAISLQDLPSYGYTF | 1100 | 17 | 0 | 912 | 879 | 1 | 0 | 0 | 1158 | 1 |
| CAITAGQGTRNEQYF | 1101 | 5 | 0 | 0 | 0 | 553 | 0 | 0 | 1093 | 0 |
| CASAPGRGVDTGELFF | 1102 | 236 | 1 | 0 | 0 | 0 | 0 | 0 | 290 | 0 |
| CASARDSYGYTF | 1103 | 0 | 2 | 0 | 2 | 267 | 1 | 578 | 537 | 2 |
| CASASRDPQDTIYF | 1104 | 348 | 0 | 0 | 0 | 238 | 0 | 0 | 0 | 0 |
| CASHGDDSAQYF | 1105 | 0 | 677 | 522 | 1 | 0 | 0 | 0 | 36 | 9 |
| CASISLRGGPYEQYF | 1106 | 361 | 0 | 0 | 0 | 171 | 0 | 0 | 0 | 0 |
| CASKQGAIDTQYF | 1107 | 0 | 174 | 0 | 240 | 0 | 529 | 0 | 154 | 0 |
| CASKVGAMGEKLFF | 1108 | 54 | 0 | 0 | 0 | 317 | 0 | 510 | 504 | 0 |
| CASRAAGTDTQYF | 1109 | 306 | 0 | 0 | 0 | 0 | 0 | 0 | 0 | 0 |
| CASREGGSSGNTIYF | 1110 | 60 | 0 | 0 | 0 | 0 | 0 | 0 | 227 | 235 |
| CASREQGPTQTGELFF | 1111 | 0 | 0 | 0 | 299 | 0 | 0 | 0 | 28 | 0 |
| CASREWTSGGNEQFF | 1112 | 29 | 0 | 1 | 0 | 780 | 0 | 0 | 1309 | 0 |
| CASRGGGTSPLHF | 1113 | 1 | 712 | 0 | 64 | 0 | 0 | 0 | 2 | 1 |
| CASRKDRDTEAFF | 1114 | 32 | 274 | 0 | 0 | 0 | 0 | 0 | 273 | 0 |
| CASRKGTQGARSGNTIYF | 1115 | 0 | 0 | 0 | 0 | 260 | 0 | 0 | 400 | 0 |

Figure 22K

| TCRB | SEQ ID NO: | TGFB | TNFA | BCL6 | TBET | GATA3 | RORC | FOXP3 | RUNX1 | RUNX3 |
|---|---|---|---|---|---|---|---|---|---|---|
| CASRMGSQETQYF | 1116 | 65 | 0 | 0 | 0 | 0 | 0 | 0 | 98 | 0 |
| CASRNQGGFGTEAFF | 1117 | 1 | 0 | 0 | 210 | 0 | 0 | 310 | 216 | 0 |
| CASRPGTGRDQPQHF | 1118 | 0 | 235 | 0 | 67 | 0 | 0 | 0 | 179 | 6 |
| CASRPREENTEAFF | 1119 | 0 | 0 | 0 | 0 | 266 | 0 | 386 | 363 | 0 |
| CASRQQTGTADTQYF | 1120 | 0 | 1 | 2 | 0 | 1 | 949 | 1 | 0 | 0 |
| CASRRAGGRYEQYF | 1121 | 0 | 0 | 0 | 983 | 713 | 0 | 0 | 1322 | 0 |
| CASRRGLAGSDTQYF | 1122 | 0 | 356 | 0 | 25 | 1 | 0 | 0 | 248 | 0 |
| CASRRQGGNSPLHF | 1123 | 0 | 5 | 480 | 385 | 0 | 0 | 0 | 296 | 0 |
| CASRSTGAGYGNTIYF | 1124 | 4 | 382 | 0 | 400 | 295 | 0 | 0 | 0 | 531 |
| CASSAAGSSGELFF | 1125 | 2 | 1181 | 0 | 0 | 1014 | 0 | 0 | 1 | 0 |
| CASSAGTGEETQYF | 1126 | 0 | 384 | 0 | 186 | 1 | 1 | 0 | 314 | 0 |
| CASSAIEGTSGELFF | 1127 | 0 | 0 | 0 | 1 | 0 | 0 | 0 | 365 | 0 |
| CASSAPGANEKLFF | 1128 | 0 | 621 | 0 | 0 | 0 | 0 | 0 | 0 | 0 |
| CASSAREQFF | 1129 | 130 | 308 | 1 | 273 | 0 | 0 | 0 | 0 | 0 |
| CASSARQDPGLSFF | 1130 | 0 | 501 | 138 | 7 | 9 | 0 | 2 | 394 | 0 |
| CASSATSGGGGRETQYF | 1131 | 15 | 1 | 0 | 269 | 0 | 0 | 0 | 2 | 532 |
| CASSAYVLGTEAFF | 1132 | 0 | 0 | 370 | 0 | 0 | 0 | 0 | 451 | 0 |
| CASSDAGGRDYGYTF | 1133 | 22 | 206 | 0 | 0 | 0 | 0 | 0 | 200 | 0 |
| CASSDGAQETQYF | 1134 | 0 | 292 | 72 | 168 | 28 | 0 | 0 | 155 | 0 |
| CASSDHERDGREQYF | 1135 | 182 | 336 | 0 | 0 | 216 | 0 | 0 | 0 | 0 |
| CASSDPGTGNYGYTF | 1136 | 46 | 0 | 0 | 0 | 456 | 0 | 0 | 724 | 0 |
| CASSDRGDSTEAFF | 1137 | 0 | 373 | 0 | 0 | 290 | 0 | 0 | 527 | 0 |
| CASSDWGGRNDEQFF | 1138 | 0 | 265 | 0 | 282 | 0 | 0 | 0 | 0 | 205 |
| CASSEAGRRTEAFF | 1139 | 343 | 0 | 0 | 0 | 1 | 0 | 0 | 678 | 0 |
| CASSEGEVTDTQYF | 1140 | 274 | 0 | 512 | 0 | 254 | 0 | 0 | 0 | 0 |
| CASSEGGQNNQPQHF | 1141 | 282 | 0 | 429 | 0 | 335 | 0 | 0 | 0 | 1 |
| CASSEGQSNQPQHF | 1142 | 0 | 482 | 0 | 0 | 289 | 0 | 0 | 0 | 0 |
| CASSEGSPYEQYF | 1143 | 0 | 238 | 0 | 100 | 10 | 0 | 0 | 182 | 0 |
| CASSEQRGGQATFYGYTF | 1144 | 169 | 0 | 0 | 228 | 0 | 0 | 307 | 224 | 121 |
| CASSESGGATYNEQFF | 1145 | 143 | 0 | 338 | 336 | 0 | 0 | 0 | 106 | 0 |
| CASSETAGGMGEQYF | 1146 | 349 | 0 | 0 | 0 | 258 | 0 | 0 | 0 | 0 |
| CASSEVGQQGYEQYF | 1147 | 0 | 369 | 0 | 23 | 0 | 0 | 0 | 14 | 0 |
| CASSEYGGRTEAFF | 1148 | 193 | 0 | 0 | 0 | 0 | 0 | 0 | 0 | 565 |
| CASSFEGTQYF | 1149 | 0 | 250 | 0 | 0 | 0 | 0 | 0 | 301 | 0 |
| CASSFERLEYNEQFF | 1150 | 0 | 310 | 0 | 299 | 1 | 167 | 0 | 169 | 0 |
| CASSFFGGNEKLFF | 1151 | 0 | 188 | 0 | 0 | 206 | 0 | 0 | 1 | 0 |

Figure 22L

| TCRB | SEQ ID NO: | TGFB | TNFA | BCL6 | TBET | GATA3 | RORC | FOXP3 | RUNX1 | RUNX3 |
|---|---|---|---|---|---|---|---|---|---|---|
| CASSFGLGEQFF | 1152 | 0 | 248 | 0 | 302 | 279 | 0 | 0 | 361 | 0 |
| CASSFMVAATDTQYF | 1153 | 0 | 230 | 226 | 0 | 0 | 0 | 0 | 101 | 0 |
| CASSFQAGANVLTF | 1154 | 169 | 0 | 1 | 0 | 1 | 0 | 0 | 241 | 249 |
| CASSFRGSNTGELFF | 1155 | 0 | 283 | 0 | 0 | 0 | 0 | 0 | 1 | 250 |
| CASSFRYTGELFF | 1156 | 10 | 0 | 0 | 0 | 453 | 0 | 0 | 674 | 0 |
| CASSFSGTSPYEQYF | 1157 | 125 | 0 | 0 | 0 | 0 | 0 | 1 | 245 | 0 |
| CASSFSSGANVLTF | 1158 | 16 | 0 | 0 | 0 | 364 | 728 | 0 | 597 | 8 |
| CASSFTGDPPLGTEAFF | 1159 | 10 | 281 | 0 | 341 | 259 | 0 | 1 | 0 | 0 |
| CASSGGGTEAFF | 1160 | 0 | 592 | 0 | 469 | 0 | 0 | 0 | 0 | 0 |
| CASSGPNYNSPLHF | 1161 | 52 | 0 | 362 | 0 | 0 | 0 | 0 | 372 | 0 |
| CASSGQSIYEQYF | 1162 | 1 | 0 | 0 | 0 | 1 | 0 | 610 | 481 | 0 |
| CASSGRENYGYTF | 1163 | 265 | 0 | 117 | 1 | 1 | 0 | 0 | 611 | 0 |
| CASSGTGGAADQPQHF | 1164 | 0 | 207 | 0 | 192 | 0 | 0 | 0 | 216 | 0 |
| CASSGTGGGPQHF | 1165 | 0 | 321 | 0 | 142 | 1 | 0 | 0 | 76 | 0 |
| CASSHGQGYADTQYF | 1166 | 13 | 309 | 0 | 343 | 205 | 429 | 0 | 0 | 481 |
| CASSIDRMAGSSYNEQFF | 1167 | 1 | 373 | 0 | 256 | 301 | 0 | 0 | 368 | 0 |
| CASSIQGGSVQETQYF | 1168 | 0 | 0 | 0 | 1 | 0 | 0 | 0 | 0 | 0 |
| CASSIREDTEAFF | 1169 | 49 | 0 | 401 | 435 | 0 | 0 | 0 | 522 | 0 |
| CASSISASGGSYNEQFF | 1170 | 1 | 0 | 0 | 239 | 0 | 462 | 360 | 374 | 0 |
| CASSKIRTGGRQAVNTDTQYF | 1171 | 0 | 323 | 294 | 0 | 1 | 0 | 0 | 404 | 0 |
| CASSKRAIEQYF | 1172 | 1 | 355 | 1 | 0 | 295 | 0 | 1 | 0 | 0 |
| CASSLAGGGSAYEQYF | 1173 | 52 | 0 | 0 | 0 | 0 | 0 | 300 | 331 | 0 |
| CASSLAGTGYEQYF | 1174 | 338 | 0 | 0 | 438 | 0 | 0 | 0 | 0 | 0 |
| CASSLAPQDQAFF | 1175 | 102 | 0 | 0 | 0 | 291 | 0 | 0 | 445 | 0 |
| CASSLARQGDRNYGYTF | 1176 | 6 | 299 | 0 | 0 | 0 | 0 | 0 | 341 | 0 |
| CASSLASATHTGELFF | 1177 | 0 | 366 | 7 | 120 | 0 | 0 | 0 | 36 | 0 |
| CASSLDGAGVSLNEQFF | 1178 | 5 | 0 | 0 | 0 | 258 | 0 | 446 | 414 | 0 |
| CASSLDGARDTGELFF | 1179 | 0 | 48 | 475 | 0 | 0 | 0 | 0 | 207 | 0 |
| CASSLDGGAGNTIYF | 1180 | 212 | 352 | 0 | 0 | 0 | 0 | 0 | 0 | 0 |
| CASSLDGLAGTDTQYF | 1181 | 216 | 0 | 0 | 0 | 1 | 0 | 0 | 330 | 0 |
| CASSLDWRQESETQYF | 1182 | 0 | 572 | 0 | 585 | 0 | 50 | 0 | 178 | 0 |
| CASSLEAGDLYEQYF | 1183 | 0 | 449 | 1 | 248 | 1 | 0 | 0 | 1 | 0 |
| CASSLEGAGYTGELFF | 1184 | 0 | 271 | 0 | 0 | 156 | 0 | 0 | 378 | 0 |
| CASSLEGQAVTGELFF | 1185 | 379 | 0 | 0 | 0 | 0 | 1 | 0 | 0 | 0 |
| CASSLEGVGQNYGYTF | 1186 | 0 | 227 | 148 | 204 | 0 | 331 | 119 | 22 | 32 |
| CASSLERGLAGVVGEQFF | 1187 | 286 | 0 | 0 | 0 | 0 | 0 | 0 | 529 | 0 |

Figure 22M

| TCRB | SEQ ID NO: | TGFB | TNFA | BCL6 | TBET | GATA3 | RORC | FOXP3 | RUNX1 | RUNX3 |
|---|---|---|---|---|---|---|---|---|---|---|
| CASSLESSGSLGEQYF | 1188 | 204 | 0 | 0 | 1 | 0 | 0 | 0 | 235 | 153 |
| CASSLETRNTEAFF | 1189 | 0 | 283 | 1 | 225 | 0 | 0 | 0 | 1 | 0 |
| CASSLFLENTEAFF | 1190 | 4 | 49 | 0 | 0 | 0 | 473 | 1 | 319 | 1 |
| CASSLFLGTGNTIYF | 1191 | 373 | 0 | 0 | 0 | 500 | 0 | 0 | 851 | 0 |
| CASSLGAGALGETQYF | 1192 | 1 | 763 | 0 | 973 | 530 | 0 | 0 | 1 | 0 |
| CASSLGAGGATDTQYF | 1193 | 17 | 1 | 0 | 0 | 456 | 0 | 0 | 681 | 663 |
| CASSLGGDRGAEKLFF | 1194 | 1 | 154 | 0 | 218 | 0 | 0 | 0 | 0 | 497 |
| CASSLGGGTEAFF | 1195 | 4 | 0 | 0 | 0 | 287 | 0 | 0 | 516 | 0 |
| CASSLGSFSYEQYF | 1196 | 40 | 529 | 0 | 605 | 1 | 0 | 0 | 1 | 0 |
| CASSLGSGASNQPQHF | 1197 | 27 | 0 | 0 | 652 | 495 | 0 | 0 | 833 | 0 |
| CASSLGTFNYGYTF | 1198 | 92 | 199 | 0 | 0 | 0 | 0 | 0 | 0 | 0 |
| CASSLGTSQETQYF | 1199 | 0 | 189 | 0 | 15 | 0 | 0 | 33 | 148 | 0 |
| CASSLGVAPTDTQYF | 1200 | 0 | 429 | 0 | 29 | 1 | 0 | 0 | 0 | 0 |
| CASSLLANEQYF | 1201 | 15 | 1 | 0 | 0 | 250 | 0 | 381 | 394 | 0 |
| CASSLLVGQTNIVSGANVLTF | 1202 | 3 | 0 | 0 | 280 | 0 | 0 | 0 | 323 | 0 |
| CASSLPAGTGTGELFF | 1203 | 174 | 1 | 0 | 0 | 0 | 0 | 0 | 426 | 0 |
| CASSLQGSSQPQHF | 1204 | 0 | 1 | 0 | 624 | 4 | 0 | 782 | 0 | 0 |
| CASSLRAGGSTDTQYF | 1205 | 273 | 0 | 0 | 2 | 0 | 0 | 0 | 396 | 0 |
| CASSLRDTGFHF | 1206 | 269 | 0 | 0 | 0 | 0 | 1 | 0 | 317 | 0 |
| CASSLSALGLAGGNTGELFF | 1207 | 0 | 272 | 309 | 0 | 0 | 0 | 0 | 274 | 0 |
| CASSLSGQGTGEQYF | 1208 | 19 | 915 | 0 | 962 | 699 | 0 | 0 | 3 | 0 |
| CASSLSRIGGGYTF | 1209 | 273 | 0 | 0 | 0 | 0 | 0 | 0 | 338 | 0 |
| CASSLSTDTQYF | 1210 | 343 | 0 | 0 | 0 | 292 | 0 | 0 | 0 | 0 |
| CASSLTDRSPQYF | 1211 | 288 | 1 | 0 | 0 | 742 | 0 | 0 | 2 | 0 |
| CASSLTGLTEAFF | 1212 | 478 | 0 | 0 | 0 | 1 | 0 | 1 | 1068 | 0 |
| CASSLTGTGIGYTF | 1213 | 147 | 277 | 0 | 0 | 0 | 0 | 0 | 331 | 0 |
| CASSLTQGITDTQYF | 1214 | 0 | 687 | 1 | 1 | 2 | 662 | 0 | 3 | 0 |
| CASSLVGMNTEAFF | 1215 | 0 | 297 | 0 | 29 | 128 | 0 | 0 | 163 | 0 |
| CASSLVLGETQYF | 1216 | 10 | 0 | 0 | 0 | 0 | 0 | 264 | 2 | 488 |
| CASSLVPTYTDTQYF | 1217 | 0 | 425 | 0 | 2 | 0 | 26 | 1 | 69 | 0 |
| CASSLVSDQSNEQFF | 1218 | 0 | 313 | 0 | 194 | 0 | 290 | 0 | 291 | 0 |
| CASSLVYSGDRTDTQYF | 1219 | 0 | 730 | 603 | 0 | 0 | 0 | 0 | 333 | 0 |
| CASSMDRGSGELFF | 1220 | 0 | 80 | 331 | 74 | 0 | 0 | 151 | 389 | 0 |
| CASSNRGLGSGANVLTF | 1221 | 55 | 277 | 0 | 0 | 0 | 0 | 0 | 302 | 0 |
| CASSPESGRYNEQFF | 1222 | 0 | 239 | 0 | 317 | 35 | 0 | 0 | 0 | 0 |
| CASSPFGRLWATNEKLFF | 1223 | 0 | 1 | 0 | 226 | 0 | 0 | 6 | 82 | 8 |

Figure 22N

| TCRB | SEQ ID NO: | TGFB | TNFA | BCL6 | TBET | GATA3 | RORC | FOXP3 | RUNX1 | RUNX3 |
|---|---|---|---|---|---|---|---|---|---|---|
| CASSPGAGEQYF | 1224 | 0 | 1 | 383 | 80 | 0 | 0 | 442 | 220 | 3 |
| CASSPGAGLNTGELFF | 1225 | 1 | 188 | 0 | 0 | 78 | 0 | 0 | 325 | 0 |
| CASSPGGTGGAYGYTF | 1226 | 206 | 0 | 0 | 0 | 0 | 0 | 0 | 303 | 0 |
| CASSPGTRAFF | 1227 | 72 | 0 | 0 | 0 | 0 | 0 | 282 | 245 | 0 |
| CASSPLLASDEQFF | 1228 | 87 | 235 | 420 | 0 | 266 | 560 | 532 | 506 | 0 |
| CASSPMAGPSFYEQYF | 1229 | 334 | 0 | 0 | 0 | 0 | 0 | 0 | 0 | 0 |
| CASSPPGGPYEQYF | 1230 | 2 | 841 | 847 | 831 | 610 | 0 | 0 | 1005 | 0 |
| CASSPQGLGNNSPLHF | 1231 | 0 | 552 | 0 | 0 | 369 | 1040 | 1 | 777 | 0 |
| CASSPQGVSFMSNQPQHF | 1232 | 274 | 0 | 0 | 0 | 0 | 0 | 0 | 220 | 0 |
| CASSPRLAGSYEQYF | 1233 | 0 | 0 | 1 | 369 | 1 | 0 | 503 | 1 | 20 |
| CASSPRQYEQFF | 1234 | 0 | 17 | 0 | 371 | 0 | 485 | 0 | 97 | 0 |
| CASSPSDRGGKLFF | 1235 | 0 | 434 | 1 | 0 | 333 | 0 | 0 | 602 | 0 |
| CASSPSGGRVSPLHF | 1236 | 292 | 188 | 0 | 0 | 278 | 0 | 0 | 502 | 0 |
| CASSPSGGVNEQFF | 1237 | 448 | 0 | 0 | 1 | 0 | 0 | 0 | 591 | 0 |
| CASSPSRVNTEAFF | 1238 | 330 | 0 | 0 | 0 | 251 | 0 | 0 | 0 | 0 |
| CASSPTAAASYNEQFF | 1239 | 0 | 207 | 1 | 238 | 18 | 2 | 0 | 0 | 0 |
| CASSPVDEGTGELFF | 1240 | 0 | 305 | 335 | 201 | 0 | 0 | 0 | 300 | 0 |
| CASSPVSGGGDTQYF | 1241 | 0 | 0 | 0 | 193 | 0 | 0 | 0 | 436 | 0 |
| CASSPWGIPEAFF | 1242 | 0 | 366 | 0 | 236 | 0 | 0 | 0 | 69 | 0 |
| CASSQAARAETQYF | 1243 | 42 | 1209 | 0 | 1330 | 868 | 0 | 0 | 0 | 0 |
| CASSQDPEGYTF | 1244 | 0 | 0 | 0 | 0 | 1 | 5 | 0 | 1045 | 0 |
| CASSQDRGAANYGYTF | 1245 | 0 | 419 | 0 | 0 | 2 | 579 | 0 | 0 | 0 |
| CASSQDRGVEQYF | 1246 | 0 | 100 | 0 | 240 | 0 | 0 | 0 | 0 | 0 |
| CASSQDSIQGSGYTF | 1247 | 0 | 0 | 909 | 0 | 572 | 0 | 0 | 1025 | 0 |
| CASSQDVSGTGGSYEQYF | 1248 | 0 | 1 | 0 | 0 | 0 | 1 | 271 | 0 | 0 |
| CASSQEEGEKLFF | 1249 | 0 | 449 | 831 | 590 | 492 | 0 | 0 | 713 | 0 |
| CASSQEGQSAAFF | 1250 | 239 | 0 | 0 | 0 | 295 | 0 | 0 | 515 | 0 |
| CASSQETSGRAYEQYF | 1251 | 0 | 313 | 0 | 0 | 0 | 0 | 0 | 218 | 0 |
| CASSQFGEGPTGGQFF | 1252 | 165 | 0 | 0 | 0 | 1 | 0 | 185 | 0 | 240 |
| CASSQGGTGELFF | 1253 | 0 | 279 | 0 | 259 | 0 | 0 | 0 | 413 | 0 |
| CASSQGPGSNQPQHF | 1254 | 0 | 0 | 0 | 0 | 0 | 0 | 275 | 288 | 0 |
| CASSQGRNTGELFF | 1255 | 23 | 0 | 0 | 0 | 0 | 0 | 0 | 361 | 0 |
| CASSQGTGGGYTF | 1256 | 0 | 0 | 0 | 0 | 0 | 0 | 339 | 260 | 133 |
| CASSQHQGAGNTIYF | 1257 | 0 | 394 | 0 | 1 | 2 | 0 | 0 | 508 | 0 |
| CASSQPTGGAYNEQFF | 1258 | 70 | 444 | 0 | 525 | 0 | 0 | 596 | 0 | 0 |
| CASSQRGDDTGELFF | 1259 | 100 | 605 | 786 | 712 | 466 | 880 | 0 | 0 | 0 |

Figure 22O

| TCRB | SEQ ID NO: | TGFB | TNFA | BCL6 | TBET | GATA 3 | RORC | FOX P3 | RUNX 1 | RUNX 3 |
|---|---|---|---|---|---|---|---|---|---|---|
| CASSQVPGEQREQYF | 1260 | 447 | 0 | 0 | 0 | 0 | 0 | 0 | 0 | 0 |
| CASSRAEASSGANVLTF | 1261 | 0 | 1143 | 0 | 0 | 0 | 0 | 0 | 1242 | 1 |
| CASSRALGDNYGYTF | 1262 | 0 | 351 | 0 | 1 | 0 | 1 | 0 | 1 | 0 |
| CASSRDLGATNEKLFF | 1263 | 41 | 0 | 0 | 0 | 509 | 0 | 0 | 528 | 631 |
| CASSRGEGKAEAFF | 1264 | 55 | 0 | 386 | 336 | 0 | 0 | 0 | 418 | 0 |
| CASSRGSYNEQFF | 1265 | 0 | 305 | 392 | 0 | 0 | 0 | 0 | 0 | 27 |
| CASSRGTDQPQHF | 1266 | 270 | 1 | 1 | 1 | 142 | 0 | 2 | 7 | 533 |
| CASSRPFGELFF | 1267 | 210 | 0 | 0 | 1 | 0 | 0 | 0 | 560 | 0 |
| CASSRQGRGEKLFF | 1268 | 0 | 188 | 0 | 0 | 0 | 0 | 0 | 0 | 0 |
| CASSRRGLNYEQYF | 1269 | 2 | 353 | 0 | 334 | 0 | 449 | 0 | 124 | 0 |
| CASSSAQVGANVLTF | 1270 | 0 | 535 | 0 | 7 | 0 | 0 | 0 | 0 | 0 |
| CASSSDRANTEAFF | 1271 | 111 | 0 | 0 | 942 | 634 | 0 | 0 | 1018 | 0 |
| CASSSGGGTEAFF | 1272 | 0 | 363 | 1 | 0 | 279 | 571 | 0 | 0 | 0 |
| CASSSGQGARTEAFF | 1273 | 759 | 0 | 0 | 1 | 498 | 0 | 0 | 2 | 0 |
| CASSSGRGFDTQYF | 1274 | 29 | 243 | 0 | 0 | 105 | 460 | 0 | 375 | 0 |
| CASSSGSETQYF | 1275 | 219 | 0 | 0 | 196 | 0 | 0 | 0 | 0 | 0 |
| CASSSKRAGGYTF | 1276 | 0 | 299 | 200 | 8 | 0 | 153 | 0 | 24 | 0 |
| CASSSLERGGRRGEQYF | 1277 | 327 | 716 | 0 | 1 | 548 | 0 | 0 | 0 | 0 |
| CASSSNQWGNEKLFF | 1278 | 125 | 0 | 0 | 215 | 0 | 0 | 0 | 194 | 102 |
| CASSSPSGNTIYF | 1279 | 0 | 379 | 0 | 234 | 107 | 0 | 0 | 0 | 0 |
| CASSSRTGASETQYF | 1280 | 0 | 0 | 0 | 664 | 0 | 0 | 822 | 1 | 0 |
| CASSSRVRQPQHF | 1281 | 11 | 0 | 1 | 259 | 0 | 0 | 0 | 358 | 0 |
| CASSSTGGNEQFF | 1282 | 111 | 593 | 0 | 636 | 498 | 1 | 0 | 1 | 0 |
| CASSSTQSTGLVEAFF | 1283 | 0 | 353 | 0 | 336 | 0 | 320 | 0 | 0 | 1 |
| CASSTGGHGTQYF | 1284 | 29 | 377 | 0 | 0 | 287 | 0 | 1 | 310 | 422 |
| CASSTLTGAGELFF | 1285 | 23 | 0 | 0 | 292 | 0 | 0 | 0 | 0 | 0 |
| CASSTLTGGRNEQFF | 1286 | 70 | 1 | 880 | 0 | 1 | 1 | 996 | 0 | 0 |
| CASSTQGNIQYF | 1287 | 289 | 0 | 244 | 0 | 1 | 0 | 338 | 0 | 0 |
| CASSTRAQSYNEQFF | 1288 | 208 | 214 | 0 | 0 | 1 | 0 | 0 | 355 | 0 |
| CASSTRTDNRGYTF | 1289 | 4 | 1 | 377 | 0 | 0 | 0 | 403 | 315 | 0 |
| CASSTRTGGKETQYF | 1290 | 0 | 270 | 378 | 0 | 0 | 0 | 1 | 412 | 0 |
| CASSTTLGTGSFQETQYF | 1291 | 148 | 181 | 0 | 0 | 0 | 0 | 0 | 279 | 3 |
| CASSTTSGGSYEQYF | 1292 | 405 | 0 | 0 | 0 | 0 | 0 | 0 | 0 | 0 |
| CASSVGDLWGPQETQYF | 1293 | 0 | 337 | 0 | 264 | 0 | 505 | 0 | 25 | 0 |
| CASSVGLAGSNEQFF | 1294 | 1 | 686 | 0 | 486 | 24 | 0 | 0 | 208 | 0 |
| CASSVGPEYEQYF | 1295 | 243 | 0 | 0 | 0 | 0 | 0 | 435 | 319 | 0 |

Figure 22P

| TCRB | SEQ ID NO: | TGFB | TNFA | BCL6 | TBET | GATA3 | RORC | FOXP3 | RUNX1 | RUNX3 |
|---|---|---|---|---|---|---|---|---|---|---|
| CASSVGRGGSNEQFF | 1296 | 60 | 0 | 0 | 0 | 567 | 0 | 1077 | 1016 | 0 |
| CASSVKIDSEAFF | 1297 | 2 | 0 | 575 | 447 | 0 | 0 | 0 | 682 | 0 |
| CASSVLAGGHNEQFF | 1298 | 16 | 0 | 0 | 0 | 0 | 0 | 0 | 0 | 0 |
| CASSVRTSVGETQYF | 1299 | 2 | 236 | 297 | 0 | 262 | 0 | 0 | 270 | 371 |
| CASSVTGDSNSPLHF | 1300 | 0 | 336 | 0 | 7 | 0 | 0 | 0 | 96 | 0 |
| CASSVVGLAATDTQYF | 1301 | 0 | 0 | 0 | 116 | 0 | 0 | 0 | 332 | 0 |
| CASSWSGDTEAFF | 1302 | 334 | 1 | 0 | 1 | 0 | 0 | 0 | 1 | 0 |
| CASSYGTSGRVIQETQYF | 1303 | 0 | 300 | 0 | 3 | 0 | 0 | 0 | 0 | 0 |
| CASSYGTSGSLGYNEQFF | 1304 | 0 | 231 | 0 | 155 | 0 | 0 | 0 | 263 | 0 |
| CASSYKPGTSGGGTPDTQYF | 1305 | 0 | 0 | 0 | 0 | 0 | 0 | 297 | 0 | 0 |
| CASSYNKVAGGNTGELFF | 1306 | 265 | 0 | 0 | 216 | 0 | 0 | 0 | 0 | 0 |
| CASSYNSPLHF | 1307 | 7 | 1 | 0 | 496 | 0 | 0 | 0 | 556 | 0 |
| CASSYREYLYNEQFF | 1308 | 17 | 487 | 0 | 465 | 0 | 0 | 648 | 574 | 0 |
| CASSYSGGTQETQYF | 1309 | 0 | 287 | 0 | 32 | 0 | 0 | 0 | 172 | 138 |
| CASSYTGGAGYTF | 1310 | 0 | 585 | 0 | 301 | 410 | 0 | 0 | 449 | 326 |
| CASTGGSTDTQYF | 1311 | 0 | 0 | 0 | 0 | 1 | 0 | 667 | 681 | 0 |
| CASTLQVSETQYF | 1312 | 14 | 0 | 349 | 0 | 0 | 0 | 0 | 433 | 0 |
| CASTPQEYQETQYF | 1313 | 35 | 0 | 0 | 576 | 0 | 0 | 1 | 721 | 0 |
| CASTQGPNEQFF | 1314 | 3 | 0 | 0 | 338 | 0 | 0 | 0 | 0 | 0 |
| CASTWDSNQPQHF | 1315 | 158 | 0 | 0 | 0 | 0 | 0 | 0 | 413 | 0 |
| CATGTGTVGETQYF | 1316 | 0 | 0 | 0 | 265 | 5 | 0 | 0 | 212 | 0 |
| CATQRDLNSPLHF | 1317 | 0 | 354 | 0 | 394 | 0 | 0 | 0 | 146 | 0 |
| CATSAPGLSGTSGYNEQFF | 1318 | 0 | 289 | 23 | 9 | 0 | 15 | 0 | 355 | 0 |
| CATSASAFGGYTF | 1319 | 0 | 306 | 0 | 45 | 144 | 2 | 0 | 316 | 0 |
| CATSDLSQPGRMGTDTQYF | 1320 | 0 | 346 | 0 | 525 | 323 | 799 | 0 | 0 | 0 |
| CATSDRAVETQYF | 1321 | 162 | 0 | 0 | 260 | 240 | 0 | 0 | 413 | 0 |
| CATSGTGDEQYF | 1322 | 249 | 0 | 275 | 0 | 0 | 0 | 0 | 353 | 0 |
| CATSRDYFSGATDTQYF | 1323 | 0 | 314 | 0 | 0 | 0 | 0 | 0 | 2 | 0 |
| CATSREASGGGGQETQYF | 1324 | 0 | 0 | 0 | 0 | 389 | 0 | 0 | 407 | 0 |
| CATSRLNNEQFF | 1325 | 428 | 0 | 0 | 0 | 267 | 0 | 0 | 0 | 0 |
| CATSSDDLGSSYNEQFF | 1326 | 2 | 0 | 0 | 292 | 0 | 0 | 0 | 316 | 0 |
| CAWAPVEGQPQHF | 1327 | 28 | 0 | 0 | 168 | 98 | 0 | 0 | 0 | 0 |
| CAWDNKGLAGGRQYF | 1328 | 305 | 0 | 0 | 0 | 0 | 0 | 0 | 465 | 0 |
| CAWETAGIGYGYTF | 1329 | 228 | 0 | 0 | 1 | 0 | 0 | 0 | 477 | 0 |
| CAWKGDREGGYTF | 1330 | 1 | 0 | 593 | 0 | 0 | 0 | 0 | 622 | 0 |
| CAWRGTSGGAQYF | 1331 | 51 | 172 | 0 | 305 | 179 | 0 | 0 | 0 | 276 |

Figure 22Q

| TCRB | SEQ ID NO: | TGFB | TNFA | BCL6 | TBET | GATA3 | RORC | FOXP3 | RUNX1 | RUNX3 |
|---|---|---|---|---|---|---|---|---|---|---|
| CAWRQDLHYGYTF | 1332 | 0 | 608 | 0 | 28 | 0 | 0 | 0 | 273 | 0 |
| CAWSGGENQPQHF | 1333 | 290 | 0 | 0 | 0 | 0 | 0 | 1 | 393 | 0 |
| CAWSGGPTNSPLHF | 1334 | 72 | 0 | 0 | 0 | 0 | 0 | 0 | 201 | 0 |
| CAWSISGTENIQYF | 1335 | 222 | 0 | 0 | 0 | 0 | 0 | 0 | 297 | 0 |
| CAWSMEAEGQPQHF | 1336 | 0 | 311 | 0 | 363 | 0 | 422 | 0 | 147 | 0 |
| CAWSPLAGVSYEQYF | 1337 | 0 | 252 | 0 | 242 | 0 | 0 | 0 | 323 | 0 |
| CAWSRLGASGNTIYF | 1338 | 0 | 372 | 0 | 216 | 0 | 0 | 0 | 0 | 0 |
| CAWSVFTGGFGTNEKLFF | 1339 | 322 | 0 | 0 | 0 | 205 | 0 | 0 | 0 | 0 |
| CAWSVIQGGTEQYF | 1340 | 252 | 0 | 0 | 0 | 0 | 0 | 0 | 255 | 0 |
| CAWTGGTGDNEQFF | 1341 | 210 | 0 | 0 | 0 | 0 | 554 | 0 | 297 | 0 |
| CSADSSAAGGQDTQYF | 1342 | 155 | 1 | 0 | 0 | 0 | 0 | 0 | 333 | 0 |
| CSAGGQGRGNTEAFF | 1343 | 0 | 0 | 1 | 0 | 0 | 0 | 366 | 383 | 0 |
| CSAGLTGGREQYF | 1344 | 0 | 442 | 0 | 0 | 165 | 0 | 1 | 37 | 0 |
| CSAGSLGGEKLFF | 1345 | 0 | 158 | 0 | 0 | 261 | 0 | 0 | 0 | 0 |
| CSAKDSSTNEKLFF | 1346 | 1 | 411 | 0 | 407 | 292 | 0 | 0 | 517 | 0 |
| CSAKTGLYYGYTF | 1347 | 0 | 294 | 0 | 0 | 242 | 647 | 0 | 411 | 0 |
| CSALGGISTDTQYF | 1348 | 188 | 1 | 406 | 0 | 1 | 1 | 471 | 371 | 0 |
| CSALGPNQETQYF | 1349 | 49 | 0 | 0 | 0 | 1 | 0 | 0 | 0 | 1138 |
| CSALLGARGYTF | 1350 | 0 | 0 | 386 | 1 | 317 | 0 | 0 | 0 | 0 |
| CSALRQGAYNEQFF | 1351 | 0 | 651 | 0 | 169 | 0 | 0 | 0 | 0 | 0 |
| CSANPGFLTDTQYF | 1352 | 383 | 0 | 0 | 765 | 562 | 0 | 0 | 940 | 0 |
| CSANSGGSEKLFF | 1353 | 217 | 0 | 0 | 0 | 183 | 0 | 308 | 0 | 0 |
| CSAPTPGTGGYGYTF | 1354 | 0 | 467 | 0 | 0 | 398 | 1 | 0 | 0 | 0 |
| CSARALALVQTQYF | 1355 | 326 | 0 | 0 | 544 | 0 | 0 | 0 | 592 | 0 |
| CSARDPRGRVITEAFF | 1356 | 830 | 0 | 0 | 0 | 539 | 0 | 0 | 2 | 0 |
| CSARDRDRAVDTGELFF | 1357 | 0 | 443 | 476 | 0 | 0 | 0 | 0 | 490 | 0 |
| CSARDRDRGTDTQYF | 1358 | 0 | 0 | 0 | 0 | 0 | 809 | 740 | 370 | 0 |
| CSARDRLRLGADTQYF | 1359 | 0 | 51 | 0 | 188 | 0 | 0 | 0 | 412 | 0 |
| CSARGGQGQYGYTF | 1360 | 0 | 0 | 451 | 0 | 0 | 0 | 0 | 544 | 0 |
| CSARGIGNTIYF | 1361 | 24 | 315 | 1 | 0 | 217 | 0 | 314 | 410 | 0 |
| CSARGSGPDTEAFF | 1362 | 473 | 0 | 0 | 1 | 398 | 0 | 0 | 0 | 0 |
| CSARGSRLRGEGVSNQPQHF | 1363 | 0 | 516 | 0 | 0 | 488 | 0 | 0 | 481 | 0 |
| CSARSPGLAGGLNEQFF | 1364 | 0 | 0 | 0 | 0 | 0 | 0 | 0 | 0 | 0 |
| CSARSPTSGRTNEQFF | 1365 | 308 | 0 | 0 | 0 | 1 | 0 | 0 | 0 | 0 |
| CSASGAYNEQFF | 1366 | 41 | 0 | 1018 | 0 | 669 | 0 | 0 | 0 | 1399 |
| CSASGWGAVF | 1367 | 771 | 0 | 0 | 0 | 779 | 0 | 0 | 1192 | 0 |

Figure 22R

| TCRB | SEQ ID NO: | TGFB | TNFA | BCL6 | TBET | GATA 3 | RORC | FOX P3 | RUNX 1 | RUNX 3 |
|---|---|---|---|---|---|---|---|---|---|---|
| CSASLGVGNQPQHF | 1368 | 32 | 0 | 415 | 1 | 294 | 0 | 0 | 525 | 0 |
| CSASPNYGYTF | 1369 | 0 | 279 | 0 | 182 | 0 | 0 | 0 | 236 | 0 |
| CSASPQIAGGYEQYF | 1370 | 1 | 242 | 0 | 107 | 0 | 0 | 0 | 111 | 0 |
| CSASQAGGSSYEQYF | 1371 | 112 | 0 | 352 | 1 | 0 | 0 | 0 | 396 | 0 |
| CSASRGNTEAFF | 1372 | 12 | 0 | 0 | 666 | 0 | 0 | 0 | 860 | 0 |
| CSATLGTADTQYF | 1373 | 118 | 0 | 0 | 0 | 0 | 0 | 0 | 860 | 0 |
| CSATNDRAYGYTF | 1374 | 0 | 223 | 0 | 1 | 0 | 0 | 0 | 140 | 0 |
| CSAYSGNPGQPQHF | 1375 | 125 | 182 | 1 | 193 | 0 | 0 | 0 | 275 | 0 |
| CSGTGEETQYF | 1376 | 8 | 0 | 658 | 0 | 0 | 0 | 682 | 739 | 0 |
| CSSIRGGPGETQYF | 1377 | 252 | 0 | 0 | 0 | 0 | 0 | 0 | 350 | 0 |
| CSVAGTGEKLFF | 1378 | 0 | 0 | 0 | 0 | 0 | 0 | 0 | 416 | 0 |
| CSVDGALAGGTYEQYF | 1379 | 0 | 0 | 0 | 0 | 0 | 0 | 0 | 0 | 0 |
| CSVEEGAGGTDTQYF | 1380 | 182 | 0 | 0 | 0 | 0 | 0 | 0 | 0 | 0 |
| CSVEGGGYGYTF | 1381 | 638 | 0 | 0 | 0 | 1301 | 0 | 0 | 2 | 0 |
| CSVEIPGLSFYEQYF | 1382 | 133 | 0 | 0 | 311 | 0 | 0 | 0 | 241 | 0 |
| CSVERERGRTEAFF | 1383 | 9 | 0 | 0 | 0 | 286 | 0 | 0 | 604 | 604 |
| CSVERSSGSFSYGYTF | 1384 | 0 | 337 | 338 | 0 | 0 | 0 | 0 | 426 | 0 |
| CSVGQGVVYGYTF | 1385 | 0 | 296 | 0 | 2 | 0 | 0 | 0 | 141 | 0 |
| CSVGQTGNYEQYF | 1386 | 1 | 27 | 0 | 72 | 0 | 0 | 0 | 0 | 0 |
| CSVGRDIQETQYF | 1387 | 71 | 1 | 0 | 299 | 277 | 0 | 0 | 306 | 65 |
| CSVIQGAGSTDTQYF | 1388 | 0 | 353 | 0 | 33 | 3 | 23 | 0 | 145 | 21 |
| CSVRTGLAKNIQYF | 1389 | 0 | 1 | 0 | 0 | 375 | 0 | 0 | 1 | 0 |
| CVTSGTVNTEAFF | 1390 | 44 | 0 | 0 | 0 | 0 | 0 | 0 | 297 | 0 | ns # SINGLE CELL ANALYSIS OF T CELLS USING HIGH-THROUGHPUT MULTIPLEX AMPLIFICATION AND DEEP SEQUENCING

CROSS-REFERENCE TO RELATED APPLICATION

This application claims benefit under 35 U.S.C. § 119(e) of provisional application 61/990,080, filed May 7, 2014, which application is hereby incorporated by reference in its entirety.

STATEMENT REGARDING FEDERALLY SPONSORED RESEARCH OR DEVELOPMENT

This invention was made with Government support under contracts AI057229 and AI090019 awarded by the National Institutes of Health. The Government has certain rights in this invention.

INCORPORATION BY REFERENCE OF SEQUENCE LISTING PROVIDED AS A TEXT FILE

A Sequence Listing is provided herewith as a text file, "STAN-1216_S13-457_SeqList_ST25.txt" created on Apr. 29, 2015 and having a size of 380 KB. The contents of the text file are incorporated by reference herein in their entirety.

INTRODUCTION

It is well established that single cell analysis can reveal important functional insights that are masked in populations of cells.[1-3] Recent technological advances have improved our ability to simultaneously query expression of multiple genes in single cells, helping to resolve the complexity inherent in populations of T cells. These technologies include cytometry-based technologies including time-of-flight mass cytometry (CyTOF), and gene expression analysis using RNA sequencing (RNA-seq) or quantitative RT-PCR.[4-7]

However, these technologies have not been applied in a high throughput manner in T cells to include the most distinctive genes a T cell expresses: the genes which encode the T cell receptor (TCR). The TCR, which determines the T cell's antigen specificity, is central to the selection and function of T cells.[8] The TCR also serves as a unique identifier of a T cell's ancestry, as any two T cells with a particular TCRαβ pair most likely arose from a common T cell predecessor.

Thus, there remains a need for the development of relatively low cost, high throughput single-cell sequencing technology capable of providing multiparameter measurements on large numbers of individual cells. Such technology would be invaluable in diagnosing and treating a wide variety of diseases, including inflammatory disorders, autoimmune diseases, infectious diseases, and cancer.

SUMMARY

The present disclosure provides oligonucleotide reagents and methods for analyzing individual T cells by high-throughput multiplex amplification and sequencing of nucleic acids encoding T cell receptors (TCRs) and various other T cell phenotypic markers. The methods generally involve sorting of single T cells into separate locations (e.g., separate wells of a multi-well titer plate) followed by nested polymerase chain reaction (PCR) amplification of nucleic acids encoding TCRs and T cell phenotypic markers. The amplicons are barcoded to identify their cell of origin, combined, and analyzed by deep sequencing. The present disclosure provides methods of reconstituting TCRs from individual T cells for functional studies, ligand discovery, or screening therapeutics.

Exemplary primers (SEQ ID NOS:7-262) are described in Example 1 (see Tables 1-3, provided in FIGS. 12A-H, 13A-B and 14A-C, respectively) for amplifying TCRs (e.g., both α and β chains of the heterodimer) and various other T cell phenotypic markers, including cytokines (e.g., pro-inflammatory and inhibitory) and transcription factors, which are important in T cell function and specific for particular T cell types, and also for adding barcodes and sequencing adapters for paired-end sequencing. Changes to the nucleotide sequences of these primers may be introduced corresponding to genetic variations in particular T cells. For example up to three nucleotide changes, including 1 nucleotide change, 2 nucleotide changes, or three nucleotide changes, may be made in a sequence selected from the group consisting of SEQ ID NOS:7-262, wherein the oligonucleotide primer is capable of hybridizing to and amplifying or sequencing a T cell target nucleic acid (e.g., TCR or other T cell phenotypic marker). In certain embodiments, the primers are chosen to detect a splice variation, somatic mutation, or genetic polymorphism in particular T cells.

In one embodiment, the present disclosure includes a composition comprising a set of primers collectively comprising the nucleotide sequences of SEQ ID NOS:7-82 or variants thereof, wherein one or more primers may comprise a nucleotide sequence that differs from a nucleotide sequence selected from the group consisting of SEQ ID NOS:7-82 by up to three nucleotide changes, wherein the primers are capable of hybridizing to and amplifying nucleotide sequences encoding T cell receptors. In certain embodiments, the composition further comprises one or more primers selected from the group consisting of: a) a primer comprising a nucleotide sequence selected from the group consisting of SEQ ID NO:157, SEQ ID NO:158, SEQ ID NO:161, SEQ ID NO:162, SEQ ID NO:165, SEQ ID NO:166, SEQ ID NO:169, SEQ ID NO:170, SEQ ID NO:173, SEQ ID NO:174, SEQ ID NO:177, SEQ ID NO:178, SEQ ID NO:181, SEQ ID NO:182, SEQ ID NO:185, SEQ ID NO:186, SEQ ID NO:189, SEQ ID NO:190, SEQ ID NO:193, SEQ ID NO:194, SEQ ID NO:197, SEQ ID NO:198, SEQ ID NO:201, SEQ ID NO:202, SEQ ID NO:205, SEQ ID NO:206, SEQ ID NO:209, SEQ ID NO:210, SEQ ID NO:213, SEQ ID NO:214, SEQ ID NO:217, SEQ ID NO:218, SEQ ID NO:221, and SEQ ID NO:222; and b) a primer comprising a nucleotide sequence that differs from a sequence selected from the group consisting of SEQ ID NO:157, SEQ ID NO:158, SEQ ID NO:161, SEQ ID NO:162, SEQ ID NO:165, SEQ ID NO:166, SEQ ID NO:169, SEQ ID NO:170, SEQ ID NO:173, SEQ ID NO:174, SEQ ID NO:177, SEQ ID NO:178, SEQ ID NO:181, SEQ ID NO:182, SEQ ID NO:185, SEQ ID NO:186, SEQ ID NO:189, SEQ ID NO:190, SEQ ID NO:193, SEQ ID NO:194, SEQ ID NO:197, SEQ ID NO:198, SEQ ID NO:201, SEQ ID NO:202, SEQ ID NO:205, SEQ ID NO:206, SEQ ID NO:209, SEQ ID NO:210, SEQ ID NO:213, SEQ ID NO:214, SEQ ID NO:217, SEQ ID NO:218, SEQ ID NO:221, and SEQ ID NO:222 by up to three nucleotide changes, wherein the primer is capable of hybridizing to and amplifying a sequence encoding a T cell phenotypic marker. In one embodiment, the composition comprises primers comprising the nucleotide sequences of SEQ ID NO:157, SEQ ID NO:158, SEQ ID NO:161, SEQ ID NO:162, SEQ ID NO:165, SEQ ID NO:166, SEQ ID NO:169, SEQ ID NO:170, SEQ ID NO:173, SEQ ID NO:174, SEQ ID NO:177, SEQ ID NO:178, SEQ ID NO:181, SEQ ID NO:182, SEQ ID NO:185, SEQ ID NO:186, SEQ ID NO:189, SEQ ID NO:190, SEQ ID NO:193, SEQ ID NO:194, SEQ ID NO:197, SEQ ID NO:198, SEQ ID NO:201, SEQ ID NO:202, SEQ ID NO:205, SEQ ID NO:206, SEQ ID NO:209, SEQ ID NO:210, SEQ ID NO:213, SEQ ID NO:214, SEQ ID NO:217, SEQ ID NO:218, SEQ ID NO:221, and SEQ ID NO:222.

In another embodiment, the present disclosure provides a composition comprising a set of primers collectively comprising the nucleotide sequences of SEQ ID NOS:83-156 or variants thereof, wherein one or more primers may comprise a nucleotide sequence that differs from a nucleotide sequence selected from the group consisting of SEQ ID NOS: 83-156 by up to three nucleotide changes, wherein the primers are capable of hybridizing to and amplifying nucleotide sequences encoding T cell receptors. In one embodiment, the composition further comprises one or more primers selected from the group consisting of: a) a primer comprising a nucleotide sequence selected from the group consisting of SEQ ID NO:159, SEQ ID NO:160, SEQ ID NO:163, SEQ ID NO:164, SEQ ID NO:167, SEQ ID NO:168, SEQ ID NO:171, SEQ ID NO:172, SEQ ID NO:175, SEQ ID NO:176, SEQ ID NO:179, SEQ ID NO:180, SEQ ID NO:183, SEQ ID NO:184, SEQ ID NO:187, SEQ ID NO:188, SEQ ID NO:191, SEQ ID NO:192, SEQ ID NO:195, SEQ ID NO:196, SEQ ID NO:199, SEQ ID NO:200, SEQ ID NO:203, SEQ ID NO:204, SEQ ID NO:207, SEQ ID NO:208, SEQ ID NO: 211, SEQ ID NO:212, SEQ ID NO:215, SEQ ID NO:216, SEQ ID NO:219, SEQ ID NO:220, SEQ ID NO:223, and SEQ ID NO:224; and b) a primer comprising a nucleotide sequence that differs from a sequence selected from the group consisting of SEQ ID NO:159, SEQ ID NO:160, SEQ ID NO:163, SEQ ID NO:164, SEQ ID NO:167, SEQ ID NO:168, SEQ ID NO:171, SEQ ID NO:172, SEQ ID NO:175, SEQ ID NO:176, SEQ ID NO:179, SEQ ID NO:180, SEQ ID NO:183, SEQ ID NO:184, SEQ ID NO:187, SEQ ID NO:188, SEQ ID NO:191, SEQ ID NO:192, SEQ ID NO:195, SEQ ID NO:196, SEQ ID NO:199, SEQ ID NO:200, SEQ ID NO:203, SEQ ID NO:204, SEQ ID NO:207, SEQ ID NO:208, SEQ ID NO: 211, SEQ ID NO:212, SEQ ID NO:215, SEQ ID NO:216, SEQ ID NO:219, SEQ ID NO:220, SEQ ID NO:223, and SEQ ID NO:224 by up to three nucleotide changes, wherein the primer is capable of hybridizing to and amplifying a sequence encoding a T cell phenotypic marker. In one embodiment, the composition comprises primers comprising the nucleotide sequences of SEQ ID NO:159, SEQ ID NO:160, SEQ ID NO:163, SEQ ID NO:164, SEQ ID NO:167, SEQ ID NO:168, SEQ ID NO:171, SEQ ID NO:172, SEQ ID NO:175, SEQ ID NO:176, SEQ ID NO:179, SEQ ID NO:180, SEQ ID NO:183, SEQ ID NO:184, SEQ ID NO:187, SEQ ID NO:188, SEQ ID NO:191, SEQ ID NO:192, SEQ ID NO:195, SEQ ID NO:196, SEQ ID NO:199, SEQ ID NO:200, SEQ ID NO:203, SEQ ID NO:204, SEQ ID NO:207, SEQ ID NO:208, SEQ ID NO: 211, SEQ ID NO:212, SEQ ID NO:215, SEQ ID NO:216, SEQ ID NO:219, SEQ ID NO:220, SEQ ID NO:223, and SEQ ID NO:224.

In certain embodiments, barcode sequences are added to primers to allow identification of the T cell from which amplified nucleic acids originated. In one embodiment, the present disclosure provides a composition comprising a set of primers collectively comprising the nucleotide sequences of SEQ ID NOS:225-248. In another embodiment, the present disclosure provides a composition comprising a set of primers collectively comprising the nucleotide sequences of SEQ ID NOS:249-260.

In certain embodiments, a sequencing adapter sequence is added to primers to allow high-throughput sequencing of nucleic acids after amplification. In one embodiment, the present disclosure provides a composition comprising primers comprising adapters for paired end sequencing, wherein the primers are selected from the group consisting of SEQ ID NO:261 and SEQ ID NO:262.

In another aspect, the present disclosure provides a method for analyzing single T cells using the compositions described herein, the method comprising: a) collecting a sample comprising T cells from a subject; b) sorting single T cells from the sample into separate locations; c) amplifying nucleic acids from each single T cell using a first set of primers capable of amplifying a plurality of nucleic acids encoding T cell receptors to produce a first set of amplicon products; d) performing nested PCR with a second set of primers to produce a second set of amplicon products, wherein each primer comprises a common sequence such that each amplicon product is capable of hybridizing to a primer comprising a barcode sequence; e) amplifying the second set of amplicon products with a third set of primers, wherein each primer comprises a barcode sequence to identify the single T cell from which each amplified nucleic acid originated; and f) sequencing the third set of amplicon products. The method may further comprise lysing each single T cell prior to amplifying the target nucleic acids. If desired, the relative expression levels of the target nucleic acids may also be determined. In certain embodiments, the method further comprises analyzing the sequences of the amplified nucleic acids for splice variations, somatic mutations, or genetic polymorphisms.

In one embodiment, the first set of primers further comprises one or more primers selected from the group consisting of SEQ ID NO:157, SEQ ID NO:158, SEQ ID NO:161, SEQ ID NO:162, SEQ ID NO:165, SEQ ID NO:166, SEQ ID NO:169, SEQ ID NO:170, SEQ ID NO:173, SEQ ID NO:174, SEQ ID NO:177, SEQ ID NO:178, SEQ ID NO:181, SEQ ID NO:182, SEQ ID NO:185, SEQ ID NO:186, SEQ ID NO:189, SEQ ID NO:190, SEQ ID NO:193, SEQ ID NO:194, SEQ ID NO:197, SEQ ID NO:198, SEQ ID NO:201, SEQ ID NO:202, SEQ ID NO:205, SEQ ID NO:206, SEQ ID NO:209, SEQ ID NO:210, SEQ ID NO:213, SEQ ID NO:214, SEQ ID NO:217, SEQ ID NO:218, SEQ ID NO:221, and SEQ ID NO:222 and a nucleotide sequence that differs from a sequence selected from the group consisting of SEQ ID NO:157, SEQ ID NO:158, SEQ ID NO:161, SEQ ID NO:162, SEQ ID NO:165, SEQ ID NO:166, SEQ ID NO:169, SEQ ID NO:170, SEQ ID NO:173, SEQ ID NO:174, SEQ ID NO:177, SEQ ID NO:178, SEQ ID NO:181, SEQ ID NO:182, SEQ ID NO:185, SEQ ID NO:186, SEQ ID NO:189, SEQ ID NO:190, SEQ ID NO:193, SEQ ID NO:194, SEQ ID NO:197, SEQ ID NO:198, SEQ ID NO:201, SEQ ID NO:202, SEQ ID NO:205, SEQ ID NO:206, SEQ ID NO:209, SEQ ID NO:210, SEQ ID NO:213, SEQ ID NO:214, SEQ ID NO:217, SEQ ID NO:218, SEQ ID NO:221, and SEQ ID NO:222 by up to three nucleotide changes, wherein the primer is capable of hybridizing to and amplifying a sequence encoding a T cell phenotypic marker. In one embodiment, the first set of primers comprises primers comprising the nucleotide sequences of SEQ ID NO:157, SEQ ID NO:158, SEQ ID NO:161, SEQ ID NO:162, SEQ ID NO:165, SEQ ID NO:166, SEQ ID NO:169, SEQ ID NO:170, SEQ ID NO:173, SEQ ID NO:174, SEQ ID NO:177, SEQ ID NO:178, SEQ ID NO:181, SEQ ID NO:182, SEQ ID NO:185, SEQ ID NO:186, SEQ ID NO:189, SEQ ID NO:190, SEQ ID NO:193, SEQ ID NO:194, SEQ ID NO:197, SEQ ID NO:198, SEQ ID NO:201, SEQ ID NO:202, SEQ ID NO:205, SEQ ID NO:206, SEQ ID NO:209, SEQ ID NO:210, SEQ ID NO:213, SEQ ID NO:214, SEQ ID NO:217, SEQ ID NO:218, SEQ ID NO:221, and SEQ ID NO:222.

In another embodiment, the second set of primers collectively comprises the nucleotide sequences of SEQ ID NOS: 83-156 or variants thereof comprising up to three nucleotide changes, wherein the primers are capable of hybridizing to and amplifying nucleotide sequences encoding T cell receptors. In one embodiment, the common sequence comprises a sequence selected from the group consisting of SEQ ID NO:3 and SEQ ID NO:6. In certain embodiments, the second set of primers further comprises one or more primers comprising a nucleotide sequence selected from the group consisting of SEQ ID NO:159, SEQ ID NO:160, SEQ ID NO:163, SEQ ID NO:164, SEQ ID NO:167, SEQ ID NO:168, SEQ ID NO:171, SEQ ID NO:172, SEQ ID NO:175, SEQ ID NO:176, SEQ ID NO:179, SEQ ID NO:180, SEQ ID NO:183, SEQ ID NO:184, SEQ ID NO:187, SEQ ID NO:188, SEQ ID NO:191, SEQ ID NO:192, SEQ ID NO:195, SEQ ID NO:196, SEQ ID NO:199, SEQ ID NO:200, SEQ ID NO:203, SEQ ID NO:204, SEQ ID NO:207, SEQ ID NO:208, SEQ ID NO: 211, SEQ ID NO:212, SEQ ID NO:215, SEQ ID NO:216, SEQ ID NO:219, SEQ ID NO:220, SEQ ID NO:223, and SEQ ID NO:224 and a nucleotide sequence that differs from a sequence selected from the group consisting of SEQ ID NO:159, SEQ ID NO:160, SEQ ID NO:163, SEQ ID NO:164, SEQ ID NO:167, SEQ ID NO:168, SEQ ID NO:171, SEQ ID NO:172, SEQ ID NO:175, SEQ ID NO:176, SEQ ID NO:179, SEQ ID NO:180, SEQ ID NO:183, SEQ ID NO:184, SEQ ID NO:187, SEQ ID NO:188, SEQ ID NO:191, SEQ ID NO:192, SEQ ID NO:195, SEQ ID NO:196, SEQ ID NO:199, SEQ ID NO:200, SEQ ID NO:203, SEQ ID NO:204, SEQ ID NO:207, SEQ ID NO:208, SEQ ID NO: 211, SEQ ID NO:212, SEQ ID NO:215, SEQ ID NO:216, SEQ ID NO:219, SEQ ID NO:220, SEQ ID NO:223, and SEQ ID NO:224 by up to three nucleotide changes, wherein the primer is capable of hybridizing to and amplifying a sequence encoding a T cell phenotypic marker. In one embodiment, the second set of primers comprises primers comprising the nucleotide sequences of SEQ ID NO:159, SEQ ID NO:160, SEQ ID NO:163, SEQ ID NO:164, SEQ ID NO:167, SEQ ID NO:168, SEQ ID NO:171, SEQ ID NO:172, SEQ ID NO:175, SEQ ID NO:176, SEQ ID NO:179, SEQ ID NO:180, SEQ ID NO:183, SEQ ID NO:184, SEQ ID NO:187, SEQ ID NO:188, SEQ ID NO:191, SEQ ID NO:192, SEQ ID NO:195, SEQ ID NO:196, SEQ ID NO:199, SEQ ID NO:200, SEQ ID NO:203, SEQ ID NO:204, SEQ ID NO:207, SEQ ID NO:208, SEQ ID NO: 211, SEQ ID NO:212, SEQ ID NO:215, SEQ ID NO:216, SEQ ID NO:219, SEQ ID NO:220, SEQ ID NO:223, and SEQ ID NO:224.

Barcodes may be added at one or both ends of each amplicon product. In one embodiment, the third set of primers collectively comprises nucleotide sequences selected from the group consisting of SEQ ID NOS:225-248. In one embodiment, the third set of primers further comprises nucleotide sequences selected from the group consisting of SEQ ID NOS:249-260.

The third set of primers may further comprise primers comprising an adapter sequence to allow high-throughput sequencing of amplified nucleic acids. In one embodiment, the primers comprise an adapter sequence for paired-end sequencing. Exemplary primers, include primers comprising a sequence selected from the group consisting of SEQ ID NO:261 and SEQ ID NO:262.

In certain embodiments, the method further comprises dividing the first set of amplicons into two pools and performing nested PCR on the first pool and the second pool separately, wherein the first pool is amplified with primers that hybridize to nucleic acids encoding TCRs and the second pool is amplified with primers that hybridize to nucleic acids encoding other T cell phenotypic markers. In one embodiment, the first pool is amplified with the primers comprising nucleotide sequences selected from the group consisting of SEQ ID NOS:83-156 or nucleotide sequences that differ from a sequence selected from the group consisting of SEQ ID NOS:83-156 by up to three nucleotide changes, wherein the primers are capable of hybridizing to and amplifying a sequence encoding a T cell receptor; and the second pool is amplified with the primers comprising nucleotide sequences selected from the group consisting of SEQ ID NO:159, SEQ ID NO:160, SEQ ID NO:163, SEQ ID NO:164, SEQ ID NO:167, SEQ ID NO:168, SEQ ID NO:171, SEQ ID NO:172, SEQ ID NO:175, SEQ ID NO:176, SEQ ID NO:179, SEQ ID NO:180, SEQ ID NO:183, SEQ ID NO:184, SEQ ID NO:187, SEQ ID NO:188, SEQ ID NO:191, SEQ ID NO:192, SEQ ID NO:195, SEQ ID NO:196, SEQ ID NO:199, SEQ ID NO:200, SEQ ID NO:203, SEQ ID NO:204, SEQ ID NO:207, SEQ ID NO:208, SEQ ID NO: 211, SEQ ID NO:212, SEQ ID NO:215, SEQ ID NO:216, SEQ ID NO:219, SEQ ID NO:220, SEQ ID NO:223, and SEQ ID NO:224, or a nucleotide sequence that differs from a sequence selected from the group consisting of SEQ ID NO:159, SEQ ID NO:160, SEQ ID NO:163, SEQ ID NO:164, SEQ ID NO:167, SEQ ID NO:168, SEQ ID NO:171, SEQ ID NO:172, SEQ ID NO:175, SEQ ID NO:176, SEQ ID NO:179, SEQ ID NO:180, SEQ ID NO:183, SEQ ID NO:184, SEQ ID NO:187, SEQ ID NO:188, SEQ ID NO:191, SEQ ID NO:192, SEQ ID NO:195, SEQ ID NO:196, SEQ ID NO:199, SEQ ID NO:200, SEQ ID NO:203, SEQ ID NO:204, SEQ ID NO:207, SEQ ID NO:208, SEQ ID NO: 211, SEQ ID NO:212, SEQ ID NO:215, SEQ ID NO:216, SEQ ID NO:219, SEQ ID NO:220, SEQ ID NO:223, and SEQ ID NO:224 by up to three nucleotide changes, wherein the primer is capable of hybridizing to and amplifying a sequence encoding a T cell phenotypic marker.

In another aspect, the present disclosure provides a kit for analyzing single T cells. The kit may comprise one or more of the primer sets described herein contained in one or more compositions. The kit may further comprise written instructions for analyzing individual T cells based on sequencing of TCRs and phenotypic markers. The kit may also comprise reagents for performing reverse transcriptase polymerase chain reaction (RT-PCR) and/or sequencing (e.g., deep sequencing).

In one embodiment, the kit comprises a set of primers collectively comprising the nucleotide sequences of SEQ ID NOS: 7-82 or variants thereof, wherein one or more primers may comprise a nucleotide sequence that differs from a nucleotide sequence selected from the group consisting of SEQ ID NOS: 7-82 by up to three nucleotide changes, wherein the primers are capable of hybridizing to and amplifying nucleotide sequences encoding T cell receptors. In certain embodiments, the kit further comprises one or more primers comprising nucleotide sequences selected from the group consisting of SEQ ID NOS:1-6 and SEQ ID NOS:83-262.

In one embodiment, the kit comprises a composition comprising a set of primers collectively comprising the nucleotide sequences of SEQ ID NOS:7-82 or variants thereof, wherein one or more primers may comprise a nucleotide sequence that differs from a nucleotide sequence selected from the group consisting of SEQ ID NOS:7-82 by up to three nucleotide changes, wherein the primers are capable of hybridizing to and amplifying nucleotide sequences encoding T cell receptors. In certain embodiments, the kit comprises a composition further comprising one or more primers selected from the group consisting of: a) a primer comprising a nucleotide sequence selected from the group consisting of SEQ ID NO:157, SEQ ID NO:158, SEQ ID NO:161, SEQ ID NO:162, SEQ ID NO:165, SEQ ID NO:166, SEQ ID NO:169, SEQ ID NO:170, SEQ ID NO:173, SEQ ID NO:174, SEQ ID NO:177, SEQ ID NO:178, SEQ ID NO:181, SEQ ID NO:182, SEQ ID NO:185, SEQ ID NO:186, SEQ ID NO:189, SEQ ID NO:190, SEQ ID NO:193, SEQ ID NO:194, SEQ ID NO:197, SEQ ID NO:198, SEQ ID NO:201, SEQ ID NO:202, SEQ ID NO:205, SEQ ID NO:206, SEQ ID NO:209, SEQ ID NO:210, SEQ ID NO:213, SEQ ID NO:214, SEQ ID NO:217, SEQ ID NO:218, SEQ ID NO:221, and SEQ ID NO:222; and b) a primer comprising a nucleotide sequence that differs from a sequence selected from the group consisting of SEQ ID NO:157, SEQ ID NO:158, SEQ ID NO:161, SEQ ID NO:162, SEQ ID NO:165, SEQ ID NO:166, SEQ ID NO:169, SEQ ID NO:170, SEQ ID NO:173, SEQ ID NO:174, SEQ ID NO:177, SEQ ID NO:178, SEQ ID NO:181, SEQ ID NO:182, SEQ ID NO:185, SEQ ID NO:186, SEQ ID NO:189, SEQ ID NO:190, SEQ ID NO:193, SEQ ID NO:194, SEQ ID NO:197, SEQ ID NO:198, SEQ ID NO:201, SEQ ID NO:202, SEQ ID NO:205, SEQ ID NO:206, SEQ ID NO:209, SEQ ID NO:210, SEQ ID NO:213, SEQ ID NO:214, SEQ ID NO:217, SEQ ID NO:218, SEQ ID NO:221, and SEQ ID NO:222 by up to three nucleotide changes, wherein the primer is capable of hybridizing to and amplifying a sequence encoding a T cell phenotypic marker. In one embodiment, the kit comprises a composition comprising primers comprising the nucleotide sequences of SEQ ID NO:157, SEQ ID NO:158, SEQ ID NO:161, SEQ ID NO:162, SEQ ID NO:165, SEQ ID NO:166, SEQ ID NO:169, SEQ ID NO:170, SEQ ID NO:173, SEQ ID NO:174, SEQ ID NO:177, SEQ ID NO:178, SEQ ID NO:181, SEQ ID NO:182, SEQ ID NO:185, SEQ ID NO:186, SEQ ID NO:189, SEQ ID NO:190, SEQ ID NO:193, SEQ ID NO:194, SEQ ID NO:197, SEQ ID NO:198, SEQ ID NO:201, SEQ ID NO:202, SEQ ID NO:205, SEQ ID NO:206, SEQ ID NO:209, SEQ ID NO:210, SEQ ID NO:213, SEQ ID NO:214, SEQ ID NO:217, SEQ ID NO:218, SEQ ID NO:221, and SEQ ID NO:222.

In another embodiment, the kit comprises a composition comprising a set of primers collectively comprising the nucleotide sequences of SEQ ID NOS:83-156 or variants thereof, wherein one or more primers may comprise a nucleotide sequence that differs from a nucleotide sequence selected from the group consisting of SEQ ID NOS: 83-156 by up to three nucleotide changes, wherein the primers are capable of hybridizing to and amplifying nucleotide sequences encoding T cell receptors. In one embodiment, the kit comprises a composition further comprising one or more primers selected from the group consisting of: a) a primer comprising a nucleotide sequence selected from the group consisting of SEQ ID NO:159, SEQ ID NO:160, SEQ ID NO:163, SEQ ID NO:164, SEQ ID NO:167, SEQ ID NO:168, SEQ ID NO:171, SEQ ID NO:172, SEQ ID NO:175, SEQ ID NO:176, SEQ ID NO:179, SEQ ID NO:180, SEQ ID NO:183, SEQ ID NO:184, SEQ ID NO:187, SEQ ID NO:188, SEQ ID NO:191, SEQ ID NO:192, SEQ ID NO:195, SEQ ID NO:196, SEQ ID NO:199, SEQ ID NO:200, SEQ ID NO:203, SEQ ID NO:204, SEQ ID NO:207, SEQ ID NO:208, SEQ ID NO: 211, SEQ ID NO:212, SEQ ID NO:215, SEQ ID NO:216, SEQ ID NO:219, SEQ ID NO:220, SEQ ID NO:223, and SEQ ID NO:224; and b) a primer comprising a nucleotide sequence that differs from a sequence selected from the group consisting of SEQ ID NO:159, SEQ ID NO:160, SEQ ID NO:163, SEQ ID NO:164, SEQ ID NO:167, SEQ ID NO:168, SEQ ID NO:171, SEQ ID NO:172, SEQ ID NO:175, SEQ ID NO:176, SEQ ID NO:179, SEQ ID NO:180, SEQ ID NO:183, SEQ ID NO:184, SEQ ID NO:187, SEQ ID NO:188, SEQ ID NO:191, SEQ ID NO:192, SEQ ID NO:195, SEQ ID NO:196, SEQ ID NO:199, SEQ ID NO:200, SEQ ID NO:203, SEQ ID NO:204, SEQ ID NO:207, SEQ ID NO:208, SEQ ID NO: 211, SEQ ID NO:212, SEQ ID NO:215, SEQ ID NO:216, SEQ ID NO:219, SEQ ID NO:220, SEQ ID NO:223, and SEQ ID NO:224 by up to three nucleotide changes, wherein the primer is capable of hybridizing to and amplifying a sequence encoding a T cell phenotypic marker. In one embodiment, the kit comprises a composition comprising primers comprising the nucleotide sequences of SEQ ID NO:159, SEQ ID NO:160, SEQ ID NO:163, SEQ ID NO:164, SEQ ID NO:167, SEQ ID NO:168, SEQ ID NO:171, SEQ ID NO:172, SEQ ID NO:175, SEQ ID NO:176, SEQ ID NO:179, SEQ ID NO:180, SEQ ID NO:183, SEQ ID NO:184, SEQ ID NO:187, SEQ ID NO:188, SEQ ID NO:191, SEQ ID NO:192, SEQ ID NO:195, SEQ ID NO:196, SEQ ID NO:199, SEQ ID NO:200, SEQ ID NO:203, SEQ ID NO:204, SEQ ID NO:207, SEQ ID NO:208, SEQ ID NO: 211, SEQ ID NO:212, SEQ ID NO:215, SEQ ID NO:216, SEQ ID NO:219, SEQ ID NO:220, SEQ ID NO:223, and SEQ ID NO:224.

In another embodiment, the kit comprises a composition comprising a set of primers collectively comprising the nucleotide sequences of SEQ ID NOS:225-248. In another embodiment, the present disclosure provides a composition comprising a set of primers collectively comprising the nucleotide sequences of SEQ ID NOS:249-260.

In another embodiment, the kit comprises a composition comprising primers comprising adapters for paired end sequencing, wherein the primers are selected from the group consisting of SEQ ID NO:261 and SEQ ID NO:262.

In another aspect, the present disclosure provides a method for producing a T cell receptor (TCR) from a single cell, the method comprising the steps of: a) analyzing a T cell as described herein; b) identifying a sequence encoding a TCRα polypeptide and a sequence encoding a TCRβ polypeptide from a single T cell; c) transforming a host cell with one or more recombinant polynucleotides encoding the TCRα polypeptide operably linked to a promoter and the TCR beta polypeptide operably linked to a promoter; d) culturing the host cell under conditions suitable for the expression of the TCRα polypeptide and the TCRβ polypeptide; and e) recovering the TCRαβ heterodimer from the host cell culture.

In another aspect, the present disclosure provides a method of screening a T cell receptor (TCR) from a single T cell for the ability to bind to a target antigen, the method comprising: a) producing a TCR from a single T cell as described herein; b) contacting the TCR with the target antigen displayed in a complex with major histocompatibility complex (MHC); and c) determining whether or not the target antigen binds to the TCR.

In another aspect, the present disclosure provides a method of screening a library of peptides for binding to a TCR from a single T cell, the method comprising: a) producing the TCR from a single T cell as described herein; b) providing a peptide library comprising a plurality of peptides displayed by major histocompatibility complex (MHC) molecules; c) contacting the plurality of peptides with the TCR; and c) identifying at least one peptide that binds to the TCR.

These and other embodiments of the present disclosure will readily occur to those of skill in the art in view of the disclosure herein.

BRIEF DESCRIPTION OF THE FIGURES

FIGS. 1A-C depict the strategy for simultaneous T cell receptor (TCR) sequence determination and phenotyping from single sorted T cells (FIG. 1A), validation of TCR sequencing (FIG. 1B), and efficiency and accuracy of TCR sequencing (FIG. 1C).

FIG. 4A shows 5' primers (SEQ ID NO:263), containing a consensus sequence having an Illumina™ Paired-End Primer site, a common sequence, and variable barcodes that specify plate number and row of a multi-well plate. FIG. 4B shows a 3' primer (SEQ ID NO:264), containing a consensus sequence having an Illumina™ Paired-End Primer site and a TCR alpha chain constant region, and variable barcodes that specify column of a multi-well plate. In some cases, the TCR alpha chain constant region may be substituted with a sequence for the TCR beta constant region (SEQ ID NO:5) or a common sequence (SEQ ID NO:6) for phenotyping genes.

FIGS. 8A-E depict increased sensitivity with increased transcript abundance, but not with increased read count.

FIG. 9 depicts two expanded TIL T cell clones sharing a highly similar TCR beta chain and an identical TCR alpha chain. The CDR3 amino acid sequence for the TCR beta chain of clone A (SEQ ID NO:265) and clone B (SEQ ID NO:267), as well as the nucleotide sequence encoding the CDR 3 region of the TCR beta chain for clone A (SEQ ID NO:266) and clone B (SEQ ID NO:268) are shown (top). The CDR3 amino acid sequence for the TCR alpha chain of clone A (SEQ ID NO:269) and clone B (SEQ ID NO:269), as well as the nucleotide sequence encoding the CDR 3 region of the TCR alpha chain for clone A (SEQ ID NO:270) and clone B (SEQ ID NO:271) are shown (bottom)s.

FIGS. 12A-H provide Table 1, which provides TCR sequences primers for the first two PCR reactions.

FIGS. 13A-B provide Table 2, which provides phenotyping primers for the first two PCR reactions.

FIGS. 14A-C provide Table 3, which provides column barcoding primers used for the third PCR reaction and Illumina® Paired-End primers.

FIGS. 15A-R provide Table 4, which provides TCR sequences from the TCR validation panel.

FIG. 16 provides Table 5, which provides multiple TCR alpha sequences obtained from single T cells.

FIGS. 17A-AA provide Table 6, which provides reads counts per well of each phenotyping parameter illustrated in FIG. 2.

FIG. 18 provides Table 7, which provides detection of single-cell phenotypes.

FIGS. 19A-AC provide Table 8, which provides paired TCR alpha/beta sequences for 597 CD4$^+$ tumor-infiltrating lymphocytes for which a TCR beta chain was obtained.

FIGS. 20A-Z provide Table 9, which provides paired TCR alpha/beta sequences for 309 CD4$^+$ T cells from adjacent colon for which a TCR beta chain was obtained.

FIGS. 21A-AV provide Table 10, which provides reads counts per well of each tumor CD4$^+$ T cell analyzed.

FIGS. 22A-R provide Table 11, which provides reads counts per well of each adjacent colon CD4$^+$ T cell analyzed.

DEFINITIONS

Figure 1A:
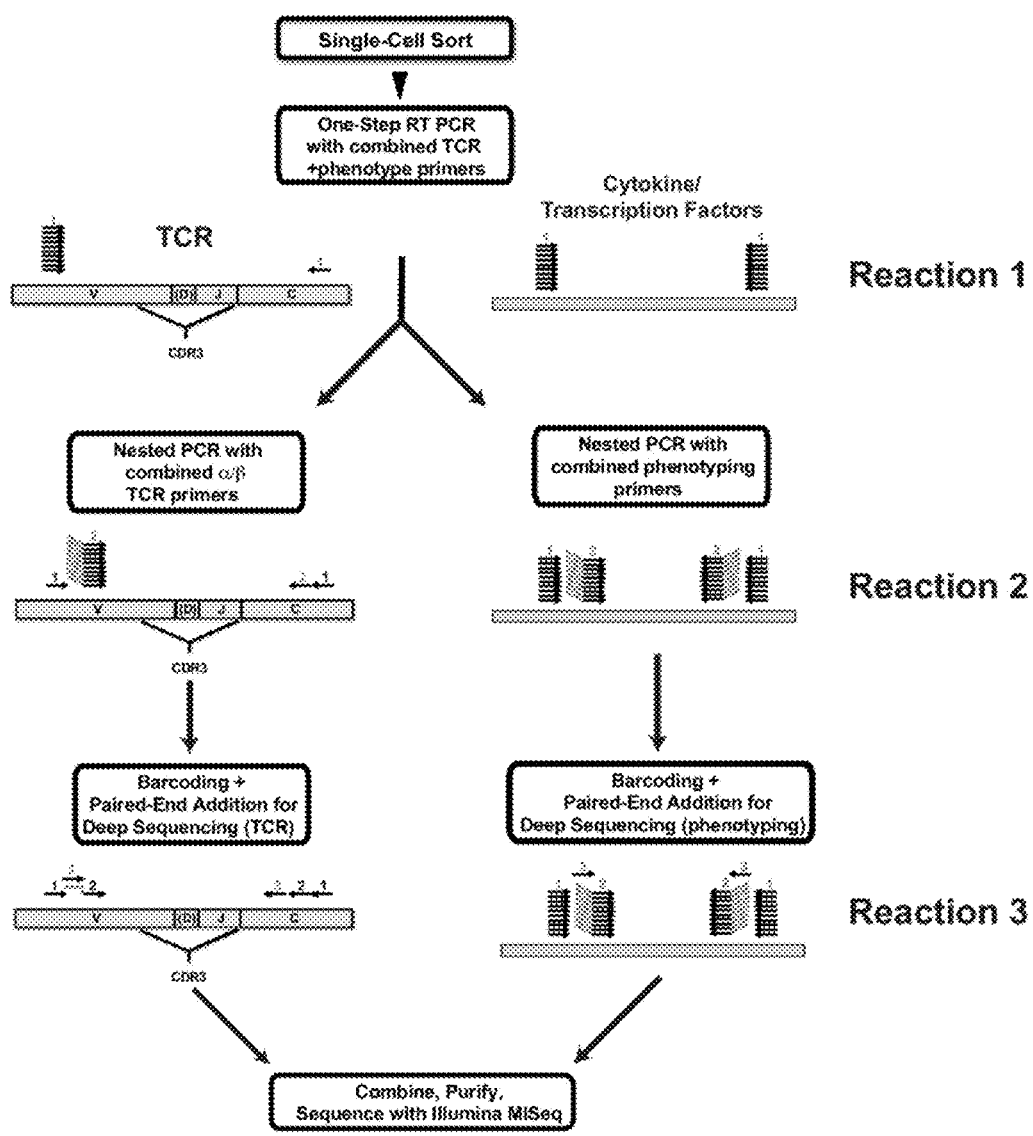

The practice of the present invention will employ, unless otherwise indicated, conventional methods of medicine, chemistry, biochemistry, immunology, cell biology, molecular biology and recombinant DNA techniques, within the skill of the art. Such techniques are explained fully in the literature. See, e.g., *T Cell Protocols* (Methods in Molecular Biology, G. De Libero ed., Humana Press; 2$^{nd}$ edition, 2009); C. W. Dieffenbach and G. S. Dveksler, *PCR Primer: A Laboratory Manual* (Cold Spring Harbor Laboratory Press; 2$^{nd}$ Lab edition, 2003); *Next Generation Sequencing: Translation to Clinical Diagnostics* (L. C. Wong ed., Springer, 2013); *Deep Sequencing Data Analysis* (Methods in Molecular Biology, N. Shomron ed., Humana Press, 2013); *Handbook of Experimental Immunology*, Vols. I-IV (D. M. Weir and C. C. Blackwell eds., Blackwell Scientific Publications); T. E. Creighton, *Proteins: Structures and Molecular Properties* (W.H. Freeman and Company, 1993); A. L. Lehninger, *Biochemistry* (Worth Publishers, Inc., current addition); Sambrook et al., *Molecular Cloning: A Laboratory Manual* (3$^{rd}$ Edition, 2001); *Methods In Enzymology* (S. Colowick and N. Kaplan eds., Academic Press, Inc.).

All publications, patents and patent applications cited herein, whether supra or infra, are hereby incorporated by reference in their entireties.

In describing the present invention, the following terms will be employed, and are intended to be defined as indicated below.

It must be noted that, as used in this specification and the appended claims, the singular forms "a", "an" and "the" include plural referents unless the content clearly dictates otherwise. Thus, for example, reference to "a primer" includes a mixture of two or more such primers, and the like. It is further noted that the claims can be drafted to exclude any optional element. As such, this statement is intended to serve as antecedent basis for use of such exclusive terminology as "solely," "only" and the like in connection with the recitation of claim elements, or use of a "negative" limitation.

"Substantially purified" generally refers to isolation of a substance (compound, polynucleotide, oligonucleotide, protein, or polypeptide) such that the substance comprises the majority percent of the sample in which it resides. Typically in a sample, a substantially purified component comprises 50%, 80%-85%, or 90-95% of the sample. Techniques for purifying polynucleotides, oliognucleotides, and polypeptides of interest are well-known in the art and include, for example, ion-exchange chromatography, affinity chromatography and sedimentation according to density.

By "isolated" is meant, when referring to a polypeptide, that the indicated molecule is separate and discrete from the whole organism with which the molecule is found in nature or is present in the substantial absence of other biological macro-molecules of the same type. The term "isolated" with respect to a polynucleotide or oligonucleotide is a nucleic acid molecule devoid, in whole or part, of sequences normally associated with it in nature; or a sequence, as it exists in nature, but having heterologous sequences in association therewith; or a molecule disassociated from the chromosome.

"Homology" refers to the percent identity between two polynucleotide or two polypeptide moieties. Two nucleic acid, or two polypeptide sequences are "substantially homologous" to each other when the sequences exhibit at least about 50% sequence identity, at least about 75% sequence identity, at least about 80%-85% sequence identity, at least about 90% sequence identity, or at least about 95%-98% sequence identity over a defined length of the molecules. As used herein, substantially homologous also refers to sequences showing complete identity to the specified sequence.

In general, "identity" refers to an exact nucleotide-to-nucleotide or amino acid-to-amino acid correspondence of two polynucleotides or polypeptide sequences, respectively. Percent identity can be determined by a direct comparison of the sequence information between two molecules by aligning the sequences, counting the exact number of matches between the two aligned sequences, dividing by the length of the shorter sequence, and multiplying the result by 100. Readily available computer programs can be used to aid in the analysis, such as ALIGN, Dayhoff, M. O. in *Atlas of Protein Sequence and Structure* M. O. Dayhoff ed., 5 Suppl. 3:353-358, National biomedical Research Foundation, Washington, D.C., which adapts the local homology algorithm of Smith and Waterman *Advances in Appl. Math.* 2:482-489, 1981 for peptide analysis. Programs for determining nucleotide sequence identity are available in the Wisconsin Sequence Analysis Package, Version 8 (available from Genetics Computer Group, Madison, Wis.) for example, the BESTFIT, FASTA and GAP programs, which also rely on the Smith and Waterman algorithm. These programs are readily utilized with the default parameters recommended by the manufacturer and described in the Wisconsin Sequence Analysis Package referred to above. For example, percent identity of a particular nucleotide sequence to a reference sequence can be determined using the homology algorithm of Smith and Waterman with a default scoring table and a gap penalty of six nucleotide positions.

Another method of establishing percent identity in the context of the present invention is to use the MPSRCH package of programs copyrighted by the University of Edinburgh, developed by John F. Collins and Shane S. Sturrok, and distributed by IntelliGenetics, Inc. (Mountain View, Calif.). From this suite of packages the Smith-Waterman algorithm can be employed where default parameters are used for the scoring table (for example, gap open penalty of 12, gap extension penalty of one, and a gap of six). From the data generated the "Match" value reflects "sequence identity." Other suitable programs for calculating the percent identity or similarity between sequences are generally known in the art, for example, another alignment program is BLAST®, used with default parameters. For example, BLAST®N and BLAST®P can be used using the following default parameters: genetic code=standard; filter=none; strand=both; cutoff=60; expect=10; Matrix=BLOSUM62; Descriptions=50 sequences; sort by=HIGH SCORE; Databases=non-redundant, GenBank®+EMBL®+DDBJ+PDB+GenBank® CDS translations+Swiss protein+Spupdate+PIR. Details of these programs are readily available.

Alternatively, homology can be determined by hybridization of polynucleotides under conditions which form stable duplexes between homologous regions, followed by digestion with single-stranded-specific nuclease(s), and size determination of the digested fragments. DNA sequences that are substantially homologous can be identified in a Southern hybridization experiment under, for example, stringent conditions, as defined for that particular system. Defining appropriate hybridization conditions is within the skill of the art. See, e.g., Sambrook et al., supra; *DNA Cloning*, supra; *Nucleic Acid Hybridization*, supra.

The terms "polynucleotide," "oligonucleotide," "nucleic acid" and "nucleic acid molecule" are used herein to include a polymeric form of nucleotides of any length, either ribonucleotides or deoxyribonucleotides. This term refers only to the primary structure of the molecule. Thus, the term includes triple-, double- and single-stranded DNA, as well as triple-, double- and single-stranded RNA. It also includes modifications, such as by methylation and/or by capping, and unmodified forms of the polynucleotide. More particularly, the terms "polynucleotide," "oligonucleotide," "nucleic acid" and "nucleic acid molecule" include polydeoxyribonucleotides (containing 2-deoxy-D-ribose), polyribonucleotides (containing D-ribose), any other type of polynucleotide which is an N- or C-glycoside of a purine or pyrimidine base, and other polymers containing nonnucleotidic backbones, for example, polyamide (e.g., peptide nucleic acids (PNAs)) and polymorpholino (commercially available from the Anti-Virals, Inc., Corvallis, Oreg., as Neugene) polymers, and other synthetic sequence-specific nucleic acid polymers providing that the polymers contain nucleobases in a configuration which allows for base pairing and base stacking, such as is found in DNA and RNA. There is no intended distinction in length between the terms "polynucleotide," "oligonucleotide," "nucleic acid" and "nucleic acid molecule," and these terms will be used interchangeably. Thus, these terms include, for example, 3'-deoxy-2',5'-DNA, oligodeoxyribonucleotide N3' P5' phosphoramidates, 2'-O-alkyl-substituted RNA, double- and single-stranded DNA, as well as double- and single-stranded RNA, DNA:RNA hybrids, and hybrids between PNAs and DNA or RNA, and also include known types of modifications, for example, labels which are known in the art, methylation, "caps," substitution of one or more of the naturally occurring nucleotides with an analog, internucleotide modifications such as, for example, those with uncharged linkages (e.g., methyl phosphonates, phosphotriesters, phosphoramidates, carbamates, etc.), with negatively charged linkages (e.g., phosphorothioates, phosphorodithioates, etc.), and with positively charged linkages (e.g., aminoalklyphosphoramidates, aminoalkylphosphotriesters), those containing pendant moieties, such as, for example, proteins (including nucleases, toxins, antibodies, signal peptides, poly-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide or oligonucleotide.

A polynucleotide "derived from" a designated sequence refers to a polynucleotide sequence which comprises a contiguous sequence of approximately at least about 6 nucleotides, at least about 8 nucleotides, at least about 10-12 nucleotides, or at least about 15-20 nucleotides corresponding, i.e., identical or complementary to, a region of the designated nucleotide sequence. The derived polynucleotide will not necessarily be derived physically from the nucleotide sequence of interest, but may be generated in any manner, including, but not limited to, chemical synthesis, replication, reverse transcription or transcription, which is based on the information provided by the sequence of bases in the region(s) from which the polynucleotide is derived. As such, it may represent either a sense or an antisense orientation of the original polynucleotide.

"Recombinant" as used herein to describe a nucleic acid molecule means a polynucleotide of genomic, cDNA, semi-synthetic, or synthetic origin which, by virtue of its origin or manipulation is not associated with all or a portion of the polynucleotide with which it is associated in nature. The term "recombinant" as used with respect to a protein or polypeptide means a polypeptide produced by expression of a recombinant polynucleotide. In general, the gene of interest is cloned and then expressed in transformed organisms, as described further below. The host organism expresses the foreign gene to produce the protein under expression conditions.

As used herein, a "solid support" refers to a solid surface such as a magnetic bead, latex bead, microtiter plate well, glass plate, nylon, agarose, acrylamide, and the like.

As used herein, the term "target nucleic acid region" or "target nucleic acid" denotes a nucleic acid molecule with a "target sequence" to be amplified. The target nucleic acid may be either single-stranded or double-stranded and may include other sequences besides the target sequence, which may not be amplified. The term "target sequence" refers to the particular nucleotide sequence of the target nucleic acid which is to be amplified. The target sequence may include a probe-hybridizing region contained within the target molecule with which a probe will form a stable hybrid under desired conditions. The "target sequence" may also include the complexing sequences to which the oligonucleotide primers complex and extended using the target sequence as a template. Where the target nucleic acid is originally single-stranded, the term "target sequence" also refers to the sequence complementary to the "target sequence" as present in the target nucleic acid. If the "target nucleic acid" is originally double-stranded, the term "target sequence" refers to both the plus (+) and minus (−) strands (or sense and antisense strands).

The term "primer" or "oligonucleotide primer" as used herein, refers to an oligonucleotide that hybridizes to the template strand of a nucleic acid and initiates synthesis of a nucleic acid strand complementary to the template strand when placed under conditions in which synthesis of a primer extension product is induced, i.e., in the presence of nucleotides and a polymerization-inducing agent such as a DNA or RNA polymerase and at suitable temperature, pH, metal concentration, and salt concentration. The primer is generally single-stranded for maximum efficiency in amplification, but may alternatively be double-stranded. If double-stranded, the primer can first be treated to separate its strands before being used to prepare extension products. This denaturation step is typically effected by heat, but may alternatively be carried out using alkali, followed by neutralization. Thus, a "primer" is complementary to a template, and complexes by hydrogen bonding or hybridization with the template to give a primer/template complex for initiation of synthesis by a polymerase, which is extended by the addition of covalently bonded bases linked at its 3' end complementary to the template in the process of DNA or RNA synthesis.

"Polymerase chain reaction," or "PCR," means a reaction for the in vitro amplification of specific DNA sequences by the simultaneous primer extension of complementary strands of DNA. In other words, PCR is a reaction for making multiple copies or replicates of a target nucleic acid flanked by primer binding sites, such reaction comprising one or more repetitions of the following steps: (i) denaturing the target nucleic acid, (ii) annealing primers to the primer binding sites, and (iii) extending the primers by a nucleic acid polymerase in the presence of nucleoside triphosphates. Usually, the reaction is cycled through different temperatures optimized for each step in a thermal cycler instrument. Particular temperatures, durations at each step, and rates of change between steps depend on many factors well-known to those of ordinary skill in the art, e.g., exemplified by the references: McPherson et al, editors, PCR: A Practical Approach and PCR2: A Practical Approach (IRL Press, Oxford, 1991 and 1995, respectively). For example, in a conventional PCR using Taq DNA polymerase, a double stranded target nucleic acid may be denatured at a temperature>90° C., primers annealed at a temperature in the range 50-75° C., and primers extended at a temperature in the range 72-78° C. The term "PCR" encompasses derivative forms of the reaction, including but not limited to, RT-PCR, real-time PCR, nested PCR, quantitative PCR, multiplexed PCR, and the like. PCR reaction volumes typically range from a few hundred nanoliters, e.g. 200 nL, to a few hundred μL, e.g. 200 μL. "Reverse transcription PCR," or "RT-PCR," means a PCR that is preceded by a reverse transcription reaction that converts a target RNA to a complementary single stranded DNA, which is then amplified, e.g. Tecott et al, U.S. Pat. No. 5,168,038, which patent is incorporated herein by reference. "Real-time PCR" means a PCR for which the amount of reaction product, i.e. amplicon, is monitored as the reaction proceeds. There are many forms of real-time PCR that differ mainly in the detection chemistries used for monitoring the reaction product, e.g., Gelfand et al, U.S. Pat. No. 5,210,015 ("taqman"); Wittwer et al, U.S. Pat. Nos. 6,174,670 and 6,569,627 (intercalating dyes); Tyagi et al, U.S. Pat. No. 5,925,517 (molecular beacons); which patents are incorporated herein by reference. Detection chemistries for real-time PCR are reviewed in Mackay et al, Nucleic Acids Research, 30: 1292-1305 (2002), which is also incorporated herein by reference. "Nested PCR" means a two-stage PCR wherein the amplicon of a first PCR becomes the sample for a second PCR using a new set of primers, at least one of which binds to an interior location of the first amplicon. As used herein, "initial primers" or "first set of primers" in reference to a nested amplification reaction mean the primers used to generate a first amplicon, and "secondary primers" or "second set of primers" mean the one or more primers used to generate a second, or nested, amplicon. "Multiplexed PCR" means a PCR wherein multiple target sequences (or a single target sequence and one or more reference sequences) are simultaneously carried out in the same reaction mixture, e.g. Bernard et al, Anal. Biochem., 273: 221-228 (1999) (two-color real-time PCR). Usually, distinct sets of primers are employed for each sequence being amplified. "Quantitative PCR" means a PCR designed to measure the abundance of one or more specific target sequences in a sample or specimen. Quantitative PCR includes both absolute quantitation and relative quantitation of such target sequences. Quantitative measurements are made using one or more reference sequences that may be assayed separately or together with a target sequence. The reference sequence may be endogenous or exogenous to a sample or specimen, and in the latter case, may comprise one or more competitor templates. Typical endogenous reference sequences include segments of transcripts of the following genes: β-actin, GAPDH, $β_2$-microglobulin, ribosomal RNA, and the like. Techniques for quantitative PCR are well-known to those of ordinary skill in the art, as exemplified in the following references that are incorporated by reference: Freeman et al, Biotechniques, 26: 112-126 (1999); Becker-Andre et al, Nucleic Acids Research, 17: 9437-9447 (1989); Zimmerman et al, Biotechniques, 21: 268-279 (1996); Diviacco et al, Gene, 122: 3013-3020 (1992); Becker-Andre et al, Nucleic Acids Research, 17: 9437-9446 (1989); and the like.

The term "amplicon" refers to the amplified nucleic acid product of a PCR reaction or other nucleic acid amplification process.

The terms "hybridize" and "hybridization" refer to the formation of complexes between nucleotide sequences which are sufficiently complementary to form complexes via Watson-Crick base pairing. Where a primer "hybridizes" with target (template), such complexes (or hybrids) are sufficiently stable to serve the priming function required by, e.g., the DNA polymerase to initiate DNA synthesis. It will be appreciated that the hybridizing sequences need not have perfect complementarity to provide stable hybrids. In many situations, stable hybrids will form where fewer than about 10% of the bases are mismatches, ignoring loops of four or more nucleotides. Accordingly, as used herein the term "complementary" refers to an oligonucleotide that forms a stable duplex with its "complement" under assay conditions, generally where there is about 90% or greater homology.

The "melting temperature" or "Tm" of double-stranded DNA is defined as the temperature at which half of the helical structure of DNA is lost due to heating or other dissociation of the hydrogen bonding between base pairs, for example, by acid or alkali treatment, or the like. The $T_m$ of a DNA molecule depends on its length and on its base composition. DNA molecules rich in GC base pairs have a higher $T_m$ than those having an abundance of AT base pairs. Separated complementary strands of DNA spontaneously reassociate or anneal to form duplex DNA when the temperature is lowered below the $T_m$. The highest rate of nucleic acid hybridization occurs approximately 25 degrees C. below the $T_m$. The $T_m$ may be estimated using the following relationship: $T_m$=69.3+0.41(GC) % (Marmur et al. (1962) *J. Mol. Biol.* 5:109-118).

The term "barcode" refers to a nucleic acid sequence that is used to identify a single cell or a subpopulation of cells. Barcode sequences can be linked to a target nucleic acid of interest during amplification and used to trace back the amplicon to the cell from which the target nucleic acid originated. A barcode sequence can be added to a target nucleic acid of interest during amplification by carrying out PCR with a primer that contains a region comprising the barcode sequence and a region that is complementary to the target nucleic acid such that the barcode sequence is incorporated into the final amplified target nucleic acid product (i.e., amplicon). Barcodes can be included in either the forward primer or the reverse primer or both primers used in PCR to amplify a target nucleic acid.

"Microfluidics device" means an integrated system of one or more chambers, ports, and channels that are interconnected and in fluid communication and designed for carrying out an analytical reaction or process, either alone or in cooperation with an appliance or instrument that provides support functions, such as sample introduction, fluid and/or reagent driving means, temperature control, detection systems, data collection and/or integration systems, and the like. Microfluidics devices may further include valves, pumps, and specialized functional coatings on interior walls, e.g. to prevent adsorption of sample components or reactants, facilitate reagent movement by electroosmosis, or the like. Such devices are usually fabricated in or as a solid substrate, which may be glass, plastic, or other solid polymeric materials, and typically have a planar format for ease of detecting and monitoring sample and reagent movement, especially via optical or electrochemical methods. Features of a microfluidic device usually have cross-sectional dimensions of less than a few hundred square micrometers and passages typically have capillary dimensions, e.g. having maximal cross-sectional dimensions of from about 500 µm to about 0.1 µm. Microfluidics devices typically have volume capacities in the range of from 1 µL to a few nL, e.g. 10-100 nL. The fabrication and operation of microfluidics devices are well-known in the art as exemplified by the following references that are incorporated by reference: Ramsey, U.S. Pat. Nos. 6,001,229; 5,858,195; 6,010,607; and 6,033,546; Soane et al, U.S. Pat. Nos. 5,126,022 and 6,054,034; Nelson et al, U.S. Pat. No. 6,613,525; Maher et al, U.S. Pat. No. 6,399,952; Ricco et al, International patent publication WO 02/24322; Bjornson et al, International patent publication WO 99/19717; Wilding et al, U.S. Pat. Nos. 5,587,128; 5,498,392; Sia et al, Electrophoresis, 24: 3563-3576 (2003); Unger et al, Science, 288: 113-116 (2000); Enzelberger et al, U.S. Pat. No. 6,960,437.

The terms "label" and "detectable label" refer to a molecule capable of detection, including, but not limited to, radioactive isotopes, fluorescers, chemiluminescers, enzymes, enzyme substrates, enzyme cofactors, enzyme inhibitors, chromophores, dyes, metal ions, metal sols, ligands (e.g., biotin or haptens) and the like. The term "fluorescer" refers to a substance or a portion thereof that is capable of exhibiting fluorescence in the detectable range. Particular examples of labels that may be used with the invention include, but are not limited to phycoerythrin, Alexa dyes, fluorescein, YPet, CyPet, Cascade blue, allophycocyanin, Cy3, Cy5, Cy7, rhodamine, dansyl, umbelliferone, Texas red, luminol, acradimum esters, biotin, green fluorescent protein (GFP), enhanced green fluorescent protein (EGFP), yellow fluorescent protein (YFP), enhanced yellow fluorescent protein (EYFP), blue fluorescent protein (BFP), red fluorescent protein (RFP), firefly luciferase, Renilla luciferase, NADPH, beta-galactosidase, horseradish peroxidase, glucose oxidase, alkaline phosphatase, chloramphenical acetyl transferase, and urease.

By "subject" is meant any member of the subphylum chordata, including, without limitation, humans and other primates, including non-human primates such as chimpanzees and other apes and monkey species; farm animals such as cattle, sheep, pigs, goats and horses; domestic mammals such as dogs and cats; birds; and laboratory animals, including rodents such as mice, rats and guinea pigs, and the like. The term does not denote a particular age. Thus, both adult and newborn individuals are intended to be covered.

"T cell receptor" or "TCR", as used herein, refers to a polypeptide expressed on the membrane surface of $CD4^+$ and $CD8^+$ T lymphocytes. TCRs are antigen receptors that function as a component of the immune system for recognition of peptides bound to self major histocompatibility complex (MHC) molecules on the surface of antigen presenting cells. The TCR may be a heterodimer of two disulfide-linked transmembrane polypeptide chains, α and β, or γ and δ. Each of these four TCR polypeptide chains is encoded by a distinct genetic locus containing multiple discontinuous gene segments. These include variable (V) region gene segments, joining (J) region gene segments and constant (C) region gene segments. Beta and delta chains contain an additional element termed the diversity (D) gene segment. The variable region contributes to the determination of the particular antigen and MHC molecule to which the TCR has binding specificity. The term TCR, as used herein, includes each of the four polypeptide chain individually, as well as biologically active fragments thereof, including fragments soluble in aqueous solutions, of either chain alone or both chains joined. Biologically active fragments may maintain the ability to bind with specificity to a specific antigen.

A TCR "subtype," as used herein, refers to a group of TCR polypeptide chains that belongs to α, β, γ or δ chains. Thus in some instances, TCR polypeptides belonging to the same subtype may have different variable regions but may have the same constant region.

"Common sequence" as used herein refers to a sequence included in a primer that is shared among a plurality of primers in a set of primers that may be used in a PCR amplification reaction. The common sequence may be a first sequence common among all forward primers and a second sequence common among all reverse primers in a set of primers that includes multiple forward and reverse primers, e.g., primer pairs. In some cases, the common sequence in a primer enables the primer to hybridize to the target nucleic acid. In some cases, the common sequence in a primer does not hybridize to the target nucleotide sequence. Thus, common sequence-containing primer pairs for amplifying TCRs may include a set of forward primers that contain a nucleic acid sequence that hybridizes to different TCR V-regions and a nucleic acid sequence common to all forward primers, and a reverse primer that contains a nucleic acid sequence that hybridizes to the same TCR C-region, which may be the common sequence for the reverse primers. The length of the common sequence may be in the range of 17 to 30 nucleotides long, e.g., 18 to 28 nucleotides long, 19 to 26 nucleotides long, including 20 to 25 nucleotides long.

"Encode," as used in reference to a nucleotide sequence of nucleic acid encoding a gene product, e.g., a protein, of interest, is meant to include instances in which a nucleic acid contains a nucleotide sequence that is the same as the endogenous sequence, or a portion thereof, of a nucleic acid found in a cell or genome that, when transcribed and/or translated into a polypeptide, produces the gene product. In some instances, a nucleotide sequence or nucleic acid encoding a gene product does not include intronic sequences. In particular instances, a nucleotide sequence or nucleic acid encoding a T cell receptor includes a nucleotide sequence that can be translated, in silico, into an amino acid sequence corresponding to variable and constant domains of a T cell receptor, with no intervening intronic sequences.

"Target nucleic acid" or "target nucleotide sequence," as used herein, refers to any nucleic acid or nucleotide sequence that is of interest for which the presence and/or expression level in a single cell is sought using a method of the present disclosure. A target nucleic acid may include a nucleic acid having a defined nucleotide sequence (e.g., a nucleotide sequence encoding a cytokine), or may encompass one or more nucleotide sequences encoding a class of proteins (e.g., a target nucleotide sequence encoding a T cell receptor alpha chain may refer to a nucleotide sequences encoding a T cell receptor alpha chain or any variants thereof that may vary at least within complementarity determining region 3 (CDR 3)).

"Originate," as used in reference to a source of an amplified piece of nucleic acid, refers to the nucleic acid being derived either directly or indirectly from the source, e.g., a well in which a single T cell is sorted. Thus in some cases, the origin of a nucleic acid obtained as a result of a sequential amplification of an original nucleic acid may be determined by reading barcode sequences that were incorporated into the nucleic acid during an amplification step performed in a location that can in turn be physically traced back to the single T cell source based on the series of sample transfers that was performed between the sequential amplification steps.

Before describing the present invention in detail, it is to be understood that this invention is not limited to particular formulations or process parameters as such may, of course, vary. It is also to be understood that the terminology used herein is for the purpose of describing particular embodiments of the invention only, and is not intended to be limiting.

Although a number of methods and materials similar or equivalent to those described herein can be used in the practice of the present invention, the preferred materials and methods are described herein.

DETAILED DESCRIPTION

The present disclosure provides oligonucleotide reagents and methods for analyzing individual T cells by high-throughput multiplex amplification and sequencing of nucleic acids encoding T cell receptors (TCRs) and various other T cell phenotypic markers. The methods generally involve sorting of single T cells into separate locations (e.g., separate wells of a multi-well titer plate) followed by nested polymerase chain reaction (PCR) amplification of nucleic acids encoding TCRs and T cell phenotypic markers. The amplicons are barcoded to identify their cell of origin, combined, and analyzed by deep sequencing. The present disclosure provides methods of reconstituting TCRs from individual T cells for functional studies, ligand discovery, or screening therapeutics.

The present invention is based on the discovery of reagents and methods for profiling T lymphocytes using high-throughput multiplex amplification and deep sequencing of single T cells. The method involves amplification of TCR gene transcripts as well as genes that specify particular T cell types and functions (see Example 1). Primers used in amplification include TCR primers for both TCR alpha and beta chain gene transcripts and phenotyping primers for multiple cytokines (e.g., pro-inflammatory and inhibitory) and transcription factors that are important in T cell function and specific for particular T cell types. Single T cells are sorted into separate locations (e.g., separate wells of a multi-well titer plate) followed by amplification of nucleic acids encoding the TCR and phenotypic markers. The amplicons are barcoded to identify their cell of origin, combined and analyzed by deep sequencing. The invention also includes methods of reconstituting TCRs from individual T cells based on knowledge of their sequences for functional studies, ligand discovery, or therapeutics.

In order to further an understanding of the invention, a more detailed discussion is provided below regarding methods of analyzing single T cells using high-throughput multiplex amplification and deep sequencing.

Methods

The present disclosure provides oligonucleotide reagents and methods for analyzing individual T cells by high-throughput multiplex amplification and sequencing of nucleic acids encoding T cell receptors (TCRs) and various other T cell phenotypic markers. The methods generally involve sorting of single T cells into separate locations (e.g., separate wells of a multi-well titer plate) followed by nested polymerase chain reaction (PCR) amplification of nucleic acids encoding TCRs and T cell phenotypic markers. The amplicons are barcoded to identify their cell of origin, combined, and analyzed by deep sequencing. The present disclosure provides methods of reconstituting TCRs from individual T cells for functional studies, ligand discovery, or screening therapeutics.

A. Amplification of Nucleic Acids from Single T Cells

A relatively low cost, high throughput single-cell sequencing technology is described capable of providing multiparameter measurements on large numbers of individual T cells. Such technology will be invaluable in diagnosing and treating a wide variety of diseases, including inflammatory disorders, autoimmune diseases, infectious diseases, and cancer.

First, a biological sample comprising T cells is collected from a subject. The biological sample can be any sample of bodily fluid or tissue containing T cells, including but not limited to, samples of blood, thymus, spleen, lymph nodes, bone marrow, a tumor biopsy, or an inflammatory lesion biopsy. In particular, samples of T cells may be taken from sites of inflamed, infected, or injured tissue, including but not limited to sites of tumors, transplant rejection, tissue damage, such as caused by traumatic injury or autoimmune disease, and organs or tissues targeted by pathogenic organisms. The biological sample may also include samples from in vitro cell culture resulting from the growth of T cells from the subject in culture. The biological sample can be obtained from a subject by conventional techniques. For example, blood can be obtained by venipuncture. Surgical techniques for obtaining solid tissue samples are well known in the art. Samples may be obtained from a subject prior to diagnosis and throughout a course of treatment.

Next, single T cells are isolated from the biological sample and sorted into separate locations. The separate locations can be separate reaction containers, such as wells of a multi-well plate (e.g., 96 well plate, 384-well plate, 1536-well plate) or microwell array, capillaries or tubes (e.g., 0.2 mL tubes, 0.5 mL tubes, 1.5 mL tubes), or chambers in a microfluidic device. Alternatively, the separate locations can be emulsion droplets that spatially separate cells.

Various methods are known in the art for isolating single cells. In some embodiments, the sample is sorted to obtain single T cells using a flow cytometer. Methods of preparing a sample of cells for flow cytometry analysis is described in, e.g., U.S. Pat. Nos. 5,378,633, 5,631,165, 6,524,858, 5,266, 269, 5,017,497 and 6,549,876; U.S. App. Pub. Nos. US20120178098, US20080153170, 20010006787, US20080158561, US20100151472, US20100099074, US20100009364, US20090269800, US20080241820, US20080182262, US20070196870 and US20080268494; PCT publication WO99/54494; Brown et al (Clin Chem. 2000 46:1221-9), McCoy et al (Hematol. Oncol. Clin. North Am. 2002 16:229-43) and Scheffold J. Clin. Immunol. 2000 20:400-7) and books such as Carey et al (*Flow Cytometry in Clinical Diagnosis*, 4*th* Edition ASCP Press, 2007), Ormerod (*Flow Cytometry—A practical approach* 3rd Edition. Oxford University Press, Oxford, UK 2000), Ormerod (*Flow Cytometry* 2nd Edition. BIOS Scientific Publishers, Oxford, UK 1999) and Ormerod (*Flow Cytometry—A basic introduction* 2009 Cytometry Part A 75A, 2009), each of which are incorporated by reference herein.

In some instances, single T cells can be isolated from a biological sample comprising T cells by appropriate dilution of a sample to allow distribution of a single cell in a small isolation volume to a separate location. In certain embodiments, a microfluidic device is used for isolating single cells and distributing single cells to separate locations in the device, such as separate wells or chambers. Alternatively, a microfluidic device can be used to generate emulsion droplets containing single cells. For a description of techniques for isolating single cells and microfluidic devices for sorting single cells, see, e.g., Huang et al. (2014) Lab Chip. 14(7): 1230-1245; Zare et al. (2010) Annu. Rev. Biomed. Eng. 12:187-201; Novak et al. (2011) Angew. Chem. Int. Ed. 50:390-395; U.S. patent publication 2010/0255471; U.S. patent publication 2010/0285975; U.S. patent publication 2010/0021984; U.S. patent publication 2010/0173394; International patent publication WO2009/145925; and U.S. patent publication 2009/0181859; herein incorporated by reference.

In certain embodiments, the sample is labeled with one or more detectable labels that bind to cells within the sample before sorting the cells. In some cases the detectable label linked to the detectable label include a binding agent that binds to a binding partner on a cell in the sample. In case of labeling T cells, the binding agent may be an antibody (e.g., anti-CD3, anti-CD4, anti-CD8, anti-αβTCR, anti-CD25, anti-CD45RA, anti-CD45RO, anti-FOXP3, etc.) that specifically binds to a binding partner on or in a T cell. Thus, in some cases the T-cell is permeabilized before labeling. In some embodiments, one or more labeling agent is used to classify a cell, e.g., T cell, within a sample, based on the amount of label bound to the cell.

In some embodiments, a subset of cells within a sample is sorted as single cells into separate locations. Thus, cells may be sorted to include a first subset and exclude a second subset of cells within the sample. The first subset and second subsets may be defined by a number of factors, including, but not limited to, amount of detectable label that is bound, size, light scattering properties, amount of staining by dyes that indicate viability or lack thereof, etc., of a cell. Thus, in some instances, a T cell that is labeled with an anti-CD4, anti-CD8, anti-CD45RA, anti-CD45RO, or a combination thereof, and is not labeled as being dead, is included to be sorted to generate single T cells in separate locations.

In some cases, sorting the T cells into separate locations as single cells may result in a subset of the separate locations having two or more T cells. These locations with potentially more than one T cells may be identified and flagged during data analysis of the sequencing data, and data from such locations in some cases may be removed from further analysis.

As explained above, the primers described herein may be used in polymerase chain reaction (PCR)-based techniques, such as RT-PCR, for amplification of T cell mRNA. PCR is a technique for amplifying a desired target nucleic acid sequence contained in a nucleic acid molecule or mixture of molecules. In PCR, a pair of primers is employed in excess to hybridize to the complementary strands of the target nucleic acid. The primers are each extended by a polymerase using the target nucleic acid as a template. The extension products become target sequences themselves after dissociation from the original target strand. New primers are then hybridized and extended by a polymerase, and the cycle is repeated to geometrically increase the number of target sequence molecules. The PCR method for amplifying target nucleic acid sequences in a sample is well known in the art and has been described in, e.g., Innis et al. (eds.) *PCR Protocols* (Academic Press, NY 1990); Taylor (1991) *Polymerase chain reaction: basic principles and automation, in PCR: A Practical Approach*, McPherson et al. (eds.) IRL Press, Oxford; Saiki et al. (1986) *Nature* 324:163; as well as in U.S. Pat. Nos. 4,683,195, 4,683,202 and 4,889,818, all incorporated herein by reference in their entireties.

In particular, PCR uses relatively short oligonucleotide primers which flank the target nucleotide sequence to be amplified, oriented such that their 3' ends face each other, each primer extending toward the other. The polynucleotide sample is extracted and denatured, e.g., by heat, and hybridized with first and second primers that are present in molar excess. Polymerization is catalyzed in the presence of the four deoxyribonucleotide triphosphates (dNTPs—dATP, dGTP, dCTP and dTTP) using a primer- and template-dependent polynucleotide polymerizing agent, such as any enzyme capable of producing primer extension products, for example, *E. coli* DNA polymerase I, Klenow fragment of DNA polymerase I, T4 DNA polymerase, thermostable DNA polymerases isolated from *Thermus aquaticus* (Taq), available from a variety of sources (for example, Perkin Elmer), *Thermus thermophilus* (United States Biochemicals), *Bacillus stereothermophilus* (Bio-Rad), or *Thermococcus litoralis* ("Vent" polymerase, New England Biolabs). This results in two "long products" which contain the respective primers at their 5' ends covalently linked to the newly synthesized complements of the original strands. The reaction mixture is then returned to polymerizing conditions, e.g., by lowering the temperature, inactivating a denaturing agent, or adding more polymerase, and a second cycle is initiated. The second cycle provides the two original strands, the two long products from the first cycle, two new long products replicated from the original strands, and two "short products" replicated from the long products. The short products have the sequence of the target sequence with a primer at each end. On each additional cycle, an additional two long products are produced, and a number of short products equal to the number of long and short products remaining at the end of the previous cycle. Thus, the number of short products containing the target sequence grows exponentially with each cycle. In some cases, PCR is carried out with a commercially available thermal cycler, e.g., Perkin Elmer.

RNA may be amplified by reverse transcribing the RNA into cDNA, and then performing PCR (RT-PCR), as described above. Alternatively, a single enzyme may be used for both steps as described in U.S. Pat. No. 5,322,770, incorporated herein by reference in its entirety. RNA may also be reverse transcribed into cDNA, followed by asymmetric gap ligase chain reaction (RT-AGLCR) as described by Marshall et al. (1994) *PCR Meth. App.* 4:80-84. Suitable DNA polymerases include reverse transcriptases, such as avian myeloblastosis virus (AMV) reverse transcriptase (available from, e.g., Seikagaku America, Inc.) and Moloney murine leukemia virus (MMLV) reverse transcriptase (available from, e.g., Bethesda Research Laboratories).

Promoters or promoter sequences suitable for incorporation in the primers are nucleic acid sequences (either naturally occurring, produced synthetically or a product of a restriction digest) that are specifically recognized by an RNA polymerase that recognizes and binds to that sequence and initiates the process of transcription whereby RNA transcripts are produced. The sequence may optionally include nucleotide bases extending beyond the actual recognition site for the RNA polymerase which may impart added stability or susceptibility to degradation processes or increased transcription efficiency. Examples of useful promoters include those which are recognized by certain bacteriophage polymerases such as those from bacteriophage T3, T7 or SP6, or a promoter from *E. coli*. These RNA polymerases are readily available from commercial sources, such as New England Biolabs and Epicentre.

Some of the reverse transcriptases suitable for use in the methods herein have an RNAse H activity, such as AMV reverse transcriptase. In some cases, exogenous RNAse H, such as *E. coli* RNAse H, is added, even when AMV reverse transcriptase is used. RNAse H is readily available from, e.g., Bethesda Research Laboratories.

The RNA transcripts produced by these methods may serve as templates to produce additional copies of the target sequence through the above-described mechanisms. The system is autocatalytic and amplification occurs autocatalytically without the need for repeatedly modifying or changing reaction conditions such as temperature, pH, ionic strength or the like.

The methods of the present disclosure utilize a multiplexed nested RT-PCR approach. For each T cell target nucleic acid, PCR is carried out in at least two steps, wherein the amplicon product from a first round of PCR becomes the template for a second round of PCR using a second set of primers, at least one of which binds to an interior location of the amplicon from the first round of PCR, to generate a second amplicon product. In certain embodiments, a third round of PCR is carried out on the second amplicon product using a third set of primers to generate a third amplicon product.

In certain embodiments, multiplexed nested PCR is carried out with multiple T cell target sequences (e.g., encoding TCRs and other T cell phenotypic markers) simultaneously in the same reaction mixture. Distinct sets of primers are employed for each sequence being amplified as described herein. Exemplary primers (SEQ ID NOS:7-262) are described in Example 1 (see Tables 1-3 provided in FIGS. 12A-H, 13A-B and 14A-C, respectively) for amplifying TCRs (e.g., both α and β chains of the heterodimer) and various other T cell phenotypic markers, including cytokines (e.g., pro-inflammatory and inhibitory) and transcription factors, which are important in T cell function and specific for particular T cell types, and also for adding barcodes and sequencing adapters for paired-end sequencing. Changes to the nucleotide sequences of these primers may be introduced corresponding to genetic variations in particular T cells. For example up to three nucleotide changes, including 1 nucleotide change, 2 nucleotide changes, or three nucleotide changes, may be made in a sequence selected from the group consisting of SEQ ID NOS:7-262, wherein the oligonucleotide primer is capable of hybridizing to and amplifying or sequencing a T cell target nucleic acid (e.g., nucleic acid encoding TCR or other T cell phenotypic marker).

In certain cases, a first set of primers used to amplify a target nucleic acid, e.g., a nucleic acid encoding a TCR or a T cell phenotypic marker, may contain a primer that specifically hybridizes to and amplifies, when paired with another appropriate primer in the first set, the target nucleic acid during a first round of PCR. A second set of primers may then be used to further amplify the target nucleic acid when the second set contains a primer that specifically hybridizes to and amplifies, when paired with another appropriate primer in the second set, a specific amplification product of the first round of PCR during a second round of PCR. Similarly, a third set of primers may then be used to further amplify the target nucleic acid when the third set contains a primer that specifically hybridizes to and amplifies, when paired with another appropriate primer in the third set, a specific amplification product of the second round of PCR during a third round of PCR.

In some embodiments, primers within a set of primers may include, in addition to a sequence that hybridizes to a target nucleic acid, or an amplification product thereof, a common sequence and/or a barcode sequence. The common sequence may be the same sequence among a plurality of primers that otherwise hybridize to and amplify, when appropriately paired with another primer, different target nucleic acids, or amplification products thereof. In some cases, the common sequence in a primer used during a round of PCR enables a primer used during a following round of PCR to anneal to and amplify, when paired with an appropriate primer, the target nucleic acid by serving as an annealing site for the primer used during a following round of PCR. As such, in some cases the common sequence in a primer used during a round of PCR is a sequence that does not hybridize to target-specific sequences of a target nucleic acid, or to a specific amplification product from a previous round of PCR. In some cases, the common sequence is a sequence that hybridizes to a target nucleic acid, if, for example, the target nucleic acid includes a sequence that is shared among different target nucleic acids, e.g., a sequence encoding a constant region of a TCR.

The multiplexed PCR reactions may be carried out in one or more of the separate locations into which single T cells from a sample have been sorted. In some cases, the amplification products of the multiplexed PCR reaction carried out in multiple separate locations are combined into one pool before sequenceing. In such cases, the barcode sequence used in one of the rounds of the multiplexed PCR reactions may be used to enable identification of the location, e.g., well, from which a particular sequenced amplification product originated, as described further below.

Primer Sets

The present disclosure provides compositions that include primers that amplify nucleotide sequences encoding T cell receptors, or a portion thereof. In some embodiments, the composition includes a first set of forward primers that includes 5 or more, e.g., 8 or more, 10 or more, 12 or more, 15 or more, 18 or more, 20 or more, 25 or more, 30 or more, 35 or more, or all of the nucleotide sequences of SEQ ID NOS:7-44, 57 and 58, or a variant thereof that differs by up to three nucleotides, and a first set of one or more reverse primers that hybridize to nucleotide sequences encoding a constant region of a T cell receptor, wherein the primers of the composition amplify nucleotide sequences encoding T cell receptors, or a portion thereof. In some embodiments, the first set of forward primers further includes 5 or more, e.g., 8 or more, 10 or more, 12 or more, 15 or more, 18 or more, 20 or more, 25 or more, 30 or more, 35 or more, or all of the nucleotide sequences of SEQ ID NOS:45-56, and 59-80, or a variant thereof that differs by up to three nucleotides, wherein the primers of the comparison amplify nucleotide sequences encoding T cell receptors, or a portion thereof.

In some embodiments, a composition of the present disclosure includes a first set of forward primers that includes 15 or more, e.g., 20 or more, 30 or more, 40 or more, 50 or more, 60 or more, 70 or more, and up to 80 different forward primers that hybridize to 15 or more, e.g., 20 or more, 30 or more, 40 or more, 50 or more, 60 or more, 70 or more, and up to 80 different nucleotide sequences that each encode a T cell receptor.

The T cell receptor encoded by the nucleotide sequence to which the primers of the present composition hybridize may be any suitable T cell receptor, and in some cases the T cell receptor is a member of different T cell receptor subtypes. Thus, in some cases, the T cell receptor may be a T cell receptor alpha chain, beta chain, delta chain or gamma chain.

The reverse primers may be any suitable reverse primer that hybridizes to a nucleotide sequence encoding a T cell receptor and that, when paired with a forward primer, as described herein, amplifies a nucleotide sequence encoding the T cell receptor, or a portion thereof. In some cases, the reverse primer of the first set of reverse primers hybridizes to nucleotide sequences encoding a constant region of a T cell receptor alpha chain, beta chain, delta chain or gamma chain. In some embodiments, the reverse primers of the first set of reverse primers includes the nucleotide sequences of SEQ ID NOS:81 and/or 82, or a variant thereof that differs by up to three nucleotides.

In one embodiment, the present disclosure provides a composition comprising a set of primers collectively comprising the nucleotide sequences of SEQ ID NOS:7-82 or variants thereof, wherein one or more primers may comprise a nucleotide sequence that differs from a nucleotide sequence selected from the group consisting of SEQ ID NOS:7-82 by up to three nucleotide changes, wherein the primers are capable of hybridizing to and amplifying nucleotide sequences encoding T cell receptors.

In some embodiments, the composition further includes a first set of phenotypic marker primers that includes one or more primer pairs that hybridize to and amplify nucleotide sequences encoding a T cell phenotypic marker, or a portion thereof. The T cell phenotypic marker may be any suitable phenotypic marker that may aid in classifying a T cell based on the expression, e.g., mRNA expression, of the phenotypic marker. Exemplary phenotypic markers include cytokines, cytokine receptors, cell-surface receptors, intracellular signaling molecules, and transcription factors. In certain embodiments, the T cell phenotypic marker is selected from IL2, IL10, IL12A, IL13, IL17A, IFNG, PRF1, GZMB TGFB, TNFA, BCL6, TBET, GATA3, RORC, FOXP3, RUNX1, RUNX3, CD4, CD8, CD11a, CD18, CD25, CD29, CCD30, CD38, CD44, CD45, CD45RA, CD45RO, CD49d, CD62, CD62L, CD69, CD71, CD103, CD137 (4-1BB), CD161, CD294, CCR5, CXCR4, HLA-DR, IL-5, IL-6, IL-9, IL-12, IL-15, IL-21, TLR2, TLR3, TLR4, TLR5, TLR6, TLR7, TLR8, TLR9 and TLR10. In some embodiments, the T cell phenotypic marker is selected from: IL2, IL10, IL12A, IL13, IL17A, IFNG, PRF1, GZMB TGFB, TNFA, BCL6, TBET, GATA3, RORC, FOXP3, RUNX1, and RUNX3. In some embodiments, the composition includes a first set of phenotypic marker primers that includes a plurality of primer pairs that collectively can amplify 10 or more, e.g., 10 or more, 15 or more, 17 or more, including 20 more, nucleotide sequences encoding a T cell phenotypic marker, or a portion thereof, and in some cases may include a plurality of primer pairs that collectively can amplify 25 or fewer, e.g., 22 or fewer, including 20 or fewer nucleotide sequences encoding a T cell phenotypic marker.

In some embodiments, the composition includes a first set of phenotypic marker primers that includes a pair of primers selected from SEQ ID NO:157 and SEQ ID NO:158, SEQ ID NO:161 and SEQ ID NO:162, SEQ ID NO:165 and SEQ ID NO:166, SEQ ID NO:169 and SEQ ID NO:170, SEQ ID NO:173 and SEQ ID NO:174, SEQ ID NO:177 and SEQ ID NO:178, SEQ ID NO:181 and SEQ ID NO:182, SEQ ID NO:185 and SEQ ID NO:186, SEQ ID NO:189 and SEQ ID NO:190, SEQ ID NO:193 and SEQ ID NO:194, SEQ ID NO:197 and SEQ ID NO:198, SEQ ID NO:201 and SEQ ID NO:202, SEQ ID NO:205 and SEQ ID NO:206, SEQ ID NO:209 and SEQ ID NO:210, SEQ ID NO:213 and SEQ ID NO:214, SEQ ID NO:217 and SEQ ID NO:218, SEQ ID NO:221 and SEQ ID NO:222, or any variant of either primer of the primer pair that differs by up to three nucleotides.

In certain embodiments, the composition further comprises one or more primers selected from the group consisting of: a) a primer comprising a nucleotide sequence selected from the group consisting of SEQ ID NO:157, SEQ ID NO:158, SEQ ID NO:161, SEQ ID NO:162, SEQ ID NO:165, SEQ ID NO:166, SEQ ID NO:169, SEQ ID NO:170, SEQ ID NO:173, SEQ ID NO:174, SEQ ID NO:177, SEQ ID NO:178, SEQ ID NO:181, SEQ ID NO:182, SEQ ID NO:185, SEQ ID NO:186, SEQ ID NO:189, SEQ ID NO:190, SEQ ID NO:193, SEQ ID NO:194, SEQ ID NO:197, SEQ ID NO:198, SEQ ID NO:201, SEQ ID NO:202, SEQ ID NO:205, SEQ ID NO:206, SEQ ID NO:209, SEQ ID NO:210, SEQ ID NO:213, SEQ ID NO:214, SEQ ID NO:217, SEQ ID NO:218, SEQ ID NO:221, and SEQ ID NO:222; and b) a primer comprising a nucleotide sequence that differs from a sequence selected from the group consisting of SEQ ID NO:157, SEQ ID NO:158, SEQ ID NO:161, SEQ ID NO:162, SEQ ID NO:165, SEQ ID NO:166, SEQ ID NO:169, SEQ ID NO:170, SEQ ID NO:173, SEQ ID NO:174, SEQ ID NO:177, SEQ ID NO:178, SEQ ID NO:181, SEQ ID NO:182, SEQ ID NO:185, SEQ ID NO:186, SEQ ID NO:189, SEQ ID NO:190, SEQ ID NO:193, SEQ ID NO:194, SEQ ID NO:197, SEQ ID NO:198, SEQ ID NO:201, SEQ ID NO:202, SEQ ID NO:205, SEQ ID NO:206, SEQ ID NO:209, SEQ ID NO:210, SEQ ID NO:213, SEQ ID NO:214, SEQ ID NO:217, SEQ ID NO:218, SEQ ID NO:221, and SEQ ID NO:222 by up to three nucleotide changes, wherein the primer is capable of hybridizing to and amplifying a sequence encoding a T cell phenotypic marker. In one embodiment, the composition comprises primers comprising the nucleotide sequences of SEQ ID NO:157, SEQ ID NO:158, SEQ ID NO:161, SEQ ID NO:162, SEQ ID NO:165, SEQ ID NO:166, SEQ ID NO:169, SEQ ID NO:170, SEQ ID NO:173, SEQ ID NO:174, SEQ ID NO:177, SEQ ID NO:178, SEQ ID NO:181, SEQ ID NO:182, SEQ ID NO:185, SEQ ID NO:186, SEQ ID NO:189, SEQ ID NO:190, SEQ ID NO:193, SEQ ID NO:194, SEQ ID NO:197, SEQ ID NO:198, SEQ ID NO:201, SEQ ID NO:202, SEQ ID NO:205, SEQ ID NO:206, SEQ ID NO:209, SEQ ID NO:210, SEQ ID NO:213, SEQ ID NO:214, SEQ ID NO:217, SEQ ID NO:218, SEQ ID NO:221, and SEQ ID NO:222.

In another embodiment, the present disclosure provides a composition comprising a set of primers collectively comprising the nucleotide sequences of SEQ ID NOS:83-156 or variants thereof, wherein one or more primers may comprise a nucleotide sequence that differs from a nucleotide sequence selected from the group consisting of SEQ ID NOS: 83-156 by up to three nucleotide changes, wherein the primers are capable of hybridizing to and amplifying nucleotide sequences encoding T cell receptors. In one embodiment, the composition further comprises one or more primers selected from the group consisting of: a) a primer comprising a nucleotide sequence selected from the group consisting of SEQ ID NO:159, SEQ ID NO:160, SEQ ID NO:163, SEQ ID NO:164, SEQ ID NO:167, SEQ ID NO:168, SEQ ID NO:171, SEQ ID NO:172, SEQ ID NO:175, SEQ ID NO:176, SEQ ID NO:179, SEQ ID NO:180, SEQ ID NO:183, SEQ ID NO:184, SEQ ID NO:187, SEQ ID NO:188, SEQ ID NO:191, SEQ ID NO:192, SEQ ID NO:195, SEQ ID NO:196, SEQ ID NO:199, SEQ ID NO:200, SEQ ID NO:203, SEQ ID NO:204, SEQ ID NO:207, SEQ ID NO:208, SEQ ID NO: 211, SEQ ID NO:212, SEQ ID NO:215, SEQ ID NO:216, SEQ ID NO:219, SEQ ID NO:220, SEQ ID NO:223, and SEQ ID NO:224; and b) a primer comprising a nucleotide sequence that differs from a sequence selected from the group consisting of SEQ ID NO:159, SEQ ID NO:160, SEQ ID NO:163, SEQ ID NO:164, SEQ ID NO:167, SEQ ID NO:168, SEQ ID NO:171, SEQ ID NO:172, SEQ ID NO:175, SEQ ID NO:176, SEQ ID NO:179, SEQ ID NO:180, SEQ ID NO:183, SEQ ID NO:184, SEQ ID NO:187, SEQ ID NO:188, SEQ ID NO:191, SEQ ID NO:192, SEQ ID NO:195, SEQ ID NO:196, SEQ ID NO:199, SEQ ID NO:200, SEQ ID NO:203, SEQ ID NO:204, SEQ ID NO:207, SEQ ID NO:208, SEQ ID NO: 211, SEQ ID NO:212, SEQ ID NO:215, SEQ ID NO:216, SEQ ID NO:219, SEQ ID NO:220, SEQ ID NO:223, and SEQ ID NO:224 by up to three nucleotide changes, wherein the primer is capable of hybridizing to and amplifying a sequence encoding a T cell phenotypic marker. In one embodiment, the composition comprises primers comprising the nucleotide sequences of SEQ ID NO:159, SEQ ID NO:160, SEQ ID NO:163, SEQ ID NO:164, SEQ ID NO:167, SEQ ID NO:168, SEQ ID NO:171, SEQ ID NO:172, SEQ ID NO:175, SEQ ID NO:176, SEQ ID NO:179, SEQ ID NO:180, SEQ ID NO:183, SEQ ID NO:184, SEQ ID NO:187, SEQ ID NO:188, SEQ ID NO:191, SEQ ID NO:192, SEQ ID NO:195, SEQ ID NO:196, SEQ ID NO:199, SEQ ID NO:200, SEQ ID NO:203, SEQ ID NO:204, SEQ ID NO:207, SEQ ID NO:208, SEQ ID NO: 211, SEQ ID NO:212, SEQ ID NO:215, SEQ ID NO:216, SEQ ID NO:219, SEQ ID NO:220, SEQ ID NO:223, and SEQ ID NO:224.

Figure 4A:
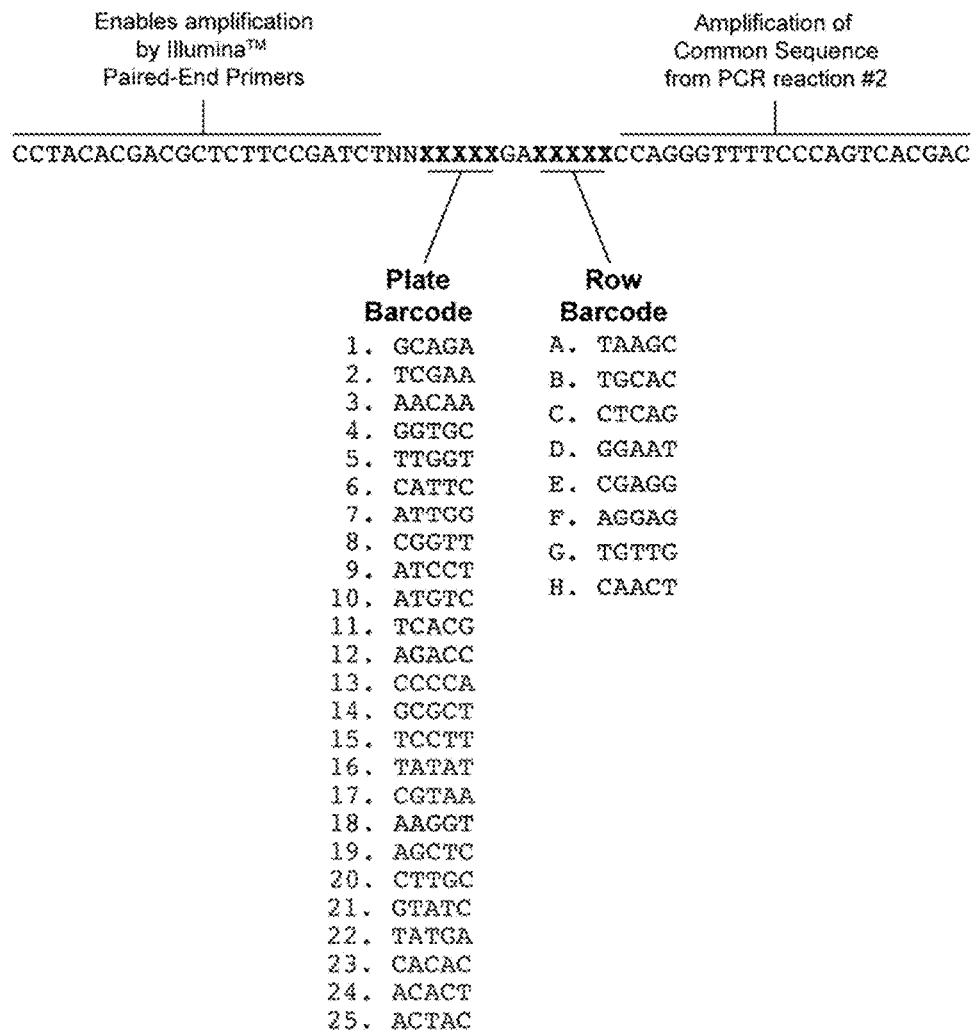
FIGS. 4A and 4B depict the barcoding primer design.

Additionally, barcode sequences can be added to amplicon products to identify the single T cell from which each amplified nucleic acid originated. The use of barcodes allows nucleic acid analytes from different cells to be pooled in a single reaction mixture for sequencing while still being able to trace back a particular target nucleic acid to the particular cell from which it originated. Each cell is identified by a unique barcode sequence comprising at least five nucleotides. A barcode sequence can be added during amplification by carrying out PCR with a primer that contains a region comprising the barcode sequence and a region that is complementary to the target nucleic acid of interest such that the barcode sequence is incorporated into the final amplified target nucleic acid product. Barcode sequences can be added at one or both ends of an amplicon. Exemplary barcode sequences are shown in FIG. 4A. In certain embodiments, single cells are initially sorted to separate locations in an ordered array or multi-well plate where the cell can be identified by its position using barcodes. See, e.g., Example 1 and FIG. 5 for a description of using barcodes to identify a cell by indexing according to the row and column of a multi-well plate. For example, barcode sequences can be added at both ends of an amplicon to identify the position of a cell in a multi-well plate by using a first barcode added at one end to identify the row and a second barcode added at the other end to identify the column of the multi-well plate.

Exemplary primers for adding barcodes are described in Example 1 (see, e.g., Table 3 provided in FIGS. 14A-C). In one embodiment, a primer for adding a barcode sequence to an amplicon of a nucleic acid encoding a TCR comprises a sequence selected from the group consisting of SEQ ID NOS: 225-248. In another embodiment, a primer for adding a barcode sequence to an amplicon of a nucleic acid encoding a T cell phenotypic marker comprises a sequence selected from the group consisting of SEQ ID NOS:249-260.

In addition, adapter sequences can be added to amplicons to facilitate high-throughput amplification or sequencing. For example, a pair of adapter sequences can be added at the 5' and 3' ends of a DNA template to allow amplification or sequencing of multiple DNA templates simultaneously by the same set of primers. Exemplary amplification adapter sequences comprise the sequences of SEQ ID NO:1 and SEQ ID NO:2. Exemplary adapter sequences for paired-end sequencing comprise the sequences of SEQ ID NO:261 and SEQ ID NO:262.

In some embodiments, the first set of forward primers and/or the first set of reverse primers, as described above, do not include a barcode sequence and/or an adapter sequence. In some embodiments, the second set of forward primers and/or the second set of reverse primers, as described above, do not include a barcode sequence.

Primers can be readily synthesized by standard techniques, e.g., solid phase synthesis via phosphoramidite chemistry, as disclosed in U.S. Pat. Nos. 4,458,066 and 4,415,732, incorporated herein by reference; Beaucage et al., *Tetrahedron* (1992) 48:2223-2311; and Applied Biosystems User Bulletin No. 13 (1 Apr. 1987). Other chemical synthesis methods include, for example, the phosphotriester method described by Narang et al., *Meth. Enzymol.* (1979) 68:90 and the phosphodiester method disclosed by Brown et al., *Meth. Enzymol.* (1979) 68:109. Poly(A) or poly(C), or other non-complementary nucleotide extensions may be incorporated into oligonucleotides using these same methods. Hexaethylene oxide extensions may be coupled to the oligonucleotides by methods known in the art. Cload et al., *J. Am. Chem. Soc.* (1991) 113:6324-6326; U.S. Pat. No. 4,914,210 to Levenson et al.; Durand et al., *Nucleic Acids Res.* (1990) 18:6353-6359; and Horn et al., *Tet. Lett.* (1986) 27:4705-4708.

Typically, the primer oligonucleotides are in the range of between 10-100 nucleotides in length, such as 15-60, 20-40 and so on, more typically in the range of between 20-40 nucleotides long, and any length between the stated ranges. In certain embodiments, a primer oligonucleotide comprises a sequence selected from the group consisting of SEQ ID NOS:1-262 or a fragment thereof comprising at least about 6 contiguous nucleotides, at least about 8 contiguous nucleotides, at least about 10-12 contiguous nucleotides, or at least about 15-20 contiguous nucleotides; or a variant thereof comprising a sequence having at least about 80-100% sequence identity thereto, including any percent identity within this range, such as 81, 82, 83, 84, 85, 86, 87, 88, 89, 90, 91, 92, 93, 94, 95, 96, 97, 98, or 99% sequence identity thereto. Changes to the nucleotide sequences of SEQ ID NOS:1-262 may be introduced corresponding to genetic variations in particular T cells. In certain embodiments, up to three nucleotide changes, including 1 nucleotide change, 2 nucleotide changes, or three nucleotide changes, may be made in a sequence selected from the group consisting of SEQ ID NOS:1-262, wherein the oligonucleotide primer is capable of hybridizing to and amplifying a particular T cell target nucleic acid.

Moreover, the oligonucleotides, particularly the primer oligonucleotides for amplification or sequencing, may be coupled to labels for detection. There are several means known for derivatizing oligonucleotides with reactive functionalities which permit the addition of a label. For example, several approaches are available for biotinylating probes so that radioactive, fluorescent, chemiluminescent, enzymatic, or electron dense labels can be attached via avidin. See, e.g., Broken et al., *Nucl. Acids Res.* (1978) 5:363-384 which discloses the use of ferritin-avidin-biotin labels; and Chollet et al., *Nucl. Acids Res.* (1985) 13:1529-1541 which discloses biotinylation of the 5' termini of oligonucleotides via an aminoalkylphosphoramide linker arm. Several methods are also available for synthesizing amino-derivatized oligonucleotides which are readily labeled by fluorescent or other types of compounds derivatized by amino-reactive groups, such as isothiocyanate, N-hydroxysuccinimide, or the like, see, e.g., Connolly, *Nucl. Acids Res.* (1987) 15:3131-3139, Gibson et al. *Nucl. Acids Res.* (1987) 15:6455-6467 and U.S. Pat. No. 4,605,735 to Miyoshi et al. Methods are also available for synthesizing sulfhydryl-derivatized oligonucleotides, which can be reacted with thiol-specific labels, see, e.g., U.S. Pat. No. 4,757,141 to Fung et al., Connolly et al., *Nucl. Acids Res.* (1985) 13:4485-4502 and Spoat et al. *Nucl. Acids Res.* (1987) 15:4837-4848. A comprehensive review of methodologies for labeling DNA fragments is provided in Matthews et al., *Anal. Biochem.* (1988) 169:1-25.

For example, oligonucleotides may be fluorescently labeled by linking a fluorescent molecule to the non-ligating terminus of the molecule. Guidance for selecting appropriate fluorescent labels can be found in Smith et al., *Meth. Enzymol.* (1987) 155:260-301; Karger et al., *Nucl. Acids Res.* (1991) 19:4955-4962; Guo et al. (2012) Anal. Bioanal. Chem. 402(10):3115-3125; and *Molecular Probes Handbook, A Guide to Fluorescent Probes and Labeling Technologies*, 11$^{th}$ edition, Johnson and Spence eds., 2010 (Molecular Probes/Life Technologies). Fluorescent labels include fluorescein and derivatives thereof, such as disclosed in U.S. Pat. No. 4,318,846 and Lee et al., *Cytometry* (1989) 10:151-164. Dyes for use in the present invention include 3-phenyl-7-isocyanatocoumarin, acridines, such as 9-isothiocyanatoacridine and acridine orange, pyrenes, benzoxadiazoles, and stilbenes, such as disclosed in U.S. Pat. No. 4,174,384. Additional dyes include SYBR green, SYBR gold, Yakima Yellow, Texas Red, 3-(ε-carboxypentyl)-3'-ethyl-5,5'-dimethyloxa-carbocyanine (CYA); 6-carboxy fluorescein (FAM); CAL Fluor Orange 560, CAL Fluor Red 610, Quasar Blue 670; 5,6-carboxyrhodamine-110 (R110); 6-carboxyrhodamine-6G (R6G); N',N',N',N'-tetramethyl-6-carboxyrhodamine (TAMRA); 6-carboxy-X-rhodamine (ROX); 2',4',5',7',-tetrachloro-4-7-dichlorofluorescein (TET); 2',7'-dimethoxy-4',5'-6 carboxyrhodamine (JOE); 6-carboxy-2',4,4',5',7,7'-hexachlorofluorescein (HEX);

Dragonfly orange; ATTO-Tec; Bodipy; ALEXA; VIC, Cy3, and Cy5. These dyes are commercially available from various suppliers such as Life Technologies (Carlsbad, Calif.), Biosearch Technologies (Novato, Calif.), and Integrated DNA Technolgies (Coralville, Iowa). Fluorescent labels include fluorescein and derivatives thereof, such as disclosed in U.S. Pat. No. 4,318,846 and Lee et al., *Cytometry* (1989) 10:151-164, and 6-FAM, JOE, TAMRA, ROX, HEX-1, HEX-2, ZOE, TET-1 or NAN-2, and the like.

Oligonucleotides can also be labeled with a minor groove binding (MGB) molecule, such as disclosed in U.S. Pat. No. 6,884,584, U.S. Pat. No. 5,801,155; Afonina et al. (2002) Biotechniques 32:940-944, 946-949; Lopez-Andreo et al. (2005) Anal. Biochem. 339:73-82; and Belousov et al. (2004) Hum Genomics 1:209-217. Oligonucleotides having a covalently attached MGB are more sequence specific for their complementary targets than unmodified oligonucleotides. In addition, an MGB group increases hybrid stability with complementary DNA target strands compared to unmodified oligonucleotides, allowing hybridization with shorter oligonucleotides.

Additionally, oligonucleotides can be labeled with an acridinium ester (AE) using the techniques described below. Current technologies allow the AE label to be placed at any location within the probe. See, e.g., Nelson et al., (1995) "Detection of Acridinium Esters by Chemiluminescence" in *Nonisotopic Probing, Blotting and Sequencing*, Kricka L. J(ed) Academic Press, San Diego, Calif.; Nelson et al. (1994) "Application of the Hybridization Protection Assay (HPA) to PCR" in *The Polymerase Chain Reaction*, Mullis et al. (eds.) Birkhauser, Boston, Mass.; Weeks et al., *Clin. Chem.* (1983) 29:1474-1479; Berry et al., *Clin. Chem.* (1988) 34:2087-2090. An AE molecule can be directly attached to the probe using non-nucleotide-based linker arm chemistry that allows placement of the label at any location within the probe. See, e.g., U.S. Pat. Nos. 5,585,481 and 5,185,439.

T cells may be pre-treated in any number of ways prior to amplification and sequencing of nucleic acids. For instance, in certain embodiments, the T cell may be treated to disrupt (or lyse) the cell membrane, for example by treating the samples with one or more detergents and/or denaturing agents (e.g., guanidinium agents). Nucleic acids may also be extracted from samples, for example, after detergent treatment and/or denaturing as described above. Total nucleic acid extraction may be performed using known techniques, for example by non-specific binding to a solid phase (e.g., silica). See, e.g., U.S. Pat. Nos. 5,234,809, 6,849,431; 6,838,243; 6,815,541; and 6,720,166.

In certain embodiments, the target nucleic acids are separated from non-homologous nucleic acids using capture oligonucleotides immobilized on a solid support. Such capture oligonucleotides contain nucleic acid sequences that are complementary to a nucleic acid sequence present in the target T cell nucleic acid analyte such that the capture oligonucleotide can "capture" the target nucleic acid. Capture oligonucleotides can be used alone or in combination to capture T cell nucleic acids. For example, multiple capture oligonucleotides can be used in combination, e.g., 2, 3, 4, 5, 6, etc. different capture oligonucleotides can be attached to a solid support to capture target T cell nucleic acids. In certain embodiments, one or more capture oligonucleotides can be used to bind T cell target nucleic acids either prior to or after amplification by primer oligonucleotides and/or sequencing.

As T cells may be sorted into single T cells in separate locations, e.g., separate wells, in the present methods, as described above, some embodiments of the present disclosure includes a composition including one or more sets of forward and reverse primers and/or sets of primer pairs, as described above, and nucleic acids from a single T cell. After single T cells are sorted to separate locations, they may be lysed in order to release cellular contents, such as nucleic acids (e.g., mRNA, miRNA, chromosomal DNA, mitochondrial DNA, etc.). The released nucleic acids may then provide templates, including any target nucleic acids, off of which PCR may be carried out using the primer compositions of the present disclosure. A composition that contains nucleic acids from a single T cell may be distinguished from a composition that contains nucleic acids from two or more T cells by, e.g., determining the number of one or more autosomal loci of chromosomal DNA using sequencing or other suitable methods, as described in, e.g., Kalisky et al., 2011. Nat Methods 8:311; Fu et al., 2011, Proc Natl Acad Sci USA. 108:9026; and Shuga et al., 2013. Nucleic Acids Res. 41:e159, which are incorporated by reference herein. Thus, in some embodiments, the composition contains one or more sets of forward and reverse primers and/or sets of primer pairs, as described above, and T cell nucleic acids from less than two T cells. In some embodiments, the composition contains no nucleases and/or contains nuclease inhibitors and/or provides buffering conditions that inhibits or reduces nucleic acid degradation at least until the first round of amplification.

B. Sequencing of Nucleic Acids

Any high-throughput technique for sequencing can be used in the practice of the invention. DNA sequencing techniques include dideoxy sequencing reactions (Sanger method) using labeled terminators or primers and gel separation in slab or capillary, sequencing by synthesis using reversibly terminated labeled nucleotides, pyrosequencing, 454 sequencing, sequencing by synthesis using allele specific hybridization to a library of labeled clones followed by ligation, real time monitoring of the incorporation of labeled nucleotides during a polymerization step, polony sequencing, SOLiD sequencing, and the like. These sequencing approaches can thus be used to sequence target nucleic acids of interest, including nucleic acids encoding TCRs and other T cell phenotypic markers amplified from single T cells.

Certain high-throughput methods of sequencing comprise a step in which individual molecules are spatially isolated on a solid surface where they are sequenced in parallel. Such solid surfaces may include nonporous surfaces (such as in Solexa sequencing, e.g. Bentley et al, Nature, 456: 53-59 (2008) or Complete Genomics sequencing, e.g. Drmanac et al, Science, 327: 78-81 (2010)), arrays of wells, which may include bead- or particle-bound templates (such as with 454, e.g. Margulies et al, Nature, 437: 376-380 (2005) or Ion Torrent sequencing, U.S. patent publication 2010/0137143 or 2010/0304982), micromachined membranes (such as with SMRT sequencing, e.g. Eid et al, Science, 323: 133-138 (2009)), or bead arrays (as with SOLiD sequencing or polony sequencing, e.g. Kim et al, Science, 316: 1481-1414 (2007)). Such methods may comprise amplifying the isolated molecules either before or after they are spatially isolated on a solid surface. Prior amplification may comprise emulsion-based amplification, such as emulsion PCR, or rolling circle amplification.

Of particular interest is sequencing on the Illumina® MiSeq platform, which uses reversible-terminator sequencing by synthesis technology (see, e.g., Shen et al. (2012) BMC Bioinformatics 13:160; Junemann et al. (2013) Nat. Biotechnol. 31(4):294-296; Glenn (2011) Mol. Ecol. Resour.

11(5):759-769; Thudi et al. (2012) Brief Funct. Genomics 11(1):3-11; herein incorporated by reference).

C. Analysis of Sequencing Data

The present disclosure also provides a method for analyzing multiplexed single cell sequencing data, such as those acquired using the method of analyzing single T cells described herein. In one implementation of the computer-implemented method, a user may access a file on a computer system, wherein the file is generated by sequencing multiplexed PCR amplification products from multiple single T cells by, e.g., a method of analyzing single T cells, as described herein. Thus, the file may include a plurality of sequencing reads for a plurality of nucleic acids derived from multiple T cells. Each of the sequencing reads may be a sequencing read of a nucleic acid that contains a target nucleic acid nucleotide sequence (e.g., a nucleotide sequence encoding T cell receptor or a T cell phenotypic marker) and one or more barcode sequences that identifies the single cell source (e.g., a single cell in a well in a multi-well plate, a capillary, a microfluidic chamber, etc.) from which the nucleic acid originated (e.g., after multiple nested PCR of the target nucleic acid expressed by a single T cell in the well). In some embodiments, the sequencing read is a paired-end sequencing read.

The sequencing reads in the file may be assembled to generate a consensus sequence of a target nucleic acid nucleotide sequence by matching the nucleotide sequence corresponding to the target nucleic acid nucleotide sequence and the barcode sequences contained in each sequencing read. Those sequencing reads that originate from the same single cell source (e.g., same well) and have a target nucleotide sequence that has a higher identity to a reference sequence than a threshold identity level may be assigned to the same target nucleic acid that was initially amplified from the single cell source, and may be grouped into a subset representing the target nucleic acid. The number of sequencing reads within the subset indicates how likely it is that the consensus sequence assembled from the sequencing reads in a subset is part of an actual nucleic acid molecule that was present in the single cell source. Thus, if the number of sequencing reads in a subset is above a background level, the consensus sequence derived from the subset may be considered to represent an actual sequence of a target nucleic acid in the single cell source. The consensus sequence may then be outputted, e.g., to a display, printout, database, etc.

In some embodiments, the reference sequence is a sequence for the targe nucleic acid in a reference database, such as GenBank®. Thus, in some embodiments, a target nucleotide sequence in a first sequencing read in a subset of sequencing reads, as described above, is 80% or more, e.g., 85% or more, 90% or more, 95% or more, or up to 100% identical to a reference sequence for the target nucleic acid from a reference database. In some embodiments, the reference sequence is one or more other sequences in sequencing reads of the same subset. Thus, in such cases, a target nucleotide sequence in a first sequencing read in a subset of sequencing reads, as described above, is 80% or more, e.g., 85% or more, 90% or more, 95% or more, or up to 100% identical to a target nucleotide sequence in a second sequencing read in the same subset. In some instances, a target nucleotide sequence in a first sequencing read in a subset is 80% or more, e.g., 85% or more, 90% or more, 95% or more, or up to 100% identical to a target nucleotide sequence in all other sequencing reads in the same subset.

In some embodiments, the present computer-implemented method includes determining whether the single cell source contained more than one variant of a target nucleotide sequence (e.g., expressed nucleotide sequences for more than one T cell receptor alpha chain that vary in CDR 3), or whether the single cell source may have had more than one cell. This may be achieved, for example, by first determining the number of subsets of sequencing reads for a T cell receptor subtype (e.g., alpha chain) from a single cell source, as defined by the barcode sequences, and then determining the percentage of sequencing reads that are present in each subset relative to the total number of sequencing reads that are assigned to all subsets of sequencing reads for all such T cell receptor subtypes (e.g., alpha chains) from the same single cell source. If the percentage is above a threshold percentage, which may be 10% or more, e.g., 20% or more, 40% or more, 60% or more, 80% or more, 85% or more, 90% or more, and up to 99.9%, the particular target nucleotide sequence variant (e.g., a T cell receptor alpha chain having a variant CDR 3) may be classified as being derived from a single cell source. In some cases, a consensus sequence for a T cell receptor alpha chain may be determined to be derived from a single cell source if the percentage of sequencing reads in the subset of sequencing reads used to assemble the consensus sequence is 10% or more, e.g., 15% or more, 20% or more, 30% or more, 40% or more, 50% or more, 80% or more, and up to 100% of the total number of sequencing reads that are assigned to all subsets of sequencing reads for T cell receptor alpha chains from the same single cell source. In some cases, a consensus sequence for a T cell receptor beta chain may be determined to be derived from a single cell source if the percentage of sequencing reads in the subset of sequencing reads used to assemble the consensus sequence is 80% or more, e.g., 85% or more, 90% or more, 95% or more, and up to 100% of the total number of sequencing reads that are assigned to all subsets of sequencing reads for T cell receptor beta chains from the same single cell source.

In certain embodiments, the sequencing reads are generated by a method of analyzing a T cell as disclosed herein. As such, in some embodiments, the target nucleic acid nucleotide sequence contained in the sequenced nucleic acid is flanked on the 5' end by a common sequence and a barcode sequence. In some cases, the sequenced nucleic acid has the structure: 5'-B1-C1-T-3', where B1 is a first barcode sequence, C1 is a first common sequence shared among all the sequenced plurality of nucleic acids, and T is the target nucleic acid nucleotide sequence. The first barcode sequence may contain one or more different barcode sequences that specify the single cell source of the target nucleic acid (e.g., the plate among a plurality of plates, the row among a plurality of rows in a multiwall plate, the column among a plurality of columns in a multiwall plate, etc.). The common sequence is incorporated into the amplified target nucleic acid during a round of the multiplex amplification process, e.g., during the second round of amplification, as described above, to provide for a primer annealing site that may be used in the next round, e.g., third round, of amplification, during which one or more barcode sequences is added 5' of the common sequence. Thus, the common sequence at the 5' end of the amplified target nucleotide sequence may be a sequence exogenous to the target nucleic acid and may not be a sequence that can hybridize to the target nucleotide sequence before the second round of amplification. The length of the common sequence may be in the range of 17 to 30 nucleotides long, e.g., 18 to 28 nucleotides long, 19 to 26 nucleotides long, including 20 to 25 nucleotides long. In some embodiments, the sequenced nucleic acid has the structure: 5'-B1-C1-T-C2-B2-3', where B1 and B2 are a first and second barcode sequences, respectively, C1 and C2 are a first and second common sequences, respectively, each shared among at least a subset of the sequenced plurality of nucleic acids, and T is the target nucleic acid nucleotide sequence. The second common sequence at the 3' end of the amplified target nucleotide sequence may or may not be a sequence exogenous to the target nucleic acid and may or may not be a sequence that can hybridize to the target nucleotide sequence before the second round of amplification.

The output of the analysis may be provided in any convenient form. In some embodiments, the output is provided on a user interface, a print out, in a database, etc. and the output may be in the form of a table, graph, raster plot, heat map etc. In some embodiments, the output is further analyzed to determine properties of the single cell from which a target nucleotide sequence was derived. Further analysis may include correlating expression of a plurality of target nucleotide sequences within single cells, principle component analysis, clustering, statistical analyses, etc.

A computer system for implementing the present computer-implemented method may include any arrangement of components as is commonly used in the art. The computer system may include a memory, a processor, input and output devices, a network interface, storage devices, power sources, and the like. The memory or storage device may be configured to store instructions that enable the processor to implement the present computer-implemented method by processing and executing the instructions stored in the memory or storage device.

D. Additional Embodiments

In certain embodiments, the present method of analyzing T cells includes stimulating T cells in a sample obtained from a subject before sorting single T cells into separate locations. The stimulating may be achieved by any convenient method. Stimulating T cells may include, but are not limited to, contacting the T cells with 12-myristate 13-acetate (PMA) and ionomycin, with PMA and anti-CD3/anti-CD28, with one or more antigens specifically recognized by one or more T cells of interest in the sample, or with extracts of cells or tissues. In some cases, a sample is divided into to a first sample whose T cells are stimulated and a second sample whose T cells are unstimulated, then the two samples are analyzed separately according to the method described herein.

In some cases, the third round of PCR in the present method of analyzing single T cells may involve splitting the amplification products encoding a TCR from the second round of PCR into two pools, and performing the third round of PCR in the first pool using a reverse primer that is specific to a first subtype of TCR, and in the second pool using a reverse primer that is specific to a second subtype of TCR. In such instances, the amplification product from the first pool and the second pool may include different T cell receptor chains (e.g., alpha, beta, delta or gamma chains). For example, the first pool may amplify a TCR with an alpha chain and the second pool a TCR with a beta chain. As with before, amplification products from the third round of PCR performed on amplification products originating from all or a subset of the separate locations containing a single T cell may be combined for sequencing.

In certain embodiments, the present method of analyzing single T cells is an efficient method of analyzing nucleic acids expressed in single T cells. The presence of a T cell receptor may be detected by the present method in 70% or more, e.g., 80% or more, 85% or more, 90% or more, 92% or more, or 94% or more, and in some cases 100% or less, e.g., 95% or less, or 94% or less of the single T cells sorted into the separate locations. In some instances, the presence of a T cell receptor may be detected by the present method in a range of 70 to 100%, e.g., a range of 80 to 98%, a range of 85 to 95%, including a range of 90 to 94% of the single T cells sorted into the separate locations. In some embodiments, presence of a T cell receptor alpha chain may be detected by the present method in 70% or more, e.g., 80% or more, 85% or more, or 90% or more, and in some cases 100% or less, e.g., 95% or less, or 90% or less of the single T cells sorted into the separate locations. In some instances, the presence of a T cell receptor alpha chain may be detected by the present method in a range of 70 to 100%, e.g., a range of 75 to 95%, a range of 80 to 92%, including a range of 85 to 90% of the single T cells sorted into the separate locations. In some embodiments, presence of a T cell receptor beta chain may be detected by the present method in 85% or more, e.g., 90% or more, or 94% or more, and in some cases 100% or less, e.g., 97% or less, or 94% or less of the single T cells sorted into the separate locations. In some instances, the presence of a T cell receptor beta chain may be detected by the present method in a range of 85 to 100%, e.g., a range of 98 to 98%, a range of 90 to 96%, including a range of 91 to 95% of the single T cells sorted into the separate locations.

In certain embodiments, the present method of analyzing single T cells is a sensitive method of analyzing nucleic acids expressed in single T cells. The present method may provide for detecting the presence of 50 molecules or less, e.g., 25 molecules or less, 20 molecules or less, 10 molecules or less, and down to 2 molecules of a target nucleic acid (e.g., mRNA for a T cell receptor) in a single T cell.

Utility

The technology described herein provides highly efficient TCR sequencing and multi-parametric phenotypic analysis of single T cells and will find numerous applications in basic research and development. This methodology requires no proprietary reagents or materials and can be performed at reasonable cost by any standardly equipped laboratory with access to flow cytometry and deep sequencing. Sequencing TCRs of single T cells provides information about the ancestry of particular T cells. The additional analysis of other phenotypic markers allows a determination of the phenotypic and functional range of T cells that arise from a single clone. Furthermore, the sequences of nucleic acids amplified from T cells can be analyzed for splice variations, somatic mutations, or genetic polymorphisms. Of particular interest are genetic variations and mutations associated with immune disorders or cancer.

This technology is complementary to recently developed methods to determine ligands for TCRs using random peptide-MHC libraries and for development of T cell based-therapies and vaccines. Such technology will be invaluable in diagnosing and treating a wide variety of diseases, including inflammatory disorders, autoimmune diseases, infectious diseases, and cancer.

Additionally, knowledge of the sequences of TCRs from individual cells allows TCRs to be reconstituted for functional studies. For example, after analyzing a T cell as described herein and identifying a sequence encoding a TCRα polypeptide and a sequence encoding a TCRβ polypeptide from a single T cell, recombinant constructs expressing the TCRαβ heterodimer can be constructed. A host cell can be transformed with one or more recombinant polynucleotides encoding the TCR (e.g., separate monocistronic constructs expressing each polypeptide chain of the TCR heterodimer or a bicistronic construct expressing both the TCRα polypeptide and the TCR beta polypeptide). The TCR of the single cell can be produced by culturing the host cell under conditions suitable for the expression of the TCRα polypeptide and the TCRβ polypeptide and recovering the TCRαβ heterodimer from the host cell culture.

The reconstituted TCR can be used in screening to determine the target antigen bound by the TCR by contacting the TCR with potential target antigens displayed in complexes with major histocompatibility complex (MHC), and determining whether or not the target antigen binds to the TCR. The TCR can be screened for antigen binding in a high-throughput manner by providing a peptide library comprising a plurality of peptides displayed by major histocompatibility complex (MHC) molecules; and contacting the plurality of peptides with the TCR; and identifying at least one peptide-MHC complex that binds to the TCR.

Any suitable antigen may find use in the present method. Exemplary antigens include, but are not limited to, antigenic molecules from infectious agents, auto-/self-antigens, tumor-/cancer-associated antigens, etc.

Tumor-associated antigens may be derived from prostate, breast, colorectal, lung, pancreatic, renal, mesothelioma, ovarian, or melanoma cancers, etc. Exemplary tumor-associated antigens or tumor cell-derived antigens include MAGE 1, 3, and MAGE 4 (or other MAGE antigens such as those disclosed in International Patent Application Publication No. WO99/40188); PRAME; BAGE; RAGE, Lage (also known as NY ESO 1); SAGE; and HAGE (see, e.g., International Patent Application Publication No. WO 99/53061) or GAGE (Robbins et al., Curr. Opin. Immunol. 8:628-36 (1996); Van den Eynde et al., Int. J. Clin. Lab. Res. 27:81-86 (1997); Van den Eynde et al., Curr. Opin. Immunol. 9:648-93 (1997); Correale et al., J. Natl. Cancer Inst. 89: 293 (1997)). These non-limiting examples of tumor antigens are expressed in a wide range of tumor types such as melanoma, lung carcinoma, sarcoma, and bladder carcinoma. See, e.g., U.S. Pat. No. 6,544,518. Prostate cancer tumor-associated antigens include, for example, prostate specific membrane antigen (PSMA), prostate-specific antigen (PSA), prostatic acid phosphates, NKX3.1, and six-transmembrane epithelial antigen of the prostate (STEAP) (Hubert et al., Proc. Natl. Acad. Sci. USA 96 14523-28, 1999); see also, e.g., Reiter et al., Proc. Nat. Acad. Sci. USA 95:1735-40, 1998; Nelson, et al., Proc. Natl. Acad. Sci. USA 96:3114-19 (1999); WO 98/12302; U.S. Pat. Nos. 5,955, 306; 5,840,871 and 5,786,148; Intl Patent Appl. Publication Nos. WO 98/20117; WO 00/04149; WO 98/137418).

Other tumor associated antigens include Plu-1 (J. Biol. Chem. 274:15633-45, 1999), HASH-1, HasH-2, Cripto (Salomon et al., Bioessays 199, 21:61-70; U.S. Pat. No. 5,654, 140) and Criptin (U.S. Pat. No. 5,981,215). Additionally, a tumor antigen may be a self peptide hormone, such as whole length gonadotrophin hormone releasing hormone (GnRH, Int'l Patent Appl. Publication No. WO 95/20600), a short 10 amino acid long peptide, useful in the treatment of many cancers.

Tumor antigens include tumor antigens derived from cancers that are characterized by tumor associated antigen expression, such as HER-2/neu expression. Tumor associated antigens of interest include lineage-specific tumor antigens such as the melanocyte-melanoma lineage antigens MART-1/Melan-A, gp100, gp75, mda-7, tyrosinase and tyrosinase-related protein. Illustrative tumor-associated antigens include, but are not limited to, tumor antigens derived from or comprising any one or more of, p53, Ras, c-Myc, cytoplasmic serine/threonine kinases (e.g., A-Raf, B-Raf, and C-Raf, cyclin-dependent kinases), MAGE-A1, MAGE-A2, MAGE-A3, MAGE-A4, MAGE-A6, MAGE-A10, MAGE-A12, MART-1, BAGE, DAM-6, -10, GAGE-1, -2, -8, GAGE-3, -4, -5, -6, -7B, NA88-A, MART-1, MC1R, Gp100, PSA, PSM, Tyrosinase, TRP-1, TRP-2, ART-4, CAMEL, CEA, Cyp-B, hTERT, hTRT, iCE, MUC1, MUC2, Phosphoinositide 3-kinases (PI3Ks), TRK receptors, PRAME, P15, RU1, RU2, SART-1, SART-3, Wilms' tumor antigen (WT1), AFP, -catenin/m, Caspase-8/m, CEA, CDK-4/m, ELF2M, GnT-V, G250, HSP70-2M, HST-2, KIAA0205, MUM-1, MUM-2, MUM-3, Myosin/m, RAGE, SART-2, TRP-2/INT2, 707-AP, Annexin II, CDC27/m, TPI/mbcr-abl, BCR-ABL, interferon regulatory factor 4 (IRF4), ETV6/AML, LDLR/FUT, Pml/RAR, Tumor-associated calcium signal transducer 1 (TACSTD1) TACSTD2, receptor tyrosine kinases (e.g., Epidermal Growth Factor receptor (EGFR) (in particular, EGFRvIII), platelet derived growth factor receptor (PDGFR), vascular endothelial growth factor receptor (VEGFR)), cytoplasmic tyrosine kinases (e.g., src-family, syk-ZAP70 family), integrin-linked kinase (ILK), signal transducers and activators of transcription STAT3, STAT5, and STATE, hypoxia inducible factors (e.g., HIF-1 and HIF-2), Nuclear Factor-Kappa B (NF-B), Notch receptors (e.g., Notch1-4), c-Met, mammalian targets of rapamycin (mTOR), WNT, extracellular signal-regulated kinases (ERKs), and their regulatory subunits, PMSA, PR-3, MDM2, Mesothelin, renal cell carcinoma-5T4, SM22-alpha, carbonic anhydrases I (CAI) and IX (CAIX) (also known as G250), STEAD, TEL/AML1, GD2, proteinase3, hTERT, sarcoma translocation breakpoints, EphA2, ML-IAP, EpCAM, ERG (TMPRSS2 ETS fusion gene), NA17, PAX3, ALK, androgen receptor, cyclin B1, polysialic acid, MYCN, RhoC, GD3, fucosyl GM1, mesothelian, PSCA, sLe, PLAC1, GM3, BORIS, Tn, GLoboH, NY-BR-1, RGsS, SART3, STn, PAX5, OY-TES1, sperm protein 17, LCK, HMWMAA, AKAP-4, SSX2, XAGE 1, B7H3, legumain, TIE2, Page4, MAD-CT-1, FAP, MAD-CT-2, fos related antigen 1, CBX2, CLDN6, SPANX, TPTE, ACTL8, ANKRD30A, CDKN2A, MAD2L1, CTAG1B, SUNC1, LRRN1 and idiotype.

Antigens may include epitopic regions or epitopic peptides derived from genes mutated in tumor cells or from genes transcribed at different levels in tumor cells compared to normal cells, such as telomerase enzyme, survivin, mesothelin, mutated ras, bcr/abl rearrangement, Her2/neu, mutated or wild-type p53, cytochrome P450 1B1, and abnormally expressed intron sequences such as N-acetylglucosaminyltransferase-V; clonal rearrangements of immunoglobulin genes generating unique idiotypes in myeloma and B-cell lymphomas; tumor antigens that include epitopic regions or epitopic peptides derived from oncoviral processes, such as human papilloma virus proteins E6 and E7; Epstein bar virus protein LMP2; nonmutated oncofetal proteins with a tumor-selective expression, such as carcinoembryonic antigen and alpha-fetoprotein. See also Boon et al., Ann. Rev. Immunol. 12:337-65 (1994); Renkvist et al., Cancer Immunol. Immunother. 50:3-15 (2001).

In other embodiments, an antigen is obtained or derived from a pathogenic microorganism or from an opportunistic pathogenic microorganism (also called herein an infectious disease microorganism), such as a virus, fungus, parasite, and bacterium. In certain embodiments, antigens derived from such a microorganism include full-length proteins.

Illustrative pathogenic organisms whose antigens are contemplated for use in the method described herein include human immunodeficiency virus (HIV), herpes simplex virus (HSV), respiratory syncytial virus (RSV), cytomegalovirus (CMV), Epstein-Barr virus (EBV), Influenza A, B, and C, vesicular stomatitis virus (VSV), vesicular stomatitis virus (VSV), *Staphylococcus* species including Methicillin-resistant *Staphylococcus aureus* (MRSA), and *Streptococcus* species including *Streptococcus pneumoniae*. As would be understood by the skilled person, proteins derived from these and other pathogenic microorganisms for use as antigen as described herein and nucleotide sequences encoding the proteins may be identified in publications and in public databases such as GENBANK®, Swiss-Prot®, and TrEMBL®.

Antigens derived from human immunodeficiency virus (HIV) include any of the HIV virion structural proteins (e.g., gp120, gp41, p17, p24), protease, reverse transcriptase, or HIV proteins encoded by tat, rev, nef, vif, vpr and vpu.

Antigens derived from herpes simplex virus (e.g., HSV 1 and HSV2) include, but are not limited to, proteins expressed from HSV late genes. The late group of genes predominantly encodes proteins that form the virion particle. Such proteins include the five proteins from (UL) which form the viral capsid: UL6, UL18, UL35, UL38 and the major capsid protein UL19, UL45, and UL27, each of which may be used as an antigen as described herein (see, e.g., McGeoch et al., Virus Res. 117:90-104 (2006); Mettenleiter et al., Curr. Opin. Microbiol. 9: 423-29 (2006)). Other illustrative HSV proteins contemplated for use as antigens herein include the ICP27 (H1, H2), glycoprotein B (gB) and glycoprotein D (gD) proteins. The HSV genome comprises at least 74 genes, each encoding a protein that could potentially be used as an antigen.

Antigens derived from cytomegalovirus (CMV) include CMV structural proteins, viral antigens expressed during the immediate early and early phases of virus replication, glycoproteins I and III, capsid protein, coat protein, lower matrix protein pp65 (ppUL83), p52 (ppUL44), IE1 and IE2 (UL123 and UL122), protein products from the cluster of genes from UL128-UL150 (Rykman, et al., J. Virol. January 2006; 80(2):710-22), envelope glycoprotein B (gB), gH, gN, and pp150. As would be understood by the skilled person, CMV proteins for use as antigens described herein may be identified in public databases such as GenBank®, Swiss-Prot®, and TrEMBL® (see e.g., Bennekov et al., Mt. Sinai J. Med. 71 (2): 86-93 (2004); Loewendorf et al., J. Intern. Med. 267(5):483-501 (2010); Marschall et al., Future Microbiol. 4:731-42 (2009)).

Antigens derived from Epstein-Ban virus (EBV) that are contemplated for use in certain embodiments include EBV lytic proteins gp350 and gp110, EBV proteins produced during latent cycle infection including Epstein-Ban nuclear antigen (EBNA)-1, EBNA-2, EBNA-3A, EBNA-3B, EBNA-3C, EBNA-leader protein (EBNA-LP) and latent membrane proteins (LMP)-1, LMP-2A and LMP-2B (see, e.g., Lockey et al., Front. Biosci. 13:5916-27 (2008)).

Antigens derived from respiratory syncytial virus (RSV) that are contemplated for use herein include any of the eleven proteins encoded by the RSV genome, or antigenic fragments thereof: NS 1, NS2, N (nucleocapsid protein), M (Matrix protein) SH, G and F (viral coat proteins), M2 (second matrix protein), M2-1 (elongation factor), M2-2 (transcription regulation), RNA polymerase, and phosphoprotein P.

Antigens derived from Vesicular stomatitis virus (VSV) that are contemplated for use include any one of the five major proteins encoded by the VSV genome, and antigenic fragments thereof: large protein (L), glycoprotein (G), nucleoprotein (N), phosphoprotein (P), and matrix protein (M) (see, e.g., Rieder et al., J. Interferon Cytokine Res. (2009) (9):499-509; Roberts et al., Adv. Virus Res. (1999) 53:301-19).

Antigens derived from an influenza virus that are contemplated for use in certain embodiments include hemagglutinin (HA), neuraminidase (NA), nucleoprotein (NP), matrix proteins M1 and M2, NS1, NS2 (NEP), PA, PB1, PB1-F2, and PB2. See e.g., Nature 437 (7062): 1162-66.

Examples viral antigens also include, but are not limited to, adenovirus polypeptides, alphavirus polypeptides, calicivirus polypeptides (e.g., a calicivirus capsid antigen), coronavirus polypeptides, distemper virus polypeptides, Ebola virus polypeptides, enterovirus polypeptides, flavivirus polypeptides, hepatitis virus (AE) polypeptides (a hepatitis B core or surface antigen, a hepatitis C virus E1 or E2 glycoproteins, core, or non-structural proteins), herpesvirus polypeptides (including a herpes simplex virus or varicella zoster virus glycoprotein), infectious peritonitis virus polypeptides, leukemia virus polypeptides, Marburg virus polypeptides, orthomyxovirus polypeptides, papilloma virus polypeptides, parainfluenza virus polypeptides (e.g., the hemagglutinin and neuraminidase polypeptides), paramyxovirus polypeptides, parvovirus polypeptides, pestivirus polypeptides, picorna virus polypeptides (e.g., a poliovirus capsid polypeptide), pox virus polypeptides (e.g., a vaccinia virus polypeptide), rabies virus polypeptides (e.g., a rabies virus glycoprotein G), reovirus polypeptides, retrovirus polypeptides, and rotavirus polypeptides.

In certain embodiments, the antigen may be bacterial antigens. In certain embodiments, a bacterial antigen of interest may be a secreted polypeptide. In other certain embodiments, bacterial antigens include antigens that have a portion or portions of the polypeptide exposed on the outer cell surface of the bacteria.

Antigens derived from *Staphylococcus* species including Methicillin-resistant *Staphylococcus aureus* (MRSA) that are contemplated for use include virulence regulators, such as the Agr system, Sar and Sae, the Arl system, Sar homologues (Rot, MgrA, SarS, SarR, SarT, SarU, SarV, SarX, SarZ and TcaR), the Srr system and TRAP. Other *Staphylococcus* proteins that may serve as antigens include Clp proteins, HtrA, MsrR, aconitase, CcpA, SvrA, Msa, CfvA and CfvB (see, e.g., *Staphylococcus*: Molecular Genetics, 2008 Caister Academic Press, Ed. Jodi Lindsay). The genomes for two species of *Staphylococcus aureus* (N315 and Mu50) have been sequenced and are publicly available, for example at PATRIC (PATRIC: The VBI PathoSystems Resource Integration Center, Snyder et al., Nucleic Acids Res. (2007) 35: 401-406). As would be understood by the skilled person, *Staphylococcus* proteins for use as antigens may also be identified in other public databases such as GenBank®, Swiss-Prot®, and TrEMBL®.

Antigens derived from *Streptococcus pneumoniae* that are contemplated for use in certain embodiments described herein include pneumolysin, PspA, choline-binding protein A (CbpA), NanA, NanB, SpnHL, PavA, LytA, Pht, and pilin proteins (RrgA; RrgB; RrgC). Antigenic proteins of *Streptococcus pneumoniae* are also known in the art and may be used as an antigen in some embodiments (see, e.g., Zysk et al., Infect. Immun. 2000 68(6):3740-43). The complete genome sequence of a virulent strain of *Streptococcus pneumoniae* has been sequenced (see, e.g., Tettelin H, et al., Science (2001) 293(5529):498-506) and, as would be understood by the skilled person, *S. pneumoniae* proteins for use herein may also be identified in other public databases such as GenBank®, Swiss-Prot®, and TrEMBL®. Proteins of particular interest for antigens according to the present disclosure include virulence factors and proteins predicted to be exposed at the surface of the pneumococci (see, e.g., Tettelin et al., supra; Frolet et al., BMC Microbiol. (2010)

July 12; 10:190; Rigden, et al., Crit. Rev. Biochem. Mol. Biol. (2003) 38(2):143-68; Jedrzejas, Microbiol. Mol. Biol. Rev. (2001) 65(2):187-207).

Examples of bacterial antigens that may be used as antigens include, but are not limited to, *Actinomyces* polypeptides, *Bacillus* polypeptides, *Bacteroides* polypeptides, *Bordetella* polypeptides, *Bartonella* polypeptides, *Borrelia* polypeptides (e.g., *B. burgdorferi* OspA), *Brucella* polypeptides, *Campylobacter* polypeptides, *Capnocytophaga* polypeptides, *Chlamydia* polypeptides, *Corynebacterium* polypeptides, *Coxiella* polypeptides, *Dermatophilus* polypeptides, *Enterococcus* polypeptides, *Ehrlichia* polypeptides, *Escherichia* polypeptides, *Francisella* polypeptides, *Fusobacterium* polypeptides, *Haemobartonella* polypeptides, *Haemophilus* polypeptides (e.g., *H. influenzae* type b outer membrane protein), *Helicobacter* polypeptides, *Klebsiella* polypeptides, L-form bacteria polypeptides, *Leptospira* polypeptides, *Listeria* polypeptides, *Mycobacteria* polypeptides, *Mycoplasma* polypeptides, *Neisseria* polypeptides, *Neorickettsia* polypeptides, *Nocardia* polypeptides, *Pasteurella* polypeptides, *Peptococcus* polypeptides, *Peptostreptococcus* polypeptides, *Pneumococcus* polypeptides (i.e., *S. pneumoniae* polypeptides) (see description herein), *Proteus* polypeptides, *Pseudomonas* polypeptides, *Rickettsia* polypeptides, *Rochalimaea* polypeptides, *Salmonella* polypeptides, *Shigella* polypeptides, *Staphylococcus* polypeptides, group A *streptococcus* polypeptides (e.g., *S. pyogenes* M proteins), group B *streptococcus* (*S. agalactiae*) polypeptides, *Treponema* polypeptides, and *Yersinia* polypeptides (e.g., *Y. pestis* F1 and V antigens).

Examples of fungal antigens include, but are not limited to, *Absidia* polypeptides, *Acremonium* polypeptides, *Alternaria* polypeptides, *Aspergillus* polypeptides, *Basidiobolus* polypeptides, *Bipolaris* polypeptides, *Blastomyces* polypeptides, *Candida* polypeptides, *Coccidioides* polypeptides, *Conidiobolus* polypeptides, *Cryptococcus* polypeptides, *Curvalaria* polypeptides, *Epidermophyton* polypeptides, *Exophiala* polypeptides, *Geotrichum* polypeptides, *Histoplasma* polypeptides, *Madurella* polypeptides, *Malassezia* polypeptides, *Microsporum* polypeptides, *Moniliella* polypeptides, *Mortierella* polypeptides, *Mucor* polypeptides, *Paecilomyces* polypeptides, *Penicillium* polypeptides, *Phialemonium* polypeptides, *Phialophora* polypeptides, *Prototheca* polypeptides, *Pseudallescheria* polypeptides, *Pseudomicrodochium* polypeptides, *Pythium* polypeptides, *Rhinosporidium* polypeptides, *Rhizopus* polypeptides, *Scolecobasidium* polypeptides, *Sporothrix* polypeptides, *Stemphylium* polypeptides, *Trichophyton* polypeptides, *Trichosporon* polypeptides, and *Xylohypha* polypeptides.

Examples of protozoan parasite antigens include, but are not limited to, *Babesia* polypeptides, *Balantidium* polypeptides, *Besnoitia* polypeptides, *Cryptosporidium* polypeptides, *Eimeria* polypeptides, *Encephalitozoon* polypeptides, *Entamoeba* polypeptides, *Giardia* polypeptides, *Hammondia* polypeptides, *Hepatozoon* polypeptides, *Isospora* polypeptides, *Leishmania* polypeptides, *Microsporidia* polypeptides, *Neospora* polypeptides, *Nosema* polypeptides, *Pentatrichomonas* polypeptides, *Plasmodium* polypeptides. Examples of helminth parasite antigens include, but are not limited to, *Acanthocheilonema* polypeptides, *Aelurostrongylus* polypeptides, *Ancylostoma* polypeptides, *Angiostrongylus* polypeptides, *Ascaris* polypeptides, *Brugia* polypeptides, *Bunostomum* polypeptides, *Capillaria* polypeptides, *Chabertia* polypeptides, *Cooperia* polypeptides, *Crenosoma* polypeptides, *Dictyocaulus* polypeptides, *Dioctophyme* polypeptides, *Dipetalonema* polypeptides, *Diphyllobothrium* polypeptides, *Diplydium* polypeptides, *Dirofilaria* polypeptides, *Dracunculus* polypeptides, *Enterobius* polypeptides, *Filaroides* polypeptides, *Haemonchus* polypeptides, *Lagochilascaris* polypeptides, *Loa* polypeptides, *Mansonella* polypeptides, *Muellerius* polypeptides, *Nanophyetus* polypeptides, *Necator* polypeptides, *Nematodirus* polypeptides, *Oesophagostomum* polypeptides, *Onchocerca* polypeptides, *Opisthorchis* polypeptides, *Ostertagia* polypeptides, *Parafilaria* polypeptides, *Paragonimus* polypeptides, *Parascaris* polypeptides, *Physaloptera* polypeptides, *Protostrongylus* polypeptides, *Setaria* polypeptides, *Spirocerca* polypeptides *Spirometra* polypeptides, *Stephanofilaria* polypeptides, *Strongyloides* polypeptides, *Strongylus* polypeptides, *Thelazia* polypeptides, *Toxascaris* polypeptides, *Toxocara* polypeptides, *Trichinella* polypeptides, *Trichostrongylus* polypeptides, *Trichuris* polypeptides, *Uncinaria* polypeptides, and *Wuchereria* polypeptides. (e.g., *P. falciparum* circumsporozoite (PfCSP)), sporozoite surface protein 2 (PfSSP2), carboxyl terminus of liver state antigen 1 (PfLSA1 c-term), and exported protein 1 (PfExp-1), *Pneumocystis* polypeptides, *Sarcocystis* polypeptides, *Schistosoma* polypeptides, *Theileria* polypeptides, *Toxoplasma* polypeptides, and *Trypanosoma* polypeptides.

Examples of ectoparasite antigens include, but are not limited to, polypeptides (including antigens as well as allergens) from fleas; ticks, including hard ticks and soft ticks; flies, such as midges, mosquitoes, sand flies, black flies, horse flies, horn flies, deer flies, tsetse flies, stable flies, myiasis-causing flies and biting gnats; ants; spiders, lice; mites; and true bugs, such as bed bugs and kissing bugs.

In some embodiments, the antigen is an autoantigen. In one embodiment, the autoantigen is a type 1 diabetes autoantigen, including, but not limited to, PDX1, AnT8, CHGA IAAP, GAD(65) and/or DiaPep277. In one embodiment, the autoantigen is an alopecia areata autoantigen, including, but not limited to, keratin 16, K18585, M10510, J01523, 022528, D04547, 005529, B20572 and/or F11552. In one embodiment, the autoantigen is a systemic lupus erythematosus autoantigen, including, but not limited to, TRIM21/Ro52/SS-A 1 and/or histone H2B. In one embodiment, the autoantigen is a Behçet's disease autoantigen, including, but not limited to, S-antigen, alpha-enolase, selenium binding partner and/or Sip1 C-ter. In one embodiment, the autoantigen is a Sjögren's syndrome autoantigen, including, but not limited to, La/SSB, KLK11 and/or a 45-kd nucleus protein. In one embodiment, the autoantigen is a rheumatoid arthritis autoantigen, including, but not limited to, vimentin, gelsolin, alpha 2 HS glycoprotein (AHSG), glial fibrillary acidic protein (GFAP), α1B-glycoprotein (A1BG), RA33 and/or citrullinated 31F4G1. In one embodiment, the autoantigen is a Grave's disease autoantigen. In one embodiment, the autoantigen is an antiphospholipid antibody syndrome autoantigen, including, but not limited to, zwitterionic phospholipids, phosphatidyl-ethanolamine, phospholipid-binding plasma protein, phospholipid-protein complexes, anionic phospholipids, cardiolipin, β2-glycoprotein I (β2GPI), phosphatidylserine, lyso(bis)phosphatidic acid, phosphatidylethanolamine, vimentin and/or annexin A5. In one embodiment, the autoantigen is a multiple sclerosis autoantigen, including, but not limited to, myelin-associated oligodendrocytic basic protein (MOBP), myelin basic protein (MBP), myelin proteolipid protein (PLP), myelin oligodendrocyte glycoprotein (MOG) and/or alpha-B-crytallin. In one embodiment, the autoantigen is an irritable bowel disease autoantigen, including, but not limited to, a ribonucleoprotein complex, a small nuclear ribonuclear polypeptide A and/or Ro-5,200 kDa. In one embodiment, the autoantigen is a Crohn's disease autoantigen, including, but not limited to, zymogen granule membrane glycoprotein 2 (GP2), an 84 by allele of CTLA-4 AT repeat polymorphism, MRP8, MRP14 and/or complex MRP8/14. In one embodiment, the autoantigen is a dermatomyositis autoantigen, including, but not limited to, aminoacyl-tRNA synthetases, Mi-2 helicase/deacetylase protein complex, signal recognition particle (SRP), T2F1-γ, MDAS, NXP2, SAE and/or HMGCR. In one embodiment, the autoantigen is an ulcerative colitis autoantigen, including, but not limited to, 7E12H12 and/or M(r) 40 kD autoantigen.

In some embodiments, the autoantigen is a collagen, e.g., collagen type II; other collagens such as collagen type IX, collagen type V, collagen type XXVII, collagen type XVIII, collagen type IV, collagen type IX; aggrecan I; pancreas-specific protein disulphide isomerise A2; interphotoreceptor retinoid binding protein (IRBP); a human IRBP peptide 1-20; protein lipoprotein; insulin 2; glutamic acid decarboxylase (GAD) 1 (GAD67 protein), BAFF, IGF2. Further examples of autoantigens include ICA69 and CYP1A2, Tph and Fabp2, Tgn, Spt1 & 2 and Mater, and the CB11 peptide from collagen.

Kits

The present disclosure provides kits for carrying out a method of the present disclosure. The above-described reagents, including the primers for amplification and sequencing of target nucleic acids encoding TCRs and other T cell phenotypic markers, and optionally other reagents for performing nucleic acid amplification (e.g., by RT-PCR) and/or sequencing can be provided in kits with suitable instructions and other necessary reagents for analyzing single T cells. The kit will normally contain in separate containers the primers and other reagents (e.g., polymerases, nucleoside triphosphates, and buffers). All primers within a set of primers may in some cases be provided in one container. In some cases, different subsets of primers within a set of primers may be provided in separate containers. Instructions (e.g., written, CD-ROM, DVD, flash drive, etc.) for carrying out the analysis of T cells usually will be included in the kit. The kit can also contain other packaged reagents and materials (i.e., wash buffers, cell lysis agents, reagents for extraction and purification of nucleic acids, and the like). Analysis of single T cells, as described herein, can be conducted using these kits.

Thus, the present disclosure provides kits that find use in performing the present methods, as described above. Embodiments of the present kit may include any embodiments of the composition containing primers described herein. In certain embodiments, the kit comprises a set of primers collectively comprising the nucleotide sequences of SEQ ID NOS:7-82 or variants thereof, wherein one or more primers may comprise a nucleotide sequence that differs from a nucleotide sequence selected from the group consisting of SEQ ID NOS:7-82 by up to three nucleotide changes, wherein the primers are capable of hybridizing to and amplifying nucleotide sequences encoding T cell receptors. In certain embodiments, the kit further comprises one or more primers comprising nucleotide sequences selected from the group consisting of SEQ ID NOS:1-6 and SEQ ID NOS:83-262.

In one embodiment, the kit comprises a composition comprising a set of primers collectively comprising the nucleotide sequences of SEQ ID NOS:7-82 or variants thereof, wherein one or more primers may comprise a nucleotide sequence that differs from a nucleotide sequence selected from the group consisting of SEQ ID NOS:7-82 by up to three nucleotide changes, wherein the primers are capable of hybridizing to and amplifying nucleotide sequences encoding T cell receptors. In certain embodiments, the kit comprises a composition further comprising one or more primers selected from the group consisting of: a) a primer comprising a nucleotide sequence selected from the group consisting of SEQ ID NO:157, SEQ ID NO:158, SEQ ID NO:161, SEQ ID NO:162, SEQ ID NO:165, SEQ ID NO:166, SEQ ID NO:169, SEQ ID NO:170, SEQ ID NO:173, SEQ ID NO:174, SEQ ID NO:177, SEQ ID NO:178, SEQ ID NO:181, SEQ ID NO:182, SEQ ID NO:185, SEQ ID NO:186, SEQ ID NO:189, SEQ ID NO:190, SEQ ID NO:193, SEQ ID NO:194, SEQ ID NO:197, SEQ ID NO:198, SEQ ID NO:201, SEQ ID NO:202, SEQ ID NO:205, SEQ ID NO:206, SEQ ID NO:209, SEQ ID NO:210, SEQ ID NO:213, SEQ ID NO:214, SEQ ID NO:217, SEQ ID NO:218, SEQ ID NO:221, and SEQ ID NO:222; and b) a primer comprising a nucleotide sequence that differs from a sequence selected from the group consisting of SEQ ID NO:157, SEQ ID NO:158, SEQ ID NO:161, SEQ ID NO:162, SEQ ID NO:165, SEQ ID NO:166, SEQ ID NO:169, SEQ ID NO:170, SEQ ID NO:173, SEQ ID NO:174, SEQ ID NO:177, SEQ ID NO:178, SEQ ID NO:181, SEQ ID NO:182, SEQ ID NO:185, SEQ ID NO:186, SEQ ID NO:189, SEQ ID NO:190, SEQ ID NO:193, SEQ ID NO:194, SEQ ID NO:197, SEQ ID NO:198, SEQ ID NO:201, SEQ ID NO:202, SEQ ID NO:205, SEQ ID NO:206, SEQ ID NO:209, SEQ ID NO:210, SEQ ID NO:213, SEQ ID NO:214, SEQ ID NO:217, SEQ ID NO:218, SEQ ID NO:221, and SEQ ID NO:222 by up to three nucleotide changes, wherein the primer is capable of hybridizing to and amplifying a sequence encoding a T cell phenotypic marker. In one embodiment, the kit comprises a composition comprising primers comprising the nucleotide sequences of SEQ ID NO:157, SEQ ID NO:158, SEQ ID NO:161, SEQ ID NO:162, SEQ ID NO:165, SEQ ID NO:166, SEQ ID NO:169, SEQ ID NO:170, SEQ ID NO:173, SEQ ID NO:174, SEQ ID NO:177, SEQ ID NO:178, SEQ ID NO:181, SEQ ID NO:182, SEQ ID NO:185, SEQ ID NO:186, SEQ ID NO:189, SEQ ID NO:190, SEQ ID NO:193, SEQ ID NO:194, SEQ ID NO:197, SEQ ID NO:198, SEQ ID NO:201, SEQ ID NO:202, SEQ ID NO:205, SEQ ID NO:206, SEQ ID NO:209, SEQ ID NO:210, SEQ ID NO:213, SEQ ID NO:214, SEQ ID NO:217, SEQ ID NO:218, SEQ ID NO:221, and SEQ ID NO:222.

In another embodiment, the kit comprises a composition comprising a set of primers collectively comprising the nucleotide sequences of SEQ ID NOS:83-156 or variants thereof, wherein one or more primers may comprise a nucleotide sequence that differs from a nucleotide sequence selected from the group consisting of SEQ ID NOS: 83-156 by up to three nucleotide changes, wherein the primers are capable of hybridizing to and amplifying nucleotide sequences encoding T cell receptors. In one embodiment, the kit comprises a composition further comprising one or more primers selected from the group consisting of: a) a primer comprising a nucleotide sequence selected from the group consisting of SEQ ID NO:159, SEQ ID NO:160, SEQ ID NO:163, SEQ ID NO:164, SEQ ID NO:167, SEQ ID NO:168, SEQ ID NO:171, SEQ ID NO:172, SEQ ID NO:175, SEQ ID NO:176, SEQ ID NO:179, SEQ ID NO:180, SEQ ID NO:183, SEQ ID NO:184, SEQ ID NO:187, SEQ ID NO:188, SEQ ID NO:191, SEQ ID NO:192, SEQ ID NO:195, SEQ ID NO:196, SEQ ID NO:199, SEQ ID NO:200, SEQ ID NO:203, SEQ ID NO:204, SEQ ID NO:207, SEQ ID NO:208, SEQ ID NO: 211, SEQ ID NO:212, SEQ ID NO:215, SEQ ID NO:216, SEQ ID NO:219, SEQ ID NO:220, SEQ ID NO:223, and SEQ ID NO:224; and b) a primer comprising a nucleotide sequence that differs from a sequence selected from the group consisting of SEQ ID NO:159, SEQ ID NO:160, SEQ ID NO:163, SEQ ID NO:164, SEQ ID NO:167, SEQ ID NO:168, SEQ ID NO:171, SEQ ID NO:172, SEQ ID NO:175, SEQ ID NO:176, SEQ ID NO:179, SEQ ID NO:180, SEQ ID NO:183, SEQ ID NO:184, SEQ ID NO:187, SEQ ID NO:188, SEQ ID NO:191, SEQ ID NO:192, SEQ ID NO:195, SEQ ID NO:196, SEQ ID NO:199, SEQ ID NO:200, SEQ ID NO:203, SEQ ID NO:204, SEQ ID NO:207, SEQ ID NO:208, SEQ ID NO: 211, SEQ ID NO:212, SEQ ID NO:215, SEQ ID NO:216, SEQ ID NO:219, SEQ ID NO:220, SEQ ID NO:223, and SEQ ID NO:224 by up to three nucleotide changes, wherein the primer is capable of hybridizing to and amplifying a sequence encoding a T cell phenotypic marker. In one embodiment, the kit comprises a composition comprising primers comprising the nucleotide sequences of SEQ ID NO:159, SEQ ID NO:160, SEQ ID NO:163, SEQ ID NO:164, SEQ ID NO:167, SEQ ID NO:168, SEQ ID NO:171, SEQ ID NO:172, SEQ ID NO:175, SEQ ID NO:176, SEQ ID NO:179, SEQ ID NO:180, SEQ ID NO:183, SEQ ID NO:184, SEQ ID NO:187, SEQ ID NO:188, SEQ ID NO:191, SEQ ID NO:192, SEQ ID NO:195, SEQ ID NO:196, SEQ ID NO:199, SEQ ID NO:200, SEQ ID NO:203, SEQ ID NO:204, SEQ ID NO:207, SEQ ID NO:208, SEQ ID NO: 211, SEQ ID NO:212, SEQ ID NO:215, SEQ ID NO:216, SEQ ID NO:219, SEQ ID NO:220, SEQ ID NO:223, and SEQ ID NO:224.

In another embodiment, the kit comprises a composition comprising a set of primers collectively comprising the nucleotide sequences of SEQ ID NOS:225-248. In another embodiment, the present disclosure provides a composition comprising a set of primers collectively comprising the nucleotide sequences of SEQ ID NOS:249-260.

In another embodiment, the kit comprises a composition comprising primers comprising adapters for paired end sequencing, wherein the primers are selected from the group consisting of SEQ ID NO:261 and SEQ ID NO:262.

EXAMPLES

Below are examples of specific embodiments for carrying out the present invention. The examples are offered for illustrative purposes only, and are not intended to limit the scope of the present invention in any way.

Efforts have been made to ensure accuracy with respect to numbers used (e.g., amounts, temperatures, etc.), but some experimental error and deviation should, of course, be allowed for.

Example 1

Linking the T Cell Receptor Repertoire to Multi-Parametric Phenotyping at the Single-Cell Level T lymphocytes recognize a vast array of different antigens through their T cell receptor (TCR) heterodimers. They have very diverse functional activities, from stimulating B cells to make high affinity antibodies to inhibiting responsiveness. In many cases, the major specificities and functional characteristics of a T cell response are not known. The TCR, which determines the T cell's antigen specificity, is central to the selection and function of T cells.[8] The TCR also serves as a unique identifier of a T cell's ancestry, as any two T cells with a particular TCRαβ pair most likely arose from a common T cell predecessor. Thus, there is great potential synergy in the pairing of TCR sequences with key phenotypic markers to better define a given T cell. It is also becoming clear that T cells responding to different antigens can have very different phenotypic and functional properties, even if these antigens are derived from the same pathogen.[9] The ability to link function and TCR specificity allows one to determine which functional groups of T cells have undergone significant clonal expansion, and which clones exhibit plasticity to produce diverse effector phenotypes. It also allows the identification of complete TCR heterodimers from individual T cells without in vitro expansion and potential loss of functional integrity. These heterodimers could also be invaluable in functional studies directed at ligand discovery[10] or in therapeutic strategies.[11]

TCR genes have been sequenced with high efficiency from single sorted T cells using a nested PCR approach and Sanger sequencing.[12-14] Here a strategy to utilize deep sequencing to simultaneously query TCR sequences and multiple phenotypic parameters on single sorted T cells with high efficiency, throughput, and reasonable cost was developed. This approach had multiple advantages over previous methods. First it was cheaper (5,000-10,000 cells can be sequenced in one sequencing run) and far less labor intensive, as individual PCR products do not need to be purified and sequenced separately. It also enabled multiple phenotypic parameters to be analyzed in parallel with TCR sequence in single cells. In terms of TCR sequencing, the method was very accurate as the major TCRs are read to great depth, often exceeding 1000-fold coverage, essentially eliminating the possibility of sequencing error. Additionally, it is well established that individual T cells can express two alpha chain genes, and that allelic exclusion is not enforced at the level of transcription[15,16]. This approach uniquely enabled multiple TCR alpha chain sequences to be readily derived from most T cells and determination of which of these alpha chains are functional.

This strategy involved the amplification of both TCR alpha and beta gene transcripts as well as genes that specify particular T cell types and functions from single T cells. These amplicons are then bar-coded, combined, and analyzed by deep sequencing. This general strategy has been successful in a number of other studies, such as BCR and HLA sequencing[17,18]. The specific scheme is depicted in FIG. 1A. Initially, single T cells are sorted into 96 well PCR plates. An RT-PCR (reverse transcriptase-PCR) reaction was performed using 76 TCR primers and 34 phenotyping primers (FIG. 4, Tables 1-3 provided in FIGS. 12A-H, 13A-B and 14A-C, respectively). The products are then used in a second PCR reaction using nested primers for TCR genes or for phenotypic markers. A third reaction was then performed that incorporated individual barcodes into each well and enabled sequencing using the Illumina® MiSeq platform (FIG. 5)[19]. The products are combined, purified, and sequenced. The resulting paired-end sequencing reads are assembled and deconvoluted using barcode identifiers at both ends of each sequence by a custom software pipeline to separate reads from every well in every plate. The resulting sequences are then analyzed using a program called VDJ-Fasta[20], which was adapted to resolve barcodes and analyze sequences with a customized gene segment database that included relevant transcription factors and cytokine genes. The population of annotated sequences in each well above background levels was then profiled for TCRα, TCRβ and phenotypic transcripts (see Methods for details on data processing and background). For TCR sequences, the CDR3 nucleotide sequences are then extracted and translated. For phenotypic parameters, the presence of a transcript in a particular well was scored.

Figure 4B:
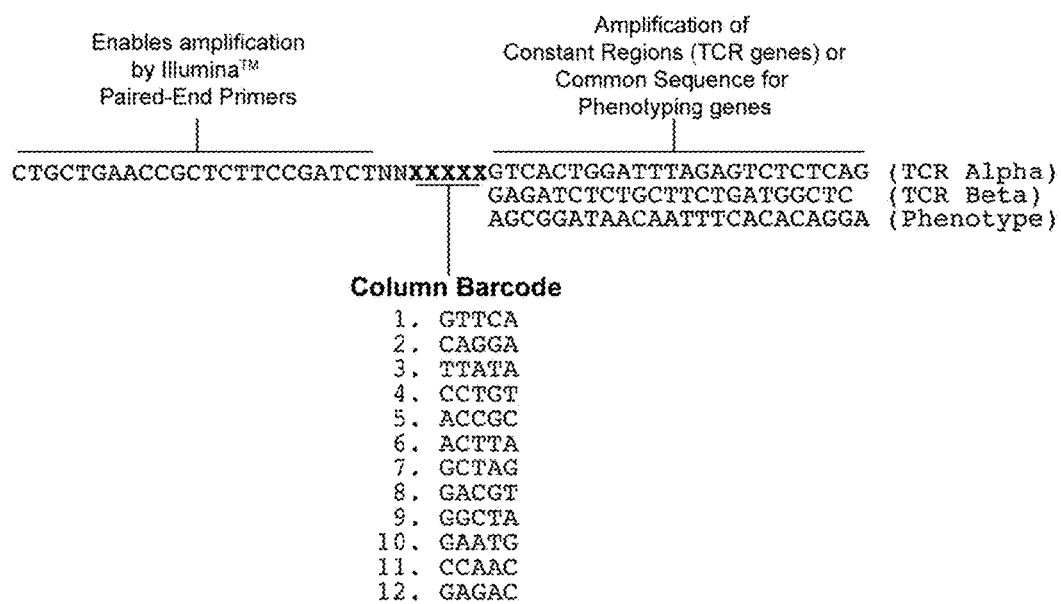

FIGS. 4A and B. FIG. 4A shows 5' primers, containing barcodes that specify plate and row, which bind and amplify a common sequence that is incorporated into all 5' primers from PCR reaction #2. The outside sequence allows for amplification using Illumina® Paired-End primers. FIG. 4B shows 3' primers containing barcodes that specify column. The primers amplify nested constant region sequences for TCRα/β or a common sequence incorporated into all 3' cytokine primers. The outside sequence allows for amplification using Illumina® Paired-End primers.

Figure 5:
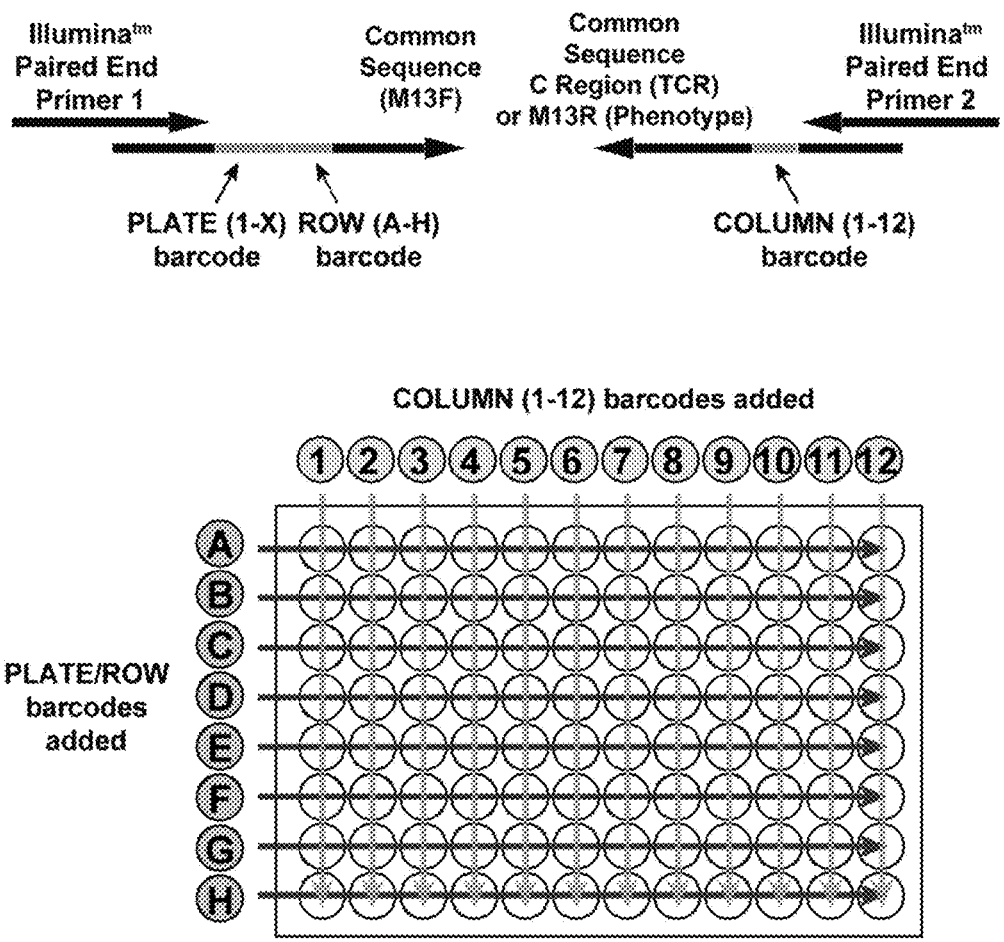
FIG. 5 depicts a schematic for barcoding the third PCR reaction.

FIG. 5. An aliquot from the second PCR reaction is used as a template for this reaction. To each well within a particular row within a given plate, a distinct 5' primer is added by multichannel pipette that specifies row. To each well within a column, a distinct 3' primer is added by multichannel pipette that specifies column. The reaction is performed with Illumina® Paired-End primers in all wells, which enable sequencing on the Illumina® MiSeq platform.

FIG. 12 (Table 1). TCR sequencing primers for the first two PCR reactions. Common sequences are indicated in bold.

FIG. 13 (Table 2). Phenotyping primers for first two PCR reactions. Common sequences are indicated in bold.

FIG. 14 (Table 3). Column barcoding primers used for the third PCR reaction and Illumina Paired-End primers. Barcodes are indicated in bold.

Figure 1B:
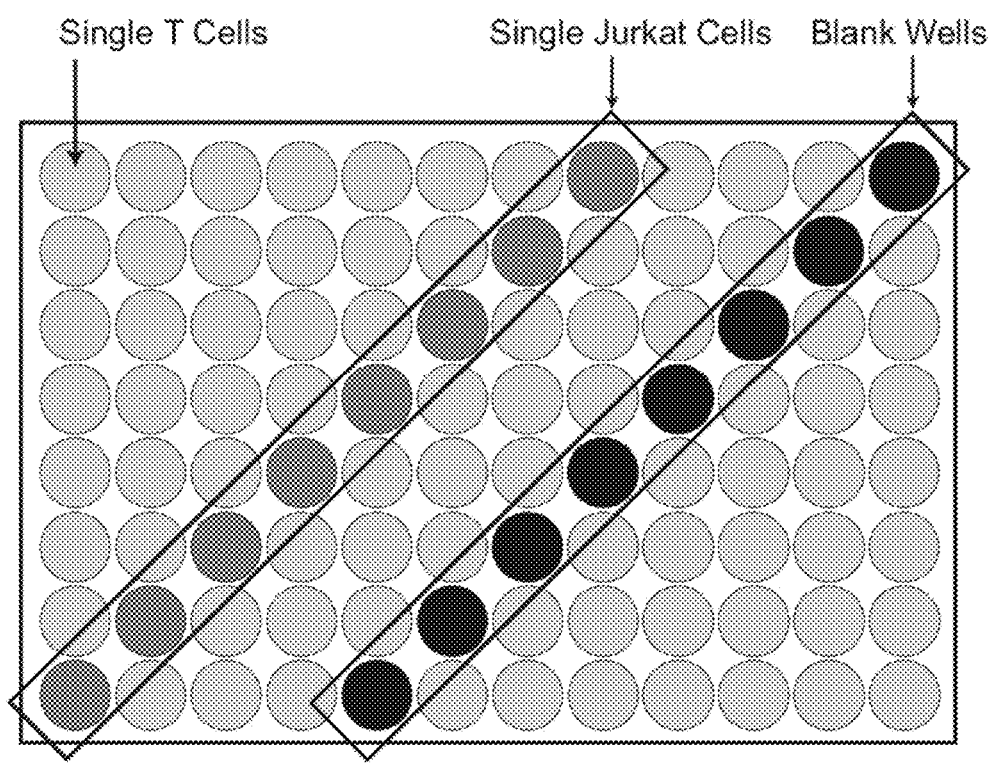

To validate the TCR sequencing methodology, two 96-well plates were sorted with freshly isolated single T cells from peripheral blood. 80 random single CD45RA+ CD4+ TCRαβ+ T cells were sorted into the first plate, and 80 random single CD4+ or CD8+ TCRαβ+ T cells were sorted into the second plate. CD45RA marks naive phenotype CD4+ T cells that are not expected to have undergone significant clonal expansion[21]. The Jurkat human T leukemic cell line was used as a positive control[22]. Into both plates, individual Jurkat T cells were sorted into 8 wells, and 8 wells were left blank (FIG. 1B). These plates were initially amplified with the first reaction containing 74 TCR V region primers, 2 C region primers, and 34 phenotyping primers. Phenotyping primers were included in the first reaction to demonstrate that the inclusion of these primers did not interfere with TCR sequencing. The subsequent nested PCR and barcoding reactions were then performed according to the protocol and products were sequenced and analyzed.

Out of 160 wells into which peripheral blood αβ T cells were randomly sorted, productive TCRβ sequences were successfully obtained in 147/160 wells (92%), and at least one productive TCRα sequence was found in 139/160 (87%) wells (FIG. 1C, Table 4 provided in FIGS. 15A-R). Paired productive TCRαβ sequences were found in 131/160 (82%) of wells. Completely identical Jurkat TCRαβ sequences were found in 16/16 wells into which Jurkat cells were sorted and found in no other wells on the plates (FIG. 1C, Table 4 provided in FIGS. 15A-R). There were no sequences above background found in the wells into which no cell was sorted. The absence of sequences from wells with no cells and the presence of Jurkat sequences only in the 16 Jurkat wells indicated that cross contamination of wells was not significant. Optimal efficiency was obtained when the third PCR reaction (barcoding) was performed in two separate plates for TCRα and TCRβ. However, the third PCR reaction for TCRα and TCRβ can be performed together in one plate with marginal loss of efficiency. When the third reaction was combined for TCR sequencing, the TCRβ efficiency 160/176 (91%) and TCRα efficiency was 138/176 (78%, FIG. 1C).

FIGS. 1A-C. FIG. 1A shows the strategy for simultaneous TCR sequence determination and phenotyping from single sorted T cells. Single T cells were sorted into 96 well plates. The initial RT-PCR (reverse transcriptase-PCR) reaction was performed using 76 TCR primers and 34 phenotyping primers. An aliquot of the first reaction was used for two separate second nested PCR reactions, one for TCR sequencing and one for phenotyping. Using an aliquot of this second PCR reaction as a template, a third PCR reaction was performed that incorporated individual barcodes into each well and enabled sequencing using the Illumina® MiSeq platform. For TCR sequencing, the third reaction can be split into a separate reaction for TCRα and TCRβ for optimal efficiency, or combined. FIG. 1B shows validation of TCR sequencing. Into each test plate, individual peripheral blood T cells were sorted into 80 wells (grey). Single Jurkat T cells were sorted into the 8 wells (medium gray), and 8 wells (black) were left blank. For sequencing of these test plates, the third reaction was initially performed separately for TCRα and TCRβ. It also was repeated with TCRα and TCRβ amplified together in the same reaction. FIG. 1C shows TCR sequencing was highly efficient and accurate. Total efficiency of TCRα and TCRβ sequencing was 88% and 93%, respectively. Identical Jurkat sequences were obtained from all Jurkat wells. No sequences were obtained from empty wells.

FIG. 15 (Table 4). TCR sequences from the TCR validation panel. Well location, V and J gene usage, CDR3 sequence, and number of reads are indicated for each TCR gene. Jurkat sequences are indicated in medium gray. Empty wells are indicated in light gray.

As discussed above, T cells often express two recombined TCR alpha genesis[15,16]. Sanger sequencing cannot be performed on heterogeneous products, therefore, methods that rely on Sanger sequencing cannot easily identify multiple TCR chains from a single cell[14]. Furthermore, the presence of multiple alpha chains can hinder the efficiency and accuracy of sequencing. Because the strategy employed deep sequencing where each template is amplified and sequenced independently, multiple TCR sequences from individual cells can be readily derived. On average (assuming twenty 96-well plates on a single sequencing run), approximately 5,000 total TCRα or β sequences were obtained with the same set of barcodes, specifying they are derived from the same well. To distinguish between TCR sequences that differ due to sequencing/PCR error and those that are likely derived from different TCR genes, the software determined a cutoff value in similarity based upon the assumed rate of sequencing/PCR error[23]. All sequences exceeding this value of similarity to one another are assumed to derive from the same TCR gene and a consensus sequence was determined. Multiple TCR gene sequences can be derived with a high degree of accuracy and redundancy from a heterogeneous group of sequences tagged with the same barcode.

In the sample set, multiple alpha chains were detectable in 80/155 (52%) wells containing at least one productive alpha chain (Table 4 provided in FIGS. 15A-R). For comparison, multiple beta chains or multiple non-productive alpha chains in wells were not detected. This indicated that cross contamination of wells or the erroneous sorting of two cells into wells was not significant. With the exception of Jurkat wells, there were no repeated TCRs present in the first plate containing 80 naïve phenotype CD45RA+ CD4+ T cells.

This was consistent with the expectation that naïve phenotype T cells are not significantly clonally expanded and therefore are unlikely to be repeated within a 96-well plate. In the second plate, which contained 80 total TCRαβ+ T cells, there were 4 repeated TCR sequences present in 11 different wells (Table 5 provided in FIG. 16). All these repeated T cells were scattered across the plates and not within close proximity to each other. For one TCRβ that was repeated across 4 wells (CAWTLGGNEQFF (SEQ ID NO:384)), each well contained sequences of the same two different productive TCRα genes. Also, for another repeated TCRβ (CASSYGDPGGLDGELFF (SEQ ID NO:355)) that was repeated across 3 wells, the same productive TCRα gene product was found in all three wells. Additionally, within 2 of these 3 wells, an identical non-productive TCRα gene was found. These findings confirm that the presence of two alpha rearrangements in a particular cell was repeatable and reliable, and not a result of contamination or error.

FIG. 16 (Table 5). Multiple TCR alpha sequences obtained from single T cells. Four T cell clones were clonally expanded and repeated within the TCR validation set. Multiple alpha chains were detected in two of these clones. Well location, V and J gene usage, CDR3 sequence, and number of reads are indicated.

Figure 7A:
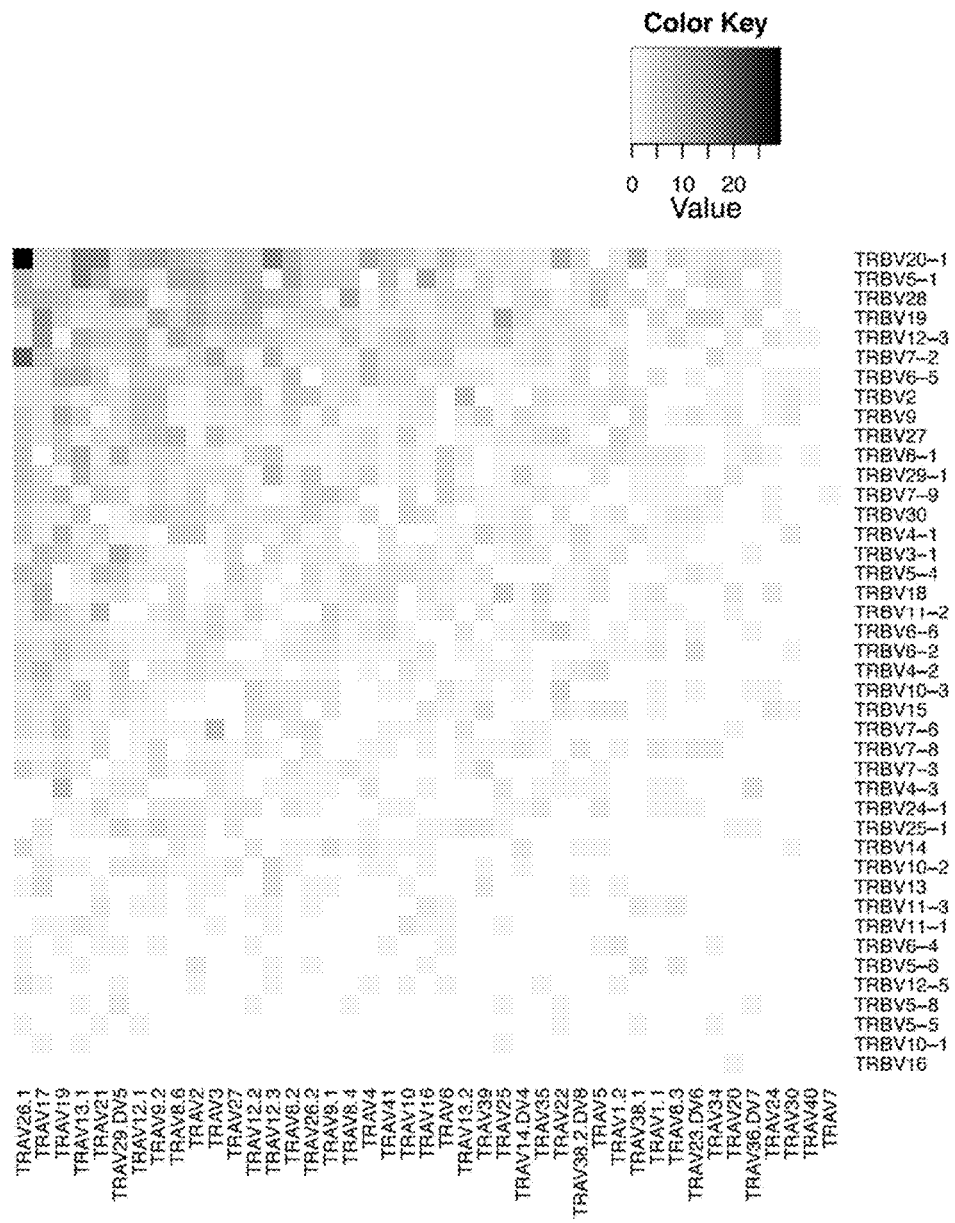
FIGS. 7A and 7B depict human TCR V-gene usage in single-cell clones.
Figure 7B:
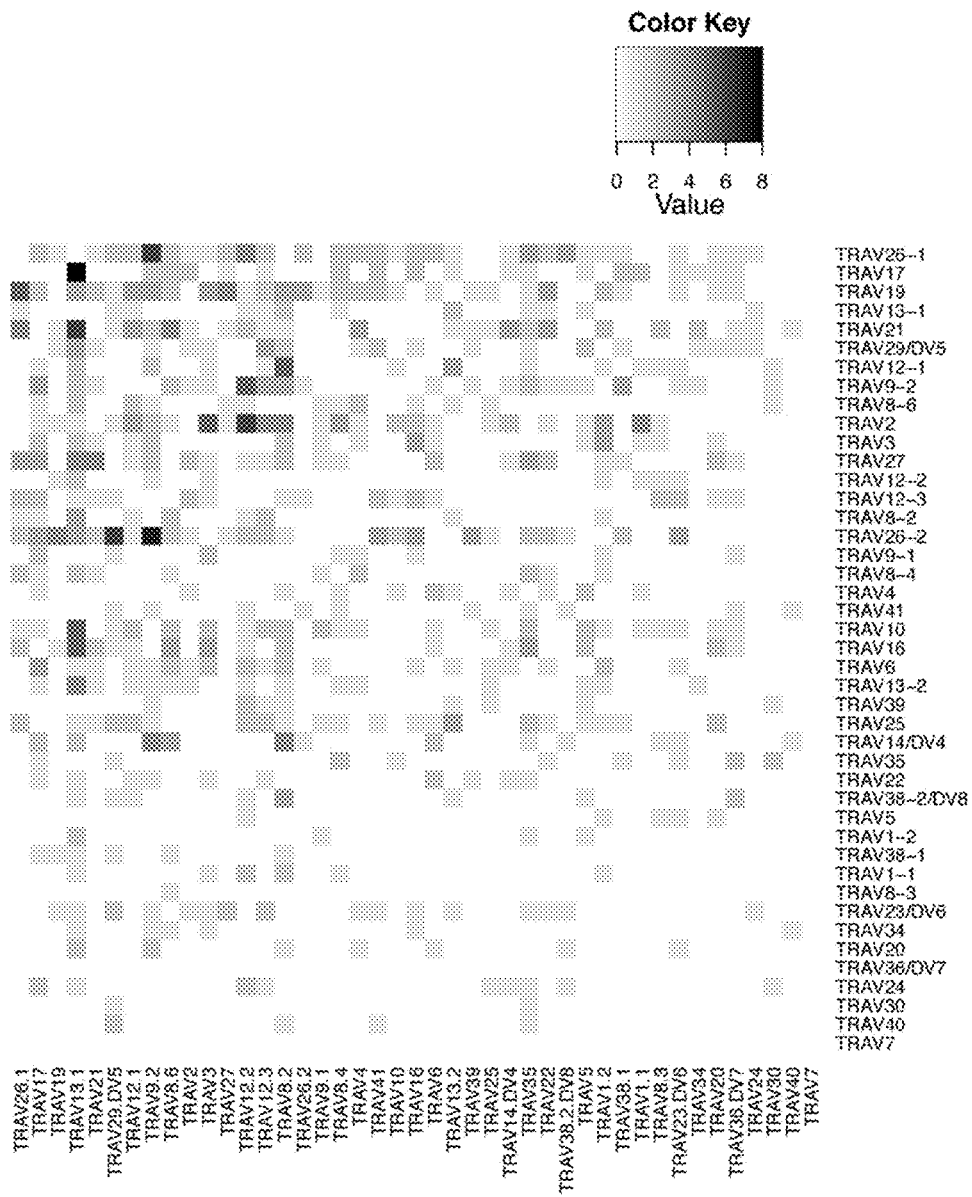

In many of the wells analyzed, a non-productively rearranged TCR alpha chain was the dominant sequence detected (Table 4 provided in FIGS. 15A-R). In most of these wells, productively rearranged alpha chain were also found. As a multiplexed PCR approach that is not meant to be quantitative was used, it cannot be concluded that the dominantly detected alpha chain sequence was present at higher levels within the cell. However, the possible presence of multiple alpha chains within a particular cell reinforced the importance of single-molecule sequencing methods to recover true TCRαβ heterodimers. Further, in cases where only one alpha chain was detected in a particular cell, there was a possibility that another productive alpha chain was present but not detected. This possibility was unlikely given the efficiency of the methodology and the fact that all V regions were detect in the TCR alpha data even in the presence of other alpha chains within the same T cell (FIGS. 7A-B). However, due to this possibility, all TCRs derived through this method that are reconstituted for use in functional studies should be validated.

FIGS. 7A-B. FIG. 7A shows the observed frequency of all possible alpha/beta combinations observed in 2,721 non-redundant TCRs where a productive beta gene and a single productive alpha gene were obtained. For both alpha and beta, some V-genes were used at a higher frequency than others, and their combinations appear largely in proportion to independent abundance. FIG. 7B shows the observed frequency of all possible double alpha combinations observed in 999 non-redundant TCRs where two alpha chains were identified, one or more being productive. The dominantly detected gene was plotted on the Y-axis, while the gene with lower read counts was plotted on the X-axis. Dual alpha cells appeared to select chains as a function of alpha frequency and there was no systemic bias observed with respect to alpha chain co-expression within a particular cell.

In summary, TCR alpha and beta chains from single T cells were sequenced with 87% and 92% efficiency, respectively, and paired productive TCRαβ sequences with 82% efficiency. This is the highest reported efficiency in sequencing TCRs from single T cells. Furthermore, the method is uniquely suited to determining multiple alpha chains from single T cells, which was demonstrated to be important in accurately determining the correct TCRα/β heterodimer that is expressed by a particular cell.

In addition to TCR sequencing, multiple phenotypic parameters from single T cells were simultaneously queried. In the phenotyping panel, multiple cytokines and transcription factors that are important in T cell function and define certain T cell types were included (Table 2 provided in FIGS. 13A-B). Flow cytometry-based detection of cytokines and transcription factors generally required cellular fixation, which compromised the integrity of nucleic acid and made it difficult to perform TCR sequencing. Furthermore, cellular fixation methods for detecting transcription factors are particularly arduous and unreliable, even compared to methods for intracellular cytokine expression[24]. Therefore, multi-parametric single-cell analysis of transcription factors through flow-cytometry based techniques is challenging.

The functional diversity of CD4+ T cells is dependent upon expression of various transcription factors. Some of these transcription factors are termed "master regulators" and have been used to specify particular T cell lineages; T-bet, GATA3, RoRyT (RAR-related orphan receptor gamma T, which is encoded by RORC), BCL-6, and FOXP3 (Forkhead box P3) have been used to specify T helper type 1 (Th1), Th2, Th17, follicular helper (TfH), and regulatory T (Treg) cells, respectively. In the phenotyping analysis, the aforementioned master regulators as well as the runt-related transcription factors Runx1 and Runx3, also appreciated to be important in T cell differentiation, were included.

Both pro-inflammatory and inhibitory cytokines that mediate T cell effector function and also define the various T cell subtypes, including IFNγ (Th1), IL-13 (Th2), IL-17 (Th17), IL-10 and TGFβ (Treg) were selected.

To validate this part of the methodology, flow cytometry-based cytokine capture assays (Miltenyi) which enable the determination of cytokine expression without the need for cell fixation[29] were used. Expression of the following cytokines for which cytokine secretion assays are commercially available: TNFα, IFNγ, IL2, IL10, IL13 and IL17 were tested. Cytokine secretion assays were performed on freshly isolated peripheral blood mononuclear cells. Into each plate 60 single CD4+ CD45RO+ memory phenotype T cells that were positive for protein expression of a particular cytokine and 36 single CD4+CD45RO+ T cells that were negative for expression were sorted (FIGS. 2A-H, Table 6 provided in FIGS. 17A-AA). These plates were initially amplified with the first reaction containing 74 TCR V-region primers, 2 C-region primers, and 34 phenotyping primers. TCR primers were included in the first reaction to demonstrate that their presence did not interfere with subsequent phenotyping reactions. Nested PCR, barcoding and sequencing analysis was performed for phenotypic parameters. Transcripts in single cytokine-positive T cells were detected with 77-97% sensitivity (FIG. 2, Table 7 provided in FIG. 18). The false positive rate was very low. The specificity of the assay was 94-100% when compared to the relevant cytokine capture assays (FIG. 2, Table 7 provided in FIG. 18).

FIG. 17 (Table 6). Reads counts per well of each phenotyping parameter illustrated in FIG. 2. Read counts for cells positive for indicated parameter are highlighted in dark gray, read counts for cells negative for indicated parameter are indicated in light gray. All raw read counts are shown, including reads below threshold levels.

FIG. 18 (Table 7). Single-cell phenotypic detection is highly sensitive and specific compared to cytokine capture assays and CD25 expression in the case of FOXP3.

Figure 2A:
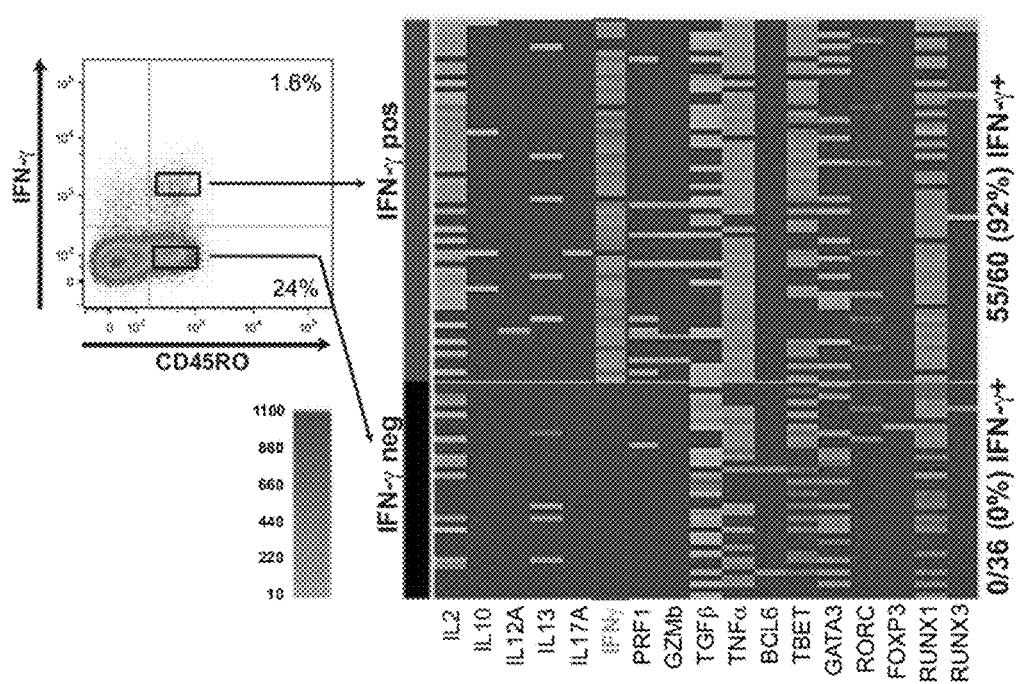
FIGS. 2A-H depict accuracy of phenotypic analysis compared to flow cytometric analysis.
Figure 2B:
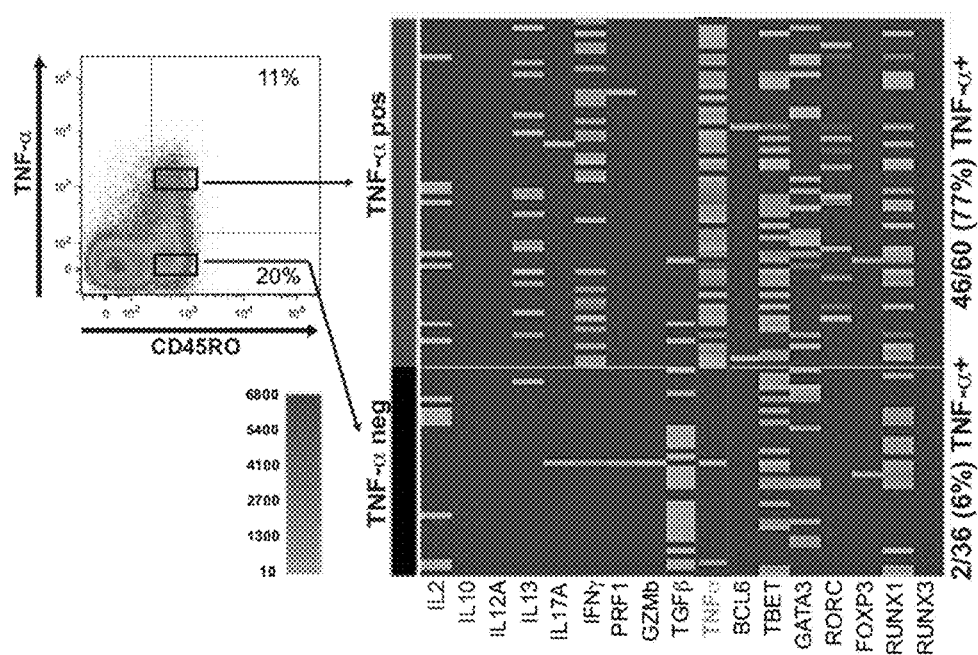
Figure 2C:
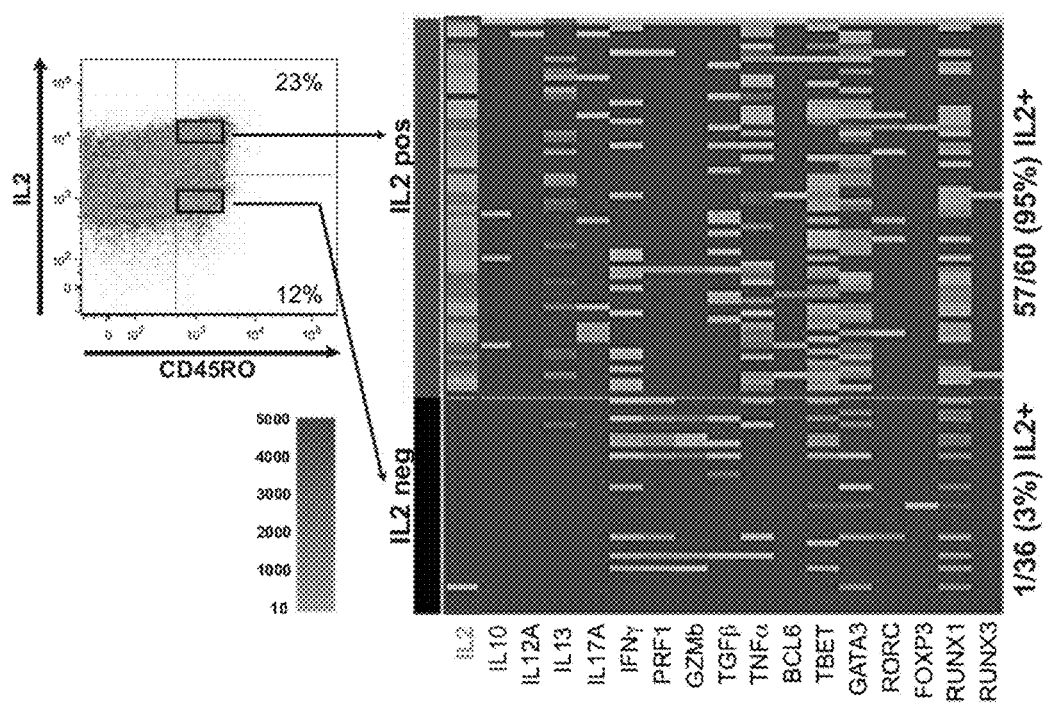
Figure 2D:
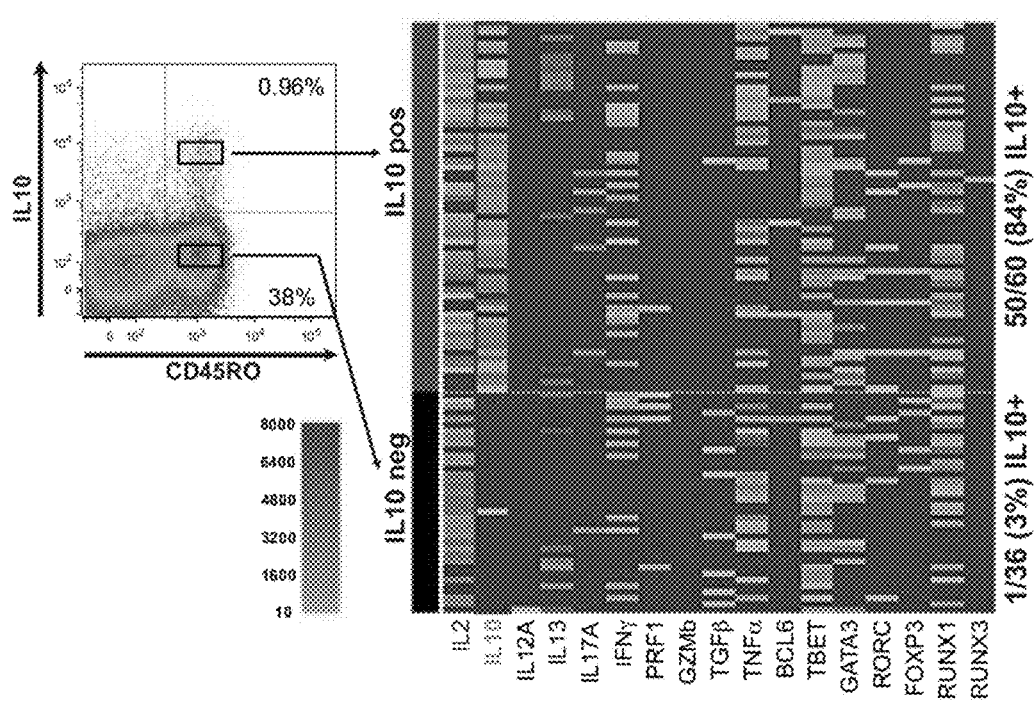
Figure 2E:
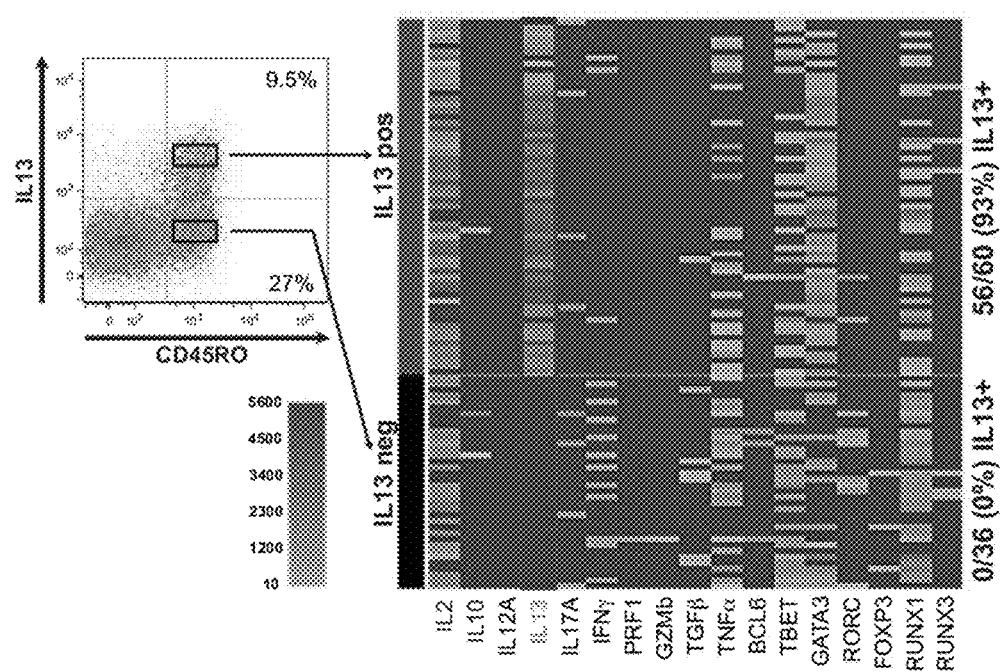
Figure 2F:
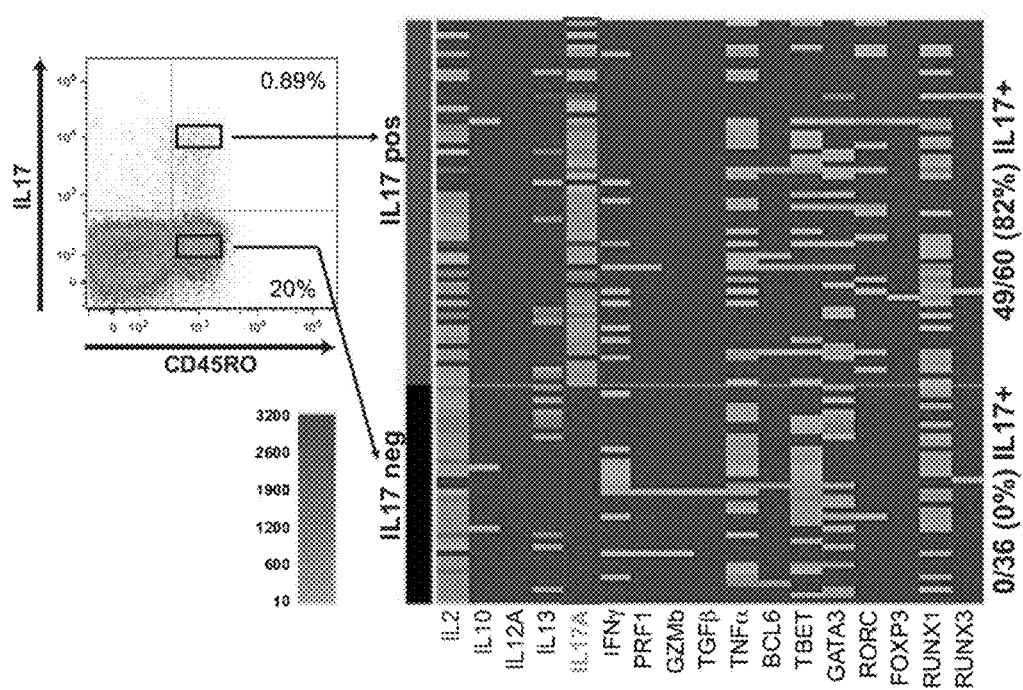
Figure 2G:
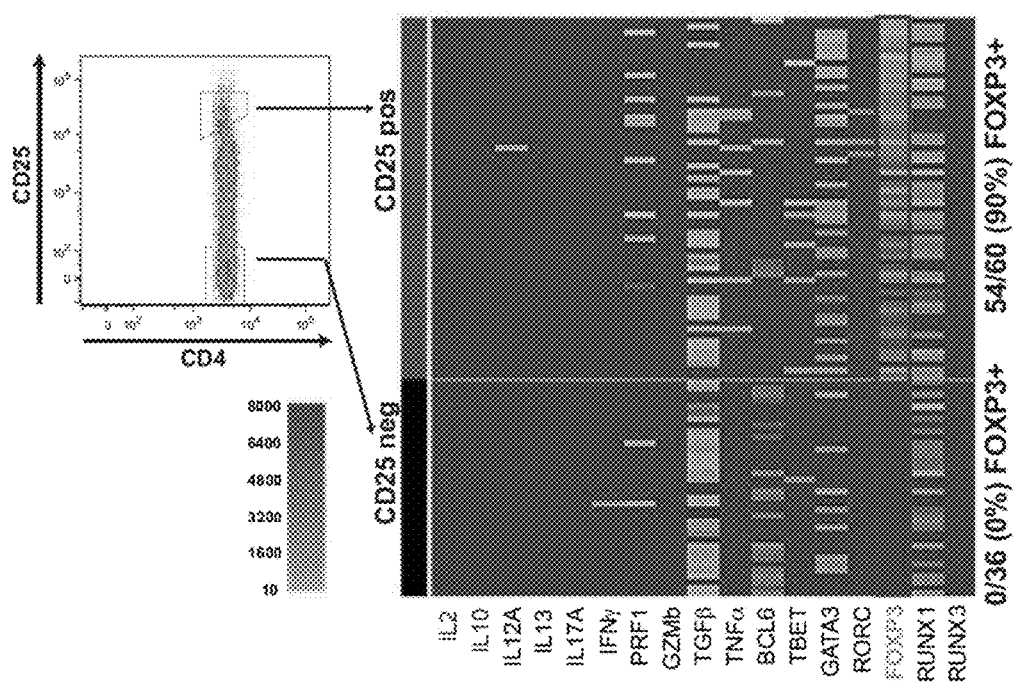
Figure 2H:
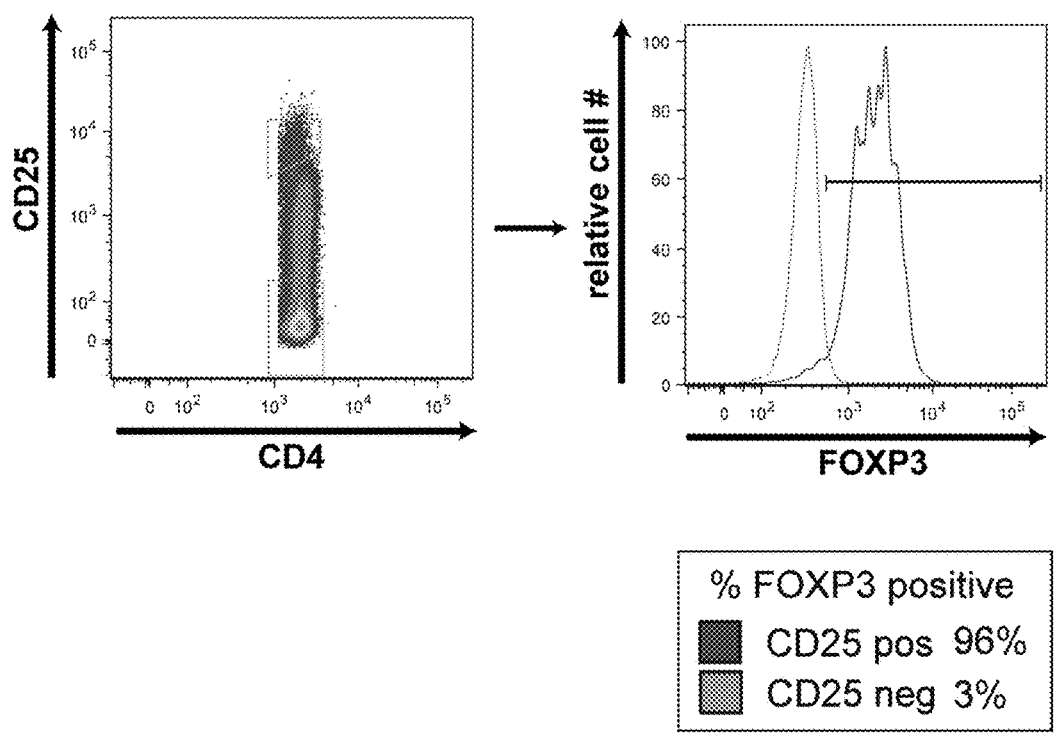

Expression of all the transcription factors in the panel in single T cells was readily detected. For most of these transcription factors, there are no available surface markers that reliably predict expression. An exception is FOXP3, whose expression correlates well with high expression of the surface marker CD25 in CD4+ T cells. To validate the methodology for FOXP3 expression, 60 single $CD25^{high}CD4^+$ T cells and 36 single $CD25^-CD4^+$ T cells were sorted into a single plate. FOXP3 was detected in 54/60 (90%) of $CD25^{high}$ cells and 0/36 (0%) of $CD25^-$ cells (FIG. 2G). T cells from the same donor with both CD25 and FOXP3 were fixed and stained to confirm the correlation between the high expression of CD25 and FOXP3 (FIG. 2H).

For some of the validated cytokines genes, there appeared to be a low false positive rate compared to cytokine secretion assays. Because these wells clearly exceed background levels (see Methods, FIGS. 6A-D for details on background), this suggested suggested that these rare cells did indeed express the particular mRNA although its protein product was not detected. This is not surprising given that cytokine genes are subject to particularly tight regulation, including translational repression that might prevent protein expression even in the presence of mRNA[31].

FIG. 6. FIGS. 6A and 6B show the validation of TCR cutoff criteria. Two plates, containing a combination of single cells and reagents, reagents but no single cells, and empty wells, were sequenced to an average depth of over 45,000 reads per well to evaluate influence of sample depth. On true-positive cutoff criteria, the plates were randomly subsampled to depths ranging from 100 to 45,000 average reads per well. Depths of 100, 1000, 10000 and 45 k are shown. While depth discrimination between true positive and true negative wells did increase with depth, a normalized depth measure, reporting the ratio between the number of domain-specific reads in this well over the average number of domain-specific reads per well in the run, provided a scale-free method to reliably exclude 100% of negative control wells across the dynamic range of 100-45,000 reads per well when a cutoff of at least 10% normalized depth in a well was asserted. For TCR analysis, samples were also evaluated based on domain dominance, a measure of dominance of a single clone in all reads of that domain type (TCR beta, TCR alpha) in the well. FIG. 6A shows that a cutoff of >85% for TCR beta was found to exclude the majority of negative control wells, as well as wells potentially containing more than one sorted cell. FIG. 6B shows that the domain dominance cutoff for TCR alpha was set at >10% to account for the possibility of multiple alpha chain expression. Both cutoffs were applied in the analysis, a domain dominance cutoff and a >10% normalized depth cutoff, to eliminate all negative control wells a dynamic range of 100-45,000 reads per well. In all positive control wells, depth was not found to ever impact successful classification of the dominant clone's identity. FIG. 6C shows the background of phenotypic parameters is proportional to total number of reads of that parameter on a given plate. Two plates, containing a combination of single stimulated T cells and reagents, reagents but no single cells, and empty wells, were sequenced. For each individual parameter, background reads (y-axis, reads per negative control well) was plotted in relation to total reads (x-axis, reads per well). The ratio of background reads/well to reads/well in all wells was ~1.23× $10^{-3}$. FIG. 6D shows that a threshold of 1 SD below mean read count provided of scale free means of excluding background signals on a plate. A single plate containing 80 wells with single T cells and 16 negative control wells was analyzed across the dynamic range of 100-45,000 reads per well. RUNX1 and GATA3, the two parameters containing the highest background, were assessed in 80 wells containing T cells and 16 negative control wells. Histogram depicts average read count per well (x-axis) and relative density (y-axis) for wells containing T cells (black) and negative control wells (light gray). Only wells containing at least 1 read for RUNX1 (left) or GATA3 (right) are shown. Dotted line represents 1 SD below the mean of log read counts per well of all wells containing reads.

As little as one molecule of template in a given cell was detected, although sensitivity improved with increased template abundance (Example 2, FIGS. 8A-E). While sensitivity of detection improved with template abundance, read number of a given transcript did not (FIGS. 8A-E). This demonstrated that the methodology was binary, and read number per well should not be used to quantify gene expression.

Figure 8A:
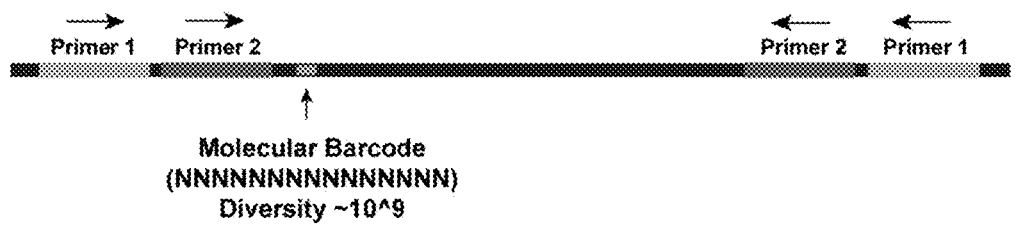
Figure 8B:
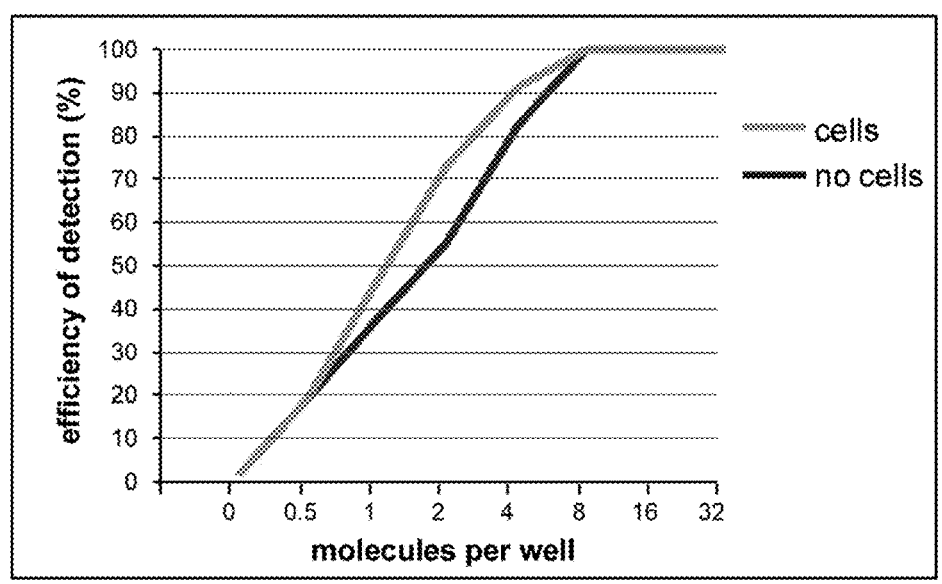
Figure 8C:
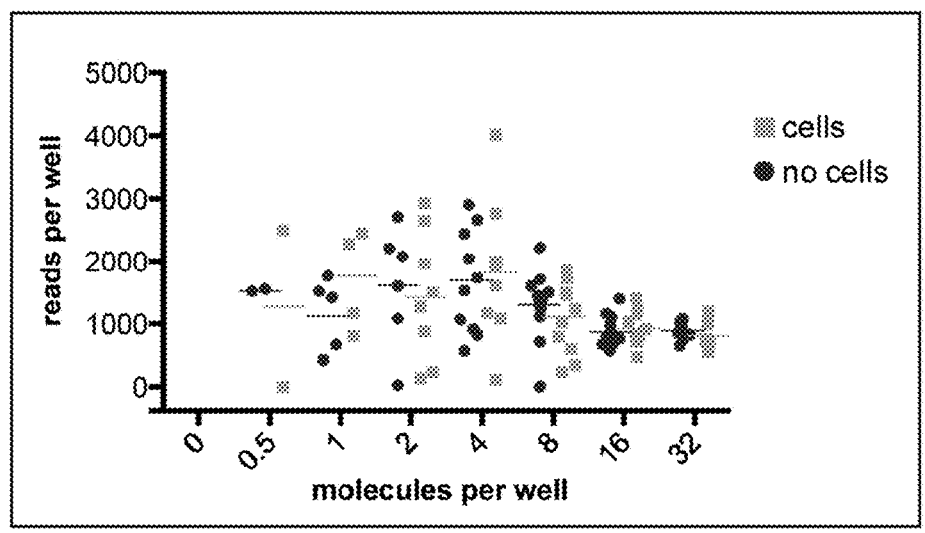
Figure 8D:
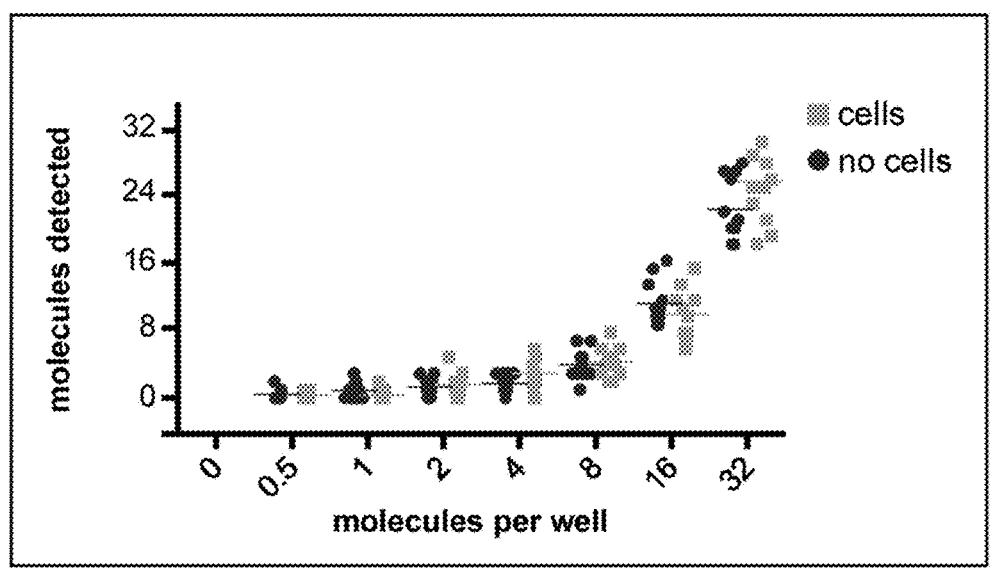

FIGS. 8A-E. A synthetic IL-17 template was spiked into 2 plates at various dilutions from 0 to 32 molecules per well (indicated on X-axis of plots). Into 1 plate, a single stimulated T cell was also sorted into each well. One well from each row was left without template as a negative control. Subsequent RT-PCR reactions were performed per protocol. FIG. 8A shows the design of the synthetic IL-17 template, which contains primer sequences for amplification and a molecular barcode containing 15 random nucleotides. FIG. 8B shows the sensitivity for detection of exogenous IL-17 template above background increases with abundance of template and does not significantly vary in the presence of other amplified phenotypic transcripts. Sensitivity was scored as a percentage of wells (out of 11 total per dilution). FIG. 8C shows that the total read number per well does not increase with template abundance. Total reads of exogenous IL-17 is wells where exogenous IL-17 was detected above background are shown. Two wells also containing endogenous IL-17 (expressed in added cells) were excluded from the analysis. FIG. 8D shows the number of uniquely barcoded molecules detected per well. To account for the presence of sequencing and PCR error, a similarity threshold was set above which molecular barcodes were scored as being equivalent. No molecules sharing the same barcode were repeated throughout the plates. FIG. 8E shows that the read counts per well of phenotypic parameters did not vary significantly. Mean read counts per well are listed for phenotypic parameters present in at least 50 cells within the tumor and colon T cell set.

It is very possible that a particular mRNA might be expressed but not detected in a particular cell, especially at lower copy number (FIGS. 8A-E). Therefore, it was expected that false negatives will occur with this method. However, the data showed that false positives do not occur at a significant rate (FIGS. 6A-D). Thus, for practical purposes, the positive predictive value of the assay exceeds its negative predictive for any given parameter. One should consider this when analyzing data using this methodology.

Despite the many factors that might contribute to discordance between mRNA and protein detection, the data correlated remarkably well with data from cytokine capture assays and with CD25 expression in the case of FOXP3 (FIGS. 2A-H, Table 6 provided in FIGS. 17A-AA). The statistical data utilized either the cytokine secretion assays or CD25 as the gold standard and did not take into account the possibility of true discordance between mRNA and protein expression. Clearly, mRNA expression does not always correlate with protein expression as many genes are subject to post-transcriptional regulation. Cytokine gene expression is subject to particularly complex regulation, including mechanisms affecting translation and/or mRNA stability[31]. Because there is likely discordance between mRNA and protein expression within cells, the data on sensitivity and specificity should only be used as a guide (Table 7 provided in FIG. 18).

FIGS. 2A-H. FIGS. 2A-2H show that phenotypic analysis was highly accurate when compared to flow cytometric analysis. FIGS. 2A-2F show that peripheral blood T cells were stimulated for 3 hours with PMA/ionomycin and analyzed for expression of the indicated cytokines by cytokine secretion assays which enable determination of cytokine expression without cell fixation. 60 single CD45RO+CD4+ T cells that were clearly positive for the indicated marker and 36 single CD45RO+CD4+ T cells that were clearly negative for expression of the indicated cytokine by flow cytometry were sorted and assayed. Heat maps indicate the read count of each parameter (X-axis) within each particular well (Y-axis). 17 independent phenotypic parameters were assayed in single sorted cells. The phenotypic parameter on which cells were sorted is indicated in light gray. Scale indicates number of reads obtained from a given well for the indicated parameter. Wells indicated in dark gray did not display any reads that reached threshold. FIG. 2G shows that unstimulated CD4+ T cells were sorted based upon CD25 expression to validate phenotypic analysis for FOXP3. 60 single CD4+ T cells with high CD25 expression and 36 single CD4+ T cells that were negative for CD25 expression flow cytometry were sorted and assayed. Heat maps indicate the level of expression of 17 independent phenotypic parameters in single sorted cells with FOXP3 indicated in light gray. FIG. 2H shows that CD25 expression correlated highly with FOXP3 expression by intracellular staining. Cells from the same donor were fixed and stained with anti-CD25 and anti-FOXP3 antibodies. Histograms on right depict FOXP3 expression by flow cytometry in indicated populations.

The strategy can also be customized or expanded. The phenotyping panel can be customized to include different genes. Since a sequence of any given parameter can be obtained, assays can be designed to include genetic polymorphisms, somatic mutations, or splice variations of genes in single cells. Because it is difficult to predict the cumulative effect of additional primers in a multiplexed PCR reaction, addition of parameters would require appropriate validation. However, the panel can likely be expanded to include more than the 17 genes assayed here. Given the current panel with 17 different phenotypic parameters, the presence of additional transcripts did not affect the sensitivity of detection of a given transcript (Example 2, FIGS. 8A-E). This suggested that significant expansion of this panel is possible even with current sequencing technology, which is continuously improving to enable higher sequencing depth. Taken together, these results show that the detection of mRNA by RT-PCR and deep sequencing is a potentially powerful and accurate way of multi-parametric phenotypic analysis in single cells.

To demonstrate one potential application of this strategy, human tumor infiltrating lymphocytes (TILs) from a human colorectal cancer were analyzed. Therapies designed to incite anti-tumor T cell responses have recently shown great promise in the treatment of human cancer[32,33]. In colorectal cancer, the presence of TILs has been shown to correlate strongly with positive prognosis[34,35]. These findings underscore the importance of T cells in anti-tumor immunity and their vast potential in cancer therapy. To date, however, phenotypic characteristics and TCR sequences of TILs have generally been studied as a population rather than single-cell level[34-37]. Thus, there is some controversy as to their function and clinical significance is different tumors[38] and no consensus view as to their specificity or functional properties.

The methodology was applied to 736 sorted human colorectal cancer infiltrating CD4+ T lymphocytes from one patient volunteer who underwent a colectomy for stage T3N1 rectal adenocarcinoma. For comparison, T cells derived from adjacent colon tissue from the same donor and peripheral blood T cells from a different healthy donor were also analyzed. TCRβ sequences were successfully obtained from 597 of the 736 CD4+ T cells (81%), and productive paired TCRαβ sequences to 503 of these (68%) were assigned. In this particular tumor, significant clonal expansion—with most highly expanded TCRβ present in 52/597 cells, and 10 TCRβ sequences seen in at least 8 cells were found (Table 8 provided in FIGS. 19A-AC). Out of 229 unique TCRβ sequences, the 10 most frequent sequences made up 215/597 (36%) of the cells where sequences were recovered, and 237 sequences (40%) were seen only once (Table 8 provided in FIGS. 19A-AC).

FIG. 19 (Table 8). Paired TCR alpha/beta sequences for 597 CD4+ tumor-infiltrating lymphocytes for which a TCR beta chain was obtained. TCR V and J gene usage, CDR3 sequence, and frequency within either the unstimulated or stimulated subset are shown. Indicated in bold are TCR clones which exhibit high sequence similarity and utilize identical TCR V and J genes. Similar clones are shaded.

For comparison, TCRs from 372 CD4+ T lymphocytes derived from resected adjacent colon tissue in the same donor were sequenced. TCRβ sequences were successfully obtained from 309 of the 372 CD4+ T cells (83%), and productive paired TCRαβ sequences were assigned to 217 of these (58%). In contrast to the tumor TCR repertoire, clonal expansion was minimal, with only 4 TCR clones present twice within the dataset (Table 9 provided in FIGS. 20A-Z). Also, there was not a single T cell clone that was shared between tumor and adjacent colon tissue. This suggested that expanded T cell clones present within tumors may be reacting to tumor antigens.

FIG. 20 (Table 9). Paired TCR alpha/beta sequences for 309 CD4+ T cells from adjacent colon for which a TCR beta chain was obtained. TCR V and J gene usage, CDR3 sequence, and frequency are shown.

Homology between tumor TCR sequences was searched to determine whether T cell expansion was due to antigen-specific responses. There were two examples of T cell clones sharing an identical alpha chain sequence and having very similar beta chain sequences (FIG. 9, Table 8 provided in FIGS. 19A-AC). One striking example of TCR similarity was found in that the most highly expanded TCRβ (CASS-LASMGVGELFF (SEQ ID NO:265)) sequence within the sample set varied by only 2 amino acids with another expanded TCRβ (CASSSASGGVGELFF (SEQ ID NO:267)). These TCRβ sequences respectively comprised 52 and 8, of 597 total T cells. These two expanded clones also used the same alpha chain (CAYRPNYGGATNKLIF (SEQ ID NO:269)). The alpha chains used different nucleotide sequences between the two clones and were not present elsewhere within the sample set, indicating that this finding was not a result of cross-contamination (Table 8 provided in FIGS. 19A-AC). Furthermore, each T cell clone expressed a different non-productive alpha chain, confirming that the common alpha chain was indeed the alpha chain that was utilized. In both T cell clones, alpha and beta chains contained significant N-nucleotide additions, indicating that these TCR sequences would not be very common by chance (FIG. 9). These findings strongly suggest that these two T cell clones comprising over 10% (60/597) total CD4+ T cells within this tumor have been selected and activated by the same peptide-MHC ligand.

FIG. 9. FIG. 9 shows that two expanded TIL T cell clones share a highly similar TCR beta chain and an identical TCR alpha chain. N-nucleotide additions and D-region sequence are indicated.

Figure 3A:
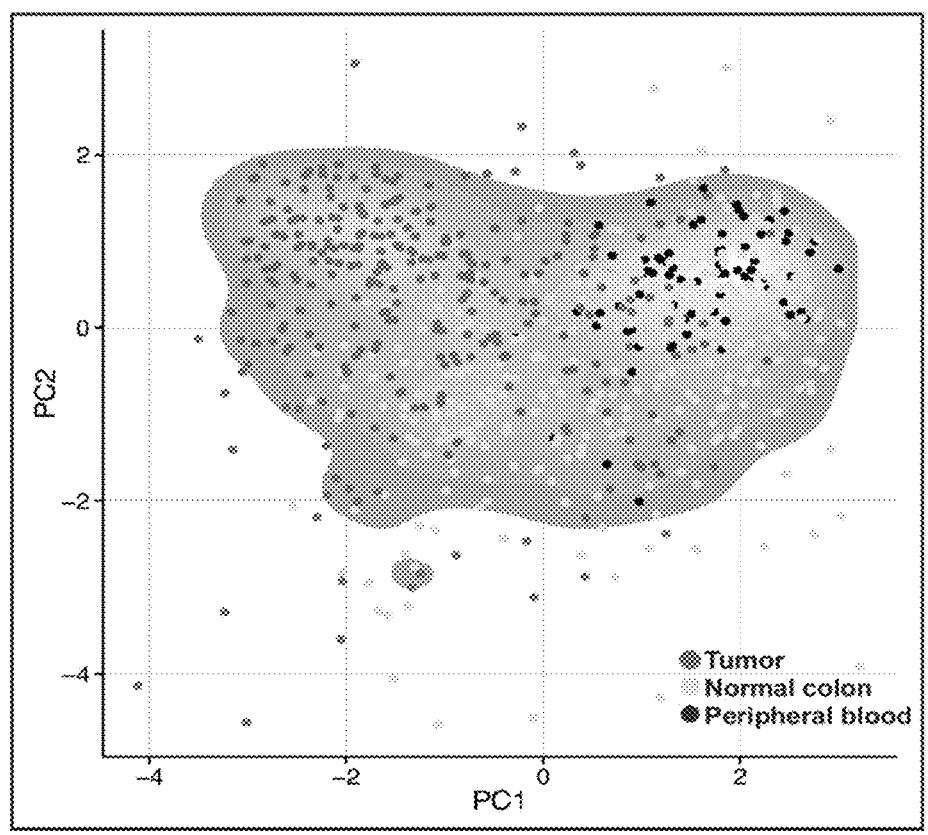
FIGS. 3A-D depict heterogeneity of human tumor infiltrating lymphocytes (TILs) based on single cell TCR sequencing and phenotypic analysis.
Figure 3B:
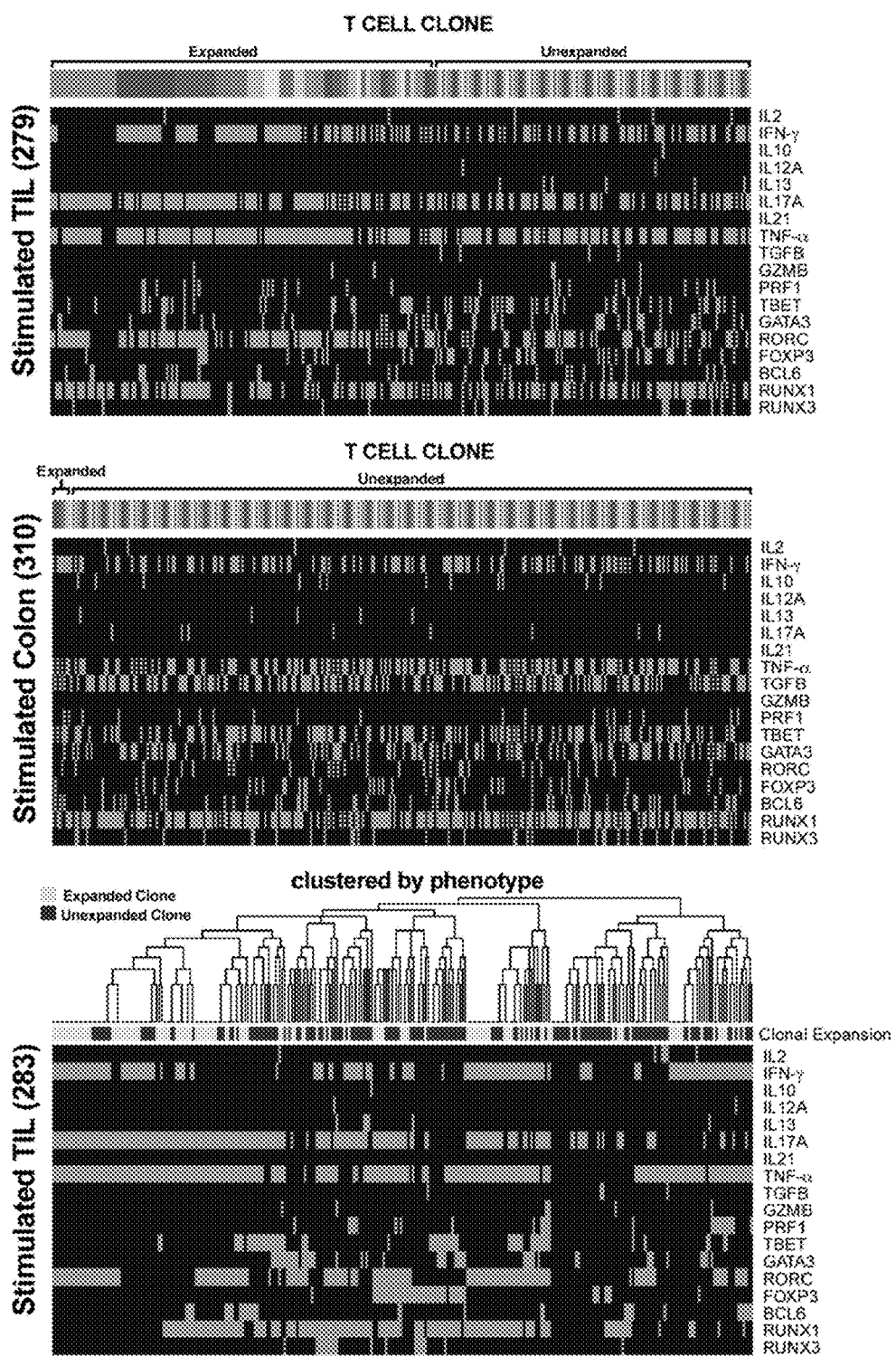
Figure 10:
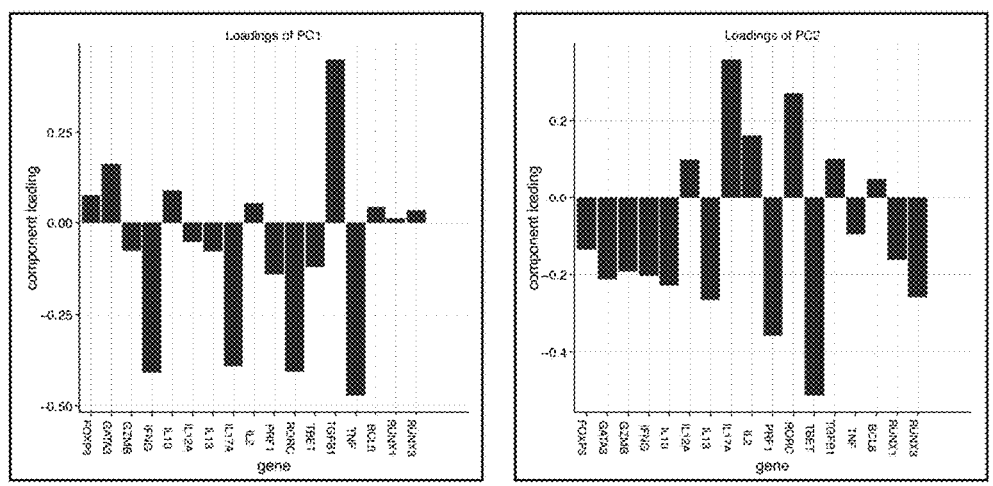
FIG. 10 depicts a principle component analysis of the parameter loadings for PC1 and PC2 shown in FIG. 3A.

In addition to TCR sequencing, these cells were phenotyped with respect to the 17 different genes discussed above. To elicit functional differences, half of the sorted TIL CD4+ T cells were stimulated for three hours with PMA/ionomycin. Consistent with previous findings[39-42], these stimulated CD4+ TILs display a distinct phenotype from stimulated CD4+ T cells from adjacent colon or peripheral blood (FIG. 3A, Table 10-11 provided in FIGS. 21A-AV and 22A-R, respectively). In this particular tumor, a high percentage of stimulated T cells expressed RORC (146/279, 52%) and were able to produce IL-17 (184/279, 66%), TNFα (217/279, 78%) and IFNγ (148/279 74%, FIG. 3B). To visualize the data, principal component analysis (PCA) was used, which acts to concentrate the most important sources of variation in larger datasets[2]. This allows us to readily visualize the phenotypic diversity of CD4+ T cells (FIGS. 3A, 3B, and 10). Although there was substantial overlap between the phenotypes between CD4+ T cells derived from tumor, colon and blood, these three population of cells cluster discretely on PCA (FIG. 3A). Such phenotypic diversity was not as apparent in the absence of stimulation (FIG. 11).

Figure 3C:
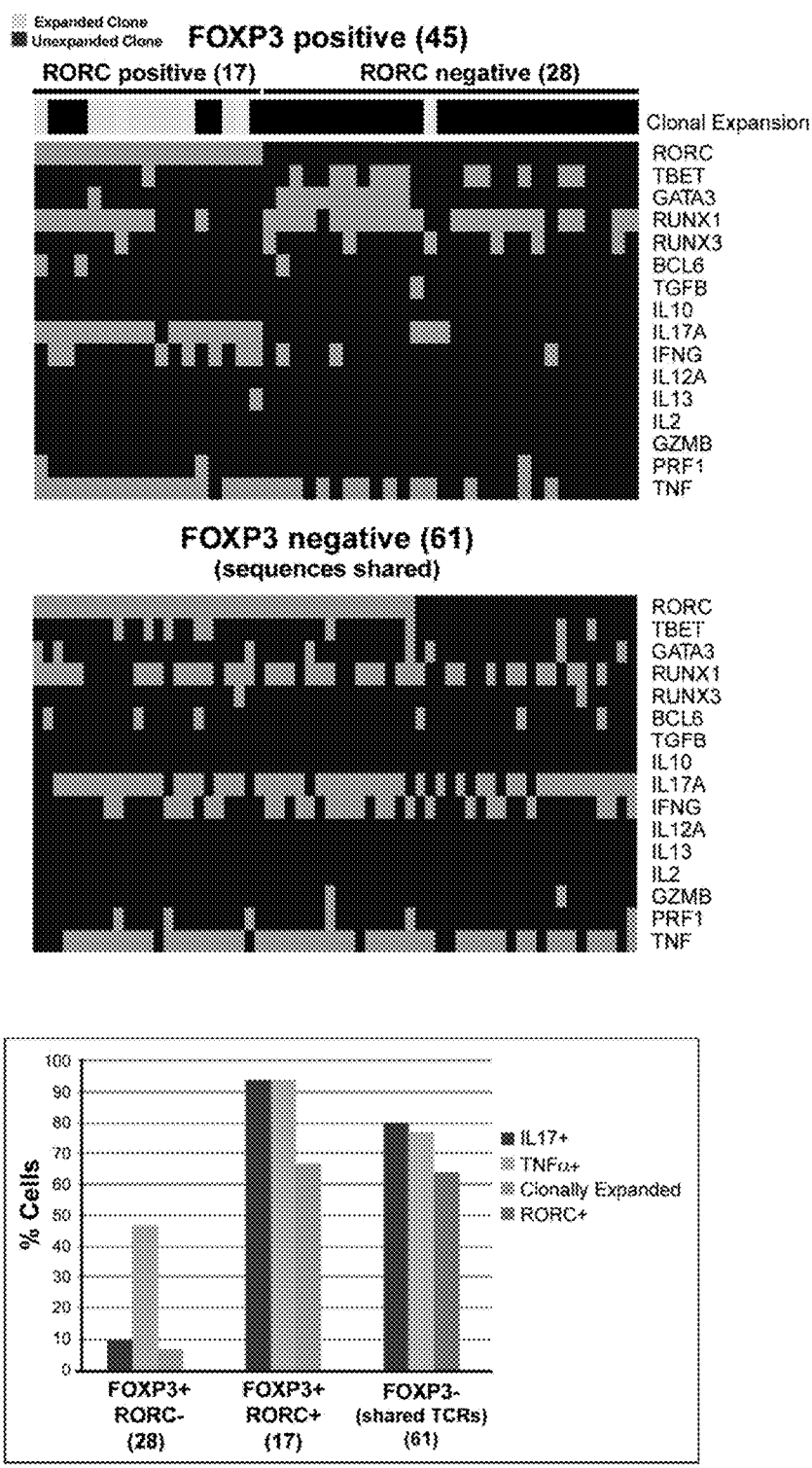
Figure 3D:
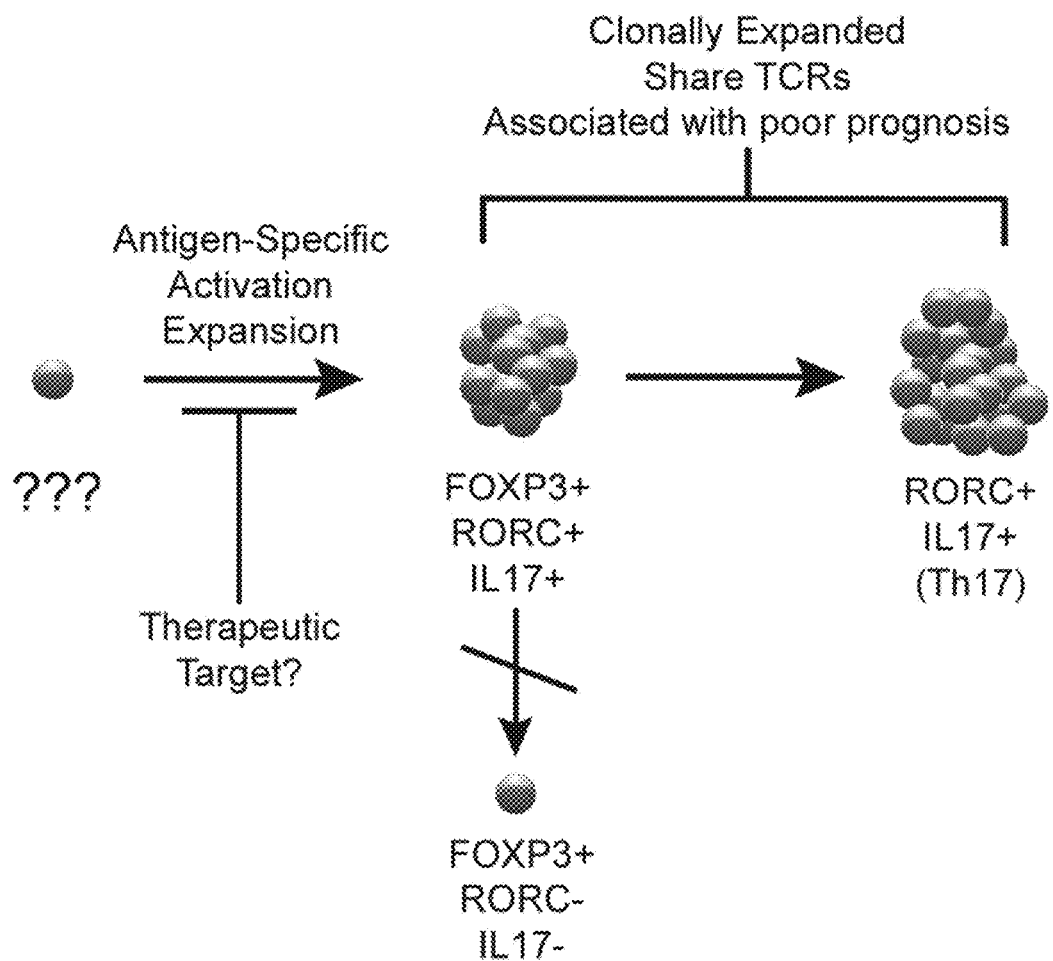

FIG. 3A-D. The number of cells analyzed for each subset is indicated in parentheses. FIG. 3A shows a principal component analysis (PCA) depicting the diversity of stimulated CD4+ T cells from tumor (medium gray), adjacent colon (light gray) and peripheral blood (black). PCA parameter loadings are shown in FIG. 10. FIG. 3B shows heat maps displaying a multi-parametric phenotypic analysis of stimulated CD4+ T cells from a tumor (top) and colon (middle). Individual T cells are grouped by TCR sequence. Each color on the bar represents a distinct TCR sequence. Hierarchical clustering of different cells by phenotype (bottom) is shown with expanded (light gray) and unexpanded (black) T cell clones. FIG. 3C shows that FOXP3+RORC− T cells and FOXP3+RORC+ T cells exhibited distinct phenotypes and degrees of clonal expansion (top). Phenotyping of T cells sharing sequences with FOXP3− RORC+ T cells (bottom) shows that FOXP3+RORC+ T cells share sequences with FOXP3−RORC+ T cells expressing IL-17. FIG. 3D shows a model suggested by analysis of TILs. A single T cell is stimulated and activated by antigen to expand and differentiate into FOXP3+RORC+ IL-17-producing T cells, which also eventually give rise to FOXP3−RORC+ IL-17-producing T cells.

Figure 11A:
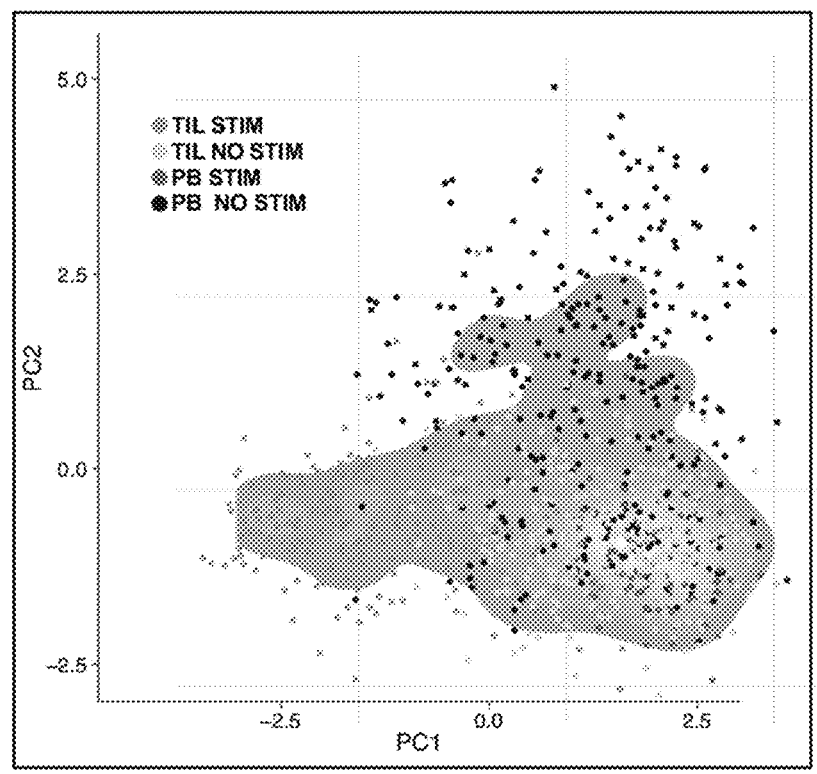
FIGS. 11A-C depict a principle component analyses and multi-parametric phenotypic analysis of CD4$^+$ T cells from tumor and peripheral blood.
Figure 11B:
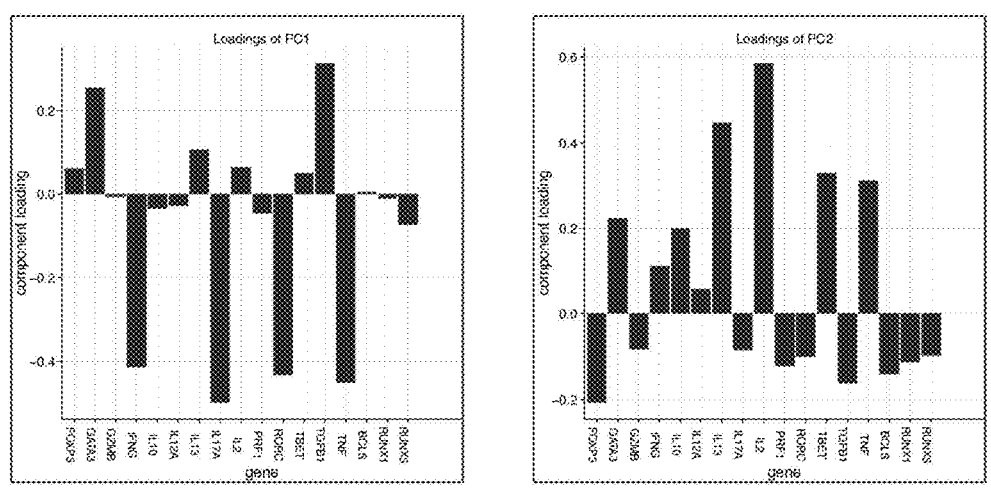
Figure 11C:
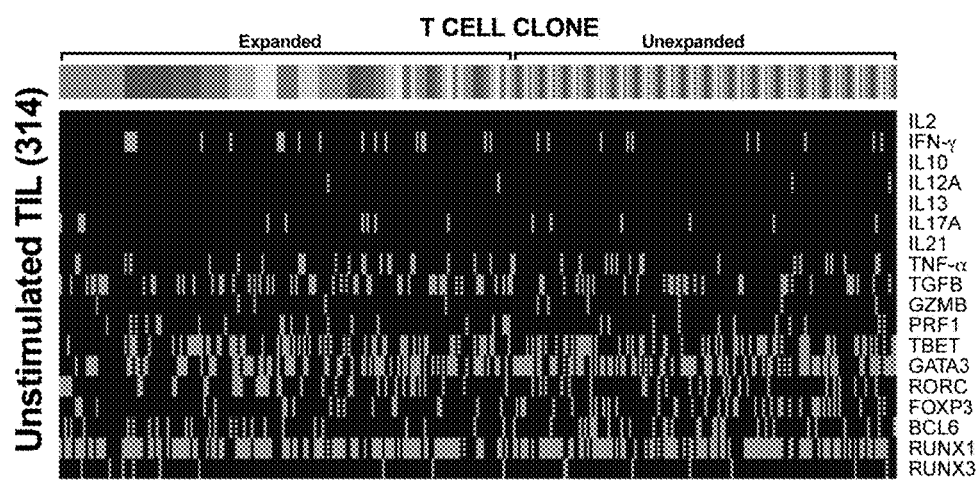

FIG. 11A-C. FIG. 11A shows a principle component analysis of unstimulated versus PMA/inomycin stimulated CD4+ T cells from tumor and peripheral blood shows that stimulation elicits functional diversity. FIG. 11B shows a principle component analysis of the parameter loadings for the PC1 and PC2 depicted in FIG. 11A. FIG. 11C shows a heat map displaying a multi-parametric phenotypic analysis of unstimulated CD4+ T cells from a tumor. Individual T cells are grouped by TCR sequence. Each color bar represents a distinct TCR sequence.

FIG. 21 (Table 10). Reads counts per well of each tumor CD4+ T cell analyzed. All raw read counts are shown, including reads below threshold levels.

FIG. 22 (Table 11). Reads counts per well of each adjacent colon CD4+ T cell analyzed. Clonally expanded clones are highlighted. All raw read counts are shown, including reads below threshold levels.

While CD4+ TILs were largely distinguished by expression of IL17, RORC, TNFα and IFNγ, there was also significant heterogeneity within each T cell population (FIG. 3B). Also, individual cells frequently co-expressed multiple different master regulator transcription factors, showing that the categorization of CD4+ T cells into specific subtypes was not always straightforward (FIGS. 3B and 3C).

A major advantage of the methodology is that it enabled us to compare the phenotypic and functional range of T cells that can arise from a single TCR clone. For instance, compared to unexpanded T cells, a significantly higher percentage of highly expanded (>10) T cell clones expressed IL-17 (70/80 vs. 65/126, p<0.005) or RORC (50/80 vs. 43/126, p<0.005). Conversely, FOXP3 was less likely to be expressed in highly expanded vs. unexpanded cells (5/80 vs. 32/126, p<0.005, FIG. 3B). When clustering analysis was applied, certain phenotypic clusters are preferentially occupied by unexpanded vs. expanded cells or vice versa (FIG. 3B).

The FOXP3+ tumor-infiltrating T cells was more closely studied. The function of Tregs in cancer has been the subject of much debate and FOXP3+ T cell infiltration in tumors has been correlated with both favorable and poor prognoses[39-42]. Within this particular tumor, two distinct subsets of FOXP3+CD4+ T cells, differentiated by the expression of RORC, were found. Within FOXP3+RORC+ cells, the overwhelming majority of cells expressed IL-17 (16/17, 94%) while IL-17 expression was rare within FOXP3+RORC− cells (3/28, 11%) (FIG. 3C). These two subsets also varied greatly with respect to the degree of clonal expansion. The FOXP3+RORC+ population consisted largely of clones that were expanded within the dataset (12/17, 71%) while clonal expansion was rare in the FOXP3+RORC− population (1/28, 4%). Incidentally, the only FOXP3+RORC− T cell that was clonally expanded expressed IL-17.

FOXP3+RORC+ IL-17-expressing T cells, described in both human colorectal cancer and in mouse models of polyposis, have been shown to have potent T-suppressive activity while being pro-inflammatory in their expression of IL-17[40,41]. While the consequences of FOXP3+ T cell infiltration into tumors are unclear, the presence of IL-17 has been associated with tumorigenesis and poor prognosis[42-44]. Based on this, RORC has been proposed as a therapeutic target. Both FOXP3+RORC+ T cells and FOXP3−RORC+ Th17-phenotype T cells may produce IL-17 within tumors, however, the relationship between these two populations of T cells was unclear. It has been proposed that they are unrelated given the discordance between their numbers within tumors[4].

To address this question, T cells that shared TCR sequences with FOXP3+RORC+ T cells were searched within the dataset. 61 instances of FOXP3− T cells sharing TCR sequences with FOXP3+RORC+ T cells were found. The majority of FOXP3− T cells sharing sequences of T cell clones within the FOXP3+RORC+ population also expressed IL-17 (49/61, 80%) and/or RORC (39/61, 64%). These findings indicate that these two populations of IL-17-expressing T cells share a common ancestry and are consistent with the idea that FOXP3+RORC+ T cells within tumors lose FOXP3 expression to become Th17 cells. The relationship between FOXP3+RORC− T cells and FOXP3+RORC+ T cells was not as clear. It was not clear whether FOXP3+ RORC+ T cells originated as FOXP3+RORC− T cells which underwent clonal expansion. However, the data suggested that FOXP3⁺RORC⁻ T cells did not originate as clonally expanded FOXP3⁺RORC⁺ T cells that lost expression of RORC. This is because FOXP3⁺RORC⁻ T cells are not clonally expanded and TCR sequences shared between those two populations of T cells were not seen.

Interestingly, for the example described above of expanded TCR clones having high similarity, both T cell clones contained cells expressing IL-17 and RORC. For the first TCRβ clone (CASSLASMGVGELFF (SEQ ID NO:265)), 27 of 52 T cell sequences were present in the stimulated sample. Of these, 24/27 cells expressed IL-17 and 16/27 cells expressed RORC. One cell co-expressed both FOXP3 and RORC. For the second TCRβ clone (CASSSASGGVGELFF (SEQ ID NO:267)), 2 of 8 sequences were present in the stimulated sample. Both of these T cells expressed IL-17 and one expressed RORC.

Taken together, the data showed clear heterogeneity between FOXP3⁺ T cells within tumors, which might help explain the why the data regarding the function of Tregs in tumors has been controversial. FOXP3⁺RORC⁺ T cells and FOXP3⁻RORC⁺ Th17-phenotype cells had also undergone significant expansion and share a common ancestry, suggesting a common initiating stimulus (FIG. 3D). Furthermore, an example of two expanded T cell clones with highly homologous TCR sequences that have members expressing IL-17 and FOXP3 were found, indicating that antigen-specificity was important to the selection of these T cells (FIG. 3D). More work is needed to understand the signals and antigens that lead to activation and clonal expansion of these IL-17 producing T cells within tumors. Also, TILs from colorectal cancer have been shown to be heterogeneous with respect IL-17 secretion so these results need to be validated on additional samples[41]. But given the association of IL-17 in tumorigenesis and poor outcomes, this initial activating event might represent an attractive target for therapy.

In summary, the technology described here enabled highly efficient TCR determination and multi-parametric phenotypic analysis in single T cells. It required no proprietary reagents or materials, and can be performed at reasonable cost by any standardly equipped laboratory with access to flow cytometry and deep sequencing. Excellent efficiency were achieved in attaining TCRαβ sequences and extensive phenotypic analysis were performed. The utility of this technology in the analysis of TILs was demonstrated, and it was shown how TCR sequences can add an invaluable dimension to multi-parametric phenotypic analysis by marking the ancestry of particular T cells, especially when the antigen is not known. This technology is also very complementary to recently developed methods to determine ligands for TCRs using random peptide-MHC libraries[10] and also the development of T cell based-therapies and vaccines.

Methods

Single Cell Sorting and Flow Cytometry

All FACS experiments were performed on ARIA II instruments (Becton Dickinson) in the Stanford Shared FACS Facility. Cytokine capture assays (Miltenyi Biotec) were performed per manufacturer's instructions on freshly isolated human peripheral blood mononuclear cells (PBMC). The Jurkat T cell leukemia cell line (Clone E6-1) was obtained from ATCC (atcc.org). The following antibody clones were used for flow cytometry: anti-CD3 (SK7, Biolegend), anti-CD4 (RPA-T4, Biolegend), anti-CD8 (OKT8, eBiosciences), anti-αβTCR (IP26, Biolegend), anti-CD25 (2A3, Becton-Dickinson), and anti-FOXP3 (PCH101, eBiosciences). Dead cells were excluded using a LIVE/DEAD Fixable Dead Cell Stain kit (Invitrogen).

Tumor Infiltrating Lymphocyte Preparation

The Stanford University Institutional Review Board approved all protocols for collection of human tissue and blood. Tissue was collected with informed consent from a patient undergoing colon resection for colon cancer at Stanford University Hospital after initially being processed by the Department of Pathology. Tumor tissue was cut into small pieces and incubated in 10 mM EDTA (ethylenediaminetetraacetic acid) in PBS (phosphate-buffered saline) for 30 minutes. Cells in suspension were collected through a 10 µM nylon cell strainer (Becton Dickinson). Tissue was then incubated in RPMI with 5% FCS containing 0.5 mg/ml of Type 4 collagenase for 30 minutes (Worthington Biochemical). Tissue was periodically disrupted during incubation by passing through a syringe topped with a blunt-ended 16-gauge needle. Lymphocytes were enriched through Percoll (GE Healthcare) gradient centrifugation. Cells were frozen in complete RPMI containing 10% DMSO (dimethylsulfoxide) and 40% FCS (fetal calf serum) for later use. Prior to use, cryopreserved lymphocytes were thawed and washed with complete RPMI before overnight recovery at 37° C. Cells were transferred to tubes, washed and resuspended in cytometry buffer (PBS+0.05% sodium azide+2 mM EDTA+2% fetal calf serum) for staining. For stimulation, cells were cultured for 3 hour at approximately $15 \times 10^6$/ml in complete RPMI (10% fetal calf serum) and 150 ng/ml PMA+1 µM ionomycin. At the end of the 3 hour stimulation, cells were pipetted vigorously to remove adherent cells from the plate and transferred to tubes, washed, and resuspended in cytometry buffer (PBS+0.05% sodium azide+2 mM EDTA+2% fetal calf serum).

TCR Sequencing and Phenotyping

Single-cell sorting was performed using an ARIA II cell sorter (Becton Dickinson). TCR sequence and gene expression analysis from single cells were obtained by a series of three nested PCR reaction as described. Cells were sorted directly into RT-PCR buffer. For the first reaction, reverse transcription and preamplification are performed with a One-Step RT-PCR kit (Qiagen) using multiplex PCR with multiple Vα and Vβ region primers, Cα and Cβ region primers, and phenotyping primers in a 20 µl reaction. For the PCR reaction #1, the final concentration of each TCR V region primer was 0.6 µM, each C region primer was 0.3 µM, each phenotyping primer was 0.1 µM. A 25 cycle first RT-PCR reaction was performed per manufacturer's instructions using the following cycling conditions: 50° 30'; 95° 15'; 94° 30", 62° 1', 72° 1'×25 cycles; 72° 5'; 4°. Next, a 1 µl aliquot of the first reaction was used as a template for second 20 µl PCR using HotStarTaq DNA polymerase (Qiagen) for either TCR sequencing or phenotyping. The following cycling conditions were: 95° 15'; 94° 30", 64° 1', 72° 1'×25 cycles (TCR) or 35 cycles (phenotyping); 72° 5'; 4°. For the TCR sequencing reaction, multiple internally nested TCRVα, TCRVβ, TCRCα and Cβ primers were used (V primers 0.6 µM, C primers 0.3 µM). For the phenotyping reaction, multiple internally nested phenotyping primers were used (0.1 µM). The second set of TCRV region primers and 5' phenotyping primers contained a common 23 base sequence at the 5' end to enable further amplification (during the third reaction) with a common 23 base primer. The second set of 3' phenotyping primers contained a common 24 base sequence to enable further amplification (during the third reaction). 1 µl aliquot of the second PCR was used as a template for the third 20 µl PCR reaction, which incorporated barcodes and enabled sequencing on the Illumina®

MiSeq platform. For the third and final PCR reaction for TCR sequencing, amplification was performed with HotStarTaq DNA polymerase for 36 cycles using a 5' barcoding primer (0.05 µM) containing the common 23 base sequence and a 3' barcoding primer (0.05 µM) containing sequence of a third internally nested Cα and/or C13 primer, and Illumina® Paired-End primers (0.5 µM each). For tumor infiltrating and colonic T cell analysis, the final barcoding PCR reaction for TCR alpha and TCR beta were combined. When the third reaction was performed together, the 3' Cα barcoding primer was used in 3-fold excess to the 3' Cβ barcoding primer (0.15 µM and 0.5 µM). In addition to the common 23 base sequence at the 3' end (that enabled amplification of products from the second reaction) and a common 23 base sequence at the 5' end (that enabled amplification with Illumina® Paired-End primers), each 5' barcoding primer contains a unique 5 base barcode that specified plate and a unique 5 base barcode that specified row within the plate. These 5' barcoding primers are added with a multichannel pipette to each of 12 wells within a particular row within a particular plate. In addition to the internally nested TCR C-region sequence and a common 23 base sequence at the 3' end (that enabled amplification with Illumina® Paired-End primers), each 3' barcoding primer contains a unique 5-nucleotide barcode that specified column. These 3' barcoding primers are added with a multichannel pipette to each of 8 wells within a column within all plates. For TCR sequencing, the third reaction can be performed separately for TCRα and TCRβ, or combined. The third reaction for phenotyping are performed in a similar manner with the TCR sequencing, except that the 3' primer contains the common 24 base sequence contained in all 3' primers from the second reaction rather than the internally nested TCR C-region primer. The same 5' barcoding primers are used for the third phenotyping reaction as the TCR sequencing reaction. After the third and final PCR reaction, each PCR product should have a unique set of barcodes incorporated that specified plate, row and column and have Illumina® Paired-End sequences that enable sequencing on the Illumina® MiSeq platform. The PCR products are combined at equal proportion by volume, run on a 1.2% agarose gel, and a band around 380 bp was cut and gel purified using a Qiaquick gel extraction kit (Qiagen). This product was then sequenced.

PCR Primer Design

All primer sequences are provided in FIG. 4 and Tables 1-3 provided in FIGS. 12A-H, 13A-B and 14A-C, respectively. All primers were designed to have a Tm of 70-72 degrees (Tm=4×[GC]+2[AT]). For TCR primers, base degeneracy was incorporated into the primers when necessary to account for TCR polymorphism and ensure amplification of all known functional Vα, Vβ, Cα and Cβ regions identified in the IMGT database (imgt(dot)org/). V-region primers were designed to be at least 50 bases from the distal end to ensure inclusion of the entire CDR3 region. All TCR and phenotyping primers for the second reaction contained the common sequence CCAGGGTTTTCCCAGTCACGAC (SEQ ID NO:3) at the 5' end, which enabled amplification with barcoding primers during the third reaction. All phenotyping primers for the second reaction contained the common sequence AGCGGATAACAATTTCACACAGGA (SEQ ID NO:6) at the 5' end, which enabled amplification with barcoding primers during the third reaction. After all reactions are performed, TCR primers amplify a segment of the TCR of approximately 250 bp. The final product for sequencing was approximately 380 bp.

Phenotyping PCR primers were designed to span introns and amplify all major variants of the genes present in the NCBI database (ncbi.nlm.nih.gov). After the second reaction was performed, phenotyping primers amplify a gene segment of approximately 200 bp, and the final sequencing product was approximately 350 bp.

Sequencing Data Analysis

Raw sequencing data was processed and demultiplexed using a custom software pipeline to separate reads from every well in every plate according to specified barcodes. All paired ends are assembled by finding a consensus of at least 100 bases in the middle of the read. The resulting paired-end reads are then assigned to wells according to barcode. Primer dimers are filtered out by establishing minimum length of 100 bases for amplicon. For example, in a recent sequencing run consisting of 2164 cells, $2.01 \times 10^7$ raw reads were obtained, $1.95 \times 10^7$ pass-filtered reads (Illumina®.com), forward/reverse consensus sequences were obtained and barcodes assigned to $1.66 \times 10^7$ reads, with $1.60 \times 10^7$ reads above 100 bases. The average read number per well was 7382±5366. A consensus sequence was obtained for each TCR gene. Because multiple TCR genes might be present in a given well, the software established a cutoff of >95% sequence identity within a given well. All sequences exceeding 95% sequence identity were assumed to derive from the same TCR gene and a consensus sequence was determined. The 95% cutoff conservatively ensured all sequences derived from the same transcript would be properly assigned even given PCR rate of 1/9,000 bases, and sequencing error rate up to 0.4%[23]. TCR V, D and J segments were assigned by VDJFasta[20]. For phenotyping transcripts, the number of reads containing a 95% match to the customized database of transcription factor and cytokine genes are scored.

Single Well Depth and Dominance Cutoff Parameter Validation

For both TCR and phenotypic parameters, there was a low background of unrelated sequences (FIG. 6). Potential background was quantified through high depth sequencing and set thresholds accordingly. For TCR sequencing, thresholds were set based upon normalized depth of detection and clonal dominance (FIG. 6). For phenotypic analysis, thresholds were set based upon normalized depth of detection.

Single Cell Sequencing Accuracy

PCR error occurs at a rate of 1/9,000 bases, and sequencing error has been reported to occur at a rate up to 0.4%. The method relied on generation of a consensus sequence from 10-10,000 reads, thus establishing single-cell transcript coverage far superior to that provided by genomic sequencing, mitigating the role of PCR error and largely eliminating sequencing error. To determine the accuracy of sequencing, the incidence of error was observed within phenotyping transcripts that are entirely germline encoded, unlike TCR genes. When consensus sequence was obtained for all phenotyping transcripts within individual wells, the sequences were always identical. This indicated that despite sequencing or PCR error, the consensus sequence derived from a given well from >10 reads was 100% accurate within the dataset.

Quantification of Background

There was an inherent level of background present even in empty wells. To quantify this background, sequencing was performed at high depth. Single stimulated T cells were sorted into two plates and processed for TCR and phenotypic analysis. Into these two plates, no cells were sorted into 16 wells, scattered through all columns and rows. 8 of these wells were processed normally with all reagents added. 8 of these wells were left completely blank throughout analysis with no reagents added. These two plates (as opposed to the usual 20-25 plates) were run on a single sequencing run to give a sequencing depth >10 fold higher than usual.

Figure 6A:
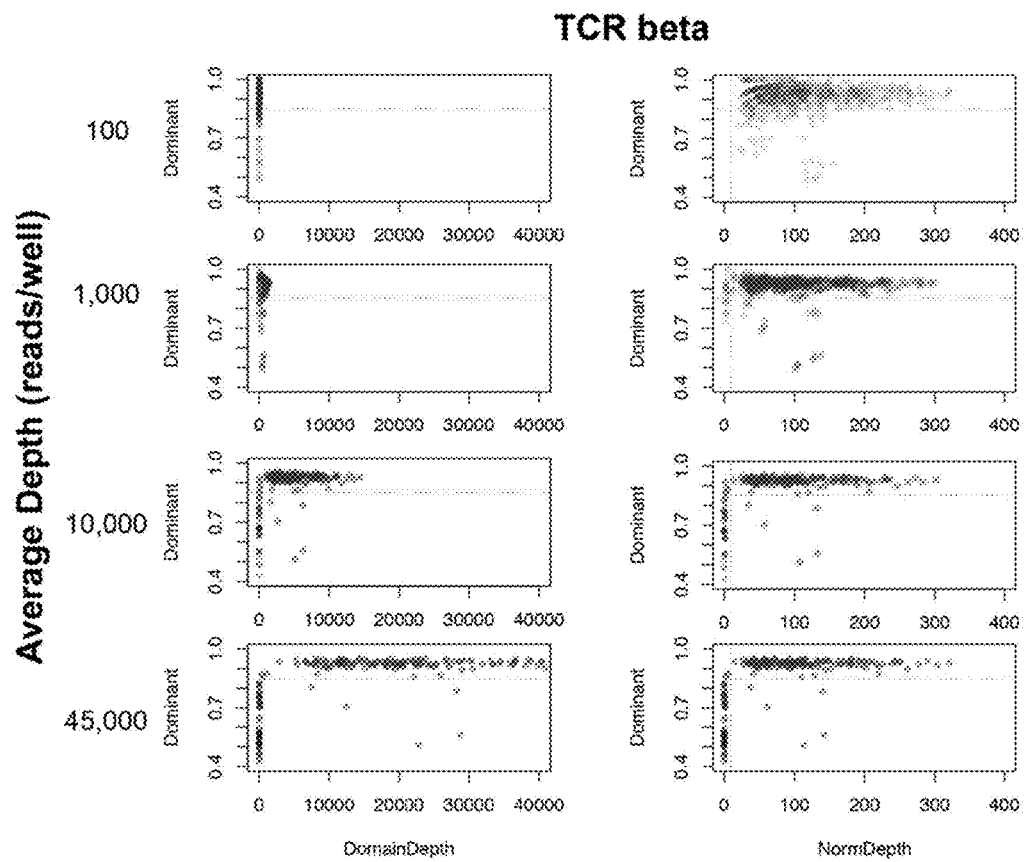
FIGS. 6A-D depict the validation of true-positive cutoff criteria by through high depth sequencing.
Figure 6B:
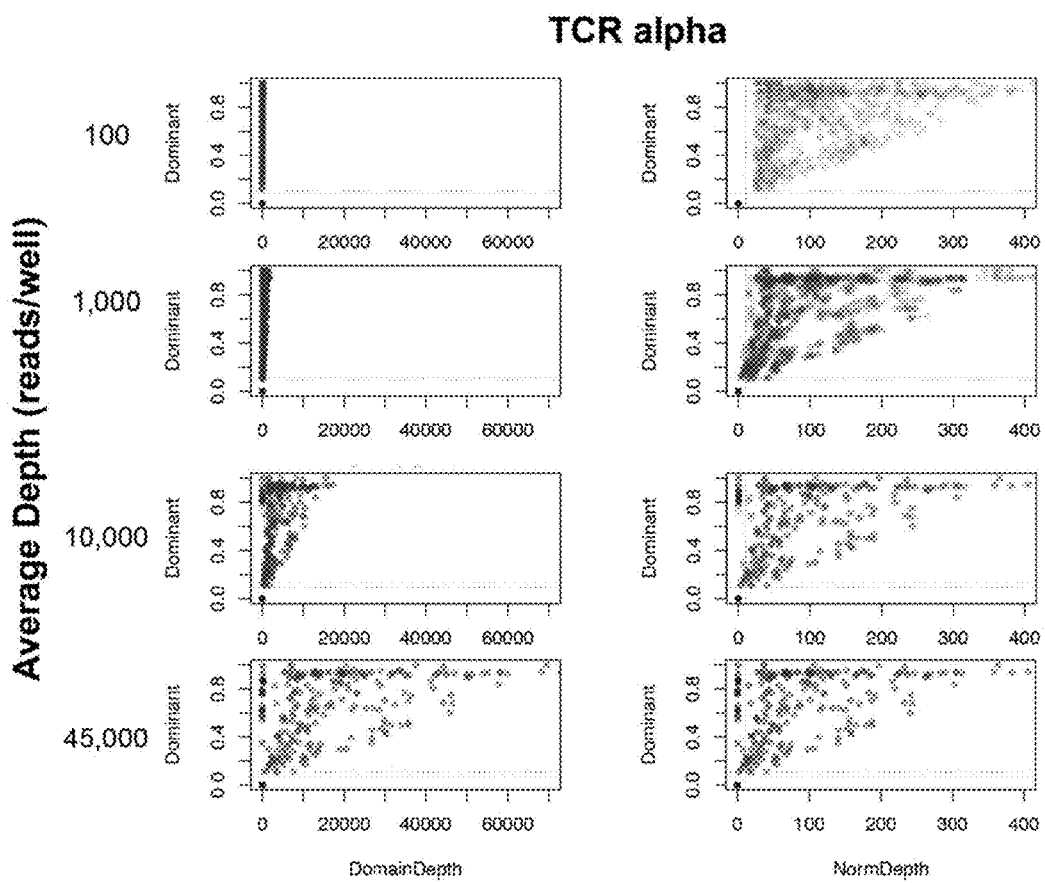

In the two test plates, there was no significant difference in TCR background reads in negative control wells without sorted T cells, regardless of whether wells were processed with reagents (FIGS. 6A and 6B). These data indicate that background was primarily due to error in PCR, sequencing or oligonucleotide synthesis within the barcodes and not due to cross contamination.

For TCR reads within the two test plates, cutoff criteria were validated by simulated subsampling (FIGS. 6A and 6B). Plates were sequenced to an average depth of >45,000 reads per well, and subsampled to depths ranging from 100 to 45,000 average reads per well. By quantifying background signal (negative control wells), justification for thresholds set in the analysis was provided. For TCR analysis, a threshold normalized depth (based up average number of reads per well in the plate) of 10% was established. Using normalized depth independently, there was a clear separation between wells containing cells and background signal in negative control wells at all depths down to 100 reads/well. For TCR analysis, establishing thresholds for clone dominance within the well further excluded the majority of negative control wells and wells potentially containing more than one cell. For beta chains, a domain dominance cutoff was set at >85%. Domain dominance was determined based on 100% identity in sequence. Thus, this threshold of 85% was considerably lower than 100% because it accounts for the presence of PCR mutation or sequencing error. Because multiple TCR alpha chains can exist within a given cell, the threshold for domain dominance was more permissive and set to 10%.

Figure 6C:
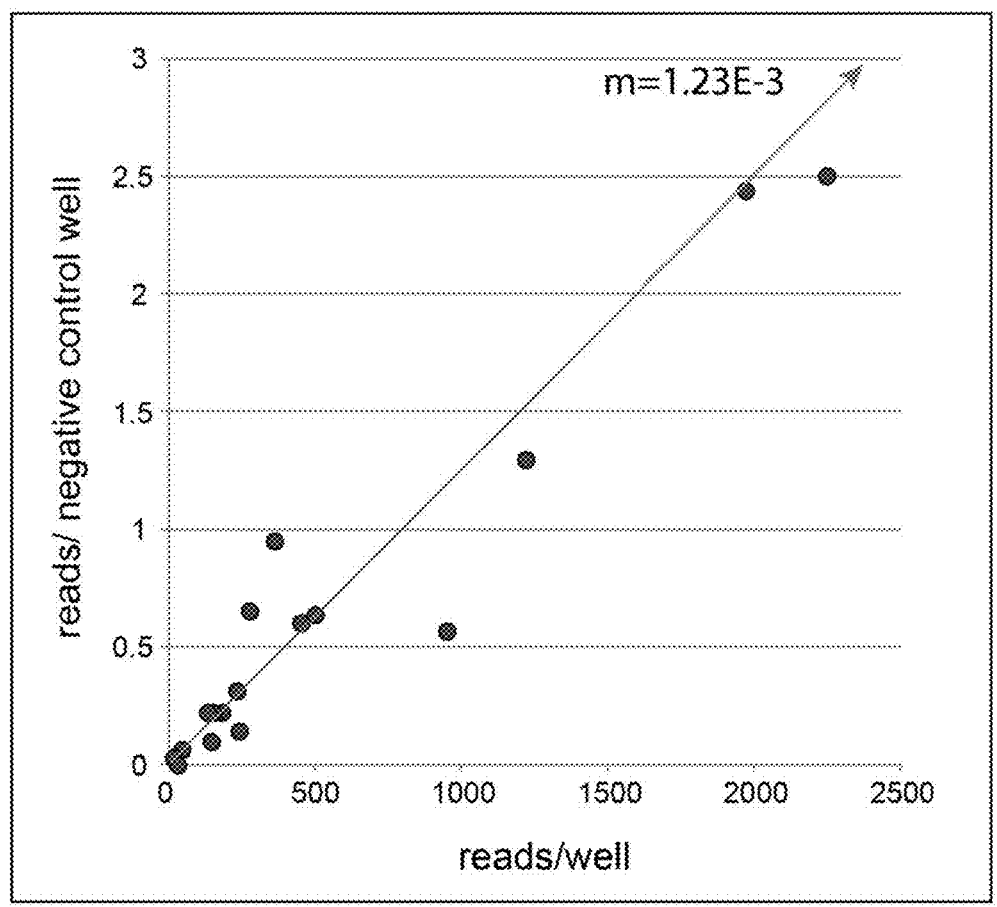

For phenotypic parameters, unlike TCR genes, not all cells express a given parameter. Thus, background was expected to depend upon number of cells expressing a given parameter as well as read depth. To investigate the background for phenotypic parameters, analysis on 2 plates containing 40 wells was performed into which stimulated IL17$^+$ T cells were sorted, 40 wells into which stimulated IL17$^-$ T cells were sorted, and 16 negative control wells. 8 of these negative control wells were processed normally with all reagents added. 8 of these wells were left completely blank throughout analysis with no reagents added. IL17$^+$ and IL17$^-$ T cells were sorted because this population gave a variable range of cells expressing all phenotypic parameters within the plate. Background levels of each phenotypic parameter signal was assessed in negative control wells. As was the case with TCR, there was no significant difference in background between negative wells processed with (0.54 background reads/well) or without reagents (0.72 background reads/well), suggesting that background was primarily due to error in PCR, sequencing or oligonucleotide synthesis within the barcodes and not due to cross contamination. The background was directly proportional to the number of reads for each particular parameter on a plate and the number of cells expressing a given parameter (FIG. 6C). The ratio of reads/negative control well versus total reads/well for each phenotypic parameter in a given plate was approximately $1.23 \times 10^{-3}$. This ratio was constant, independent of the frequency of the cells expressing a given parameter.

Figure 6D:
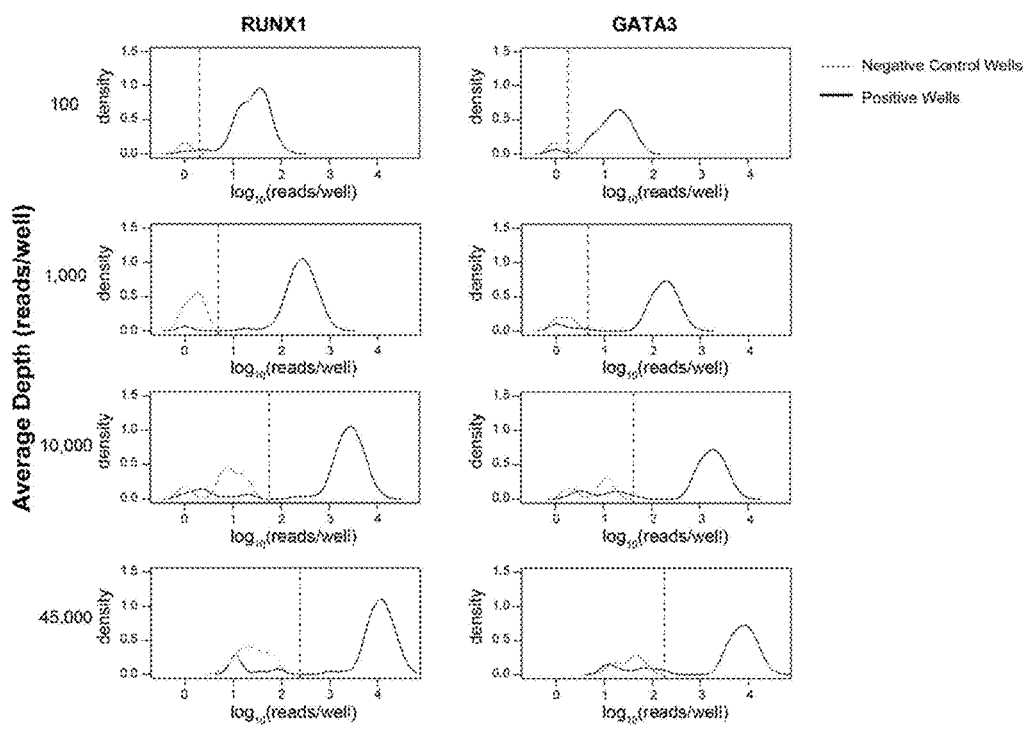

High depth analysis was performed on one plate containing 80 wells with single T cells and 16 negative control wells to further investigate background per well. The plate was sequenced to an average depth of >45,000 reads per well, and subsampled to depths ranging from 100 to 45,000 average reads per well. The two phenotypic parameters with the highest level of background on this plate, RUNX1 and GATA3, were individually assessed. For RUNX1 and GATA3, respectively, the ratio of reads/negative control well vs total reads/well was $1.30 \times 10^{-3}$ and $1.71 \times 10^{-3}$ consistent with levels established in the analysis of the prior plate (FIG. 6C). This indicated that relative background did not vary significantly, even at high read depth. RUNX1 and GATA3 signal in 80 wells containing T cells and 16 negative control wells was assessed (FIG. 6D). Setting a threshold to 1 SD below the mean of log read counts per well (in all wells within a sequencing run expressing a given parameter) provided a scale-free means of conservatively excluding all background signals for phenotypic parameters. The accuracy of this threshold did not vary as a function of frequency of cells expressing the parameter, as only wells expressing a given parameter are included.

Example 2

Sensitivity of Detection, but not Read Count, Increased with Template Abundance

The sensitivity of the method for detection of a particular transcript was further investigated. A synthetic dsDNA was constructed that contains binding sites for the IL-17 primers (FIG. 8A). The construct was identical to the exogenous IL-17 amplicon except 15 nucleotides of endogenous IL-17 sequence was replaced with a 15 nucleotide random molecular barcode giving a theoretical diversity of $4^{15}$ ($>10^9$). This synthetic construct was made by PCR using a 124 base 5' primer incorporating the primer sequences and the molecular barcode (5' GCG TAA TAC GAC TCA CTA TAG GGA GAC AGA CAA GAA CTT CCC CCG GAC TGT GAT GGT CAA CCT GAA CAT CCA TAA CCG GAA CAT NNN NNN NNN NNN NNN CAA AAG GTC CTC AGA TTA CTA CAA C (SEQ ID NO:1644)). To ensure that unique barcodes were not amplified, the template was first amplified by 60 cycle reaction using only the 5' primer, and then 1 cycle was performed after addition of the 3' primer. The PCR product was purified and quantified. The product was quantified by Nanodrop™ 2000 (Thermo Scientific) and Bioanalyzer™ 2100 (Agilent). Based upon these calculations, serial dilutions were performed and quantities were further verified by performing 50 cycle PCRs using primers within the template sequence. This synthetic construct was spiked into wells at different serial dilutions indicated and performed reactions and analysis on two plates. These two plates were processed identically, except a single stimulated T cell was added to one of the plates. Into both plates, 8 negative control wells were processed without spiked template or cells.

The method could detect as little as 1 molecule of dsDNA template (equivalent to 2 molecules of mRNA) (FIG. 8B). Sensitivity improved with increased copy number and 100% sensitivity was achieved when 8 molecules of dsDNA (equivalent of 16 molecules of mRNA) were spiked into the initial reaction (FIG. 11B). Although sensitivity did improve with increased copy number, read count per well did not significantly change (FIG. 8C). This indicated that the readout was binary and read depth will not significantly affect sensitivity (i.e., sequencing at a higher depth will not improve identification of low abundance transcripts in cells). Furthermore, the sensitivity of detection for one particular phenotypic parameter was not affected by the presence of other transcripts, as the sensitivity of detection for this template did not differ when stimulated T cells are added to the reaction and other amplified transcripts are present (FIG.

8C). As more molecules were added per well, more molecular barcodes were detected (FIG. 8D). No molecular barcodes were repeated in different wells in the dataset after accounting for background and the presence of PCR or sequencing error (FIG. 8D).

Mean read counts per well for each phenotypic parameter did not vary significantly for phenotypic parameters present in at least 50 cells in the tumor and colon dataset, which were sequenced to similar read depth (FIG. 5E).

REFERENCES

1 Wills, Q. F. et al. Single-cell gene expression analysis reveals genetic associations masked in whole-tissue experiments. *Nature biotechnology* 31, 748-752, doi:10.1038/nbt.2642 (2013).
2 Newell, E. W., Sigal, N., Bendall, S. C., Nolan, G. P. & Davis, M. M. Cytometry by time-of-flight shows combinatorial cytokine expression and virus-specific cell niches within a continuum of CD8+ T cell phenotypes. *Immunity* 36, 142-152, doi:10.1016/j.immuni.2012.01.002 (2012).
3 Shapiro, E., Biezuner, T. & Linnarsson, S. Single-cell sequencing-based technologies will revolutionize whole-organism science. *Nature reviews. Genetics* 14, 618-630, doi:10.1038/nrg3542 (2013).
4 Bendall, S. C., Nolan, G. P., Roederer, M. & Chattopadhyay, P. K. A deep profiler's guide to cytometry. *Trends in immunology* 33, 323-332, doi:10.1016/j.it.2012.02.010 (2012).
5 Spurgeon, S. L., Jones, R. C. & Ramakrishnan, R. High throughput gene expression measurement with real time PCR in a microfluidic dynamic array. *PloS one* 3, e1662, doi:10.1371/journal.pone.0001662 (2008).
6 Wu, A. R. et al. Quantitative assessment of single-cell RNA-sequencing methods. *Nature methods*, doi:10.1038/nmeth.2694 (2013).
7 Newell, E. W. & Davis, M. M. Beyond model antigens: high-dimensional methods for the analysis of antigen-specific T cells. *Nature biotechnology* 32, 149-157, doi:10.1038/nbt.2783 (2014).
8 Krogsgaard, M. & Davis, M. M. How T cells 'see' antigen. *Nature immunology* 6, 239-245, doi:10.1038/ni1173 (2005).
9 Newell, E. W. et al. Combinatorial tetramer staining and mass cytometry analysis facilitate T-cell epitope mapping and characterization. *Nature biotechnology* 31, 623-629, doi:10.1038/nbt.2593 (2013).
10 Birnbaum, M. E. et al. Deconstructing the peptide-MHC specificity of T cell recognition. In press, *Cell* (2014).
11 Hinrichs, C. S. & Restifo, N. P. Reassessing target antigens for adoptive T-cell therapy. *Nature biotechnology* 31, 999-1008, doi:10.1038/nbt.2725 (2013).
12 Han, A. et al. Dietary gluten triggers concomitant activation of CD4+ and CD8+ alphabeta T cells and gammadelta T cells in celiac disease. *Proceedings of the National Academy of Sciences of the United States of America* 110, 13073-13078, doi:10.1073/pnas.1311861110 (2013).
13 Kim, S. M. et al. Analysis of the paired TCR alpha- and beta-chains of single human T cells. *PloS one* 7, e37338, doi:10.1371/journal.pone.0037338 (2012).
14 Dash, P. et al. Paired analysis of TCRalpha and TCRbeta chains at the single-cell level in mice. *The Journal of clinical investigation* 121, 288-295, doi:10.1172/JCI44752 (2011).
15 Gascoigne, N. R. & Alam, S. M. Allelic exclusion of the T cell receptor alpha-chain: developmental regulation of a post-translational event. *Seminars in immunology* 11, 337-347, doi:10.1006/smim.1999.0190 (1999).
16 Malissen, M. et al. Regulation of TCR alpha and beta gene allelic exclusion during T-cell development. *Immunology today* 13, 315-322 (1992).
17 DeKosky, B. J. et al. High-throughput sequencing of the paired human immunoglobulin heavy and light chain repertoire. *Nature biotechnology* 31, 166-169, doi:10.1038/nbt.2492 (2013).
18 Wang, C. et al. High-throughput, high-fidelity HLA genotyping with deep sequencing. *Proceedings of the National Academy of Sciences of the United States of America* 109, 8676-8681, doi:10.1073/pnas.1206614109 (2012).
19 Bentley, D. R. et al. Accurate whole human genome sequencing using reversible terminator chemistry. *Nature* 456, 53-59, doi:10.1038/nature07517 (2008).
20 Glanville, J. et al. Precise determination of the diversity of a combinatorial antibody library gives insight into the human immunoglobulin repertoire. *Proceedings of the National Academy of Sciences of the United States of America* 106, 20216-20221, doi:10.1073/pnas.0909775106 (2009).
21 De Rosa, S. C., Herzenberg, L. A., Herzenberg, L. A. & Roederer, M. 11-color, 13-parameter flow cytometry: identification of human naive T cells by phenotype, function, and T-cell receptor diversity. *Nature medicine* 7, 245-248, doi:10.1038/84701 (2001).
22 Yanagi, Y., Chan, A., Chin, B., Minden, M. & Mak, T. W. Analysis of cDNA clones specific for human T cells and the alpha and beta chains of the T-cell receptor heterodimer from a human T-cell line. *Proceedings of the National Academy of Sciences of the United States of America* 82, 3430-3434 (1985).
23 Nakamura, K. et al. Sequence-*specific error profile of Illumina sequencers. Nucleic acids research* 39, e90, doi:10.1093/nar/gkr344 (2011).
24 Law, J. P. et al. The importance of Foxp3 antibody and fixation/permeabilization buffer combinations in identifying CD4+CD25+Foxp3+ regulatory T cells. *Cytometry. Part A: the journal of the International Society for Analytical Cytology* 75, 1040-1050, doi:10.1002/cyto.a.20815 (2009).
25 Vahedi, G., Kanno, Y., Sartorelli, V. & O'Shea, J. J. Transcription factors and CD4 T cells seeking identity: masters, minions, setters and spikers. *Immunology* 139, 294-298, doi:10.1111/imm.12113 (2013).
26 Oestreich, K. J. & Weinmann, A. S. Master regulators or lineage-specifying? Changing views on CD4+ T cell transcription factors. *Nature reviews. Immunology* 12, 799-804, doi:10.1038/nri3321 (2012).
27 Wilson, C. B., Rowell, E. & Sekimata, M. Epigenetic control of T-helper-cell differentiation. *Nature reviews. Immunology* 9, 91-105, doi:10.1038/nri2487 (2009).
28 Collins, A., Littman, D. R. & Taniuchi, I. RUNX proteins in transcription factor networks that regulate T-cell lineage choice. *Nature reviews. Immunology* 9, 106-115, doi:10.1038/nri2489 (2009).
29 Assenmacher, M., Lohning, M. & Radbruch, A. Detection and isolation of cytokine secreting cells using the cytometric cytokine secretion assay. *Current protocols in immunology*/edited by John E. Coligan . . . [et al.] Chapter 6, Unit 6 27, doi:10.1002/0471142735.im0627s46 (2002).
30 Fontenot, J. D., Gavin, M. A. & Rudensky, A. Y. Foxp3 programs the development and function of CD4+CD25+ regulatory T cells. *Nature immunology* 4, 330-336, doi:10.1038/ni904 (2003).

31 Anderson, P. Post-transcriptional control of cytokine production. *Nature immunology* 9, 353-359, doi:10.1038/ni1584 (2008).

32 Ribas, A. Tumor immunotherapy directed at PD-1. *The New England journal of medicine* 366, 2517-2519, doi: 10.1056/NEJMe1205943 (2012).

33 Sliwkowski, M. X. & Mellman, I. Antibody therapeutics in cancer. *Science* 341, 1192-1198, doi:10.1126/science.1241145 (2013).

34 Pages, F. et al. Effector memory T cells, early metastasis, and survival in colorectal cancer. *The New England journal of medicine* 353, 2654-2666, doi:10.1056/NEJMoa051424 (2005).

35 Galon, J. et al. Type, density, and location of immune cells within human colorectal tumors predict clinical outcome. *Science* 313, 1960-1964, doi:10.1126/science.1129139 (2006).

36 Gerlinger, M. et al. Ultra-deep T-cell receptor sequencing reveals the complexity and intratumour heterogeneity of T-cell clones in renal cell carcinomas. *The Journal of pathology*, doi:10.1002/path.4284 (2013).

37 Sherwood, A. M. et al. Tumor-infiltrating lymphocytes in colorectal tumors display a diversity of T cell receptor sequences that differ from the T cells in adjacent mucosal tissue. *Cancer immunology, immunotherapy: CII* 62, 1453-1461, doi:10.1007/s00262-013-1446-2 (2013).

38 Sasada, T. & Suekane, S. Variation of tumor-infiltrating lymphocytes in human cancers: controversy on clinical significance. *Immunotherapy* 3, 1235-1251, doi:10.2217/imt.11.106 (2011).

39 deLeeuw, R. J., Kost, S. E., Kakal, J. A. & Nelson, B. H. The prognostic value of FoxP3+ tumor-infiltrating lymphocytes in cancer: a critical review of the literature. *Clinical cancer research: an official journal of the American Association for Cancer Research* 18, 3022-3029, doi:10.1158/1078-0432.CCR-11-3216 (2012).

40 Scurr, M., Gallimore, A. & Godkin, A. T cell subsets and colorectal cancer: discerning the good from the bad. *Cellular immunology* 279, 21-24, doi:10.1016/j.cellimm.2012.08.004 (2012).

41 Tosolini, M. et al. Clinical impact of different classes of infiltrating T cytotoxic and helper cells (Th1, th2, treg, th17) in patients with colorectal cancer. *Cancer research* 71, 1263-1271, doi:10.1158/0008-5472.CAN-10-2907 (2011).

42 Ladoire, S., Martin, F. & Ghiringhelli, F. Prognostic role of FOXP3+ regulatory T cells infiltrating human carcinomas: the paradox of colorectal cancer. *Cancer immunology, immunotherapy: CII* 60, 909-918, doi:10.1007/s00262-011-1046-y (2011).

43 Blatner, N. R. et al. Expression of RORgammat marks a pathogenic regulatory T cell subset in human colon cancer. *Science translational medicine* 4, 164ra159, doi: 10.1126/scitranslmed.3004566 (2012).

44 Gounaris, E. et al. T-regulatory cells shift from a protective anti-inflammatory to a cancer-promoting proinflammatory phenotype in polyposis. *Cancer research* 69, 5490-5497, doi:10.1158/0008-5472.CAN-09-0304 (2009).

45 Miyara, M. et al. Functional delineation and differentiation dynamics of human CD4+ T cells expressing the FoxP3 transcription factor. *Immunity* 30, 899-911, doi: 10.1016/j.immuni.2009.03.019 (2009).

46 Zhou, L., Chong, M. M. & Littman, D. R. Plasticity of CD4+ T cell lineage differentiation. *Immunity* 30, 646-655, doi:10.1016/j.immuni.2009.05.001 (2009).

Although preferred embodiments of the subject invention have been described in some detail, it is understood that obvious variations can be made without departing from the spirit and the scope of the invention as defined herein.

What is claimed is:

1. A kit for analyzing a single T cell comprising:
a) a first container comprising a first set of primers, wherein the first set of primers comprises:
   i) a first set of forward primers comprising 5 or more of the nucleotide sequences of SEQ ID NOS:7-82 having a length ranging from 20-40 nucleotides,
   ii) a first set of reverse primers comprising reverse primers that hybridize to a nucleotide sequence encoding a constant region of a T cell receptor, wherein primers from the first set of forward primers and the first set of reverse primers amplify nucleotide sequences encoding T cell receptors, or a portion thereof, and
   iii) a first set of phenotypic marker primers comprising one or more primer pairs that hybridize to and amplify nucleotide sequences encoding a phenotypic marker, or a portion thereof;
b) a second container comprising a second set of primers, wherein the second set of primers comprises:
   i) a second set of forward primers, wherein each primer in the second set of forward primers comprises a first common sequence, and
   ii) a second set of reverse primers, wherein each primer in the second set of reverse primers comprises either a sequence that amplifies a T cell receptor constant region, or a second common sequence; and
c) a third container comprising a third set of primers, wherein the third set of primers comprises:
   i) a third set of forward primers that hybridizes to the first common sequence,
   ii) a third set of reverse primers comprising a sequence that hybridizes to the T cell receptor constant region, or the second common sequence, wherein the third set of forward and reverse primers collectively comprises nucleotide sequences selected from the group consisting of SEQ ID NOS:225-248 and having a length ranging from 50-60 nucleotides, and
   iii) a set of primers comprising an adapter sequence for paired-end sequencing.

2. A method for analyzing single T cells, comprising:
a) sorting single T cells from a sample comprising a plurality of T cells into separate locations;
b) amplifying target nucleic acids from one or more single T cells using the first set of primers from the kit of claim 1 to produce a first set of amplicon products in one or more locations of the separate locations;
c) performing nested polymerase chain reaction (PCR) on the amplified target nucleic acids in the first set of amplicon products with the second set of primers from the kit of claim 1 to produce a second set of amplicon products;
d) amplifying the second set of amplicon products with the third set of forward and reverse primers from the kit of claim 1 to produce a third set of amplicon products, wherein each forward and reverse primer of the third set of primers further comprises a barcode sequence; and
e) sequencing the third set of amplicon products.

3. The method of claim 2, wherein the target nucleic acids are RNAs.

4. The method of claim 3, wherein the RNAs are mRNAs.

5. The method of claim 2, wherein the sample is collected from a subject.

6. The method of claim 2, wherein the second set of forward primers comprises 5 or more of the nucleotide sequences of SEQ ID NOS:83-154 having a length ranging from 40-60 nucleotides, and the second set of reverse primers comprises one or more reverse primers that hybridize to either nucleotide sequences encoding a constant region of a T cell receptor, or the second common sequence.

7. The method of claim 2, wherein a first primer from the third set of forward primers that comprises a sequence that hybridizes to the first common sequence does not hybridize to the T cell receptor constant region or the second common sequence, and a second primer from the third set of reverse primers that comprises a sequence that hybridizes to the second common sequence does not hybridize to the first common sequence.

8. The method of claim 7, wherein the first common sequence comprises SEQ ID NO:3, and the third set of reverse primers comprises a sequence selected from the group consisting of SEQ ID NO:4, SEQ ID NO:5, SEQ ID NO:6 and a nucleotide sequence that hybridizes to a sequence encoding a constant region of a T cell receptor or to the second common sequence from the second set of amplicon products, wherein the first and second common sequences are different sequences.

9. The kit method of claim 1, wherein the primers comprising an adapter sequence for paired-end sequencing are selected from the group consisting of SEQ ID NO:261 and SEQ ID NO:262.

10. The method of claim 2, wherein the phenotypic marker is selected from the group consisting of IL2, IL10, IL12A, IL13, IL17A, IFNG, PRF1, GZMB, TGFB, TNFA, BCL6, TBET, GATA3, RORC, FOXP3, RUNX1, and RUNX3.

11. The method of claim 10, wherein the first set of phenotypic marker primers comprise a pair of primers having a length ranging from 20-40 nucleotides and are selected from the group consisting of SEQ ID NO:157 and SEQ ID NO:158, SEQ ID NO:161 and SEQ ID NO:162, SEQ ID NO:165 and SEQ ID NO:166, SEQ ID NO:169 and SEQ ID NO:170, SEQ ID NO:173 and SEQ ID NO:174, SEQ ID NO:177 and SEQ ID NO:178, SEQ ID NO:181 and SEQ ID NO:182, SEQ ID NO:185 and SEQ ID NO:186, SEQ ID NO:189 and SEQ ID NO:190, SEQ ID NO:193 and SEQ ID NO:194, SEQ ID NO:197 and SEQ ID NO:198, SEQ ID NO:201 and SEQ ID NO:202, SEQ ID NO:205 and SEQ ID NO:206, SEQ ID NO:209 and SEQ ID NO:210, SEQ ID NO:213 and SEQ ID NO:214, SEQ ID NO:217 and SEQ ID NO:218, SEQ ID NO:221 and SEQ ID NO:222.

12. The method of claim 11, wherein the first set of phenotypic marker primers comprise primers comprising the nucleotide sequences of SEQ ID NO:157, SEQ ID NO:158, SEQ ID NO:161, SEQ ID NO:162, SEQ ID NO:165, SEQ ID NO:166, SEQ ID NO:169, SEQ ID NO:170, SEQ ID NO:173, SEQ ID NO:174, SEQ ID NO:177, SEQ ID NO:178, SEQ ID NO:181, SEQ ID NO:182, SEQ ID NO:185, SEQ ID NO:186, SEQ ID NO:189, SEQ ID NO:190, SEQ ID NO:193, SEQ ID NO:194, SEQ ID NO:197, SEQ ID NO:198, SEQ ID NO:201, SEQ ID NO:202, SEQ ID NO:205, SEQ ID NO:206, SEQ ID NO:209, SEQ ID NO:210, SEQ ID NO:213, SEQ ID NO:214, SEQ ID NO:217, SEQ ID NO:218, SEQ ID NO:221, and SEQ ID NO:222.

13. The method of claim 2, wherein the second set of primers further comprises a second set of phenotypic marker primers comprising one or more primer pairs that hybridize to and amplify an amplification product of the first set of amplicon products encoding the phenotypic marker, or a portion thereof, and wherein each primer comprises a common sequence.

14. The method of claim 13, wherein the second set of phenotypic marker primers comprise a plurality of primers each comprising a nucleotide sequence having a length ranging from 15-60 nucleotides and are selected from the group consisting of SEQ ID NO:159, SEQ ID NO:160, SEQ ID NO:163, SEQ ID NO:164, SEQ ID NO:167, SEQ ID NO:168, SEQ ID NO:171, SEQ ID NO:172, SEQ ID NO:175, SEQ ID NO:176, SEQ ID NO:179, SEQ ID NO:180, SEQ ID NO:183, SEQ ID NO:184, SEQ ID NO:187, SEQ ID NO:188, SEQ ID NO:191, SEQ ID NO:192, SEQ ID NO:195, SEQ ID NO:196, SEQ ID NO:199, SEQ ID NO:200, SEQ ID NO:203, SEQ ID NO:204, SEQ ID NO:207, SEQ ID NO:208, SEQ ID NO:211, SEQ ID NO:212, SEQ ID NO:215, SEQ ID NO:216, SEQ ID NO:219, SEQ ID NO:220, SEQ ID NO:223, and SEQ ID NO:224.

15. The method of claim 13, wherein the performing step c) comprises:
  i) dividing the first set of amplicon products into two pools; and
  ii) performing nested PCR on the first pool and second pool separately,
  wherein the first pool is amplified with the second set of forward primers comprising 5 or more of the nucleotide sequences having a length ranging from 40-60 nucleotides and are selected from the group consisting of SEQ ID NOS:83-154, and the second set of one or more reverse primers that hybridize to nucleotide sequences encoding the constant region of the T cell receptor, and wherein the second pool is amplified with the second set of phenotypic marker primers.

16. The method of claim 15, wherein the method comprises, between steps c) and d), dividing one or more of the second set of amplicon products into two secondary amplicon pools, and wherein the amplifying step (d) comprises:
  i) amplifying the second set of amplicon products in a first secondary amplicon pool with the third set of primers, wherein the third set of primers comprises a third set of forward primers that hybridizes to an amplified target nucleic acid of the second set of amplicon products encoding a first T cell receptor encoded by the second set of amplicon products and a reverse primer that hybridizes to a nucleotide sequence encoding the constant region of the first T cell receptor; and
  ii) amplifying the second set of amplicon products in a second secondary amplicon pool with the third set of primers, wherein the third set of primers comprises a third set of forward primers that hybridizes to an amplified target nucleic acid of the second set of amplicon products encoding a second T cell receptor encoded by the second set of amplicon products and a reverse primer that hybridizes to a nucleotide sequence encoding the constant region of the second T cell receptor, wherein the first and second T cell receptors have different constant regions.

17. The method of claim 16, wherein the first T cell receptor comprises a T cell receptor alpha chain and the second T cell receptor comprises a T cell receptor beta chain.

18. The method of claim 13, wherein the third set of primers further comprises a third set of phenotypic marker primers comprising comprises nucleotide sequences selected from the group consisting of SEQ ID NOS:249-260.

19. The method of claim 2, wherein the amplifying step b) is done in a plurality of locations of the separate locations, and wherein the method comprises between steps d) and e), combining the third set of amplicon products, or a portion thereof, from the plurality of locations into a third set of combined amplicon products, and wherein the sequencing step e) comprises sequencing the third set of combined amplicon products.

20. The method of claim 2, wherein barcode sequences are added at both ends of each amplicon product.

21. The method of claim 15, wherein the amplifying step d) comprises amplifying the second set of amplicon products amplified from the first pool with the third set of primers to produce the third set of amplicon products.

* * * * *

SEQUENCE LISTING

```
<160> NUMBER OF SEQ ID NOS: 1644

<210> SEQ ID NO 1
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 1
cctacacgac gctcttccga tct                                              23

<210> SEQ ID NO 2
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 2
ctgctgaacc gctcttccga tct                                              23

<210> SEQ ID NO 3
<211> LENGTH: 22
<212> TYPE: DNA
<213> ORGANISM: Artificial sequence
<220> FEATURE:
<223> OTHER INFORMATION: Synthetic oligonucleotide
```

<400> SEQUENCE: 3
ccagggtttt cccagtcacg ac                                    22

<210> SEQ ID NO 4
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 4
gtcactggat ttagagtctc tcag                                  24

<210> SEQ ID NO 5
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 5
gagatctctg cttctgatgg ctc                                   23

<210> SEQ ID NO 6
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 6
agcggataac aatttcacac agga                                  24

<210> SEQ ID NO 7
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 7
ctgcacgtac cagacatctg ggtt                                  24

<210> SEQ ID NO 8
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 8
ggctcaaagc cttctcagca gg                                    22

<210> SEQ ID NO 9
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 9
ggataacctg gttaaaggca gcta                                  24

<210> SEQ ID NO 10
<211> LENGTH: 26

```
<212> TYPE: DNA
<213> ORGANISM: Artificial sequence
<220> FEATURE:
<223> OTHER INFORMATION: Synthetic oligonucleotide

<400> SEQUENCE: 10
ggatacaaga caaaagttac aaacga                                        26

<210> SEQ ID NO 11
<211> LENGTH: 27
<212> TYPE: DNA
<213> ORGANISM: Artificial sequence
<220> FEATURE:
<223> OTHER INFORMATION: Synthetic oligonucleotide

<400> SEQUENCE: 11
gctgacgtat atttttcaa atatgga                                        27

<210> SEQ ID NO 12
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 12
ggaagaggcc ctgttttctt gct                                           23

<210> SEQ ID NO 13
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 13
gctggatatg agaagcagaa agga                                          24

<210> SEQ ID NO 14
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 14
aggactccag cttctcctga agta                                          24

<210> SEQ ID NO 15
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 15
gtatgtccaa tatcctggag aaggt                                         25

<210> SEQ ID NO 16
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 16
```
cagtgagaac acaaagtcga acgg                                          24

<210> SEQ ID NO 17
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 17
cctaagttgc tgatgtccgt atac                                          24

<210> SEQ ID NO 18
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 18
gggaaaagcc ctgagttgat aatgt                                         25

<210> SEQ ID NO 19
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 19
gctgatgtac acatactcca gtgg                                          24

<210> SEQ ID NO 20
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 20
cccttggtat aagcaagaac ttgg                                          24

<210> SEQ ID NO 21
<211> LENGTH: 26
<212> TYPE: DNA
<213> ORGANISM: Artificial sequence
<220> FEATURE:
<223> OTHER INFORMATION: Synthetic oligonucleotide

<400> SEQUENCE: 21
cctcaattca ttatagacat tcgttc                                        26

<210> SEQ ID NO 22
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 22
gcaaaatgca acagaaggtc gcta                                          24

<210> SEQ ID NO 23
<211> LENGTH: 24
<212> TYPE: DNA
<213> ORGANISM: Artificial sequence

```
<220> FEATURE:
<223> OTHER INFORMATION: Synthetic oligonucleotide

<400> SEQUENCE: 23
tagagagagc atcaaaggct tcac                                              24

<210> SEQ ID NO 24
<211> LENGTH: 26
<212> TYPE: DNA
<213> ORGANISM: Artificial sequence
<220> FEATURE:
<223> OTHER INFORMATION: Synthetic oligonucleotide

<400> SEQUENCE: 24
cgttcaaatg aaagagagaa acacag                                            26

<210> SEQ ID NO 25
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 25
cctgaaaagt tcagaaaacc aggag                                             25

<210> SEQ ID NO 26
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 26
ggtcggtatt cttggaactt ccag                                              24

<210> SEQ ID NO 27
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 27
gctggggaag aaaaggagaa agaaa                                             25

<210> SEQ ID NO 28
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 28
gtcagagaga gcaaacaagt ggaa                                              24

<210> SEQ ID NO 29
<211> LENGTH: 26
<212> TYPE: DNA
<213> ORGANISM: Artificial sequence
<220> FEATURE:
<223> OTHER INFORMATION: Synthetic oligonucleotide

<400> SEQUENCE: 29
ggacaaaaca gaatggaaga ttaagc                                            26
```

<210> SEQ ID NO 30
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 30
ccagatgtga gtgaaaagaa agaag                                        25

<210> SEQ ID NO 31
<211> LENGTH: 26
<212> TYPE: DNA
<213> ORGANISM: Artificial sequence
<220> FEATURE:
<223> OTHER INFORMATION: Synthetic oligonucleotide

<400> SEQUENCE: 31
gactttaaat ggggatgaaa agaaga                                       26

<210> SEQ ID NO 32
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 32
ggagaagtga agaagcagaa aagac                                        25

<210> SEQ ID NO 33
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 33
ccaatgaaat ggcctctctg atca                                         24

<210> SEQ ID NO 34
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 34
gcaatgtgaa caacagaatg gcct                                         24

<210> SEQ ID NO 35
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 35
ggtggagaag tgaagaagct gaag                                         24

<210> SEQ ID NO 36
<211> LENGTH: 27
<212> TYPE: DNA
<213> ORGANISM: Artificial sequence
<220> FEATURE:
<223> OTHER INFORMATION: Synthetic oligonucleotide

<400> SEQUENCE: 36
ggataaaaat gaagatggaa gattcac                                          27

<210> SEQ ID NO 37
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 37
cctgatgata ttactgaagg gtgga                                            25

<210> SEQ ID NO 38
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 38
ggtggggaag agaaaagtca tgaa                                             24

<210> SEQ ID NO 39
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 39
ggtgaattga cctcaaatgg aagac                                            25

<210> SEQ ID NO 40
<211> LENGTH: 26
<212> TYPE: DNA
<213> ORGANISM: Artificial sequence
<220> FEATURE:
<223> OTHER INFORMATION: Synthetic oligonucleotide

<400> SEQUENCE: 40
gctaacttca agtggaattg aaaaga                                           26

<210> SEQ ID NO 41
<211> LENGTH: 26
<212> TYPE: DNA
<213> ORGANISM: Artificial sequence
<220> FEATURE:
<223> OTHER INFORMATION: Synthetic oligonucleotide

<400> SEQUENCE: 41
gaagcttata agcaacagaa tgcaac                                           26

<210> SEQ ID NO 42
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 42
ggagcagtga agcaggaggg ac                                               22

<210> SEQ ID NO 43

```
<211> LENGTH: 26
<212> TYPE: DNA
<213> ORGANISM: Artificial sequence
<220> FEATURE:
<223> OTHER INFORMATION: Synthetic oligonucleotide

<400> SEQUENCE: 43
gagagacaat ggaaaacagc aaaaac                                              26

<210> SEQ ID NO 44
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 44
gctgagctca gggaagaaga agc                                                 23

<210> SEQ ID NO 45
<211> LENGTH: 27
<212> TYPE: DNA
<213> ORGANISM: Artificial sequence
<220> FEATURE:
<223> OTHER INFORMATION: Synthetic oligonucleotide

<400> SEQUENCE: 45
ctgaaatatt cgatgatcaa ttctcag                                             27

<210> SEQ ID NO 46
<211> LENGTH: 28
<212> TYPE: DNA
<213> ORGANISM: Artificial sequence
<220> FEATURE:
<223> OTHER INFORMATION: Synthetic oligonucleotide

<400> SEQUENCE: 46
tcattataaa tgaaacagtt ccaaatcg                                            28

<210> SEQ ID NO 47
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 47
agtgtgccaa gtcgcttctc ac                                                  22

<210> SEQ ID NO 48
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 48
cagaggaaac tyccctccta gatt                                                24

<210> SEQ ID NO 49
<211> LENGTH: 27
<212> TYPE: DNA
<213> ORGANISM: Artificial sequence
<220> FEATURE:
<223> OTHER INFORMATION: Synthetic oligonucleotide

<400> SEQUENCE: 49
```
gagacacaga gaaacaaagg aaacttc       27

<210> SEQ ID NO 50
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 50
ggtaccactg acaaaggaga agtcc       25

<210> SEQ ID NO 51
<211> LENGTH: 26
<212> TYPE: DNA
<213> ORGANISM: Artificial sequence
<220> FEATURE:
<223> OTHER INFORMATION: Synthetic oligonucleotide

<400> SEQUENCE: 51
gagggtacaa ctgccaaagg agaggt       26

<210> SEQ ID NO 52
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 52
ggcaaaggag aagtccctga tggtt       25

<210> SEQ ID NO 53
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 53
aaggagaagt cccsaatggc tacaa       25

<210> SEQ ID NO 54
<211> LENGTH: 26
<212> TYPE: DNA
<213> ORGANISM: Artificial sequence
<220> FEATURE:
<223> OTHER INFORMATION: Synthetic oligonucleotide

<400> SEQUENCE: 54
ctgacaaaga agtccccaat ggctac       26

<210> SEQ ID NO 55
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 55
cactgacaaa ggagaagtcc ccgat       25

<210> SEQ ID NO 56
<211> LENGTH: 24
<212> TYPE: DNA

```
<213> ORGANISM: Artificial sequence
<220> FEATURE:
<223> OTHER INFORMATION: Synthetic oligonucleotide

<400> SEQUENCE: 56
agacaaatca gggctgccca gtga                                          24

<210> SEQ ID NO 57
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 57
gactcagggc tgcccaacga t                                             21

<210> SEQ ID NO 58
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 58
ccagaatgaa gctcaactag acaa                                          24

<210> SEQ ID NO 59
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 59
ggttctctgc agagaggcct gag                                           23

<210> SEQ ID NO 60
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 60
ggctgcccag tgatcggttc tc                                            22

<210> SEQ ID NO 61
<211> LENGTH: 27
<212> TYPE: DNA
<213> ORGANISM: Artificial sequence
<220> FEATURE:
<223> OTHER INFORMATION: Synthetic oligonucleotide

<400> SEQUENCE: 61
gacttacttc cagaatgaag ctcaact                                       27

<210> SEQ ID NO 62
<211> LENGTH: 28
<212> TYPE: DNA
<213> ORGANISM: Artificial sequence
<220> FEATURE:
<223> OTHER INFORMATION: Synthetic oligonucleotide

<400> SEQUENCE: 62
gagcaaaagg aaacattctt gaacgatt                                      28
```

<210> SEQ ID NO 63
<211> LENGTH: 26
<212> TYPE: DNA
<213> ORGANISM: Artificial sequence
<220> FEATURE:
<223> OTHER INFORMATION: Synthetic oligonucleotide

<400> SEQUENCE: 63
ggctratcca ttactcatat ggtgtt                                 26

<210> SEQ ID NO 64
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 64
gataaaggag aagtccccga tggct                                  25

<210> SEQ ID NO 65
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 65
gattcacagt tgcctaagga tcgat                                  25

<210> SEQ ID NO 66
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 66
gattcaggga tgcccgagga tcg                                    23

<210> SEQ ID NO 67
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 67
gattcgggga tgccgaagga tcg                                    23

<210> SEQ ID NO 68
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 68
gcagagcgat aaaggaagca tccct                                  25

<210> SEQ ID NO 69
<211> LENGTH: 25
<212> TYPE: DNA
<213> ORGANISM: Artificial sequence
<220> FEATURE:

<223> OTHER INFORMATION: Synthetic oligonucleotide

<400> SEQUENCE: 69
tccggtatgc ccaacaatcg attct                                    25

<210> SEQ ID NO 70
<211> LENGTH: 27
<212> TYPE: DNA
<213> ORGANISM: Artificial sequence
<220> FEATURE:
<223> OTHER INFORMATION: Synthetic oligonucleotide

<400> SEQUENCE: 70
gattttaaca atgaagcaga cacccct                                  27

<210> SEQ ID NO 71
<211> LENGTH: 26
<212> TYPE: DNA
<213> ORGANISM: Artificial sequence
<220> FEATURE:
<223> OTHER INFORMATION: Synthetic oligonucleotide

<400> SEQUENCE: 71
gatgaaacag gtatgcccaa ggaaag                                   26

<210> SEQ ID NO 72
<211> LENGTH: 28
<212> TYPE: DNA
<213> ORGANISM: Artificial sequence
<220> FEATURE:
<223> OTHER INFORMATION: Synthetic oligonucleotide

<400> SEQUENCE: 72
tatcatagat gagtcaggaa tgccaaag                                 28

<210> SEQ ID NO 73
<211> LENGTH: 27
<212> TYPE: DNA
<213> ORGANISM: Artificial sequence
<220> FEATURE:
<223> OTHER INFORMATION: Synthetic oligonucleotide

<400> SEQUENCE: 73
gactttcaga aaggagatat agctgaa                                  27

<210> SEQ ID NO 74
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 74
caaggccaca tacgagcaag gcgtc                                    25

<210> SEQ ID NO 75
<211> LENGTH: 28
<212> TYPE: DNA
<213> ORGANISM: Artificial sequence
<220> FEATURE:
<223> OTHER INFORMATION: Synthetic oligonucleotide

<400> SEQUENCE: 75
caaagatata aacaaggag agatctct                                  28

```
<210> SEQ ID NO 76
<211> LENGTH: 26
<212> TYPE: DNA
<213> ORGANISM: Artificial sequence
<220> FEATURE:
<223> OTHER INFORMATION: Synthetic oligonucleotide

<400> SEQUENCE: 76
agagaaggga gatctttcct ctgagt                                      26

<210> SEQ ID NO 77
<211> LENGTH: 26
<212> TYPE: DNA
<213> ORGANISM: Artificial sequence
<220> FEATURE:
<223> OTHER INFORMATION: Synthetic oligonucleotide

<400> SEQUENCE: 77
gactgataag ggagatgttc ctgaag                                      26

<210> SEQ ID NO 78
<211> LENGTH: 28
<212> TYPE: DNA
<213> ORGANISM: Artificial sequence
<220> FEATURE:
<223> OTHER INFORMATION: Synthetic oligonucleotide

<400> SEQUENCE: 78
ggctgatcta tttctcatat gatgttaa                                    28

<210> SEQ ID NO 79
<211> LENGTH: 27
<212> TYPE: DNA
<213> ORGANISM: Artificial sequence
<220> FEATURE:
<223> OTHER INFORMATION: Synthetic oligonucleotide

<400> SEQUENCE: 79
gccacatatg agagtggatt tgtcatt                                     27

<210> SEQ ID NO 80
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 80
ggtgccccag aatctctcag cct                                         23

<210> SEQ ID NO 81
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 81
cggtgaatag gcagacagac ttgt                                        24

<210> SEQ ID NO 82
<211> LENGTH: 23
<212> TYPE: DNA
<213> ORGANISM: Artificial sequence
<220> FEATURE:
<223> OTHER INFORMATION: Synthetic oligonucleotide
```

<400> SEQUENCE: 82
accagtgtgg cctttgggt gtg                                      23

<210> SEQ ID NO 83
<211> LENGTH: 48
<212> TYPE: DNA
<213> ORGANISM: Artificial sequence
<220> FEATURE:
<223> OTHER INFORMATION: Synthetic oligonucleotide

<400> SEQUENCE: 83
ccagggtttt cccagtcacg acaggtcgtt tttcttcatt ccttagtc           48

<210> SEQ ID NO 84
<211> LENGTH: 47
<212> TYPE: DNA
<213> ORGANISM: Artificial sequence
<220> FEATURE:
<223> OTHER INFORMATION: Synthetic oligonucleotide

<400> SEQUENCE: 84
ccagggtttt cccagtcacg acacgataca acatgaccta tgaacgg            47

<210> SEQ ID NO 85
<211> LENGTH: 48
<212> TYPE: DNA
<213> ORGANISM: Artificial sequence
<220> FEATURE:
<223> OTHER INFORMATION: Synthetic oligonucleotide

<400> SEQUENCE: 85
ccagggtttt cccagtcacg acctttgaag ctgaatttaa caagagcc           48

<210> SEQ ID NO 86
<211> LENGTH: 44
<212> TYPE: DNA
<213> ORGANISM: Artificial sequence
<220> FEATURE:
<223> OTHER INFORMATION: Synthetic oligonucleotide

<400> SEQUENCE: 86
ccagggtttt cccagtcacg acctccctgt ttatccctgc cgac               44

<210> SEQ ID NO 87
<211> LENGTH: 47
<212> TYPE: DNA
<213> ORGANISM: Artificial sequence
<220> FEATURE:
<223> OTHER INFORMATION: Synthetic oligonucleotide

<400> SEQUENCE: 87
ccagggtttt cccagtcacg acaaacaaga ccaaagactc actgttc            47

<210> SEQ ID NO 88
<211> LENGTH: 47
<212> TYPE: DNA
<213> ORGANISM: Artificial sequence
<220> FEATURE:
<223> OTHER INFORMATION: Synthetic oligonucleotide

<400> SEQUENCE: 88
ccagggtttt cccagtcacg acaagactga aggtcacctt tgatacc            47

<210> SEQ ID NO 89
<211> LENGTH: 49

```
<212> TYPE: DNA
<213> ORGANISM: Artificial sequence
<220> FEATURE:
<223> OTHER INFORMATION: Synthetic oligonucleotide

<400> SEQUENCE: 89
ccagggtttt cccagtcacg acactaaatg ctacattact gaagaatgg        49

<210> SEQ ID NO 90
<211> LENGTH: 50
<212> TYPE: DNA
<213> ORGANISM: Artificial sequence
<220> FEATURE:
<223> OTHER INFORMATION: Synthetic oligonucleotide

<400> SEQUENCE: 90
ccagggtttt cccagtcacg acgcatcaac ggttttgagg ctgaatttaa       50

<210> SEQ ID NO 91
<211> LENGTH: 48
<212> TYPE: DNA
<213> ORGANISM: Artificial sequence
<220> FEATURE:
<223> OTHER INFORMATION: Synthetic oligonucleotide

<400> SEQUENCE: 91
ccagggtttt cccagtcacg acgaaaccac ttctttccac ttggagaa         48

<210> SEQ ID NO 92
<211> LENGTH: 46
<212> TYPE: DNA
<213> ORGANISM: Artificial sequence
<220> FEATURE:
<223> OTHER INFORMATION: Synthetic oligonucleotide

<400> SEQUENCE: 92
ccagggtttt cccagtcacg actacagcaa ctctggatgc agacac           46

<210> SEQ ID NO 93
<211> LENGTH: 45
<212> TYPE: DNA
<213> ORGANISM: Artificial sequence
<220> FEATURE:
<223> OTHER INFORMATION: Synthetic oligonucleotide

<400> SEQUENCE: 93
ccagggtttt cccagtcacg acgaagatgg aaggtttaca gcaca            45

<210> SEQ ID NO 94
<211> LENGTH: 46
<212> TYPE: DNA
<213> ORGANISM: Artificial sequence
<220> FEATURE:
<223> OTHER INFORMATION: Synthetic oligonucleotide

<400> SEQUENCE: 94
ccagggtttt cccagtcacg acgacattcg ttcaaatgtg ggcgaa           46

<210> SEQ ID NO 95
<211> LENGTH: 44
<212> TYPE: DNA
<213> ORGANISM: Artificial sequence
<220> FEATURE:
<223> OTHER INFORMATION: Synthetic oligonucleotide

<400> SEQUENCE: 95
```

```
ccagggtttt cccagtcacg acggcaaggc caaagagtca ccgt              44
```

<210> SEQ ID NO 96
<211> LENGTH: 46
<212> TYPE: DNA
<213> ORGANISM: Artificial sequence
<220> FEATURE:
<223> OTHER INFORMATION: Synthetic oligonucleotide

<400> SEQUENCE: 96

```
ccagggtttt cccagtcacg actccagaag gcaagaaaat ccgcca            46
```

<210> SEQ ID NO 97
<211> LENGTH: 46
<212> TYPE: DNA
<213> ORGANISM: Artificial sequence
<220> FEATURE:
<223> OTHER INFORMATION: Synthetic oligonucleotide

<400> SEQUENCE: 97

```
ccagggtttt cccagtcacg acgctgacct taacaaaggc gagaca            46
```

<210> SEQ ID NO 98
<211> LENGTH: 47
<212> TYPE: DNA
<213> ORGANISM: Artificial sequence
<220> FEATURE:
<223> OTHER INFORMATION: Synthetic oligonucleotide

<400> SEQUENCE: 98

```
ccagggtttt cccagtcacg acttaagagt cacgcttgac acttcca           47
```

<210> SEQ ID NO 99
<211> LENGTH: 45
<212> TYPE: DNA
<213> ORGANISM: Artificial sequence
<220> FEATURE:
<223> OTHER INFORMATION: Synthetic oligonucleotide

<400> SEQUENCE: 99

```
ccaggtttt cccagtcacg acgcagaggt tttcaggcca gtcct              45
```

<210> SEQ ID NO 100
<211> LENGTH: 46
<212> TYPE: DNA
<213> ORGANISM: Artificial sequence
<220> FEATURE:
<223> OTHER INFORMATION: Synthetic oligonucleotide

<400> SEQUENCE: 100

```
ccagggtttt cccagtcacg actccaccag ttccttcaac ttcacc            46
```

<210> SEQ ID NO 101
<211> LENGTH: 47
<212> TYPE: DNA
<213> ORGANISM: Artificial sequence
<220> FEATURE:
<223> OTHER INFORMATION: Synthetic oligonucleotide

<400> SEQUENCE: 101

```
ccagggtttt cccagtcacg acgccacatt aacaaagaag gaaagct           47
```

<210> SEQ ID NO 102
<211> LENGTH: 46
<212> TYPE: DNA
<213> ORGANISM: Artificial sequence

```
<220> FEATURE:
<223> OTHER INFORMATION: Synthetic oligonucleotide

<400> SEQUENCE: 102
ccagggtttt cccagtcacg acgcctcgct ggataaatca tcagga                    46

<210> SEQ ID NO 103
<211> LENGTH: 45
<212> TYPE: DNA
<213> ORGANISM: Artificial sequence
<220> FEATURE:
<223> OTHER INFORMATION: Synthetic oligonucleotide

<400> SEQUENCE: 103
ccagggtttt cccagtcacg acacgactgt cgctacggaa cgcta                     45

<210> SEQ ID NO 104
<211> LENGTH: 48
<212> TYPE: DNA
<213> ORGANISM: Artificial sequence
<220> FEATURE:
<223> OTHER INFORMATION: Synthetic oligonucleotide

<400> SEQUENCE: 104
ccagggtttt cccagtcacg accacaatct ccttcaataa aagtgcca                  48

<210> SEQ ID NO 105
<211> LENGTH: 48
<212> TYPE: DNA
<213> ORGANISM: Artificial sequence
<220> FEATURE:
<223> OTHER INFORMATION: Synthetic oligonucleotide

<400> SEQUENCE: 105
ccagggtttt cccagtcacg acacgaataa gtgccactct taatacca                  48

<210> SEQ ID NO 106
<211> LENGTH: 48
<212> TYPE: DNA
<213> ORGANISM: Artificial sequence
<220> FEATURE:
<223> OTHER INFORMATION: Synthetic oligonucleotide

<400> SEQUENCE: 106
ccagggtttt cccagtcacg acgtttggag aagcaaaaaa gaacagct                  48

<210> SEQ ID NO 107
<211> LENGTH: 46
<212> TYPE: DNA
<213> ORGANISM: Artificial sequence
<220> FEATURE:
<223> OTHER INFORMATION: Synthetic oligonucleotide

<400> SEQUENCE: 107
ccagggtttt cccagtcacg accagaagac agaaagtcca gcacct                    46

<210> SEQ ID NO 108
<211> LENGTH: 46
<212> TYPE: DNA
<213> ORGANISM: Artificial sequence
<220> FEATURE:
<223> OTHER INFORMATION: Synthetic oligonucleotide

<400> SEQUENCE: 108
ccagggtttt cccagtcacg acatcgctga agacagaaag tccagt                    46
```

<210> SEQ ID NO 109
<211> LENGTH: 48
<212> TYPE: DNA
<213> ORGANISM: Artificial sequence
<220> FEATURE:
<223> OTHER INFORMATION: Synthetic oligonucleotide

<400> SEQUENCE: 109
ccagggtttt cccagtcacg acactaacct ttcagtttgg tgatgcaa            48

<210> SEQ ID NO 110
<211> LENGTH: 47
<212> TYPE: DNA
<213> ORGANISM: Artificial sequence
<220> FEATURE:
<223> OTHER INFORMATION: Synthetic oligonucleotide

<400> SEQUENCE: 110
ccagggtttt cccagtcacg accttaaaca aaagtgccaa gcacctc             47

<210> SEQ ID NO 111
<211> LENGTH: 51
<212> TYPE: DNA
<213> ORGANISM: Artificial sequence
<220> FEATURE:
<223> OTHER INFORMATION: Synthetic oligonucleotide

<400> SEQUENCE: 111
ccagggtttt cccagtcacg acaatatctg cttcatttaa tgaaaaaag c         51

<210> SEQ ID NO 112
<211> LENGTH: 47
<212> TYPE: DNA
<213> ORGANISM: Artificial sequence
<220> FEATURE:
<223> OTHER INFORMATION: Synthetic oligonucleotide

<400> SEQUENCE: 112
ccagggtttt cccagtcacg acccaagttg gatgagaaaa agcagca             47

<210> SEQ ID NO 113
<211> LENGTH: 47
<212> TYPE: DNA
<213> ORGANISM: Artificial sequence
<220> FEATURE:
<223> OTHER INFORMATION: Synthetic oligonucleotide

<400> SEQUENCE: 113
ccagggtttt cccagtcacg acctcagttt ggtataacca gaaagga            47

<210> SEQ ID NO 114
<211> LENGTH: 49
<212> TYPE: DNA
<213> ORGANISM: Artificial sequence
<220> FEATURE:
<223> OTHER INFORMATION: Synthetic oligonucleotide

<400> SEQUENCE: 114
ccagggtttt cccagtcacg acggaagact aagtagcata ttagataag           49

<210> SEQ ID NO 115
<211> LENGTH: 46
<212> TYPE: DNA
<213> ORGANISM: Artificial sequence
<220> FEATURE:
<223> OTHER INFORMATION: Synthetic oligonucleotide

```
<400> SEQUENCE: 115
ccagggtttt cccagtcacg acctgtgaac ttccagaaag cagcca                46

<210> SEQ ID NO 116
<211> LENGTH: 45
<212> TYPE: DNA
<213> ORGANISM: Artificial sequence
<220> FEATURE:
<223> OTHER INFORMATION: Synthetic oligonucleotide

<400> SEQUENCE: 116
ccagggtttt cccagtcacg accctcactt gataccaaag cccgt                 45

<210> SEQ ID NO 117
<211> LENGTH: 49
<212> TYPE: DNA
<213> ORGANISM: Artificial sequence
<220> FEATURE:
<223> OTHER INFORMATION: Synthetic oligonucleotide

<400> SEQUENCE: 117
ccagggtttt cccagtcacg acaggcggaa atattaaaga caaaaactc             49

<210> SEQ ID NO 118
<211> LENGTH: 49
<212> TYPE: DNA
<213> ORGANISM: Artificial sequence
<220> FEATURE:
<223> OTHER INFORMATION: Synthetic oligonucleotide

<400> SEQUENCE: 118
ccagggtttt cccagtcacg acgattaatt gccacaataa acatacagg             49

<210> SEQ ID NO 119
<211> LENGTH: 47
<212> TYPE: DNA
<213> ORGANISM: Artificial sequence
<220> FEATURE:
<223> OTHER INFORMATION: Synthetic oligonucleotide

<400> SEQUENCE: 119
ccagggtttt cccagtcacg acgcctgatg gatcaaattt cactctg               47

<210> SEQ ID NO 120
<211> LENGTH: 48
<212> TYPE: DNA
<213> ORGANISM: Artificial sequence
<220> FEATURE:
<223> OTHER INFORMATION: Synthetic oligonucleotide

<400> SEQUENCE: 120
ccagggtttt cccagtcacg actctcacct aaatctccag acaaagct              48

<210> SEQ ID NO 121
<211> LENGTH: 44
<212> TYPE: DNA
<213> ORGANISM: Artificial sequence
<220> FEATURE:
<223> OTHER INFORMATION: Synthetic oligonucleotide

<400> SEQUENCE: 121
ccagggtttt cccagtcacg accctgaatg ccccaacagc tctc                  44

<210> SEQ ID NO 122
```

```
<211> LENGTH: 45
<212> TYPE: DNA
<213> ORGANISM: Artificial sequence
<220> FEATURE:
<223> OTHER INFORMATION: Synthetic oligonucleotide

<400> SEQUENCE: 122
ccagggtttt cccagtcacg acctctgagc tgaatgtgaa cgcct                45

<210> SEQ ID NO 123
<211> LENGTH: 46
<212> TYPE: DNA
<213> ORGANISM: Artificial sequence
<220> FEATURE:
<223> OTHER INFORMATION: Synthetic oligonucleotide

<400> SEQUENCE: 123
ccagggtttt cccagtcacg accgattctc agggcgccag ttctct               46

<210> SEQ ID NO 124
<211> LENGTH: 49
<212> TYPE: DNA
<213> ORGANISM: Artificial sequence
<220> FEATURE:
<223> OTHER INFORMATION: Synthetic oligonucleotide

<400> SEQUENCE: 124
ccagggtttt cccagtcacg actggctaca atgtctccag attaaacaa            49

<210> SEQ ID NO 125
<211> LENGTH: 47
<212> TYPE: DNA
<213> ORGANISM: Artificial sequence
<220> FEATURE:
<223> OTHER INFORMATION: Synthetic oligonucleotide

<400> SEQUENCE: 125
ccagggtttt cccagtcacg acccctgatg gctacaatgt ctccaga              47

<210> SEQ ID NO 126
<211> LENGTH: 49
<212> TYPE: DNA
<213> ORGANISM: Artificial sequence
<220> FEATURE:
<223> OTHER INFORMATION: Synthetic oligonucleotide

<400> SEQUENCE: 126
ccagggtttt cccagtcacg acgtgtctcc agagcaaaca cagatgatt            49

<210> SEQ ID NO 127
<211> LENGTH: 46
<212> TYPE: DNA
<213> ORGANISM: Artificial sequence
<220> FEATURE:
<223> OTHER INFORMATION: Synthetic oligonucleotide

<400> SEQUENCE: 127
ccagggtttt cccagtcacg acgtctccag atcaaccaca gaggat               46

<210> SEQ ID NO 128
<211> LENGTH: 49
<212> TYPE: DNA
<213> ORGANISM: Artificial sequence
<220> FEATURE:
<223> OTHER INFORMATION: Synthetic oligonucleotide

<400> SEQUENCE: 128
```
ccagggtttt cccagtcacg acgtctctag attaaacaca gaggatttc        49

<210> SEQ ID NO 129
<211> LENGTH: 47
<212> TYPE: DNA
<213> ORGANISM: Artificial sequence
<220> FEATURE:
<223> OTHER INFORMATION: Synthetic oligonucleotide

<400> SEQUENCE: 129
ccagggtttt cccagtcacg acggctacaa tgtatccaga tcaaaca           47

<210> SEQ ID NO 130
<211> LENGTH: 46
<212> TYPE: DNA
<213> ORGANISM: Artificial sequence
<220> FEATURE:
<223> OTHER INFORMATION: Synthetic oligonucleotide

<400> SEQUENCE: 130
ccagggtttt cccagtcacg actcgcttct ctgcagagag gactgg            46

<210> SEQ ID NO 131
<211> LENGTH: 45
<212> TYPE: DNA
<213> ORGANISM: Artificial sequence
<220> FEATURE:
<223> OTHER INFORMATION: Synthetic oligonucleotide

<400> SEQUENCE: 131
ccagggtttt cccagtcacg accggttctt tgcagtcagg cctga             45

<210> SEQ ID NO 132
<211> LENGTH: 46
<212> TYPE: DNA
<213> ORGANISM: Artificial sequence
<220> FEATURE:
<223> OTHER INFORMATION: Synthetic oligonucleotide

<400> SEQUENCE: 132
ccagggtttt cccagtcacg acccagtgat cgcttctttg cagaaa            46

<210> SEQ ID NO 133
<211> LENGTH: 46
<212> TYPE: DNA
<213> ORGANISM: Artificial sequence
<220> FEATURE:
<223> OTHER INFORMATION: Synthetic oligonucleotide

<400> SEQUENCE: 133
ccagggtttt cccagtcacg actctccact ctgamgatcc agcgca            46

<210> SEQ ID NO 134
<211> LENGTH: 45
<212> TYPE: DNA
<213> ORGANISM: Artificial sequence
<220> FEATURE:
<223> OTHER INFORMATION: Synthetic oligonucleotide

<400> SEQUENCE: 134
ccagggtttt cccagtcacg acgcagagag gcctgaggga tccat             45

<210> SEQ ID NO 135
<211> LENGTH: 45
<212> TYPE: DNA

```
<213> ORGANISM: Artificial sequence
<220> FEATURE:
<223> OTHER INFORMATION: Synthetic oligonucleotide

<400> SEQUENCE: 135
ccagggtttt cccagtcacg acctgcagag aggcctaagg gatct                45

<210> SEQ ID NO 136
<211> LENGTH: 46
<212> TYPE: DNA
<213> ORGANISM: Artificial sequence
<220> FEATURE:
<223> OTHER INFORMATION: Synthetic oligonucleotide

<400> SEQUENCE: 136
ccagggtttt cccagtcacg acctccgcac aacagttccc tgactt               46

<210> SEQ ID NO 137
<211> LENGTH: 50
<212> TYPE: DNA
<213> ORGANISM: Artificial sequence
<220> FEATURE:
<223> OTHER INFORMATION: Synthetic oligonucleotide

<400> SEQUENCE: 137
ccagggtttt cccagtcacg accagatggc tayagtgtct ctagatcaaa           50

<210> SEQ ID NO 138
<211> LENGTH: 48
<212> TYPE: DNA
<213> ORGANISM: Artificial sequence
<220> FEATURE:
<223> OTHER INFORMATION: Synthetic oligonucleotide

<400> SEQUENCE: 138
ccagggtttt cccagtcacg acgttgtctc cagatccaag acagagaa             48

<210> SEQ ID NO 139
<211> LENGTH: 47
<212> TYPE: DNA
<213> ORGANISM: Artificial sequence
<220> FEATURE:
<223> OTHER INFORMATION: Synthetic oligonucleotide

<400> SEQUENCE: 139
ccagggtttt cccagtcacg acgcagagag gctcaaagga gtagact              47

<210> SEQ ID NO 140
<211> LENGTH: 48
<212> TYPE: DNA
<213> ORGANISM: Artificial sequence
<220> FEATURE:
<223> OTHER INFORMATION: Synthetic oligonucleotide

<400> SEQUENCE: 140
ccagggtttt cccagtcacg acgctaagat gcctaatgca tcattctc             48

<210> SEQ ID NO 141
<211> LENGTH: 47
<212> TYPE: DNA
<213> ORGANISM: Artificial sequence
<220> FEATURE:
<223> OTHER INFORMATION: Synthetic oligonucleotide

<400> SEQUENCE: 141
ccagggtttt cccagtcacg acctcagcag agatgcctga tgcaact              47
```

<210> SEQ ID NO 142
<211> LENGTH: 47
<212> TYPE: DNA
<213> ORGANISM: Artificial sequence
<220> FEATURE:
<223> OTHER INFORMATION: Synthetic oligonucleotide

<400> SEQUENCE: 142
ccagggtttt cccagtcacg actctcagct caacagttca gtgacta        47

<210> SEQ ID NO 143
<211> LENGTH: 46
<212> TYPE: DNA
<213> ORGANISM: Artificial sequence
<220> FEATURE:
<223> OTHER INFORMATION: Synthetic oligonucleotide

<400> SEQUENCE: 143
ccagggtttt cccagtcacg acgctgaaag gactggaggg acgtat        46

<210> SEQ ID NO 144
<211> LENGTH: 46
<212> TYPE: DNA
<213> ORGANISM: Artificial sequence
<220> FEATURE:
<223> OTHER INFORMATION: Synthetic oligonucleotide

<400> SEQUENCE: 144
ccagggtttt cccagtcacg acgataactt ccaatccagg aggccg        46

<210> SEQ ID NO 145
<211> LENGTH: 46
<212> TYPE: DNA
<213> ORGANISM: Artificial sequence
<220> FEATURE:
<223> OTHER INFORMATION: Synthetic oligonucleotide

<400> SEQUENCE: 145
ccagggtttt cccagtcacg acgctaagtg cctcccaaat tcaccc        46

<210> SEQ ID NO 146
<211> LENGTH: 48
<212> TYPE: DNA
<213> ORGANISM: Artificial sequence
<220> FEATURE:
<223> OTHER INFORMATION: Synthetic oligonucleotide

<400> SEQUENCE: 146
ccagggtttt cccagtcacg acggaacgat tttctgctga atttccca        48

<210> SEQ ID NO 147
<211> LENGTH: 46
<212> TYPE: DNA
<213> ORGANISM: Artificial sequence
<220> FEATURE:
<223> OTHER INFORMATION: Synthetic oligonucleotide

<400> SEQUENCE: 147
ccagggtttt cccagtcacg acggtacagc gtctctcggg agaaga        46

<210> SEQ ID NO 148
<211> LENGTH: 48
<212> TYPE: DNA
<213> ORGANISM: Artificial sequence
<220> FEATURE:

<223> OTHER INFORMATION: Synthetic oligonucleotide

<400> SEQUENCE: 148
ccagggtttt cccagtcacg acggacaagt ttctcatcaa ccatgcaa       48

<210> SEQ ID NO 149
<211> LENGTH: 46
<212> TYPE: DNA
<213> ORGANISM: Artificial sequence
<220> FEATURE:
<223> OTHER INFORMATION: Synthetic oligonucleotide

<400> SEQUENCE: 149
ccagggtttt cccagtcacg actggataca gtgtctctcg acaggc         46

<210> SEQ ID NO 150
<211> LENGTH: 47
<212> TYPE: DNA
<213> ORGANISM: Artificial sequence
<220> FEATURE:
<223> OTHER INFORMATION: Synthetic oligonucleotide

<400> SEQUENCE: 150
ccagggtttt cccagtcacg accaacagtc tccagaataa ggacgga        47

<210> SEQ ID NO 151
<211> LENGTH: 50
<212> TYPE: DNA
<213> ORGANISM: Artificial sequence
<220> FEATURE:
<223> OTHER INFORMATION: Synthetic oligonucleotide

<400> SEQUENCE: 151
ccagggtttt cccagtcacg actacaaagt ctctcgaaaa gagaagagga     50

<210> SEQ ID NO 152
<211> LENGTH: 45
<212> TYPE: DNA
<213> ORGANISM: Artificial sequence
<220> FEATURE:
<223> OTHER INFORMATION: Synthetic oligonucleotide

<400> SEQUENCE: 152
ccagggtttt cccagtcacg acggggtaca gtgtctctag agaga          45

<210> SEQ ID NO 153
<211> LENGTH: 47
<212> TYPE: DNA
<213> ORGANISM: Artificial sequence
<220> FEATURE:
<223> OTHER INFORMATION: Synthetic oligonucleotide

<400> SEQUENCE: 153
ccagggtttt cccagtcacg acgtttccca tcagccgccc aaaccta        47

<210> SEQ ID NO 154
<211> LENGTH: 46
<212> TYPE: DNA
<213> ORGANISM: Artificial sequence
<220> FEATURE:
<223> OTHER INFORMATION: Synthetic oligonucleotide

<400> SEQUENCE: 154
ccagggtttt cccagtcacg accagacccc aggaccggca gttcat         46

```
<210> SEQ ID NO 155
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 155
cagacagact tgtcactgga tttag                                    25

<210> SEQ ID NO 156
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 156
cttttgggtg tgggagatct ctg                                      23

<210> SEQ ID NO 157
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 157
gacgcggcgc agtacccgct                                          20

<210> SEQ ID NO 158
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 158
ggagaagggg ctgagattcc ag                                       22

<210> SEQ ID NO 159
<211> LENGTH: 44
<212> TYPE: DNA
<213> ORGANISM: Artificial sequence
<220> FEATURE:
<223> OTHER INFORMATION: Synthetic oligonucleotide

<400> SEQUENCE: 159
ccagggtttt cccagtcacg acgccggagg aggtggatgt gctt               44

<210> SEQ ID NO 160
<211> LENGTH: 44
<212> TYPE: DNA
<213> ORGANISM: Artificial sequence
<220> FEATURE:
<223> OTHER INFORMATION: Synthetic oligonucleotide

<400> SEQUENCE: 160
agcggataac aatttcacac aggaggggag gcggtgtggt ggct               44

<210> SEQ ID NO 161
<211> LENGTH: 21
<212> TYPE: DNA
<213> ORGANISM: Artificial sequence
<220> FEATURE:
<223> OTHER INFORMATION: Synthetic oligonucleotide
```

```
<400> SEQUENCE: 161
gcctgtacgt ccacccggac t                                    21

<210> SEQ ID NO 162
<211> LENGTH: 26
<212> TYPE: DNA
<213> ORGANISM: Artificial sequence
<220> FEATURE:
<223> OTHER INFORMATION: Synthetic oligonucleotide

<400> SEQUENCE: 162
ctgggtttct tggaaagtaa agatat                               26

<210> SEQ ID NO 163
<211> LENGTH: 43
<212> TYPE: DNA
<213> ORGANISM: Artificial sequence
<220> FEATURE:
<223> OTHER INFORMATION: Synthetic oligonucleotide

<400> SEQUENCE: 163
ccagggtttt cccagtcacg accccaacac aggagcgcac tgg            43

<210> SEQ ID NO 164
<211> LENGTH: 46
<212> TYPE: DNA
<213> ORGANISM: Artificial sequence
<220> FEATURE:
<223> OTHER INFORMATION: Synthetic oligonucleotide

<400> SEQUENCE: 164
agcggataac aatttcacac aggacgtgtt ggaagcgttg caggct         46

<210> SEQ ID NO 165
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 165
ggctcctgct gcatcgtagc tgct                                 24

<210> SEQ ID NO 166
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 166
gtccgctgct tctctggagc ct                                   22

<210> SEQ ID NO 167
<211> LENGTH: 42
<212> TYPE: DNA
<213> ORGANISM: Artificial sequence
<220> FEATURE:
<223> OTHER INFORMATION: Synthetic oligonucleotide

<400> SEQUENCE: 167
ccagggtttt cccagtcacg acggcagcca aggccctgtc gt             42

<210> SEQ ID NO 168
<211> LENGTH: 45
```

<212> TYPE: DNA
<213> ORGANISM: Artificial sequence
<220> FEATURE:
<223> OTHER INFORMATION: Synthetic oligonucleotide

<400> SEQUENCE: 168
agcggataac aatttcacac aggaccagga tggcccagcg gatga    45

<210> SEQ ID NO 169
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 169
cccgggagga agtgactggc ta    22

<210> SEQ ID NO 170
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 170
ccatgccacc gtatttgcct tcaa    24

<210> SEQ ID NO 171
<211> LENGTH: 46
<212> TYPE: DNA
<213> ORGANISM: Artificial sequence
<220> FEATURE:
<223> OTHER INFORMATION: Synthetic oligonucleotide

<400> SEQUENCE: 171
ccagggtttt cccagtcacg acagaggaag tccatgtggg agatgt    46

<210> SEQ ID NO 172
<211> LENGTH: 48
<212> TYPE: DNA
<213> ORGANISM: Artificial sequence
<220> FEATURE:
<223> OTHER INFORMATION: Synthetic oligonucleotide

<400> SEQUENCE: 172
agcggataac aatttcacac aggatcagca ttgtaggccc ggcacatc    48

<210> SEQ ID NO 173
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 173
ccgcagcatg gtggaggtgc t    21

<210> SEQ ID NO 174
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 174
ggtcattaaa tcttgcaacc tggtt                                                      25

<210> SEQ ID NO 175
<211> LENGTH: 43
<212> TYPE: DNA
<213> ORGANISM: Artificial sequence
<220> FEATURE:
<223> OTHER INFORMATION: Synthetic oligonucleotide

<400> SEQUENCE: 175
ccagggtttt cccagtcacg acgcgagctg gtgcgcaccg aca                                  43

<210> SEQ ID NO 176
<211> LENGTH: 47
<212> TYPE: DNA
<213> ORGANISM: Artificial sequence
<220> FEATURE:
<223> OTHER INFORMATION: Synthetic oligonucleotide

<400> SEQUENCE: 176
agcggataac aatttcacac aggaggctgc ggtagcattt ctcagct                              47

<210> SEQ ID NO 177
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 177
gcgctcgatg gtggacgtgc t                                                          21

<210> SEQ ID NO 178
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 178
agcacgtcca ccatcgagcg c                                                          21

<210> SEQ ID NO 179
<211> LENGTH: 43
<212> TYPE: DNA
<213> ORGANISM: Artificial sequence
<220> FEATURE:
<223> OTHER INFORMATION: Synthetic oligonucleotide

<400> SEQUENCE: 179
ccagggtttt cccagtcacg acggaccacg caggcgagct cgt                                  43

<210> SEQ ID NO 180
<211> LENGTH: 45
<212> TYPE: DNA
<213> ORGANISM: Artificial sequence
<220> FEATURE:
<223> OTHER INFORMATION: Synthetic oligonucleotide

<400> SEQUENCE: 180
agcggataac aatttcacac aggacggccg aggcattgcg cagct                                45

<210> SEQ ID NO 181
<211> LENGTH: 21
<212> TYPE: DNA
<213> ORGANISM: Artificial sequence

```
<220> FEATURE:
<223> OTHER INFORMATION: Synthetic oligonucleotide

<400> SEQUENCE: 181
gccaaaccag aggggcctga g                                               21

<210> SEQ ID NO 182
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 182
gagagccgca ggacgtgcac tt                                              22

<210> SEQ ID NO 183
<211> LENGTH: 43
<212> TYPE: DNA
<213> ORGANISM: Artificial sequence
<220> FEATURE:
<223> OTHER INFORMATION: Synthetic oligonucleotide

<400> SEQUENCE: 183
ccagggtttt cccagtcacg accctacacg gccccacctg cct                       43

<210> SEQ ID NO 184
<211> LENGTH: 47
<212> TYPE: DNA
<213> ORGANISM: Artificial sequence
<220> FEATURE:
<223> OTHER INFORMATION: Synthetic oligonucleotide

<400> SEQUENCE: 184
agcggataac aatttcacac aggagggtgc atgtagagtg gtgagtg                   47

<210> SEQ ID NO 185
<211> LENGTH: 26
<212> TYPE: DNA
<213> ORGANISM: Artificial sequence
<220> FEATURE:
<223> OTHER INFORMATION: Synthetic oligonucleotide

<400> SEQUENCE: 185
ctcacattta agttttacat gcccaa                                          26

<210> SEQ ID NO 186
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 186
gacaaaaggt aatccatctg ttcag                                           25

<210> SEQ ID NO 187
<211> LENGTH: 46
<212> TYPE: DNA
<213> ORGANISM: Artificial sequence
<220> FEATURE:
<223> OTHER INFORMATION: Synthetic oligonucleotide

<400> SEQUENCE: 187
ccagggtttt cccagtcacg acccacagaa ctgaaacatc ttcagt                    46
```

<210> SEQ ID NO 188
<211> LENGTH: 46
<212> TYPE: DNA
<213> ORGANISM: Artificial sequence
<220> FEATURE:
<223> OTHER INFORMATION: Synthetic oligonucleotide

<400> SEQUENCE: 188
agcggataac aatttcacac aggattctac aatggttgct gtctca          46

<210> SEQ ID NO 189
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 189
ccagttttac ctggaggagg tga          23

<210> SEQ ID NO 190
<211> LENGTH: 26
<212> TYPE: DNA
<213> ORGANISM: Artificial sequence
<220> FEATURE:
<223> OTHER INFORMATION: Synthetic oligonucleotide

<400> SEQUENCE: 190
gtaggcttct atgtagttga tgaaga          26

<210> SEQ ID NO 191
<211> LENGTH: 45
<212> TYPE: DNA
<213> ORGANISM: Artificial sequence
<220> FEATURE:
<223> OTHER INFORMATION: Synthetic oligonucleotide

<400> SEQUENCE: 191
ccagggtttt cccagtcacg accccaagct gagaaccaag accca          45

<210> SEQ ID NO 192
<211> LENGTH: 48
<212> TYPE: DNA
<213> ORGANISM: Artificial sequence
<220> FEATURE:
<223> OTHER INFORMATION: Synthetic oligonucleotide

<400> SEQUENCE: 192
agcggataac aatttcacac aggagtcaaa ctcactcatg gctttgta          48

<210> SEQ ID NO 193
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 193
gggagttgcc tggcctccag aa          22

<210> SEQ ID NO 194
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 194
cggttcttca agggaggatt tttgt                                              25

<210> SEQ ID NO 195
<211> LENGTH: 46
<212> TYPE: DNA
<213> ORGANISM: Artificial sequence
<220> FEATURE:
<223> OTHER INFORMATION: Synthetic oligonucleotide

<400> SEQUENCE: 195
ccagggtttt cccagtcacg acagacctct tttatgatgg ccctgt                       46

<210> SEQ ID NO 196
<211> LENGTH: 49
<212> TYPE: DNA
<213> ORGANISM: Artificial sequence
<220> FEATURE:
<223> OTHER INFORMATION: Synthetic oligonucleotide

<400> SEQUENCE: 196
agcggataac aatttcacac aggaggcaca gtctcactgt tgaaattca                    49

<210> SEQ ID NO 197
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 197
cccagaacca gaaggctccg ct                                                 22

<210> SEQ ID NO 198
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 198
ccctcgcgaa aaagtttctt taaat                                              25

<210> SEQ ID NO 199
<211> LENGTH: 45
<212> TYPE: DNA
<213> ORGANISM: Artificial sequence
<220> FEATURE:
<223> OTHER INFORMATION: Synthetic oligonucleotide

<400> SEQUENCE: 199
ccagggtttt cccagtcacg acggtatgga gcatcaacct gacag                        45

<210> SEQ ID NO 200
<211> LENGTH: 46
<212> TYPE: DNA
<213> ORGANISM: Artificial sequence
<220> FEATURE:
<223> OTHER INFORMATION: Synthetic oligonucleotide

<400> SEQUENCE: 200
agcggataac aatttcacac aggaggtcct ttacaaactg ggccac                       46

<210> SEQ ID NO 201

```
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 201
gacaagaact tcccccggac tg                                                  22

<210> SEQ ID NO 202
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 202
ggaccaggat ctcttgctgg at                                                  22

<210> SEQ ID NO 203
<211> LENGTH: 46
<212> TYPE: DNA
<213> ORGANISM: Artificial sequence
<220> FEATURE:
<223> OTHER INFORMATION: Synthetic oligonucleotide

<400> SEQUENCE: 203
ccagggtttt cccagtcacg accaacctga acatccataa ccggaa                        46

<210> SEQ ID NO 204
<211> LENGTH: 47
<212> TYPE: DNA
<213> ORGANISM: Artificial sequence
<220> FEATURE:
<223> OTHER INFORMATION: Synthetic oligonucleotide

<400> SEQUENCE: 204
agcggataac aatttcacac aggaggggac agagttcatg tggtagt                       47

<210> SEQ ID NO 205
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 205
ggcttttcag ctctgcatcg tttt                                                24

<210> SEQ ID NO 206
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 206
ggatgctctg gtcatctttta aagtt                                              25

<210> SEQ ID NO 207
<211> LENGTH: 44
<212> TYPE: DNA
<213> ORGANISM: Artificial sequence
<220> FEATURE:
<223> OTHER INFORMATION: Synthetic oligonucleotide

<400> SEQUENCE: 207
```
ccagggtttt cccagtcacg acgggttctc ttggctgtta ctgc     44

<210> SEQ ID NO 208
<211> LENGTH: 49
<212> TYPE: DNA
<213> ORGANISM: Artificial sequence
<220> FEATURE:
<223> OTHER INFORMATION: Synthetic oligonucleotide

<400> SEQUENCE: 208
agcggataac aatttcacac aggagtttga agtaaaagga gacaatttg     49

<210> SEQ ID NO 209
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 209
catgatccgg gacgtggagc t     21

<210> SEQ ID NO 210
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 210
gggctacagg cttgtcactc g     21

<210> SEQ ID NO 211
<211> LENGTH: 43
<212> TYPE: DNA
<213> ORGANISM: Artificial sequence
<220> FEATURE:
<223> OTHER INFORMATION: Synthetic oligonucleotide

<400> SEQUENCE: 211
ccagggtttt cccagtcacg acggaggcgc tccccaagaa gac     43

<210> SEQ ID NO 212
<211> LENGTH: 47
<212> TYPE: DNA
<213> ORGANISM: Artificial sequence
<220> FEATURE:
<223> OTHER INFORMATION: Synthetic oligonucleotide

<400> SEQUENCE: 212
agcggataac aatttcacac aggacgagaa gatgatctga ctgcctg     47

<210> SEQ ID NO 213
<211> LENGTH: 26
<212> TYPE: DNA
<213> ORGANISM: Artificial sequence
<220> FEATURE:
<223> OTHER INFORMATION: Synthetic oligonucleotide

<400> SEQUENCE: 213
gcatatatat gttcttcaac acatca     26

<210> SEQ ID NO 214
<211> LENGTH: 20
<212> TYPE: DNA

```
<213> ORGANISM: Artificial sequence
<220> FEATURE:
<223> OTHER INFORMATION: Synthetic oligonucleotide

<400> SEQUENCE: 214
ccctccacgg ctcaaccact                                              20

<210> SEQ ID NO 215
<211> LENGTH: 43
<212> TYPE: DNA
<213> ORGANISM: Artificial sequence
<220> FEATURE:
<223> OTHER INFORMATION: Synthetic oligonucleotide

<400> SEQUENCE: 215
ccagggtttt cccagtcacg acccgagaag cggtacctga acc                    43

<210> SEQ ID NO 216
<211> LENGTH: 46
<212> TYPE: DNA
<213> ORGANISM: Artificial sequence
<220> FEATURE:
<223> OTHER INFORMATION: Synthetic oligonucleotide

<400> SEQUENCE: 216
agcggataac aatttcacac aggaccgcac aactccggtg acatca                 46

<210> SEQ ID NO 217
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 217
gtgtctgtgg ccggctcaca c                                            21

<210> SEQ ID NO 218
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 218
ccgatatgcg gccacccagc t                                            21

<210> SEQ ID NO 219
<211> LENGTH: 44
<212> TYPE: DNA
<213> ORGANISM: Artificial sequence
<220> FEATURE:
<223> OTHER INFORMATION: Synthetic oligonucleotide

<400> SEQUENCE: 219
ccagggtttt cccagtcacg acgccaactt tgcagcccag aaga                   44

<210> SEQ ID NO 220
<211> LENGTH: 46
<212> TYPE: DNA
<213> ORGANISM: Artificial sequence
<220> FEATURE:
<223> OTHER INFORMATION: Synthetic oligonucleotide

<400> SEQUENCE: 220
agcggataac aatttcacac aggagggtgc cgtagttgga gataag                 46
```

<210> SEQ ID NO 221
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 221
gggaagctcc ataaatgtca cctt                                             24

<210> SEQ ID NO 222
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 222
gttttcccag gggggccgtc t                                                21

<210> SEQ ID NO 223
<211> LENGTH: 46
<212> TYPE: DNA
<213> ORGANISM: Artificial sequence
<220> FEATURE:
<223> OTHER INFORMATION: Synthetic oligonucleotide

<400> SEQUENCE: 223
ccagggtttt cccagtcacg acccacaata tcaaagaaca ggagcc                     46

<210> SEQ ID NO 224
<211> LENGTH: 45
<212> TYPE: DNA
<213> ORGANISM: Artificial sequence
<220> FEATURE:
<223> OTHER INFORMATION: Synthetic oligonucleotide

<400> SEQUENCE: 224
agcggataac aatttcacac aggagccaca ctgcatgtct gccct                      45

<210> SEQ ID NO 225
<211> LENGTH: 54
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (24)..(25)
<223> OTHER INFORMATION: n is a, c, g, or t

<400> SEQUENCE: 225
ctgctgaacc gctcttccga tctnngttca gtcactggat ttagagtctc tcag            54

<210> SEQ ID NO 226
<211> LENGTH: 54
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (24)..(25)
<223> OTHER INFORMATION: n is a, c, g, or t

<400> SEQUENCE: 226
ctgctgaacc gctcttccga tctnncagga gtcactggat ttagagtctc tcag        54

<210> SEQ ID NO 227
<211> LENGTH: 54
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (24)..(25)
<223> OTHER INFORMATION: n is a, c, g, or t

<400> SEQUENCE: 227
ctgctgaacc gctcttccga tctnnttata gtcactggat ttagagtctc tcag        54

<210> SEQ ID NO 228
<211> LENGTH: 54
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (24)..(25)
<223> OTHER INFORMATION: n is a, c, g, or t

<400> SEQUENCE: 228
ctgctgaacc gctcttccga tctnncctgt gtcactggat ttagagtctc tcag        54

<210> SEQ ID NO 229
<211> LENGTH: 54
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (24)..(25)
<223> OTHER INFORMATION: n is a, c, g, or t

<400> SEQUENCE: 229
ctgctgaacc gctcttccga tctnnaccgc gtcactggat ttagagtctc tcag        54

<210> SEQ ID NO 230
<211> LENGTH: 54
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (24)..(25)
<223> OTHER INFORMATION: n is a, c, g, or t

<400> SEQUENCE: 230
ctgctgaacc gctcttccga tctnnactta gtcactggat ttagagtctc tcag        54

<210> SEQ ID NO 231
<211> LENGTH: 54
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (24)..(25)
<223> OTHER INFORMATION: n is a, c, g, or t

<400> SEQUENCE: 231
ctgctgaacc gctcttccga tctnngctag gtcactggat ttagagtctc tcag    54

<210> SEQ ID NO 232
<211> LENGTH: 54
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (24)..(25)
<223> OTHER INFORMATION: n is a, c, g, or t

<400> SEQUENCE: 232
ctgctgaacc gctcttccga tctnngacgt gtcactggat ttagagtctc tcag    54

<210> SEQ ID NO 233
<211> LENGTH: 54
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (24)..(25)
<223> OTHER INFORMATION: n is a, c, g, or t

<400> SEQUENCE: 233
ctgctgaacc gctcttccga tctnnggcta gtcactggat ttagagtctc tcag    54

<210> SEQ ID NO 234
<211> LENGTH: 54
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (24)..(25)
<223> OTHER INFORMATION: n is a, c, g, or t

<400> SEQUENCE: 234
ctgctgaacc gctcttccga tctnngaatg gtcactggat ttagagtctc tcag    54

<210> SEQ ID NO 235
<211> LENGTH: 54
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (24)..(25)
<223> OTHER INFORMATION: n is a, c, g, or t

<400> SEQUENCE: 235
ctgctgaacc gctcttccga tctnnccaac gtcactggat ttagagtctc tcag    54

<210> SEQ ID NO 236
<211> LENGTH: 54
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (24)..(25)
<223> OTHER INFORMATION: n is a, c, g, or t

<400> SEQUENCE: 236
ctgctgaacc gctcttccga tctnngagac gtcactggat ttagagtctc tcag            54

<210> SEQ ID NO 237
<211> LENGTH: 53
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (24)..(25)
<223> OTHER INFORMATION: n is a, c, g, or t

<400> SEQUENCE: 237
ctgctgaacc gctcttccga tctnngttca gagatctctg cttctgatgg ctc             53

<210> SEQ ID NO 238
<211> LENGTH: 53
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (24)..(25)
<223> OTHER INFORMATION: n is a, c, g, or t

<400> SEQUENCE: 238
ctgctgaacc gctcttccga tctnncagga gagatctctg cttctgatgg ctc             53

<210> SEQ ID NO 239
<211> LENGTH: 53
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (24)..(25)
<223> OTHER INFORMATION: n is a, c, g, or t

<400> SEQUENCE: 239
ctgctgaacc gctcttccga tctnnttata gagatctctg cttctgatgg ctc             53

<210> SEQ ID NO 240
<211> LENGTH: 53
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (24)..(25)
<223> OTHER INFORMATION: n is a, c, g, or t

<400> SEQUENCE: 240
ctgctgaacc gctcttccga tctnncctgt gagatctctg cttctgatgg ctc             53

<210> SEQ ID NO 241
<211> LENGTH: 53
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (24)..(25)
<223> OTHER INFORMATION: n is a, c, g, or t

<400> SEQUENCE: 241
ctgctgaacc gctcttccga tctnnaccgc gagatctctg cttctgatgg ctc        53

<210> SEQ ID NO 242
<211> LENGTH: 53
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (24)..(25)
<223> OTHER INFORMATION: n is a, c, g, or t

<400> SEQUENCE: 242
ctgctgaacc gctcttccga tctnnactta gagatctctg cttctgatgg ctc        53

<210> SEQ ID NO 243
<211> LENGTH: 53
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (24)..(25)
<223> OTHER INFORMATION: n is a, c, g, or t

<400> SEQUENCE: 243
ctgctgaacc gctcttccga tctnngctag gagatctctg cttctgatgg ctc        53

<210> SEQ ID NO 244
<211> LENGTH: 53
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (24)..(25)
<223> OTHER INFORMATION: n is a, c, g, or t

<400> SEQUENCE: 244
ctgctgaacc gctcttccga tctnngacgt gagatctctg cttctgatgg ctc        53

<210> SEQ ID NO 245
<211> LENGTH: 53
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (24)..(25)
<223> OTHER INFORMATION: n is a, c, g, or t

<400> SEQUENCE: 245
ctgctgaacc gctcttccga tctnnggcta gagatctctg cttctgatgg ctc        53

<210> SEQ ID NO 246
<211> LENGTH: 53
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (24)..(25)

<223> OTHER INFORMATION: n is a, c, g, or t

<400> SEQUENCE: 246
ctgctgaacc gctcttccga tctnngaatg gagatctctg cttctgatgg ctc    53

<210> SEQ ID NO 247
<211> LENGTH: 53
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (24)..(25)
<223> OTHER INFORMATION: n is a, c, g, or t

<400> SEQUENCE: 247
ctgctgaacc gctcttccga tctnnccaac gagatctctg cttctgatgg ctc    53

<210> SEQ ID NO 248
<211> LENGTH: 53
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (24)..(25)
<223> OTHER INFORMATION: n is a, c, g, or t

<400> SEQUENCE: 248
ctgctgaacc gctcttccga tctnngagac gagatctctg cttctgatgg ctc    53

<210> SEQ ID NO 249
<211> LENGTH: 54
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (24)..(25)
<223> OTHER INFORMATION: n is a, c, g, or t

<400> SEQUENCE: 249
ctgctgaacc gctcttccga tctnngttca agcggataac aatttcacac agga    54

<210> SEQ ID NO 250
<211> LENGTH: 54
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (24)..(25)
<223> OTHER INFORMATION: n is a, c, g, or t

<400> SEQUENCE: 250
ctgctgaacc gctcttccga tctnncagga agcggataac aatttcacac agga    54

<210> SEQ ID NO 251
<211> LENGTH: 54
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (24)..(25)
<223> OTHER INFORMATION: n is a, c, g, or t

<400> SEQUENCE: 251
ctgctgaacc gctcttccga tctnnttata agcggataac aatttcacac agga       54

<210> SEQ ID NO 252
<211> LENGTH: 54
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (24)..(25)
<223> OTHER INFORMATION: n is a, c, g, or t

<400> SEQUENCE: 252
ctgctgaacc gctcttccga tctnncctgt agcggataac aatttcacac agga       54

<210> SEQ ID NO 253
<211> LENGTH: 54
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (24)..(25)
<223> OTHER INFORMATION: n is a, c, g, or t

<400> SEQUENCE: 253
ctgctgaacc gctcttccga tctnnaccgc agcggataac aatttcacac agga       54

<210> SEQ ID NO 254
<211> LENGTH: 54
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (24)..(25)
<223> OTHER INFORMATION: n is a, c, g, or t

<400> SEQUENCE: 254
ctgctgaacc gctcttccga tctnnactta agcggataac aatttcacac agga       54

<210> SEQ ID NO 255
<211> LENGTH: 54
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (24)..(25)
<223> OTHER INFORMATION: n is a, c, g, or t

<400> SEQUENCE: 255
ctgctgaacc gctcttccga tctnngctag agcggataac aatttcacac agga       54

<210> SEQ ID NO 256
<211> LENGTH: 54
<212> TYPE: DNA
<213> ORGANISM: Artificial sequence
<220> FEATURE:
<223> OTHER INFORMATION: Synthetic oligonucleotide
<220> FEATURE:

```
<221> NAME/KEY: misc_feature
<222> LOCATION: (24)..(25)
<223> OTHER INFORMATION: n is a, c, g, or t

<400> SEQUENCE: 256
ctgctgaacc gctcttccga tctnngacgt agcggataac aatttcacac agga         54

<210> SEQ ID NO 257
<211> LENGTH: 54
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (24)..(25)
<223> OTHER INFORMATION: n is a, c, g, or t

<400> SEQUENCE: 257
ctgctgaacc gctcttccga tctnnggcta agcggataac aatttcacac agga         54

<210> SEQ ID NO 258
<211> LENGTH: 54
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (24)..(25)
<223> OTHER INFORMATION: n is a, c, g, or t

<400> SEQUENCE: 258
ctgctgaacc gctcttccga tctnngaatg agcggataac aatttcacac agga         54

<210> SEQ ID NO 259
<211> LENGTH: 54
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (24)..(25)
<223> OTHER INFORMATION: n is a, c, g, or t

<400> SEQUENCE: 259
ctgctgaacc gctcttccga tctnnccaac agcggataac aatttcacac agga         54

<210> SEQ ID NO 260
<211> LENGTH: 54
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (24)..(25)
<223> OTHER INFORMATION: n is a, c, g, or t

<400> SEQUENCE: 260
ctgctgaacc gctcttccga tctnngagac agcggataac aatttcacac agga         54

<210> SEQ ID NO 261
<211> LENGTH: 58
<212> TYPE: DNA
<213> ORGANISM: Artificial sequence
<220> FEATURE:
<223> OTHER INFORMATION: Synthetic oligonucleotide
```

```
<400> SEQUENCE: 261
aatgatacgg cgaccaccga gatctacact ctttccctac acgacgctct tccgatct        58

<210> SEQ ID NO 262
<211> LENGTH: 60
<212> TYPE: DNA
<213> ORGANISM: Artificial sequence
<220> FEATURE:
<223> OTHER INFORMATION: Synthetic oligonucleotide

<400> SEQUENCE: 262
aagcagaaga cggcatacga gatcggtctc ggcattcctg ctgaaccgct cttccgatct      60

<210> SEQ ID NO 263
<211> LENGTH: 59
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (24)..(30)
<223> OTHER INFORMATION: n is a, c, g, or t
<220> FEATURE:
<221> NAME/KEY: misc_feature
<222> LOCATION: (33)..(37)
<223> OTHER INFORMATION: n is a, c, g, or t

<400> SEQUENCE: 263
cctacacgac gctcttccga tctnnnnnnn gannnnncca gggttttccc agtcacgac       59

<210> SEQ ID NO 264
<211> LENGTH: 54
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (24)..(30)
<223> OTHER INFORMATION: n is a, c, g, or t

<400> SEQUENCE: 264
ctgctgaacc gctcttccga tctnnnnnnn gtcactggat ttagagtctc tcag           54

<210> SEQ ID NO 265
<211> LENGTH: 15
<212> TYPE: PRT
<213> ORGANISM: Artificial sequence
<220> FEATURE:
<223> OTHER INFORMATION: Synthetic oligonucleotide

<400> SEQUENCE: 265

Cys Ala Ser Ser Leu Ala Ser Met Gly Val Gly Glu Leu Phe Phe
1               5                   10                  15

<210> SEQ ID NO 266
<211> LENGTH: 45
<212> TYPE: DNA
<213> ORGANISM: Artificial sequence
<220> FEATURE:
<223> OTHER INFORMATION: Synthetic oligonucleotide

<400> SEQUENCE: 266
tgtgccagca gcctagcgag tatgggtgtc ggggagctgt ttttt                     45
```

<210> SEQ ID NO 267
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 267

Cys Ala Ser Ser Ser Ala Ser Gly Gly Val Gly Glu Leu Phe Phe
1               5                   10                  15

<210> SEQ ID NO 268
<211> LENGTH: 45
<212> TYPE: DNA
<213> ORGANISM: Artificial sequence
<220> FEATURE:
<223> OTHER INFORMATION: Synthetic oligonucleotide

<400> SEQUENCE: 268
tgtgccagca gctcggcaag cgggggagtc ggggagctgt ttttt             45

<210> SEQ ID NO 269
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 269

Cys Ala Tyr Arg Pro Asn Tyr Gly Gly Ala Thr Asn Lys Leu Ile Phe
1               5                   10                  15

<210> SEQ ID NO 270
<211> LENGTH: 48
<212> TYPE: DNA
<213> ORGANISM: Artificial sequence
<220> FEATURE:
<223> OTHER INFORMATION: Synthetic oligonucleotide

<400> SEQUENCE: 270
tgtgcttata ggccaaatta tggtggtgct acaaacaagc tcatctttt            48

<210> SEQ ID NO 271
<211> LENGTH: 48
<212> TYPE: DNA
<213> ORGANISM: Artificial sequence
<220> FEATURE:
<223> OTHER INFORMATION: Synthetic oligonucleotide

<400> SEQUENCE: 271
tgtgcttata ggccgaatta tggtggtgct acaaacaagc tcatctttt            48

<210> SEQ ID NO 272
<211> LENGTH: 13
<212> TYPE: PRT
<213> ORGANISM: Artificial Sequence
<220> FEATURE:
<223> OTHER INFORMATION: Synthetic polypeptide

<400> SEQUENCE: 272

Cys Ala Ser Ser Phe Phe Gly Asn Gln Pro Gln His Phe
1               5                   10

<210> SEQ ID NO 273
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 273

Cys Ala Ser Ser Leu Leu Ser Gly Ala His Glu Gln Tyr Phe
1               5                   10

<210> SEQ ID NO 274
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 274

Cys Ala Ser Ser Ser Leu Thr Ser Gly Arg Ala Asp Thr Gln Tyr Phe
1               5                   10                  15

<210> SEQ ID NO 275
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 275

Cys Ala Ser Ser Leu Gln Gly Ser Met Asn Thr Glu Ala Phe Phe
1               5                   10                  15

<210> SEQ ID NO 276
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 276

Cys Ala Ser Ser Glu Ala Gly Arg Val Asn Ile Gln Tyr Phe
1               5                   10

<210> SEQ ID NO 277
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 277

Cys Ala Ser Ser Leu Val Gln Val Asn Ser Pro Leu His Phe
1               5                   10

<210> SEQ ID NO 278
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 278

Cys Ala Thr Gln Asp Arg Arg Gly Thr Glu Ala Phe Phe
1               5                   10

<210> SEQ ID NO 279
<211> LENGTH: 16
<212> TYPE: PRT
<213> ORGANISM: Artificial sequence
<220> FEATURE:

<223> OTHER INFORMATION: Synthetic polypeptide

<400> SEQUENCE: 279

Cys Ala Ser Ser Phe Ser Thr Cys Ser Ala Asn Tyr Gly Tyr Thr Phe
1               5                   10                  15

<210> SEQ ID NO 280
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 280

Cys Ala Ser Thr Asn Leu Arg Gly Ser Gly Gly Tyr Thr Phe
1               5                   10

<210> SEQ ID NO 281
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 281

Cys Ala Ser Ser Leu Arg Thr Arg Pro Gly Ala Gly Glu Leu Phe Phe
1               5                   10                  15

<210> SEQ ID NO 282
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 282

Cys Ala Ile Ser Glu Asn Ala Ser Gln Asn Ser Pro Leu His Phe
1               5                   10                  15

<210> SEQ ID NO 283
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 283

Cys Ala Ser Arg Ala Thr Gly Asn Gly Ser Pro Leu His Phe
1               5                   10

<210> SEQ ID NO 284
<211> LENGTH: 17
<212> TYPE: PRT
<213> ORGANISM: Artificial sequence
<220> FEATURE:
<223> OTHER INFORMATION: Synthetic polypeptide

<400> SEQUENCE: 284

Cys Ala Ser Ser Gln Glu Gly Thr Ser Gly Ala Tyr Asn Glu Gln Phe
1               5                   10                  15

Phe

<210> SEQ ID NO 285
<211> LENGTH: 11
<212> TYPE: PRT
<213> ORGANISM: Artificial sequence

```
<220> FEATURE:
<223> OTHER INFORMATION: Synthetic polypeptide

<400> SEQUENCE: 285

Cys Ser Val His Gly Gly Glu Thr Gln Tyr Phe
1               5                   10

<210> SEQ ID NO 286
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 286

Cys Ala Ser Ser Pro Glu Ala Leu Glu Thr Gln Tyr Phe
1               5                   10

<210> SEQ ID NO 287
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 287

Cys Ser Val Glu Gly Glu Gly Val Ala Phe Phe
1               5                   10

<210> SEQ ID NO 288
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 288

Cys Ala Ser Arg Ala Gly Leu Phe Tyr Asp Asn Glu Gln Phe Phe
1               5                   10                  15

<210> SEQ ID NO 289
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 289

Cys Ala Ser Ser Gln Gly Pro Gly Ala Asp Thr Gln Tyr Phe
1               5                   10

<210> SEQ ID NO 290
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 290

Cys Ala Ser Ser Arg Thr Trp Arg Gly Tyr Glu Gln Tyr Phe
1               5                   10

<210> SEQ ID NO 291
<211> LENGTH: 13
<212> TYPE: PRT
<213> ORGANISM: Artificial sequence
<220> FEATURE:
```

<223> OTHER INFORMATION: Synthetic polypeptide

<400> SEQUENCE: 291

Cys Ser Val Ala Pro Ser Gly Ile Gly Glu Gln Phe Phe
1               5                   10

<210> SEQ ID NO 292
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 292

Cys Ala Ser Ser Leu Ile Gly Gly Asn Gln Pro Gln His Phe
1               5                   10

<210> SEQ ID NO 293
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 293

Cys Ala Ser Ser Phe Ser Gly Gly Arg Pro Thr Glu Ala Phe Phe
1               5                   10                  15

<210> SEQ ID NO 294
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 294

Cys Ala Ser Ser Pro Ile Leu Gly Val Glu Gln Tyr Phe
1               5                   10

<210> SEQ ID NO 295
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 295

Cys Ala Ser Ser Val Thr Gly Gly Met Gly Thr Asp Thr Gln Tyr Phe
1               5                   10                  15

<210> SEQ ID NO 296
<211> LENGTH: 17
<212> TYPE: PRT
<213> ORGANISM: Artificial sequence
<220> FEATURE:
<223> OTHER INFORMATION: Synthetic polypeptide

<400> SEQUENCE: 296

Cys Ala Ser Ser Pro Gly Ile Ala Gly Tyr Leu Gly Asn Glu Gln Phe
1               5                   10                  15
Phe

<210> SEQ ID NO 297
<211> LENGTH: 14
<212> TYPE: PRT
<213> ORGANISM: Artificial sequence

```
<220> FEATURE:
<223> OTHER INFORMATION: Synthetic polypeptide

<400> SEQUENCE: 297

Cys Ala Ser Ser Leu Glu Gly Arg Asn Thr Glu Ala Phe Phe
1               5                   10

<210> SEQ ID NO 298
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 298

Cys Ala Ser Ser Trp Thr Ser Gly Ser Thr Asp Thr Gln Tyr Phe
1               5                   10                  15

<210> SEQ ID NO 299
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 299

Cys Ala Ser Thr Arg Asp Gly Glu Ile Tyr Gly Tyr Thr Phe
1               5                   10

<210> SEQ ID NO 300
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 300

Cys Ala Ser Ser Leu Ala Arg Pro Ser Thr Asn Glu Lys Leu Phe Phe
1               5                   10                  15

<210> SEQ ID NO 301
<211> LENGTH: 17
<212> TYPE: PRT
<213> ORGANISM: Artificial sequence
<220> FEATURE:
<223> OTHER INFORMATION: Synthetic polypeptide

<400> SEQUENCE: 301

Cys Ala Ser Ser Ser Leu Gly Gly Thr Gly Lys Pro Tyr Glu Gln Tyr
1               5                   10                  15

Phe

<210> SEQ ID NO 302
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 302

Cys Ala Ser Ser Gly Gly Asp Gly Thr Phe Ser Glu Gln Phe Phe
1               5                   10                  15

<210> SEQ ID NO 303
<211> LENGTH: 12
<212> TYPE: PRT
```

<213> ORGANISM: Artificial sequence
<220> FEATURE:
<223> OTHER INFORMATION: Synthetic polypeptide

<400> SEQUENCE: 303

Cys Ser Ala Arg Gly Gln Gly Gly Glu Gln Tyr Phe
1               5                   10

<210> SEQ ID NO 304
<211> LENGTH: 17
<212> TYPE: PRT
<213> ORGANISM: Artificial sequence
<220> FEATURE:
<223> OTHER INFORMATION: Synthetic polypeptide

<400> SEQUENCE: 304

Cys Ala Ser Ser Tyr Ser Ile Ala Gly Gly Ser Tyr Asn Glu Gln Phe
1               5                   10                  15

Phe

<210> SEQ ID NO 305
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 305

Cys Ala Ser Arg Gly Leu Ala Gly Arg Thr Glu Ala Phe Phe
1               5                   10

<210> SEQ ID NO 306
<211> LENGTH: 18
<212> TYPE: PRT
<213> ORGANISM: Artificial sequence
<220> FEATURE:
<223> OTHER INFORMATION: Synthetic polypeptide

<400> SEQUENCE: 306

Cys Ala Ser Ser Ser Gly Leu Ala Gly Gly Gly Ser Thr Asp Thr Gln
1               5                   10                  15

Tyr Phe

<210> SEQ ID NO 307
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 307

Cys Ala Ser Ser Pro Ser Gly Gly Arg Ser Tyr Glu Gln Tyr Phe
1               5                   10                  15

<210> SEQ ID NO 308
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 308

Cys Ala Ser Ser Phe Asn Ser Asn Thr Glu Ala Phe Phe
1               5                   10

```
<210> SEQ ID NO 309
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 309

Cys Ala Ser Arg Leu Ser Gly Ser Gly Lys Gly Asn Glu Gln Phe Phe
1               5                   10                  15

<210> SEQ ID NO 310
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 310

Cys Ala Ser Ser Val Gly Gly Ala Ala Gln Glu Thr Gln Tyr Phe
1               5                   10                  15

<210> SEQ ID NO 311
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 311

Cys Ala Ser Ser Leu Ile Ser Pro Pro Pro Tyr Glu Gln Tyr Phe
1               5                   10                  15

<210> SEQ ID NO 312
<211> LENGTH: 10
<212> TYPE: PRT
<213> ORGANISM: Artificial sequence
<220> FEATURE:
<223> OTHER INFORMATION: Synthetic polypeptide

<400> SEQUENCE: 312

Cys Ala Ser Ser Val Asn Glu Gln Phe Phe
1               5                   10

<210> SEQ ID NO 313
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 313

Cys Ala Ser Ser Trp Thr Ser Val Gly Glu Thr Asp Thr Gln Tyr Phe
1               5                   10                  15

<210> SEQ ID NO 314
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 314

Cys Ala Ser Gly Pro Arg Asp Arg Gly Gly Tyr Glu Gln Tyr Phe
1               5                   10                  15

<210> SEQ ID NO 315
```

```
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 315

Cys Ala Ser Ser Glu Thr Thr Ala Thr Val Gln Glu Thr Gln Tyr Phe
1               5                   10                  15

<210> SEQ ID NO 316
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 316

Cys Ala Ser Ser Gly Gly Gly Arg Thr Gln Glu Thr Gln Tyr Phe
1               5                   10                  15

<210> SEQ ID NO 317
<211> LENGTH: 17
<212> TYPE: PRT
<213> ORGANISM: Artificial sequence
<220> FEATURE:
<223> OTHER INFORMATION: Synthetic polypeptide

<400> SEQUENCE: 317

Cys Ala Ser Ser Gln Gly Gly Ser Gly Asp Tyr Tyr Asn Glu Gln Phe
1               5                   10                  15

Phe

<210> SEQ ID NO 318
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 318

Cys Ala Ser Ser Leu Arg Gln Gly Gly Ser Thr Gly Glu Leu Phe Phe
1               5                   10                  15

<210> SEQ ID NO 319
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 319

Cys Ala Ser Ser Pro Thr Thr Asp Arg His Trp Ala Glu Ala Phe Phe
1               5                   10                  15

<210> SEQ ID NO 320
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 320

Cys Ala Ser Ser Gln Gly Gly Ala Gly Asn Gly Glu Gln Phe Phe
1               5                   10                  15
```

```
<210> SEQ ID NO 321
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 321

Cys Ala Ser Ser Glu Gly Gly Thr Thr Ile Gln Pro Gln His Phe
1               5                   10                  15

<210> SEQ ID NO 322
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 322

Cys Ala Ser Ser Val Gly Arg Ala Gly Glu Leu Phe Phe
1               5                   10

<210> SEQ ID NO 323
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 323

Cys Ala Ser Ser Ser Ala Gly Tyr Glu Gln Tyr Phe
1               5                   10

<210> SEQ ID NO 324
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 324

Cys Ser Ala Arg Glu Ala Gly Val Thr Gly Glu Leu Phe Phe
1               5                   10

<210> SEQ ID NO 325
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 325

Cys Ala Ser Ser Leu Leu Gly Gly Asn Asn Ser Pro Leu His Phe
1               5                   10                  15

<210> SEQ ID NO 326
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 326

Cys Ala Ser Ser Pro Asn Ser Asn Gln Pro Gln His Phe
1               5                   10

<210> SEQ ID NO 327
```

```
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 327

Cys Ala Ser Ser Phe Pro Gly Ala Gly Asn Gln Pro Gln His Phe
1               5                   10                  15

<210> SEQ ID NO 328
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 328

Cys Ala Ser Ser Glu Val Trp Ala Gly Asn Gln Pro Gln His Phe
1               5                   10                  15

<210> SEQ ID NO 329
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 329

Cys Ala Thr Arg Asp Arg Gly Leu Gln Glu Thr Gln Tyr Phe
1               5                   10

<210> SEQ ID NO 330
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 330

Cys Ala Ser Ser Arg Glu Ala Gly Gly Ser Tyr Asn Glu Gln Phe Phe
1               5                   10                  15

<210> SEQ ID NO 331
<211> LENGTH: 17
<212> TYPE: PRT
<213> ORGANISM: Artificial sequence
<220> FEATURE:
<223> OTHER INFORMATION: Synthetic polypeptide

<400> SEQUENCE: 331

Cys Ala Ser Ser Phe Gly Leu Ala Gly Ser Leu Ser Tyr Glu Gln Tyr
1               5                   10                  15

Phe

<210> SEQ ID NO 332
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 332

Cys Ala Trp Ser Ile Asn Leu Gly His Arg Ser Tyr Glu Gln Tyr Phe
1               5                   10                  15
```

<210> SEQ ID NO 333
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 333

Cys Ser Ala Arg Met Gly Pro Tyr Glu Gln Tyr Phe
1               5                   10

<210> SEQ ID NO 334
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 334

Cys Ala Ser Ser Pro Ser Gly Asp Tyr Asn Glu Gln Phe Phe
1               5                   10

<210> SEQ ID NO 335
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 335

Cys Ala Ser Ser Pro Glu Thr Gly Ser Ser Tyr Glu Gln Tyr Phe
1               5                   10                  15

<210> SEQ ID NO 336
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 336

Cys Ala Ser Ser Leu Pro Gly Gly Val Gly Gln Thr Gln Tyr Phe
1               5                   10                  15

<210> SEQ ID NO 337
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 337

Cys Ala Ser Ser His Gly Gly Asp Asn Glu Gln Phe Phe
1               5                   10

<210> SEQ ID NO 338
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 338

Cys Ala Ser Ser Leu Gly Asn Tyr Gly Tyr Thr Phe
1               5                   10

<210> SEQ ID NO 339

```
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 339

Cys Ala Ser Ser Val Ser Met Asn Thr Glu Ala Phe Phe
1               5                   10

<210> SEQ ID NO 340
<211> LENGTH: 17
<212> TYPE: PRT
<213> ORGANISM: Artificial sequence
<220> FEATURE:
<223> OTHER INFORMATION: Synthetic polypeptide

<400> SEQUENCE: 340

Cys Ala Thr Ser Glu Gly Gly Leu Ala Gly Val Lys Asn Ile Gln Tyr
1               5                   10                  15

Phe

<210> SEQ ID NO 341
<211> LENGTH: 20
<212> TYPE: PRT
<213> ORGANISM: Artificial sequence
<220> FEATURE:
<223> OTHER INFORMATION: Synthetic polypeptide

<400> SEQUENCE: 341

Cys Ser Ala Arg Asp Gly Lys Ala Ser Thr Ser Phe Ser Ser Tyr Asn
1               5                   10                  15

Glu Gln Phe Phe
            20

<210> SEQ ID NO 342
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 342

Cys Ala Ser Ser Val Thr Thr Gly Gly Gly Glu Gln Tyr Phe
1               5                   10

<210> SEQ ID NO 343
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 343

Cys Ala Gly Arg Gly Thr Ser Tyr Glu Gln Tyr Phe
1               5                   10

<210> SEQ ID NO 344
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 344

Cys Ala Ser Lys Gln Gly Ala Tyr Thr Glu Ala Phe Phe
```

<210> SEQ ID NO 345
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 345

Cys Ala Ser Ser Gln Glu Arg Val Ser Tyr Asn Glu Gln Phe Phe
1               5                   10                  15

<210> SEQ ID NO 346
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 346

Cys Ala Ser Asn Leu Ala Gly Gly Asn Glu Gln Phe Phe
1               5                   10

<210> SEQ ID NO 347
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 347

Cys Ala Ser Thr Arg Asp Thr Asn Thr Gly Glu Leu Phe Phe
1               5                   10

<210> SEQ ID NO 348
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 348

Cys Ala Ser Ser Ser Leu Asp Arg Tyr Asn Glu Gln Phe Phe
1               5                   10

<210> SEQ ID NO 349
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 349

Cys Ala Ser Tyr Arg Gly Ser Gly Pro Leu Ser Tyr Glu Gln Tyr Phe
1               5                   10                  15

<210> SEQ ID NO 350
<211> LENGTH: 17
<212> TYPE: PRT
<213> ORGANISM: Artificial sequence
<220> FEATURE:
<223> OTHER INFORMATION: Synthetic polypeptide

<400> SEQUENCE: 350

Cys Ala Ser Ser Pro Gly Ala Ile Glu Gly Ile Ser Tyr Glu Gln Tyr
1               5                   10                  15

Phe

<210> SEQ ID NO 351
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 351

Cys Ala Ser Gln Lys Ser Thr Tyr Asn Ser Pro Leu His Phe
1               5                   10

<210> SEQ ID NO 352
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 352

Cys Ala Ser Thr Thr Thr Arg Ala Pro Gly Tyr Gly Tyr Thr Phe
1               5                   10                  15

<210> SEQ ID NO 353
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 353

Cys Ala Ser Ser Gly Ser Pro Ser Tyr Asn Glu Gln Phe Phe
1               5                   10

<210> SEQ ID NO 354
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 354

Cys Ala Ser Ser Leu Leu Gly Trp Thr Asp Asn Glu Gln Phe Phe
1               5                   10                  15

<210> SEQ ID NO 355
<211> LENGTH: 17
<212> TYPE: PRT
<213> ORGANISM: Artificial sequence
<220> FEATURE:
<223> OTHER INFORMATION: Synthetic polypeptide

<400> SEQUENCE: 355

Cys Ala Ser Ser Tyr Gly Asp Pro Gly Gly Leu Asp Gly Glu Leu Phe
1               5                   10                  15

Phe

<210> SEQ ID NO 356
<211> LENGTH: 17
<212> TYPE: PRT
<213> ORGANISM: Artificial sequence
<220> FEATURE:
<223> OTHER INFORMATION: Synthetic polypeptide

<400> SEQUENCE: 356

Cys Ala Ser Ser Gln Tyr Leu Ala Val Thr Ser Gly Glu Thr Gln Tyr
1               5                   10                  15

Phe

<210> SEQ ID NO 357
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 357

Cys Ala Ser Ser Pro Asp Arg Gly Gly Ala Asn Val Leu Thr Phe
1               5                   10                  15

<210> SEQ ID NO 358
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 358

Cys Ala Ser Ser Leu Asp Asn Ser Gly Ala Asn Val Leu Thr Phe
1               5                   10                  15

<210> SEQ ID NO 359
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 359

Cys Ser Ala Glu Leu Val Arg Gly Thr Glu Ala Phe Phe
1               5                   10

<210> SEQ ID NO 360
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 360

Cys Ala Ser Arg Leu Thr Gly Ser Ala Thr Asn Glu Lys Leu Phe Phe
1               5                   10                  15

<210> SEQ ID NO 361
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 361

Cys Ala Ser Ser Gln Asp Pro Ser Gly Glu Tyr Asn Glu Gln Phe Phe
1               5                   10                  15

<210> SEQ ID NO 362
<211> LENGTH: 11
<212> TYPE: PRT
<213> ORGANISM: Artificial sequence
<220> FEATURE:
<223> OTHER INFORMATION: Synthetic polypeptide

```
<400> SEQUENCE: 362

Cys Ala Ser Ser Thr Asn Ile Gln Tyr Phe
1               5                   10

<210> SEQ ID NO 363
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 363

Cys Ala Ser Ser Thr Gly Ala Gly Asp Pro Glu Ala Phe Phe
1               5                   10

<210> SEQ ID NO 364
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 364

Cys Ser Ala Gln Thr Glu Leu Ser Ser Tyr Glu Gln Tyr Phe
1               5                   10

<210> SEQ ID NO 365
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 365

Cys Ala Ser Ser Tyr Arg Tyr Gly Asp Tyr Gly Tyr Thr Phe
1               5                   10

<210> SEQ ID NO 366
<211> LENGTH: 18
<212> TYPE: PRT
<213> ORGANISM: Artificial sequence
<220> FEATURE:
<223> OTHER INFORMATION: Synthetic polypeptide

<400> SEQUENCE: 366

Cys Ala Ser Ser Trp Thr Ser Gly Arg Ser Asn Ser Pro Arg Glu Leu
1               5                   10                  15

Phe Phe

<210> SEQ ID NO 367
<211> LENGTH: 17
<212> TYPE: PRT
<213> ORGANISM: Artificial sequence
<220> FEATURE:
<223> OTHER INFORMATION: Synthetic polypeptide

<400> SEQUENCE: 367

Cys Ser Ala Arg Lys His Gln Arg Ala Glu Ser Tyr Asn Glu Gln Phe
1               5                   10                  15

Phe

<210> SEQ ID NO 368
<211> LENGTH: 15
<212> TYPE: PRT
<213> ORGANISM: Artificial sequence
```

```
<220> FEATURE:
<223> OTHER INFORMATION: Synthetic polypeptide

<400> SEQUENCE: 368

Cys Ser Ala Thr Ile Asp Ser Ala Thr Asn Glu Lys Leu Phe Phe
1               5                   10                  15

<210> SEQ ID NO 369
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 369

Cys Ser Val Ala Lys Thr Gly Gly Ser Asp Glu Gln Phe Phe
1               5                   10

<210> SEQ ID NO 370
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 370

Cys Ala Ser Ser Thr Gly Gly Thr Asp Thr Gln Tyr Phe
1               5                   10

<210> SEQ ID NO 371
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 371

Cys Ala Ser Ser Leu Gly Ser Gly Asn Gln Pro Gln His Phe
1               5                   10

<210> SEQ ID NO 372
<211> LENGTH: 17
<212> TYPE: PRT
<213> ORGANISM: Artificial sequence
<220> FEATURE:
<223> OTHER INFORMATION: Synthetic polypeptide

<400> SEQUENCE: 372

Cys Ala Thr Ser Asp Lys Leu Ala Gly Val Ser Tyr Asn Glu Gln Phe
1               5                   10                  15

Phe

<210> SEQ ID NO 373
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 373

Cys Ala Ser Ser Glu Gly Lys Gly Pro Gln His Phe
1               5                   10

<210> SEQ ID NO 374
<211> LENGTH: 14
<212> TYPE: PRT
```

```
<213> ORGANISM: Artificial sequence
<220> FEATURE:
<223> OTHER INFORMATION: Synthetic polypeptide

<400> SEQUENCE: 374

Cys Ala Ser Ser Val Gly Leu Thr Ala Thr Glu Ala Phe Phe
1               5                   10

<210> SEQ ID NO 375
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 375

Cys Ala Ser Arg Ser Ser Pro Leu Asn Glu Gln Phe Phe
1               5                   10

<210> SEQ ID NO 376
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 376

Cys Ala Ser Ser Gly Ala Ser Gly Ser Lys Asn Ile Gln Tyr Phe
1               5                   10                  15

<210> SEQ ID NO 377
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 377

Cys Ala Ser Ser Gln Thr Trp Asp Thr Glu Ala Phe Phe
1               5                   10

<210> SEQ ID NO 378
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 378

Cys Ser Ala Arg Met Thr Leu Asp Gly Asp Glu Gln Tyr Phe
1               5                   10

<210> SEQ ID NO 379
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 379

Cys Ala Ser Ser Thr Thr Ala Gly Gly Arg Ser Glu Gln Phe Phe
1               5                   10                  15

<210> SEQ ID NO 380
<211> LENGTH: 16
<212> TYPE: PRT
<213> ORGANISM: Artificial sequence
```

```
<220> FEATURE:
<223> OTHER INFORMATION: Synthetic polypeptide

<400> SEQUENCE: 380

Cys Ala Ser Ser Gly Ala Pro Arg Arg Asn Thr Gly Glu Leu Phe Phe
1               5                   10                  15

<210> SEQ ID NO 381
<211> LENGTH: 18
<212> TYPE: PRT
<213> ORGANISM: Artificial sequence
<220> FEATURE:
<223> OTHER INFORMATION: Synthetic polypeptide

<400> SEQUENCE: 381

Cys Ala Ser Thr Leu Leu Gly Leu Ala Ala Pro Gly Thr Asp Thr Gln
1               5                   10                  15

Tyr Phe

<210> SEQ ID NO 382
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 382

Cys Ser Ala Arg Gly Gly Gly Arg Trp Thr Asp Thr Gln Tyr Phe
1               5                   10                  15

<210> SEQ ID NO 383
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 383

Cys Ser Val Ala Gln Gly Arg Thr Glu Ala Phe Phe
1               5                   10

<210> SEQ ID NO 384
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 384

Cys Ala Trp Thr Leu Gly Gly Asn Glu Gln Phe Phe
1               5                   10

<210> SEQ ID NO 385
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 385

Cys Ser Ala Arg Leu Ala Gly Gly Ser Ser Tyr Asn Glu Gln Phe Phe
1               5                   10                  15

<210> SEQ ID NO 386
<211> LENGTH: 14
<212> TYPE: PRT
```

```
<213> ORGANISM: Artificial sequence
<220> FEATURE:
<223> OTHER INFORMATION: Synthetic polypeptide

<400> SEQUENCE: 386

Cys Ala Thr Ser Arg Val Glu Gly Arg Gln Pro Gln His Phe
1               5                   10

<210> SEQ ID NO 387
<211> LENGTH: 7
<212> TYPE: PRT
<213> ORGANISM: Artificial sequence
<220> FEATURE:
<223> OTHER INFORMATION: Synthetic polypeptide

<400> SEQUENCE: 387

Cys Ala Leu Gly Tyr Thr Phe
1               5

<210> SEQ ID NO 388
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 388

Cys Ala Ser Ser Ala Gly Pro Lys Asn Gln Pro Gln His Phe
1               5                   10

<210> SEQ ID NO 389
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 389

Cys Ala Ser Ser Pro Asp Arg Gly Arg Glu Gln Tyr Phe
1               5                   10

<210> SEQ ID NO 390
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 390

Cys Ala Ser Ser Leu Pro Gly Gly Gly His Ser Thr Glu Ala Phe Phe
1               5                   10                  15

<210> SEQ ID NO 391
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 391

Cys Ala Ser Ser Ala Gly Gln Gly Glu Gln Lys Leu Phe Phe
1               5                   10

<210> SEQ ID NO 392
<211> LENGTH: 13
<212> TYPE: PRT
<213> ORGANISM: Artificial sequence
```

<220> FEATURE:
<223> OTHER INFORMATION: Synthetic polypeptide

<400> SEQUENCE: 392

Cys Ala Ile Thr Pro Arg Gln Asp Tyr Glu Gln Tyr Phe
1               5                   10

<210> SEQ ID NO 393
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 393

Cys Ala Ser Ser Glu Ile Gly Val Ser Trp Glu Gln Tyr Phe
1               5                   10

<210> SEQ ID NO 394
<211> LENGTH: 17
<212> TYPE: PRT
<213> ORGANISM: Artificial sequence
<220> FEATURE:
<223> OTHER INFORMATION: Synthetic polypeptide

<400> SEQUENCE: 394

Cys Ala Ser Ser Val Gly Leu Ala Gly Gly Pro Arg Asp Thr Gln Tyr
1               5                   10                  15

Phe

<210> SEQ ID NO 395
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 395

Cys Ala Ser Leu Gly Pro Gly Thr Thr Gln Tyr Phe
1               5                   10

<210> SEQ ID NO 396
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 396

Cys Ala Ser Ser Tyr Ala Ala Gly Leu Gln Ala Phe Phe
1               5                   10

<210> SEQ ID NO 397
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 397

Cys Ala Ser Ser Ala Gln Thr Gly Gly Trp Asp Gly Tyr Thr Phe
1               5                   10                  15

<210> SEQ ID NO 398
<211> LENGTH: 19
<212> TYPE: PRT

<213> ORGANISM: Artificial sequence
<220> FEATURE:
<223> OTHER INFORMATION: Synthetic polypeptide

<400> SEQUENCE: 398

Cys Ala Ser Asn Gly Leu Ala Gly Gly Arg Ser Ser Ser Tyr Asn Glu
1               5                   10                  15

Gln Phe Phe

<210> SEQ ID NO 399
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 399

Cys Ala Ser Ser Glu Ala Leu Arg Gly Ser Lys Phe Phe
1               5                   10

<210> SEQ ID NO 400
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 400

Cys Ser Ala Ala Gly Leu Gly His Asn Ser Pro Leu His Phe
1               5                   10

<210> SEQ ID NO 401
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 401

Cys Ala Ser Arg Pro Gly Gln Gly Val Thr Glu Ala Phe Phe
1               5                   10

<210> SEQ ID NO 402
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 402

Cys Ala Ser Ser Pro Gly Val Gly Thr Gly Glu Leu Phe Phe
1               5                   10

<210> SEQ ID NO 403
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 403

Cys Ala Ser Ser Pro Tyr Gly Thr Ser Thr Asp Thr Gln Tyr Phe
1               5                   10                  15

<210> SEQ ID NO 404
<211> LENGTH: 14

```
<212> TYPE: PRT
<213> ORGANISM: Artificial sequence
<220> FEATURE:
<223> OTHER INFORMATION: Synthetic polypeptide

<400> SEQUENCE: 404

Cys Ala Ser Ser Gly Arg Asp Tyr Lys Tyr Glu Gln Tyr Phe
1               5                   10

<210> SEQ ID NO 405
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 405

Cys Ala Ser Ser Trp Arg Pro Asn Tyr Glu Gln Tyr Phe
1               5                   10

<210> SEQ ID NO 406
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 406

Cys Ala Ser Ser Leu Val Asn Thr Glu Ala Phe Phe
1               5                   10

<210> SEQ ID NO 407
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 407

Cys Ala Ser Ser Pro His Tyr Arg Gly Gly Asn Thr Ile Tyr Phe
1               5                   10                  15

<210> SEQ ID NO 408
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 408

Cys Ala Ser Ser Leu Gly Gly Ser Pro His Asn Glu Gln Phe Phe
1               5                   10                  15

<210> SEQ ID NO 409
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 409

Cys Ala Ile Ser Glu Ser Gly Thr Leu Gln Glu Thr Gln Tyr Phe
1               5                   10                  15

<210> SEQ ID NO 410
<211> LENGTH: 16
<212> TYPE: PRT
```

<213> ORGANISM: Artificial sequence
<220> FEATURE:
<223> OTHER INFORMATION: Synthetic polypeptide

<400> SEQUENCE: 410

```
Cys Ala Ser Ser Gln Trp Gly Ala Gly Val Gly Glu Thr Gln Tyr Phe
1               5                   10                  15
```

<210> SEQ ID NO 411
<211> LENGTH: 17
<212> TYPE: PRT
<213> ORGANISM: Artificial sequence
<220> FEATURE:
<223> OTHER INFORMATION: Synthetic polypeptide

<400> SEQUENCE: 411

```
Cys Ala Ser Ser Pro Pro Trp Ala Ser Gly Arg Val Asp Glu Gln Phe
1               5                   10                  15

Phe
```

<210> SEQ ID NO 412
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 412

```
Cys Ala Ser Ser Phe Ser Gly Gly Asn Lys Asn Ile Gln Tyr Phe
1               5                   10                  15
```

<210> SEQ ID NO 413
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 413

```
Cys Ala Ser Ser Gly Thr Ser Ser His Glu Gln Phe Phe
1               5                   10
```

<210> SEQ ID NO 414
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 414

```
Cys Ala Val Thr Gln Gly Gly Ser Glu Lys Leu Val Phe
1               5                   10
```

<210> SEQ ID NO 415
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 415

```
Cys Ala Val Lys His Gln Ala Gly Thr Ala Leu Ile Phe
1               5                   10
```

<210> SEQ ID NO 416
<211> LENGTH: 14

```
<212> TYPE: PRT
<213> ORGANISM: Artificial sequence
<220> FEATURE:
<223> OTHER INFORMATION: Synthetic polypeptide

<400> SEQUENCE: 416

Cys Ala Val Arg Asp Asn Ser Gly Tyr Ser Thr Leu Thr Phe
1               5                   10

<210> SEQ ID NO 417
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 417

Cys Ala Val Arg Asp Ala Gly Gly Gly Phe Gly Asn Val Leu His Cys
1               5                   10                  15

<210> SEQ ID NO 418
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 418

Cys Val Val Pro Ile Thr Gly Thr Ala Ser Lys Leu Thr Phe
1               5                   10

<210> SEQ ID NO 419
<211> LENGTH: 8
<212> TYPE: PRT
<213> ORGANISM: Artificial sequence
<220> FEATURE:
<223> OTHER INFORMATION: Synthetic polypeptide

<400> SEQUENCE: 419

Cys Ala Leu Glu Asn Phe Val Phe
1               5

<210> SEQ ID NO 420
<211> LENGTH: 17
<212> TYPE: PRT
<213> ORGANISM: Artificial sequence
<220> FEATURE:
<223> OTHER INFORMATION: Synthetic polypeptide

<400> SEQUENCE: 420

Cys Ala Val Ser Asp Leu Glu Pro Asn Ser Ser Ala Ser Lys Ile Ile
1               5                   10                  15

Phe

<210> SEQ ID NO 421
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 421

Cys Ala Ala Ser Met Ala Asn Thr Gly Asn Gln Phe Tyr Phe
1               5                   10

<210> SEQ ID NO 422
```

```
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 422

Cys Ala Val Arg Leu Pro Ser Asn Thr Gly Asn Gln Phe Tyr Phe
1               5                   10                  15

<210> SEQ ID NO 423
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 423

Cys Ala Ser Val Phe Gln Gly Ala Gln Lys Leu Val Phe
1               5                   10

<210> SEQ ID NO 424
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 424

Cys Ala Thr Ala Arg Trp Gly Ala Thr Asn Lys Leu Ile Phe
1               5                   10

<210> SEQ ID NO 425
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 425

Cys Ala Glu Leu Gly Ala Asp Gly Leu Thr Phe
1               5                   10

<210> SEQ ID NO 426
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 426

Cys Ala Leu Ser Pro Leu Gly Asn Thr Gly Lys Leu Ile Phe
1               5                   10

<210> SEQ ID NO 427
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 427

Cys Ala Ser Arg His Gly Ser Gly Asn Thr Gly Lys Leu Ile Phe
1               5                   10                  15

<210> SEQ ID NO 428
<211> LENGTH: 14
```

```
<212> TYPE: PRT
<213> ORGANISM: Artificial sequence
<220> FEATURE:
<223> OTHER INFORMATION: Synthetic polypeptide

<400> SEQUENCE: 428

Cys Ala Phe Met Leu Thr Gly Thr Ala Ser Lys Leu Thr Phe
1               5                   10

<210> SEQ ID NO 429
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 429

Cys Ala Leu Gly Ser Ala Arg Gln Leu Thr Phe
1               5                   10

<210> SEQ ID NO 430
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 430

Cys Leu Val Gly Ala Gly Gln Ala Gly Thr Ala Leu Ile Phe
1               5                   10

<210> SEQ ID NO 431
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 431

Cys Ala Gly Pro Trp Val Ala Asp Gly Ser Glu Lys Leu Val Phe
1               5                   10                  15

<210> SEQ ID NO 432
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 432

Cys Ala Val Ser Asp Gln Gly Ala Arg Leu Met Phe
1               5                   10

<210> SEQ ID NO 433
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 433

Cys Ala Ala Ser Leu Gly Ser Tyr Ile Pro Thr Phe
1               5                   10

<210> SEQ ID NO 434
<211> LENGTH: 15
<212> TYPE: PRT
```

```
<213> ORGANISM: Artificial sequence
<220> FEATURE:
<223> OTHER INFORMATION: Synthetic polypeptide

<400> SEQUENCE: 434

Cys Ile Leu Arg Asp Val His Asn Gln Gly Gly Lys Leu Ile Phe
1               5                   10                  15

<210> SEQ ID NO 435
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 435

Cys Ala Ser Ser Arg Gly Asn Gln Phe Tyr Phe
1               5                   10

<210> SEQ ID NO 436
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 436

Cys Ala Val Asn Asn Pro Ser Ser Ala Ser Lys Ile Ile Phe
1               5                   10

<210> SEQ ID NO 437
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 437

Cys Ala Glu Thr Pro Ile Tyr Thr Arg Leu Met Phe
1               5                   10

<210> SEQ ID NO 438
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 438

Cys Ala Tyr Arg Lys Trp Met Gly Asp Asp Lys Ile Ile Phe
1               5                   10

<210> SEQ ID NO 439
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 439

Cys Ala Ala Ser Ile Glu Thr Ser Gly Ser Arg Leu Thr Phe
1               5                   10

<210> SEQ ID NO 440
<211> LENGTH: 14
<212> TYPE: PRT
<213> ORGANISM: Artificial sequence
```

```
<220> FEATURE:
<223> OTHER INFORMATION: Synthetic polypeptide

<400> SEQUENCE: 440

Cys Val Val Ser Ala Asn Asn Gln Gly Gly Lys Leu Ile Phe
1               5                   10

<210> SEQ ID NO 441
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 441

Cys Val Val Thr Thr Gly Phe Gln Lys Leu Val Phe
1               5                   10

<210> SEQ ID NO 442
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 442

Cys Ala Phe Arg Ser Gly Gly Ser Asn Tyr Lys Leu Thr Phe
1               5                   10

<210> SEQ ID NO 443
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 443

Cys Leu Val Gly Asp Met Asp Ser Ser Tyr Lys Leu Ile Phe
1               5                   10

<210> SEQ ID NO 444
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 444

Cys Ala Val Arg Arg Gly Ala Asn Asn Leu Phe Phe
1               5                   10

<210> SEQ ID NO 445
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 445

Cys Leu Phe Ala Ala Gly Ser Ala Arg Gln Leu Thr Phe
1               5                   10

<210> SEQ ID NO 446
<211> LENGTH: 16
<212> TYPE: PRT
<213> ORGANISM: Artificial sequence
<220> FEATURE:
```

<223> OTHER INFORMATION: Synthetic polypeptide

<400> SEQUENCE: 446

Cys Ala Ala Thr Thr Tyr Trp Gln Gly Gly Ala Asp Gly Leu Thr Phe
1               5                   10                  15

<210> SEQ ID NO 447
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 447

Cys Ala Thr Val Ser Ile Gln Gly Ala Gln Lys Leu Val Phe
1               5                   10

<210> SEQ ID NO 448
<211> LENGTH: 17
<212> TYPE: PRT
<213> ORGANISM: Artificial sequence
<220> FEATURE:
<223> OTHER INFORMATION: Synthetic polypeptide

<400> SEQUENCE: 448

Cys Leu Val Gly Pro Ser Ala Met Asp Thr Gly Arg Arg Ala Leu Thr
1               5                   10                  15

Phe

<210> SEQ ID NO 449
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 449

Cys Leu Val Gly Ser Gly Gly Lys Leu Ile Phe
1               5                   10

<210> SEQ ID NO 450
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 450

Cys Ala Val Arg Leu Trp Asn Ser Gly Asn Thr Pro Leu Val Phe
1               5                   10                  15

<210> SEQ ID NO 451
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 451

Cys Ala Val Glu Pro Gly Ser Gly Asn Thr Gly Lys Leu Ile Phe
1               5                   10                  15

<210> SEQ ID NO 452
<211> LENGTH: 14
<212> TYPE: PRT
<213> ORGANISM: Artificial sequence

```
<220> FEATURE:
<223> OTHER INFORMATION: Synthetic polypeptide

<400> SEQUENCE: 452

Cys Ile Val Arg Val Ala Asn Ser Gly Tyr Ala Leu Asn Phe
1               5                   10

<210> SEQ ID NO 453
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 453

Cys Ala Val Ile Glu Gly Gly Ser Tyr Ile Pro Thr Phe
1               5                   10

<210> SEQ ID NO 454
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 454

Cys Ala Val Arg Glu Val Tyr Asn Phe Asn Lys Phe Tyr Phe
1               5                   10

<210> SEQ ID NO 455
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 455

Cys Ala Val Pro Asn Asn Ala Arg Leu Met Phe
1               5                   10

<210> SEQ ID NO 456
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 456

Cys Ala Val Glu Asp Asp Gly Gln Lys Leu Leu Phe
1               5                   10

<210> SEQ ID NO 457
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 457

Cys Ala Leu Ser Asp Arg Gly Phe Gly Asn Val Leu His Cys
1               5                   10

<210> SEQ ID NO 458
<211> LENGTH: 14
<212> TYPE: PRT
<213> ORGANISM: Artificial sequence
<220> FEATURE:
```

<223> OTHER INFORMATION: Synthetic polypeptide

<400> SEQUENCE: 458

Cys Ala Phe Met Lys Pro Asn Thr Gly Asn Gln Phe Tyr Phe
1               5                   10

<210> SEQ ID NO 459
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 459

Cys Ala Ala Gly Gly Thr Ser Tyr Gly Lys Leu Thr Phe
1               5                   10

<210> SEQ ID NO 460
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 460

Cys Ala Glu Asn Ile Pro Gly Gly Gly Ser Asn Tyr Lys Leu Thr Phe
1               5                   10                  15

<210> SEQ ID NO 461
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 461

Cys Ala Gly Thr His Ser Gly Asn Thr Gly Lys Leu Ile Phe
1               5                   10

<210> SEQ ID NO 462
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 462

Cys Ile Val Arg Ala Gly Thr Asp Lys Leu Ile Phe
1               5                   10

<210> SEQ ID NO 463
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 463

Cys Ala Met Ser Leu Thr Phe Ser Gly Asn Thr Pro Leu Val Phe
1               5                   10                  15

<210> SEQ ID NO 464
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 464

Cys Ala Leu Ser Glu Val Gly Pro Gly Thr Ala Ser Lys Leu Thr Phe
1               5                   10                  15

<210> SEQ ID NO 465
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 465

Cys Ala Val Ser Lys Ser Ser Ala Ser Lys Ile Ile Phe
1               5                   10

<210> SEQ ID NO 466
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 466

Cys Ala Val Arg Pro Thr Asn Ala Gly Lys Ser Thr Phe
1               5                   10

<210> SEQ ID NO 467
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 467

Cys Ala Leu Ser Glu Ala Gly Asn Thr Asp Lys Leu Ile Phe
1               5                   10

<210> SEQ ID NO 468
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 468

Cys Ile Leu Arg Val Leu Gly Thr Pro Leu Val Phe
1               5                   10

<210> SEQ ID NO 469
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 469

Cys Ala Ala Asp Arg Asn Thr Asp Lys Leu Ile Phe
1               5                   10

<210> SEQ ID NO 470
<211> LENGTH: 13
<212> TYPE: PRT
<213> ORGANISM: Artificial sequence
<220> FEATURE:
<223> OTHER INFORMATION: Synthetic polypeptide

```
<400> SEQUENCE: 470

Cys Ala Gly Val Lys Ala Ala Gly Asn Lys Leu Thr Phe
1               5                   10

<210> SEQ ID NO 471
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 471

Cys Ala Ala Ser Ile Arg Asn Ala Gly Asn Met Leu Thr Phe
1               5                   10

<210> SEQ ID NO 472
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 472

Cys Ala Val Glu Thr Thr Ser Gly Thr Tyr Lys Tyr Ile Phe
1               5                   10

<210> SEQ ID NO 473
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 473

Cys Ala Ala Arg Asn Asn Ala Arg Leu Met Phe
1               5                   10

<210> SEQ ID NO 474
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 474

Cys Ala Arg Leu Gly Ala Gly Asn Met Leu Thr Phe
1               5                   10

<210> SEQ ID NO 475
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 475

Cys Ala Leu Pro Gly Arg Gly Tyr Gln Lys Val Thr Phe
1               5                   10

<210> SEQ ID NO 476
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 476
```

Cys Ala Val Ser Pro Pro Arg Asn Asp Tyr Lys Leu Ser Phe
1               5                   10

<210> SEQ ID NO 477
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 477

Cys Ala Leu Ser Glu Ala Lys Ala Ala Gly Asn Lys Leu Thr Phe
1               5                   10                  15

<210> SEQ ID NO 478
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 478

Cys Ala Trp Thr Tyr Gly Gln Asn Phe Val Phe
1               5                   10

<210> SEQ ID NO 479
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 479

Cys Ala Ala Pro Ser Gly Gly Gly Ala Asp Gly Leu Thr Phe
1               5                   10

<210> SEQ ID NO 480
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 480

Cys Val Val Asn Val Val Thr Ser Tyr Gly Lys Leu Thr Phe
1               5                   10

<210> SEQ ID NO 481
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 481

Cys Ala Met Ser Leu Arg Ser Arg Thr Gly Arg Arg Ala Leu Thr Phe
1               5                   10                  15

<210> SEQ ID NO 482
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 482

Cys Ala Val Asn Ser Gly Gly Gly Ala Asp Gly Leu Thr Phe
1               5                   10

<210> SEQ ID NO 483
<211> LENGTH: 17
<212> TYPE: PRT
<213> ORGANISM: Artificial sequence
<220> FEATURE:
<223> OTHER INFORMATION: Synthetic polypeptide

<400> SEQUENCE: 483

Cys Ala Val Gln Ser Pro His Gly Ser Gly Asn Thr Gly Lys Leu Ile
1               5                   10                  15

Phe

<210> SEQ ID NO 484
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 484

Cys Val Val Phe Met Asn Thr Gly Phe Gln Lys Leu Val Phe
1               5                   10

<210> SEQ ID NO 485
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 485

Cys Ala Val Asn Thr Asn Ser Gly Asn Thr Gly Lys Leu Ile Phe
1               5                   10                  15

<210> SEQ ID NO 486
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 486

Cys Ala Met Arg Asp Ser Gly Asn Thr Gly Lys Leu Ile Phe
1               5                   10

<210> SEQ ID NO 487
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 487

Cys Ala Val Asn Asn Asn Ala Arg Leu Met Phe
1               5                   10

<210> SEQ ID NO 488
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 488

```
Cys Val Val Ser Pro Lys Ile Lys Ala Ala Gly Asn Lys Leu Thr Phe
1               5                   10                  15
```

<210> SEQ ID NO 489
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 489

```
Cys Ala Pro Ile Asn Ser Asn Ser Gly Tyr Ala Leu Asn Phe
1               5                   10
```

<210> SEQ ID NO 490
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 490

```
Cys Ala Val Gly Gly Ala Gly Gly Ser Tyr Ile Pro Thr Phe
1               5                   10
```

<210> SEQ ID NO 491
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 491

```
Cys Ala Leu Ser Gly Gly Tyr Gln Lys Val Thr Phe
1               5                   10
```

<210> SEQ ID NO 492
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 492

```
Cys Ala Met Ser Ala Ser Gly Asn Gln Phe Tyr Phe
1               5                   10
```

<210> SEQ ID NO 493
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 493

```
Cys Ala Val Arg Ile Ser Asn Thr Gly Asn Gln Phe Tyr Phe
1               5                   10
```

<210> SEQ ID NO 494
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 494

Cys Ala Val Ile Ser Phe Gln Lys Leu Val Phe
1               5                   10

<210> SEQ ID NO 495
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 495

Cys Ala Met Ser Ala Ala Gly Gly Ser Tyr Ile Pro Thr Phe
1               5                   10

<210> SEQ ID NO 496
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 496

Cys Ala Leu His Thr Ser Gly Thr Tyr Lys Tyr Ile Phe
1               5                   10

<210> SEQ ID NO 497
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 497

Cys Ala Ala Ser Asn Gly Gly Ala Thr Asn Lys Leu Ile Phe
1               5                   10

<210> SEQ ID NO 498
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 498

Cys Val Asn Asp Tyr Lys Leu Ser Phe
1               5

<210> SEQ ID NO 499
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 499

Cys Ala Leu Lys Thr Ser Tyr Asp Lys Val Ile Phe
1               5                   10

<210> SEQ ID NO 500
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 500

Cys Ala Leu Ser Ala Tyr Gly Asn Asn Arg Leu Ala Phe

```
1               5                   10
```

<210> SEQ ID NO 501
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 501

```
Cys Ala Leu Ser Arg Gly Asn Thr Pro Leu Val Phe
1               5                   10
```

<210> SEQ ID NO 502
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 502

```
Cys Leu Val Gly Gly Tyr Gly Gly Ala Thr Asn Lys Leu Ile Phe
1               5                   10                  15
```

<210> SEQ ID NO 503
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 503

```
Cys Ala Glu Asn Thr Gly Thr Asp Lys Leu Ile Phe
1               5                   10
```

<210> SEQ ID NO 504
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 504

```
Cys Ala Met Arg Glu Gly Lys Asp Ser Ser Tyr Lys Leu Ile Phe
1               5                   10                  15
```

<210> SEQ ID NO 505
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 505

```
Cys Ala Gly Ala Gly Ala Gly Asn Asn Arg Lys Leu Ile Trp
1               5                   10
```

<210> SEQ ID NO 506
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 506

```
Cys Ala Met Arg Glu Gly Lys Asp Ser Ser Tyr Lys Leu Ile Phe
1               5                   10                  15
```

<210> SEQ ID NO 507
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 507

Cys Ala Val Ser Leu Ile Ser Asn Phe Gly Asn Glu Lys Leu Thr Phe
1               5                   10                  15

<210> SEQ ID NO 508
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 508

Cys Ala Val Gly Ser Gly Asn Thr Gly Lys Leu Ile Phe
1               5                   10

<210> SEQ ID NO 509
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 509

Cys Ile Val Ser Pro Ala Ser Gly Gly Gly Ala Asp Gly Leu Thr Phe
1               5                   10                  15

<210> SEQ ID NO 510
<211> LENGTH: 17
<212> TYPE: PRT
<213> ORGANISM: Artificial sequence
<220> FEATURE:
<223> OTHER INFORMATION: Synthetic polypeptide

<400> SEQUENCE: 510

Cys Ala Ala Ser Arg Ser Thr Ala Gly Gly Gly Ala Asp Gly Leu Thr
1               5                   10                  15

Phe

<210> SEQ ID NO 511
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 511

Cys Ala Leu Val Phe Ser Gly Asn Thr Gly Lys Leu Ile Phe
1               5                   10

<210> SEQ ID NO 512
<211> LENGTH: 17
<212> TYPE: PRT
<213> ORGANISM: Artificial sequence
<220> FEATURE:
<223> OTHER INFORMATION: Synthetic polypeptide

<400> SEQUENCE: 512

Cys Val Val Ile Ser Thr Tyr Ser Gly Gly Gly Ala Asp Gly Leu Thr

Phe

<210> SEQ ID NO 513
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 513

Cys Ala Val Arg Asp Arg Gln Gly Tyr Gln Lys Val Thr Phe
1               5                   10

<210> SEQ ID NO 514
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 514

Cys Ala Val Arg Asn Gln Gly Gly Lys Leu Ile Phe
1               5                   10

<210> SEQ ID NO 515
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 515

Cys Ile Arg Thr Ile Asn Asn Ala Gly Asn Met Leu Thr Phe
1               5                   10

<210> SEQ ID NO 516
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 516

Cys Ala Val Ser Asp Asn Pro Gly Gly Ser Tyr Ile Pro Thr Phe
1               5                   10                  15

<210> SEQ ID NO 517
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 517

Cys Ala Leu Asp Asp Gly Ala Asn Asn Leu Phe Phe
1               5                   10

<210> SEQ ID NO 518
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 518

Cys Ile Val Gly Gly Phe Tyr Asn Gln Gly Gly Lys Leu Ile Phe
1               5                   10                  15

<210> SEQ ID NO 519
<211> LENGTH: 10
<212> TYPE: PRT
<213> ORGANISM: Artificial sequence
<220> FEATURE:
<223> OTHER INFORMATION: Synthetic polypeptide

<400> SEQUENCE: 519

Cys Ala Arg Gly Gly Ser Arg Leu Thr Phe
1               5                   10

<210> SEQ ID NO 520
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 520

Cys Ala Val Arg Val Arg Arg Asn Asn Arg Leu Ala Phe
1               5                   10

<210> SEQ ID NO 521
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 521

Cys Ala Ser Lys Ile Lys Ala Ala Gly Asn Lys Leu Thr Phe
1               5                   10

<210> SEQ ID NO 522
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 522

Cys Ala Leu Ser Gly Ser Gly Gly Tyr Gln Lys Val Thr Phe
1               5                   10

<210> SEQ ID NO 523
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 523

Cys Ala Val Arg Asp Ser Asn Tyr Gln Leu Ile Trp
1               5                   10

<210> SEQ ID NO 524
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 524

Cys Ala Gly Ala Ser Tyr Gly Gly Lys Leu Ile Phe

```
1               5                   10
```

```
<210> SEQ ID NO 525
<211> LENGTH: 18
<212> TYPE: PRT
<213> ORGANISM: Artificial sequence
<220> FEATURE:
<223> OTHER INFORMATION: Synthetic polypeptide

<400> SEQUENCE: 525

Cys Ala Phe Met Asn Thr Leu Arg Gly Glu Thr Ser Gly Ser Arg Leu
1               5                   10                  15

Thr Phe

<210> SEQ ID NO 526
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 526

Cys Ala Pro Arg Gly Asn Thr Asp Lys Leu Ile Phe
1               5                   10

<210> SEQ ID NO 527
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 527

Cys Ile Leu Phe Asn Thr Gly Gly Phe Lys Thr Ile Phe
1               5                   10

<210> SEQ ID NO 528
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 528

Cys Ala Val Asn Asn Gln Gly Gly Lys Leu Ile Phe
1               5                   10

<210> SEQ ID NO 529
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 529

Cys Ala Leu Ala Ala Gly Tyr Ala Leu Asn Phe
1               5                   10

<210> SEQ ID NO 530
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 530
```

Cys Ala Leu Gly Arg Thr Gly Thr Ala Ser Lys Leu Thr Phe
1               5                   10

<210> SEQ ID NO 531
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 531

Cys Val Val Pro Leu Ile Ser Gly Asn Thr Gly Lys Leu Ile Phe
1               5                   10                  15

<210> SEQ ID NO 532
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 532

Cys Ala Val Asn Pro Leu Thr Gly Gly Gly Asn Lys Leu Thr Phe
1               5                   10                  15

<210> SEQ ID NO 533
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 533

Cys Ala Glu Asn Ala Gly Gly Thr Ser Tyr Gly Lys Leu Thr Phe
1               5                   10                  15

<210> SEQ ID NO 534
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 534

Cys Ala Glu Arg Asn Asn Asn Ala Arg Leu Met Phe
1               5                   10

<210> SEQ ID NO 535
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 535

Cys Ala Val Ser Asp Glu Ala Ala Gly Asn Lys Leu Thr Phe
1               5                   10

<210> SEQ ID NO 536
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 536

Cys Leu Val Gly Gly Asn Thr Asn Ala Gly Lys Ser Thr Phe

<210> SEQ ID NO 537
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 537

Cys Ala Gly Phe Ser Gly Asn Thr Pro Leu Val Phe
1               5                   10

<210> SEQ ID NO 538
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 538

Cys Gly Thr Glu Ile Trp Gly Ala Gln Lys Leu Val Phe
1               5                   10

<210> SEQ ID NO 539
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 539

Cys Ala Gly Tyr Asn Asn Thr Asp Lys Leu Ile Phe
1               5                   10

<210> SEQ ID NO 540
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 540

Cys Ala Val Ser Met Asn Thr Gly Phe Gln Lys Leu Val Phe
1               5                   10

<210> SEQ ID NO 541
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 541

Cys Ala Ala Ser Val Val Gly Ala Gln Lys Leu Val Phe
1               5                   10

<210> SEQ ID NO 542
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 542

Cys Ala Gly Gln Gly Pro Tyr Ser Gly Ser Ala Arg Gln Leu Thr Phe
1               5                   10                  15

<210> SEQ ID NO 543
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 543

Cys Gly Thr Gly Arg Gly Ser Thr Leu Gly Arg Leu Tyr Phe
1               5                   10

<210> SEQ ID NO 544
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 544

Cys Ala Ala Asn Gly Arg Tyr Ser Ser Ala Ser Lys Ile Ile Phe
1               5                   10                  15

<210> SEQ ID NO 545
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 545

Cys Ala Ala Pro Arg Ser Asn Tyr Gln Leu Ile Trp
1               5                   10

<210> SEQ ID NO 546
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 546

Cys Ala Glu Ser Pro Tyr Asn Tyr Gly Gln Asn Phe Val Phe
1               5                   10

<210> SEQ ID NO 547
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 547

Cys Ala Val Ser Asn Thr Gly Asn Gln Phe Tyr Phe
1               5                   10

<210> SEQ ID NO 548
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 548

Cys Ala Leu Ser Asp Gly Asn Tyr Gly Gln Asn Phe Val Phe
1               5                   10

<210> SEQ ID NO 549
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 549

Cys Gly Thr Gly Gly Ala Thr Asn Lys Leu Ile Phe
1               5                   10

<210> SEQ ID NO 550
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 550

Cys Ala Thr Leu Gln Thr Gly Ala Asn Asn Leu Phe Phe
1               5                   10

<210> SEQ ID NO 551
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 551

Cys Ala Phe His Gly Ser Gly Asn Thr Gly Lys Leu Ile Phe
1               5                   10

<210> SEQ ID NO 552
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 552

Cys Ala Val Asn Thr Asn Ser Gly Asn Thr Gly Lys Leu Ile Phe
1               5                   10                  15

<210> SEQ ID NO 553
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 553

Cys Ala Ala Ser Ile Ala Gly Gly Tyr Gln Lys Val Thr Phe
1               5                   10

<210> SEQ ID NO 554
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 554

Cys Ala Leu Lys Thr Ser Tyr Asp Lys Val Ile Phe
1               5                   10

<210> SEQ ID NO 555
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 555

Cys Ala Val Ile Ser Gly Gly Tyr Asn Lys Leu Ile Phe
1               5                   10

<210> SEQ ID NO 556
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 556

Cys Ala Leu Ser Ala Tyr Gly Asn Asn Arg Leu Ala Phe
1               5                   10

<210> SEQ ID NO 557
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 557

Cys Ile Arg Thr Gly Gly Tyr Gln Lys Val Thr Phe
1               5                   10

<210> SEQ ID NO 558
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 558

Cys Ala Ala Ser Ala Val Asp Thr Asp Lys Leu Ile Phe
1               5                   10

<210> SEQ ID NO 559
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 559

Cys Ala Gly Arg Ala Gly Gly Phe Lys Thr Ile Phe
1               5                   10

<210> SEQ ID NO 560
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 560

Cys Ala Leu Gly Asp Ala Gly Asn Asn Arg Lys Leu Ile Trp
1               5                   10

<210> SEQ ID NO 561

```
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 561

Cys Ile Leu Phe Asn Thr Gly Gly Phe Lys Thr Ile Phe
1               5                   10

<210> SEQ ID NO 562
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 562

Cys Ala Ala Pro Asp Tyr Gly Asn Asn Arg Leu Ala Phe
1               5                   10

<210> SEQ ID NO 563
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 563

Cys Ala Ser Pro Gly Gly Trp Thr Gly Gly Asn Glu Gln Phe Phe
1               5                   10                  15

<210> SEQ ID NO 564
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 564

Cys Ala Ser Asn Thr Leu Gly Ala Gly Gly Arg Glu Gln Tyr Phe
1               5                   10                  15

<210> SEQ ID NO 565
<211> LENGTH: 17
<212> TYPE: PRT
<213> ORGANISM: Artificial sequence
<220> FEATURE:
<223> OTHER INFORMATION: Synthetic polypeptide

<400> SEQUENCE: 565

Cys Ala Ser Ser Glu Ala Gly Gly Gln Asp Tyr Gly Asn Glu Gln Phe
1               5                   10                  15

Phe

<210> SEQ ID NO 566
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 566

Cys Ala Ser Ser Gln Gly Leu Ala Ala Pro Tyr Glu Gln Tyr Phe
1               5                   10                  15
```

```
<210> SEQ ID NO 567
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 567

Cys Ala Trp Ser Asp Gly Val Val Gly Glu Lys Leu Phe Phe
1               5                   10

<210> SEQ ID NO 568
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 568

Cys Ala Ser Arg Glu Asn Ser Gly Ala Asn Val Leu Thr Phe
1               5                   10

<210> SEQ ID NO 569
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 569

Cys Ser Ala Gly Thr Tyr Arg Thr Asp Thr Gln Tyr Phe
1               5                   10

<210> SEQ ID NO 570
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 570

Cys Ala Ser Ser Leu Gly Gly Gly Ser Tyr Asn Glu Gln Phe Phe
1               5                   10                  15

<210> SEQ ID NO 571
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 571

Cys Ala Ser Ser Gln Asp Gly Ala Gly Gly Arg Glu Gln Phe Phe
1               5                   10                  15

<210> SEQ ID NO 572
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 572

Cys Ala Trp Ser Pro Gly Gly Glu Thr Gln Tyr Phe
1               5                   10

<210> SEQ ID NO 573
```

```
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 573

Cys Ala Ser Ser Phe Ser Pro Gly Leu Glu Thr Gln Tyr Phe
1               5                   10

<210> SEQ ID NO 574
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 574

Cys Ala Ser Ser Leu Val Ser Ser Pro Leu His Phe
1               5                   10

<210> SEQ ID NO 575
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 575

Cys Ala Ser Ser Ser Gly Thr Gly Gly Leu Glu Thr Gln Tyr Phe
1               5                   10                  15

<210> SEQ ID NO 576
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 576

Cys Ala Thr Ser Arg Asp Gly Thr Asp Tyr Gly Tyr Thr Phe
1               5                   10

<210> SEQ ID NO 577
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 577

Cys Ala Thr Ser Arg Glu Trp Gly Glu Ala Tyr Glu Gln Tyr Phe
1               5                   10                  15

<210> SEQ ID NO 578
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 578

Cys Ser Ala Ala Thr Leu Asp Gly Ser Asn Gln Pro Gln His Phe
1               5                   10                  15

<210> SEQ ID NO 579
<211> LENGTH: 17
```

```
<212> TYPE: PRT
<213> ORGANISM: Artificial sequence
<220> FEATURE:
<223> OTHER INFORMATION: Synthetic polypeptide

<400> SEQUENCE: 579

Cys Ala Ser Ser Ala Thr Gly Leu Ala Gly Gly Gly Glu Thr Gln Tyr
1               5                   10                  15

Phe

<210> SEQ ID NO 580
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 580

Cys Ala Ser Ser Glu Pro Gly Glu Gln Phe Phe
1               5                   10

<210> SEQ ID NO 581
<211> LENGTH: 19
<212> TYPE: PRT
<213> ORGANISM: Artificial sequence
<220> FEATURE:
<223> OTHER INFORMATION: Synthetic polypeptide

<400> SEQUENCE: 581

Cys Ala Ser Ser Leu Ala Pro Leu Gln Gly Thr Phe Arg Ala Asp Thr
1               5                   10                  15

Gln Tyr Phe

<210> SEQ ID NO 582
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 582

Cys Ala Ser Ser Leu Ser Gly Glu Lys Leu Phe Phe
1               5                   10

<210> SEQ ID NO 583
<211> LENGTH: 17
<212> TYPE: PRT
<213> ORGANISM: Artificial sequence
<220> FEATURE:
<223> OTHER INFORMATION: Synthetic polypeptide

<400> SEQUENCE: 583

Cys Ala Ser Ser Pro Thr Gly Gly Thr Thr Tyr Asn Ser Pro Leu His
1               5                   10                  15

Phe

<210> SEQ ID NO 584
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 584

Cys Ala Ser Ser Gln Asp Glu Val Gly Gly Arg Arg Ala Phe Phe
```

```
1               5               10              15
```

<210> SEQ ID NO 585
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 585

```
Cys Ala Ser Ser Gln Asp Trp Gly Asp Tyr Gly Tyr Thr Phe
1               5                   10
```

<210> SEQ ID NO 586
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 586

```
Cys Ala Ser Ser Gln Asp Tyr Gln Gly Leu Asp Gly Glu Gln Phe Phe
1               5                   10                  15
```

<210> SEQ ID NO 587
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 587

```
Cys Ala Ser Ser Ser Pro Gly Val Gly Ala Asn Val Leu Thr Phe
1               5                   10                  15
```

<210> SEQ ID NO 588
<211> LENGTH: 20
<212> TYPE: PRT
<213> ORGANISM: Artificial sequence
<220> FEATURE:
<223> OTHER INFORMATION: Synthetic polypeptide

<400> SEQUENCE: 588

```
Cys Ala Ser Ser Trp Ile Ala Gly Val Ala Gly Gly Ala Val Ala Asp
1               5                   10                  15

Thr Gln Tyr Phe
            20
```

<210> SEQ ID NO 589
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 589

```
Cys Ala Ile Ser Ala Val Gly Asp Arg Gly Thr Gly Glu Leu Phe Phe
1               5                   10                  15
```

<210> SEQ ID NO 590
<211> LENGTH: 18
<212> TYPE: PRT
<213> ORGANISM: Artificial sequence
<220> FEATURE:
<223> OTHER INFORMATION: Synthetic polypeptide

<400> SEQUENCE: 590

-continued

```
Cys Ala Ser Ile Pro Pro Arg Ala Gly Pro Ile Ala Asn Glu Lys Leu
1               5                   10                  15

Phe Phe

<210> SEQ ID NO 591
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 591

Cys Ala Ser Arg Asp Gly Val Gln Pro Gln His Phe
1               5                   10

<210> SEQ ID NO 592
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 592

Cys Ala Ser Arg Lys Gly Thr Glu Gly Thr Gln Tyr Phe
1               5                   10

<210> SEQ ID NO 593
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 593

Cys Ala Ser Arg Thr Glu Arg Glu Ser Ile Asn Glu Gln Phe Phe
1               5                   10                  15

<210> SEQ ID NO 594
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 594

Cys Ala Ser Ser Glu Gly Gly Asp His Glu Gln Phe Phe
1               5                   10

<210> SEQ ID NO 595
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 595

Cys Ala Ser Ser Glu Val Trp Gly Ser Thr His Asn Glu Gln Phe Phe
1               5                   10                  15

<210> SEQ ID NO 596
<211> LENGTH: 15
<212> TYPE: PRT
<213> ORGANISM: Artificial sequence
<220> FEATURE:
<223> OTHER INFORMATION: Synthetic polypeptide
```

```
<400> SEQUENCE: 596

Cys Ala Ser Ser Phe His Thr Gly Glu Ala Tyr Glu Gln Tyr Phe
1               5                   10                  15

<210> SEQ ID NO 597
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 597

Cys Ala Ser Ser Leu Ala Gly Thr Gly Gln Phe Phe
1               5                   10

<210> SEQ ID NO 598
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 598

Cys Ala Ser Ser Leu Glu Gly Gln Gly Asn Gly Tyr Thr Phe
1               5                   10

<210> SEQ ID NO 599
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 599

Cys Ala Ser Ser Leu Ser Gln Arg Pro Asn Thr Gly Glu Leu Phe Phe
1               5                   10                  15

<210> SEQ ID NO 600
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 600

Cys Ala Ser Ser Leu Thr Gly Ala Asp Ser Pro Leu His Phe
1               5                   10

<210> SEQ ID NO 601
<211> LENGTH: 17
<212> TYPE: PRT
<213> ORGANISM: Artificial sequence
<220> FEATURE:
<223> OTHER INFORMATION: Synthetic polypeptide

<400> SEQUENCE: 601

Cys Ala Ser Ser Pro Pro Thr Ser Glu Asp Ala Tyr Asn Glu Gln Phe
1               5                   10                  15

Phe

<210> SEQ ID NO 602
<211> LENGTH: 14
<212> TYPE: PRT
<213> ORGANISM: Artificial sequence
<220> FEATURE:
<223> OTHER INFORMATION: Synthetic polypeptide
```

<400> SEQUENCE: 602

Cys Ala Ser Ser Pro Thr Ile Arg Asp Ser Gly Tyr Thr Phe
1               5                   10

<210> SEQ ID NO 603
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 603

Cys Ala Ser Ser Gln Ala Ser His Leu Ser Gly Asn Thr Ile Tyr Phe
1               5                   10                  15

<210> SEQ ID NO 604
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 604

Cys Ala Ser Ser Gln Asp Ala Val Gln Arg Leu Tyr Gly Tyr Thr Phe
1               5                   10                  15

<210> SEQ ID NO 605
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 605

Cys Ala Ser Ser Arg Gly Asn Ser Pro Leu His Phe
1               5                   10

<210> SEQ ID NO 606
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 606

Cys Ala Ser Ser Ser Gly Gln Leu Val His Glu Gln Phe Phe
1               5                   10

<210> SEQ ID NO 607
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 607

Cys Ala Ser Ser Ser Gln Ser Asn Thr Glu Ala Phe Phe
1               5                   10

<210> SEQ ID NO 608
<211> LENGTH: 15
<212> TYPE: PRT
<213> ORGANISM: Artificial sequence
<220> FEATURE:
<223> OTHER INFORMATION: Synthetic polypeptide

```
<400> SEQUENCE: 608

Cys Ala Ser Ser Thr Gly Thr Gly Gly Glu Glu Thr Gln Tyr Phe
1               5                   10                  15

<210> SEQ ID NO 609
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 609

Cys Ala Ser Ser Val Asp Met Val Gly Ala Asn Val Leu Thr Phe
1               5                   10                  15

<210> SEQ ID NO 610
<211> LENGTH: 18
<212> TYPE: PRT
<213> ORGANISM: Artificial sequence
<220> FEATURE:
<223> OTHER INFORMATION: Synthetic polypeptide

<400> SEQUENCE: 610

Cys Ala Ser Ser Val Phe Gly Ile Gly Val Gly Gly Thr Tyr Glu Gln
1               5                   10                  15

Tyr Phe

<210> SEQ ID NO 611
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 611

Cys Ala Ser Ser Tyr Pro Ser Gly Arg Ile Cys Glu Gln Tyr Phe
1               5                   10                  15

<210> SEQ ID NO 612
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 612

Cys Ala Ser Thr Ser Gly Gly Ala Tyr Glu Gln Tyr Phe
1               5                   10

<210> SEQ ID NO 613
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 613

Cys Ala Thr Ser Arg Asp Leu Val Gly Gly Asn Glu Gln Phe Phe
1               5                   10                  15

<210> SEQ ID NO 614
<211> LENGTH: 15
<212> TYPE: PRT
<213> ORGANISM: Artificial sequence
<220> FEATURE:
<223> OTHER INFORMATION: Synthetic polypeptide
```

```
<400> SEQUENCE: 614

Cys Ala Trp Ser Ala Gly Gln Gly Ile Leu Asn Glu Gln Phe Phe
1               5                   10                  15

<210> SEQ ID NO 615
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 615

Cys Ser Ala Ala Pro Gly Thr Gly Asp Asn Ser Pro Leu His Phe
1               5                   10                  15

<210> SEQ ID NO 616
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 616

Cys Ser Ala Pro Thr Arg Ala Gly Ala Asn Val Leu Thr Phe
1               5                   10

<210> SEQ ID NO 617
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 617

Cys Ser Ala Arg Ala Gly Gly Gly Asp Gly Glu Leu Phe Phe
1               5                   10

<210> SEQ ID NO 618
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 618

Cys Ser Ala Arg Asp Gly Thr Gly Ile Gly Asp Thr Gln Tyr Phe
1               5                   10                  15

<210> SEQ ID NO 619
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 619

Cys Ser Ala Arg Asp Arg Asp Arg Tyr Tyr Glu Gln Tyr Phe
1               5                   10

<210> SEQ ID NO 620
<211> LENGTH: 20
<212> TYPE: PRT
<213> ORGANISM: Artificial sequence
<220> FEATURE:
<223> OTHER INFORMATION: Synthetic polypeptide
```

```
<400> SEQUENCE: 620

Cys Ser Ala Arg Asp Ser Ala Lys Leu Ala Gly Ala Leu Arg Gly Gly
1               5                   10                  15

Glu Leu Phe Phe
            20

<210> SEQ ID NO 621
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 621

Cys Ser Val Ala Tyr Pro Gly Gln Ser Tyr Gly Tyr Thr Phe
1               5                   10

<210> SEQ ID NO 622
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 622

Cys Ser Val Gly Val Met Thr Tyr Asn Glu Gln Phe Phe
1               5                   10

<210> SEQ ID NO 623
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 623

Cys Ala Ser Asn Leu Gly Thr Ala Asp Ser Asn Gln Pro Gln His Phe
1               5                   10                  15

<210> SEQ ID NO 624
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 624

Cys Ala Ile Arg Glu Gln Gly Glu Ala Phe Phe
1               5                   10

<210> SEQ ID NO 625
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 625

Cys Ala Ile Ser Glu Asn Gly Lys Ala Asn Tyr Gly Tyr Thr Phe
1               5                   10                  15

<210> SEQ ID NO 626
<211> LENGTH: 15
<212> TYPE: PRT
<213> ORGANISM: Artificial sequence
<220> FEATURE:
```

<223> OTHER INFORMATION: Synthetic polypeptide

<400> SEQUENCE: 626

Cys Ala Ile Ser Glu Ser Ser Gly Gly Asp Glu Lys Leu Phe Phe
1               5                   10                  15

<210> SEQ ID NO 627
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 627

Cys Ala Ile Ser Gly Gly Gln Asp Ser Asn Gln Pro Gln His Phe
1               5                   10                  15

<210> SEQ ID NO 628
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 628

Cys Ala Ile Ser Ser Pro Ser Ser Gly Asn Tyr Glu Gln Tyr Phe
1               5                   10                  15

<210> SEQ ID NO 629
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 629

Cys Ala Leu Asp Gly Thr Gly Gly Asn Thr Ile Tyr Phe
1               5                   10

<210> SEQ ID NO 630
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 630

Cys Ala Ser Ala Ala Gly Trp Asp Thr Glu Ala Phe Phe
1               5                   10

<210> SEQ ID NO 631
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 631

Cys Ala Ser Ala Arg Glu Gly Pro Asp Thr Gln Tyr Phe
1               5                   10

<210> SEQ ID NO 632
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 632

Cys Ala Ser Gly Asp Ile Asp Ser Ala Arg Lys Gln Tyr Phe
1               5                   10

<210> SEQ ID NO 633
<211> LENGTH: 10
<212> TYPE: PRT
<213> ORGANISM: Artificial sequence
<220> FEATURE:
<223> OTHER INFORMATION: Synthetic polypeptide

<400> SEQUENCE: 633

Cys Ala Ser Gly Gly Thr Glu Ala Phe Phe
1               5                   10

<210> SEQ ID NO 634
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 634

Cys Ala Ser His Leu Val Asp Phe Thr Asp Thr Gln Tyr Phe
1               5                   10

<210> SEQ ID NO 635
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 635

Cys Ala Ser His Ser Thr Gln Ala Gly Tyr Asn Glu Gln Phe Phe
1               5                   10                  15

<210> SEQ ID NO 636
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 636

Cys Ala Ser Ile Arg Glu Gly Ser His Tyr Asn Glu Gln Phe Phe
1               5                   10                  15

<210> SEQ ID NO 637
<211> LENGTH: 19
<212> TYPE: PRT
<213> ORGANISM: Artificial sequence
<220> FEATURE:
<223> OTHER INFORMATION: Synthetic polypeptide

<400> SEQUENCE: 637

Cys Ala Ser Ile Ser Met Gly Ala Gly Gly Leu Ser Gly Ala Asn Val
1               5                   10                  15

Leu Thr Phe

<210> SEQ ID NO 638
<211> LENGTH: 15
<212> TYPE: PRT
<213> ORGANISM: Artificial sequence
<220> FEATURE:

<223> OTHER INFORMATION: Synthetic polypeptide

<400> SEQUENCE: 638

Cys Ala Ser Ile Thr Ser Gly Gly Ala Thr Gly Glu Leu Phe Phe
1               5                   10                  15

<210> SEQ ID NO 639
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 639

Cys Ala Ser Lys Lys Gly Thr Gly Gly Asn Gln Pro Gln His Phe
1               5                   10                  15

<210> SEQ ID NO 640
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 640

Cys Ala Ser Leu Arg Gly Tyr Glu Gln Tyr Phe
1               5                   10

<210> SEQ ID NO 641
<211> LENGTH: 17
<212> TYPE: PRT
<213> ORGANISM: Artificial sequence
<220> FEATURE:
<223> OTHER INFORMATION: Synthetic polypeptide

<400> SEQUENCE: 641

Cys Ala Ser Leu Ser Asp Phe Gly Ser Ala Asn Thr Gly Glu Leu Phe
1               5                   10                  15

Phe

<210> SEQ ID NO 642
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 642

Cys Ala Ser Met Lys Asp Val Gly Ala Gly Ala Asn Val Leu Thr Phe
1               5                   10                  15

<210> SEQ ID NO 643
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 643

Cys Ala Ser Gln Gly Gln Gly Glu Gln Tyr Phe
1               5                   10

<210> SEQ ID NO 644
<211> LENGTH: 13
<212> TYPE: PRT
<213> ORGANISM: Artificial sequence

```
<220> FEATURE:
<223> OTHER INFORMATION: Synthetic polypeptide

<400> SEQUENCE: 644

Cys Ala Ser Arg Ala Gly Gly Glu Ala Pro Ala Phe Phe
1               5                   10

<210> SEQ ID NO 645
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 645

Cys Ala Ser Arg Gly Asp Arg Gly Asp Tyr Gly Tyr Thr Phe
1               5                   10

<210> SEQ ID NO 646
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 646

Cys Ala Ser Arg Ile Gly Thr Gly Ser Asn Gln Pro Gln His Phe
1               5                   10                  15

<210> SEQ ID NO 647
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 647

Cys Ala Ser Arg Leu Ala Gly Ala Asp Asn Gln Pro Gln His Phe
1               5                   10                  15

<210> SEQ ID NO 648
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 648

Cys Ala Ser Arg Leu Gly Leu Ala Glu Asn Glu Gln Phe Phe
1               5                   10

<210> SEQ ID NO 649
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 649

Cys Ala Ser Arg Leu Ser Arg Asp Asn Ser Pro Leu His Phe
1               5                   10

<210> SEQ ID NO 650
<211> LENGTH: 14
<212> TYPE: PRT
<213> ORGANISM: Artificial sequence
<220> FEATURE:
```

<223> OTHER INFORMATION: Synthetic polypeptide

<400> SEQUENCE: 650

Cys Ala Ser Arg Pro Gly Leu Ala Gly Asp Glu Gln Tyr Phe
1               5                   10

<210> SEQ ID NO 651
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 651

Cys Ala Ser Arg Pro Gly Gln Tyr Ser Tyr Glu Gln Tyr Phe
1               5                   10

<210> SEQ ID NO 652
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 652

Cys Ala Ser Arg Pro Gly Thr Gly Arg Asp Gln Pro Gln His Phe
1               5                   10                  15

<210> SEQ ID NO 653
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 653

Cys Ala Ser Arg Pro Gly Thr Val Asn Thr Gly Glu Leu Phe Phe
1               5                   10                  15

<210> SEQ ID NO 654
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 654

Cys Ala Ser Arg Gln Arg Asp Arg Val Leu Glu Gln Tyr Phe
1               5                   10

<210> SEQ ID NO 655
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 655

Cys Ala Ser Arg Gln Thr Gly Thr Ser Thr Asp Thr Gln Tyr Phe
1               5                   10                  15

<210> SEQ ID NO 656
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 656

Cys Ala Ser Arg Gln Thr Ser Gly Gln Glu Thr Gln Tyr Phe
1               5                   10

<210> SEQ ID NO 657
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 657

Cys Ala Ser Arg Arg Thr Gly Met Ser Thr Asp Thr Gln Tyr Phe
1               5                   10                  15

<210> SEQ ID NO 658
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 658

Cys Ala Ser Arg Ser Gly Ile Tyr Thr Glu Ala Phe Phe
1               5                   10

<210> SEQ ID NO 659
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 659

Cys Ala Ser Arg Ser Gly Leu Ala Gly Thr Thr Asp Thr Gln Tyr Phe
1               5                   10                  15

<210> SEQ ID NO 660
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 660

Cys Ala Ser Arg Thr Gly Leu Asn Gly Glu Leu Phe Phe
1               5                   10

<210> SEQ ID NO 661
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 661

Cys Ala Ser Ser Ala Gly Gln Asp Ser Asp Thr Gln Tyr Phe
1               5                   10

<210> SEQ ID NO 662
<211> LENGTH: 17
<212> TYPE: PRT
<213> ORGANISM: Artificial sequence
<220> FEATURE:
<223> OTHER INFORMATION: Synthetic polypeptide

```
<400> SEQUENCE: 662

Cys Ala Ser Ser Ala Pro Gly Leu Ala Gly Thr Gly Glu Thr Gln Tyr
1               5                   10                  15

Phe

<210> SEQ ID NO 663
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 663

Cys Ala Ser Ser Ala Pro Gly Thr Gly Asp Thr Asp Thr Gln Tyr Phe
1               5                   10                  15

<210> SEQ ID NO 664
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 664

Cys Ala Ser Ser Ala Thr Leu Gly Ser Leu His Tyr Gly Tyr Thr Phe
1               5                   10                  15

<210> SEQ ID NO 665
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 665

Cys Ala Ser Ser Ala Val Glu Ala Gly Asn Thr Ile Tyr Phe
1               5                   10

<210> SEQ ID NO 666
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 666

Cys Ala Ser Ser Asp Asp Gly Thr Gly Asp Gln Pro Gln His Phe
1               5                   10                  15

<210> SEQ ID NO 667
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 667

Cys Ala Ser Ser Asp Pro Gly Gly Gly Val Thr Gly Glu Leu Phe Phe
1               5                   10                  15

<210> SEQ ID NO 668
<211> LENGTH: 13
<212> TYPE: PRT
<213> ORGANISM: Artificial sequence
<220> FEATURE:
<223> OTHER INFORMATION: Synthetic polypeptide
```

```
<400> SEQUENCE: 668

Cys Ala Ser Ser Asp Arg Gly Asn Thr Glu Ala Phe Phe
1               5                   10

<210> SEQ ID NO 669
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 669

Cys Ala Ser Ser Glu Ala Gly Asp Tyr Glu Gln Tyr Phe
1               5                   10

<210> SEQ ID NO 670
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 670

Cys Ala Ser Ser Glu Ala Gly Gly Asn Thr Ile Tyr Phe
1               5                   10

<210> SEQ ID NO 671
<211> LENGTH: 17
<212> TYPE: PRT
<213> ORGANISM: Artificial sequence
<220> FEATURE:
<223> OTHER INFORMATION: Synthetic polypeptide

<400> SEQUENCE: 671

Cys Ala Ser Ser Glu Ala Gly Val Arg Leu Val Ser Tyr Glu Gln Tyr
1               5                   10                  15

Phe

<210> SEQ ID NO 672
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 672

Cys Ala Ser Ser Glu Arg Ala Gly Gly Asp Thr Gly Glu Leu Phe Phe
1               5                   10                  15

<210> SEQ ID NO 673
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 673

Cys Ala Ser Ser Glu Trp Gly Gln Gly Gly Ala Glu Gln Tyr Phe
1               5                   10                  15

<210> SEQ ID NO 674
<211> LENGTH: 14
<212> TYPE: PRT
<213> ORGANISM: Artificial sequence
<220> FEATURE:
```

<223> OTHER INFORMATION: Synthetic polypeptide

<400> SEQUENCE: 674

Cys Ala Ser Ser Glu Tyr Lys Ala Thr Tyr Glu Gln Tyr Phe
1               5                   10

<210> SEQ ID NO 675
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 675

Cys Ala Ser Ser Phe Asp Glu Gly Thr Gln His Phe
1               5                   10

<210> SEQ ID NO 676
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 676

Cys Ala Ser Ser Phe Glu Arg Pro Tyr Glu Gln Tyr Phe
1               5                   10

<210> SEQ ID NO 677
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 677

Cys Ala Ser Ser Phe Gly Ala Glu Asp Thr Gln Tyr Phe
1               5                   10

<210> SEQ ID NO 678
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 678

Cys Ala Ser Ser Phe Gly Gly Pro Ser Tyr Glu Gln Tyr Phe
1               5                   10

<210> SEQ ID NO 679
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 679

Cys Ala Ser Ser Phe Gly Arg Trp Val Asp Ser Pro Leu His Phe
1               5                   10                  15

<210> SEQ ID NO 680
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 680

Cys Ala Ser Ser Phe Pro Tyr Thr Glu Ala Phe Phe
1               5                   10

<210> SEQ ID NO 681
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 681

Cys Ala Ser Ser Phe Arg Gly Asp Asp Lys Asn Ile Gln Tyr Phe
1               5                   10                  15

<210> SEQ ID NO 682
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 682

Cys Ala Ser Ser Phe Ser Gly Arg Glu Gly Val Asp Thr Gln Tyr Phe
1               5                   10                  15

<210> SEQ ID NO 683
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 683

Cys Ala Ser Ser Phe Ser Gly Ser Ala Tyr Glu Gln Tyr Phe
1               5                   10

<210> SEQ ID NO 684
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 684

Cys Ala Ser Ser Phe Ser Thr Ser Gly Glu Gln Tyr Phe
1               5                   10

<210> SEQ ID NO 685
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 685

Cys Ala Ser Ser Phe Ser Thr Ser Gly Asn Thr Gly Glu Leu Phe Phe
1               5                   10                  15

<210> SEQ ID NO 686
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 686

Cys Ala Ser Ser Phe Val Asn Ser Pro Leu His Phe
1               5                   10

<210> SEQ ID NO 687
<211> LENGTH: 18
<212> TYPE: PRT
<213> ORGANISM: Artificial sequence
<220> FEATURE:
<223> OTHER INFORMATION: Synthetic polypeptide

<400> SEQUENCE: 687

Cys Ala Ser Ser Phe Val Arg Ala Leu Gly Ser Tyr Asn Ser Pro Leu
1               5                   10                  15

His Phe

<210> SEQ ID NO 688
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 688

Cys Ala Ser Ser Gly Gly Thr Gly Asn Asn Tyr Glu Gln Tyr Phe
1               5                   10                  15

<210> SEQ ID NO 689
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 689

Cys Ala Ser Ser Gly Ile Leu Glu Thr Gln Tyr Phe
1               5                   10

<210> SEQ ID NO 690
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 690

Cys Ala Ser Ser Gly Thr Gly Gly His Gln Pro Gln His Phe
1               5                   10

<210> SEQ ID NO 691
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 691

Cys Ala Ser Ser His Ser Ala Thr His Asn Glu Gln Phe Phe
1               5                   10

<210> SEQ ID NO 692
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 692

Cys Ala Ser Ser Ile Gly Ala Arg Gly Tyr Thr Phe
1               5                   10

<210> SEQ ID NO 693
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 693

Cys Ala Ser Ser Ile Gly Arg Thr Tyr Glu Gln Tyr Phe
1               5                   10

<210> SEQ ID NO 694
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 694

Cys Ala Ser Ser Ile Arg Arg Asn Asn Glu Gln Phe Phe
1               5                   10

<210> SEQ ID NO 695
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 695

Cys Ala Ser Ser Ile Trp Gly Ser Glu Ala Phe Phe
1               5                   10

<210> SEQ ID NO 696
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 696

Cys Ala Ser Ser Lys Glu Gly Arg Ile Thr Asp Thr Gln Tyr Phe
1               5                   10                  15

<210> SEQ ID NO 697
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 697

Cys Ala Ser Ser Lys Gly Thr Asp Leu Asn Thr Glu Ala Phe Phe
1               5                   10                  15

<210> SEQ ID NO 698
<211> LENGTH: 14
<212> TYPE: PRT
<213> ORGANISM: Artificial sequence
<220> FEATURE:
<223> OTHER INFORMATION: Synthetic polypeptide

```
<400> SEQUENCE: 698

Cys Ala Ser Ser Leu Ala Ala Gly Pro Tyr Gly Tyr Thr Phe
1               5                   10

<210> SEQ ID NO 699
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 699

Cys Ala Ser Ser Leu Ala Ala Asn Ser Pro Leu His Phe
1               5                   10

<210> SEQ ID NO 700
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 700

Cys Ala Ser Ser Leu Ala Gly Ser Val Tyr Glu Gln Tyr Phe
1               5                   10

<210> SEQ ID NO 701
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 701

Cys Ala Ser Ser Leu Ala Pro Gly Val Gly Glu Thr Gln Tyr Phe
1               5                   10                  15

<210> SEQ ID NO 702
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 702

Cys Ala Ser Ser Leu Ala Ser Gly Ile Tyr Glu Gln Phe Phe
1               5                   10

<210> SEQ ID NO 703
<211> LENGTH: 17
<212> TYPE: PRT
<213> ORGANISM: Artificial sequence
<220> FEATURE:
<223> OTHER INFORMATION: Synthetic polypeptide

<400> SEQUENCE: 703

Cys Ala Ser Ser Leu Ala Ser Arg Gly Pro Gln Gly Glu Thr Gln Tyr
1               5                   10                  15

Phe

<210> SEQ ID NO 704
<211> LENGTH: 14
<212> TYPE: PRT
<213> ORGANISM: Artificial sequence
<220> FEATURE:
<223> OTHER INFORMATION: Synthetic polypeptide
```

```
<400> SEQUENCE: 704

Cys Ala Ser Ser Leu Ala Tyr Gly Thr Asp Thr Gln Tyr Phe
1               5                   10

<210> SEQ ID NO 705
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 705

Cys Ala Ser Ser Leu Asp Gly Gly Val Val Gly Gly Tyr Thr Phe
1               5                   10                  15

<210> SEQ ID NO 706
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 706

Cys Ala Ser Ser Leu Asp Gly Thr Ser Thr Tyr Glu Gln Tyr Phe
1               5                   10                  15

<210> SEQ ID NO 707
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 707

Cys Ala Ser Ser Leu Asp Ser Gln Asn Thr Gly Glu Leu Phe Phe
1               5                   10                  15

<210> SEQ ID NO 708
<211> LENGTH: 17
<212> TYPE: PRT
<213> ORGANISM: Artificial sequence
<220> FEATURE:
<223> OTHER INFORMATION: Synthetic polypeptide

<400> SEQUENCE: 708

Cys Ala Ser Ser Leu Asp Ser Thr Gly Thr Gly Lys Glu Thr Gln Tyr
1               5                   10                  15

Phe

<210> SEQ ID NO 709
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 709

Cys Ala Ser Ser Leu Glu Ala Thr Ser Arg Thr Gln Pro Gln His Phe
1               5                   10                  15

<210> SEQ ID NO 710
<211> LENGTH: 14
<212> TYPE: PRT
<213> ORGANISM: Artificial sequence
<220> FEATURE:
```

-continued

<223> OTHER INFORMATION: Synthetic polypeptide

<400> SEQUENCE: 710

Cys Ala Ser Ser Leu Glu Gly Pro Arg Asp Thr Gln Tyr Phe
1               5                   10

<210> SEQ ID NO 711
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 711

Cys Ala Ser Ser Leu Glu Gly Ser Gly Gly Thr Glu Ala Phe Phe
1               5                   10                  15

<210> SEQ ID NO 712
<211> LENGTH: 19
<212> TYPE: PRT
<213> ORGANISM: Artificial sequence
<220> FEATURE:
<223> OTHER INFORMATION: Synthetic polypeptide

<400> SEQUENCE: 712

Cys Ala Ser Ser Leu Glu Leu Ala Gly Val Thr Arg Ser Thr Asp Thr
1               5                   10                  15

Gln Tyr Phe

<210> SEQ ID NO 713
<211> LENGTH: 18
<212> TYPE: PRT
<213> ORGANISM: Artificial sequence
<220> FEATURE:
<223> OTHER INFORMATION: Synthetic polypeptide

<400> SEQUENCE: 713

Cys Ala Ser Ser Leu Glu Pro Gly Arg Gln Gly Asn Thr Gly Glu Leu
1               5                   10                  15

Phe Phe

<210> SEQ ID NO 714
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 714

Cys Ala Ser Ser Leu Gly Asp Thr Gly Glu Leu Phe Phe
1               5                   10

<210> SEQ ID NO 715
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 715

Cys Ala Ser Ser Leu Gly Gly Gly Ala Glu Gly Pro Gln His Phe
1               5                   10                  15

<210> SEQ ID NO 716
<211> LENGTH: 14

```
<212> TYPE: PRT
<213> ORGANISM: Artificial sequence
<220> FEATURE:
<223> OTHER INFORMATION: Synthetic polypeptide

<400> SEQUENCE: 716

Cys Ala Ser Ser Leu Gly Gly Thr Pro Glu Pro Gln His Phe
1               5                   10

<210> SEQ ID NO 717
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 717

Cys Ala Ser Ser Leu Gly Gly Val Thr Tyr Asn Glu Gln Phe Phe
1               5                   10                  15

<210> SEQ ID NO 718
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 718

Cys Ala Ser Ser Leu Gly Pro Gly Leu Ala Ser Tyr Glu Gln Tyr Phe
1               5                   10                  15

<210> SEQ ID NO 719
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 719

Cys Ala Ser Ser Leu Gly Pro Gly Gln Glu Thr Gln Tyr Phe
1               5                   10

<210> SEQ ID NO 720
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 720

Cys Ala Ser Ser Leu Gly Gln Glu Glu Asn Ser Pro Leu His Phe
1               5                   10                  15

<210> SEQ ID NO 721
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 721

Cys Ala Ser Ser Leu Gly Ser Gly Thr Asn Thr Gly Glu Leu Phe Phe
1               5                   10                  15

<210> SEQ ID NO 722
<211> LENGTH: 14
<212> TYPE: PRT
```

```
<213> ORGANISM: Artificial sequence
<220> FEATURE:
<223> OTHER INFORMATION: Synthetic polypeptide

<400> SEQUENCE: 722

Cys Ala Ser Ser Leu Gly Thr Glu Arg Thr Glu Ala Phe Phe
1               5                   10

<210> SEQ ID NO 723
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 723

Cys Ala Ser Ser Leu Ile Gly Ala Ser Gly Pro Gly Glu Leu Phe Phe
1               5                   10                  15

<210> SEQ ID NO 724
<211> LENGTH: 17
<212> TYPE: PRT
<213> ORGANISM: Artificial sequence
<220> FEATURE:
<223> OTHER INFORMATION: Synthetic polypeptide

<400> SEQUENCE: 724

Cys Ala Ser Ser Leu Leu Ala Gly Gly Leu Ile Val Asn Glu Gln Phe
1               5                   10                  15

Phe

<210> SEQ ID NO 725
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 725

Cys Ala Ser Ser Leu Leu Arg Asn Ser Gly Asn Thr Ile Tyr Phe
1               5                   10                  15

<210> SEQ ID NO 726
<211> LENGTH: 18
<212> TYPE: PRT
<213> ORGANISM: Artificial sequence
<220> FEATURE:
<223> OTHER INFORMATION: Synthetic polypeptide

<400> SEQUENCE: 726

Cys Ala Ser Ser Leu Asn Ala Pro Gly Leu Gly Ser Thr Gly Glu Leu
1               5                   10                  15

Phe Phe

<210> SEQ ID NO 727
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 727

Cys Ala Ser Ser Leu Asn Gln Asp Gly Tyr Thr Phe
1               5                   10
```

```
<210> SEQ ID NO 728
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 728

Cys Ala Ser Ser Leu Gln Ala Gly Ser Gly Glu Gln Tyr Phe
1               5                   10

<210> SEQ ID NO 729
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 729

Cys Ala Ser Ser Leu Gln Gly Ala Leu Gly Asn Thr Ile Tyr Phe
1               5                   10                  15

<210> SEQ ID NO 730
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 730

Cys Ala Ser Ser Leu Gln Val Tyr Asn Glu Gln Phe Phe
1               5                   10

<210> SEQ ID NO 731
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 731

Cys Ala Ser Ser Leu Arg Ala Ser Gly Thr Arg Gly Glu Gln Phe Phe
1               5                   10                  15

<210> SEQ ID NO 732
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 732

Cys Ala Ser Ser Leu Arg Gly Gln Gly Asn Glu Lys Leu Phe Phe
1               5                   10                  15

<210> SEQ ID NO 733
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 733

Cys Ala Ser Ser Leu Arg Gly Arg Glu Thr Gln Tyr Phe
1               5                   10

<210> SEQ ID NO 734
```

```
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 734

Cys Ala Ser Ser Leu Arg Arg Asp Tyr Gly Tyr Thr Phe
1               5                   10

<210> SEQ ID NO 735
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 735

Cys Ala Ser Ser Leu Ser Ser Ser Glu Val Asp Thr Gln Tyr Phe
1               5                   10                  15

<210> SEQ ID NO 736
<211> LENGTH: 18
<212> TYPE: PRT
<213> ORGANISM: Artificial sequence
<220> FEATURE:
<223> OTHER INFORMATION: Synthetic polypeptide

<400> SEQUENCE: 736

Cys Ala Ser Ser Leu Ser Val Thr Asp Ser Arg Ser Gly Asn Thr Ile
1               5                   10                  15

Tyr Phe

<210> SEQ ID NO 737
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 737

Cys Ala Ser Ser Leu Thr Leu Ala Gly Gly Gln Asn Glu Gln Tyr Phe
1               5                   10                  15

<210> SEQ ID NO 738
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 738

Cys Ala Ser Ser Leu Val Gly Gly Gly Asn Gln Pro Gln His Phe
1               5                   10                  15

<210> SEQ ID NO 739
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 739

Cys Ala Ser Ser Leu Val Ile Gln Pro Gln His Phe
1               5                   10
```

```
<210> SEQ ID NO 740
<211> LENGTH: 18
<212> TYPE: PRT
<213> ORGANISM: Artificial sequence
<220> FEATURE:
<223> OTHER INFORMATION: Synthetic polypeptide

<400> SEQUENCE: 740

Cys Ala Ser Ser Leu Tyr Pro Arg Arg Ile Ser Ser Gly Asn Thr Ile
1               5                   10                  15

Tyr Phe

<210> SEQ ID NO 741
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 741

Cys Ala Ser Ser Leu Tyr Thr Gly Gly Gly Ser Gly Glu Leu Phe Phe
1               5                   10                  15

<210> SEQ ID NO 742
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 742

Cys Ala Ser Ser Met Val Ala Gly Asn Gly Glu Leu Phe Phe
1               5                   10

<210> SEQ ID NO 743
<211> LENGTH: 18
<212> TYPE: PRT
<213> ORGANISM: Artificial sequence
<220> FEATURE:
<223> OTHER INFORMATION: Synthetic polypeptide

<400> SEQUENCE: 743

Cys Ala Ser Ser Asn Pro Tyr Arg Gly Trp Gly Gln Asn Gln Pro Gln
1               5                   10                  15

His Phe

<210> SEQ ID NO 744
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 744

Cys Ala Ser Ser Pro Ala Gly Pro Phe Tyr Glu Gln Tyr Phe
1               5                   10

<210> SEQ ID NO 745
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 745

Cys Ala Ser Ser Pro Ala Pro Gly Pro Asp Thr Gln Tyr Phe
```

```
1               5               10
```

<210> SEQ ID NO 746
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 746

```
Cys Ala Ser Ser Pro Asp Asn Asp Glu Glu Thr Gln Tyr Phe
1               5                   10
```

<210> SEQ ID NO 747
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 747

```
Cys Ala Ser Ser Pro Phe Trp Asp Ser Asn Tyr Gly Tyr Thr Phe
1               5                   10                  15
```

<210> SEQ ID NO 748
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 748

```
Cys Ala Ser Ser Pro Gly Gly Ala Asp Tyr Gly Tyr Thr Phe
1               5                   10
```

<210> SEQ ID NO 749
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 749

```
Cys Ala Ser Ser Pro Gly Gly Glu Ser Asn Gln Pro Gln His Phe
1               5                   10                  15
```

<210> SEQ ID NO 750
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 750

```
Cys Ala Ser Ser Pro Gly Pro Pro Gly Leu Gly Pro Gln His Phe
1               5                   10                  15
```

<210> SEQ ID NO 751
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 751

```
Cys Ala Ser Ser Pro Gly Thr Gln Val Tyr Glu Gln Tyr Phe
1               5                   10
```

<210> SEQ ID NO 752
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 752

Cys Ala Ser Ser Pro Gly Thr Ser Gly Val Gly Glu Leu Phe Phe
1               5                   10                  15

<210> SEQ ID NO 753
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 753

Cys Ala Ser Ser Pro Pro Thr Ala Ser Gly Ser Val Gly Gln Tyr Phe
1               5                   10                  15

<210> SEQ ID NO 754
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 754

Cys Ala Ser Ser Pro Pro Val Trp Pro Thr Gly Glu Leu Phe Phe
1               5                   10                  15

<210> SEQ ID NO 755
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 755

Cys Ala Ser Ser Pro Gln Gln Ala Gly Asp Thr Glu Ala Phe Phe
1               5                   10                  15

<210> SEQ ID NO 756
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 756

Cys Ala Ser Ser Pro Arg Gly Gly Ala Tyr Glu Gln Tyr Phe
1               5                   10

<210> SEQ ID NO 757
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 757

Cys Ala Ser Ser Pro Arg Gly Tyr Glu Gln Tyr Phe
1               5                   10

<210> SEQ ID NO 758
<211> LENGTH: 17
<212> TYPE: PRT
<213> ORGANISM: Artificial sequence
<220> FEATURE:
<223> OTHER INFORMATION: Synthetic polypeptide

<400> SEQUENCE: 758

Cys Ala Ser Ser Pro Arg Asn Ser Ala Gly Gly Pro Glu Thr Gln Tyr
1               5                   10                  15

Phe

<210> SEQ ID NO 759
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 759

Cys Ala Ser Ser Pro Ser Gly Arg Glu Asp Gly Tyr Thr Phe
1               5                   10

<210> SEQ ID NO 760
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 760

Cys Ala Ser Ser Pro Ser Trp Ala Gly Gly Asp Tyr Glu Gln Tyr Phe
1               5                   10                  15

<210> SEQ ID NO 761
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 761

Cys Ala Ser Ser Pro Thr Ser Gly Glu Thr Thr Gln Tyr Phe
1               5                   10

<210> SEQ ID NO 762
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 762

Cys Ala Ser Ser Pro Trp Ser Gln Ser Ser Gly Asn Thr Ile Tyr Phe
1               5                   10                  15

<210> SEQ ID NO 763
<211> LENGTH: 19
<212> TYPE: PRT
<213> ORGANISM: Artificial sequence
<220> FEATURE:
<223> OTHER INFORMATION: Synthetic polypeptide

<400> SEQUENCE: 763

Cys Ala Ser Ser Pro Trp Thr Gly Thr Gly Ser Tyr Ser Asn Gln Pro
1               5                   10                  15

Gln His Phe

<210> SEQ ID NO 764
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 764

Cys Ala Ser Ser Pro Tyr Arg Asp Leu Tyr Glu Gln Tyr Phe
1               5                   10

<210> SEQ ID NO 765
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 765

Cys Ala Ser Ser Gln Ala Gly Gly Asn Ser Pro Leu His Phe
1               5                   10

<210> SEQ ID NO 766
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 766

Cys Ala Ser Ser Gln Asp Ala Gly Val Gly Val Gly Tyr Thr Phe
1               5                   10                  15

<210> SEQ ID NO 767
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 767

Cys Ala Ser Ser Gln Asp Gly Pro Arg Gly Leu Glu Thr Gln Tyr Phe
1               5                   10                  15

<210> SEQ ID NO 768
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 768

Cys Ala Ser Ser Gln Asp Tyr Gln Gly Val Asp Asn Glu Gln Phe Phe
1               5                   10                  15

<210> SEQ ID NO 769
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 769

Cys Ala Ser Ser Gln Glu Pro Asp Arg Arg Ala Gln Tyr Phe

<210> SEQ ID NO 770
<211> LENGTH: 17
<212> TYPE: PRT
<213> ORGANISM: Artificial sequence
<220> FEATURE:
<223> OTHER INFORMATION: Synthetic polypeptide

<400> SEQUENCE: 770

Cys Ala Ser Ser Gln Glu Arg Gly Gly Lys Trp Ala Tyr Glu Gln Tyr
1               5                   10                  15
Phe

<210> SEQ ID NO 771
<211> LENGTH: 18
<212> TYPE: PRT
<213> ORGANISM: Artificial sequence
<220> FEATURE:
<223> OTHER INFORMATION: Synthetic polypeptide

<400> SEQUENCE: 771

Cys Ala Ser Ser Gln Glu Ser Arg Gly Gly Pro Val Ser Tyr Glu Gln
1               5                   10                  15
Tyr Phe

<210> SEQ ID NO 772
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 772

Cys Ala Ser Ser Gln Gly Ala Ala Gly Glu Gln Gln Tyr Phe
1               5                   10

<210> SEQ ID NO 773
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 773

Cys Ala Ser Ser Gln Gly Glu Thr Gly Glu Tyr Gly Tyr Thr Phe
1               5                   10                  15

<210> SEQ ID NO 774
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 774

Cys Ala Ser Ser Gln Gly Phe Val Val Asn Ser Pro Leu His Phe
1               5                   10                  15

<210> SEQ ID NO 775
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 775

Cys Ala Ser Ser Gln Gly Arg Gly Val Gly Thr Asp Thr Gln Tyr Phe
1               5                   10                  15

<210> SEQ ID NO 776
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 776

Cys Ala Ser Ser Gln Gly Arg Pro Asn Ser Pro Leu His Phe
1               5                   10

<210> SEQ ID NO 777
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 777

Cys Ala Ser Ser Gln Gly Thr Ser Gly Trp Thr Asp Thr Gln Tyr Phe
1               5                   10                  15

<210> SEQ ID NO 778
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 778

Cys Ala Ser Ser Gln Leu Ser Ser Gly Asp Tyr Asn Glu Gln Phe Phe
1               5                   10                  15

<210> SEQ ID NO 779
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 779

Cys Ala Ser Ser Gln Arg Val Gly Gly Leu Asp Thr Gln Tyr Phe
1               5                   10                  15

<210> SEQ ID NO 780
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 780

Cys Ala Ser Ser Gln Thr Asp Ala Asn Thr Gly Glu Leu Phe Phe
1               5                   10                  15

<210> SEQ ID NO 781
<211> LENGTH: 17
<212> TYPE: PRT
<213> ORGANISM: Artificial sequence
<220> FEATURE:
<223> OTHER INFORMATION: Synthetic polypeptide

<400> SEQUENCE: 781

```
Cys Ala Ser Ser Gln Thr Gln Asn Arg Gly Gly Asn Tyr Gly Tyr Thr
1               5                   10                  15

Phe
```

<210> SEQ ID NO 782
<211> LENGTH: 18
<212> TYPE: PRT
<213> ORGANISM: Artificial sequence
<220> FEATURE:
<223> OTHER INFORMATION: Synthetic polypeptide

<400> SEQUENCE: 782

```
Cys Ala Ser Ser Gln Val Gly Gly Ala Phe Ala Asn Thr Gly Glu Leu
1               5                   10                  15

Phe Phe
```

<210> SEQ ID NO 783
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 783

```
Cys Ala Ser Ser Arg Glu Ser Phe Ala Pro Asp Gly Tyr Thr Phe
1               5                   10                  15
```

<210> SEQ ID NO 784
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 784

```
Cys Ala Ser Ser Arg Gly Leu Tyr Asn Glu Gln Phe Phe
1               5                   10
```

<210> SEQ ID NO 785
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 785

```
Cys Ala Ser Ser Arg Ser Ser Gly Ala Ser Ser Tyr Glu Gln Tyr Phe
1               5                   10                  15
```

<210> SEQ ID NO 786
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 786

```
Cys Ala Ser Ser Arg Ser Thr Glu Asn Asn Ser Pro Leu His Phe
1               5                   10                  15
```

<210> SEQ ID NO 787
<211> LENGTH: 16
<212> TYPE: PRT
<213> ORGANISM: Artificial sequence
<220> FEATURE:

<223> OTHER INFORMATION: Synthetic polypeptide

<400> SEQUENCE: 787

Cys Ala Ser Ser Arg Thr Gly Gly Asn Ser Gly Asn Thr Ile Tyr Phe
1               5                   10                  15

<210> SEQ ID NO 788
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 788

Cys Ala Ser Ser Ser Ala Gly Gly Ala Phe Ser His Glu Gln Tyr Phe
1               5                   10                  15

<210> SEQ ID NO 789
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 789

Cys Ala Ser Ser Ser Gly Gln Gly Asn Gln Pro Gln His Phe
1               5                   10

<210> SEQ ID NO 790
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 790

Cys Ala Ser Ser Ser Gly Gln Gln Leu Ala Gly Glu Leu Phe Phe
1               5                   10              15

<210> SEQ ID NO 791
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 791

Cys Ala Ser Ser Ser Pro Gly Gln Gly Trp Asn Glu Gln Phe Phe
1               5                   10              15

<210> SEQ ID NO 792
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 792

Cys Ala Ser Ser Ser Pro Ser Leu Ala Gly Pro Tyr Glu Gln Tyr Phe
1               5                   10                  15

<210> SEQ ID NO 793
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 793

Cys Ala Ser Ser Ser Arg Gly Pro Pro Ala Tyr Glu Gln Tyr Phe
1               5                   10                  15

<210> SEQ ID NO 794
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 794

Cys Ala Ser Ser Ser Ser Asp Arg Ala His Phe
1               5                   10

<210> SEQ ID NO 795
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 795

Cys Ala Ser Ser Ser Ser Asp Ser Tyr Asn Glu Gln Phe Phe
1               5                   10

<210> SEQ ID NO 796
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 796

Cys Ala Ser Ser Ser Ser Gly Ser Arg Thr Asp Thr Gln Tyr Phe
1               5                   10                  15

<210> SEQ ID NO 797
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 797

Cys Ala Ser Ser Ser Thr Gly Gln Ser Trp Asp Thr Gln Tyr Phe
1               5                   10                  15

<210> SEQ ID NO 798
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 798

Cys Ala Ser Ser Ser Thr Gly Thr Ser Gly Arg Met Arg Ile Phe
1               5                   10                  15

<210> SEQ ID NO 799
<211> LENGTH: 15
<212> TYPE: PRT
<213> ORGANISM: Artificial sequence
<220> FEATURE:
<223> OTHER INFORMATION: Synthetic polypeptide

```
<400> SEQUENCE: 799

Cys Ala Ser Ser Thr Ser Gly Gln Glu Glu Thr Gln Tyr Phe
1               5                   10                  15

<210> SEQ ID NO 800
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 800

Cys Ala Ser Ser Thr Asp Ser Ala Asn Tyr Gly Tyr Thr Phe
1               5                   10

<210> SEQ ID NO 801
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 801

Cys Ala Ser Ser Thr His Ser Gly Arg Thr Glu Ala Phe Phe
1               5                   10

<210> SEQ ID NO 802
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 802

Cys Ala Ser Ser Thr Ser Arg Asp Arg Val Asn Gln Pro Gln His Phe
1               5                   10                  15

<210> SEQ ID NO 803
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 803

Cys Ala Ser Ser Thr Thr Gly Gly Thr Gly Thr Glu Ala Phe Phe
1               5                   10                  15

<210> SEQ ID NO 804
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 804

Cys Ala Ser Ser Thr Trp Thr Ala Tyr Asn Glu Lys Leu Phe Phe
1               5                   10                  15

<210> SEQ ID NO 805
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 805
```

Cys Ala Ser Ser Val Gly Gly Thr Ser Thr Asp Thr Gln Tyr Phe
1               5                   10                  15

<210> SEQ ID NO 806
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 806

Cys Ala Ser Ser Val Ser Gly Ala Arg Gly Tyr Asn Glu Gln Phe Phe
1               5                   10                  15

<210> SEQ ID NO 807
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 807

Cys Ala Ser Ser Tyr Leu Ser Gly Gly Glu His Asn Glu Gln Phe Phe
1               5                   10                  15

<210> SEQ ID NO 808
<211> LENGTH: 17
<212> TYPE: PRT
<213> ORGANISM: Artificial sequence
<220> FEATURE:
<223> OTHER INFORMATION: Synthetic polypeptide

<400> SEQUENCE: 808

Cys Ala Ser Ser Tyr Pro Ala Pro Ser Gly Gly Pro Glu Thr Gln Tyr
1               5                   10                  15

Phe

<210> SEQ ID NO 809
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 809

Cys Ala Ser Ser Tyr Pro Leu Val Leu Ser Glu Gln Phe Phe
1               5                   10

<210> SEQ ID NO 810
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 810

Cys Ala Ser Ser Tyr Ser Ser Gly Glu Tyr Thr Gly Glu Leu Phe Phe
1               5                   10                  15

<210> SEQ ID NO 811
<211> LENGTH: 15
<212> TYPE: PRT
<213> ORGANISM: Artificial sequence
<220> FEATURE:
<223> OTHER INFORMATION: Synthetic polypeptide

```
<400> SEQUENCE: 811

Cys Ala Ser Ser Tyr Ser Tyr Arg Asp Asn Ser Pro Leu His Phe
1               5                   10                  15

<210> SEQ ID NO 812
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 812

Cys Ala Ser Thr Ser Ser Gly Gly Ser Pro Tyr Glu Gln Tyr Phe
1               5                   10                  15

<210> SEQ ID NO 813
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 813

Cys Ala Ser Thr Tyr Trp Ala Gly Ala Glu Ala Phe Phe
1               5                   10

<210> SEQ ID NO 814
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 814

Cys Ala Thr Ser Leu Met Gly Gln Pro Gln His Phe
1               5                   10

<210> SEQ ID NO 815
<211> LENGTH: 19
<212> TYPE: PRT
<213> ORGANISM: Artificial sequence
<220> FEATURE:
<223> OTHER INFORMATION: Synthetic polypeptide

<400> SEQUENCE: 815

Cys Ala Thr Ser Arg Ala Phe Asp Trp Asp Arg Gly Leu Asp Thr Glu
1               5                   10                  15

Ala Phe Phe

<210> SEQ ID NO 816
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 816

Cys Ala Thr Ser Arg Asp Phe Gly Asp Ser Tyr Glu Gln Tyr Phe
1               5                   10                  15

<210> SEQ ID NO 817
<211> LENGTH: 15
<212> TYPE: PRT
<213> ORGANISM: Artificial sequence
<220> FEATURE:
<223> OTHER INFORMATION: Synthetic polypeptide
```

<400> SEQUENCE: 817

Cys Ala Thr Ser Arg Asp Pro Gly Leu Ala Ser Thr Gln Tyr Phe
1               5                   10                  15

<210> SEQ ID NO 818
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 818

Cys Ala Thr Ser Arg Asp Arg Ala Asp Thr Glu Ala Phe Phe
1               5                   10

<210> SEQ ID NO 819
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 819

Cys Ala Trp Glu Lys Ala Gly Ala Gly Gly Thr Gln Tyr Phe
1               5                   10

<210> SEQ ID NO 820
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 820

Cys Ala Trp Gly Thr Asn Tyr Gly Tyr Thr Phe
1               5                   10

<210> SEQ ID NO 821
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 821

Cys Ala Trp Met Glu Val His Glu Gln Phe Phe
1               5                   10

<210> SEQ ID NO 822
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 822

Cys Ala Trp Gln Tyr Pro Ala Asp Ser Glu Lys Leu Phe Phe
1               5                   10

<210> SEQ ID NO 823
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 823

Cys Ala Trp Arg Ser Gly Gly Ala Ser Pro Leu His Phe
1               5                   10

<210> SEQ ID NO 824
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 824

Cys Ala Trp Ser Ala Gly Thr Gly Val Arg Glu Leu Phe Phe
1               5                   10

<210> SEQ ID NO 825
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 825

Cys Ala Trp Ser Ala Ser Arg Asp Ala Glu Gln Phe Phe
1               5                   10

<210> SEQ ID NO 826
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 826

Cys Ala Trp Ser Glu Gly Gly Ile Gly Gln Pro Gln His Phe
1               5                   10

<210> SEQ ID NO 827
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 827

Cys Ala Trp Ser Gly Ala Asn Tyr Gly Tyr Thr Phe
1               5                   10

<210> SEQ ID NO 828
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 828

Cys Ala Trp Ser Ser Gly Thr Gly Thr Ser Glu Gln Tyr Phe
1               5                   10

<210> SEQ ID NO 829
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 829

```
Cys Ala Trp Ser Val Gly Gly Arg Ile Tyr Gly Tyr Thr Phe
1               5                   10
```

<210> SEQ ID NO 830
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 830

```
Cys Ala Trp Ser Val Leu Arg Gly Gln Tyr Phe
1               5                   10
```

<210> SEQ ID NO 831
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 831

```
Cys Ile Ser Gln Ser Gly Ile Gly Phe Asp Thr Phe
1               5                   10
```

<210> SEQ ID NO 832
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 832

```
Cys Ser Ala Ala Ile Val Gly Gln Pro Gln His Phe
1               5                   10
```

<210> SEQ ID NO 833
<211> LENGTH: 18
<212> TYPE: PRT
<213> ORGANISM: Artificial sequence
<220> FEATURE:
<223> OTHER INFORMATION: Synthetic polypeptide

<400> SEQUENCE: 833

```
Cys Ser Ala Glu Arg Ser Gly Leu Ala Gly Ala Pro Ala Tyr Glu Gln
1               5                   10                  15

Tyr Phe
```

<210> SEQ ID NO 834
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 834

```
Cys Ser Ala Gly Pro Val Gly Ala Gly Gly Ala Gly Glu Gln Phe Phe
1               5                   10                  15
```

<210> SEQ ID NO 835
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 835

Cys Ser Ala Leu Leu Pro Thr Gly Gly Gly Glu Gln Tyr Phe
1               5                   10

<210> SEQ ID NO 836
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 836

Cys Ser Ala Asn Gly Leu Gly Gly Leu Asn Thr Glu Ala Phe Phe
1               5                   10                  15

<210> SEQ ID NO 837
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 837

Cys Ser Ala Pro Gln Gly Gln Glu Thr Gln Tyr Phe
1               5                   10

<210> SEQ ID NO 838
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 838

Cys Ser Ala Arg Asp Gly Ala Gly Val Gly Asp Thr Gln Tyr Phe
1               5                   10                  15

<210> SEQ ID NO 839
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 839

Cys Ser Ala Arg Asp Ser Asp Gly Glu Lys Leu Phe Phe
1               5                   10

<210> SEQ ID NO 840
<211> LENGTH: 18
<212> TYPE: PRT
<213> ORGANISM: Artificial sequence
<220> FEATURE:
<223> OTHER INFORMATION: Synthetic polypeptide

<400> SEQUENCE: 840

Cys Ser Ala Arg Gly Gly Gly Gly Ala Leu Gly Ser Tyr Asn Glu Gln
1               5                   10                  15

Phe Phe

<210> SEQ ID NO 841
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 841

Cys Ser Ala Arg Gly Ser Gly Thr Gly Asp Leu Tyr Gly Tyr Thr Phe
1               5                   10                  15

<210> SEQ ID NO 842
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 842

Cys Ser Ala Arg Trp Glu Gln Gly Ala Arg Gly Tyr Thr Phe
1               5                   10

<210> SEQ ID NO 843
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 843

Cys Ser Ala Ser Glu Ser Leu Leu Leu Gly Tyr Thr Phe
1               5                   10

<210> SEQ ID NO 844
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 844

Cys Ser Ala Ser Gly Arg Ala Gly Glu Ser Asn Glu Gln Phe Phe
1               5                   10                  15

<210> SEQ ID NO 845
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 845

Cys Ser Ala Ser Lys Thr Gly Val His Glu Gln Tyr Phe
1               5                   10

<210> SEQ ID NO 846
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 846

Cys Ser Ala Ser Arg Gly Asn Thr Glu Ala Phe Phe
1               5                   10

<210> SEQ ID NO 847
<211> LENGTH: 15
<212> TYPE: PRT
<213> ORGANISM: Artificial sequence
<220> FEATURE:
<223> OTHER INFORMATION: Synthetic polypeptide

```
<400> SEQUENCE: 847

Cys Ser Ala Thr His Arg Glu Asn Leu Thr Asp Thr Gln Tyr Phe
1               5                   10                  15

<210> SEQ ID NO 848
<211> LENGTH: 18
<212> TYPE: PRT
<213> ORGANISM: Artificial sequence
<220> FEATURE:
<223> OTHER INFORMATION: Synthetic polypeptide

<400> SEQUENCE: 848

Cys Ser Ala Thr Ser Pro Leu Ser Ala Gly Ala Tyr Gln Glu Thr Gln
1               5                   10                  15

Tyr Phe

<210> SEQ ID NO 849
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 849

Cys Ser Ala Val Gly Gly Pro Val Ser Gln Pro Gln His Phe
1               5                   10

<210> SEQ ID NO 850
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 850

Cys Ser Ala Val Arg Thr Gly Gly Tyr Tyr Glu Gln Tyr Phe
1               5                   10

<210> SEQ ID NO 851
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 851

Cys Ser Ile Gly Gly Gln Gly Leu Glu Ala Phe Phe
1               5                   10

<210> SEQ ID NO 852
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 852

Cys Ser Val Asp Gly Ala Leu Ala Gly Gly Thr Tyr Glu Gln Tyr Phe
1               5                   10                  15

<210> SEQ ID NO 853
<211> LENGTH: 10
<212> TYPE: PRT
<213> ORGANISM: Artificial sequence
<220> FEATURE:
<223> OTHER INFORMATION: Synthetic polypeptide
```

<400> SEQUENCE: 853

Cys Ser Val Asp Gly Ser Trp Gln Phe Phe
1               5                   10

<210> SEQ ID NO 854
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 854

Cys Ser Val Glu Glu Gly Asp Ile Arg Pro Tyr Glu Gln Tyr Phe
1               5                   10                  15

<210> SEQ ID NO 855
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 855

Cys Ser Val Glu Leu Gln Gly Asn Lys Val Gly Glu Leu Phe Phe
1               5                   10                  15

<210> SEQ ID NO 856
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 856

Cys Ser Val Leu Ala Ala Tyr Asn Glu Gln Phe Phe
1               5                   10

<210> SEQ ID NO 857
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 857

Cys Ser Val Arg Thr Gly Asn Ser Asn Gln Pro Gln His Phe
1               5                   10

<210> SEQ ID NO 858
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 858

Cys Ser Val Ser Gln Gly Arg Gly Gly Asp Thr Gln Tyr Phe
1               5                   10

<210> SEQ ID NO 859
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 859

Cys Ser Thr Gly Gly Met Gln Pro Gln His Phe
1               5                   10

<210> SEQ ID NO 860
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 860

Cys Ala Val Asp Gly Glu Gly Gly Ser Gln Gly Asn Leu Ile Phe
1               5                   10                  15

<210> SEQ ID NO 861
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 861

Cys Ile Val Arg Val Lys Gly Gln Tyr Asn Asn Asn Asp Met Arg Phe
1               5                   10                  15

<210> SEQ ID NO 862
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 862

Cys Ala Val Asn Gly Tyr Ser Thr Leu Thr Phe
1               5                   10

<210> SEQ ID NO 863
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 863

Cys Ala Ala Thr Thr Gly Gly Gly Asn Lys Leu Thr Phe
1               5                   10

<210> SEQ ID NO 864
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 864

Cys Ala Leu Lys Gly Gly Thr Gly Gly Gly Asn Lys Leu Thr Phe
1               5                   10                  15

<210> SEQ ID NO 865
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 865

Cys Ala Ala Lys Leu Gly Gly Ser Glu Lys Leu Val Phe
1               5                   10

<210> SEQ ID NO 866
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 866

Cys Ala Phe Ser Met Tyr Ser Gly Gly Gly Ala Asp Gly Leu Thr Phe
1               5                   10                  15

<210> SEQ ID NO 867
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 867

Cys Ala Leu Ser Tyr Asn Gln Gly Gly Lys Leu Ile Phe
1               5                   10

<210> SEQ ID NO 868
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 868

Cys Ala Ala Asn Phe Gly Ser Phe Gly Asn Val Leu His Cys
1               5                   10

<210> SEQ ID NO 869
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 869

Cys Ala Tyr Val Gly Ser Ser Asn Thr Gly Lys Leu Ile Phe
1               5                   10

<210> SEQ ID NO 870
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 870

Cys Ala Ala Ser Lys Gly Asn Tyr Gly Gln Asn Phe Val Phe
1               5                   10

<210> SEQ ID NO 871
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 871

Cys Ile Val Arg Val Glu Gly Asn Asn Arg Leu Ala Phe
1               5                   10

<210> SEQ ID NO 872
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 872

Cys Ala Leu Ser Pro Gly Gly Gly Gly Asn Lys Leu Thr Phe
1               5                   10

<210> SEQ ID NO 873
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 873

Cys Ala Val Ser Tyr Asn Ala Arg Leu Met Phe
1               5                   10

<210> SEQ ID NO 874
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 874

Cys Ala Met Ser Thr Asn Thr Gly Gly Phe Lys Thr Ile Phe
1               5                   10

<210> SEQ ID NO 875
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 875

Cys Ala Val Arg Arg Gly Gly Gly Ser Tyr Ile Pro Thr Phe
1               5                   10

<210> SEQ ID NO 876
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 876

Cys Ile Val Arg Ser Tyr Asn Gln Gly Ala Gln Lys Leu Val Phe
1               5                   10                  15

<210> SEQ ID NO 877
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 877

Cys Ala Leu Thr Pro Asn Ser Gly Asn Thr Pro Leu Val Phe

```
                 1               5                  10

<210> SEQ ID NO 878
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 878

Cys Ala Val Gln Ala Pro Gly Gly Tyr Gln Lys Val Thr Phe
  1               5                  10

<210> SEQ ID NO 879
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 879

Cys Ala Gly Gln Leu Leu Ile Gly Gln Ala Gly Thr Ala Leu Ile Phe
  1               5                  10                  15

<210> SEQ ID NO 880
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 880

Cys Ile Val Arg Val Phe Gly Gly Ala Thr Asn Lys Leu Ile Phe
  1               5                  10                  15

<210> SEQ ID NO 881
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 881

Cys Ala Ala Glu Arg Glu Gly Asn Lys Leu Val Phe
  1               5                  10

<210> SEQ ID NO 882
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 882

Cys Ala Ser Gly Gly Ser Asn Tyr Lys Leu Thr Phe
  1               5                  10

<210> SEQ ID NO 883
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 883

Cys Ala Val Gln Ala Pro Gly Gly Ser Asn Tyr Lys Leu Thr Phe
  1               5                  10                  15
```

```
<210> SEQ ID NO 884
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 884

Cys Ala Leu Pro Leu Asn Asp Tyr Lys Leu Ser Phe
1               5                   10

<210> SEQ ID NO 885
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 885

Cys Ala Tyr Arg Ser Pro Asn Ser Gly Tyr Ala Leu Asn Phe
1               5                   10

<210> SEQ ID NO 886
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 886

Cys Val Val Ser Asp His Ala Arg Leu Met Phe
1               5                   10

<210> SEQ ID NO 887
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 887

Cys Ile Val Arg Val Val Ser Phe Gln Lys Leu Val Phe
1               5                   10

<210> SEQ ID NO 888
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 888

Cys Val Val Asn Glu Gly Asn Asp Met Arg Phe
1               5                   10

<210> SEQ ID NO 889
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 889

Cys Ala Ala Thr Asp Ser Trp Gly Lys Leu Gln Phe
1               5                   10
```

<210> SEQ ID NO 890
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 890

Cys Ala Val Val Asn Thr Gly Asn Gln Phe Tyr Phe
1               5                   10

<210> SEQ ID NO 891
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 891

Cys Ala Arg Asn Arg Asp Asp Lys Ile Ile Phe
1               5                   10

<210> SEQ ID NO 892
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 892

Cys Ala Phe Lys Gly Ser Gly Gly Ser Asn Tyr Lys Leu Thr Phe
1               5                   10                  15

<210> SEQ ID NO 893
<211> LENGTH: 17
<212> TYPE: PRT
<213> ORGANISM: Artificial sequence
<220> FEATURE:
<223> OTHER INFORMATION: Synthetic polypeptide

<400> SEQUENCE: 893

Cys Ala Gly Glu Leu Leu Val Ser Val Gly Asn Thr Gly Lys Leu Ile
1               5                   10                  15

Phe

<210> SEQ ID NO 894
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 894

Cys Ala Gly Pro Thr Lys Ala Gly Asn Met Leu Thr Phe
1               5                   10

<210> SEQ ID NO 895
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 895

Cys Ala Val Ser Gly Ile Val Arg Leu Met Phe
1               5                   10

<210> SEQ ID NO 896
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 896

Cys Ala Leu Ser Glu Ala Ser Asn Gly Asn Asn Arg Lys Leu Ile Trp
1               5                   10                  15

<210> SEQ ID NO 897
<211> LENGTH: 17
<212> TYPE: PRT
<213> ORGANISM: Artificial sequence
<220> FEATURE:
<223> OTHER INFORMATION: Synthetic polypeptide

<400> SEQUENCE: 897

Cys Ile Val Arg Ser Leu Ile Arg Gly Gly Ser Gln Gly Asn Leu Ile
1               5                   10                  15

Phe

<210> SEQ ID NO 898
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 898

Cys Ala Ala Pro Pro Gln Leu Lys Ala Ala Gly Asn Lys Leu Thr Phe
1               5                   10                  15

<210> SEQ ID NO 899
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 899

Cys Thr Ala Ser Ala Val Ser Phe Gly Asn Val Leu His Cys
1               5                   10

<210> SEQ ID NO 900
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 900

Cys Ala Ala Ile Gly Ser Ser Asn Thr Gly Lys Leu Ile Phe
1               5                   10

<210> SEQ ID NO 901
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 901

Cys Ala Ala Ser Lys Asp Phe Gly Asn Glu Lys Leu Thr Phe

```
1               5               10
```

<210> SEQ ID NO 902
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 902

```
Cys Ala Val Arg Asp Ser Thr Asn Arg Asp Asp Lys Ile Ile Phe
1               5                   10                  15
```

<210> SEQ ID NO 903
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 903

```
Cys Ala Val Thr Pro Ala Tyr Lys Tyr Ile Phe
1               5                   10
```

<210> SEQ ID NO 904
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 904

```
Cys Ala Leu Ser Thr Thr Asn Gln Ala Gly Thr Ala Leu Ile Phe
1               5                   10                  15
```

<210> SEQ ID NO 905
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 905

```
Cys Val Val Lys Lys Asp Ser Trp Gly Lys Leu Gln Phe
1               5                   10
```

<210> SEQ ID NO 906
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 906

```
Cys Ala Ala Ser Met Ala Gly Asn Gln Phe Tyr Phe
1               5                   10
```

<210> SEQ ID NO 907
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 907

```
Cys Ile Val Arg Val Glu Asp Ser Ser Tyr Lys Leu Ile Phe
1               5                   10
```

<210> SEQ ID NO 908
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 908

Cys Ala Ala Ser Lys Ser Gly Asn Asn Asp Met Arg Phe
1               5                   10

<210> SEQ ID NO 909
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 909

Cys Ala Phe Met Lys Glu Gly Ala Gln Lys Leu Val Phe
1               5                   10

<210> SEQ ID NO 910
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 910

Cys Ala Met Ser Ala Trp Asn Asn Asn Asp Met Arg Phe
1               5                   10

<210> SEQ ID NO 911
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 911

Cys Ala Leu Gly Arg Asp Asp Lys Ile Ile Phe
1               5                   10

<210> SEQ ID NO 912
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 912

Cys Ala Ala Leu Gln Gly Ala Gln Lys Leu Val Phe
1               5                   10

<210> SEQ ID NO 913
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 913

Cys Val Val Ser Asp Gln Asn Ser Gly Tyr Ala Leu Asn Phe
1               5                   10

<210> SEQ ID NO 914
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 914

Cys Ala Met Ser Ala Arg Tyr Gly Gly Ala Thr Asn Lys Leu Ile Phe
1               5                   10                  15

<210> SEQ ID NO 915
<211> LENGTH: 17
<212> TYPE: PRT
<213> ORGANISM: Artificial sequence
<220> FEATURE:
<223> OTHER INFORMATION: Synthetic polypeptide

<400> SEQUENCE: 915

Cys Ala Tyr Arg Ser Ala Arg Gly Ser Ser Asn Thr Gly Lys Leu Ile
1               5                   10                  15

Phe

<210> SEQ ID NO 916
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 916

Cys Ala Leu Gly Ser Trp Gly Lys Leu Gln Phe
1               5                   10

<210> SEQ ID NO 917
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 917

Cys Ala Val Val Asn Ser Gly Gly Gly Ala Asp Gly Leu Thr Phe
1               5                   10                  15

<210> SEQ ID NO 918
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 918

Cys Ala Leu Thr Asn Asp Tyr Lys Leu Ser Phe
1               5                   10

<210> SEQ ID NO 919
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 919

Cys Ala Phe Arg Thr Asn Thr Gly Asn Gln Phe Tyr Phe
1               5                   10

```
<210> SEQ ID NO 920
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 920

Cys Val Val Thr Thr Tyr Asn Thr Asp Lys Leu Ile Phe
1               5                   10

<210> SEQ ID NO 921
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 921

Cys Ala Ala Ser Asp Ser Gln Trp Tyr Asp Met Arg Phe
1               5                   10

<210> SEQ ID NO 922
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 922

Cys Ile Leu Arg Arg Asn Glu Lys Leu Thr Phe
1               5                   10

<210> SEQ ID NO 923
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 923

Cys Ile Val Arg Val Ala Gly Asn Thr Gly Gly Phe Lys Thr Ile Phe
1               5                   10                  15

<210> SEQ ID NO 924
<211> LENGTH: 18
<212> TYPE: PRT
<213> ORGANISM: Artificial sequence
<220> FEATURE:
<223> OTHER INFORMATION: Synthetic polypeptide

<400> SEQUENCE: 924

Cys Val Val Ser Val Ser Asn Asp Ser Gly Gly Ser Asn Tyr Lys Leu
1               5                   10                  15

Thr Phe

<210> SEQ ID NO 925
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 925

Cys Ala Leu Arg Pro Asp Thr Gly Arg Arg Ala Leu Thr Phe
```

<210> SEQ ID NO 926
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 926

Cys Ala Tyr Arg Ser Tyr Arg Thr Gly Asn Gln Phe Tyr Phe
1               5                   10

<210> SEQ ID NO 927
<211> LENGTH: 8
<212> TYPE: PRT
<213> ORGANISM: Artificial sequence
<220> FEATURE:
<223> OTHER INFORMATION: Synthetic polypeptide

<400> SEQUENCE: 927

Cys Ala Pro Asp Lys Leu Ile Phe
1               5

<210> SEQ ID NO 928
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 928

Cys Ala Met Ser Gln Thr Gln Gly Gly Ser Glu Lys Leu Val Phe
1               5                   10                  15

<210> SEQ ID NO 929
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 929

Cys Ala Val Ser Ser Tyr Ser Gly Gly Tyr Gln Lys Val Thr Phe
1               5                   10                  15

<210> SEQ ID NO 930
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 930

Cys Ala Ala Ser Thr Arg Gly Ser Gln Gly Asn Leu Ile Phe
1               5                   10

<210> SEQ ID NO 931
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 931

Cys Val Val Asn His Asn Thr Asp Lys Leu Ile Phe
1               5                   10

```
<210> SEQ ID NO 932
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 932

Cys Val Val Thr Leu Arg Pro Trp Ser Asn Tyr Gln Leu Ile Trp
1               5                   10                  15

<210> SEQ ID NO 933
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 933

Cys Ala Ala Ser Glu Trp Thr Ala Gly Asn Met Leu Thr Phe
1               5                   10

<210> SEQ ID NO 934
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 934

Cys Ala Val Asp Glu Gly Leu Gly Asn Thr Gly Lys Leu Ile Phe
1               5                   10                  15

<210> SEQ ID NO 935
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 935

Cys Ala Val Lys Asp Ser Gly Tyr Ala Leu Asn Phe
1               5                   10

<210> SEQ ID NO 936
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 936

Cys Val Val Ser Pro Gly Gly Tyr Gln Lys Val Thr Phe
1               5                   10

<210> SEQ ID NO 937
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 937

Cys Ala Ala Ser Arg Asn Ser Gly Asn Thr Pro Leu Val Phe
1               5                   10
```

<210> SEQ ID NO 938
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 938

Cys Ala Leu Ser Asp Gln Gly Ile Gln Gly Ala Gln Lys Leu Val Phe
1               5                   10                  15

<210> SEQ ID NO 939
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 939

Cys Ala Thr Asp Glu Thr Ala Gly Gly Ser Arg Leu Thr Phe
1               5                   10

<210> SEQ ID NO 940
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 940

Cys Ala Thr Gly Leu Ser Ser Gly Ser Ala Arg Gln Leu Thr Phe
1               5                   10                  15

<210> SEQ ID NO 941
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 941

Cys Ala Val Glu Asp Gln Ala Gly Thr Ala Leu Ile Phe
1               5                   10

<210> SEQ ID NO 942
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 942

Cys Ala Val Asn Arg Ser Thr Asp Lys Leu Ile Phe
1               5                   10

<210> SEQ ID NO 943
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 943

Cys Ala Tyr Arg Val Gly Gly Ser Gln Gly Asn Leu Ile Phe
1               5                   10

```
<210> SEQ ID NO 944
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 944

Cys Ala Val Arg Gly Ala Gly Gly Ser Tyr Ile Pro Thr Phe
1               5                   10

<210> SEQ ID NO 945
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 945

Cys Ala Phe Met Lys His Phe Gly Asn Glu Lys Leu Thr Phe
1               5                   10

<210> SEQ ID NO 946
<211> LENGTH: 17
<212> TYPE: PRT
<213> ORGANISM: Artificial sequence
<220> FEATURE:
<223> OTHER INFORMATION: Synthetic polypeptide

<400> SEQUENCE: 946

Cys Ala Val Asn Thr Gly Leu Ser Asn Phe Gly Asn Glu Lys Leu Thr
1               5                   10                  15

Phe

<210> SEQ ID NO 947
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 947

Cys Ala Leu Asp Glu Ser Asn Thr Gly Lys Leu Ile Phe
1               5                   10

<210> SEQ ID NO 948
<211> LENGTH: 17
<212> TYPE: PRT
<213> ORGANISM: Artificial sequence
<220> FEATURE:
<223> OTHER INFORMATION: Synthetic polypeptide

<400> SEQUENCE: 948

Cys Ala Ala Gly Gly Ile Leu Gly Glu Thr Ser Gly Ser Arg Leu Thr
1               5                   10                  15

Phe

<210> SEQ ID NO 949
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 949

Cys Ala Thr His Asn Ser Gly Thr Tyr Lys Tyr Ile Phe
```

```
<210> SEQ ID NO 950
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 950

Cys Ile Val Arg Val Gly Gly Thr Gly Gly Phe Lys Thr Ile Phe
1               5                   10                  15

<210> SEQ ID NO 951
<211> LENGTH: 17
<212> TYPE: PRT
<213> ORGANISM: Artificial sequence
<220> FEATURE:
<223> OTHER INFORMATION: Synthetic polypeptide

<400> SEQUENCE: 951

Cys Ala Val Thr Arg Gly Ile Leu Thr Gly Gly Gly Asn Lys Leu Thr
1               5                   10                  15

Phe

<210> SEQ ID NO 952
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 952

Cys Ala Glu Ser Gly Ser Phe Gly Asn Val Leu His Cys
1               5                   10

<210> SEQ ID NO 953
<211> LENGTH: 17
<212> TYPE: PRT
<213> ORGANISM: Artificial sequence
<220> FEATURE:
<223> OTHER INFORMATION: Synthetic polypeptide

<400> SEQUENCE: 953

Cys Val Val Asn Met Phe Ala Gly Gly Thr Ser Tyr Gly Lys Leu Thr
1               5                   10                  15

Phe

<210> SEQ ID NO 954
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 954

Cys Val Val Thr Pro Trp Gly Gly Gly Ser Gln Gly Asn Leu Ile Phe
1               5                   10                  15

<210> SEQ ID NO 955
<211> LENGTH: 13
<212> TYPE: PRT
<213> ORGANISM: Artificial sequence
<220> FEATURE:
<223> OTHER INFORMATION: Synthetic polypeptide
```

```
<400> SEQUENCE: 955

Cys Ala Val Asn Arg Gly Gly Ser Tyr Ile Pro Thr Phe
1               5                   10

<210> SEQ ID NO 956
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 956

Cys Val Val Ser Asp Arg Thr Pro Gly Thr Tyr Lys Tyr Ile Phe
1               5                   10                  15

<210> SEQ ID NO 957
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 957

Cys Ala Val Ser Asn Asn Ala Arg Leu Met Phe
1               5                   10

<210> SEQ ID NO 958
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 958

Cys Ala Leu Ala Thr Gly Gly Gly Asn Lys Leu Thr Phe
1               5                   10

<210> SEQ ID NO 959
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 959

Cys Ala Ala Ser Ile Ala Gly Ser Asn Tyr Lys Leu Thr Phe
1               5                   10

<210> SEQ ID NO 960
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 960

Cys Leu Val Gly Gly Asp Asn Gln Gly Gly Lys Leu Ile Phe
1               5                   10

<210> SEQ ID NO 961
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 961
```

```
Cys Ala Ala Ser Lys Tyr Gly Asn Lys Leu Val Phe
1               5                   10
```

<210> SEQ ID NO 962
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 962

```
Cys Ala Met Gly Gly Gly Gly Ser Glu Lys Leu Val Phe
1               5                   10
```

<210> SEQ ID NO 963
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 963

```
Cys Ala Val Ser Pro Asn Ser Gly Gly Tyr Gln Lys Val Thr Phe
1               5                   10                  15
```

<210> SEQ ID NO 964
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 964

```
Cys Ile Val Thr Gly Ser Ala Arg Gln Leu Thr Phe
1               5                   10
```

<210> SEQ ID NO 965
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 965

```
Cys Ala Ala Arg Gly Met Asp Ser Ser Tyr Lys Leu Ile Phe
1               5                   10
```

<210> SEQ ID NO 966
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 966

```
Cys Ala Thr Glu Gly Gly Ser Asn Tyr Lys Leu Thr Phe
1               5                   10
```

<210> SEQ ID NO 967
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 967

```
Cys Ala Pro Val Ser Gly Thr Tyr Lys Tyr Ile Phe
1               5                   10
```

<210> SEQ ID NO 968
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 968

```
Cys Ala Ser Tyr Ser Leu Gln Gly Ala Gln Lys Leu Val Phe
1               5                   10
```

<210> SEQ ID NO 969
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 969

```
Cys Ala Gly Ala Val Gly Ala Val Gly Ser Gln Gly Asn Leu Ile Phe
1               5                   10                  15
```

<210> SEQ ID NO 970
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 970

```
Cys Ala Val Leu Ser Gly Gly Gly Ala Asp Gly Leu Thr Phe
1               5                   10
```

<210> SEQ ID NO 971
<211> LENGTH: 10
<212> TYPE: PRT
<213> ORGANISM: Artificial sequence
<220> FEATURE:
<223> OTHER INFORMATION: Synthetic polypeptide

<400> SEQUENCE: 971

```
Cys Ala Tyr Ser Leu Gly Lys Leu Ile Phe
1               5                   10
```

<210> SEQ ID NO 972
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 972

```
Cys Ala Val Gly Asn Glu Gly Phe Gln Lys Leu Val Phe
1               5                   10
```

<210> SEQ ID NO 973
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 973

```
Cys Val Val Ser Arg Asn Thr Gly Gly Phe Lys Thr Ile Phe
```

-continued

```
1               5                  10

<210> SEQ ID NO 974
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 974

Cys Val Val Ala Asn Asn Ala Arg Leu Met Phe
1               5                  10

<210> SEQ ID NO 975
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 975

Cys Gly Ala Asp Arg Gly Ser Thr Leu Gly Arg Leu Tyr Phe
1               5                  10

<210> SEQ ID NO 976
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 976

Cys Ala Tyr Asn Asn Pro Gly Thr Tyr Lys Tyr Ile Phe
1               5                  10

<210> SEQ ID NO 977
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 977

Cys Ala Val Thr Leu Pro His Thr Gly Ala Asn Ser Lys Leu Thr Phe
1               5                  10                  15

<210> SEQ ID NO 978
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 978

Cys Ala Leu Ser Asp Asn Ala Gly Asn Met Leu Thr Phe
1               5                  10

<210> SEQ ID NO 979
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 979

Cys Ala Val Ser Gly Gly Ser Ser Asn Thr Gly Lys Leu Ile Phe
1               5                  10                  15
```

<210> SEQ ID NO 980
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 980

Cys Ala Tyr Ile Gly Ser Ser Asn Thr Gly Lys Leu Ile Phe
1               5                   10

<210> SEQ ID NO 981
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 981

Cys Ala Pro Arg Ala Phe Gly Tyr Ala Leu Asn Phe
1               5                   10

<210> SEQ ID NO 982
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 982

Cys Ala Val Ser Tyr Asn Asn Asp Met Arg Phe
1               5                   10

<210> SEQ ID NO 983
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 983

Cys Ala Gly Arg Pro Arg His Thr Asn Ala Gly Lys Ser Thr Phe
1               5                   10                  15

<210> SEQ ID NO 984
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 984

Cys Ala Ala Ser Thr Phe Ala Ala Gly Asn Lys Leu Thr Phe
1               5                   10

<210> SEQ ID NO 985
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 985

Cys Ala Ala Ile Ser Met Asp Ser Ser Tyr Lys Leu Ile Phe
1               5                   10

<210> SEQ ID NO 986
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 986

Cys Ala Val Thr Asn Ser Gly Gly Tyr Gln Lys Val Thr Phe
1               5                   10

<210> SEQ ID NO 987
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 987

Cys Ala Val Thr Val Ser Asn Asn Asp Met Arg Phe
1               5                   10

<210> SEQ ID NO 988
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 988

Cys Ala Val Asp Glu Gly Leu Gly Asn Thr Gly Lys Leu Ile Phe
1               5                   10                  15

<210> SEQ ID NO 989
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 989

Cys Ala Val Gln Tyr Thr Thr Ser Gly Thr Tyr Lys Tyr Ile Phe
1               5                   10                  15

<210> SEQ ID NO 990
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 990

Cys Ala Val Pro Gly Lys Gly Gly Gly Ala Asp Gly Leu Thr Phe
1               5                   10                  15

<210> SEQ ID NO 991
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 991

Cys Ala Val Lys Arg Pro Gly Gly Gly Asn Lys Leu Thr Phe
1               5                   10

```
<210> SEQ ID NO 992
<211> LENGTH: 17
<212> TYPE: PRT
<213> ORGANISM: Artificial sequence
<220> FEATURE:
<223> OTHER INFORMATION: Synthetic polypeptide

<400> SEQUENCE: 992

Cys Ala Met Arg Glu Gly Gln Gly Gln Gly Gly Ser Glu Lys Leu Val
1               5                   10                  15

Phe

<210> SEQ ID NO 993
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 993

Cys Ala Val Arg Asp Leu Leu Asn Ser Gly Asn Thr Pro Leu Val Phe
1               5                   10                  15

<210> SEQ ID NO 994
<211> LENGTH: 17
<212> TYPE: PRT
<213> ORGANISM: Artificial sequence
<220> FEATURE:
<223> OTHER INFORMATION: Synthetic polypeptide

<400> SEQUENCE: 994

Cys Ala Leu Arg Gly Tyr Gly Ser Gly Ala Gly Ser Tyr Gln Leu Thr
1               5                   10                  15

Phe

<210> SEQ ID NO 995
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 995

Cys Ala Tyr Arg Ser Thr Val Ser Gly Thr Ala Ser Lys Leu Thr Phe
1               5                   10                  15

<210> SEQ ID NO 996
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 996

Cys Ala Val Thr Tyr Ser Ser Asn Thr Gly Lys Leu Ile Phe
1               5                   10

<210> SEQ ID NO 997
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 997

Cys Ala Thr Gly Thr Pro Tyr Tyr Gly Asn Asn Arg Leu Ala Phe
```

<210> SEQ ID NO 998
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 998

Cys Ala Leu Glu Thr Gln Ala Gly Thr Ala Leu Ile Phe
1               5                   10

<210> SEQ ID NO 999
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 999

Cys Val Leu Glu Asp Thr Gly Phe Gln Lys Leu Val Phe
1               5                   10

<210> SEQ ID NO 1000
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 1000

Cys Ala Tyr Arg Thr Glu Thr Ser Gly Ser Arg Leu Thr Phe
1               5                   10

<210> SEQ ID NO 1001
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 1001

Cys Ala Ser Arg Gly Thr Gly Thr Tyr Lys Tyr Ile Phe
1               5                   10

<210> SEQ ID NO 1002
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 1002

Cys Ala Tyr Arg Ser Ala Tyr Gly Gly Ala Thr Asn Lys Leu Ile Phe
1               5                   10                  15

<210> SEQ ID NO 1003
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 1003

Cys Ala Val Glu Glu Gly Gly Gln Asn Phe Val Phe
1               5                   10

<210> SEQ ID NO 1004
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 1004

Cys Ala Thr Ser Glu Gly Gly Phe Lys Thr Ile Phe
1               5                   10

<210> SEQ ID NO 1005
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 1005

Cys Leu Asp Gln Ala Arg Asn Gln Gly Gly Lys Leu Ile Phe
1               5                   10

<210> SEQ ID NO 1006
<211> LENGTH: 17
<212> TYPE: PRT
<213> ORGANISM: Artificial sequence
<220> FEATURE:
<223> OTHER INFORMATION: Synthetic polypeptide

<400> SEQUENCE: 1006

Cys Ala Met Arg Pro Gly Pro Pro Thr Asp Ser Trp Gly Lys Leu Gln
1               5                   10                  15

Phe

<210> SEQ ID NO 1007
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 1007

Cys Ala Leu Ser Asp Asp Asn Asn Asp Met Arg Phe
1               5                   10

<210> SEQ ID NO 1008
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 1008

Cys Ala Ala Glu Tyr Gly Asn Lys Leu Val Phe
1               5                   10

<210> SEQ ID NO 1009
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 1009

Cys Ala Leu Ser Glu Asp Ser Gly Gly Ser Asn Tyr Lys Leu Thr Phe

```
                1               5                  10                  15

<210> SEQ ID NO 1010
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 1010

Cys Ala Met Arg Glu Gly Tyr Thr Gly Ala Asn Ser Lys Leu Thr Phe
1               5                  10                  15

<210> SEQ ID NO 1011
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 1011

Cys Ala Thr Gly Gly Ser Asn Tyr Lys Leu Thr Phe
1               5                  10

<210> SEQ ID NO 1012
<211> LENGTH: 10
<212> TYPE: PRT
<213> ORGANISM: Artificial sequence
<220> FEATURE:
<223> OTHER INFORMATION: Synthetic polypeptide

<400> SEQUENCE: 1012

Cys Ala Glu Asn Phe Asn Lys Phe Tyr Phe
1               5                  10

<210> SEQ ID NO 1013
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 1013

Cys Val Val Asn Thr Pro Asp Ser Trp Gly Lys Leu Gln Phe
1               5                  10

<210> SEQ ID NO 1014
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 1014

Cys Ala Leu Ser Glu Phe Ala Ser Gly Asn Thr Pro Leu Val Phe
1               5                  10                  15

<210> SEQ ID NO 1015
<211> LENGTH: 17
<212> TYPE: PRT
<213> ORGANISM: Artificial sequence
<220> FEATURE:
<223> OTHER INFORMATION: Synthetic polypeptide

<400> SEQUENCE: 1015

Cys Leu Val Gly Asp Ser Asn Tyr Gly Gly Ala Thr Asn Lys Leu Ile
1               5                  10                  15
```

Phe

<210> SEQ ID NO 1016
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 1016

Cys Ile Leu Met Ser Gly Ala Gly Asn Asn Arg Lys Leu Ile Trp
1               5                   10                  15

<210> SEQ ID NO 1017
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 1017

Cys Ala Met Arg Glu Arg Gly Asn Asn Ala Arg Leu Met Phe
1               5                   10

<210> SEQ ID NO 1018
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 1018

Cys Ala Tyr Arg Ser Ala Ser Gly Trp Gly Asn Thr Pro Leu Val Phe
1               5                   10                  15

<210> SEQ ID NO 1019
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 1019

Cys Ala Ala Ser Asn Thr Gly Asn Gln Phe Tyr Phe
1               5                   10

<210> SEQ ID NO 1020
<211> LENGTH: 17
<212> TYPE: PRT
<213> ORGANISM: Artificial sequence
<220> FEATURE:
<223> OTHER INFORMATION: Synthetic polypeptide

<400> SEQUENCE: 1020

Cys Ala Val Ser Val Pro Asn Ser Gly Gly Ser Asn Tyr Lys Leu Thr
1               5                   10                  15

Phe

<210> SEQ ID NO 1021
<211> LENGTH: 18
<212> TYPE: PRT
<213> ORGANISM: Artificial sequence
<220> FEATURE:
<223> OTHER INFORMATION: Synthetic polypeptide

<400> SEQUENCE: 1021

```
Cys Ala Val Ser Asp Pro Asn Ala Gly Gly Thr Ser Tyr Gly Lys Leu
1               5                   10                  15

Thr Phe

<210> SEQ ID NO 1022
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 1022

Cys Ala Gly Pro Asn Thr Gly Gly Phe Lys Thr Ile Phe
1               5                   10

<210> SEQ ID NO 1023
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 1023

Cys Ala Gly Gln Arg Gly Arg Ile Gln Gly Ala Gln Lys Leu Val Phe
1               5                   10                  15

<210> SEQ ID NO 1024
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 1024

Cys Gly Ala Asp Lys Tyr Gly Gly Ser Gln Gly Asn Leu Ile Phe
1               5                   10                  15

<210> SEQ ID NO 1025
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 1025

Cys Val Val Asn Lys Ala Ala Gly Asn Lys Leu Thr Phe
1               5                   10

<210> SEQ ID NO 1026
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 1026

Cys Ala Val Ser Glu Arg Leu Met Glu Tyr Gly Asn Lys Leu Val Phe
1               5                   10                  15

<210> SEQ ID NO 1027
<211> LENGTH: 13
<212> TYPE: PRT
<213> ORGANISM: Artificial sequence
<220> FEATURE:
<223> OTHER INFORMATION: Synthetic polypeptide
```

<400> SEQUENCE: 1027

Cys Ala Leu Thr Gly Asp Gly Asn Asn Arg Leu Ala Phe
1               5                   10

<210> SEQ ID NO 1028
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 1028

Cys Ala Met Gly Gly Arg Asp Ser Ser Tyr Lys Leu Ile Phe
1               5                   10

<210> SEQ ID NO 1029
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 1029

Cys Ala Gly Glu Gly Ile Ser Asn Phe Gly Asn Glu Lys Leu Thr Phe
1               5                   10                  15

<210> SEQ ID NO 1030
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 1030

Cys Ala Val Pro Ser Asn Ser Gly Tyr Ala Leu Asn Phe
1               5                   10

<210> SEQ ID NO 1031
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 1031

Cys Ala Leu Leu Ala Gly Asn Asn Arg Lys Leu Ile Trp
1               5                   10

<210> SEQ ID NO 1032
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 1032

Cys Ala Thr His His Ala Gly Gly Thr Ser Tyr Gly Lys Leu Thr Phe
1               5                   10                  15

<210> SEQ ID NO 1033
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 1033

```
Cys Val Val Ser Glu Ser Gly Asn Phe Gly Asn Glu Lys Leu Thr Phe
1               5                   10                  15

<210> SEQ ID NO 1034
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 1034

Cys Ala Leu Ser Val Gly Ser Gln Gly Asn Leu Ile Phe
1               5                   10

<210> SEQ ID NO 1035
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 1035

Cys Ala Ala Ser Arg Tyr Gly Gln Asn Phe Val Phe
1               5                   10

<210> SEQ ID NO 1036
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 1036

Cys Ala Val Gln Thr Gly Asp Ser Asn Tyr Gln Leu Ile Trp
1               5                   10

<210> SEQ ID NO 1037
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 1037

Cys Ala Thr Val Val Asn Thr Gly Thr Ala Ser Lys Leu Thr Phe
1               5                   10                  15

<210> SEQ ID NO 1038
<211> LENGTH: 19
<212> TYPE: PRT
<213> ORGANISM: Artificial sequence
<220> FEATURE:
<223> OTHER INFORMATION: Synthetic polypeptide

<400> SEQUENCE: 1038

Cys Ala Val Ser Val Arg Ala Glu Ala Gly Gly Thr Ser Tyr Gly Lys
1               5                   10                  15

Leu Thr Phe

<210> SEQ ID NO 1039
<211> LENGTH: 14
<212> TYPE: PRT
<213> ORGANISM: Artificial sequence
<220> FEATURE:
<223> OTHER INFORMATION: Synthetic polypeptide
```

<400> SEQUENCE: 1039

Cys Ala Leu Pro Asn Ser Gly Gly Tyr Gln Lys Val Thr Phe
1               5                   10

<210> SEQ ID NO 1040
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 1040

Cys Ala Ala Thr Asn Thr Gly Asn Gln Phe Tyr Phe
1               5                   10

<210> SEQ ID NO 1041
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 1041

Cys Ala Leu Ser Gln Ser Asn Ala Gly Asn Met Leu Thr Phe
1               5                   10

<210> SEQ ID NO 1042
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 1042

Cys Ala Val Ser Asp Ser Gly Gly Gly Ala Asp Gly Leu Thr Phe
1               5                   10                  15

<210> SEQ ID NO 1043
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 1043

Cys Ala Ala Ile Gly Gly Gly Ala Asp Gly Leu Thr Phe
1               5                   10

<210> SEQ ID NO 1044
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 1044

Cys Ala Ala Tyr Ser Gly Tyr Ser Thr Leu Thr Phe
1               5                   10

<210> SEQ ID NO 1045
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 1045

Cys Ala Val Arg Asp Ile Ile Asn Asp Met Arg Phe
1               5                   10

<210> SEQ ID NO 1046
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 1046

Cys Ala Phe Gly Pro Gly Val Asn Tyr Gly Gln Asn Phe Val Phe
1               5                   10                  15

<210> SEQ ID NO 1047
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 1047

Cys Ala Pro Pro Ser Gly Ser Arg Leu Thr Phe
1               5                   10

<210> SEQ ID NO 1048
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 1048

Cys Ala Val Ser Asp Arg Arg Gly Gly Asn Lys Leu Thr Phe
1               5                   10

<210> SEQ ID NO 1049
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 1049

Cys Ala Val Asp Asn Tyr Gly Gln Asn Phe Val Phe
1               5                   10

<210> SEQ ID NO 1050
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 1050

Cys Ala Gly Ser Lys Thr Ser Gly Ser Arg Leu Thr Phe
1               5                   10

<210> SEQ ID NO 1051
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 1051

```
Cys Ala Met Gln Pro Val Asn Ser Gly Tyr Ala Leu Asn Phe
1               5                   10
```

<210> SEQ ID NO 1052
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 1052

```
Cys Ile Val Arg Pro Ala Asn Ser Gly Gly Tyr Gln Lys Val Thr Phe
1               5                   10                  15
```

<210> SEQ ID NO 1053
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 1053

```
Cys Ala Val Asn Pro Ser Ser Asn Thr Gly Lys Leu Ile Phe
1               5                   10
```

<210> SEQ ID NO 1054
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 1054

```
Cys Ala Ile Pro Glu Asp Ser Asn Tyr Gln Leu Ile Trp
1               5                   10
```

<210> SEQ ID NO 1055
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 1055

```
Cys Ile Val Tyr Asn Gln Ala Gly Thr Ala Leu Ile Phe
1               5                   10
```

<210> SEQ ID NO 1056
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 1056

```
Cys Ala Leu Ala Thr Ser Asn Thr Gly Lys Leu Ile Phe
1               5                   10
```

<210> SEQ ID NO 1057
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 1057

```
Cys Val Gly Arg Ala Gln Gly Gly Ala Gly Ser Tyr Gln Leu Thr Phe
```

<210> SEQ ID NO 1058
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 1058

Cys Ala Val Asn Lys Gly Gly Ser Glu Lys Leu Val Phe
1               5                   10

<210> SEQ ID NO 1059
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 1059

Cys Ile Val Ser Leu Asn Thr Gly Asn Gln Phe Tyr Phe
1               5                   10

<210> SEQ ID NO 1060
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 1060

Cys Ala Leu Arg Gly Asn Thr Gly Thr Ala Ser Lys Leu Thr Phe
1               5                   10                  15

<210> SEQ ID NO 1061
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 1061

Cys Ala Val Ile Gly Pro Gly Gly Thr Ser Tyr Gly Lys Leu Thr Phe
1               5                   10                  15

<210> SEQ ID NO 1062
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 1062

Cys Ala Val Ile Gly Leu Thr Gly Gly Gly Asn Lys Leu Thr Phe
1               5                   10                  15

<210> SEQ ID NO 1063
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 1063

Cys Val Val Ser Glu Ser Gln Ala Gly Thr Ala Leu Ile Phe
1               5                   10

```
<210> SEQ ID NO 1064
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 1064

Cys Val Val Asn Ile Ile Lys Gly Ser Ser Tyr Lys Leu Ile Phe
1               5                   10                  15

<210> SEQ ID NO 1065
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 1065

Cys Ala Val Arg Asp Phe Ser Gly Thr Tyr Lys Tyr Ile Phe
1               5                   10

<210> SEQ ID NO 1066
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 1066

Cys Ile Val Arg Val Gly Leu Ser Gly Asn Thr Pro Leu Val Phe
1               5                   10                  15

<210> SEQ ID NO 1067
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 1067

Cys Ala Thr Asp Ala Asn Asp Tyr Lys Leu Ser Phe
1               5                   10

<210> SEQ ID NO 1068
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 1068

Cys Ala Val Glu Gly Gly Gly Arg Arg Ala Leu Thr Phe
1               5                   10

<210> SEQ ID NO 1069
<211> LENGTH: 10
<212> TYPE: PRT
<213> ORGANISM: Artificial sequence
<220> FEATURE:
<223> OTHER INFORMATION: Synthetic polypeptide

<400> SEQUENCE: 1069

Cys Ala Ser Tyr Gly Asn Lys Leu Val Phe
1               5                   10
```

```
<210> SEQ ID NO 1070
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 1070

Cys Ala Ala Ser Lys Glu Asp Tyr Lys Leu Ser Phe
1               5                   10

<210> SEQ ID NO 1071
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 1071

Cys Ala Ala Asn Phe Gly Ser Phe Gly Asn Met Leu His Cys
1               5                   10

<210> SEQ ID NO 1072
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 1072

Cys Ile Val Arg Val Glu Glu Asn Asn Arg Leu Ala Phe
1               5                   10

<210> SEQ ID NO 1073
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 1073

Cys Ala Val Arg Gly Ala Asn Gln Gly Gly Lys Leu Ile Phe
1               5                   10

<210> SEQ ID NO 1074
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 1074

Cys Ala Ala Thr Thr Gly Gly Gly Asn Lys Leu Thr Phe
1               5                   10

<210> SEQ ID NO 1075
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 1075

Cys Ala Val Asn Glu Pro Asn Phe Gly Asn Glu Lys Leu Thr Phe
1               5                   10                  15
```

```
<210> SEQ ID NO 1076
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 1076

Cys Ala Ala Ile Asp Ser Ser Asn Thr Gly Lys Leu Ile Phe
1               5                   10

<210> SEQ ID NO 1077
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 1077

Cys Ala Ala Ser Asp Ser Gly Asn Thr Pro Leu Val Phe
1               5                   10

<210> SEQ ID NO 1078
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 1078

Cys Val Val Asn Lys Gly Ile Asp Gln Gly Gly Lys Leu Ile Phe
1               5                   10                  15

<210> SEQ ID NO 1079
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 1079

Cys Ala Tyr Arg Thr Thr Gln Gly Gly Ser Glu Lys Leu Val Phe
1               5                   10                  15

<210> SEQ ID NO 1080
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 1080

Cys Ala Val Arg Gly Arg Gly Ser Thr Leu Gly Arg Leu Tyr Phe
1               5                   10                  15

<210> SEQ ID NO 1081
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 1081

Cys Ala Gly Pro Thr Thr Asp Ser Trp Gly Lys Leu Gln Phe
1               5                   10

<210> SEQ ID NO 1082
```

```
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 1082

Cys Ala Tyr Arg Ser Ala Val Gly Ala Tyr Lys Tyr Ile Phe
1               5                   10

<210> SEQ ID NO 1083
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 1083

Cys Ile Val Arg Val Glu Gly Ala Asp Gly Leu Thr Phe
1               5                   10

<210> SEQ ID NO 1084
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 1084

Cys Ala Gly Val Asn Asp Tyr Lys Leu Ser Phe
1               5                   10

<210> SEQ ID NO 1085
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 1085

Cys Ala Ala Ile Asn Ala Gly Asn Met Leu Thr Phe
1               5                   10

<210> SEQ ID NO 1086
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 1086

Cys Ala Ser Arg Pro Gly Pro Gly Val Gly Asn Glu Gln Phe Phe
1               5                   10                  15

<210> SEQ ID NO 1087
<211> LENGTH: 19
<212> TYPE: PRT
<213> ORGANISM: Artificial sequence
<220> FEATURE:
<223> OTHER INFORMATION: Synthetic polypeptide

<400> SEQUENCE: 1087

Cys Ala Ser Ser Leu Ile Met Gly Thr Ser Gly Gly Ala Thr Asp Thr
1               5                   10                  15

Gln Tyr Phe
```

```
<210> SEQ ID NO 1088
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 1088

Cys Ala Ser Ser Leu Leu Gly Gln Leu Asn Thr Glu Ala Phe Phe
1               5                   10                  15

<210> SEQ ID NO 1089
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 1089

Cys Ala Ser Ser Gln Gly Pro Val Gly Tyr Glu Gln Tyr Phe
1               5                   10

<210> SEQ ID NO 1090
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 1090

Cys Ala Glu Gly Ser Asn Ser Gly Ala Asn Val Leu Thr Phe
1               5                   10

<210> SEQ ID NO 1091
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 1091

Cys Ala Ile Arg Asp Arg Gln Glu Thr Gln Tyr Phe
1               5                   10

<210> SEQ ID NO 1092
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 1092

Cys Ala Ile Arg Thr Gly Ser Ser Ser Tyr Glu Gln Tyr Phe
1               5                   10

<210> SEQ ID NO 1093
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 1093

Cys Ala Ile Arg Val Gly Asn Gly Asn Glu Gln Phe Phe
1               5                   10

<210> SEQ ID NO 1094
```

```
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 1094

Cys Ala Ile Ser Glu Leu Ala Gly Val Val Asn Glu Gln Phe Phe
1               5                   10                  15

<210> SEQ ID NO 1095
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 1095

Cys Ala Ile Ser Glu Ser Ala Met Asp Thr Glu Ala Phe Phe
1               5                   10

<210> SEQ ID NO 1096
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 1096

Cys Ala Ile Ser Glu Ser Lys Gly Gly Thr Glu Ala Phe Phe
1               5                   10

<210> SEQ ID NO 1097
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 1097

Cys Ala Ile Ser Glu Ser Thr Val Gln Asn Gly Tyr Thr Phe
1               5                   10

<210> SEQ ID NO 1098
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 1098

Cys Ala Ile Ser Phe Asp Arg Gly Thr Glu Ala Phe Phe
1               5                   10

<210> SEQ ID NO 1099
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 1099

Cys Ala Ile Ser Gly Gly Leu Ala Glu Trp His Glu Gln Phe Phe
1               5                   10                  15

<210> SEQ ID NO 1100
<211> LENGTH: 15
```

```
<212> TYPE: PRT
<213> ORGANISM: Artificial sequence
<220> FEATURE:
<223> OTHER INFORMATION: Synthetic polypeptide

<400> SEQUENCE: 1100

Cys Ala Ile Ser Leu Gln Asp Leu Pro Ser Tyr Gly Tyr Thr Phe
1               5                   10                  15

<210> SEQ ID NO 1101
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 1101

Cys Ala Ile Thr Ala Gly Gln Gly Thr Arg Asn Glu Gln Tyr Phe
1               5                   10                  15

<210> SEQ ID NO 1102
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 1102

Cys Ala Ser Ala Pro Gly Arg Gly Val Asp Thr Gly Glu Leu Phe Phe
1               5                   10                  15

<210> SEQ ID NO 1103
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 1103

Cys Ala Ser Ala Arg Asp Ser Tyr Gly Tyr Thr Phe
1               5                   10

<210> SEQ ID NO 1104
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 1104

Cys Ala Ser Ala Ser Arg Asp Pro Gln Asp Thr Ile Tyr Phe
1               5                   10

<210> SEQ ID NO 1105
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 1105

Cys Ala Ser His Gly Asp Asp Ser Ala Gln Tyr Phe
1               5                   10

<210> SEQ ID NO 1106
<211> LENGTH: 15
<212> TYPE: PRT
```

```
<213> ORGANISM: Artificial sequence
<220> FEATURE:
<223> OTHER INFORMATION: Synthetic polypeptide

<400> SEQUENCE: 1106

Cys Ala Ser Ile Ser Leu Arg Gly Gly Pro Tyr Glu Gln Tyr Phe
1               5                   10                  15

<210> SEQ ID NO 1107
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 1107

Cys Ala Ser Lys Gln Gly Ala Ile Asp Thr Gln Tyr Phe
1               5                   10

<210> SEQ ID NO 1108
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 1108

Cys Ala Ser Lys Val Gly Ala Met Gly Glu Lys Leu Phe Phe
1               5                   10

<210> SEQ ID NO 1109
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 1109

Cys Ala Ser Arg Ala Ala Gly Thr Asp Thr Gln Tyr Phe
1               5                   10

<210> SEQ ID NO 1110
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 1110

Cys Ala Ser Arg Glu Gly Gly Ser Ser Gly Asn Thr Ile Tyr Phe
1               5                   10                  15

<210> SEQ ID NO 1111
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 1111

Cys Ala Ser Arg Glu Gln Gly Pro Thr Gln Thr Gly Glu Leu Phe Phe
1               5                   10                  15

<210> SEQ ID NO 1112
<211> LENGTH: 15
<212> TYPE: PRT
<213> ORGANISM: Artificial sequence
```

```
<220> FEATURE:
<223> OTHER INFORMATION: Synthetic polypeptide

<400> SEQUENCE: 1112

Cys Ala Ser Arg Glu Trp Thr Ser Gly Gly Asn Glu Gln Phe Phe
1               5                   10                  15

<210> SEQ ID NO 1113
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 1113

Cys Ala Ser Arg Gly Gly Gly Thr Ser Pro Leu His Phe
1               5                   10

<210> SEQ ID NO 1114
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 1114

Cys Ala Ser Arg Lys Asp Arg Asp Thr Glu Ala Phe Phe
1               5                   10

<210> SEQ ID NO 1115
<211> LENGTH: 18
<212> TYPE: PRT
<213> ORGANISM: Artificial sequence
<220> FEATURE:
<223> OTHER INFORMATION: Synthetic polypeptide

<400> SEQUENCE: 1115

Cys Ala Ser Arg Lys Gly Thr Gln Gly Ala Arg Ser Gly Asn Thr Ile
1               5                   10                  15

Tyr Phe

<210> SEQ ID NO 1116
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 1116

Cys Ala Ser Arg Met Gly Ser Gln Glu Thr Gln Tyr Phe
1               5                   10

<210> SEQ ID NO 1117
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 1117

Cys Ala Ser Arg Asn Gln Gly Gly Phe Gly Thr Glu Ala Phe Phe
1               5                   10                  15

<210> SEQ ID NO 1118
<211> LENGTH: 15
<212> TYPE: PRT
```

<213> ORGANISM: Artificial sequence
<220> FEATURE:
<223> OTHER INFORMATION: Synthetic polypeptide

<400> SEQUENCE: 1118

Cys Ala Ser Arg Pro Gly Thr Gly Arg Asp Gln Pro Gln His Phe
1               5                   10                  15

<210> SEQ ID NO 1119
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 1119

Cys Ala Ser Arg Pro Arg Glu Glu Asn Thr Glu Ala Phe Phe
1               5                   10

<210> SEQ ID NO 1120
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 1120

Cys Ala Ser Arg Gln Gln Thr Gly Thr Ala Asp Thr Gln Tyr Phe
1               5                   10                  15

<210> SEQ ID NO 1121
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 1121

Cys Ala Ser Arg Arg Ala Gly Gly Arg Tyr Glu Gln Tyr Phe
1               5                   10

<210> SEQ ID NO 1122
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 1122

Cys Ala Ser Arg Arg Gly Leu Ala Gly Ser Asp Thr Gln Tyr Phe
1               5                   10                  15

<210> SEQ ID NO 1123
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 1123

Cys Ala Ser Arg Arg Gln Gly Gly Asn Ser Pro Leu His Phe
1               5                   10

<210> SEQ ID NO 1124
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 1124

Cys Ala Ser Arg Ser Thr Gly Ala Gly Tyr Gly Asn Thr Ile Tyr Phe
1               5                   10                  15

<210> SEQ ID NO 1125
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 1125

Cys Ala Ser Ser Ala Ala Gly Ser Ser Gly Glu Leu Phe Phe
1               5                   10

<210> SEQ ID NO 1126
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 1126

Cys Ala Ser Ser Ala Gly Thr Gly Glu Glu Thr Gln Tyr Phe
1               5                   10

<210> SEQ ID NO 1127
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 1127

Cys Ala Ser Ser Ala Ile Glu Gly Thr Ser Gly Glu Leu Phe Phe
1               5                   10                  15

<210> SEQ ID NO 1128
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 1128

Cys Ala Ser Ser Ala Pro Gly Ala Asn Glu Lys Leu Phe Phe
1               5                   10

<210> SEQ ID NO 1129
<211> LENGTH: 10
<212> TYPE: PRT
<213> ORGANISM: Artificial sequence
<220> FEATURE:
<223> OTHER INFORMATION: Synthetic polypeptide

<400> SEQUENCE: 1129

Cys Ala Ser Ser Ala Arg Glu Gln Phe Phe
1               5                   10

<210> SEQ ID NO 1130
<211> LENGTH: 14
<212> TYPE: PRT
<213> ORGANISM: Artificial sequence
<220> FEATURE:

<223> OTHER INFORMATION: Synthetic polypeptide

<400> SEQUENCE: 1130

Cys Ala Ser Ser Ala Arg Gln Asp Pro Gly Leu Ser Phe Phe
1               5                   10

<210> SEQ ID NO 1131
<211> LENGTH: 17
<212> TYPE: PRT
<213> ORGANISM: Artificial sequence
<220> FEATURE:
<223> OTHER INFORMATION: Synthetic polypeptide

<400> SEQUENCE: 1131

Cys Ala Ser Ser Ala Thr Ser Gly Gly Gly Gly Arg Glu Thr Gln Tyr
1               5                   10                  15

Phe

<210> SEQ ID NO 1132
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 1132

Cys Ala Ser Ser Ala Tyr Val Leu Gly Thr Glu Ala Phe Phe
1               5                   10

<210> SEQ ID NO 1133
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 1133

Cys Ala Ser Ser Asp Ala Gly Gly Arg Asp Tyr Gly Tyr Thr Phe
1               5                   10                  15

<210> SEQ ID NO 1134
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 1134

Cys Ala Ser Ser Asp Gly Ala Gln Glu Thr Gln Tyr Phe
1               5                   10

<210> SEQ ID NO 1135
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 1135

Cys Ala Ser Ser Asp His Glu Arg Asp Gly Arg Glu Gln Tyr Phe
1               5                   10                  15

<210> SEQ ID NO 1136
<211> LENGTH: 15
<212> TYPE: PRT
<213> ORGANISM: Artificial sequence

```
<220> FEATURE:
<223> OTHER INFORMATION: Synthetic polypeptide

<400> SEQUENCE: 1136

Cys Ala Ser Ser Asp Pro Gly Thr Gly Asn Tyr Gly Tyr Thr Phe
1               5                   10                  15

<210> SEQ ID NO 1137
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 1137

Cys Ala Ser Ser Asp Arg Gly Asp Ser Thr Glu Ala Phe Phe
1               5                   10

<210> SEQ ID NO 1138
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 1138

Cys Ala Ser Ser Asp Trp Gly Gly Arg Asn Asp Glu Gln Phe Phe
1               5                   10                  15

<210> SEQ ID NO 1139
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 1139

Cys Ala Ser Ser Glu Ala Gly Arg Arg Thr Glu Ala Phe Phe
1               5                   10

<210> SEQ ID NO 1140
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 1140

Cys Ala Ser Ser Glu Gly Glu Val Thr Asp Thr Gln Tyr Phe
1               5                   10

<210> SEQ ID NO 1141
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 1141

Cys Ala Ser Ser Glu Gly Gly Gln Asn Asn Gln Pro Gln His Phe
1               5                   10                  15

<210> SEQ ID NO 1142
<211> LENGTH: 14
<212> TYPE: PRT
<213> ORGANISM: Artificial sequence
<220> FEATURE:
```

<223> OTHER INFORMATION: Synthetic polypeptide

<400> SEQUENCE: 1142

Cys Ala Ser Ser Glu Gly Gln Ser Asn Gln Pro Gln His Phe
1               5                   10

<210> SEQ ID NO 1143
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 1143

Cys Ala Ser Ser Glu Gly Ser Pro Tyr Glu Gln Tyr Phe
1               5                   10

<210> SEQ ID NO 1144
<211> LENGTH: 18
<212> TYPE: PRT
<213> ORGANISM: Artificial sequence
<220> FEATURE:
<223> OTHER INFORMATION: Synthetic polypeptide

<400> SEQUENCE: 1144

Cys Ala Ser Ser Glu Gln Arg Gly Gly Gln Ala Thr Phe Tyr Gly Tyr
1               5                   10                  15

Thr Phe

<210> SEQ ID NO 1145
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 1145

Cys Ala Ser Ser Glu Ser Gly Gly Ala Thr Tyr Asn Glu Gln Phe Phe
1               5                   10                  15

<210> SEQ ID NO 1146
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 1146

Cys Ala Ser Ser Glu Thr Ala Gly Gly Met Gly Glu Gln Tyr Phe
1               5                   10                  15

<210> SEQ ID NO 1147
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 1147

Cys Ala Ser Ser Glu Val Gly Gln Gln Gly Tyr Glu Gln Tyr Phe
1               5                   10                  15

<210> SEQ ID NO 1148
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 1148

Cys Ala Ser Ser Glu Tyr Gly Gly Arg Thr Glu Ala Phe Phe
1               5                   10

<210> SEQ ID NO 1149
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 1149

Cys Ala Ser Ser Phe Glu Gly Thr Gln Tyr Phe
1               5                   10

<210> SEQ ID NO 1150
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 1150

Cys Ala Ser Ser Phe Glu Arg Leu Glu Tyr Asn Glu Gln Phe Phe
1               5                   10                  15

<210> SEQ ID NO 1151
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 1151

Cys Ala Ser Ser Phe Phe Gly Gly Asn Glu Lys Leu Phe Phe
1               5                   10

<210> SEQ ID NO 1152
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 1152

Cys Ala Ser Ser Phe Gly Leu Gly Glu Gln Phe Phe
1               5                   10

<210> SEQ ID NO 1153
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 1153

Cys Ala Ser Ser Phe Met Val Ala Ala Thr Asp Thr Gln Tyr Phe
1               5                   10                  15

<210> SEQ ID NO 1154
<211> LENGTH: 14
<212> TYPE: PRT
<213> ORGANISM: Artificial sequence
<220> FEATURE:

```
<223> OTHER INFORMATION: Synthetic polypeptide

<400> SEQUENCE: 1154

Cys Ala Ser Ser Phe Gln Ala Gly Ala Asn Val Leu Thr Phe
1               5                   10

<210> SEQ ID NO 1155
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 1155

Cys Ala Ser Ser Phe Arg Gly Ser Asn Thr Gly Glu Leu Phe Phe
1               5                   10                  15

<210> SEQ ID NO 1156
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 1156

Cys Ala Ser Ser Phe Arg Tyr Thr Gly Glu Leu Phe Phe
1               5                   10

<210> SEQ ID NO 1157
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 1157

Cys Ala Ser Ser Phe Ser Gly Thr Ser Pro Tyr Glu Gln Tyr Phe
1               5                   10                  15

<210> SEQ ID NO 1158
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 1158

Cys Ala Ser Ser Phe Ser Ser Gly Ala Asn Val Leu Thr Phe
1               5                   10

<210> SEQ ID NO 1159
<211> LENGTH: 17
<212> TYPE: PRT
<213> ORGANISM: Artificial sequence
<220> FEATURE:
<223> OTHER INFORMATION: Synthetic polypeptide

<400> SEQUENCE: 1159

Cys Ala Ser Ser Phe Thr Gly Asp Pro Pro Leu Gly Thr Glu Ala Phe
1               5                   10                  15

Phe

<210> SEQ ID NO 1160
<211> LENGTH: 12
<212> TYPE: PRT
<213> ORGANISM: Artificial sequence
```

<220> FEATURE:
<223> OTHER INFORMATION: Synthetic polypeptide

<400> SEQUENCE: 1160

Cys Ala Ser Ser Gly Gly Gly Thr Glu Ala Phe Phe
1               5                   10

<210> SEQ ID NO 1161
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 1161

Cys Ala Ser Ser Gly Pro Asn Tyr Asn Ser Pro Leu His Phe
1               5                   10

<210> SEQ ID NO 1162
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 1162

Cys Ala Ser Ser Gly Gln Ser Ile Tyr Glu Gln Tyr Phe
1               5                   10

<210> SEQ ID NO 1163
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 1163

Cys Ala Ser Ser Gly Arg Glu Asn Tyr Gly Tyr Thr Phe
1               5                   10

<210> SEQ ID NO 1164
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 1164

Cys Ala Ser Ser Gly Thr Gly Gly Ala Ala Asp Gln Pro Gln His Phe
1               5                   10                  15

<210> SEQ ID NO 1165
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 1165

Cys Ala Ser Ser Gly Thr Gly Gly Gly Pro Gln His Phe
1               5                   10

<210> SEQ ID NO 1166
<211> LENGTH: 15
<212> TYPE: PRT
<213> ORGANISM: Artificial sequence
<220> FEATURE:

<223> OTHER INFORMATION: Synthetic polypeptide

<400> SEQUENCE: 1166

Cys Ala Ser Ser His Gly Gln Gly Tyr Ala Asp Thr Gln Tyr Phe
1               5                   10                  15

<210> SEQ ID NO 1167
<211> LENGTH: 18
<212> TYPE: PRT
<213> ORGANISM: Artificial sequence
<220> FEATURE:
<223> OTHER INFORMATION: Synthetic polypeptide

<400> SEQUENCE: 1167

Cys Ala Ser Ser Ile Asp Arg Met Ala Gly Ser Ser Tyr Asn Glu Gln
1               5                   10                  15

Phe Phe

<210> SEQ ID NO 1168
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 1168

Cys Ala Ser Ser Ile Gln Gly Gly Ser Val Gln Glu Thr Gln Tyr Phe
1               5                   10                  15

<210> SEQ ID NO 1169
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 1169

Cys Ala Ser Ser Ile Arg Glu Asp Thr Glu Ala Phe Phe
1               5                   10

<210> SEQ ID NO 1170
<211> LENGTH: 17
<212> TYPE: PRT
<213> ORGANISM: Artificial sequence
<220> FEATURE:
<223> OTHER INFORMATION: Synthetic polypeptide

<400> SEQUENCE: 1170

Cys Ala Ser Ser Ile Ser Ala Ser Gly Gly Ser Tyr Asn Glu Gln Phe
1               5                   10                  15

Phe

<210> SEQ ID NO 1171
<211> LENGTH: 21
<212> TYPE: PRT
<213> ORGANISM: Artificial sequence
<220> FEATURE:
<223> OTHER INFORMATION: Synthetic polypeptide

<400> SEQUENCE: 1171

Cys Ala Ser Ser Lys Ile Arg Thr Gly Gly Arg Gln Ala Val Asn Thr
1               5                   10                  15

Asp Thr Gln Tyr Phe
            20

```
<210> SEQ ID NO 1172
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 1172

Cys Ala Ser Ser Lys Arg Ala Ile Glu Gln Tyr Phe
1               5                   10

<210> SEQ ID NO 1173
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 1173

Cys Ala Ser Ser Leu Ala Gly Gly Gly Ser Ala Tyr Glu Gln Tyr Phe
1               5                   10                  15

<210> SEQ ID NO 1174
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 1174

Cys Ala Ser Ser Leu Ala Gly Thr Gly Tyr Glu Gln Tyr Phe
1               5                   10

<210> SEQ ID NO 1175
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 1175

Cys Ala Ser Ser Leu Ala Pro Gln Asp Gln Ala Phe Phe
1               5                   10

<210> SEQ ID NO 1176
<211> LENGTH: 17
<212> TYPE: PRT
<213> ORGANISM: Artificial sequence
<220> FEATURE:
<223> OTHER INFORMATION: Synthetic polypeptide

<400> SEQUENCE: 1176

Cys Ala Ser Ser Leu Ala Arg Gln Gly Asp Arg Asn Tyr Gly Tyr Thr
1               5                   10                  15

Phe

<210> SEQ ID NO 1177
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 1177

Cys Ala Ser Ser Leu Ala Ser Ala Thr His Thr Gly Glu Leu Phe Phe
1               5                   10                  15
```

```
<210> SEQ ID NO 1178
<211> LENGTH: 17
<212> TYPE: PRT
<213> ORGANISM: Artificial sequence
<220> FEATURE:
<223> OTHER INFORMATION: Synthetic polypeptide

<400> SEQUENCE: 1178

Cys Ala Ser Ser Leu Asp Gly Ala Gly Val Ser Leu Asn Glu Gln Phe
1               5                   10                  15

Phe

<210> SEQ ID NO 1179
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 1179

Cys Ala Ser Ser Leu Asp Gly Ala Arg Asp Thr Gly Glu Leu Phe Phe
1               5                   10                  15

<210> SEQ ID NO 1180
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 1180

Cys Ala Ser Ser Leu Asp Gly Gly Ala Gly Asn Thr Ile Tyr Phe
1               5                   10                  15

<210> SEQ ID NO 1181
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 1181

Cys Ala Ser Ser Leu Asp Gly Leu Ala Gly Thr Asp Thr Gln Tyr Phe
1               5                   10                  15

<210> SEQ ID NO 1182
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 1182

Cys Ala Ser Ser Leu Asp Trp Arg Gln Glu Ser Glu Thr Gln Tyr Phe
1               5                   10                  15

<210> SEQ ID NO 1183
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 1183

Cys Ala Ser Ser Leu Glu Ala Gly Asp Leu Tyr Glu Gln Tyr Phe
```

<210> SEQ ID NO 1184
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 1184

Cys Ala Ser Ser Leu Glu Gly Ala Gly Tyr Thr Gly Glu Leu Phe Phe
1               5                   10                  15

<210> SEQ ID NO 1185
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 1185

Cys Ala Ser Ser Leu Glu Gly Gln Ala Val Thr Gly Glu Leu Phe Phe
1               5                   10                  15

<210> SEQ ID NO 1186
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 1186

Cys Ala Ser Ser Leu Glu Gly Val Gly Gln Asn Tyr Gly Tyr Thr Phe
1               5                   10                  15

<210> SEQ ID NO 1187
<211> LENGTH: 18
<212> TYPE: PRT
<213> ORGANISM: Artificial sequence
<220> FEATURE:
<223> OTHER INFORMATION: Synthetic polypeptide

<400> SEQUENCE: 1187

Cys Ala Ser Ser Leu Glu Arg Gly Leu Ala Gly Val Val Gly Glu Gln
1               5                   10                  15

Phe Phe

<210> SEQ ID NO 1188
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 1188

Cys Ala Ser Ser Leu Glu Ser Ser Gly Ser Leu Gly Glu Gln Tyr Phe
1               5                   10                  15

<210> SEQ ID NO 1189
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 1189

Cys Ala Ser Ser Leu Glu Thr Arg Asn Thr Glu Ala Phe Phe
1               5                   10

<210> SEQ ID NO 1190
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 1190

Cys Ala Ser Ser Leu Phe Leu Glu Asn Thr Glu Ala Phe Phe
1               5                   10

<210> SEQ ID NO 1191
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 1191

Cys Ala Ser Ser Leu Phe Leu Gly Thr Gly Asn Thr Ile Tyr Phe
1               5                   10                  15

<210> SEQ ID NO 1192
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 1192

Cys Ala Ser Ser Leu Gly Ala Gly Ala Leu Gly Glu Thr Gln Tyr Phe
1               5                   10                  15

<210> SEQ ID NO 1193
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 1193

Cys Ala Ser Ser Leu Gly Ala Gly Gly Ala Thr Asp Thr Gln Tyr Phe
1               5                   10                  15

<210> SEQ ID NO 1194
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 1194

Cys Ala Ser Ser Leu Gly Gly Asp Arg Gly Ala Glu Lys Leu Phe Phe
1               5                   10                  15

<210> SEQ ID NO 1195
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 1195

Cys Ala Ser Ser Leu Gly Gly Gly Thr Glu Ala Phe Phe

```
1               5                   10
```

<210> SEQ ID NO 1196
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 1196

```
Cys Ala Ser Ser Leu Gly Ser Phe Ser Tyr Glu Gln Tyr Phe
1               5                   10
```

<210> SEQ ID NO 1197
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 1197

```
Cys Ala Ser Ser Leu Gly Ser Gly Ala Ser Asn Gln Pro Gln His Phe
1               5                   10                  15
```

<210> SEQ ID NO 1198
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 1198

```
Cys Ala Ser Ser Leu Gly Thr Phe Asn Tyr Gly Tyr Thr Phe
1               5                   10
```

<210> SEQ ID NO 1199
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 1199

```
Cys Ala Ser Ser Leu Gly Thr Ser Gln Glu Thr Gln Tyr Phe
1               5                   10
```

<210> SEQ ID NO 1200
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 1200

```
Cys Ala Ser Ser Leu Gly Val Ala Pro Thr Asp Thr Gln Tyr Phe
1               5                   10                  15
```

<210> SEQ ID NO 1201
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 1201

```
Cys Ala Ser Ser Leu Leu Ala Asn Glu Gln Tyr Phe
1               5                   10
```

<210> SEQ ID NO 1202
<211> LENGTH: 21
<212> TYPE: PRT
<213> ORGANISM: Artificial sequence
<220> FEATURE:
<223> OTHER INFORMATION: Synthetic polypeptide

<400> SEQUENCE: 1202

Cys Ala Ser Ser Leu Leu Val Gly Gln Thr Asn Ile Val Ser Gly Ala
1               5                   10                  15

Asn Val Leu Thr Phe
            20

<210> SEQ ID NO 1203
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 1203

Cys Ala Ser Ser Leu Pro Ala Gly Thr Gly Thr Gly Glu Leu Phe Phe
1               5                   10                  15

<210> SEQ ID NO 1204
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 1204

Cys Ala Ser Ser Leu Gln Gly Ser Ser Gln Pro Gln His Phe
1               5                   10

<210> SEQ ID NO 1205
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 1205

Cys Ala Ser Ser Leu Arg Ala Gly Gly Ser Thr Asp Thr Gln Tyr Phe
1               5                   10                  15

<210> SEQ ID NO 1206
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 1206

Cys Ala Ser Ser Leu Arg Asp Thr Gly Phe His Phe
1               5                   10

<210> SEQ ID NO 1207
<211> LENGTH: 20
<212> TYPE: PRT
<213> ORGANISM: Artificial sequence
<220> FEATURE:
<223> OTHER INFORMATION: Synthetic polypeptide

<400> SEQUENCE: 1207

Cys Ala Ser Ser Leu Ser Ala Leu Gly Leu Ala Gly Gly Asn Thr Gly
1               5                   10                  15

Glu Leu Phe Phe
            20

<210> SEQ ID NO 1208
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 1208

Cys Ala Ser Ser Leu Ser Gly Gln Gly Thr Gly Glu Gln Tyr Phe
1               5                   10                  15

<210> SEQ ID NO 1209
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 1209

Cys Ala Ser Ser Leu Ser Arg Ile Gly Gly Gly Tyr Thr Phe
1               5                   10

<210> SEQ ID NO 1210
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 1210

Cys Ala Ser Ser Leu Ser Thr Asp Thr Gln Tyr Phe
1               5                   10

<210> SEQ ID NO 1211
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 1211

Cys Ala Ser Ser Leu Thr Asp Arg Ser Pro Gln Tyr Phe
1               5                   10

<210> SEQ ID NO 1212
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 1212

Cys Ala Ser Ser Leu Thr Gly Leu Thr Glu Ala Phe Phe
1               5                   10

<210> SEQ ID NO 1213
<211> LENGTH: 14
<212> TYPE: PRT
<213> ORGANISM: Artificial sequence
<220> FEATURE:
<223> OTHER INFORMATION: Synthetic polypeptide

```
<400> SEQUENCE: 1213

Cys Ala Ser Ser Leu Thr Gly Thr Gly Ile Gly Tyr Thr Phe
1               5                   10

<210> SEQ ID NO 1214
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 1214

Cys Ala Ser Ser Leu Thr Gln Gly Ile Thr Asp Thr Gln Tyr Phe
1               5                   10                  15

<210> SEQ ID NO 1215
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 1215

Cys Ala Ser Ser Leu Val Gly Met Asn Thr Glu Ala Phe Phe
1               5                   10

<210> SEQ ID NO 1216
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 1216

Cys Ala Ser Ser Leu Val Leu Gly Glu Thr Gln Tyr Phe
1               5                   10

<210> SEQ ID NO 1217
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 1217

Cys Ala Ser Ser Leu Val Pro Thr Tyr Thr Asp Thr Gln Tyr Phe
1               5                   10                  15

<210> SEQ ID NO 1218
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 1218

Cys Ala Ser Ser Leu Val Ser Asp Gln Ser Asn Glu Gln Phe Phe
1               5                   10                  15

<210> SEQ ID NO 1219
<211> LENGTH: 17
<212> TYPE: PRT
<213> ORGANISM: Artificial sequence
<220> FEATURE:
<223> OTHER INFORMATION: Synthetic polypeptide

<400> SEQUENCE: 1219
```

-continued

```
Cys Ala Ser Ser Leu Val Tyr Ser Gly Asp Arg Thr Asp Thr Gln Tyr
1               5                   10                  15

Phe

<210> SEQ ID NO 1220
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 1220

Cys Ala Ser Ser Met Asp Arg Gly Ser Gly Glu Leu Phe Phe
1               5                   10

<210> SEQ ID NO 1221
<211> LENGTH: 17
<212> TYPE: PRT
<213> ORGANISM: Artificial sequence
<220> FEATURE:
<223> OTHER INFORMATION: Synthetic polypeptide

<400> SEQUENCE: 1221

Cys Ala Ser Ser Asn Arg Gly Leu Gly Ser Gly Ala Asn Val Leu Thr
1               5                   10                  15

Phe

<210> SEQ ID NO 1222
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 1222

Cys Ala Ser Ser Pro Glu Ser Gly Arg Tyr Asn Glu Gln Phe Phe
1               5                   10                  15

<210> SEQ ID NO 1223
<211> LENGTH: 18
<212> TYPE: PRT
<213> ORGANISM: Artificial sequence
<220> FEATURE:
<223> OTHER INFORMATION: Synthetic polypeptide

<400> SEQUENCE: 1223

Cys Ala Ser Ser Pro Phe Gly Arg Leu Trp Ala Thr Asn Glu Lys Leu
1               5                   10                  15

Phe Phe

<210> SEQ ID NO 1224
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 1224

Cys Ala Ser Ser Pro Gly Ala Gly Glu Gln Tyr Phe
1               5                   10

<210> SEQ ID NO 1225
<211> LENGTH: 16
<212> TYPE: PRT
```

<213> ORGANISM: Artificial sequence
<220> FEATURE:
<223> OTHER INFORMATION: Synthetic polypeptide

<400> SEQUENCE: 1225

Cys Ala Ser Ser Pro Gly Ala Gly Leu Asn Thr Gly Glu Leu Phe Phe
1               5                   10                  15

<210> SEQ ID NO 1226
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 1226

Cys Ala Ser Ser Pro Gly Gly Thr Gly Gly Ala Tyr Gly Tyr Thr Phe
1               5                   10                  15

<210> SEQ ID NO 1227
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 1227

Cys Ala Ser Ser Pro Gly Thr Arg Ala Phe Phe
1               5                   10

<210> SEQ ID NO 1228
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 1228

Cys Ala Ser Ser Pro Leu Leu Ala Ser Asp Glu Gln Phe Phe
1               5                   10

<210> SEQ ID NO 1229
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 1229

Cys Ala Ser Ser Pro Met Ala Gly Pro Ser Phe Tyr Glu Gln Tyr Phe
1               5                   10                  15

<210> SEQ ID NO 1230
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 1230

Cys Ala Ser Ser Pro Pro Gly Gly Pro Tyr Glu Gln Tyr Phe
1               5                   10

<210> SEQ ID NO 1231
<211> LENGTH: 16
<212> TYPE: PRT
<213> ORGANISM: Artificial sequence

```
<220> FEATURE:
<223> OTHER INFORMATION: Synthetic polypeptide

<400> SEQUENCE: 1231

Cys Ala Ser Ser Pro Gln Gly Leu Gly Asn Asn Ser Pro Leu His Phe
1               5                   10                  15

<210> SEQ ID NO 1232
<211> LENGTH: 18
<212> TYPE: PRT
<213> ORGANISM: Artificial sequence
<220> FEATURE:
<223> OTHER INFORMATION: Synthetic polypeptide

<400> SEQUENCE: 1232

Cys Ala Ser Ser Pro Gln Gly Val Ser Phe Met Ser Asn Gln Pro Gln
1               5                   10                  15

His Phe

<210> SEQ ID NO 1233
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 1233

Cys Ala Ser Ser Pro Arg Leu Ala Gly Ser Tyr Glu Gln Tyr Phe
1               5                   10                  15

<210> SEQ ID NO 1234
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 1234

Cys Ala Ser Ser Pro Arg Gln Tyr Glu Gln Phe Phe
1               5                   10

<210> SEQ ID NO 1235
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 1235

Cys Ala Ser Ser Pro Ser Asp Arg Gly Gly Lys Leu Phe Phe
1               5                   10

<210> SEQ ID NO 1236
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 1236

Cys Ala Ser Ser Pro Ser Gly Gly Arg Val Ser Pro Leu His Phe
1               5                   10                  15

<210> SEQ ID NO 1237
<211> LENGTH: 14
<212> TYPE: PRT
```

```
<213> ORGANISM: Artificial sequence
<220> FEATURE:
<223> OTHER INFORMATION: Synthetic polypeptide

<400> SEQUENCE: 1237

Cys Ala Ser Ser Pro Ser Gly Gly Val Asn Glu Gln Phe Phe
1               5                   10

<210> SEQ ID NO 1238
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 1238

Cys Ala Ser Ser Pro Ser Arg Val Asn Thr Glu Ala Phe Phe
1               5                   10

<210> SEQ ID NO 1239
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 1239

Cys Ala Ser Ser Pro Thr Ala Ala Ala Ser Tyr Asn Glu Gln Phe Phe
1               5                   10                  15

<210> SEQ ID NO 1240
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 1240

Cys Ala Ser Ser Pro Val Asp Glu Gly Thr Gly Glu Leu Phe Phe
1               5                   10                  15

<210> SEQ ID NO 1241
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 1241

Cys Ala Ser Ser Pro Val Ser Gly Gly Gly Asp Thr Gln Tyr Phe
1               5                   10                  15

<210> SEQ ID NO 1242
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 1242

Cys Ala Ser Ser Pro Trp Gly Ile Pro Glu Ala Phe Phe
1               5                   10

<210> SEQ ID NO 1243
<211> LENGTH: 14
<212> TYPE: PRT
<213> ORGANISM: Artificial sequence
```

```
<220> FEATURE:
<223> OTHER INFORMATION: Synthetic polypeptide

<400> SEQUENCE: 1243

Cys Ala Ser Ser Gln Ala Ala Arg Ala Glu Thr Gln Tyr Phe
1               5                   10

<210> SEQ ID NO 1244
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 1244

Cys Ala Ser Ser Gln Asp Pro Glu Gly Tyr Thr Phe
1               5                   10

<210> SEQ ID NO 1245
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 1245

Cys Ala Ser Ser Gln Asp Arg Gly Ala Ala Asn Tyr Gly Tyr Thr Phe
1               5                   10                  15

<210> SEQ ID NO 1246
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 1246

Cys Ala Ser Ser Gln Asp Arg Gly Val Glu Gln Tyr Phe
1               5                   10

<210> SEQ ID NO 1247
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 1247

Cys Ala Ser Ser Gln Asp Ser Ile Gln Gly Ser Gly Tyr Thr Phe
1               5                   10                  15

<210> SEQ ID NO 1248
<211> LENGTH: 18
<212> TYPE: PRT
<213> ORGANISM: Artificial sequence
<220> FEATURE:
<223> OTHER INFORMATION: Synthetic polypeptide

<400> SEQUENCE: 1248

Cys Ala Ser Ser Gln Asp Val Ser Gly Thr Gly Gly Ser Tyr Glu Gln
1               5                   10                  15

Tyr Phe

<210> SEQ ID NO 1249
<211> LENGTH: 13
<212> TYPE: PRT
```

<213> ORGANISM: Artificial sequence
<220> FEATURE:
<223> OTHER INFORMATION: Synthetic polypeptide

<400> SEQUENCE: 1249

Cys Ala Ser Ser Gln Glu Glu Gly Glu Lys Leu Phe Phe
1               5                   10

<210> SEQ ID NO 1250
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 1250

Cys Ala Ser Ser Gln Glu Gly Gln Ser Ala Ala Phe Phe
1               5                   10

<210> SEQ ID NO 1251
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 1251

Cys Ala Ser Ser Gln Glu Thr Ser Gly Arg Ala Tyr Glu Gln Tyr Phe
1               5                   10                  15

<210> SEQ ID NO 1252
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 1252

Cys Ala Ser Ser Gln Phe Gly Glu Gly Pro Thr Gly Gly Gln Phe Phe
1               5                   10                  15

<210> SEQ ID NO 1253
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 1253

Cys Ala Ser Ser Gln Gly Gly Thr Gly Glu Leu Phe Phe
1               5                   10

<210> SEQ ID NO 1254
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 1254

Cys Ala Ser Ser Gln Gly Pro Gly Ser Asn Gln Pro Gln His Phe
1               5                   10                  15

<210> SEQ ID NO 1255
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 1255

Cys Ala Ser Ser Gln Gly Arg Asn Thr Gly Glu Leu Phe Phe
1               5                   10

<210> SEQ ID NO 1256
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 1256

Cys Ala Ser Ser Gln Gly Thr Gly Gly Gly Tyr Thr Phe
1               5                   10

<210> SEQ ID NO 1257
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 1257

Cys Ala Ser Ser Gln His Gln Gly Ala Gly Asn Thr Ile Tyr Phe
1               5                   10                  15

<210> SEQ ID NO 1258
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 1258

Cys Ala Ser Ser Gln Pro Thr Gly Gly Ala Tyr Asn Glu Gln Phe Phe
1               5                   10                  15

<210> SEQ ID NO 1259
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 1259

Cys Ala Ser Ser Gln Arg Gly Asp Asp Thr Gly Glu Leu Phe Phe
1               5                   10                  15

<210> SEQ ID NO 1260
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 1260

Cys Ala Ser Ser Gln Val Pro Gly Glu Gln Arg Glu Gln Tyr Phe
1               5                   10                  15

<210> SEQ ID NO 1261
<211> LENGTH: 17
<212> TYPE: PRT
<213> ORGANISM: Artificial sequence
<220> FEATURE:

<223> OTHER INFORMATION: Synthetic polypeptide

<400> SEQUENCE: 1261

Cys Ala Ser Ser Arg Ala Glu Ala Ser Ser Gly Ala Asn Val Leu Thr
1               5                   10                  15

Phe

<210> SEQ ID NO 1262
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 1262

Cys Ala Ser Ser Arg Ala Leu Gly Asp Asn Tyr Gly Tyr Thr Phe
1               5                   10                  15

<210> SEQ ID NO 1263
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 1263

Cys Ala Ser Ser Arg Asp Leu Gly Ala Thr Asn Glu Lys Leu Phe Phe
1               5                   10                  15

<210> SEQ ID NO 1264
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 1264

Cys Ala Ser Ser Arg Gly Glu Gly Lys Ala Glu Ala Phe Phe
1               5                   10

<210> SEQ ID NO 1265
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 1265

Cys Ala Ser Ser Arg Gly Ser Tyr Asn Glu Gln Phe Phe
1               5                   10

<210> SEQ ID NO 1266
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 1266

Cys Ala Ser Ser Arg Gly Thr Asp Gln Pro Gln His Phe
1               5                   10

<210> SEQ ID NO 1267
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 1267

Cys Ala Ser Ser Arg Pro Phe Gly Glu Leu Phe Phe
1               5                   10

<210> SEQ ID NO 1268
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 1268

Cys Ala Ser Ser Arg Gln Gly Arg Gly Glu Lys Leu Phe Phe
1               5                   10

<210> SEQ ID NO 1269
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 1269

Cys Ala Ser Ser Arg Arg Gly Leu Asn Tyr Glu Gln Tyr Phe
1               5                   10

<210> SEQ ID NO 1270
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 1270

Cys Ala Ser Ser Ser Ala Gln Val Gly Ala Asn Val Leu Thr Phe
1               5                   10                  15

<210> SEQ ID NO 1271
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 1271

Cys Ala Ser Ser Ser Asp Arg Ala Asn Thr Glu Ala Phe Phe
1               5                   10

<210> SEQ ID NO 1272
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 1272

Cys Ala Ser Ser Ser Gly Gly Gly Thr Glu Ala Phe Phe
1               5                   10

<210> SEQ ID NO 1273
<211> LENGTH: 15
<212> TYPE: PRT
<213> ORGANISM: Artificial sequence
<220> FEATURE:

```
<223> OTHER INFORMATION: Synthetic polypeptide

<400> SEQUENCE: 1273

Cys Ala Ser Ser Ser Gly Gln Gly Ala Arg Thr Glu Ala Phe Phe
1               5                   10                  15

<210> SEQ ID NO 1274
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 1274

Cys Ala Ser Ser Ser Gly Arg Gly Phe Asp Thr Gln Tyr Phe
1               5                   10

<210> SEQ ID NO 1275
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 1275

Cys Ala Ser Ser Ser Gly Ser Glu Thr Gln Tyr Phe
1               5                   10

<210> SEQ ID NO 1276
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 1276

Cys Ala Ser Ser Ser Lys Arg Ala Gly Gly Tyr Thr Phe
1               5                   10

<210> SEQ ID NO 1277
<211> LENGTH: 17
<212> TYPE: PRT
<213> ORGANISM: Artificial sequence
<220> FEATURE:
<223> OTHER INFORMATION: Synthetic polypeptide

<400> SEQUENCE: 1277

Cys Ala Ser Ser Ser Leu Glu Arg Gly Gly Arg Arg Gly Glu Gln Tyr
1               5                   10                  15

Phe

<210> SEQ ID NO 1278
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 1278

Cys Ala Ser Ser Ser Asn Gln Trp Gly Asn Glu Lys Leu Phe Phe
1               5                   10                  15

<210> SEQ ID NO 1279
<211> LENGTH: 13
<212> TYPE: PRT
<213> ORGANISM: Artificial sequence
```

```
<220> FEATURE:
<223> OTHER INFORMATION: Synthetic polypeptide

<400> SEQUENCE: 1279

Cys Ala Ser Ser Pro Ser Gly Asn Thr Ile Tyr Phe
1               5                   10

<210> SEQ ID NO 1280
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 1280

Cys Ala Ser Ser Ser Arg Thr Gly Ala Ser Glu Thr Gln Tyr Phe
1               5                   10                  15

<210> SEQ ID NO 1281
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 1281

Cys Ala Ser Ser Ser Arg Val Arg Gln Pro Gln His Phe
1               5                   10

<210> SEQ ID NO 1282
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 1282

Cys Ala Ser Ser Ser Thr Gly Gly Asn Glu Gln Phe Phe
1               5                   10

<210> SEQ ID NO 1283
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 1283

Cys Ala Ser Ser Ser Thr Gln Ser Thr Gly Leu Val Glu Ala Phe Phe
1               5                   10                  15

<210> SEQ ID NO 1284
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 1284

Cys Ala Ser Ser Thr Gly Gly His Gly Thr Gln Tyr Phe
1               5                   10

<210> SEQ ID NO 1285
<211> LENGTH: 14
<212> TYPE: PRT
<213> ORGANISM: Artificial sequence
<220> FEATURE:
```

<223> OTHER INFORMATION: Synthetic polypeptide

<400> SEQUENCE: 1285

Cys Ala Ser Ser Thr Leu Thr Gly Ala Gly Glu Leu Phe Phe
1               5                   10

<210> SEQ ID NO 1286
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 1286

Cys Ala Ser Ser Thr Leu Thr Gly Gly Arg Asn Glu Gln Phe Phe
1               5                   10                  15

<210> SEQ ID NO 1287
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 1287

Cys Ala Ser Ser Thr Gln Gly Asn Ile Gln Tyr Phe
1               5                   10

<210> SEQ ID NO 1288
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 1288

Cys Ala Ser Ser Thr Arg Ala Gln Ser Tyr Asn Glu Gln Phe Phe
1               5                   10                  15

<210> SEQ ID NO 1289
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 1289

Cys Ala Ser Ser Thr Arg Thr Asp Asn Arg Gly Tyr Thr Phe
1               5                   10

<210> SEQ ID NO 1290
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 1290

Cys Ala Ser Ser Thr Arg Thr Gly Gly Lys Glu Thr Gln Tyr Phe
1               5                   10                  15

<210> SEQ ID NO 1291
<211> LENGTH: 18
<212> TYPE: PRT
<213> ORGANISM: Artificial sequence
<220> FEATURE:
<223> OTHER INFORMATION: Synthetic polypeptide

```
<400> SEQUENCE: 1291

Cys Ala Ser Ser Thr Thr Leu Gly Thr Gly Ser Phe Gln Glu Thr Gln
1               5                   10                  15

Tyr Phe

<210> SEQ ID NO 1292
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 1292

Cys Ala Ser Ser Thr Thr Ser Gly Gly Ser Tyr Glu Gln Tyr Phe
1               5                   10                  15

<210> SEQ ID NO 1293
<211> LENGTH: 17
<212> TYPE: PRT
<213> ORGANISM: Artificial sequence
<220> FEATURE:
<223> OTHER INFORMATION: Synthetic polypeptide

<400> SEQUENCE: 1293

Cys Ala Ser Ser Val Gly Asp Leu Trp Gly Pro Gln Glu Thr Gln Tyr
1               5                   10                  15

Phe

<210> SEQ ID NO 1294
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 1294

Cys Ala Ser Ser Val Gly Leu Ala Gly Ser Asn Glu Gln Phe Phe
1               5                   10                  15

<210> SEQ ID NO 1295
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 1295

Cys Ala Ser Ser Val Gly Pro Glu Tyr Glu Gln Tyr Phe
1               5                   10

<210> SEQ ID NO 1296
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 1296

Cys Ala Ser Ser Val Gly Arg Gly Gly Ser Asn Glu Gln Phe Phe
1               5                   10                  15

<210> SEQ ID NO 1297
<211> LENGTH: 13
<212> TYPE: PRT
```

<213> ORGANISM: Artificial sequence
<220> FEATURE:
<223> OTHER INFORMATION: Synthetic polypeptide

<400> SEQUENCE: 1297

Cys Ala Ser Ser Val Lys Ile Asp Ser Glu Ala Phe Phe
1               5                   10

<210> SEQ ID NO 1298
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 1298

Cys Ala Ser Ser Val Leu Ala Gly Gly His Asn Glu Gln Phe Phe
1               5                   10                  15

<210> SEQ ID NO 1299
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 1299

Cys Ala Ser Ser Val Arg Thr Ser Val Gly Glu Thr Gln Tyr Phe
1               5                   10                  15

<210> SEQ ID NO 1300
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 1300

Cys Ala Ser Ser Val Thr Gly Asp Ser Asn Ser Pro Leu His Phe
1               5                   10                  15

<210> SEQ ID NO 1301
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 1301

Cys Ala Ser Ser Val Val Gly Leu Ala Ala Thr Asp Thr Gln Tyr Phe
1               5                   10                  15

<210> SEQ ID NO 1302
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 1302

Cys Ala Ser Ser Trp Ser Gly Asp Thr Glu Ala Phe Phe
1               5                   10

<210> SEQ ID NO 1303
<211> LENGTH: 18
<212> TYPE: PRT
<213> ORGANISM: Artificial sequence

```
<220> FEATURE:
<223> OTHER INFORMATION: Synthetic polypeptide

<400> SEQUENCE: 1303

Cys Ala Ser Ser Tyr Gly Thr Ser Gly Arg Val Ile Gln Glu Thr Gln
1               5                   10                  15

Tyr Phe

<210> SEQ ID NO 1304
<211> LENGTH: 18
<212> TYPE: PRT
<213> ORGANISM: Artificial sequence
<220> FEATURE:
<223> OTHER INFORMATION: Synthetic polypeptide

<400> SEQUENCE: 1304

Cys Ala Ser Ser Tyr Gly Thr Ser Gly Ser Leu Gly Tyr Asn Glu Gln
1               5                   10                  15

Phe Phe

<210> SEQ ID NO 1305
<211> LENGTH: 20
<212> TYPE: PRT
<213> ORGANISM: Artificial sequence
<220> FEATURE:
<223> OTHER INFORMATION: Synthetic polypeptide

<400> SEQUENCE: 1305

Cys Ala Ser Ser Tyr Lys Pro Gly Thr Ser Gly Gly Gly Thr Pro Asp
1               5                   10                  15

Thr Gln Tyr Phe
            20

<210> SEQ ID NO 1306
<211> LENGTH: 18
<212> TYPE: PRT
<213> ORGANISM: Artificial sequence
<220> FEATURE:
<223> OTHER INFORMATION: Synthetic polypeptide

<400> SEQUENCE: 1306

Cys Ala Ser Ser Tyr Asn Lys Val Ala Gly Gly Asn Thr Gly Glu Leu
1               5                   10                  15

Phe Phe

<210> SEQ ID NO 1307
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 1307

Cys Ala Ser Ser Tyr Asn Ser Pro Leu His Phe
1               5                   10

<210> SEQ ID NO 1308
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 1308
```

Cys Ala Ser Ser Tyr Arg Glu Tyr Leu Tyr Asn Glu Gln Phe Phe
1               5                   10                  15

<210> SEQ ID NO 1309
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 1309

Cys Ala Ser Ser Tyr Ser Gly Gly Thr Gln Glu Thr Gln Tyr Phe
1               5                   10                  15

<210> SEQ ID NO 1310
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 1310

Cys Ala Ser Ser Tyr Thr Gly Gly Ala Gly Tyr Thr Phe
1               5                   10

<210> SEQ ID NO 1311
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 1311

Cys Ala Ser Thr Gly Gly Ser Thr Asp Thr Gln Tyr Phe
1               5                   10

<210> SEQ ID NO 1312
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 1312

Cys Ala Ser Thr Leu Gln Val Ser Glu Thr Gln Tyr Phe
1               5                   10

<210> SEQ ID NO 1313
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 1313

Cys Ala Ser Thr Pro Gln Glu Tyr Gln Glu Thr Gln Tyr Phe
1               5                   10

<210> SEQ ID NO 1314
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 1314

Cys Ala Ser Thr Gln Gly Pro Asn Glu Gln Phe Phe

```
1               5                   10
```

<210> SEQ ID NO 1315
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 1315

```
Cys Ala Ser Thr Trp Asp Ser Asn Gln Pro Gln His Phe
1               5                   10
```

<210> SEQ ID NO 1316
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 1316

```
Cys Ala Thr Gly Thr Gly Thr Val Gly Glu Thr Gln Tyr Phe
1               5                   10
```

<210> SEQ ID NO 1317
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 1317

```
Cys Ala Thr Gln Arg Asp Leu Asn Ser Pro Leu His Phe
1               5                   10
```

<210> SEQ ID NO 1318
<211> LENGTH: 19
<212> TYPE: PRT
<213> ORGANISM: Artificial sequence
<220> FEATURE:
<223> OTHER INFORMATION: Synthetic polypeptide

<400> SEQUENCE: 1318

```
Cys Ala Thr Ser Ala Pro Gly Leu Ser Gly Thr Ser Gly Tyr Asn Glu
1               5                   10                  15

Gln Phe Phe
```

<210> SEQ ID NO 1319
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 1319

```
Cys Ala Thr Ser Ala Ser Ala Phe Gly Gly Tyr Thr Phe
1               5                   10
```

<210> SEQ ID NO 1320
<211> LENGTH: 19
<212> TYPE: PRT
<213> ORGANISM: Artificial sequence
<220> FEATURE:
<223> OTHER INFORMATION: Synthetic polypeptide

<400> SEQUENCE: 1320

Cys Ala Thr Ser Asp Leu Ser Gln Pro Gly Arg Met Gly Thr Asp Thr
1               5                   10                  15

Gln Tyr Phe

<210> SEQ ID NO 1321
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 1321

Cys Ala Thr Ser Asp Arg Ala Val Glu Thr Gln Tyr Phe
1               5                   10

<210> SEQ ID NO 1322
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 1322

Cys Ala Thr Ser Gly Thr Gly Asp Glu Gln Tyr Phe
1               5                   10

<210> SEQ ID NO 1323
<211> LENGTH: 17
<212> TYPE: PRT
<213> ORGANISM: Artificial sequence
<220> FEATURE:
<223> OTHER INFORMATION: Synthetic polypeptide

<400> SEQUENCE: 1323

Cys Ala Thr Ser Arg Asp Tyr Phe Ser Gly Ala Thr Asp Thr Gln Tyr
1               5                   10                  15

Phe

<210> SEQ ID NO 1324
<211> LENGTH: 18
<212> TYPE: PRT
<213> ORGANISM: Artificial sequence
<220> FEATURE:
<223> OTHER INFORMATION: Synthetic polypeptide

<400> SEQUENCE: 1324

Cys Ala Thr Ser Arg Glu Ala Ser Gly Gly Gly Gly Gln Glu Thr Gln
1               5                   10                  15

Tyr Phe

<210> SEQ ID NO 1325
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 1325

Cys Ala Thr Ser Arg Leu Asn Asn Glu Gln Phe Phe
1               5                   10

<210> SEQ ID NO 1326
<211> LENGTH: 17
<212> TYPE: PRT
<213> ORGANISM: Artificial sequence
<220> FEATURE:
<223> OTHER INFORMATION: Synthetic polypeptide

<400> SEQUENCE: 1326

Cys Ala Thr Ser Ser Asp Asp Leu Gly Ser Ser Tyr Asn Glu Gln Phe
1               5                   10                  15

Phe

<210> SEQ ID NO 1327
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 1327

Cys Ala Trp Ala Pro Val Glu Gly Gln Pro Gln His Phe
1               5                   10

<210> SEQ ID NO 1328
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 1328

Cys Ala Trp Asp Asn Lys Gly Leu Ala Gly Gly Arg Gln Tyr Phe
1               5                   10                  15

<210> SEQ ID NO 1329
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 1329

Cys Ala Trp Glu Thr Ala Gly Ile Gly Tyr Gly Tyr Thr Phe
1               5                   10

<210> SEQ ID NO 1330
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 1330

Cys Ala Trp Lys Gly Asp Arg Glu Gly Gly Tyr Thr Phe
1               5                   10

<210> SEQ ID NO 1331
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 1331

Cys Ala Trp Arg Gly Thr Ser Gly Gly Ala Gln Tyr Phe
1               5                   10

<210> SEQ ID NO 1332
<211> LENGTH: 13
<212> TYPE: PRT

<213> ORGANISM: Artificial sequence
<220> FEATURE:
<223> OTHER INFORMATION: Synthetic polypeptide

<400> SEQUENCE: 1332

Cys Ala Trp Arg Gln Asp Leu His Tyr Gly Tyr Thr Phe
1               5                   10

<210> SEQ ID NO 1333
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 1333

Cys Ala Trp Ser Gly Gly Glu Asn Gln Pro Gln His Phe
1               5                   10

<210> SEQ ID NO 1334
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 1334

Cys Ala Trp Ser Gly Gly Pro Thr Asn Ser Pro Leu His Phe
1               5                   10

<210> SEQ ID NO 1335
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 1335

Cys Ala Trp Ser Ile Ser Gly Thr Glu Asn Ile Gln Tyr Phe
1               5                   10

<210> SEQ ID NO 1336
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 1336

Cys Ala Trp Ser Met Glu Ala Glu Gly Gln Pro Gln His Phe
1               5                   10

<210> SEQ ID NO 1337
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 1337

Cys Ala Trp Ser Pro Leu Ala Gly Val Ser Tyr Glu Gln Tyr Phe
1               5                   10                  15

<210> SEQ ID NO 1338
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 1338

Cys Ala Trp Ser Arg Leu Gly Ala Ser Gly Asn Thr Ile Tyr Phe
1               5                   10                  15

<210> SEQ ID NO 1339
<211> LENGTH: 18
<212> TYPE: PRT
<213> ORGANISM: Artificial sequence
<220> FEATURE:
<223> OTHER INFORMATION: Synthetic polypeptide

<400> SEQUENCE: 1339

Cys Ala Trp Ser Val Phe Thr Gly Gly Phe Gly Thr Asn Glu Lys Leu
1               5                   10                  15

Phe Phe

<210> SEQ ID NO 1340
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 1340

Cys Ala Trp Ser Val Ile Gln Gly Gly Thr Glu Gln Tyr Phe
1               5                   10

<210> SEQ ID NO 1341
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 1341

Cys Ala Trp Thr Gly Gly Thr Gly Asp Asn Glu Gln Phe Phe
1               5                   10

<210> SEQ ID NO 1342
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 1342

Cys Ser Ala Asp Ser Ser Ala Ala Gly Gly Gln Asp Thr Gln Tyr Phe
1               5                   10                  15

<210> SEQ ID NO 1343
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 1343

Cys Ser Ala Gly Gly Gln Gly Arg Gly Asn Thr Glu Ala Phe Phe
1               5                   10                  15

<210> SEQ ID NO 1344
<211> LENGTH: 13
<212> TYPE: PRT

<213> ORGANISM: Artificial sequence
<220> FEATURE:
<223> OTHER INFORMATION: Synthetic polypeptide

<400> SEQUENCE: 1344

Cys Ser Ala Gly Leu Thr Gly Gly Arg Glu Gln Tyr Phe
1               5                   10

<210> SEQ ID NO 1345
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 1345

Cys Ser Ala Gly Ser Leu Gly Gly Glu Lys Leu Phe Phe
1               5                   10

<210> SEQ ID NO 1346
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 1346

Cys Ser Ala Lys Asp Ser Ser Thr Asn Glu Lys Leu Phe Phe
1               5                   10

<210> SEQ ID NO 1347
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 1347

Cys Ser Ala Lys Thr Gly Leu Tyr Tyr Gly Tyr Thr Phe
1               5                   10

<210> SEQ ID NO 1348
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 1348

Cys Ser Ala Leu Gly Gly Ile Ser Thr Asp Thr Gln Tyr Phe
1               5                   10

<210> SEQ ID NO 1349
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 1349

Cys Ser Ala Leu Gly Pro Asn Gln Glu Thr Gln Tyr Phe
1               5                   10

<210> SEQ ID NO 1350
<211> LENGTH: 12
<212> TYPE: PRT
<213> ORGANISM: Artificial sequence

```
<220> FEATURE:
<223> OTHER INFORMATION: Synthetic polypeptide

<400> SEQUENCE: 1350

Cys Ser Ala Leu Leu Gly Ala Arg Gly Tyr Thr Phe
1               5                   10

<210> SEQ ID NO 1351
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 1351

Cys Ser Ala Leu Arg Gln Gly Ala Tyr Asn Glu Gln Phe Phe
1               5                   10

<210> SEQ ID NO 1352
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 1352

Cys Ser Ala Asn Pro Gly Phe Leu Thr Asp Thr Gln Tyr Phe
1               5                   10

<210> SEQ ID NO 1353
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 1353

Cys Ser Ala Asn Ser Gly Gly Ser Glu Lys Leu Phe Phe
1               5                   10

<210> SEQ ID NO 1354
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 1354

Cys Ser Ala Pro Thr Pro Gly Thr Gly Gly Tyr Gly Tyr Thr Phe
1               5                   10                  15

<210> SEQ ID NO 1355
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 1355

Cys Ser Ala Arg Ala Leu Ala Leu Val Gln Thr Gln Tyr Phe
1               5                   10

<210> SEQ ID NO 1356
<211> LENGTH: 16
<212> TYPE: PRT
<213> ORGANISM: Artificial sequence
<220> FEATURE:
```

<223> OTHER INFORMATION: Synthetic polypeptide

<400> SEQUENCE: 1356

Cys Ser Ala Arg Asp Pro Arg Gly Arg Val Ile Thr Glu Ala Phe Phe
1               5                   10                  15

<210> SEQ ID NO 1357
<211> LENGTH: 17
<212> TYPE: PRT
<213> ORGANISM: Artificial sequence
<220> FEATURE:
<223> OTHER INFORMATION: Synthetic polypeptide

<400> SEQUENCE: 1357

Cys Ser Ala Arg Asp Arg Asp Arg Ala Val Asp Thr Gly Glu Leu Phe
1               5                   10                  15

Phe

<210> SEQ ID NO 1358
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 1358

Cys Ser Ala Arg Asp Arg Asp Arg Gly Thr Asp Thr Gln Tyr Phe
1               5                   10                  15

<210> SEQ ID NO 1359
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 1359

Cys Ser Ala Arg Asp Arg Leu Arg Leu Gly Ala Asp Thr Gln Tyr Phe
1               5                   10                  15

<210> SEQ ID NO 1360
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 1360

Cys Ser Ala Arg Gly Gly Gln Gly Gln Tyr Gly Tyr Thr Phe
1               5                   10

<210> SEQ ID NO 1361
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 1361

Cys Ser Ala Arg Gly Ile Gly Asn Thr Ile Tyr Phe
1               5                   10

<210> SEQ ID NO 1362
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 1362

Cys Ser Ala Arg Gly Ser Gly Pro Asp Thr Glu Ala Phe Phe
1               5                   10

<210> SEQ ID NO 1363
<211> LENGTH: 20
<212> TYPE: PRT
<213> ORGANISM: Artificial sequence
<220> FEATURE:
<223> OTHER INFORMATION: Synthetic polypeptide

<400> SEQUENCE: 1363

Cys Ser Ala Arg Gly Ser Arg Leu Arg Gly Glu Gly Val Ser Asn Gln
1               5                   10                  15

Pro Gln His Phe
            20

<210> SEQ ID NO 1364
<211> LENGTH: 17
<212> TYPE: PRT
<213> ORGANISM: Artificial sequence
<220> FEATURE:
<223> OTHER INFORMATION: Synthetic polypeptide

<400> SEQUENCE: 1364

Cys Ser Ala Arg Ser Pro Gly Leu Ala Gly Gly Leu Asn Glu Gln Phe
1               5                   10                  15

Phe

<210> SEQ ID NO 1365
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 1365

Cys Ser Ala Arg Ser Pro Thr Ser Gly Arg Thr Asn Glu Gln Phe Phe
1               5                   10                  15

<210> SEQ ID NO 1366
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 1366

Cys Ser Ala Ser Gly Ala Tyr Asn Glu Gln Phe Phe
1               5                   10

<210> SEQ ID NO 1367
<211> LENGTH: 10
<212> TYPE: PRT
<213> ORGANISM: Artificial sequence
<220> FEATURE:
<223> OTHER INFORMATION: Synthetic polypeptide

<400> SEQUENCE: 1367

Cys Ser Ala Ser Gly Trp Gly Ala Val Phe
1               5                   10

```
<210> SEQ ID NO 1368
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 1368

Cys Ser Ala Ser Leu Gly Val Gly Asn Gln Pro Gln His Phe
1               5                   10

<210> SEQ ID NO 1369
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 1369

Cys Ser Ala Ser Pro Asn Tyr Gly Tyr Thr Phe
1               5                   10

<210> SEQ ID NO 1370
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 1370

Cys Ser Ala Ser Pro Gln Ile Ala Gly Gly Tyr Glu Gln Tyr Phe
1               5                   10                  15

<210> SEQ ID NO 1371
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 1371

Cys Ser Ala Ser Gln Ala Gly Gly Ser Ser Tyr Glu Gln Tyr Phe
1               5                   10                  15

<210> SEQ ID NO 1372
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 1372

Cys Ser Ala Ser Arg Gly Asn Thr Glu Ala Phe Phe
1               5                   10

<210> SEQ ID NO 1373
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 1373

Cys Ser Ala Thr Leu Gly Thr Ala Asp Thr Gln Tyr Phe
1               5                   10

<210> SEQ ID NO 1374
```

```
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 1374

Cys Ser Ala Thr Asn Asp Arg Ala Tyr Gly Tyr Thr Phe
1               5                   10

<210> SEQ ID NO 1375
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 1375

Cys Ser Ala Tyr Ser Gly Asn Pro Gly Gln Pro Gln His Phe
1               5                   10

<210> SEQ ID NO 1376
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 1376

Cys Ser Gly Thr Gly Glu Glu Thr Gln Tyr Phe
1               5                   10

<210> SEQ ID NO 1377
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 1377

Cys Ser Ser Ile Arg Gly Gly Pro Gly Glu Thr Gln Tyr Phe
1               5                   10

<210> SEQ ID NO 1378
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 1378

Cys Ser Val Ala Gly Thr Gly Glu Lys Leu Phe Phe
1               5                   10

<210> SEQ ID NO 1379
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 1379

Cys Ser Val Asp Gly Ala Leu Ala Gly Gly Thr Tyr Glu Gln Tyr Phe
1               5                   10                  15

<210> SEQ ID NO 1380
<211> LENGTH: 15
```

```
<212> TYPE: PRT
<213> ORGANISM: Artificial sequence
<220> FEATURE:
<223> OTHER INFORMATION: Synthetic polypeptide

<400> SEQUENCE: 1380

Cys Ser Val Glu Glu Gly Ala Gly Gly Thr Asp Thr Gln Tyr Phe
1               5                   10                  15

<210> SEQ ID NO 1381
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 1381

Cys Ser Val Glu Gly Gly Gly Tyr Gly Tyr Thr Phe
1               5                   10

<210> SEQ ID NO 1382
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 1382

Cys Ser Val Glu Ile Pro Gly Leu Ser Phe Tyr Glu Gln Tyr Phe
1               5                   10                  15

<210> SEQ ID NO 1383
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 1383

Cys Ser Val Glu Arg Glu Arg Gly Arg Thr Glu Ala Phe Phe
1               5                   10

<210> SEQ ID NO 1384
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 1384

Cys Ser Val Glu Arg Ser Ser Gly Ser Phe Ser Tyr Gly Tyr Thr Phe
1               5                   10                  15

<210> SEQ ID NO 1385
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 1385

Cys Ser Val Gly Gln Gly Val Val Tyr Gly Tyr Thr Phe
1               5                   10

<210> SEQ ID NO 1386
<211> LENGTH: 13
<212> TYPE: PRT
```

<213> ORGANISM: Artificial sequence
<220> FEATURE:
<223> OTHER INFORMATION: Synthetic polypeptide

<400> SEQUENCE: 1386

Cys Ser Val Gly Gln Thr Gly Asn Tyr Glu Gln Tyr Phe
1               5                   10

<210> SEQ ID NO 1387
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 1387

Cys Ser Val Gly Arg Asp Ile Gln Glu Thr Gln Tyr Phe
1               5                   10

<210> SEQ ID NO 1388
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 1388

Cys Ser Val Ile Gln Gly Ala Gly Ser Thr Asp Thr Gln Tyr Phe
1               5                   10                  15

<210> SEQ ID NO 1389
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 1389

Cys Ser Val Arg Thr Gly Leu Ala Lys Asn Ile Gln Tyr Phe
1               5                   10

<210> SEQ ID NO 1390
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 1390

Cys Val Thr Ser Gly Thr Val Asn Thr Glu Ala Phe Phe
1               5                   10

<210> SEQ ID NO 1391
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 1391

Cys Ala Ala Ser Met Ile Gly Ser Ser Ala Ser Lys Ile Ile Phe
1               5                   10                  15

<210> SEQ ID NO 1392
<211> LENGTH: 12
<212> TYPE: PRT
<213> ORGANISM: Artificial sequence

```
<220> FEATURE:
<223> OTHER INFORMATION: Synthetic polypeptide

<400> SEQUENCE: 1392

Cys Ala Leu Arg Pro Asn Asn Asn Asp Met Arg Phe
1               5                   10

<210> SEQ ID NO 1393
<211> LENGTH: 17
<212> TYPE: PRT
<213> ORGANISM: Artificial sequence
<220> FEATURE:
<223> OTHER INFORMATION: Synthetic polypeptide

<400> SEQUENCE: 1393

Cys Ala Thr Ala Pro Asn Ala Gly Gly Thr Ser Tyr Gly Lys Leu Thr
1               5                   10                  15

Phe

<210> SEQ ID NO 1394
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 1394

Cys Ala Val Thr Gly Gly Asp Thr Gly Asn Gln Phe Tyr Phe
1               5                   10

<210> SEQ ID NO 1395
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 1395

Cys Ala Leu Ser Gly Arg Asp Gly Gly Ser Gln Gly Asn Leu Ile Phe
1               5                   10                  15

<210> SEQ ID NO 1396
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 1396

Cys Ala Val Arg Asp Asn Asn Ala Arg Leu Met Phe
1               5                   10

<210> SEQ ID NO 1397
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 1397

Cys Val Val Tyr Val Pro Thr Gly Asn Gln Phe Tyr Phe
1               5                   10

<210> SEQ ID NO 1398
<211> LENGTH: 12
<212> TYPE: PRT
```

<213> ORGANISM: Artificial sequence
<220> FEATURE:
<223> OTHER INFORMATION: Synthetic polypeptide

<400> SEQUENCE: 1398

Cys Ala Val Met Gly Ala Gly Asn Lys Leu Thr Phe
1               5                   10

<210> SEQ ID NO 1399
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 1399

Cys Ala Thr Asp Ala Ser Lys Asn Thr Asp Lys Leu Ile Phe
1               5                   10

<210> SEQ ID NO 1400
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 1400

Cys Ala Ala Ser Ile Ser Gly Asn Gln Phe Tyr Phe
1               5                   10

<210> SEQ ID NO 1401
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 1401

Cys Ile Leu Arg Asp Ser Gly Asn Ala Gly Asn Met Leu Thr Phe
1               5                   10                  15

<210> SEQ ID NO 1402
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 1402

Cys Val Ile His Gly Ser Ser Asn Thr Gly Lys Leu Ile Phe
1               5                   10

<210> SEQ ID NO 1403
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 1403

Cys Ala Thr Leu Thr Arg Ser Gly Tyr Ala Leu Asn Phe
1               5                   10

<210> SEQ ID NO 1404
<211> LENGTH: 16
<212> TYPE: PRT
<213> ORGANISM: Artificial sequence

```
<220> FEATURE:
<223> OTHER INFORMATION: Synthetic polypeptide

<400> SEQUENCE: 1404

Cys Ile Val Arg Gly His Ser Gly Gly Gly Ala Asp Gly Leu Thr Phe
1               5                   10                  15

<210> SEQ ID NO 1405
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 1405

Cys Ala Val Ser Asn Arg Asp Asp Lys Ile Ile Phe
1               5                   10

<210> SEQ ID NO 1406
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 1406

Cys Ala Val Ser Asn Arg Asp Asp Lys Ile Ile Phe
1               5                   10

<210> SEQ ID NO 1407
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 1407

Cys Ala Val Arg Asp Thr Ser Gly Thr Tyr Lys Tyr Ile Phe
1               5                   10

<210> SEQ ID NO 1408
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 1408

Cys Ile Val Arg Gly Leu Ser Asn Phe Gly Asn Glu Lys Leu Thr Phe
1               5                   10                  15

<210> SEQ ID NO 1409
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 1409

Cys Ala Arg Thr Ser Gly Thr Tyr Lys Tyr Ile Phe
1               5                   10

<210> SEQ ID NO 1410
<211> LENGTH: 12
<212> TYPE: PRT
<213> ORGANISM: Artificial sequence
<220> FEATURE:
```

<223> OTHER INFORMATION: Synthetic polypeptide

<400> SEQUENCE: 1410

Cys Ala Leu Asn Asn Ala Gly Asn Met Leu Thr Phe
1               5                   10

<210> SEQ ID NO 1411
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 1411

Cys Pro Lys Ile Gln Thr Gly Ala Asn Asn Leu Phe Phe
1               5                   10

<210> SEQ ID NO 1412
<211> LENGTH: 17
<212> TYPE: PRT
<213> ORGANISM: Artificial sequence
<220> FEATURE:
<223> OTHER INFORMATION: Synthetic polypeptide

<400> SEQUENCE: 1412

Cys Ala Glu Asn Ile Gly His Arg Gly Ser Thr Leu Gly Arg Leu Tyr
1               5                   10                  15

Phe

<210> SEQ ID NO 1413
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 1413

Cys Ala Met Arg Glu Gly Met Gly Asn Ala Gly Asn Met Leu Thr Phe
1               5                   10                  15

<210> SEQ ID NO 1414
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 1414

Cys Ala Gly Gly Ala Thr Asn Lys Leu Ile Phe
1               5                   10

<210> SEQ ID NO 1415
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 1415

Cys Ala Ala Glu Arg Glu Gly Asn Lys Leu Val Phe
1               5                   10

<210> SEQ ID NO 1416
<211> LENGTH: 12
<212> TYPE: PRT
<213> ORGANISM: Artificial sequence

```
<220> FEATURE:
<223> OTHER INFORMATION: Synthetic polypeptide

<400> SEQUENCE: 1416

Cys Ala Gly Phe Glu Tyr Gly Asn Lys Leu Val Phe
1               5                   10

<210> SEQ ID NO 1417
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 1417

Cys Ala Leu Ser Gly Thr Ser Tyr Gly Lys Leu Thr Phe
1               5                   10

<210> SEQ ID NO 1418
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 1418

Cys Leu Val Gly Asp Pro Ser Gly Ala Gly Ser Tyr Gln Leu Thr Phe
1               5                   10                  15

<210> SEQ ID NO 1419
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 1419

Cys Ile Val Arg Val Gly Thr Ser Gly Thr Tyr Lys Tyr Ile Phe
1               5                   10                  15

<210> SEQ ID NO 1420
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 1420

Cys Ala Leu Asp Ile Ser Tyr Gln Leu Ile Trp
1               5                   10

<210> SEQ ID NO 1421
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 1421

Cys Ala Met Arg Glu Phe Arg Ser Asn Asp Tyr Lys Leu Ser Phe
1               5                   10                  15

<210> SEQ ID NO 1422
<211> LENGTH: 11
<212> TYPE: PRT
<213> ORGANISM: Artificial sequence
<220> FEATURE:
```

<223> OTHER INFORMATION: Synthetic polypeptide

<400> SEQUENCE: 1422

Cys Ala Leu Tyr Asn Phe Asn Lys Phe Tyr Phe
1               5                   10

<210> SEQ ID NO 1423
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 1423

Cys Ala Ala Ser Ile Leu Thr Gly Gly Gly Asn Lys Leu Thr Phe
1               5                   10                  15

<210> SEQ ID NO 1424
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 1424

Cys Ala Val Pro Lys Met Glu Tyr Gly Asn Lys Leu Val Phe
1               5                   10

<210> SEQ ID NO 1425
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 1425

Cys Ala Val Asp Pro Ser Gly Thr Tyr Lys Tyr Ile Phe
1               5                   10

<210> SEQ ID NO 1426
<211> LENGTH: 17
<212> TYPE: PRT
<213> ORGANISM: Artificial sequence
<220> FEATURE:
<223> OTHER INFORMATION: Synthetic polypeptide

<400> SEQUENCE: 1426

Cys Ile Val Arg Gly Val Asn Ser Gly Gly Ser Asn Tyr Lys Leu Thr
1               5                   10                  15

Phe

<210> SEQ ID NO 1427
<211> LENGTH: 18
<212> TYPE: PRT
<213> ORGANISM: Artificial sequence
<220> FEATURE:
<223> OTHER INFORMATION: Synthetic polypeptide

<400> SEQUENCE: 1427

Cys Ala Leu Ser Glu Ala Asn Arg Val Lys Ala Ala Gly Asn Lys Leu
1               5                   10                  15

Thr Phe

<210> SEQ ID NO 1428
<211> LENGTH: 11

<212> TYPE: PRT
<213> ORGANISM: Artificial sequence
<220> FEATURE:
<223> OTHER INFORMATION: Synthetic polypeptide

<400> SEQUENCE: 1428

Cys Ile Leu Lys Pro Gly Asn Gln Phe Tyr Phe
1               5                   10

<210> SEQ ID NO 1429
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 1429

Cys Ala Ala Thr Lys Lys Ser Ser Gly Asp Lys Leu Thr Phe
1               5                   10

<210> SEQ ID NO 1430
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 1430

Cys Ala Leu Ser Ala Gly Asp Tyr Lys Leu Ser Phe
1               5                   10

<210> SEQ ID NO 1431
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 1431

Cys Ala Leu Ser Gln Phe Tyr Gly Asn Asn Arg Leu Ala Phe
1               5                   10

<210> SEQ ID NO 1432
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 1432

Cys Ala Val Arg Ala Ala Gly Asn Lys Leu Thr Phe
1               5                   10

<210> SEQ ID NO 1433
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 1433

Cys Val Val Leu Gly Ala Gly Ser Tyr Gln Leu Thr Phe
1               5                   10

<210> SEQ ID NO 1434
<211> LENGTH: 15
<212> TYPE: PRT

<213> ORGANISM: Artificial sequence
<220> FEATURE:
<223> OTHER INFORMATION: Synthetic polypeptide

<400> SEQUENCE: 1434

Cys Ala Val Arg Pro Arg Ser Ser Asn Thr Gly Lys Leu Ile Phe
1               5                   10                  15

<210> SEQ ID NO 1435
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 1435

Cys Ala Glu Ser Gly Gly Gly Ser Thr Leu Gly Arg Leu Tyr Phe
1               5                   10                  15

<210> SEQ ID NO 1436
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 1436

Cys Ala Tyr Arg Ser Ala Gly Asn Asn Ala Arg Leu Met Phe
1               5                   10

<210> SEQ ID NO 1437
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 1437

Cys Ala Val Asn Glu Gly Phe Gln Lys Leu Val Phe
1               5                   10

<210> SEQ ID NO 1438
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 1438

Cys Ala Ala Ser Ser Leu Val Tyr Gly Gln Asn Phe Val Phe
1               5                   10

<210> SEQ ID NO 1439
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 1439

Cys Ala Tyr Arg Asn Thr Leu Asn Gln Ala Gly Thr Ala Leu Ile Phe
1               5                   10                  15

<210> SEQ ID NO 1440
<211> LENGTH: 16
<212> TYPE: PRT
<213> ORGANISM: Artificial sequence

```
<220> FEATURE:
<223> OTHER INFORMATION: Synthetic polypeptide

<400> SEQUENCE: 1440

Cys Ala Val Gly Gly Val Ser Ser Gly Ser Ala Arg Gln Leu Thr Phe
1               5                   10                  15

<210> SEQ ID NO 1441
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 1441

Cys Ala Ala Ser Ala His Asp Asn Tyr Gln Leu Ile Trp
1               5                   10

<210> SEQ ID NO 1442
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 1442

Cys Val Val Pro Asn Ser Gly Gly Tyr Gln Lys Val Thr Phe
1               5                   10

<210> SEQ ID NO 1443
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 1443

Cys Ala Ala Met Ser Ser Asn Ser Gly Tyr Ala Leu Asn Phe
1               5                   10

<210> SEQ ID NO 1444
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 1444

Cys Ala Leu Gly Ser Gly Gly Ser Tyr Ile Pro Thr Phe
1               5                   10

<210> SEQ ID NO 1445
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 1445

Cys Ala Val Thr Asn Ala Gly Gly Thr Ser Tyr Gly Lys Leu Thr Phe
1               5                   10                  15

<210> SEQ ID NO 1446
<211> LENGTH: 11
<212> TYPE: PRT
<213> ORGANISM: Artificial sequence
<220> FEATURE:
```

```
<223> OTHER INFORMATION: Synthetic polypeptide

<400> SEQUENCE: 1446

Cys Ala Gly Ala Asp Asp Tyr Lys Leu Ser Phe
1               5                   10

<210> SEQ ID NO 1447
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 1447

Cys Ala Phe Asn Trp Gly Ala Gln Lys Leu Val Phe
1               5                   10

<210> SEQ ID NO 1448
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 1448

Cys Ala Val Gly Asp Phe Asn Lys Phe Tyr Phe
1               5                   10

<210> SEQ ID NO 1449
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 1449

Cys Ala Ala Ser Val Ala Phe Ser Gly Asn Thr Pro Leu Val Phe
1               5                   10                  15

<210> SEQ ID NO 1450
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 1450

Cys Ala Val Arg Asp Ile Ser Asp Asn Asp Met Arg Phe
1               5                   10

<210> SEQ ID NO 1451
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 1451

Cys Ala Val Arg Pro Phe Pro Thr Asn Ala Gly Lys Ser Thr Phe
1               5                   10                  15

<210> SEQ ID NO 1452
<211> LENGTH: 12
<212> TYPE: PRT
<213> ORGANISM: Artificial sequence
<220> FEATURE:
<223> OTHER INFORMATION: Synthetic polypeptide
```

<400> SEQUENCE: 1452

Cys Ala Val Asp Ser Ser Ala Ser Lys Ile Ile Phe
1               5                   10

<210> SEQ ID NO 1453
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 1453

Cys Ala Met Arg Met Met Asn Thr Gly Asn Gln Phe Tyr Phe
1               5                   10

<210> SEQ ID NO 1454
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 1454

Cys Ala Ala Ala Asn Tyr Gly Gly Ala Thr Asn Lys Leu Ile Phe
1               5                   10                  15

<210> SEQ ID NO 1455
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 1455

Cys Val Val Ile Arg Ser Tyr Ile Pro Thr Phe
1               5                   10

<210> SEQ ID NO 1456
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 1456

Cys Ala Pro Asp Phe Gly Asn Glu Lys Leu Thr Phe
1               5                   10

<210> SEQ ID NO 1457
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 1457

Cys Ala Val Asn Ile Gly Gly Gly Phe Lys Thr Ile Phe
1               5                   10

<210> SEQ ID NO 1458
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 1458

Cys Val Val Arg Ser Gln Ala Gly Thr Ala Leu Ile Phe
1               5                   10

<210> SEQ ID NO 1459
<211> LENGTH: 17
<212> TYPE: PRT
<213> ORGANISM: Artificial sequence
<220> FEATURE:
<223> OTHER INFORMATION: Synthetic polypeptide

<400> SEQUENCE: 1459

Cys Ile Val Arg Gly Asn Ala Gly Gly Thr Ser Tyr Gly Lys Leu Thr
1               5                   10                  15

Phe

<210> SEQ ID NO 1460
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 1460

Cys Ala Val Ser Asn Asp Tyr Lys Leu Ser Phe
1               5                   10

<210> SEQ ID NO 1461
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 1461

Cys Ala Ala Ser Ala Gly Thr Gly Arg Arg Ala Leu Thr Phe
1               5                   10

<210> SEQ ID NO 1462
<211> LENGTH: 17
<212> TYPE: PRT
<213> ORGANISM: Artificial sequence
<220> FEATURE:
<223> OTHER INFORMATION: Synthetic polypeptide

<400> SEQUENCE: 1462

Cys Ala Leu Ser Glu Ser Gly Gly Gly Thr Ser Tyr Gly Lys Leu Thr
1               5                   10                  15

Phe

<210> SEQ ID NO 1463
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 1463

Cys Ala Val Gly Asn Tyr Asn Asp Tyr Lys Leu Ser Phe
1               5                   10

<210> SEQ ID NO 1464
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 1464

Cys Ile Val Ile Glu Ser Gly Gly Ser Asn Tyr Lys Leu Thr Phe
1               5                   10                  15

<210> SEQ ID NO 1465
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 1465

Cys Ala Val Arg Glu Thr Gly Ala Asn Ser Lys Leu Thr Phe
1               5                   10

<210> SEQ ID NO 1466
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 1466

Cys Ala Val Asp Arg Trp Ser Asn Tyr Gln Leu Ile Trp
1               5                   10

<210> SEQ ID NO 1467
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 1467

Cys Ala Leu Glu Arg Gly Asn Thr Pro Leu Val Phe
1               5                   10

<210> SEQ ID NO 1468
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 1468

Cys Ala Gly Val Gln Ala Gly Thr Ala Leu Ile Phe
1               5                   10

<210> SEQ ID NO 1469
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 1469

Cys Ala Leu Arg Leu Thr Gly Gly Gly Asn Lys Leu Thr Phe
1               5                   10

<210> SEQ ID NO 1470
<211> LENGTH: 13
<212> TYPE: PRT
<213> ORGANISM: Artificial sequence
<220> FEATURE:

<223> OTHER INFORMATION: Synthetic polypeptide

<400> SEQUENCE: 1470

Cys Ala Ala Leu Leu Tyr Asn Phe Asn Lys Phe Tyr Phe
1               5                   10

<210> SEQ ID NO 1471
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 1471

Cys Ala Val Ser Val Thr Ser Gly Ser Arg Leu Thr Phe
1               5                   10

<210> SEQ ID NO 1472
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 1472

Cys Ala Leu Glu Asn Ser Gly Thr Tyr Lys Tyr Ile Phe
1               5                   10

<210> SEQ ID NO 1473
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 1473

Cys Ile Val Arg Gly Ile Asp Asp Tyr Lys Leu Ser Phe
1               5                   10

<210> SEQ ID NO 1474
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 1474

Cys Gly Thr Lys Leu Gln Thr Gly Ala Asn Asn Leu Phe Phe
1               5                   10

<210> SEQ ID NO 1475
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 1475

Cys Val Val Asn Asp Gln Ala Gly Thr Ala Leu Ile Phe
1               5                   10

<210> SEQ ID NO 1476
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 1476

Cys Ala Leu Arg Gly Leu Arg Asn Tyr Gly Gln Asn Phe Val Phe
1               5                   10                  15

<210> SEQ ID NO 1477
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 1477

Cys Ala Val Asp Thr Asn Ala Gly Lys Ser Thr Phe
1               5                   10

<210> SEQ ID NO 1478
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 1478

Cys Ala Lys Gly Ile Thr Gly Gly Gly Asn Lys Leu Thr Phe
1               5                   10

<210> SEQ ID NO 1479
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 1479

Cys Ala Val Ser Val Gly Ser Gly Gly Gly Ala Asp Gly Leu Thr Phe
1               5                   10                  15

<210> SEQ ID NO 1480
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 1480

Cys Ala Val Phe Tyr Gly Asn Asn Arg Leu Ala Phe
1               5                   10

<210> SEQ ID NO 1481
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 1481

Cys Val Val Glu Thr Gln Thr Gly Ala Asn Asn Leu Phe Phe
1               5                   10

<210> SEQ ID NO 1482
<211> LENGTH: 15
<212> TYPE: PRT
<213> ORGANISM: Artificial sequence
<220> FEATURE:
<223> OTHER INFORMATION: Synthetic polypeptide

```
<400> SEQUENCE: 1482

Cys Ala Leu Lys Ile Ser Ser Gly Ser Ala Arg Gln Leu Thr Phe
1               5                   10                  15

<210> SEQ ID NO 1483
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 1483

Cys Ile Val Met Gly Gly Ala Gln Lys Leu Val Phe
1               5                   10

<210> SEQ ID NO 1484
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 1484

Cys Ile Val Arg Val Ala Gln Gly Gly Ser Glu Lys Leu Val Phe
1               5                   10                  15

<210> SEQ ID NO 1485
<211> LENGTH: 10
<212> TYPE: PRT
<213> ORGANISM: Artificial sequence
<220> FEATURE:
<223> OTHER INFORMATION: Synthetic polypeptide

<400> SEQUENCE: 1485

Cys Ala Gly Arg Asn Asn Asp Met Arg Phe
1               5                   10

<210> SEQ ID NO 1486
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 1486

Cys Ala Leu Glu Asn Ala Gly Asn Met Leu Thr Phe
1               5                   10

<210> SEQ ID NO 1487
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 1487

Cys Ala Leu Ser Glu Lys Arg Thr Gly Asn Gln Phe Tyr Phe
1               5                   10

<210> SEQ ID NO 1488
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 1488
```

```
Cys Ala Glu Asn Lys Ser Gly Asn Asn Arg Leu Ala Phe
1               5                   10
```

<210> SEQ ID NO 1489
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 1489

```
Cys Ala Val His Leu Ile Gln Gly Ala Gln Lys Leu Val Phe
1               5                   10
```

<210> SEQ ID NO 1490
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 1490

```
Cys Ala Val Gly Ile Gln Gly Ala Gln Lys Leu Val Phe
1               5                   10
```

<210> SEQ ID NO 1491
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 1491

```
Cys Ile Val Arg Gly Asn Ser Gly Gly Ser Asn Tyr Lys Leu Thr Phe
1               5                   10                  15
```

<210> SEQ ID NO 1492
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 1492

```
Cys Ala Val Arg Glu Ser Thr Gly Ala Asn Asn Leu Phe Phe
1               5                   10
```

<210> SEQ ID NO 1493
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 1493

```
Cys Ala Ala Ser Leu Asn Gln Gly Gly Lys Leu Ile Phe
1               5                   10
```

<210> SEQ ID NO 1494
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 1494

Cys Ala Ala Ser Leu Asn Gln Gly Gly Lys Leu Ile Phe
1               5                   10

<210> SEQ ID NO 1495
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 1495

Cys Ala Gly His Leu Thr Gly Asn Gln Phe Tyr Phe
1               5                   10

<210> SEQ ID NO 1496
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 1496

Cys Ala Val Arg Glu Gly Tyr Gly Gly Ala Thr Asn Lys Leu Ile Phe
1               5                   10                  15

<210> SEQ ID NO 1497
<211> LENGTH: 15
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<222> LOCATION: (5)..(5)
<223> OTHER INFORMATION: Xaa can be any naturally occurring amino acid

<400> SEQUENCE: 1497

Cys Ala Val Ala Xaa Asp Pro Gly Thr Ala Ser Lys Leu Thr Phe
1               5                   10                  15

<210> SEQ ID NO 1498
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 1498

Cys Ala Met Ser Gly Phe Asp Ser Asn Tyr Gln Leu Ile Trp
1               5                   10

<210> SEQ ID NO 1499
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 1499

Cys Ala Val Arg Trp Gly Gly Gly Gly Ala Asp Gly Leu Thr Phe
1               5                   10                  15

<210> SEQ ID NO 1500
<211> LENGTH: 14
<212> TYPE: PRT
<213> ORGANISM: Artificial sequence
<220> FEATURE:
<223> OTHER INFORMATION: Synthetic polypeptide

```
<400> SEQUENCE: 1500

Cys Ala Val Arg Gly Thr Thr Gly Ala Asn Asn Leu Phe Phe
1               5                   10

<210> SEQ ID NO 1501
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 1501

Cys Ala Leu Gly Leu Gln Asn Ala Gly Lys Ser Thr Phe
1               5                   10

<210> SEQ ID NO 1502
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 1502

Cys Ala Thr Gly Leu Val Glu Tyr Gly Asn Lys Leu Val Phe
1               5                   10

<210> SEQ ID NO 1503
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 1503

Cys Ala Thr Ser Gly Thr Tyr Lys Tyr Ile Phe
1               5                   10

<210> SEQ ID NO 1504
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 1504

Cys Ala Val Val Arg Gly Gly Gly Asn Lys Leu Thr Phe
1               5                   10

<210> SEQ ID NO 1505
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 1505

Cys Ala Leu Tyr Thr Gly Gly Gly Asn Lys Leu Thr Phe
1               5                   10

<210> SEQ ID NO 1506
<211> LENGTH: 14
<212> TYPE: PRT
<213> ORGANISM: Artificial sequence
<220> FEATURE:
<223> OTHER INFORMATION: Synthetic polypeptide
```

<400> SEQUENCE: 1506

Cys Ala Val Ser Ala Pro Ser Gly Tyr Ser Thr Leu Thr Phe
1               5                   10

<210> SEQ ID NO 1507
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 1507

Cys Ala Val Gln Ser Gly Gly Gly Ala Asp Gly Leu Thr Phe
1               5                   10

<210> SEQ ID NO 1508
<211> LENGTH: 10
<212> TYPE: PRT
<213> ORGANISM: Artificial sequence
<220> FEATURE:
<223> OTHER INFORMATION: Synthetic polypeptide

<400> SEQUENCE: 1508

Pro Tyr Asn Tyr Gly Gln Asn Phe Val Phe
1               5                   10

<210> SEQ ID NO 1509
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 1509

Cys Val Val Asn Met Ser Trp Gly Ala Gln Lys Leu Val Phe
1               5                   10

<210> SEQ ID NO 1510
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 1510

Cys Ala Pro Ser Gly Asn Thr Pro Leu Val Phe
1               5                   10

<210> SEQ ID NO 1511
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 1511

Cys Ile Val Met Gly Gly Ala Gln Lys Leu Val Phe
1               5                   10

<210> SEQ ID NO 1512
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 1512

Cys Ala Thr Val Leu Thr Gly Ala Asn Asn Leu Phe Phe
1               5                   10

<210> SEQ ID NO 1513
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 1513

Cys Ala Thr Val Leu Asn Asn Ala Gly Asn Met Leu Thr Phe
1               5                   10

<210> SEQ ID NO 1514
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 1514

Cys Leu Thr Pro Gln Gly Gly Ser Glu Lys Leu Val Phe
1               5                   10

<210> SEQ ID NO 1515
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 1515

Cys Val Val Asn Ile Gln Ser Gly Gly Ser Tyr Ile Pro Thr Phe
1               5                   10                  15

<210> SEQ ID NO 1516
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 1516

Cys Ala Val Glu Ala Pro Glu Thr Asp Lys Leu Ile Phe
1               5                   10

<210> SEQ ID NO 1517
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 1517

Cys Ala Val Arg Gly Gly Gly Tyr Gln Leu Ile Trp
1               5                   10

<210> SEQ ID NO 1518
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 1518

```
Cys Ala Val Gln Ala Ala Glu Thr Ser Gly Ser Arg Leu Thr Phe
1               5                   10                  15
```

<210> SEQ ID NO 1519
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 1519

```
Cys Ala Val Glu Asp Thr Gly Arg Arg Ala Leu Thr Phe
1               5                   10
```

<210> SEQ ID NO 1520
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 1520

```
Cys Ala Leu Ser Val Ala Asn Gln Gly Gly Lys Leu Ile Phe
1               5                   10
```

<210> SEQ ID NO 1521
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 1521

```
Cys Ala Leu Arg Phe Arg Gly Thr Asn Ala Gly Lys Ser Thr Phe
1               5                   10                  15
```

<210> SEQ ID NO 1522
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 1522

```
Cys Ala Val Ser Glu Asn Thr Gly Phe Gln Lys Leu Val Phe
1               5                   10
```

<210> SEQ ID NO 1523
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 1523

```
Cys Ala Val Ser Tyr Gly Gly Ala Thr Asn Lys Leu Ile Phe
1               5                   10
```

<210> SEQ ID NO 1524
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 1524

Cys Ala Met Val Glu Tyr Gly Asn Lys Leu Val Phe

-continued

```
1               5                   10

<210> SEQ ID NO 1525
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 1525

Cys Ala Ala Thr Thr Ser Gly Thr Tyr Lys Tyr Ile Phe
1               5                   10

<210> SEQ ID NO 1526
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 1526

Cys Ile Val Gly Arg Thr Asn Phe Gly Asn Glu Lys Leu Thr Phe
1               5                   10                  15

<210> SEQ ID NO 1527
<211> LENGTH: 10
<212> TYPE: PRT
<213> ORGANISM: Artificial sequence
<220> FEATURE:
<223> OTHER INFORMATION: Synthetic polypeptide

<400> SEQUENCE: 1527

Cys Ala Val Thr Gly Asn Gln Phe Tyr Phe
1               5                   10

<210> SEQ ID NO 1528
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 1528

Cys Ala Ala Ser Glu Gly Gly Gly Thr Tyr Lys Tyr Ile Phe
1               5                   10

<210> SEQ ID NO 1529
<211> LENGTH: 17
<212> TYPE: PRT
<213> ORGANISM: Artificial sequence
<220> FEATURE:
<223> OTHER INFORMATION: Synthetic polypeptide

<400> SEQUENCE: 1529

Cys Ala Leu Ser Glu Ile Gly Tyr Gly Gly Ala Thr Asn Lys Leu Ile
1               5                   10                  15

Phe

<210> SEQ ID NO 1530
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 1530
```

Cys Ala Pro Ser Lys Gly Ala Asn Asn Leu Phe Phe
1               5                   10

<210> SEQ ID NO 1531
<211> LENGTH: 17
<212> TYPE: PRT
<213> ORGANISM: Artificial sequence
<220> FEATURE:
<223> OTHER INFORMATION: Synthetic polypeptide

<400> SEQUENCE: 1531

Cys Ile Val Arg Val Ser His Gly Ser Ser Asn Thr Gly Lys Leu Ile
1               5                   10                  15

Phe

<210> SEQ ID NO 1532
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 1532

Cys Ala Val Pro Gln Ala Gly Thr Ala Leu Ile Phe
1               5                   10

<210> SEQ ID NO 1533
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 1533

Cys Ala Met Ala Asn Thr Gly Gly Phe Lys Thr Ile Phe
1               5                   10

<210> SEQ ID NO 1534
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 1534

Cys Ala Leu Ser Asp Gln Gly Thr Asn Ala Gly Lys Ser Thr Phe
1               5                   10                  15

<210> SEQ ID NO 1535
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 1535

Cys Ala Phe Met Lys Ala Thr Gly Thr Ala Ser Lys Leu Thr Phe
1               5                   10                  15

<210> SEQ ID NO 1536
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 1536

```
Cys Ile Val Arg Ala Pro Gly Gly Ser Gln Gly Asn Leu Ile Phe
1               5                   10                  15
```

<210> SEQ ID NO 1537
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 1537

```
Cys Ala Val Gln Thr Met Asp Ser Ser Tyr Lys Leu Ile Phe
1               5                   10
```

<210> SEQ ID NO 1538
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 1538

```
Cys Ala Val Ser Gly Asn Thr Gly Gly Phe Lys Thr Ile Phe
1               5                   10
```

<210> SEQ ID NO 1539
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 1539

```
Cys Ala Leu Ser Ala Gly Asp Tyr Lys Leu Ser Phe
1               5                   10
```

<210> SEQ ID NO 1540
<211> LENGTH: 10
<212> TYPE: PRT
<213> ORGANISM: Artificial sequence
<220> FEATURE:
<223> OTHER INFORMATION: Synthetic polypeptide

<400> SEQUENCE: 1540

```
Cys Ala Val Thr Gly Asn Gln Phe Tyr Phe
1               5                   10
```

<210> SEQ ID NO 1541
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 1541

```
Cys Ala Val Glu Asp Thr Gly Arg Arg Ala Leu Thr Phe
1               5                   10
```

<210> SEQ ID NO 1542
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 1542

Cys Ala Val Gln Ala Val Glu Thr Ser Gly Ser Arg Leu Thr Phe
1               5                   10                  15

<210> SEQ ID NO 1543
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 1543

Cys Ala Tyr Ser Leu Arg Ser Gly Thr Ala Ser Lys Leu Thr Phe
1               5                   10                  15

<210> SEQ ID NO 1544
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 1544

Cys Ala Gly Leu Gly Gln Gly Asn Leu Ile Phe
1               5                   10

<210> SEQ ID NO 1545
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 1545

Cys Ala Ala Thr His Leu Asn Thr Asp Lys Leu Ile Phe
1               5                   10

<210> SEQ ID NO 1546
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 1546

Cys Ala Val Thr Thr Arg Gly Gly Ser Tyr Ile Pro Thr Phe
1               5                   10

<210> SEQ ID NO 1547
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 1547

Cys Ala Val Ser Ala Trp Gly Ser Ser Asn Thr Gly Lys Leu Ile Phe
1               5                   10                  15

<210> SEQ ID NO 1548
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 1548

Cys Ala Leu Arg Asn Asn Asn Ala Arg Leu Met Phe

```
                1               5                   10

<210> SEQ ID NO 1549
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 1549

Cys Ala Ala Pro Asn Asn Asn Asn Asp Met Arg Phe
1               5                   10

<210> SEQ ID NO 1550
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 1550

Cys Ala Ala Ser Val Ser Gly Gly Ser Tyr Ile Pro Thr Phe
1               5                   10

<210> SEQ ID NO 1551
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 1551

Cys Ala Tyr Arg Thr Asn Thr Gly Asn Gln Phe Tyr Phe
1               5                   10

<210> SEQ ID NO 1552
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 1552

Cys Ala Val Ser Lys Gly Ala Gln Lys Leu Val Phe
1               5                   10

<210> SEQ ID NO 1553
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 1553

Cys Ala Gly Gln Leu Pro Gly Asn Asn Arg Leu Ala Phe
1               5                   10

<210> SEQ ID NO 1554
<211> LENGTH: 11
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<222> LOCATION: (7)..(7)
<223> OTHER INFORMATION: Xaa can be any naturally occurring amino acid
```

```
<400> SEQUENCE: 1554

Cys Ile Leu Lys Ile Thr Xaa Met Leu Asn Phe
1               5                   10

<210> SEQ ID NO 1555
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 1555

Cys Ala Pro Asn Asn Ala Gly Asn Met Leu Thr Phe
1               5                   10

<210> SEQ ID NO 1556
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 1556

Cys Val Val Ile Leu Pro Pro Ser Gly Thr Tyr Lys Tyr Ile Phe
1               5                   10                  15

<210> SEQ ID NO 1557
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 1557

Cys Ala Ala Ser Glu Glu Gly Gly Ser Glu Lys Leu Val Phe
1               5                   10

<210> SEQ ID NO 1558
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 1558

Cys Leu Pro Gly Arg Gly Asn Glu Lys Leu Thr Phe
1               5                   10

<210> SEQ ID NO 1559
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 1559

Cys Ala Gly Tyr Gly Gly Ala Thr Asn Lys Leu Ile Phe
1               5                   10

<210> SEQ ID NO 1560
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 1560
```

```
Cys Ala Leu Met Gly Ser Asn Tyr Lys Leu Thr Phe
1               5                   10
```

<210> SEQ ID NO 1561
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 1561

```
Cys Ala Val Ser Glu Ala Asn Thr Gly Gly Gly Asn Lys Leu Thr Phe
1               5                   10                  15
```

<210> SEQ ID NO 1562
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 1562

```
Cys Ala Leu Thr Pro Gly Gly Ala Thr Asn Lys Leu Ile Phe
1               5                   10
```

<210> SEQ ID NO 1563
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 1563

```
Cys Ala Val Ser Asn Arg Asp Asp Lys Ile Ile Phe
1               5                   10
```

<210> SEQ ID NO 1564
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 1564

```
Cys Ile Val Arg Val Ser Ser Arg Thr Asn Asp Met Arg Phe
1               5                   10
```

<210> SEQ ID NO 1565
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 1565

```
Cys Ala Thr His Gly Ser Ser Asn Thr Gly Lys Leu Ile Phe
1               5                   10
```

<210> SEQ ID NO 1566
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 1566

Cys Ile Val Arg Val Asp Leu Val Asn Arg Asp Asp Lys Ile Ile Phe
1               5                   10                  15

<210> SEQ ID NO 1567
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 1567

Cys Ile Leu Thr Ser Ser Asn Thr Gly Lys Leu Ile Phe
1               5                   10

<210> SEQ ID NO 1568
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 1568

Cys Ala Phe Met Lys Leu Arg Gly Asp Met Arg Phe
1               5                   10

<210> SEQ ID NO 1569
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 1569

Cys Ile Val Asp Asn Asn Ala Gly Asn Met Leu Thr Phe
1               5                   10

<210> SEQ ID NO 1570
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 1570

Cys Ala Leu Asp Asp Asn Phe Gly Asn Glu Lys Leu Thr Phe
1               5                   10

<210> SEQ ID NO 1571
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 1571

Cys Ala Thr Val Pro Pro Gly Gly Ser Glu Lys Leu Val Phe
1               5                   10

<210> SEQ ID NO 1572
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 1572

Cys Ile Leu Arg Asp Gly Arg Asn Ser Gly Tyr Ala Leu Asn Phe

-continued

<210> SEQ ID NO 1573
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 1573

Cys Ile Val Arg Ala Pro Gly Gly Ser Gln Gly Asn Leu Ile Phe
1               5                   10                  15

<210> SEQ ID NO 1574
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 1574

Cys Ala Glu Thr Gly Gly Thr Ser Tyr Gly Lys Leu Thr Phe
1               5                   10

<210> SEQ ID NO 1575
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 1575

Cys Ala Gly Val Gln Ala Gly Thr Ala Leu Ile Phe
1               5                   10

<210> SEQ ID NO 1576
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 1576

Cys Ala Leu Thr Ser Gln Gly Gly Ser Glu Lys Leu Val Phe
1               5                   10

<210> SEQ ID NO 1577
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 1577

Cys Ile Val Arg Val Ala Asp Asp Tyr Lys Leu Ser Phe
1               5                   10

<210> SEQ ID NO 1578
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 1578

Cys Ala Leu Arg Gly Gly Gly Thr Gly Gly Phe Lys Thr Ile Phe
1               5                   10                  15

<210> SEQ ID NO 1579
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 1579

Cys Ala Ala Lys Met Gly Gly Ser Asn Tyr Lys Leu Thr Phe
1               5                   10

<210> SEQ ID NO 1580
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 1580

Cys Ala Ala Arg Asp Ser Asn Tyr Gln Leu Ile Trp
1               5                   10

<210> SEQ ID NO 1581
<211> LENGTH: 17
<212> TYPE: PRT
<213> ORGANISM: Artificial sequence
<220> FEATURE:
<223> OTHER INFORMATION: Synthetic polypeptide

<400> SEQUENCE: 1581

Cys Ala Phe Met Lys His Ala Ser Gly Gly Ser Asn Tyr Lys Leu Thr
1               5                   10                  15

Phe

<210> SEQ ID NO 1582
<211> LENGTH: 10
<212> TYPE: PRT
<213> ORGANISM: Artificial sequence
<220> FEATURE:
<223> OTHER INFORMATION: Synthetic polypeptide

<400> SEQUENCE: 1582

Cys Ala Val Asp Tyr Ser Thr Leu Thr Phe
1               5                   10

<210> SEQ ID NO 1583
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 1583

Cys Ala Leu Asp Ile Ser Tyr Gln Leu Ile Trp
1               5                   10

<210> SEQ ID NO 1584
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 1584

Cys Ala Val Ser Gly Phe Gly Gly Gly Ala Asp Gly Leu Thr Phe

```
1               5                   10                  15
```

<210> SEQ ID NO 1585
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 1585

```
Cys Ile Val Gln Gly Asn Thr Gly Lys Leu Ile Phe
1               5                   10
```

<210> SEQ ID NO 1586
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 1586

```
Cys Ala Met Ser Ala Asn Thr Asn Ala Gly Lys Ser Thr Phe
1               5                   10
```

<210> SEQ ID NO 1587
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 1587

```
Cys Ala Thr Asp Pro Asn Thr Gly Asn Gln Phe Tyr Phe
1               5                   10
```

<210> SEQ ID NO 1588
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 1588

```
Cys Val Val Thr Arg Asn Ser Gly Tyr Ser Thr Leu Thr Phe
1               5                   10
```

<210> SEQ ID NO 1589
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 1589

```
Cys Ala Leu Ser Arg Asn Thr Gly Thr Ala Ser Lys Leu Thr Phe
1               5                   10                  15
```

<210> SEQ ID NO 1590
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 1590

```
Cys Ala Val Gly Ala Tyr Val Gly Gly Lys Leu Ile Phe
1               5                   10
```

<210> SEQ ID NO 1591
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 1591

Cys Ala Val Ser Glu Ser Ser Gly Asp Lys Leu Thr Phe
1               5                   10

<210> SEQ ID NO 1592
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 1592

Cys Ala Gly Arg Glu Asn Asn Asn Ala Arg Leu Met Phe
1               5                   10

<210> SEQ ID NO 1593
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 1593

Cys Ala Pro Asp Phe Gly Asn Glu Lys Leu Thr Phe
1               5                   10

<210> SEQ ID NO 1594
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 1594

Cys Leu Val Gly Pro Ser Phe Gly Asn Glu Lys Leu Thr Phe
1               5                   10

<210> SEQ ID NO 1595
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 1595

Cys Ala Val Gly Gln Ala Gly Thr Ala Leu Ile Phe
1               5                   10

<210> SEQ ID NO 1596
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 1596

Cys Ala Gly Gly Ala Gly Gly Thr Ser Tyr Gly Lys Leu Thr Phe
1               5                   10                  15

<210> SEQ ID NO 1597
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 1597

Cys Gly Ala Gly Gly Ser Gln Gly Asn Leu Ile Phe
1               5                   10

<210> SEQ ID NO 1598
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 1598

Cys Ala Thr Asp Ser Ser Tyr Lys Leu Ile Phe
1               5                   10

<210> SEQ ID NO 1599
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 1599

Cys Ala Val Ser Asn Tyr Asn Gln Gly Gly Lys Leu Ile Phe
1               5                   10

<210> SEQ ID NO 1600
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 1600

Cys Ala Val Arg Val Ser Asn Ser Asn Ser Gly Tyr Ala Leu Asn Phe
1               5                   10                  15

<210> SEQ ID NO 1601
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 1601

Cys Ala Leu Tyr Thr Gly Gly Gly Asn Lys Leu Thr Phe
1               5                   10

<210> SEQ ID NO 1602
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 1602

Cys Ala Tyr Arg Ser Pro Asp Asn Asn Ala Arg Leu Met Phe
1               5                   10

```
<210> SEQ ID NO 1603
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 1603

Cys Ser Glu Trp Glu Ala Asn Ser Gly Asn Thr Pro Leu Val Phe
1               5                   10                  15

<210> SEQ ID NO 1604
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 1604

Cys Ala Val Ser Thr Pro Asn Arg Asp Asp Lys Ile Ile Phe
1               5                   10

<210> SEQ ID NO 1605
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 1605

Cys Ala Tyr Glu Ile Thr Gln Gly Gly Ser Glu Lys Leu Val Phe
1               5                   10                  15

<210> SEQ ID NO 1606
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 1606

Cys Ala Val Arg Glu Asp Ser Asn Tyr Gln Leu Ile Trp
1               5                   10

<210> SEQ ID NO 1607
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 1607

Cys Ala Val Arg Pro Arg Asn Gln Gly Gly Lys Leu Ile Phe
1               5                   10

<210> SEQ ID NO 1608
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 1608

Cys Ala Leu Lys Pro Gly Gly Thr Gly Gly Phe Lys Thr Ile Phe
1               5                   10                  15

<210> SEQ ID NO 1609
```

```
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 1609

Cys Ile Val Arg Val Ser Ser Arg Thr Asn Asp Met Arg Phe
1               5                   10

<210> SEQ ID NO 1610
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 1610

Cys Ala Ser Asn Asn Tyr Gly Gln Asn Phe Val Phe
1               5                   10

<210> SEQ ID NO 1611
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 1611

Cys Ala Leu Ser Asp Pro Asn Thr Gly Asn Gln Phe Tyr Phe
1               5                   10

<210> SEQ ID NO 1612
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 1612

Cys Ala Thr Gly Glu Val Ser Gly Asn Thr Pro Leu Val Phe
1               5                   10

<210> SEQ ID NO 1613
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 1613

Cys Ala Val Arg Leu Leu Gly Gly Gly Ala Asp Gly Leu Thr Phe
1               5                   10                  15

<210> SEQ ID NO 1614
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 1614

Cys Ala Val Glu Arg Ser Ser Gly Ala Thr Asn Lys Leu Ile Phe
1               5                   10                  15

<210> SEQ ID NO 1615
<211> LENGTH: 13
```

```
<212> TYPE: PRT
<213> ORGANISM: Artificial sequence
<220> FEATURE:
<223> OTHER INFORMATION: Synthetic polypeptide

<400> SEQUENCE: 1615

Cys Ala Met Ser Val Pro Ser Gln Gly Asn Leu Ile Phe
1               5                   10

<210> SEQ ID NO 1616
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 1616

Cys Ala Val Ser Tyr Asn Thr Asn Ala Gly Lys Ser Thr Phe
1               5                   10

<210> SEQ ID NO 1617
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 1617

Cys Ala Leu Ser Gly Ser Gly Ala Gly Ser Tyr Gln Leu Thr Phe
1               5                   10                  15

<210> SEQ ID NO 1618
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 1618

Cys Ala Thr Ser Gly Ser Ala Arg Gln Leu Thr Phe
1               5                   10

<210> SEQ ID NO 1619
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 1619

Cys Ala Leu Ser Ala Gly Arg Asp Asp Lys Ile Ile Phe
1               5                   10

<210> SEQ ID NO 1620
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 1620

Cys Ala Ala Ala Tyr Thr Gly Arg Arg Ala Leu Thr Phe
1               5                   10

<210> SEQ ID NO 1621
<211> LENGTH: 13
<212> TYPE: PRT
```

```
<213> ORGANISM: Artificial sequence
<220> FEATURE:
<223> OTHER INFORMATION: Synthetic polypeptide

<400> SEQUENCE: 1621

Cys Ala Pro Pro Thr Ser Gly Thr Tyr Lys Tyr Ile Phe
1               5                   10

<210> SEQ ID NO 1622
<211> LENGTH: 17
<212> TYPE: PRT
<213> ORGANISM: Artificial sequence
<220> FEATURE:
<223> OTHER INFORMATION: Synthetic polypeptide

<400> SEQUENCE: 1622

Cys Leu Val Gly Asp Tyr Glu Trp Gly Gly Ala Thr Asn Lys Leu Ile
1               5                   10                  15

Phe

<210> SEQ ID NO 1623
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 1623

Cys Ala Val Met Thr Ile Gln Gly Ala Gln Lys Leu Val Phe
1               5                   10

<210> SEQ ID NO 1624
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 1624

Cys Ala Thr Asp Ser Gly Ala Asn Ser Lys Leu Thr Phe
1               5                   10

<210> SEQ ID NO 1625
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 1625

Cys Ala Leu Arg Leu Tyr Asn Gln Gly Gly Lys Leu Ile Phe
1               5                   10

<210> SEQ ID NO 1626
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 1626

Cys Ile Val Arg Val Trp Asn Asn Phe Asn Lys Phe Tyr Phe
1               5                   10

<210> SEQ ID NO 1627
<211> LENGTH: 13
```

```
<212> TYPE: PRT
<213> ORGANISM: Artificial sequence
<220> FEATURE:
<223> OTHER INFORMATION: Synthetic polypeptide

<400> SEQUENCE: 1627

Cys Ala Phe Met Lys His Thr Gly Asn Met Leu Thr Phe
1               5                   10

<210> SEQ ID NO 1628
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 1628

Cys Ala Ile Lys Arg Arg Asp Gly Ala Thr Asn Lys Leu Ile Phe
1               5                   10                  15

<210> SEQ ID NO 1629
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 1629

Cys Ala Val Arg Asp Met Asn Asn Asn Ala Gly Asn Met Leu Thr Phe
1               5                   10                  15

<210> SEQ ID NO 1630
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 1630

Cys Ala Ala Arg Asp Ser Gly Gly Tyr Gln Lys Val Thr Phe
1               5                   10

<210> SEQ ID NO 1631
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 1631

Cys Ala Gly Arg Ala Ser Gly Thr Tyr Lys Tyr Ile Phe
1               5                   10

<210> SEQ ID NO 1632
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 1632

Cys Ala Pro Pro Val Gly Ser Asn Thr Gly Lys Leu Ile Phe
1               5                   10

<210> SEQ ID NO 1633
<211> LENGTH: 12
<212> TYPE: PRT
```

<213> ORGANISM: Artificial sequence
<220> FEATURE:
<223> OTHER INFORMATION: Synthetic polypeptide

<400> SEQUENCE: 1633

Cys Ala Ala Val Gly Asn Asn Asn Asp Met Arg Phe
1               5                   10

<210> SEQ ID NO 1634
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 1634

Cys Ala Gly Arg Pro Thr Ser Gly Ser Ala Arg Gln Leu Thr Phe
1               5                   10                  15

<210> SEQ ID NO 1635
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 1635

Cys Ala Ala Arg Val Ile His Asn Gln Gly Gly Lys Leu Ile Phe
1               5                   10                  15

<210> SEQ ID NO 1636
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 1636

Cys Ala Met Ser Lys Gln Thr Gly Ala Asn Asn Leu Phe Phe
1               5                   10

<210> SEQ ID NO 1637
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 1637

Cys Ala Val Ser Asp Pro Asn Ser Trp Gly Lys Leu Gln Phe
1               5                   10

<210> SEQ ID NO 1638
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 1638

Cys Leu Val Gly Ser Asn Ser Gly Asn Thr Pro Leu Val Phe
1               5                   10

<210> SEQ ID NO 1639
<211> LENGTH: 12
<212> TYPE: PRT
<213> ORGANISM: Artificial sequence

```
<220> FEATURE:
<223> OTHER INFORMATION: Synthetic polypeptide

<400> SEQUENCE: 1639

Cys Leu Val Gly Val Asn Thr Asp Lys Leu Ile Phe
1               5                   10

<210> SEQ ID NO 1640
<211> LENGTH: 11
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<222> LOCATION: (4)..(4)
<223> OTHER INFORMATION: Xaa can be any naturally occurring amino acid

<400> SEQUENCE: 1640

Cys Ala Met Xaa Asp Asp Tyr Lys Leu Ser Phe
1               5                   10

<210> SEQ ID NO 1641
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 1641

Cys Val Val Thr Asp Tyr Gly Gln Asn Phe Val Phe
1               5                   10

<210> SEQ ID NO 1642
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 1642

Cys Ala Val Arg Glu Gly Tyr Gly Gly Ala Thr Asn Lys Leu Ile Phe
1               5                   10                  15

<210> SEQ ID NO 1643
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 1643

Pro Arg Arg Asn Thr Gly Asn Gln Phe Tyr Phe
1               5                   10

<210> SEQ ID NO 1644
<211> LENGTH: 124
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (85)..(99)
<223> OTHER INFORMATION: n is a, c, g, or t

<400> SEQUENCE: 1644
gcgtaatacg actcactata gggagacaga caagaacttc ccccggactg tgatggtcaa      60
```

```
cctgaacatc cataaccgga acatnnnnnn nnnnnnnnnc aaaaggtcct cagattacta    120
caac                                                                124
```